US012364773B2

(12) United States Patent
Katikaneni et al.

(10) Patent No.: US 12,364,773 B2
(45) Date of Patent: Jul. 22, 2025

(54) LIPID NANOPARTICLE COMPOSITIONS AND USES THEREOF

(71) Applicant: ReCode Therapeutics, Inc., Menlo Park, CA (US)

(72) Inventors: Sahitya Katikaneni, Menlo Park, CA (US); Neda Mahmoudi, Menlo Park, CA (US); Peng Wang, Menlo Park, CA (US); Sakya Sing Mohapatra, Menlo Park, CA (US); Vladimir Grigor'evich Kharitonov, Menlo Park, CA (US)

(73) Assignee: ReCode Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 18/433,161

(22) Filed: Feb. 5, 2024

(65) Prior Publication Data

US 2025/0177562 A1 Jun. 5, 2025

Related U.S. Application Data

(60) Provisional application No. 63/605,191, filed on Dec. 1, 2023.

(51) Int. Cl.

| | |
|---|---|
| *A61K 48/00* | (2006.01) |
| *A61K 9/00* | (2006.01) |
| *A61K 9/51* | (2006.01) |
| *A61K 31/7088* | (2006.01) |
| *A61K 38/17* | (2006.01) |
| *A61K 38/46* | (2006.01) |
| *A61P 11/00* | (2006.01) |

(52) U.S. Cl.
CPC ........ *A61K 48/0033* (2013.01); *A61K 9/0078* (2013.01); *A61K 9/5123* (2013.01); *A61K 31/7088* (2013.01); *A61K 38/1709* (2013.01); *A61K 38/465* (2013.01); *A61P 11/00* (2018.01)

(58) Field of Classification Search
CPC .... A61K 31/713; A61K 48/00; A61K 47/544; A61K 9/12; A61K 47/28; A61K 47/543; A61K 9/1271; A61P 31/14
USPC .......................................................... 424/501
See application file for complete search history.

(56) References Cited

U.S. PATENT DOCUMENTS

| | | | |
|---|---|---|---|
| 5,518,179 | A | 5/1996 | Humberstone et al. |
| 5,820,873 | A | 10/1998 | Choi et al. |
| 7,404,969 | B2 | 7/2008 | Chen et al. |

(Continued)

FOREIGN PATENT DOCUMENTS

| | | | |
|---|---|---|---|
| WO | 2008103276 | A2 | 8/2008 |
| WO | 2010021865 | A1 | 2/2010 |

(Continued)

OTHER PUBLICATIONS

Ndeupen et al. iscience 2021, 249103479) pp. 1-15.*

(Continued)

*Primary Examiner* — Robert B Mondesi
*Assistant Examiner* — Mohammad Y Meah
(74) *Attorney, Agent, or Firm* — Mintz Levin Cohn Ferris Glovsky and Popeo, P.C.

(57) ABSTRACT

Provided are aerosolized pharmaceutical compositions including comprising aerosol particles, the aerosol particles comprising lipid nanoparticles (LNPs). Also provided herein are methods of administering the aerosolized pharmaceutical compositions described herein.

39 Claims, 215 Drawing Sheets

Specification includes a Sequence Listing.

(56) References Cited

U.S. PATENT DOCUMENTS

| | | | |
|---|---|---|---|
| 7,893,302 | B2 | 2/2011 | Chen et al. |
| 8,283,333 | B2 | 10/2012 | Yaworski et al. |
| 8,450,298 | B2 | 5/2013 | Mahon et al. |
| 8,466,122 | B2 | 6/2013 | Heyes et al. |
| 9,061,303 | B2 | 6/2015 | Waldner et al. |
| 10,221,127 | B2 * | 3/2019 | Du et al. .............. C07D 295/13 |
| 10,717,982 | B2 | 7/2020 | Eberle et al. |
| 10,898,574 | B2 | 1/2021 | De Fougerolles et al. |
| 11,135,312 | B2 | 10/2021 | Von Der Mülbe et al. |
| 11,173,190 | B2 | 11/2021 | Heartlein et al. |
| 2005/0006359 | A1 | 1/2005 | Blakey |
| 2008/0060640 | A1 | 3/2008 | Waldner et al. |
| 2008/0311648 | A1 | 12/2008 | Chang et al. |
| 2010/0036115 | A1 | 2/2010 | Beigelman et al. |
| 2012/0202871 | A1 | 8/2012 | Heyes et al. |
| 2013/0064894 | A1 | 3/2013 | Martin et al. |
| 2013/0129785 | A1 | 5/2013 | Manoharan et al. |
| 2013/0150625 | A1 | 6/2013 | Budzik et al. |
| 2013/0178541 | A1 | 7/2013 | Stanton et al. |
| 2013/0225836 | A1 | 8/2013 | Stanton et al. |
| 2014/0200257 | A1 | 7/2014 | Rajeev et al. |
| 2021/0259980 | A1 | 8/2021 | Cheng et al. |
| 2022/0071916 | A1 | 3/2022 | Cheng et al. |

FOREIGN PATENT DOCUMENTS

| | | |
|---|---|---|
| WO | 2010080724 A1 | 7/2010 |
| WO | 2010141069 A2 | 12/2010 |
| WO | 2010144740 A1 | 12/2010 |
| WO | 2011022460 A1 | 2/2011 |
| WO | 2011043913 A2 | 4/2011 |
| WO | 2011068810 A1 | 6/2011 |
| WO | 2011090965 A1 | 7/2011 |
| WO | 2011149733 A2 | 12/2011 |
| WO | 2011153120 A1 | 12/2011 |
| WO | 2012040184 A2 | 3/2012 |
| WO | 2012044638 A1 | 4/2012 |
| WO | 2012046203 A1 | 4/2012 |
| WO | 2012054365 A2 | 4/2012 |
| WO | 2012061259 A2 | 5/2012 |
| WO | 2012099755 A1 | 7/2012 |
| WO | 2012170930 A1 | 12/2012 |
| WO | 2013063468 A1 | 5/2013 |
| WO | 2013086354 A1 | 6/2013 |
| WO | 2013086373 A1 | 6/2013 |
| WO | 2013149140 A1 | 10/2013 |
| WO | 2013151663 A1 | 10/2013 |
| WO | 2013151664 A1 | 10/2013 |
| WO | 2013151667 A1 | 10/2013 |
| WO | 2013151736 A2 | 10/2013 |
| WO | 2014153052 A2 | 9/2014 |
| WO | 2015095340 A1 | 6/2015 |
| WO | 2015184256 A2 | 12/2015 |
| WO | 2015199952 A1 | 12/2015 |
| WO | 2016004202 A1 | 1/2016 |
| WO | 2016094342 A1 | 6/2016 |
| WO | 2016118724 A1 | 7/2016 |
| WO | 2016118725 A1 | 7/2016 |
| WO | 2016205691 A1 | 12/2016 |
| WO | 2017004143 A1 | 1/2017 |
| WO | 2017048789 A1 | 3/2017 |
| WO | 2017049245 A2 | 3/2017 |
| WO | 2017075531 A1 | 5/2017 |
| WO | 2017117528 A1 | 7/2017 |
| WO | 2017173054 A1 | 10/2017 |
| WO | 2017201091 A1 | 11/2017 |
| WO | 2017205767 A1 | 11/2017 |
| WO | 2018157154 A2 | 8/2018 |
| WO | 2018213476 A1 | 11/2018 |
| WO | 2020051220 A1 | 3/2020 |
| WO | 2020051223 A1 | 3/2020 |
| WO | 2020106946 A1 | 5/2020 |
| WO | 2021155274 A1 | 8/2021 |
| WO | 2021216577 A1 | 10/2021 |
| WO | 2021222801 A2 | 11/2021 |
| WO | 2022032154 A2 | 2/2022 |
| WO | 2022169508 A1 | 8/2022 |
| WO | 2022204053 A1 | 9/2022 |
| WO | 2022204215 A1 | 9/2022 |
| WO | 2022204219 A1 | 9/2022 |
| WO | 2022204270 A1 | 9/2022 |
| WO | 2022216619 A1 | 10/2022 |
| WO | 2022226344 A1 | 10/2022 |
| WO | 2022261185 A1 | 12/2022 |

OTHER PUBLICATIONS

Zhou et al. (Jan. 19, 2016) "Modular Degradable Dendrimers Enable Small RNAs to Extend Survival in an Aggressive Liver Cancer Model", Proceedings of the National Academy of Sciences of the United States of America, 113(3):520-525.

Tam et al. (Sep. 1, 2022) "Lipid Nanoparticle Formulations for Optimal RNA-based Topical Delivery to Murine Airways", European Journal of Pharmaceutical Sciences, 176(20):106234.

Uner et al. (Sep. 2007) "Importance of Solid Lipid Nanoparticles (SLN) in Various Administration Routes and Future Perspectives", International Journal of Nanomedicine, 2(3):289-300.

Wang et al. (Jan. 2023) "Preparation of Selective Organ-targeting (SORT) Lipid Nanoparticles (LNPs) Using Multiple Technical Methods for Tissue-specific mRNA Delivery", Nature Protocols, 18:265-291.

Wei et al. (Nov. 11, 2023) "Lung SORT Lnps Enable Precise Homology Directed Repair Mediated CRISPR/Cas Genome Correction in Cystic Fibrosis Models", Nature communications, 14(1):7322.

Wei et al. (Jun. 26, 2020) "Systemic Nanoparticle Delivery of CRISPR-Cas9 Ribonucleoproteins for Effective Tissue Specific Genome Editing", Nature Communications, 11(1):3232.

Zhang et al. (Oct. 30, 2020) "Aerosolizable Lipid Nanoparticles for Pulmonary Delivery of mRNA through Design of Experiments", Pharmaceutics, 12(11):1042.

Zhang et al. (Jul. 2022) "Enhancing CRISPR/Cas Gene Editing Through Modulating Cellular Mechanical Properties for Cancer Therapy", Nature nanotechnology, 17(7):777-787.

Bauer, et al. (Jan. 3, 2015) Generation of Genomic Deletions in Mammalian Cell Lines via CRISPR/Cas9, Journal of Visualized Experiments, (95): e52118.

Allen et al. (Jan. 2013) "Liposomal Drug Delivery Systems: From Concept to Clinical Applications", Proceedings of the National Academy of Sciences of the United States of America, 65(1):36-48.

Álvarez-Benedicto et al. (Jan. 18, 2022) "Optimization of Phospholipid Chemistry for Improved Lipid Nanoparticle (LNP) Delivery of Messenger RNA (mRNA)", Biomaterials Science, 10(2):549-559.

Anderson et al. (Oct. 10, 2019) "Inhalable Nanotherapeutics to Improve Treatment Efficacy for Common Lung Diseases", WIREs Nanomedicine and Nanobiotechnology, 12(1):e1586.

Arteta et al. (Mar. 27, 2018) "Successful Reprogramming of Cellular Protein Production Through mRNA Delivered by Functionalized Lipid Nanoparticles", Proceedings of the National Academy of Sciences of the United States of America, 115(15):E3351-E3360.

Brigham et al. (Oct. 1989) "In vivo Transfection of Murine Lungs with a Functioning Prokaryotic Gene using a Liposome Vehicle", The American Journal of the Medical Sciences, 298(4):278-281.

Bryson et al. (May 20, 2022) "Aerosolized Therapy Restores CFTR in Patient-derived Cells", Cystic Fibrosis News Today, 5 pages.

Calcedo et al. (Sep. 2013) "Self-Reactive CFTR T Cells in Humans: Implications for Gene Therapy", Human Gene Therapy Clinical Development, 24(3):108-115.

Cao et al. (Aug. 15, 2022) "Helper-Polymer Based Five-Element Nanoparticles (FNPs) for Lung-Specific mRNA Delivery with Long-Term Stability after Lyophilization", Nano Letters, 22(16):6580-6589.

Chang et al. (Oct. 6, 2021) "Lipid Nanoparticles for The Inhalation of mRNA", Nature Biomedical Engineering, 5 (9):949-950.

Cheng et al. (Apr. 6, 2020) "Selective Organ Targeting (SORT) Nanoparticles for Tissue-Specific mRNA Delivery and CRISPR-Cas Gene Editing", Nature Nanotechnology, 15(4):313-320.

(56) References Cited

OTHER PUBLICATIONS

Chow et al. (Oct. 2020) "Inhaled RNA Therapy: From Promise to Reality", Trends in Pharmacological Sciences, 41(10):715-729.
Deltcheva et al. (Mar. 31, 2011) "CRISPR RNA Maturation by Trans-Encoded Small RNA and Host Factor RNase III", Nature, 471(7340):602-607.
Dillard et al. (2023) "Passive, Active and Endogenous Organ-targeted Lipid and Polymer Nanoparticles for Delivery of Genetic Drugs", Nature Reviews Materials, 8(4):282-300.
Dilliard et al. (Dec. 28, 2021) "On the Mechanism of Tissue-specific mRNA Delivery by Selective Organ Targeting Nanoparticles", Proceedings of the National Academy of Sciences of the United States of America, 118(52): e2109256118.
Farbiak et al. (Jun. 17, 2021) "All-In-One Dendrimer-Based Lipid Nanoparticles Enable Precise HDR-Mediated Gene Editing In Vivo", Advanced Materials, 33(30):32006619.
Ferguson et al. (Jan. 2018) "Co-Suspension Delivery Technology in Pressurized Metered-Dose Inhalers for Multi-drug Dosing in the Treatment of Respiratory Diseases", Respiratory Medicine, 134:16-23.
Gibson et al. (Oct. 15, 2003) "Pathophysiology and Management of Pulmonary Infections in Cystic Fibrosis", American journal of respiratory and critical care medicine, 168(8):918-951.
Graham et al. (Jun. 2021) "CRISPR/Cas9 Gene Editing Therapies for Cystic Fibrosis", Expert Opinion on Biological Therapy, 21(6):767-780.
Guo et al. (Aug. 2021) "Pharmaceutical Strategies to Extend Pulmonary Exposure of Inhaled Medicines", Acta Pharmaceutica Sinica B, 11(8):2565-2584.
Han et al. (Dec. 13, 2021) "An Ionizable Lipid Toolbox for RNA Delivery", Nature Communications, 12(1):7233.
Haque et al. (Nov. 13, 2018) "Chemically Modified hCFTR mRNAs Recuperate Lung Function in a Mouse Model of Cystic Fibrosis", Scientific reports, 8(1):1-14.
Hou et al. (2021) "Lipid Nanoparticles for mRNA Delivery", Nature Reviews Materials, 6(12):1078-1094.
Jinek et al. (Aug. 17, 2012) "A Programmable Dual-RNA-Guided DNA Endonuclease in Adaptive Bacterial Immunity", Science, 337(6096):816-821.
Karra et al. (Dec. 2019) "Drug Delivery for Traditional and Emerging Airway Models", Organs-on-a-Chip, 1:100002.
Kim et al. (Aug. 29, 2022) "Engineering Lipid Nanoparticles for Enhanced Intracellular Delivery of mRNA through Inhalation", ACS Nano, 16:14792-14806.
Kon et al. (Nov. 2023) "Targeting Cancer with mRNA-Lipid Nanoparticles: Key Considerations and Future Prospects", Nature reviews clinical oncology, 16 Pages.
Koonin et al. (Jun. 2017) "Diversity, Classification and Evolution of CRISPR-Cas Systems", Current Opinion in Microbiology, 37:67-78.
Leong et al. (Sep. 2, 2022) "Lipid Nanoparticles as Delivery Vehicles for Inhaled Therapeutics", Biomedicines, 10(9):2179.
Liu et al. (May 25, 2021) "Membrane-Destabilizing Ionizable Phospholipids for Organ-Selective mRNA Delivery and CRISPR-Cas Gene Editing", Nature Materials, 20(5):701-710.
Lokugamage et al. (Sep. 2021) "Optimization of Lipid Nanoparticles for the Delivery of Nebulized Therapeutic mRNA to the Lungs", Nature Biomedical Engineering, 5(9):1059-1068.
Makarova et al. (Sep. 28, 2015) "An Update Eevolutionary Classification of CRISPR-Cas Systems", Nature Reviews Microbiology, 13:722-736.
McClellan et al. (Apr. 16, 2010) "Genetic Heterogeneity in Human Disease", Cell, 141(2):210-217.
Micklefield, Jason, (Aug. 2001) "Backbone Modification of Nucleic Acids: Synthesis, Structure and Therapeutic Applications", Current Medicinal Chemistry, 8(10):1157-1179.
Miller et al. (Jan. 19, 2017) "Non-Viral CRISPR/Cas Gene Editing In Vitro and In Vivo Enabled by Synthetic Nanoparticle Co-Delivery of Cas9 mRNA and sgRNA", Angewandte Chemie, 56(4):1059-1063.
Moran et al. (2008) "On the Measurement of the Functional Properties of the CFTR", Journal of Cystic Fibrosis, 7 (6):483-494.
Needleman et al. (Mar. 28, 1970) "A General Method Applicable to the Search for Similarities in the Amino Acid Sequence of Two Proteins", Journal of molecular biology, 48:443-453.
O'Sullivan et al. (May 30, 2009) "Cystic Fibrosis", Lancet, 373(9678):1891-1904.
Paranjpe et al. (Apr. 2014) "Nanoparticle-Mediated Pulmonary Drug Delivery: A Review", International Journal of Molecular Sciences, 15(4):5852-5873.
Pardi et al. (Nov. 10, 2015) "Expression Kinetics of Nucleoside-modified mRNA Delivered in Lipid Nanoparticles to Mice by Various Routes", Journal of Controlled Release, 217:345-351.
Pei et al. (Mar. 2022) "Synthesis and Bioactivity of Readily Hydrolysable Novel Cationic Lipids for Potential Lung Delivery Application of mRNAs", Chemistry and Physics of Lipids, 243:105178.
Pillai et al. (Nov. 1998) "Ultrasonic Nebulization of Cationic Lipid-based Gene Delivery Systems for Airway Administration", Pharmaceutical Research, 15(11):1743-1747.
Qiu et al. (Feb. 22, 2022) "Lung-selective mRNA Delivery of Synthetic Lipid Nanoparticles for the Treatment of Pulmonary Lymphangioleiomyomatosis", Proceedings of the National Academy of Sciences of the United States of America, 119(8):e2116271119.
Ratjen et al. (Feb. 22, 2003) "Cystic Fibrosis", Lancet, 361(9358):681-689.
Robinson et al. (2018) "Lipid Nanoparticle-Delivered Chemically Modified mRNA Restores Chloride Secretion in Cystic Fibrosis", Molecular Therapy, 26(8):2034-2046.
Rowe et al. (May 12, 2005) "Cystic Fibrosis", The New England Journal of Medicine, 352(19):1992-2001.
Samaridou et al. (2020) "Lipid Nanoparticles for Nucleic Acid Delivery: Current Perspectives", Advanced Drug Delivery Reviews, 154-155:37-63.
Sanchez et al. (Jan. 2023) "Substituting Racemic Ionizable Lipids With Stereopure Ionizable Lipids Can Increase mRNA Delivery", Journal of Controlled Release, 353:270-277.
Shaffer et al. (Oct. 5, 2020) "Mist Begins to Clear for Lung Delivery of RNA", Nature Biotechnology, 38 (10):1110-1112.
Shmakov et al. (Nov. 5, 2015) "Discovery and Functional Characterization of Diverse Class 2 CRISPR-Cas Systems", Molecular Cell, 60(3):385-397.
Srinivasan et al. (Apr. 2015) "TEER Measurement Techniques for In Vitro Barrier Model Systems", Journal of Laboratory Automation, 20(2):1-20.

\* cited by examiner

Percent recovery of lipids using different extraction solutions and volume

| | Exp 1 | Exp 2 | Exp 3 | Exp 4 | Exp 5 |
|---|---|---|---|---|---|
| Extraction solution | Water / Isopropanol (20:80 v/v) | Water / Isopropanol (40:60 v/v) | Water / Isopropanol (40:60 v/v) | Water / Isopropanol (40:60 v/v) | 50 mM ammonium acetate / Isopropanol (40:60 v/v) |
| Extraction volume | 4 mL | 4 mL | 8 mL | 8 mL | 8 mL |
| Extraction time | 30 min | 30 min | 30 min | 60 min | 60 min |
| 14:0 EPC | 65.52 ± 0.32 | 72.84 ± 1.39 | 83.08 ± 1.80 | 88.41 ± 1.05 | 94.65 ± 2.38 |
| 4A3-SC7 | 85.52 ± 0.92 | 93.31 ± 2.97 | 102.51 ± 0.37 | 102.93 ± 0.59 | 95.74 ± 3.52 |
| Cholesterol | 90.71 ± 2.37 | 95.64 ± 2.01 | 102.34 ± 1.47 | 103.51 ± 1.20 | 95.78 ± 1.16 |
| DMG-PEG2k | 84.46 ± 3.15 | 90.45 ± 1.72 | 101.89 ± 0.58 | 103.37 ± 1.52 | 96.47 ± 1.27 |
| DOPE | 90.23 ± 3.30 | 95.96 ± 1.67 | 102.07 ± 0.88 | 104.71 ± 2.90 | 97.59 ± 1.43 |

FIG. 17A

| Storage Condition | Exp 6<br>4 °C for 24 hours | Exp 7<br>-80 °C for 24 hours |
| --- | --- | --- |
| 14:0 EPC | 95.77 ± 3.25 | 97.22 ± 0.90 |
| 4A3-SC7 | 94.59 ± 1.63 | 97.05 ± 2.27 |
| Cholesterol | 96.21 ± 1.54 | 96.04 ± 1.65 |
| DMG-PEG2k | 96.24 ± 1.08 | 96.78 ± 2.64 |
| DOPE | 94.68 ± 1.16 | 94.69 ± 1.87 |

FIG. 20A

| | Pre-Dialysis Details | | | Post Dialysis Details* | | Post Nebulization | | | Aprroximate Nebulization Output | |
|---|---|---|---|---|---|---|---|---|---|---|
| Sample # | Manufacturing Process Details | Initial Formulation Buffer | Particle Size (nm) Pre-Dialysis | Post Dialysis Buffer | Particle Size (nm) Post Dialysis | Particle Size (nm) | Pre-neb EE% | Solo Post Neb EE% | Solo (uL/min) | PDAP (uL/min) |
| 1 | | | | 15mM Tris 75mM NaCl, pH 7.5, 5% Sucrose | 90.5 | 302 | 90.1 | 55.6 | 200 | 400 |
| 2 | Knauer Pump + TFF | 15mM Citrate pH 4.0, 10% Sucrose | 68.3 | 1X DPBS | 88.3 | 477 | 92.6 | 3.2 | 200 | 400 |
| 3 | | | | 15mM Citrate pH 4.0 | 72.9 | 273 | 91.1 | 91.1 | 70 | N/A |
| 4 | Knauer Pump + TFF | 15mM Tris 75mM NaCl, pH 7.5, 5% Sucrose | 63.2 | 15mM Citrate pH 4.0, 10% Sucrose | 76.7 | 174 | 92.8 | 90.1 | 70 | N/A |
| 5 | Knauer Pump + TFF | 15mM Tris 75mM NaCl, pH 7.5, 5% Sucrose | 62.9 | N/A | N/A | 400 | 93.2 | 26.0 (Solo); 29.0 (PDAP) | 200 | 400 |

| Sample # | |
|---|---|
| 1 | Composition X-CFTR, 1mg/mL |
| 2 | Composition X-CFTR, 1mg/mL |
| 3 | Composition X-CFTR, 1mg/mL |
| 4 | Composition B-CFTR, 1mg/mL |
| 5 | Composition B-CFTR, 1mg/mL (300mg ITR Techtrial Batch) |

FIG. 60

| Sample | Scale + Process | Storage at 2-8°C | | | | Freeze-Thaw (Storage at -80°C) | | | |
|---|---|---|---|---|---|---|---|---|---|
| | | Z avg (nm) | PDI | EE (%) | RNA (mg/ml) Ribogreen-AL | Z avg (nm) | PDI | EE (%) | RNA (mg/ml) Ribogreen-AL |
| Composition X-CFTR-HA 6mL 1mg/mL RCD2100-22-KP-TFF-001 DOM: 12SEP2022 Storage Buffer: 15mM Citrate, 10% Sucrose w/v | 0.5g (Knauer Pump + TFF) Tech Trial Batch | 59.8 | 0.10 | 94.1 | 1.11 | 63.0 | 0.10 | 94.5 | 1.01 |
| 20220824-Composition X-CFTR 15mM Citrate 10% sucrose pH 4 | 3mg (Syinge Pump Mixing + PD10) | 56.3 | 0.10 | 93.5 | 1.21 | 64.7 | 0.08 | 92.2 | 1.11 |
| 20220830-Composition X-CFTR | 6mg (Syinge Pump Mixing + PD10) | 56.6 | 0.11 | 94.0 | 1.08 | 74.7 | 0.08 | 93.4 | 1.06 |

FIG. 61

| Sample # | Starting mRNA Buffer/ Citrate Inline Dilution | Formulation Buffer | Sucrose % (w/v) |
|---|---|---|---|
| 1 | 10mM Citrate, pH4.0 | 15mM Citrate pH 4.0 | 5 |
| 2 | | 15mM Citrate pH 5.2 | |
| 3 | | 15mM Sodium Acetate pH 4.0 | |
| 4 | | 15mM Sodium Acetate pH 5.2 | |
| 5 | | 15mM Tris pH 5.2 | |
| 6 | | 15mM Tris pH 7.5 | |
| 7 | 10mM Citrate, pH6.0 | 15mM Citrate pH 4.0 | 10 |
| 8 | | 15mM Citrate pH 5.2 | |
| 9 | | 15mM Sodium Acetate pH 4.0 | |
| 10 | | 15mM Sodium Acetate pH 5.2 | |
| 11 | | 15mM Tris pH 5.2 | |
| 12 | | 15mM Tris pH 7.5 | |
| 13 | | 15mM Citrate pH 4.0 | |
| 14 | | 15mM Citrate pH 5.2 | |
| 15 | | 15mM Sodium Acetate pH 4.0 | |
| 16 | | 15mM Sodium Acetate pH 5.2 | |
| 17 | | 15mM Tris pH 7.5 | |

FIG. 62B

| Sample# | F/T cycle 1 | | | F/T cycle 2 | | | F/T cycle 3 | | |
|---|---|---|---|---|---|---|---|---|---|
| | Particle Size (nm) | Polydispersity Index | % Encapsulation efficiency | Particle Size (nm) | Polydispersity Index | % Encapsulation efficiency | Particle Size (nm) | Polydispersity Index | % Encapsulation efficiency |
| 1 | 72 | 0.153 | 91 | 81 | 0.098 | 91 | 90 | 0.138 | 90 |
| 2 | 78 | 0.095 | 93 | 97 | 0.124 | 88 | 111 | 0.124 | 83 |
| 3 | 75 | 0.061 | 94 | 82 | 0.083 | 91 | 99 | 0.154 | 91 |
| 4 | 98 | 0.157 | 86 | 134 | 0.181 | 80 | 200 | 0.214 | 69 |
| 5 | 212 | 0.088 | 92 | 120 | 0.118 | 83 | 133 | 0.093 | 80 |
| 6 | 109 | 0.107 | 84 | 140 | 0.178 | 79 | 175 | 0.165 | 67 |
| 7 | 64 | 0.145 | 91 | 67 | 0.125 | 91 | 97 | 0.255 | 90 |
| 8 | 72 | 0.094 | 92 | 87 | 0.122 | 86 | 94 | 0.110 | 73 |
| 9 | 61 | 0.082 | 91 | 64 | 0.069 | 91 | 67 | 0.084 | 89 |
| 10 | 75 | 0.133 | 92 | 85 | 0.128 | 83 | 96 | 0.185 | 83 |
| 11 | 198 | 0.074 | 94 | 97 | 0.124 | 91 | 106 | 0.124 | 86 |
| 13 | 67 | 0.120 | 94 | 69 | 0.109 | 95 | 71 | 0.103 | 93 |
| 14 | 84 | 0.088 | 93 | 89 | 0.117 | 88 | 99 | 0.153 | 84 |
| 15 | 73 | 0.067 | 93 | 82 | 0.121 | 80 | 84 | 0.110 | 85 |
| 16 | 87 | 0.119 | 87 | 102 | 0.189 | 77 | 103 | 0.180 | 77 |
| 17 | 125 | 0.184 | 91 | 126 | 0.211 | 90 | 130 | 0.169 | 87 |

FIG. 62C

| Sample# | Week 1 | | | Week 2 | | | Week 3 | | | Week 4 | | | Week 7 | | |
|---|---|---|---|---|---|---|---|---|---|---|---|---|---|---|---|
| | Particle Size (nm) | Polydispersity Index | % Encapsulation efficiency | Particle Size (nm) | Polydispersity Index | % Encapsulation efficiency | Particle Size (nm) | Polydispersity Index | % Encapsulation efficiency | Particle Size (nm) | Polydispersity Index | % Encapsulation efficiency | Particle Size (nm) | Polydispersity Index | % Encapsulation efficiency |
| 1 | 85 | 0.137 | 91 | 78 | 0.128 | 91 | x | x | x | x | x | x | x | x | x |
| 2 | 87 | 0.082 | 92 | 117 | 0.139 | 91 | x | x | x | x | x | x | x | x | x |
| 3 | 79 | 0.065 | 92 | 78 | 0.058 | 91 | x | x | x | x | x | x | x | x | x |
| 4 | 102 | 0.192 | 87 | 91 | 0.158 | 87 | x | x | x | x | x | x | x | x | x |
| 5 | 108 | 0.097 | 90 | 103 | 0.152 | 90 | x | x | x | x | x | x | x | x | x |
| 6 | 124 | 0.160 | 84 | 114 | 0.132 | 85 | x | x | x | x | x | x | x | x | x |
| 7 | 69 | 0.169 | 91 | 64 | 0.130 | 91 | 69 | 0.209 | 91 | 66 | 0.126 | 88 | 66 | 0.159 | 90 |
| 8 | 85 | 0.124 | 86 | 122 | 0.121 | 90 | 129 | 0.113 | 90 | x | x | x | x | x | x |
| 9 | 62 | 0.099 | 92 | 61 | 0.080 | 91 | 63 | 0.132 | 91 | 70 | 0.189 | 89 | 62 | 0.079 | 91 |
| 10 | 82 | 0.175 | 91 | 75 | 0.112 | 90 | 93 | 0.243 | 91 | 78 | 0.138 | 88 | 83 | 0.163 | 90 |
| 11 | 91 | 0.187 | 92 | 93 | 0.159 | 92 | 102 | 0.186 | 91 | 94 | 0.178 | 89 | 94 | 0.136 | 91 |
| 13 | 67 | 0.126 | 93 | 67 | 0.101 | 94 | 67 | 0.133 | 93 | 78 | 0.192 | 91 | 69 | 0.099 | 93 |
| 14 | 86 | 0.126 | 92 | 112 | 0.055 | 92 | 130 | 0.057 | 92 | 114 | 0.096 | 90 | 159 | 0.081 | 91 |
| 15 | 74 | 0.136 | 92 | 73 | 0.087 | 92 | 74 | 0.117 | 92 | 75 | 0.110 | 92 | 76 | 0.056 | 92 |
| 16 | 87 | 0.129 | 88 | 86 | 0.134 | 89 | 88 | 0.111 | 87 | 89 | 0.164 | 86 | 98 | 0.133 | 81 |
| 17 | 122 | 0.205 | 91 | 117 | 0.168 | 91 | 111 | 0.185 | 90 | 108 | 0.191 | 88 | 133 | 0.213 | 92 |

FIG. 62D

| Sample# | Starting mRNA Buffer/ Citrate Inline dilution | Formulation Buffer | Sucrose % (w/v) | P188 %(w/v) |
|---|---|---|---|---|
| 1 | | 15mM Citrate pH 4.0 | | |
| 2 | | 15mM Sodium Acetate pH 4.0 | | 0 |
| 3 | | 15mM Sodium Acetate pH 4.9 | | |
| 4 | 10mM Citrate, pH4.0 | 15mM Histidine, pH 6.0 | 10 | |
| 5 | | 15mM Citrate pH 4.0 | | |
| 6 | | 15mM Sodium Acetate pH 4.0 | | 0.005 |
| 7 | | 15mM Sodium Acetate pH 4.9 | | |
| 8 | | 15mM Histidine, pH 6.0 | | |
| 9 | 10mM Citrate, pH6.0 | 15mM Citrate pH 4.0 | | 0 |
| 10 | | 15mM Citrate pH 4.0 | | 0.005 |

FIG. 62E

| Sample# | F/T cycle 1 | | | F/T cycle 2 | | | F/T cycle 3 | | |
|---|---|---|---|---|---|---|---|---|---|
| | Particle Size (nm) | Polydispersity Index | % Encapsulation efficiency | Particle Size (nm) | Polydispersity Index | % Encapsulation efficiency | Particle Size (nm) | Polydispersity Index | % Encapsulation efficiency |
| 1 | 62 | 0.058 | 92 | 68 | 0.048 | 92 | 72 | 0.090 | 91 |
| 2 | 64 | 0.042 | 91 | 68 | 0.068 | 91 | 71 | 0.030 | 90 |
| 3 | 61 | 0.107 | 92 | 63 | 0.128 | 92 | 64 | 0.119 | 92 |
| 4 | 82 | 0.155 | 91 | 87 | 0.149 | 91 | 91 | 0.169 | 91 |
| 5 | 63 | 0.080 | 93 | 68 | 0.065 | 93 | 72 | 0.061 | 92 |
| 6 | 61 | 0.089 | 93 | 64 | 0.072 | 93 | 65 | 0.054 | 92 |
| 7 | 60 | 0.097 | 93 | 62 | 0.102 | 93 | 64 | 0.107 | 92 |
| 8 | 89 | 0.141 | 92 | 94 | 0.173 | 90 | 99 | 0.144 | 89 |
| 9 | 72 | 0.122 | 93 | 76 | 0.099 | 92 | 79 | 0.117 | 91 |
| 10 | 75 | 0.130 | 94 | 78 | 0.140 | 93 | 81 | 0.129 | 93 |

FIG. 62F

| Sample# | Week 1 | | | Week 3 | | | Week 4 | | | Week 6 | | |
|---|---|---|---|---|---|---|---|---|---|---|---|---|
| | Particle Size (nm) | Polydispersity Index | % Encapsulation efficiency | Particle Size (nm) | Polydispersity Index | % Encapsulation efficiency | Particle Size (nm) | Polydispersity Index | % Encapsulation efficiency | Particle Size (nm) | Polydispersity Index | % Encapsulation efficiency |
| 1 | 61 | 0.076 | 93 | 62 | 0.062 | 91 | 63 | 0.070 | 91 | 62 | 0.070 | 90 |
| 2 | 65 | 0.058 | 92 | 64 | 0.072 | 91 | 67 | 0.069 | 91 | 64 | 0.062 | 89 |
| 3 | 61 | 0.117 | 93 | 65 | 0.135 | 91 | 62 | 0.127 | 92 | 63 | 0.118 | 91 |
| 4 | 79 | 0.146 | 92 | 85 | 0.153 | 91 | 87 | 0.163 | 91 | 86 | 0.142 | 91 |
| 5 | 61 | 0.076 | 93 | 61 | 0.069 | 92 | 65 | 0.054 | 93 | 65 | 0.068 | 91 |
| 6 | 60 | 0.066 | 93 | 60 | 0.066 | 92 | 63 | 0.085 | 93 | 61 | 0.070 | 92 |
| 7 | 57 | 0.113 | 93 | 63 | 0.142 | 92 | 63 | 0.099 | 92 | 64 | 0.145 | 92 |
| 8 | 83 | 0.141 | 92 | 85 | 0.152 | 91 | 87 | 0.148 | 91 | 89 | 0.140 | 90 |
| 9 | 72 | 0.159 | 93 | 74 | 0.114 | 92 | 75 | 0.143 | 92 | 75 | 0.122 | 91 |
| 10 | 73 | 0.147 | 94 | 76 | * | 93 | 78 | 0.135 | 93 | 78 | 0.142 | 92 |

\* Missing datapoint

| Formulation | Buffer Strength & Species | pH | P-188 (%w/v) | Sucrose (%w/v) | Solo Output Rate (uL/min) | Analyst 01 | | Analyst 02 | |
|---|---|---|---|---|---|---|---|---|---|
| | | | | | | %EE Pre-Neb | %EE Post Neb | %EE Pre-Neb | %EE Post Neb |
| Composition X-HA-CFTR | 15mM Citrate | 4.0 | 0 | 10 | 50-90* | - | - | 93.0 | 87.8 |
| | 15mM Acetate | 5.0 | 0 | 10 | 85.1 | 93.24 | 87.12 | 93.79 | 86.45 |
| | 15mM Citrate | 5.5 | 0 | 10 | 94.5 | 92.78 | 88.13 | 92.89 | 88.2 |
| | 15mM Citrate | 6.0 | 0 | 10 | 113.5 | 92.81 | 78.6 | 93.06 | 82.59 |
| | 15mM Tris | 7.0 | 0 | 10 | 114 | 92.64 | 53.7 | 91.47 | 54.79 |
| | 15mM Tris | 7.5 | 0.005 | 10 | 148.5 | 92.4 | 22.06 | 92.17 | 21.44 |

FIG. 63

| Sample # | Formulation | Formulation Buffer | mRNA | pH | NaCl (mM) | % Sucrose (w/v) | Solo Output Rate (uL/min) | %EE Pre-Neb | | Solo %EE Post-Neb | |
|---|---|---|---|---|---|---|---|---|---|---|---|
| | | | | | | | | Analyst 01 | Analyst 02 | Analyst 01 | Analyst 02 |
| 1 | Composition X | 15mM Citrate | CFTR | 6.0 | 0 | 10 | 94 | 90.92 | 92.58 | 76.54 | 80.33 |
| 2 | | | CFTR | 6.5 | 0 | 10 | 127 | 89.00 | 89.93 | 70.32 | 71.36 |
| 3 | | | CFTR | 6.0 | 50 | 10 | 122 | 90.48 | 91.34 | 71.66 | 70.58 |
| 4 | | | CFTR | 6.5 | 50 | 10 | 134 | 92.76 | 93.21 | 70.52 | 70.17 |

FIG. 64

Extracted from Goldfarbmuren et al. (2020) Nat Commun. 11: 2485.

| Genotype | Donor Codes |
|---|---|
| ΔF508/ΔF508 | TXCF042716<br>KKD012K<br>KKD025L<br>KKD003K<br>20160524CF<br>KKD017N |
| W1282X/W1282X | UI0014 |
| R553X/W1282X | UI0009 |
| K710X/L467P | ND13816 |
| G542X/ΔF508 | KKCFFT0051 |

FIG. 67B

| Cell type | Antibody |
|---|---|
| Ionocytes | FoxI1 |
| Proliferating basal, secretory, ionocyte, and SMG basal | KRT8 |
| Basal cells | KRT5 |
| Club cells | CC10 |
| Secretory cells | Mucin |
| Ciliated cells | Tubulin |

FIG. 67C

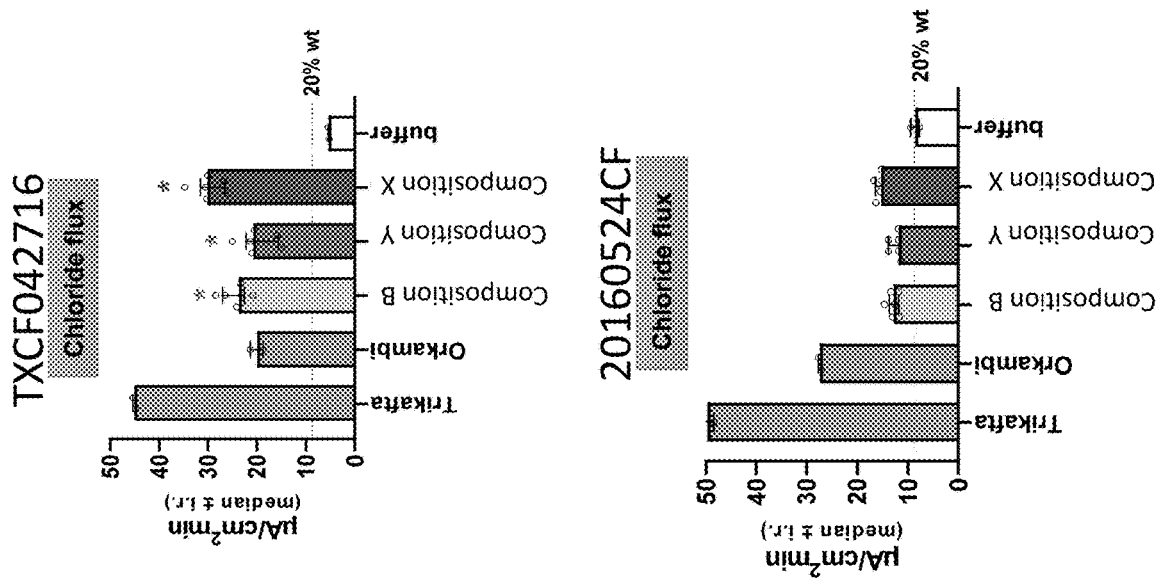
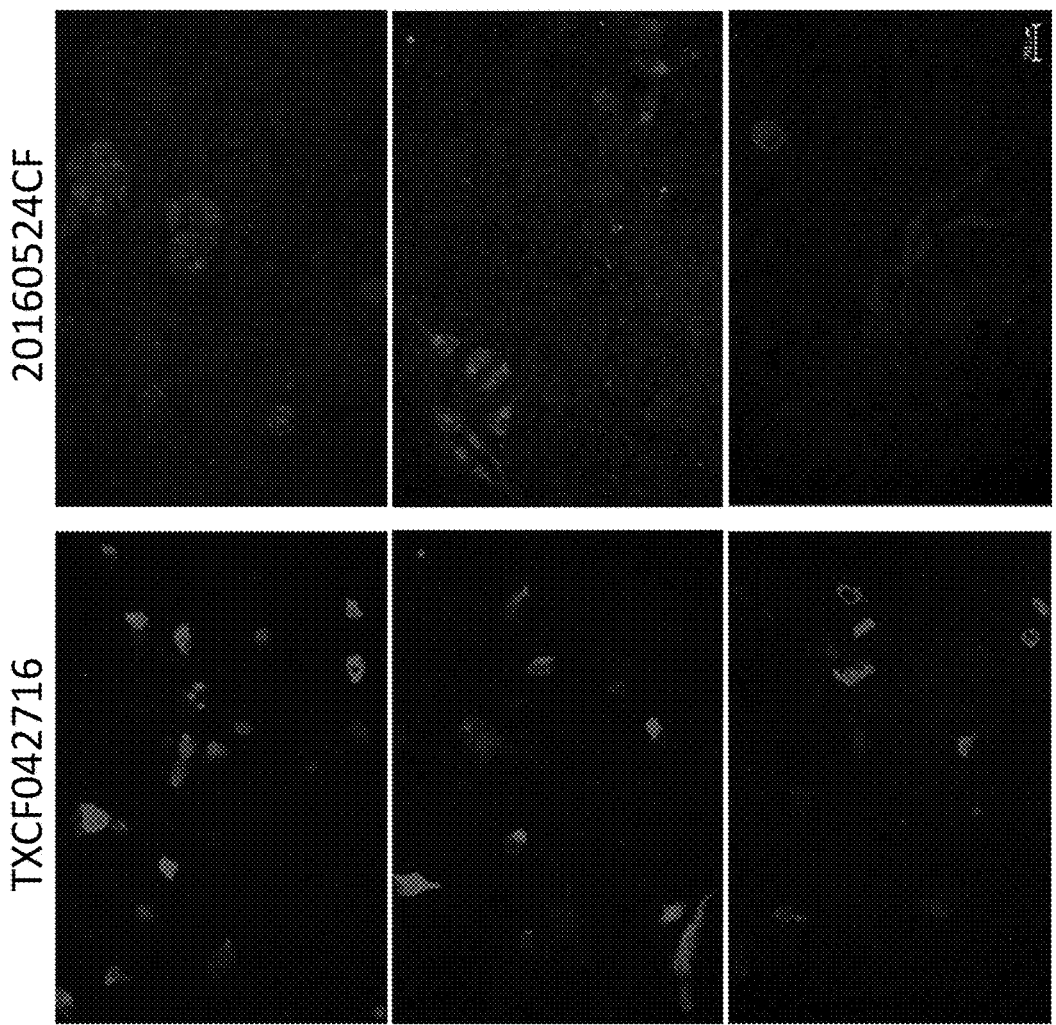
FIG. 72

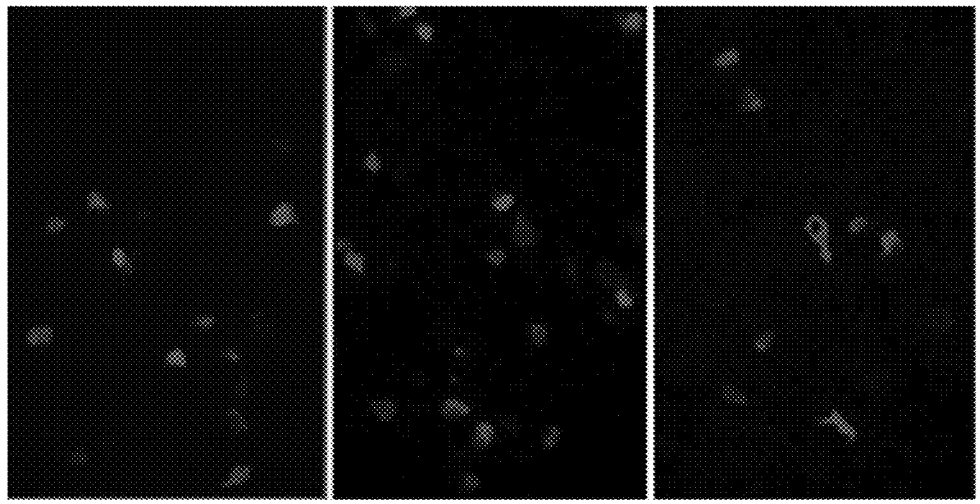
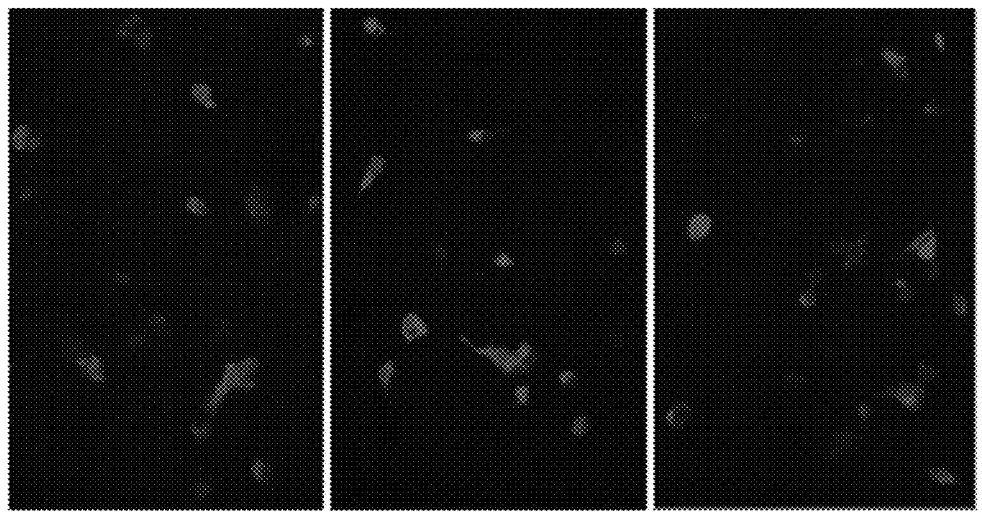
FIG. 75

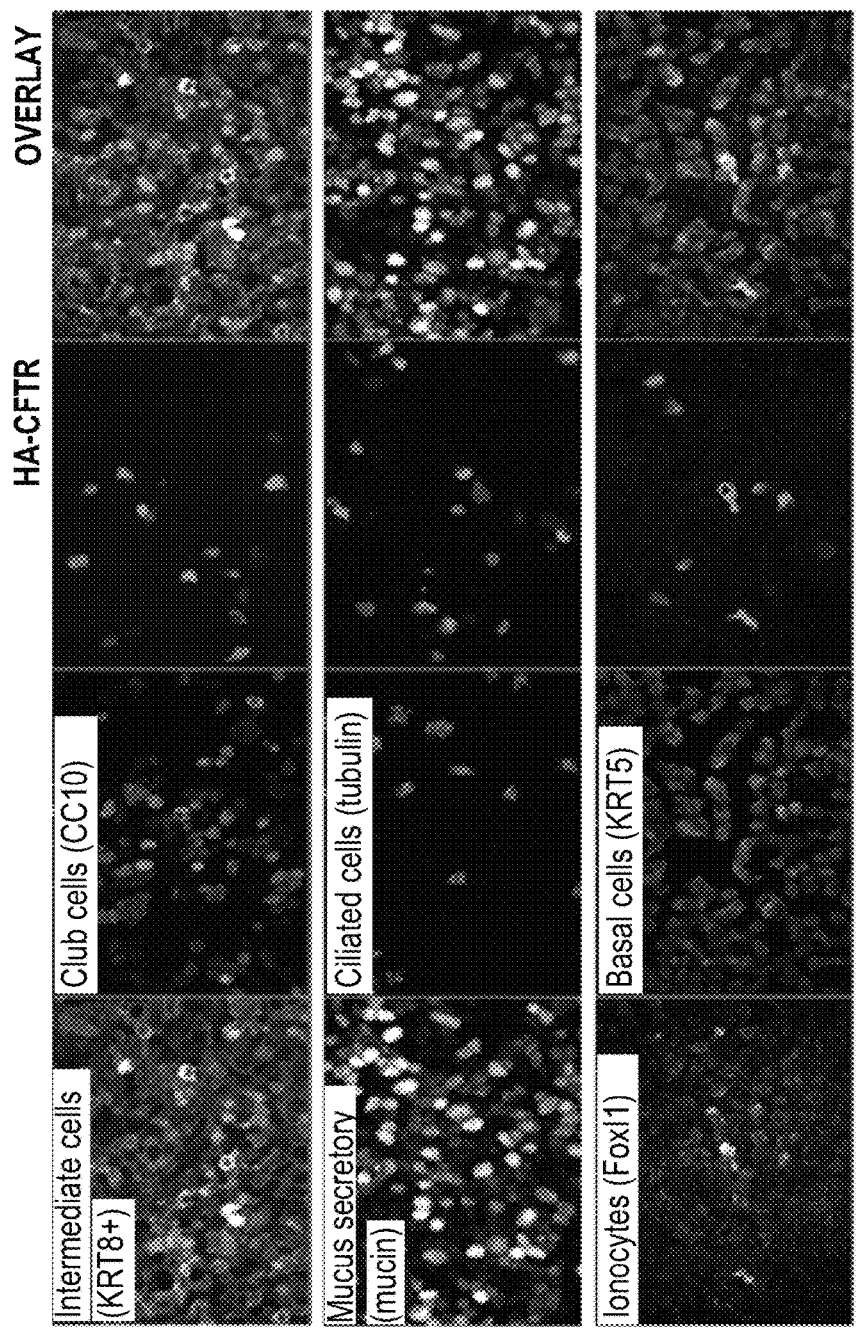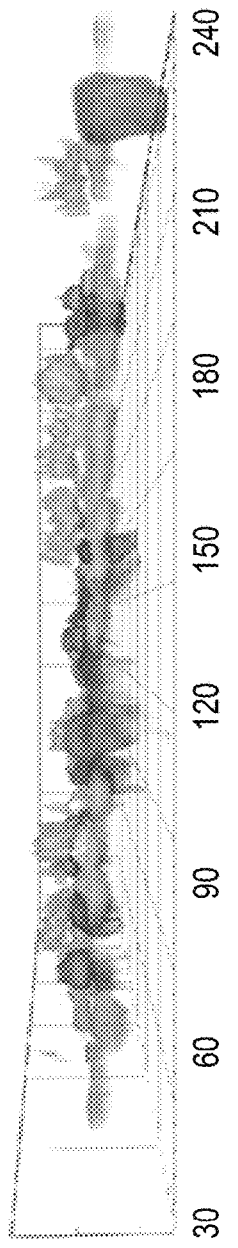
FIG. 76A

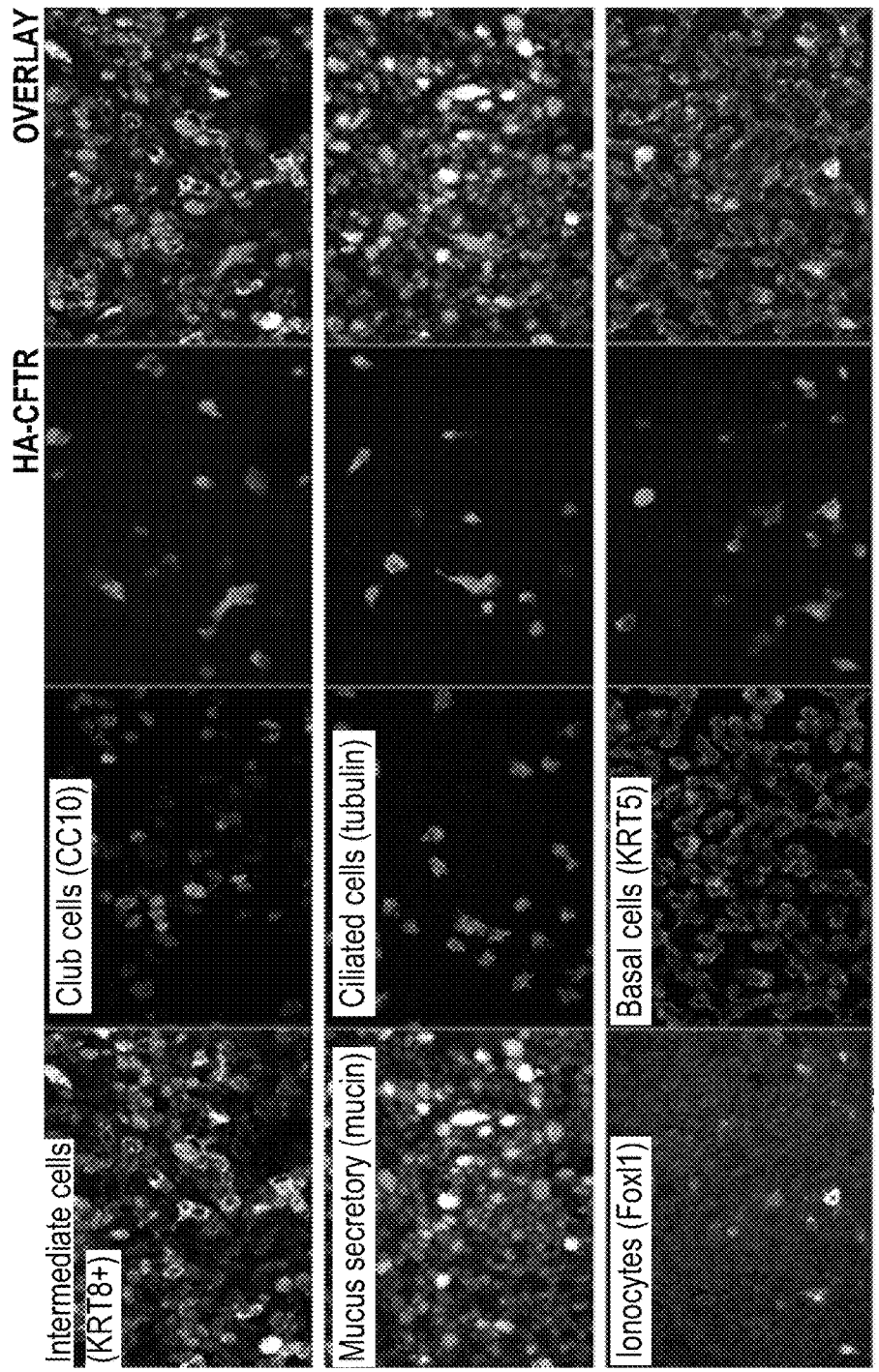
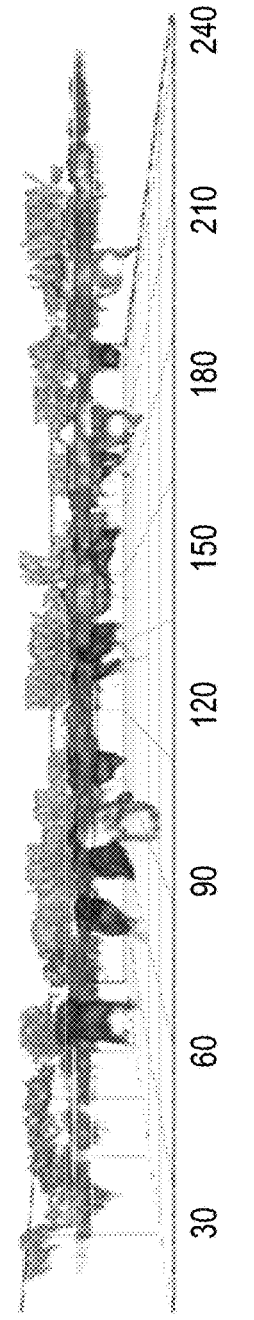
FIG. 77A

| Cohort | Planned Dose | Number of Participants |
|---|---|---|
| Cohort 1 | 2.5 mg | 8 (6 active, 2 placebo) |
| Cohort 2 | 5.0 mg | 8 (6 active, 2 placebo) |
| Cohort 3 | 10.0 mg | 8 (6 active, 2 placebo) |
| Cohort 4 | 20.0 mg | 8 (6 active, 2 placebo) |

Abbreviation: SRC, safety review committee.

Notes:

Dose units refer to the nominal dose of the study drug that will be loaded into the nebulizer.

Doses for Cohorts 1 to 4 are planned. As new safety and/or laboratory data become available, the planned dose escalation scheme may change following a review of the data by the SRC.

If needed based on the recommendation of the SRC, dose levels may be adjusted and/or additional cohorts added or expanded as necessary to adequately characterize the safety of the study drug.

The maximum dose strength administered is planned to be 20.0 mg and the maximum increase between dose strengths is planned to be approximately 2×.

FIG. 79

| Phase | Screening | Check-in | Treatment Period | | | | | | | Follow-up | | |
|---|---|---|---|---|---|---|---|---|---|---|---|---|
| Day | −28 to −2 | −1 | 1 | | | | | | | 8 | 15 | 29 |
| Hours Postdose | | | Predose | 0 | 0.5 | 1 | 4 | 24 | 48 | | | EOS / ET |
| Time Window | | | | | ±5 min | ±10 min | ±10 min | ±60 min | ±60 min | ±1 day | ±1 day | ±1 day |
| Procedure[a] | | | | | | | | | | | | |
| Admission to clinic | | X | | | | | | | | | | |
| Discharge from clinic[b] | | | | | | | | | X | | | |
| Outpatient visit | X | | | | | | | | | X | | X |
| Informed consent | X | | | | | | | | | | | |
| Demographics | X | | | | | | | | | | | |
| Serology[c] | X | | | | | | | | | | | |
| Serum FSH[d] | X | | | | | | | | | | | |
| Inclusion/exclusion criteria | X | X | | | | | | | | | | |
| Medical history | X | X | | | | | | | | | | |
| Height, weight, and BMI[e] | X | X | | | | | | | | | | |
| Physical examination[f] | X | X | | | | | | | | | | X |
| Vital sign measurements[g] | X | X | X | | X | X | X | X | | X | X | X |
| 12-lead ECG[h] | X | X | | | | X | X | X | X | X | X | X |
| Clinical laboratory testing[i] | X | X | | | | | X | X | X | X | X | X |
| Cytokines[j] | | X | | | | X | X | X | X | | | |
| Urinalysis[j] | X | X | | | | X | | X | X | | | |
| Spirometry[j] | X | X | X[l] | | | X | X | X | X | | | |
| Alcohol breath/urine drug and cotinine screen[k] | X | X | | | | | | | | | | |
| SARS-CoV-2 screening[l] | X | | | X | | | | | | | | |
| Salbutamol HTA administration[m] | | | | | | | | | | | | |
| Study drug administration[n] | | | | | | | | | | | | |
| AntiDNA11 binding antibodies, antiPEG antibodies | | X | | | | | | | | X | X | X |
| DNA11 mRNA | | X | | | X | X | X | X | X | X | X | |
| LNP SORT components[o] | | X | | | X | X | X | X | X | X | X | |
| AEs[p] | | | | | | | | | | | | |
| Prior/concomitant medications | | | | | | | | | | | | |

FIG. 80

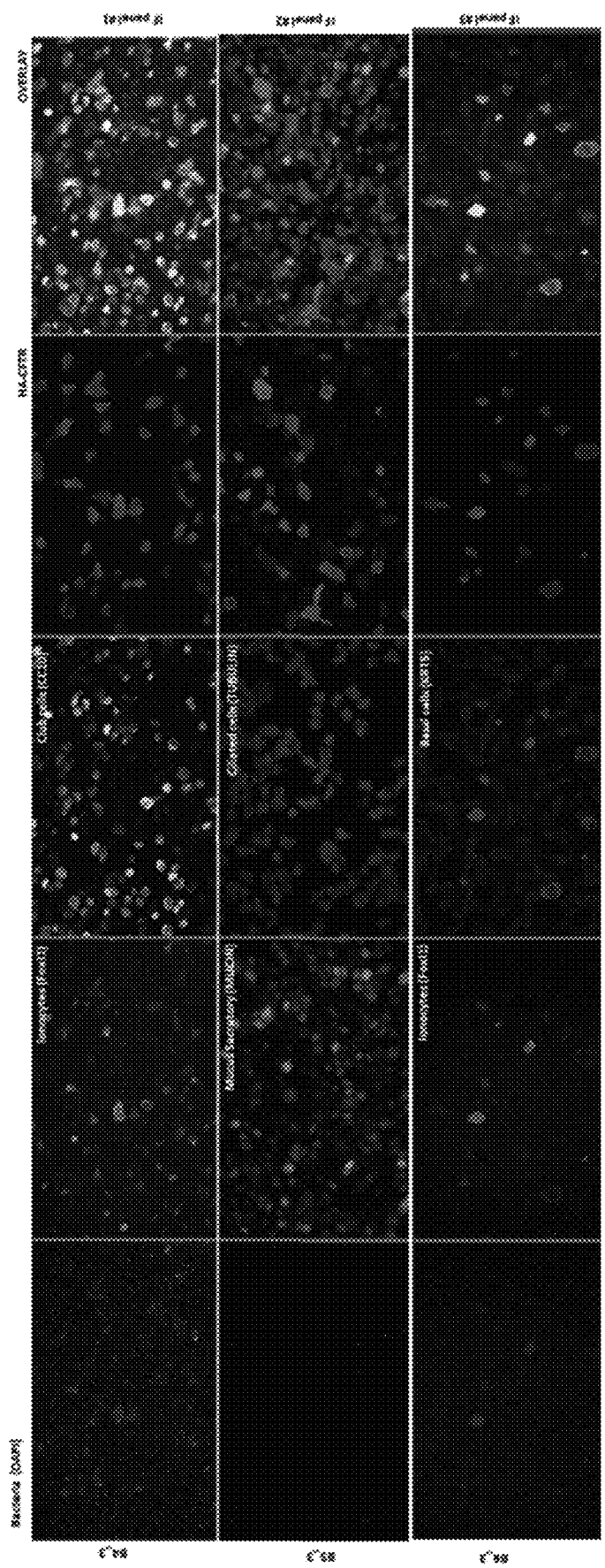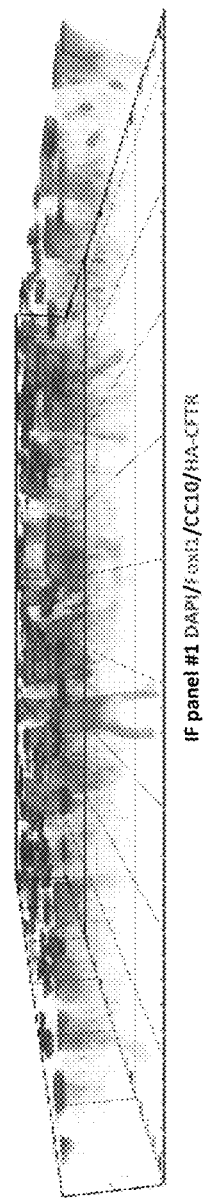
FIG. 81

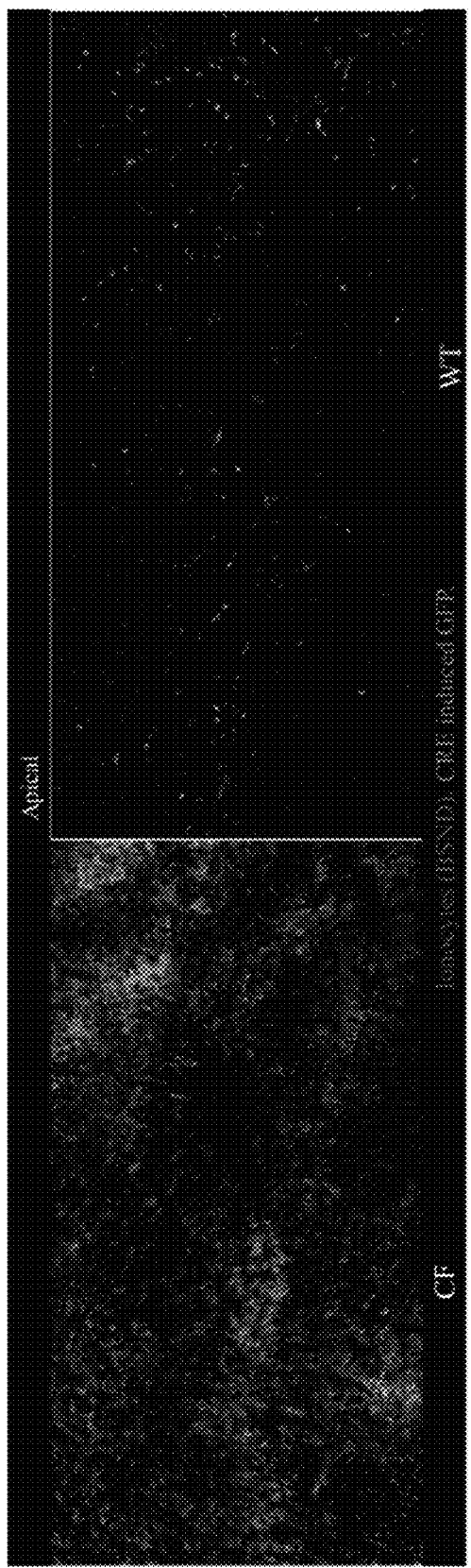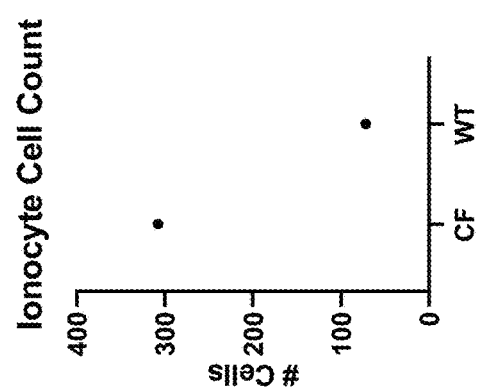
FIG. 130A

LIPID NANOPARTICLE COMPOSITIONS AND USES THEREOF

CROSS-REFERENCE TO RELATED APPLICATION

This application claims the benefit of U.S. Provisional Patent Application No. 63/605,191 filed Dec. 1, 2023 which is incorporated by reference herein in its entirety.

INCORPORATION BY REFERENCE OF SEQUENCE LISTING

This application contains a Sequence Listing which has been submitted in .XML format via EFS-WEB and is hereby incorporated by reference in its entirety. The .XML file, created on Feb. 5, 2024, is named 06529-509001US_SeqList_ST26.xml and is 16 kilobytes in size.

BACKGROUND

Delivery of therapeutic agents to lungs may be achieved either through systemic administration of the agents to a subject or through administration directly to the lungs via mouth or nose. In either case, a vehicle may be used to protect and aide the delivery of the agents. One type of vehicle for the therapeutics agents (such proteins, nucleic acids, or small molecules) is lipid nanoparticles (LNPs). This type of vehicle is used, for example in mRNA-based vaccines. LNP vaccines are generally administered subcutaneously, and like most LNPs, by default they primarily traffic to liver. By contrast, WO 2020/051220 A1 discloses compositions with preferential targeting or delivery of a nucleic acid composition to a particular organ, such as lungs. Accordingly, one approach to delivery of LNPs to lungs is systemic administration of LNPs in a pharmaceutical composition that has not been nebulized to form aerosols but rather is injected into the subject for systemic distribution (e.g., injected intravenously).

For delivery to lungs via mouth or nose, a pharmaceutical composition containing the therapeutic agents, or a vehicle containing the therapeutic agents, may be nebulized to form fine particles (generally less than 10 microns in aerodynamic diameter). However, size control is an important consideration. Aerosol particles smaller than 2 microns can reach deep into alveolar regions. Nebulization of pharmaceutical composition containing the therapeutic agents in a manner that preserves therapeutic efficacy and generates aerosol particles with desired physical characteristics for delivery to appropriate regions of lungs remain challenging. In particular, nebulization of pharmaceutical compositions containing LNPs may result in degradation of the LNPs, de-encapsulation of the therapeutic agents, formations of aerosol particles having physical properties that prevent targeted to delivery to desired regions of lungs, or other undesired effects on the LNPs, and their payload, or both.

Accordingly, there is a long-felt and unmet need for aerosolized pharmaceutical compositions that comprise aerosol particles comprising lipid nanoparticles (LNPs) capable of delivering the LNPs to lungs of a subject—for example, to a tracheobronchial region of a subject—and/or having desired physical characteristics. The present disclosure provides such aerosolized pharmaceutical compositions, methods of making and using thereof, and further related compositions and methods.

SUMMARY

In one aspect, the present disclosure provides a lipid nanoparticle (LNP) composition, comprising at least two selective organ targeting (SORT) lipids and/or at least six lipids.

In some embodiments, the LNP composition comprises an ionizable cationic lipid, optionally two or more ionizable lipids; and a permanently cationic lipid, optionally two or more permanently cationic lipids.

In some embodiments, the LNP composition comprises an ionizable cationic lipid, a permanently cationic lipid, optionally a phospholipid, optionally a polyethylene-glycol (PEG)-lipid, and/or optionally a sterol.

In some embodiments, the LNP composition comprises at least six lipids.

In some embodiments, the LNP composition comprises an ionizable cationic lipid, a permanently cationic lipid, optionally a phospholipid, optionally a polyethylene-glycol (PEG)-lipid, and/or optionally a sterol.

In some embodiments, the LNP composition comprises at least two selective organ targeting (SORT) lipids. In some embodiments, the ionizable cationic lipid is a dendrimeric lipid, optionally 4A3-SC7 or 5A2-SC8. In some embodiments, the ionizable cationic lipid is a SORT lipid; and/or the permanently cationic lipid is a SORT lipid. In some embodiments, the ionizable cationic lipid is 1,2-dioleoyl-3-dimethylammonium-propane (DODAP). In some embodiments, the permanently cationic lipid is trimethylammonium-propane, optionally 1,2-dimyristoyl-3-trimethylammonium-propane(14:0 TAP), 1,2-dipalmitoyl-3-trimethylammonium-propane (16:0 TAP), 1,2-stearoyl-3-trimethylammonium-propane (18:0 TAP), 1,2-dioleoyl-3-trimethylammonium-propane (DOTAP). In some embodiments, the permanently cationic lipid is ethylphosphocholine (EPC), optionally 1,2-dilauroyl-sn-glycero-3-ethylphosphocholine (12:0 EPC), 1,2-dimyristoyl-sn-glycero-3-ethylphosphocholine (14:0 EPC), 1,2-dipalmitoyl-sn-glycero-3-ethylphosphocholine (16:0 EPC), 1,2-distearoyl-sn-glycero-3-ethylphosphocholine (18:0 EPC).

In some embodiments, the LNP specifically transduces a lung cell; and/or the LNP delivers mRNA to a lung cell in an amount effective to increase expression and/or function of a protein encoded by the mRNA. In some embodiments, the lung cell is ionocyte. In some embodiments, the lung cell is ciliated cell. In some embodiments, the lung cell is secretory cell.

In some embodiments, the LNP comprises the ionizable cationic lipid at a molar percentage greater than 15%. In some embodiments, the ionizable cationic lipid is the dendrimeric lipid at a molar percentage between 10% and 30%. In some embodiments, the LNP comprises DODAP at a molar percentage between 5% and 40%. In some embodiments, the LNP comprises permanently cationic lipids at a molar percentage less than 40%. In some embodiments, the permanently cationic lipids at a molar percentage between 5% and 25%, between 5% and 20%, between 5% and 15%, between 5% and 10%, between 10% and 20%, between 15% and 20%. In some embodiments, the permanently cationic lipid is trimethylammonium-propane (TAP). In some embodiments, the TAP is 1,2-dimyristoyl-3-trimethylammonium-propane(14:0 TAP). In some embodiments, the permanently cationic lipid is 14:0 TAP at a molar percentage between 10% and 15%. In some embodiments, the permanently cationic lipid is ethylphosphocholine (EPC). In some embodiments, the TAP is 1,2-dimyristoyl-sn-glycero-3-ethylphosphocholine (14:0 EPC). In some embodiments, the permanently cationic lipid is 14:0 EPC at a molar percentage between 10% and 15%.

In some embodiments, the LNP comprises phospholipid at a molar percentage between 10% and 30%. In some embodiments, the LNP comprises cholesterol at a molar percentage greater than 25%. In some embodiments, the cholesterol at a molar percentage between 25% and 50%, between 30% and 50%, between 30% and 45%, between 30% and 40%, or between 30% and 35%. In some embodiments, the LNP comprises polyethylene-glycol (PEG)-lipid at a molar percentage between 0.5% and 10% or between 1% and 4%.

In some embodiments, the LNP comprises messenger RNA (mRNA). In some embodiments, the LNP comprises mRNA at a lipid:mRNA ratio less than 40:1. In some embodiments, the lipid:mRNA ratio is 36:1. In some embodiments, the lipid:mRNA ratio is 33:1. In some embodiments, the lipid:mRNA ratio is 30:1.

In some embodiments, the LNP comprises gene editing payload. In some embodiments, the gene editing payload comprises a nuclease, and/or one or more guide RNAs, and optionally a repair template. In some embodiments, the LNP comprises polypeptide, or protein.

In some embodiments, the LNP comprising the cationic ionizable lipid is 5A2-SC8 or 4A3-SC7, the cationic ionizable SORT lipid is DODAP, the permanently cationic lipid is 14:0 TAP or 14:0 EPC, phospholipid is 1,2-dioleoyl-sn-glycero-3-phosphoethanolamine (DOPE) or 1,2-distearoyl-sn-glycero-3-phosphocholine (DSPC), the sterol is cholesterol or sitosterol, and/or the polyethylene-glycol (PEG)-lipid is DMG-PEG, optionally DMG-PEG2000.

In some embodiments, the LNP comprising the cationic ionizable lipid is 4A3-SC7, the cationic ionizable SORT lipid is DODAP, the permanently cationic lipid is 14:0 TAP, the phospholipid is DOPE, the sterol is cholesterol, and/or the polyethylene-glycol (PEG)-lipid is DMG-PEG.

In some embodiments, the LNP comprising the cationic ionizable lipid is 4A3-SC7, the cationic ionizable SORT lipid is DODAP, the permanently cationic lipid is 14:0 EPC, the phospholipid is DOPE, the sterol is cholesterol, and/or the polyethylene-glycol (PEG)-lipid is DMG-PEG.

In some embodiments, the cationic ionizable lipid is 4A3-SC7 and the LNP comprises 4A3-SC7 at a molar percentage between about 10% and about 30%. In some embodiments, the cationic ionizable SORT lipid is DODAP and the LNP comprises DODAP at a molar percentage between about 5% and about 40%. In some embodiments, the permanently cationic lipid is 14:0 TAP and the LNP comprises 14:0 TAP at a molar percentage between about 5% and about 25%. In some embodiments, the permanently cationic lipid is 14:0 EPC and the LNP comprises 14:0 EPC at a molar percentage between about 5% and about 25%.

In some embodiments, the LNP comprises 4A3-SC7 at a molar percentage between about 10% and about 30%, DODAP at a molar percentage between about 5% and about 40%, 14:0 TAP at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises 4A3-SC7 at a molar percentage between about 10% and about 15%, (DODAP at a molar percentage between about 5% and about 20%, 14:0 TAP at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises 4A3-SC7 at a molar percentage between about 10% and about 30%, DODAP at a molar percentage between about 5% and about 40%, 14:0 EPC at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises 4A3-SC7 at a molar percentage between about 10% and about 15%, DODAP at a molar percentage between about 5% and about 20%, 14:0 EPC at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about about 30%, and DMG-PEG at a molar percentage of about about 3%.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about about 32%, and DMG-PEG at a molar percentage of about about 3%.

In some embodiments, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%.

In some embodiments, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises a payload. In some embodiments, the payload is a messenger RNA (mRNA). In some embodiments, the mRNA comprises between 100 bases and 8 kilobases (kb). In some embodiments, the mRNA comprises between 1 kb and 8 kb, or between 2 kb and 8 kb, between 3 kb and 8 kb, or between 4 kb and 8 kb. In some embodiments, the mRNA comprises (about) 2 kb. In some embodiments, the mRNA comprises (about) 4.6 kb. In some embodiments, the mRNA encodes a cystic fibrosis transmembrane conductance regulator (CFTR) protein. In some embodiments, the mRNA encodes a Dynein axonemal intermediate chain 1 (DNAI1) protein. In some embodiments, the mRNA encodes a gene-editing system or components thereof. In some embodiments, wherein the payload is an shRNA or a polynucleotide encoding an shRNA. In some embodiments, the payload is a microRNA or a polynucleotide encoding a microRNA. In some embodiments, the payload is polypeptide. In some embodiments, the payload is protein.

In some embodiments, the composition is a pharmaceutical composition. In some embodiments, the composition is an aerosolized composition.

In some embodiments, wherein the LNP has an encapsulation efficiency of between 50% and 99%, between 60% and 99%, between 70% and 99%, or between 80% and 99%. In some embodiments, the LNP has an encapsulation efficiency of between 50% and 95%, between 60% and 95%, between 70% and 95%, or between 80% and 95%. In some embodiments, the LNP composition is a liquid. In some embodiments, the LNP composition is an aerosol.

In another aspect, the disclosure provides a method of delivering a payload to a cell, comprising contacting a cell with the LNP composition disclosed herein. In another aspect, the disclosure provides a method of delivering expressing a protein or an RNA in a cell, comprises contacting a cell with an LNP composition disclosed herein. In some embodiments, the cell is a lung cell. In some embodiments, the lung cell is a secretory cell. In some embodiments, the lung cell is an ionocyte. In some embodiments, the lung cell is a ciliated cell. In some embodiments, the method specifically transduces the secretory cells compared to other lung cells. In some embodiments, the method specifically transduces the ionocyte compared to other lung cells. In some embodiments, the method specifically transduces the ciliated cell compared to other lung cells. In some embodiments, the method comprises nebulizing the LNP composition to generate an aerosolized composition, then contacting the aerosolized composition with the cell. In some embodiments, the LNP composition is an aerosolized composition, and the method comprises contacting the aerosolized composition with the cell.

In another aspect, the disclosure provides a method of delivering a payload to lungs of a subject, comprising administering to the subject a composition disclosed herein.

In another aspect, the disclosure provides a method of treating or preventing lung disease in a subject, comprising administering to the subject a composition disclosed herein.

In some embodiments, the method comprising nebulizing the composition prior to the administering step. In some embodiments of the method, the LNP composition is administered, as an aerosolized composition, by inhalation. In some embodiments, the method delivers an effective amount of the LNP composition to the lungs. In some embodiments, the method delivers an effective amount of the LNP composition to the lungs to treat the lung disease.

In another aspect, the disclosure provides use of a composition described herein for treatment of a lung disease.

In another aspect, the disclosure provides a composition described herein for treatment of a lung disease.

In another aspect, the disclosure provides a kit comprising a composition described herein and a nebulizer mask and/or a mesh suitable for use in a nebulizer.

In another aspect, the disclosure provides a method of making an LNP composition described herein, comprising mixing the lipid components and the payload in conditions effective to assemble the LNPs comprising the payload. In some embodiments, the method comprising nebulizing the composition to generate an aerosolized LNP composition.

In another aspect, the disclosure provides an aerosolized pharmaceutical composition comprising the LNP composition described herein. In some embodiments of the aerosolized pharmaceutical composition comprises at least two selective organ targeting (SORT) lipids and/or at least six lipids. In some embodiments of the aerosolized pharmaceutical composition, the LNP composition comprises an ionizable cationic lipid, optionally two or more ionizable lipids; and a permanently cationic lipid, optionally two or more permanently cationic lipids.

In some embodiments of the aerosolized pharmaceutical composition, the LNP composition comprises an ionizable cationic lipid, a permanently cationic lipid, optionally a phospholipid, optionally a polyethylene-glycol (PEG)-lipid, and/or optionally a sterol.

In some embodiments of the aerosolized pharmaceutical composition, the LNP composition comprises at least six lipids.

In some embodiments of the aerosolized pharmaceutical composition, the LNP composition comprises an ionizable cationic lipid, a permanently cationic lipid, optionally a phospholipid, optionally a polyethylene-glycol (PEG)-lipid, and/or optionally a sterol.

In some embodiments of the aerosolized pharmaceutical composition, the LNP composition comprises at least two selective organ targeting (SORT) lipids.

In some embodiments, the ionizable cationic lipid is a dendrimeric lipid, optionally 4A3-SC7 or 5A2-SC8. In some embodiments of the aerosolized pharmaceutical composition, the ionizable cationic lipid is a SORT lipid; and/or the permanently cationic lipid is a SORT lipid. In some embodiments of the aerosolized pharmaceutical composition, the ionizable cationic lipid is 1,2-dioleoyl-3-dimethylammonium-propane (DODAP). In some embodiments of the aerosolized pharmaceutical composition, the permanently cationic lipid is trimethylammonium-propane, optionally 1,2-dimyristoyl-3-trimethylammonium-propane(14:0 TAP), 1,2-dipalmitoyl-3-trimethylammonium-propane (16:0 TAP), 1,2-stearoyl-3-trimethylammonium-propane (18:0 TAP), 1,2-dioleoyl-3-trimethylammonium-propane (DO-TAP). In some embodiments of the aerosolized pharmaceutical composition, the permanently cationic lipid is ethylphosphocholine (EPC), optionally 1,2-dilauroyl-sn-glycero-3-ethylphosphocholine (12:0 EPC), 1,2-dimyristoyl-sn-glycero-3-ethylphosphocholine (14:0 EPC), 1,2-dipalmitoyl-sn-glycero-3-ethylphosphocholine (16:0 EPC), 1,2-distearoyl-sn-glycero-3-ethylphosphocholine (18:0 EPC).

In some embodiments of the aerosolized pharmaceutical composition, the LNP specifically transduces a lung cell; and/or the LNP delivers mRNA to a lung cell in an amount effective to increase expression and/or function of a protein encoded by the mRNA. In some embodiments of the aerosolized pharmaceutical composition, the lung cell is ionocyte. In some embodiments of the aerosolized pharmaceutical composition, the lung cell is ciliated cell. In some embodiments of the aerosolized pharmaceutical composition, the lung cell is secretory cell.

In some embodiments of the aerosolized pharmaceutical composition, the LNP comprises the ionizable cationic lipid at a molar percentage greater than 15%. In some embodiments of the aerosolized pharmaceutical composition, the the ionizable cationic lipid is the dendrimeric lipid at a molar percentage between 10% and 30%. In some embodiments of the aerosolized pharmaceutical composition, the LNP comprises DODAP at a molar percentage between 5% and 40%. In some embodiments of the aerosolized pharmaceutical composition, the LNP comprises permanently cationic lipids at a molar percentage less than 40%. In some embodiments of the aerosolized pharmaceutical composition, the permanently cationic lipids at a molar percentage between 5% and 25%, between 5% and 20%, between 5% and 15%, between 5% and 10%, between 10% and 20%, between 15% and 20%. In some embodiments of the aerosolized pharmaceutical composition, the permanently cationic lipid is trimethylammonium-propane (TAP). In some embodiments of the aerosolized pharmaceutical composition, the TAP is 1,2-dimyristoyl-3-trimethylammonium-propane(14:0 TAP). In some embodiments of the aerosolized pharmaceutical composition, the permanently cationic lipid is 14:0 TAP at a molar percentage between 10% and 15%. In some embodiments of the aerosolized pharmaceutical composition, the permanently cationic lipid is ethylphosphocholine (EPC). In some embodiments of the aerosolized pharmaceutical composition, the EPC is 1,2-dimyristoyl-sn-glycero-3-ethylphosphocholine (14:0 EPC). In some embodiments of the aerosolized pharmaceutical composition, the permanently cationic lipid is 14:0 EPC at a molar percentage between 10% and 15%. In some embodiments of the aerosolized pharmaceutical composition, the LNP comprises phospholipid at a molar percentage between 10% and 30%. In some embodiments of the aerosolized pharmaceutical composition, the LNP comprises cholesterol at a molar percentage greater than 25%. In some embodiments of the aerosolized pharmaceutical composition, the cholesterol at a molar percentage between 25% and 50%, between 30% and 50%, between 30% and 45%, between 30% and 40%, or between 30% and 35%. In some embodiments of the aerosolized pharmaceutical composition, the LNP comprises polyethylene-glycol (PEG)-lipid at a molar percentage between 0.5% and 10% or between 1% and 4%.

In some embodiments of the aerosolized pharmaceutical composition, the LNP comprises messenger RNA (mRNA). In some embodiments of the aerosolized pharmaceutical composition, the LNP comprises mRNA at a lipid:mRNA ratio less than 40:1. In some embodiments of the aerosolized pharmaceutical composition, the lipid:mRNA ratio is 36:1. In some embodiments of the aerosolized pharmaceutical composition, the lipid:mRNA ratio is 33:1. In some embodiments of the aerosolized pharmaceutical composition, the lipid:mRNA ratio is 30:1.

In some embodiments of the aerosolized pharmaceutical composition, the LNP comprises gene editing payload. In some embodiments of the aerosolized pharmaceutical composition, the gene editing payload comprises Cas9, sgRNA, and/or ss DNA.

In some embodiments of the aerosolized pharmaceutical composition, the LNP comprise the cationic ionizable lipid is 5A2-SC8 or 4A3-SC7, the cationic ionizable SORT lipid is DODAP, the permanently cationic lipid is 14:0 TAP or 14:0 EPC, phospholipid is 1,2-dioleoyl-sn-glycero-3-phosphoethanolamine (DOPE) or 1,2-distearoyl-sn-glycero-3-phosphocholine (DSPC), the sterol is cholesterol or sitosterol, and/or the polyethylene-glycol (PEG)-lipid is DMG-PEG, optionally DMG-PEG2000.

In some embodiments of the aerosolized pharmaceutical composition, the LNP comprise the cationic ionizable lipid is 4A3-SC7, the cationic ionizable SORT lipid is DODAP, the permanently cationic lipid is 14:0 TAP, the phospholipid is DOPE, the sterol is cholesterol, and/or the polyethylene-glycol (PEG)-lipid is DMG-PEG.

In some embodiments of the aerosolized pharmaceutical composition, the LNP comprise the cationic ionizable lipid is 4A3-SC7, the cationic ionizable SORT lipid is DODAP, the permanently cationic lipid is 14:0 EPC, the phospholipid is DOPE, the sterol is cholesterol, and/or the polyethylene-glycol (PEG)-lipid is DMG-PEG.

In some embodiments of the aerosolized pharmaceutical composition, the cationic ionizable lipid is 4A3-SC7 and the LNP comprises 4A3-SC7 at a molar percentage between about 10% and about 30%. In some embodiments of the aerosolized pharmaceutical composition, the cationic ionizable SORT lipid is DODAP and the LNP comprises DODAP at a molar percentage between about 5% and about 40%. In some embodiments of the aerosolized pharmaceutical composition, the permanently cationic lipid is 14:0 TAP and the LNP comprises 14:0 TAP at a molar percentage between about 5% and about 25%. In some embodiments of the aerosolized pharmaceutical composition, the permanently cationic lipid is 14:0 EPC and the LNP comprises 14:0 EPC at a molar percentage between about 5% and about 25%.

In some embodiments of the aerosolized pharmaceutical composition, the LNP comprises 4A3-SC7 at a molar percentage between about 10% and about 30%, DODAP at a molar percentage between about 5% and about 40%, 14:0 TAP at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments of the aerosolized pharmaceutical composition, the LNP comprises 4A3-SC7 at a molar percentage between about 10% and about 15%, DODAP at a molar percentage between about 5% and about 20%, 14:0 TAP at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments of the aerosolized pharmaceutical composition, the LNP comprises 4A3-SC7 at a molar percentage between about 10% and about 30%, DODAP at a molar percentage between about 5% and about 40%, 14:0 EPC at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments of the aerosolized pharmaceutical composition, the LNP comprises 4A3-SC7 at a molar percentage between about 10% and about 15%, DODAP at a molar percentage between about 5% and about 20%, 14:0 EPC at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments of the aerosolized pharmaceutical composition, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments of the aerosolized pharmaceutical composition, the LNP comprises a payload. In some embodiments of the aerosolized pharmaceutical composition, the payload is a messenger RNA (mRNA). In some embodiments of the aerosolized pharmaceutical composition, the mRNA encodes a gene-editing system or components thereof. In some embodiments of the aerosolized pharmaceutical composition, the payload is an shRNA or a polynucleotide encoding an shRNA. In some embodiments of the aerosolized pharmaceutical composition, the payload is a microRNA or a polynucleotide encoding a microRNA. In some embodiments of the aerosolized pharmaceutical composition, the composition is a pharmaceutical composition.

In another aspect, the disclosure provides a liquid pharmaceutical composition for use in making the aerosolized pharmaceutical compositions described herein.

In another aspect, the disclosure provides a method for delivering lipid nanoparticles (LNPs) to a lung cell of a subject, the method comprising nebulizing the liquid pharmaceutical composition described herein to generate an aerosolized pharmaceutical composition, and administering the aerosolized pharmaceutical composition to the subject.

In another aspect, the disclosure provides a method of delivering a payload to a lung cell of a subject, the method comprising administering the aerosolized pharmaceutical composition described herein to the subject, wherein optionally the payload is a polynucleotide.

In another aspect, the disclosure provides a method for expressing a protein in the lung of a subject, the method comprising administering the aerosolized pharmaceutical composition described herein to the subject.

In another aspect, the disclosure provides a method for treating a lung disease in a subject, the method comprising administering the aerosolized pharmaceutical composition described herein to the subject.

In another aspect, the disclosure provides a kit comprising a lipid nanoparticle composition comprising at least two selective organ targeting (SORT) lipids and/or at least six lipids, optionally comprising a polynucleotide.

Further aspects and embodiments of the invention are provided by the Detailed Description that follows. The scope of the invention is limited only by the claims. Those of skill in the art will be able to envision and implement numerous variations of the disclosed embodiments.

BRIEF DESCRIPTION OF THE DRAWINGS

FIG. 1 shows a schematic of criteria used to evaluate aerosolized pharmaceutical compositions.

FIG. 2 shows a chart of output rate with various nebulizer heads on the PARI® eFlow® nebulizer system.

FIG. 3 shows a chart of output rate of composition A with various nebulizer heads on the PARI® eFlow® nebulizer system.

FIGS. 4A-4B show predicted and actual nebulization time of either baseline or Composition A/DNAI1 lipid nanoparticles. FIG. 4A shows predicted and actual nebulization time of baseline (PBS). FIG. 4B shows predicted and actual nebulization time of Composition A/DNAI1 lipid nanoparticles.

FIG. 5 shows encapsulation efficiency (%) of various nebulizer heads on the PARI® eFlow® nebulizer system.

FIG. 6 shows encapsulation efficiency (%) data for 40 HO V of PARI® eFlow® nebulizer system.

FIG. 7 shows mRNA integrity for either 35 V or 40 HO V of PARI® eFlow® nebulizer system.

FIGS. 8A-8C show encapsulation efficiency (%) of various head of PARI© eFlow® nebulizer system. FIG. 8A shows encapsulation efficiency (%) of PARI® eFlow® nebulizer at slow flow. FIG. 8B shows encapsulation efficiency (%) of PARI® eFlow® nebulizer at median flow. FIG. 8C shows encapsulation efficiency (%) of PARI® eFlow® nebulizer at fast flow.

FIGS. 9A-9C show hydrodynamic diameter (nm) of various head of PARI© eFlow® nebulizer system. FIG. 9A shows hydrodynamic diameter (nm) of PARI® eFlow® nebulizer at slow flow. FIG. 9B shows hydrodynamic diameter (nm) of PARI® eFlow® nebulizer at median flow. FIG. 9C shows hydrodynamic diameter (nm) of PARI® eFlow® nebulizer at fast flow.

FIGS. 10A-10C show polydispersity index of various head of PARI© eFlow® nebulizer system. FIG. 10A shows polydispersity index of PARI® eFlow® nebulizer at slow flow. FIG. 10B shows polydispersity index of PARI® eFlow® nebulizer at median flow. FIG. 10C shows polydispersity index of PARI® eFlow® nebulizer at fast flow.

FIG. 11 shows hydrodynamic diameter (nm) over course of nebulization of various head of PARI® eFlow® nebulizer system.

FIG. 12 shows polydispersity index over course of nebulization of various head of PARI® eFlow® nebulizer system.

FIGS. 13A-13D show characteristics of lipid nanoparticles for 40 HO V of PARI® eFlow® nebulizer system. FIG. 13A shows concentration of lipid nanoparticles. FIG. 13B shows encapsulation efficiency (%) of lipid nanoparticles. FIG. 13C shows hydrodynamic diameter (nm) of lipid nanoparticles. FIG. 13D shows polydispersity index of lipid nanoparticles.

FIGS. 14A-14B show drug deposition (μg) in various stages for either 40 HO V or 30 HO V of PARI® eFlow® nebulizer system. FIG. 14A shows drug deposition (μg) in various stages at 40 HO V. FIG. 14B shows drug deposition (μg) in various stages at 30 HO V.

FIG. 14C shows aerosol characterizations in a next generation impactor (NGI).

FIGS. 15A-15B show deposition fraction of multiple-path particle dosimetry (MPPD) of either Aerogen® Solo or PDAP. FIG. 15A shows deposition fraction of multiple-path particle dosimetry (MPPD) of Aerogen® Solo. FIG. 15B shows deposition fraction of multiple-path particle dosimetry (MPPD) of PDAP.

FIGS. 16A-16E show deposition fraction of multiple-path particle dosimetry (MPPD) of various nebulizer heads on the PARI® eFlow® nebulizer system. FIG. 16A shows deposition fraction of multiple-path particle dosimetry (MPPD) at 30NV. FIG. 16B shows deposition fraction of multiple-path particle dosimetry (MPPD) at 35NV. FIG. 16C shows deposition fraction of multiple-path particle dosimetry (MPPD) at 30V. FIG. 16D shows deposition fraction of multiple-path particle dosimetry (MPPD) at 35V. FIG. 16E shows deposition fraction of multiple-path particle dosimetry (MPPD) at 40HO.

FIGS. 17A-17B show percent recovery of lipids using different lipid extraction solutions and volume. FIG. 17A shows percent recovery of lipids. FIG. 17B shows quantitative data of percent recovery of lipids.

FIGS. 18A-18C show comparison result of Gravimetric, Ribogreen and high-performance liquid chromatography with charged aerosol detector (HPLC-CAD) method. FIG. 18A shows quantitative data showing comparison result of different methods. FIG. 18B shows comparison of Gravimetric and HPLC-CAD. FIG. 18C shows comparison of RiboGreen and HPLC-CAD.

FIGS. 19A-19B show lipid weight fraction of various lipid extraction solutions and volume. FIG. 19A shows lipid weight fraction in Rat GLP-tox experiment. FIG. 19B shows lipid weight fraction in NHP GLP-tox experiment.

FIGS. 20A-20B show percent recovery of lipids by different filter storage. FIG. 20A shows percent recovery of lipids at different condition. FIG. 20B shows quantitative data of percent recovery of lipids.

FIGS. 21A-21E shows total lipid mass comparison of Gravimetric, HPLC-CAD and LC-MS on Composition B. FIG. 21A shows percent recovery of lipids. FIG. 21B shows quantitative data of percent recovery of lipids. FIG. 21C shows total lipid mass comparison of Gravimetric, HPLC-CAD and LC-MS. FIG. 21D shows comparison of LC-MS and Gravimetric.

Figure 24A:
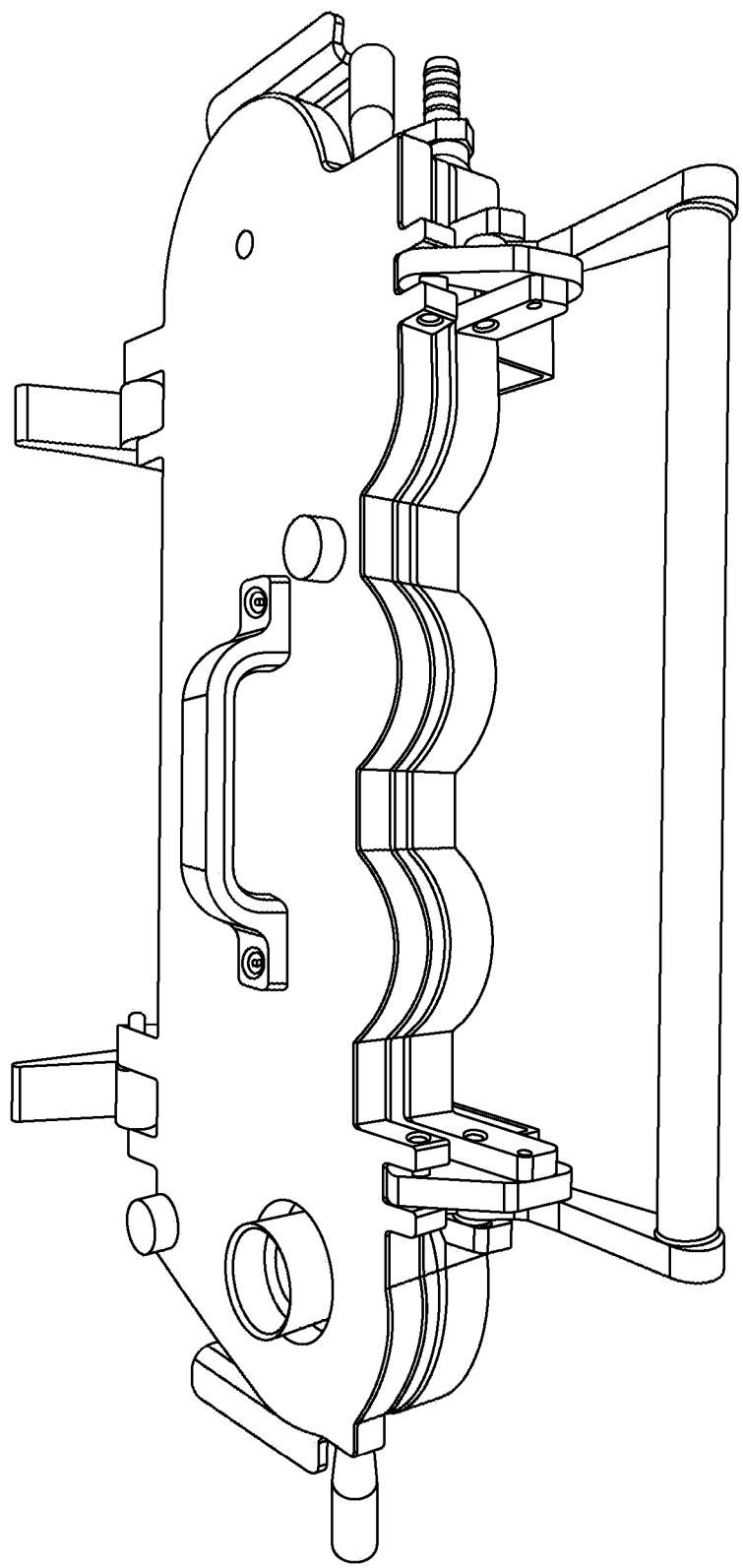
Figure 24C:
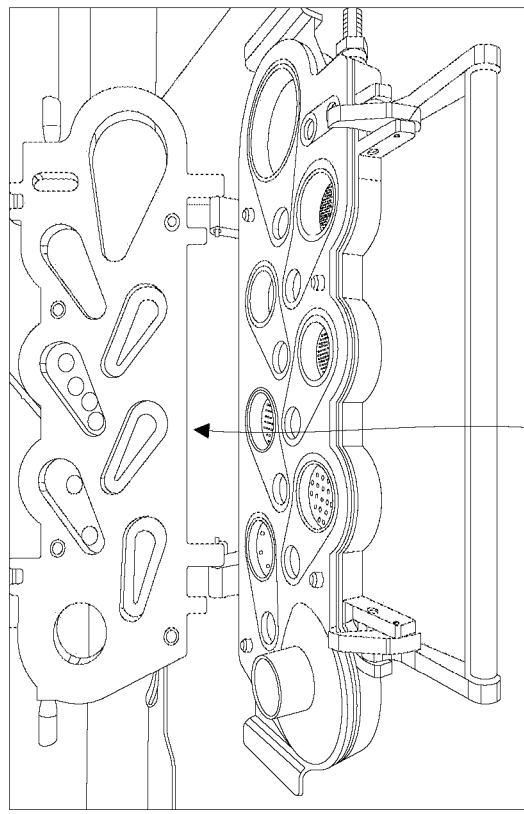
Figure 24B:
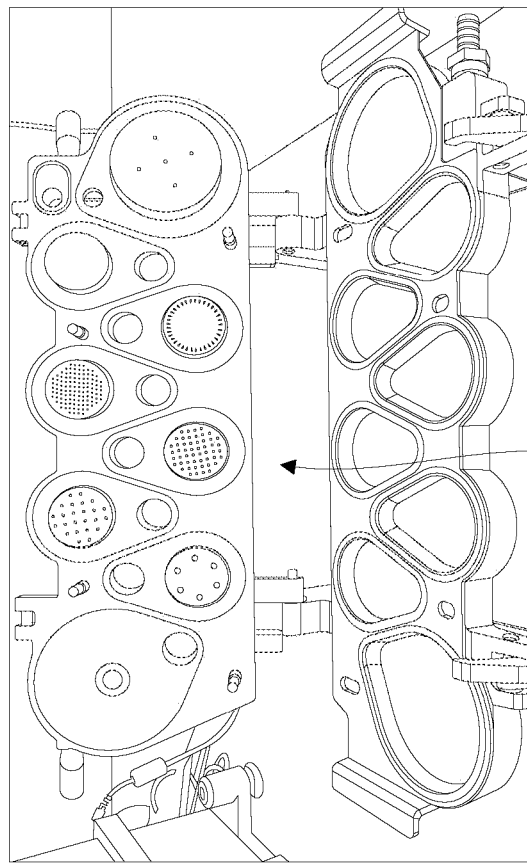

FIGS. 24A-24C are images of a next generation impactor (NGI). FIG. 24A shows images of a next generation impactor (NGI). FIG. 24B shows NGI seal body (stage nozzles).

FIG. 24C shows NIG lid (inter-stage passageways).

Figure 25B:
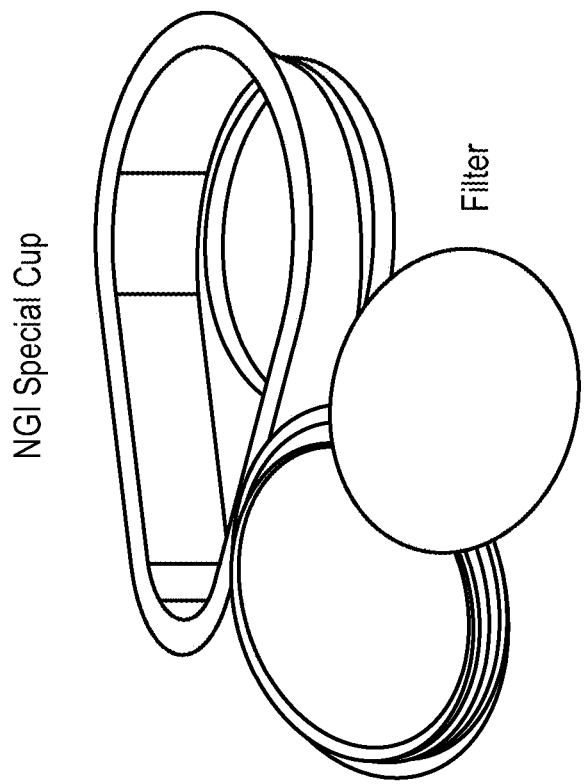
Figure 25A:
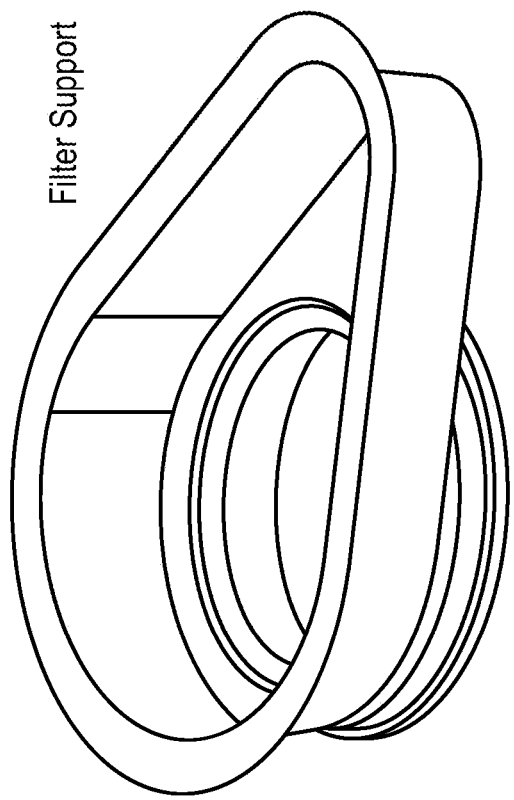

FIGS. 25A-25B are images of an NGI gravimetric cup. FIG. 25A shows image of an NGI gravimetric cup. FIG. 25B shows images of an NGI gravimetric cup parts (NGI special cup, filter, and filter support).

Figure 26B:
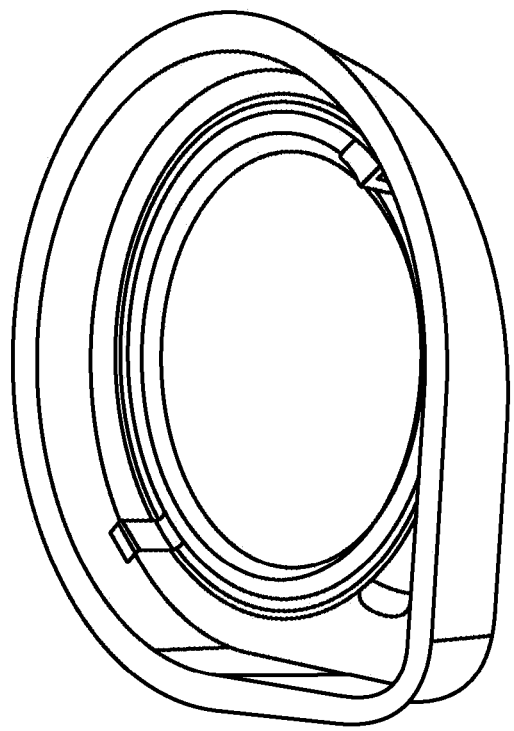
Figure 26A:
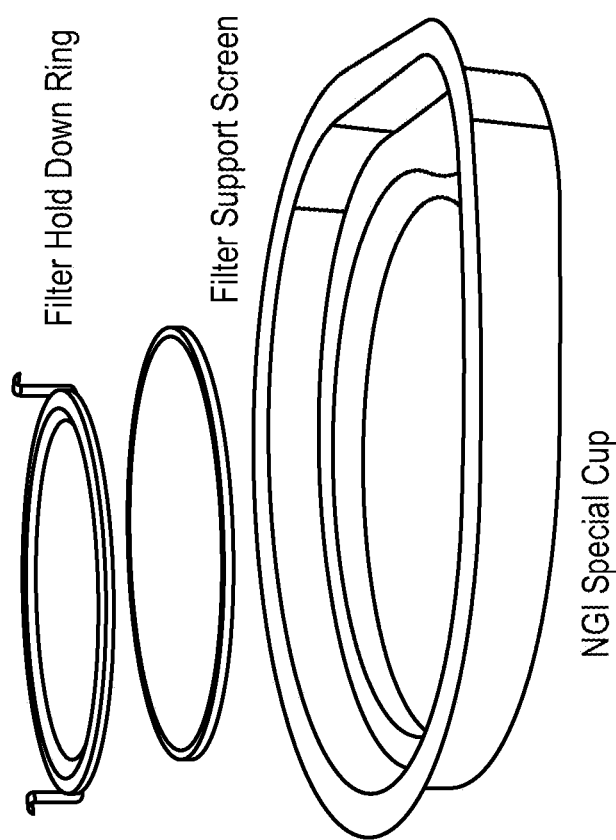

FIGS. 26A-26B are images of an NGI internal filter holder. FIG. 26A shows images of an NGI internal filter holder (NGI special cup, filter support screen and filter hold down ring).

FIG. 26B shows image of an NGI internal filter holder.

Figure 27:
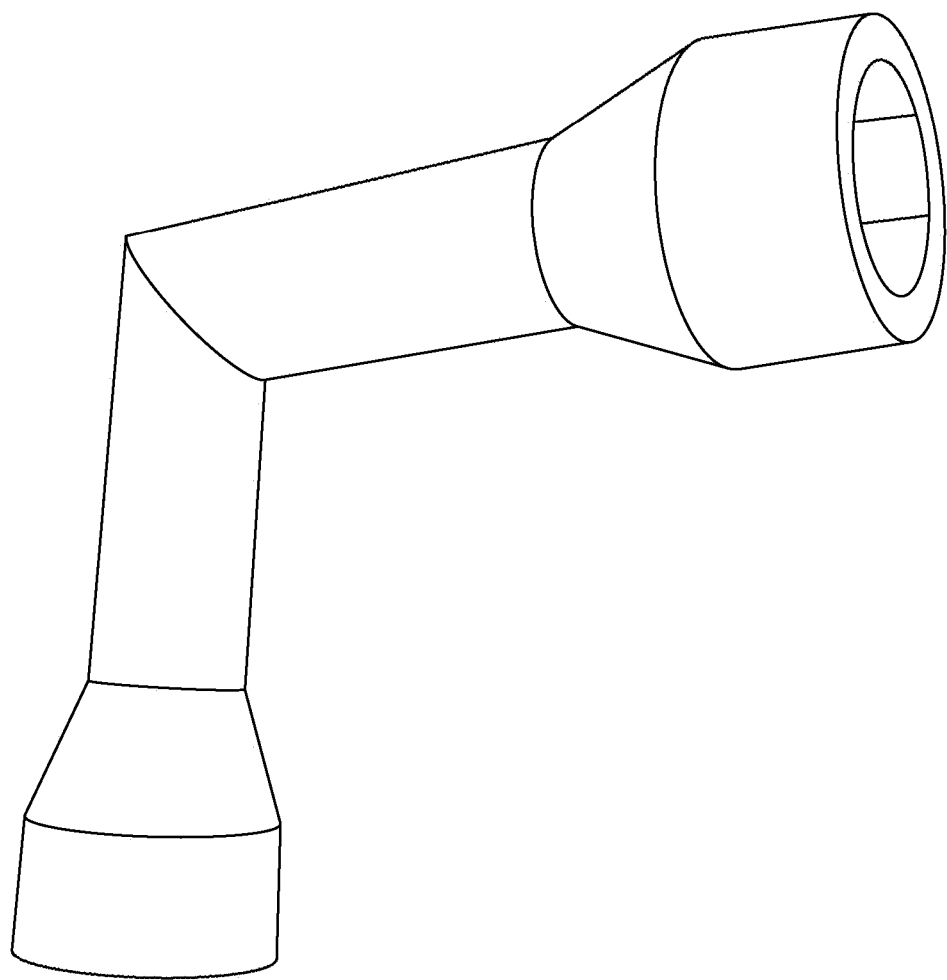

FIG. 27 is an image of a USP (United States Pharmacopeia) induction port.

Figure 28B:
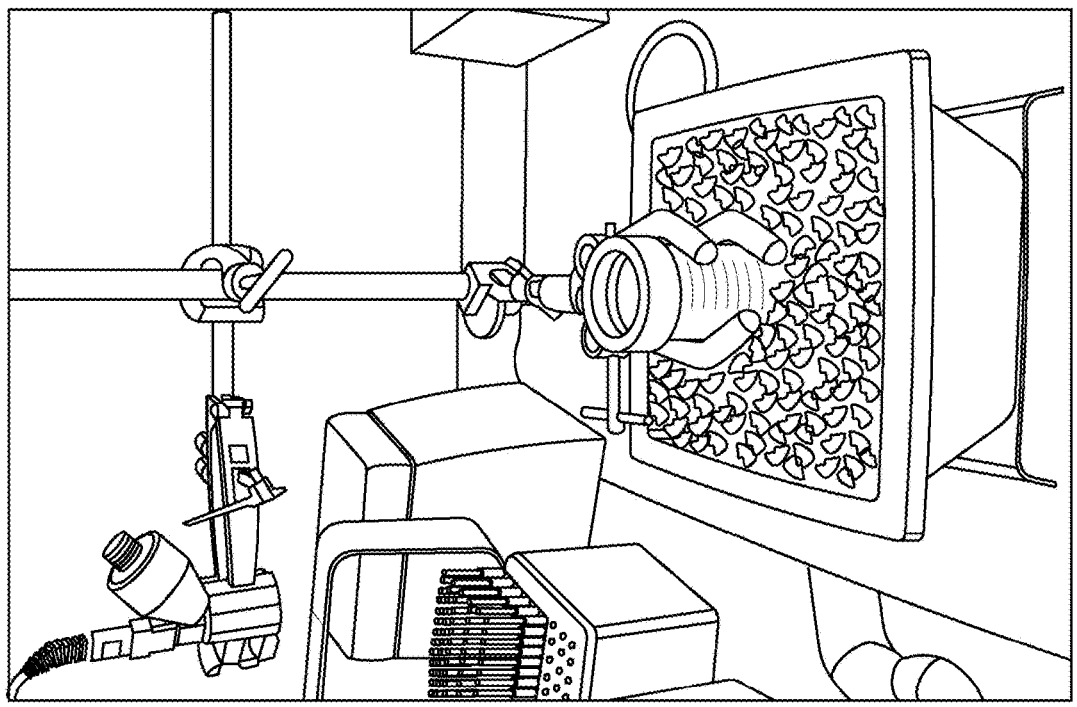
Figure 28A:
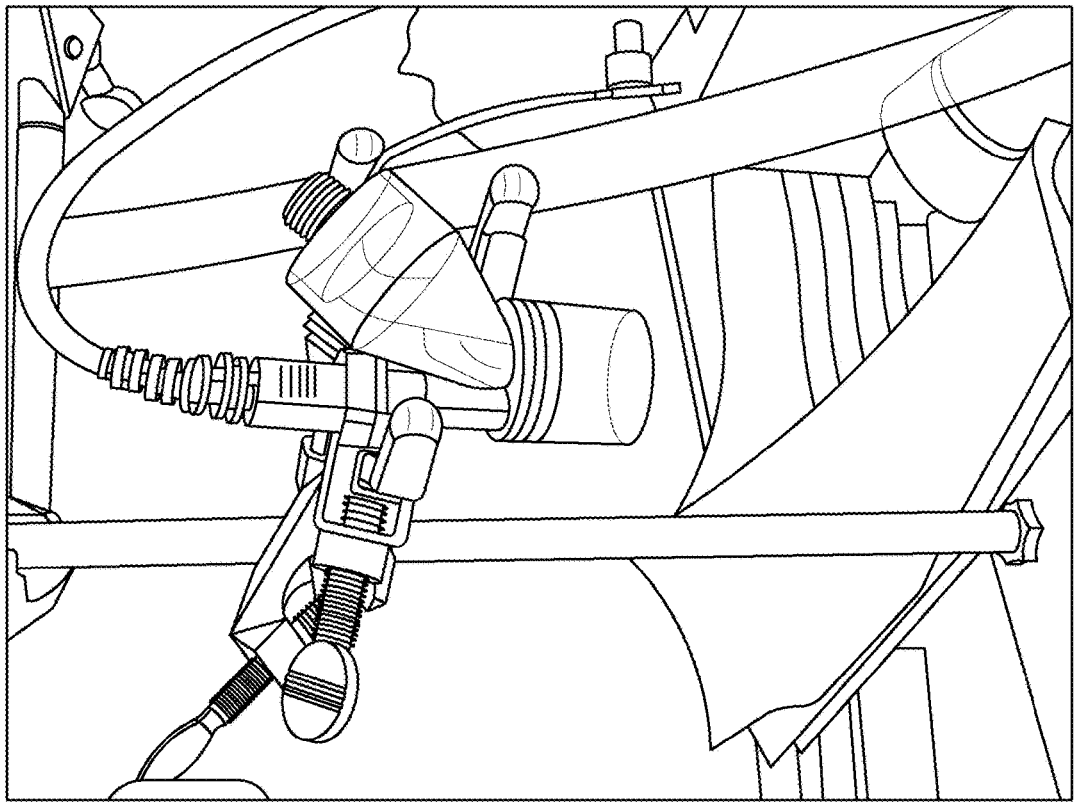
Figure 29:
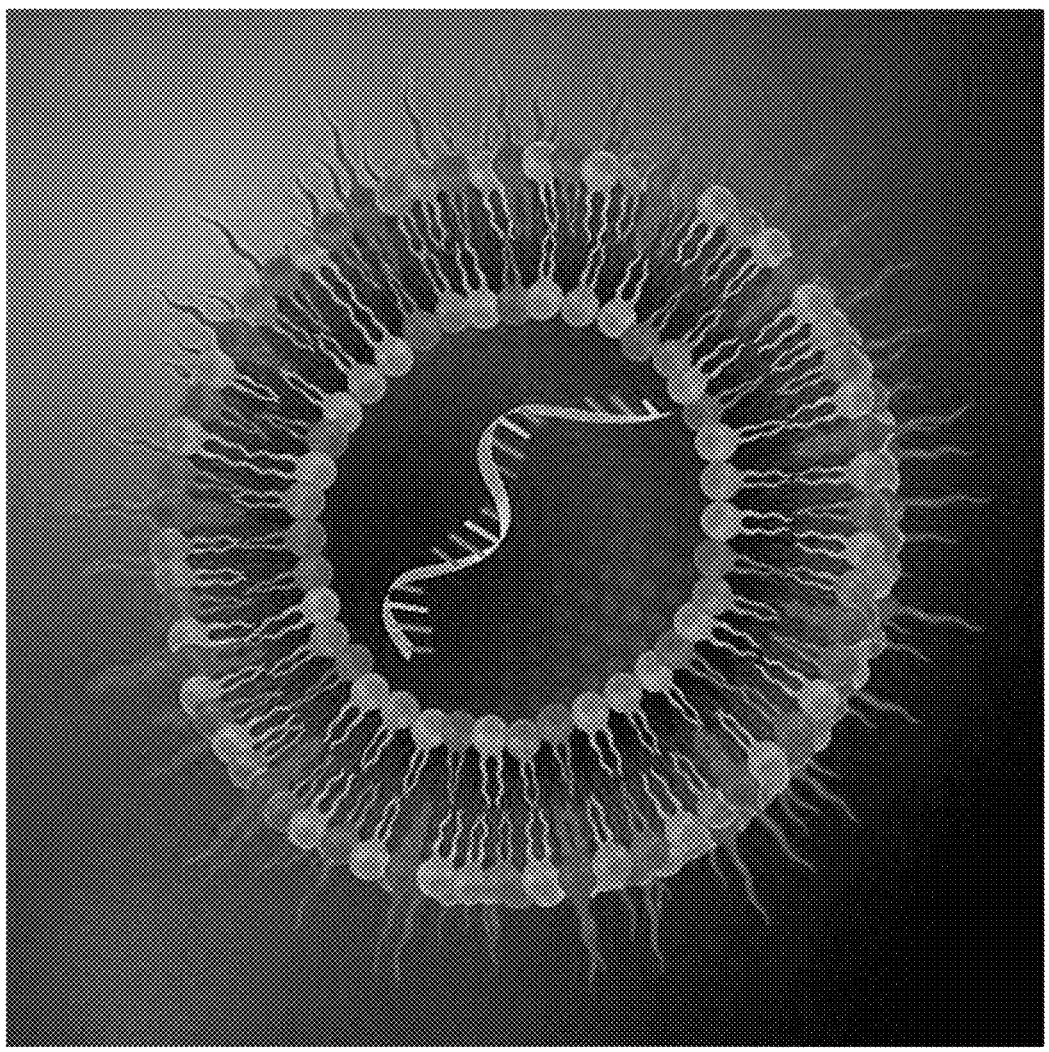
Figure 46A:
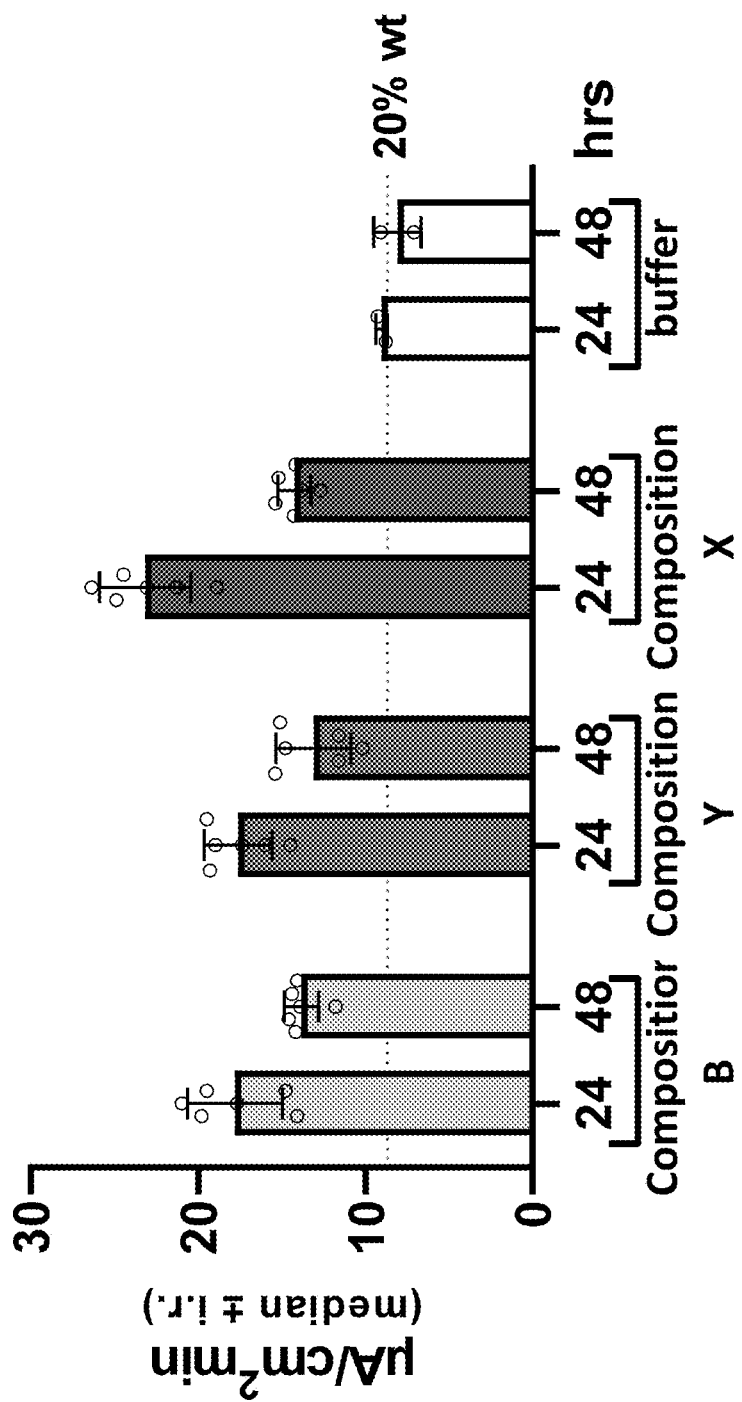
Figure 46B:
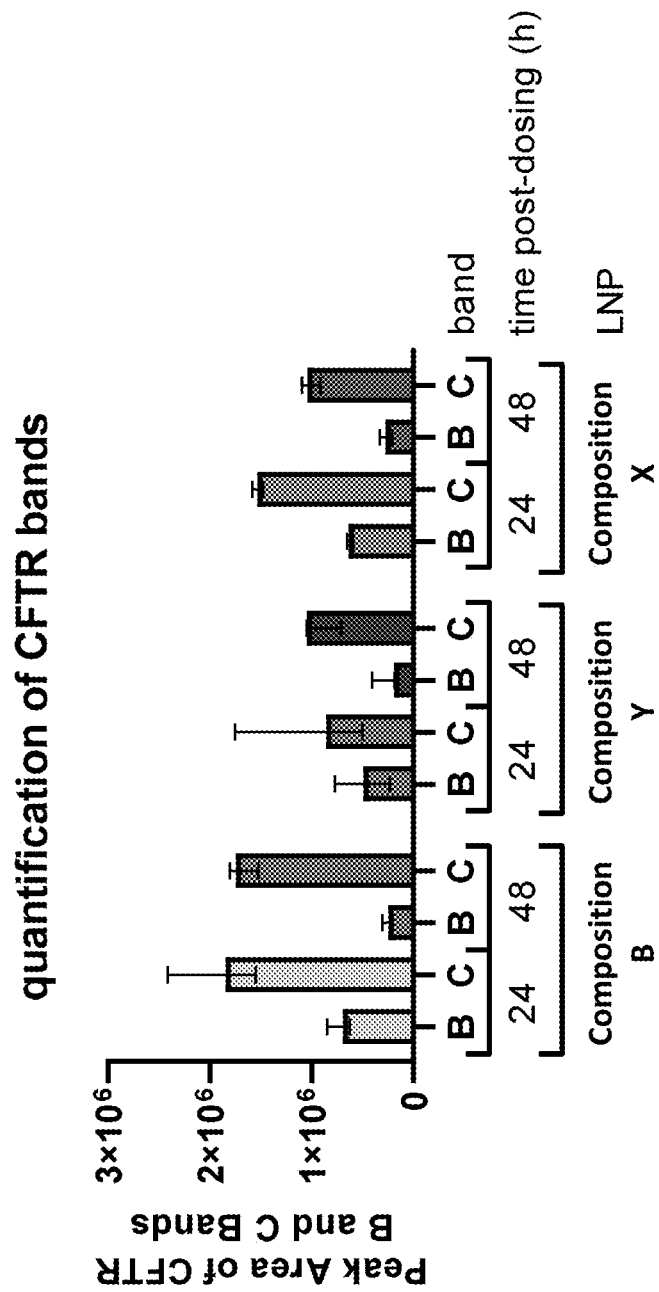
Figure 46C:
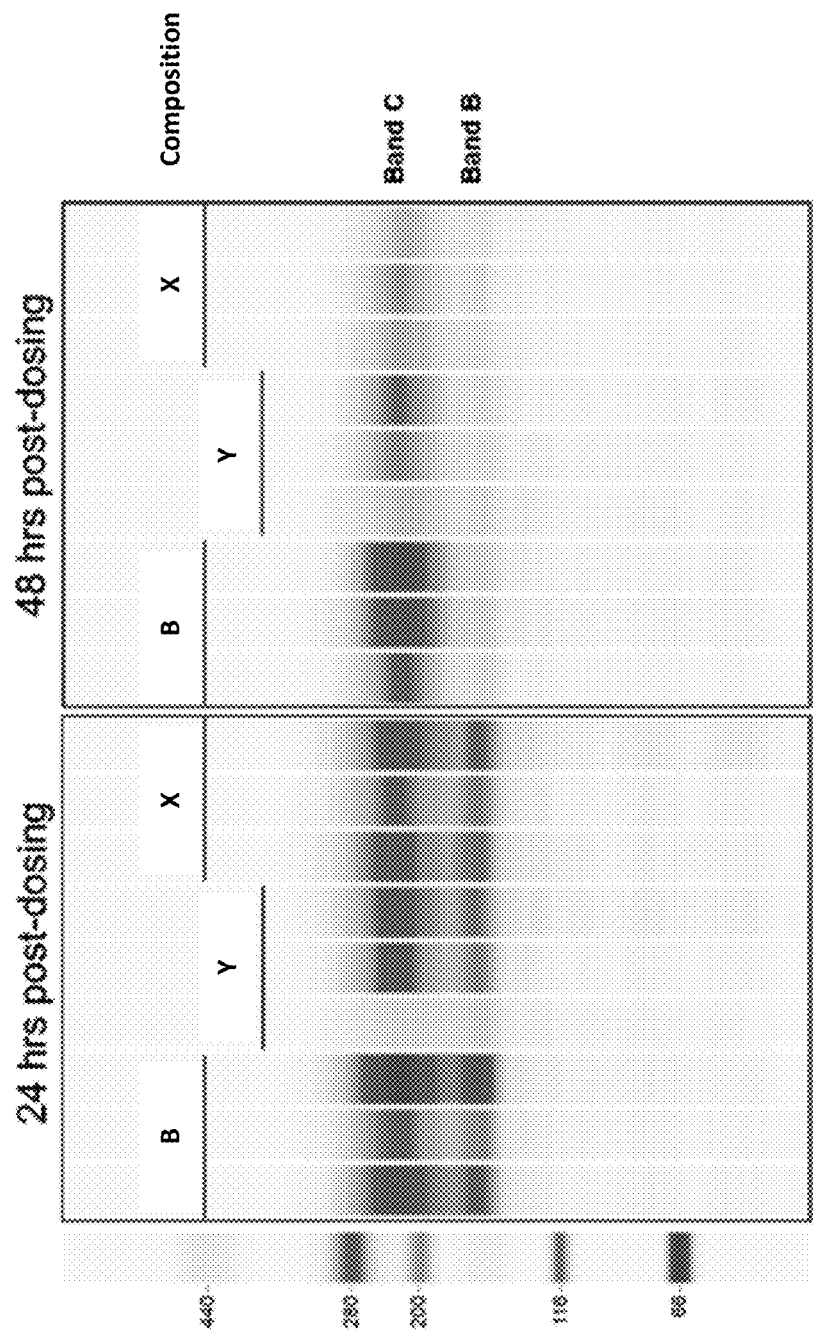

FIG. 28A shows image of a laboratory stand with a claw nebulizer. FIG. 28B shows collecting nebula using a chilled 50 mL conical tube with cut-out lid to fit nebulizer.

FIG. 29 shows a schematic depiction of a lipid nanoparticle (LNP) encapsulating an mRNA.

FIG. 30 shows AUC/min of non-DOTAP LNPs.

FIG. 31 shows AUC/min of DODAP-based LNPs.

FIG. 32 shows AUC/min of Composition B with different buffers.

FIG. 33A shows screening results of Compound B and Composition R with different buffers. FIG. 33B shows screening results of Compound B and Composition U with different buffers.

FIGS. 34A-34D show lipid nanoparticle characterization summary of various lipid nanoparticles in different pH buffer. FIG. 34A shows size of lipid nanoparticles. FIG. 34B shows polydispersity index of lipid nanoparticles. FIG. 34C shows encapsulation efficiency (%) of lipid nanoparticles. FIG. 34D shows zeta potential (mV) of lipid nanoparticles.

FIG. 35A shows TNS assay of Composition B in different buffers. FIG. 35B shows TNS assay of Composition C in different buffers. FIG. 35C shows TNS assay of Composition A.

FIGS. 36A-36D show lipid nanoparticle characterization summary of Composition B and Composition C in different pH buffer. FIG. 36A shows size of lipid nanoparticles. FIG. 36B shows polydispersity index of lipid nanoparticles. FIG. 36C shows encapsulation efficiency (%) of lipid nanoparticles. FIG. 36D shows zeta potential (mV) of lipid nanoparticles.

FIG. 37A shows TNS assay of Composition B. FIG. 37B shows TNS assay of Composition C.

FIGS. 38A-38D show lipid nanoparticle characterization summary of Composition B in either pH 4, pH 5 or pH 6. FIG. 38A shows size of lipid nanoparticles. FIG. 38B shows polydispersity index of lipid nanoparticles. FIG. 38C shows encapsulation efficiency (%) of lipid nanoparticles. FIG. 38D shows zeta potential (mV) of lipid nanoparticles.

FIGS. 39A-39D show lipid nanoparticle characterization summary of Composition F in either pH 4, pH 5 or pH 6. FIG. 39A shows size of lipid nanoparticles. FIG. 39B shows polydispersity index of lipid nanoparticles. FIG. 39C shows encapsulation efficiency (%) of lipid nanoparticles. FIG. 39D shows zeta potential (mV) of lipid nanoparticles.

FIG. 40 shows AUC/min of Composition B variants.

FIG. 41 shows AUC/min of various with 50% cholesterol.

FIG. 42 shows experimental conditions.

FIG. 43A-43D show rescue of CFTR function in two nonresponsive genotype hBEs. FIG. 43A shows rescue of CFTR function in R553X/W1282X genotype hBEs. FIG. 43B shows measurement of transepithelial resistance (TEER) (top) and LDH release (bottom) in R553X/W1282X genotype hBEs. FIG. 43C shows rescue of CFTR function in W1282X/W1282X genotype hBEs. FIG. 43C shows measurement of transepithelial resistance (TEER) (top) and LDH release (bottom) in W1282X/W1282X genotype hBEs.

FIG. 44 shows a summary of benchmarking data across several CF genotypes and donors.

FIG. 45A shows rescue of CFTR function in donor TXCF042716 cells. FIG. 45B shows measurements of LDH release in donor TXCF042716 cells to detect cytotoxicity from aerosolized formulations. FIG. 45C shows rescue of CFTR function in donor KKD012K cells.

FIG. 45D shows measurements of LDH release in donor KKD012K cells to detect cytotoxicity from aerosolized formulations. FIG. 45E shows rescue of CFTR function in donor KKD025L cells. FIG. 45F shows measurements of LDH release in donor KKD025L cells to detect cytotoxicity from aerosolized formulations. FIG. 45G shows rescue of CFTR function in donor KKD003K cells. FIG. 45H shows measurements of LDH release in donor KKD003K cells to detect cytotoxicity from aerosolized formulations. FIG. 45I shows rescue of CFTR function in donor 20160524CF cells. FIG. 45J shows measurements of LDH release in donor 20160524CF cells to detect cytotoxicity from aerosolized formulations. FIG. 45K shows rescue of CFTR function in donor KK017N cells.

FIG. 46A shows rescue of CFTR function in donor KKD003K cells by various lipid nanoparticles at 24 h and 48 h. FIG. 46B shows quantification of CFTR bands. FIG. 46C shows expression of CFTR protein by Western blot analysis.

Figure 47A:
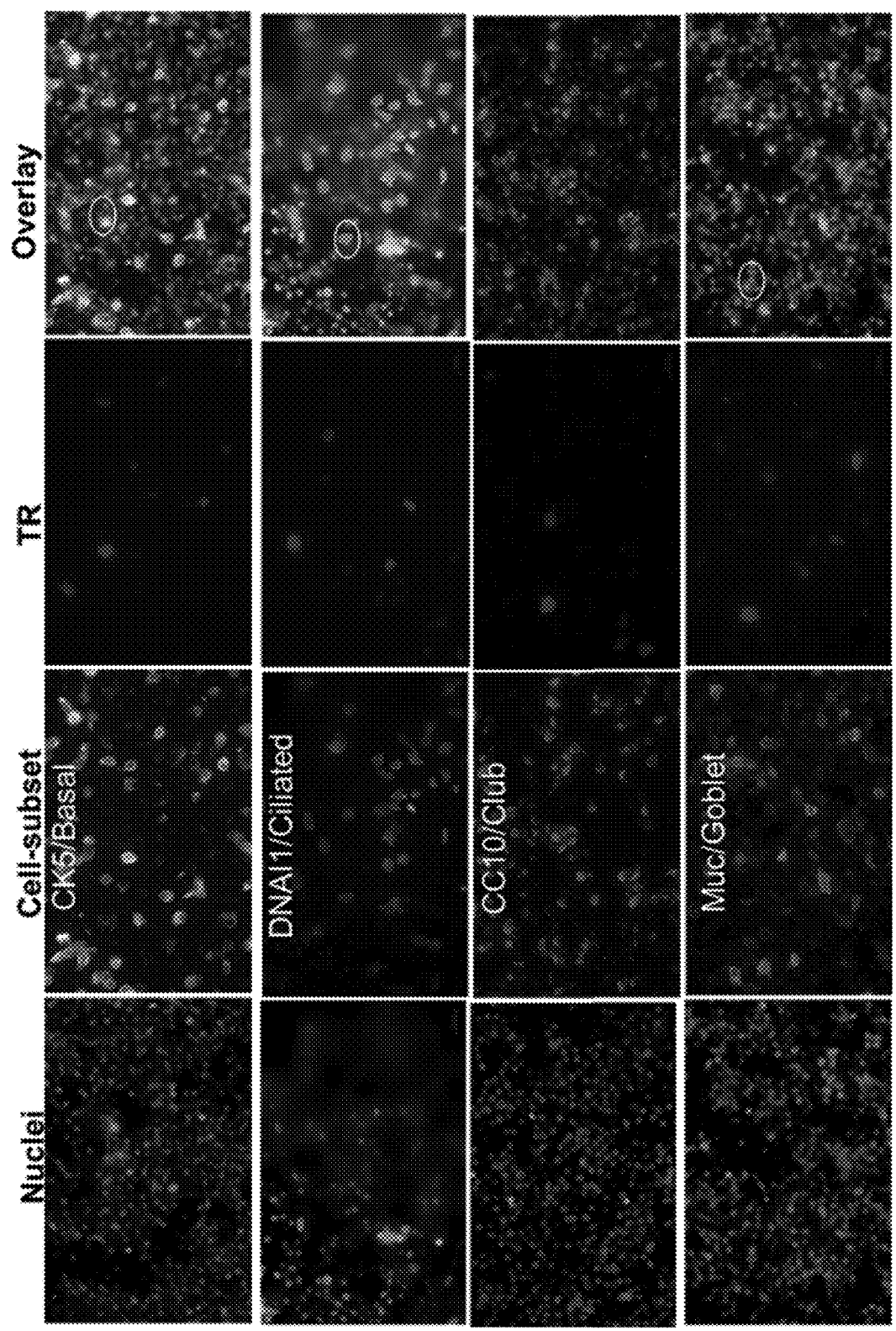

FIG. 47A shows preliminary assessment of lipid nanoparticles targeting secretory cells (e.g., goblet cells) in ΔF508/ΔF508 (donor TXCF042716) hBE cells. FIG. 48B shows quantification of TR positive cells.

Figure 48A:
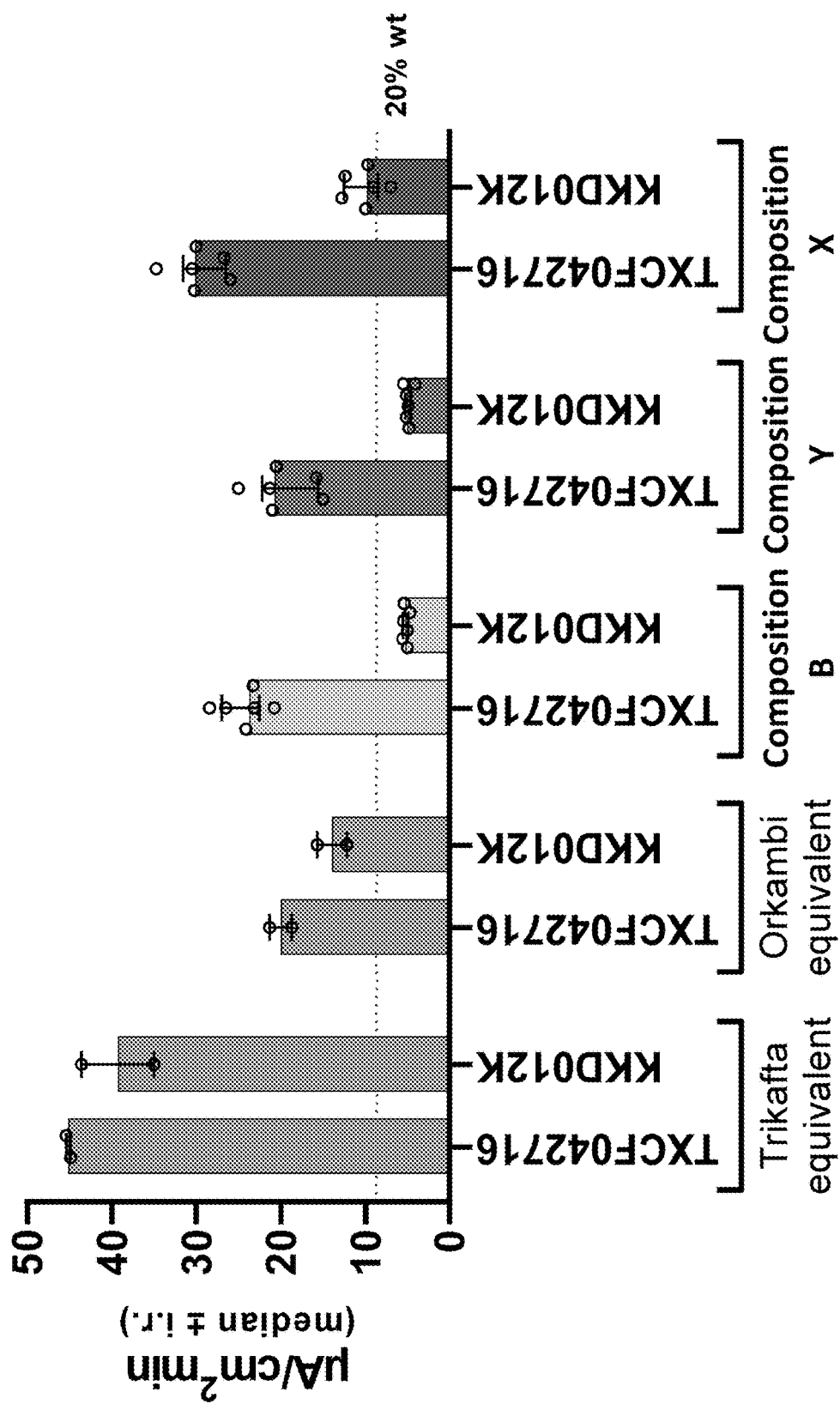
Figure 48B:
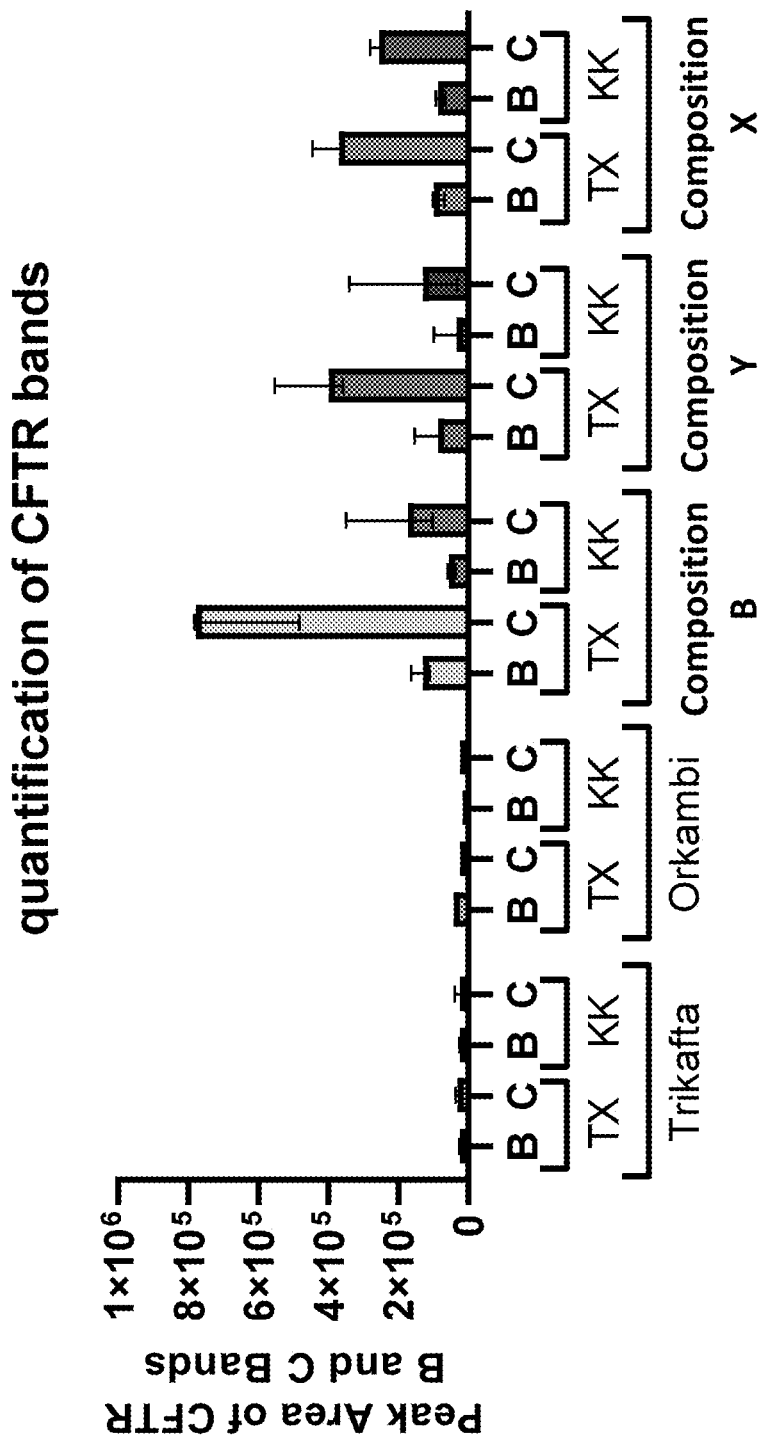
Figure 48C:
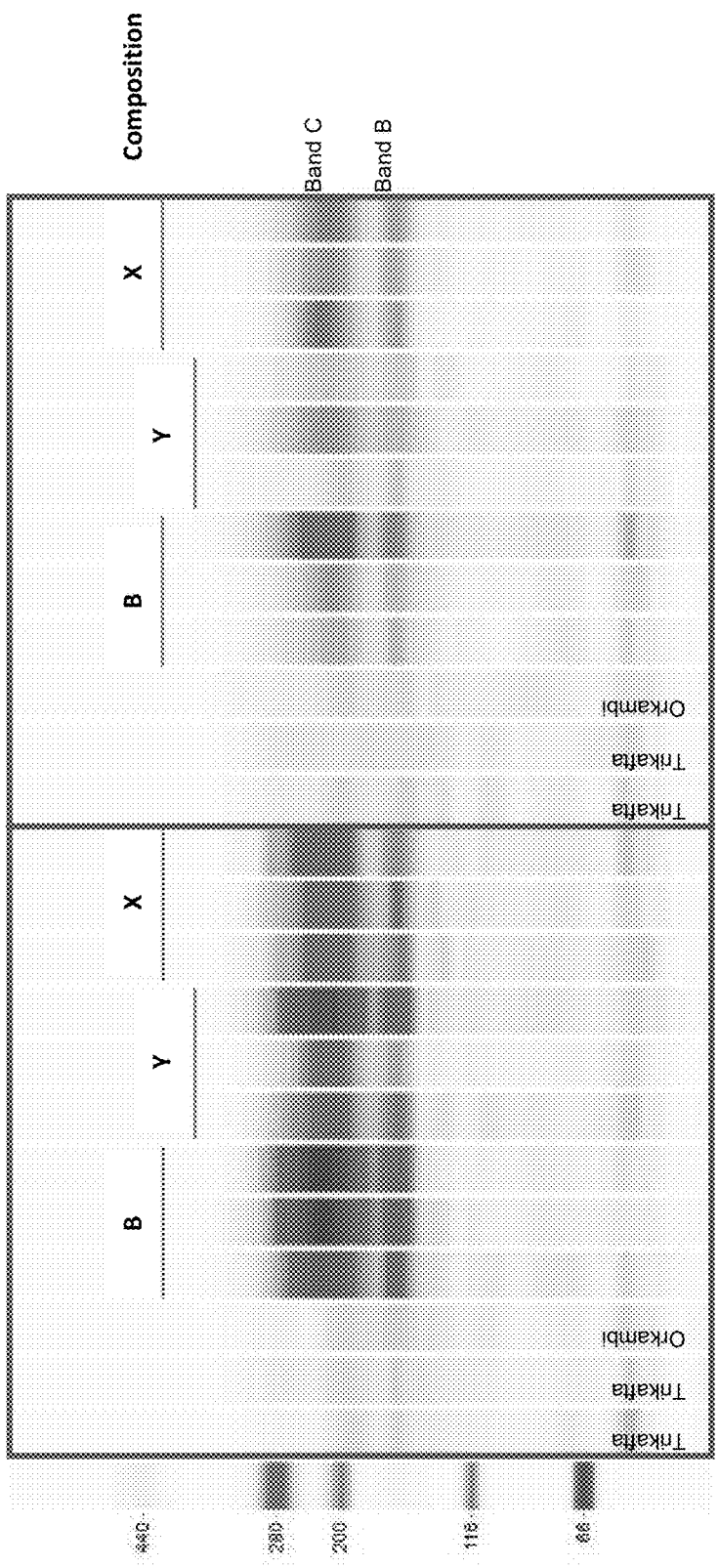

FIGS. 48A-48C show correlation of CFTR function with CFTR protein level. FIG. 48A shows rescue of CFTR function in either donor KKD003K or donor KKD012K cells. FIG. 48B shows quantification of CFTR bands. FIG. 48C shows expression of CFTR protein in either donor KKD003K or donor KKD012K cells by Western blot analysis.

Figure 49:
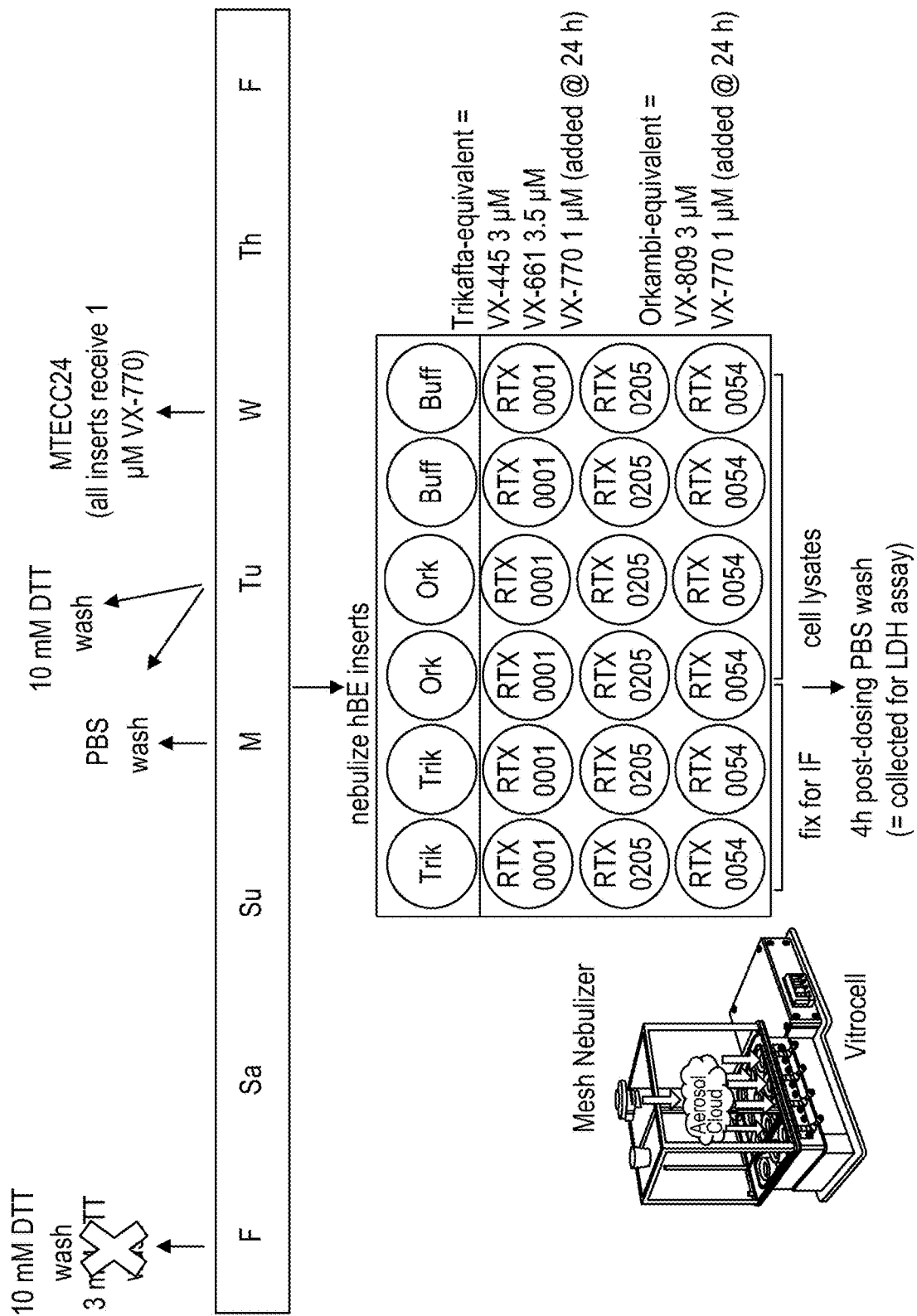

FIG. 49 shows experimental conditions for benchmark studies.

Figure 50A:
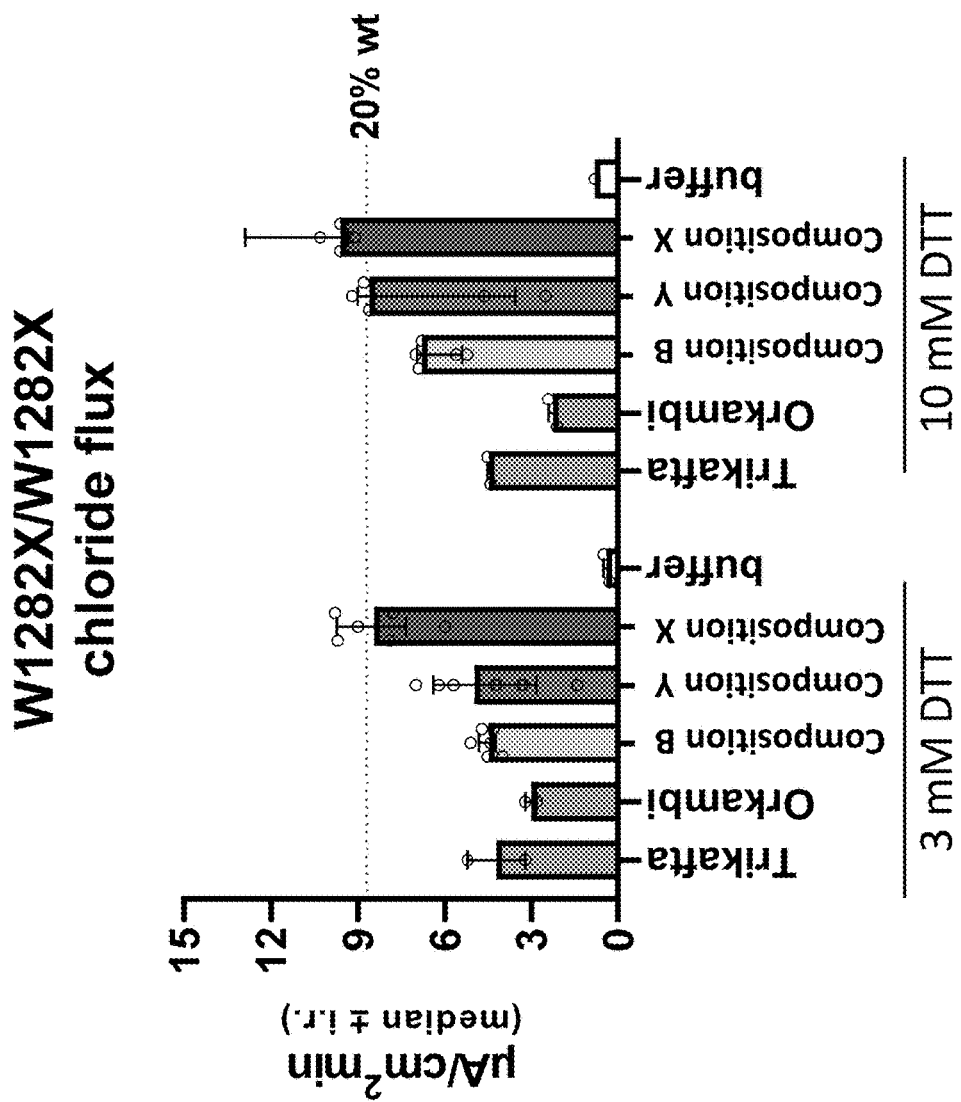
Figure 50B:
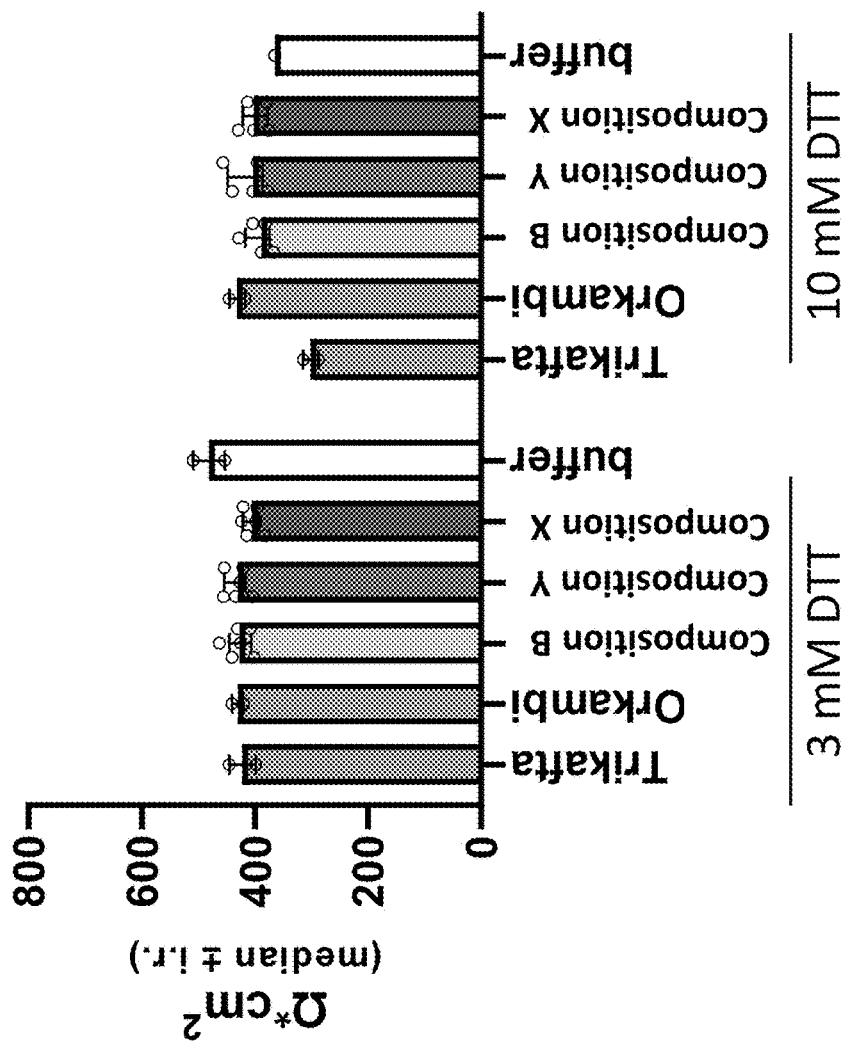

FIGS. 50A-50B show effect of mucus on transfection efficiency of aerosolized SORT lipid nanoparticles in W1282X/W1282X hBEs. FIG. 50A shows rescue of CFTR function. FIG. 50B shows measurement of transepithelial resistance (TEER).

Figure 51A:
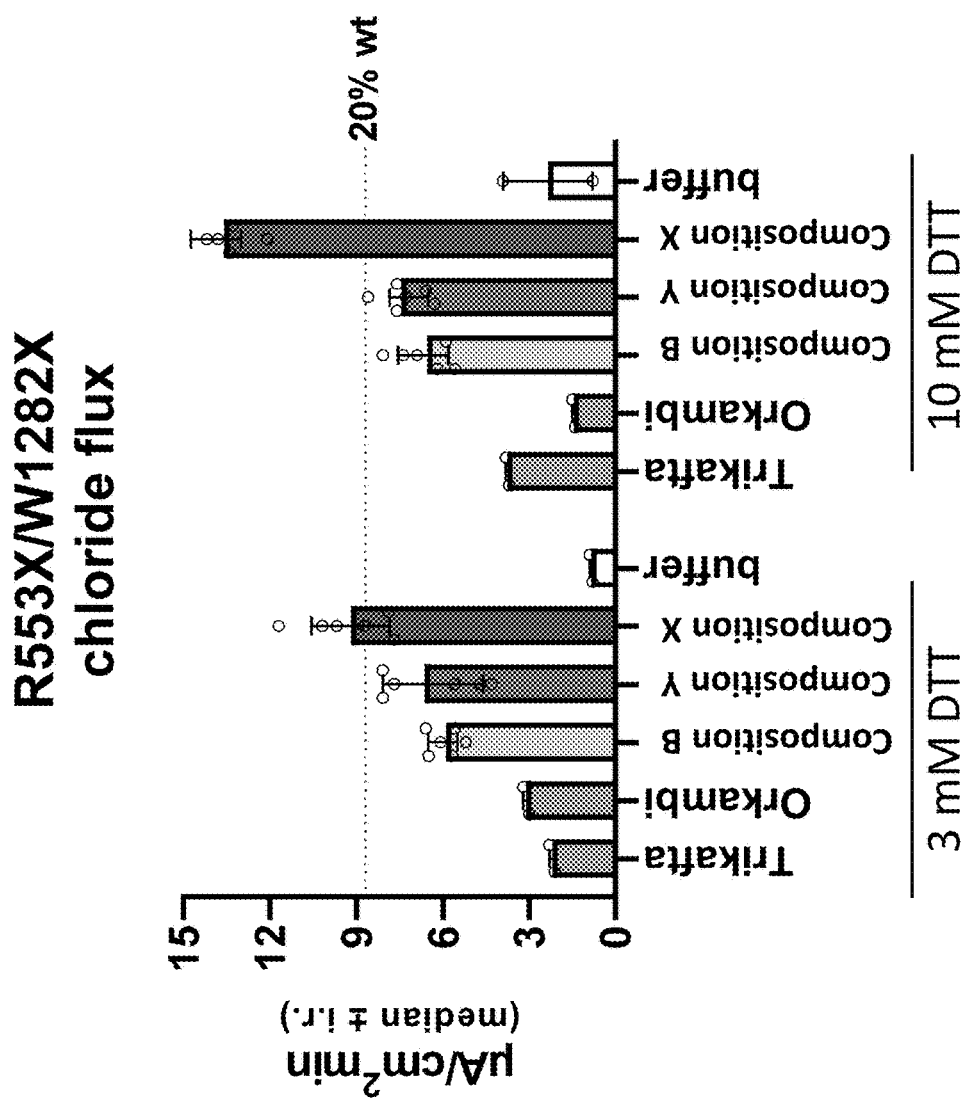
Figure 51B:
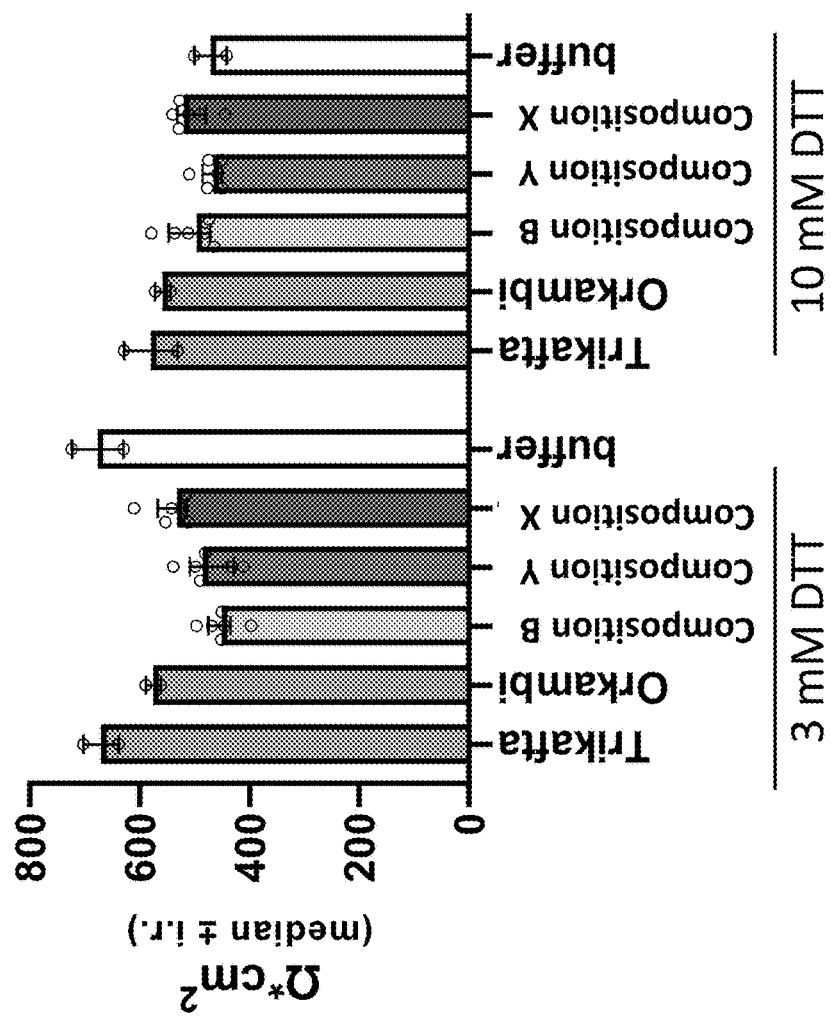

FIGS. 51A-51B show effect of mucus on transfection efficiency of aerosolized SORT lipid nanoparticles in R553X/W1282X hBEs. FIG. 51A shows rescue of CFTR function. FIG. 51B shows measurement of transepithelial resistance (TEER).

Figure 52A:
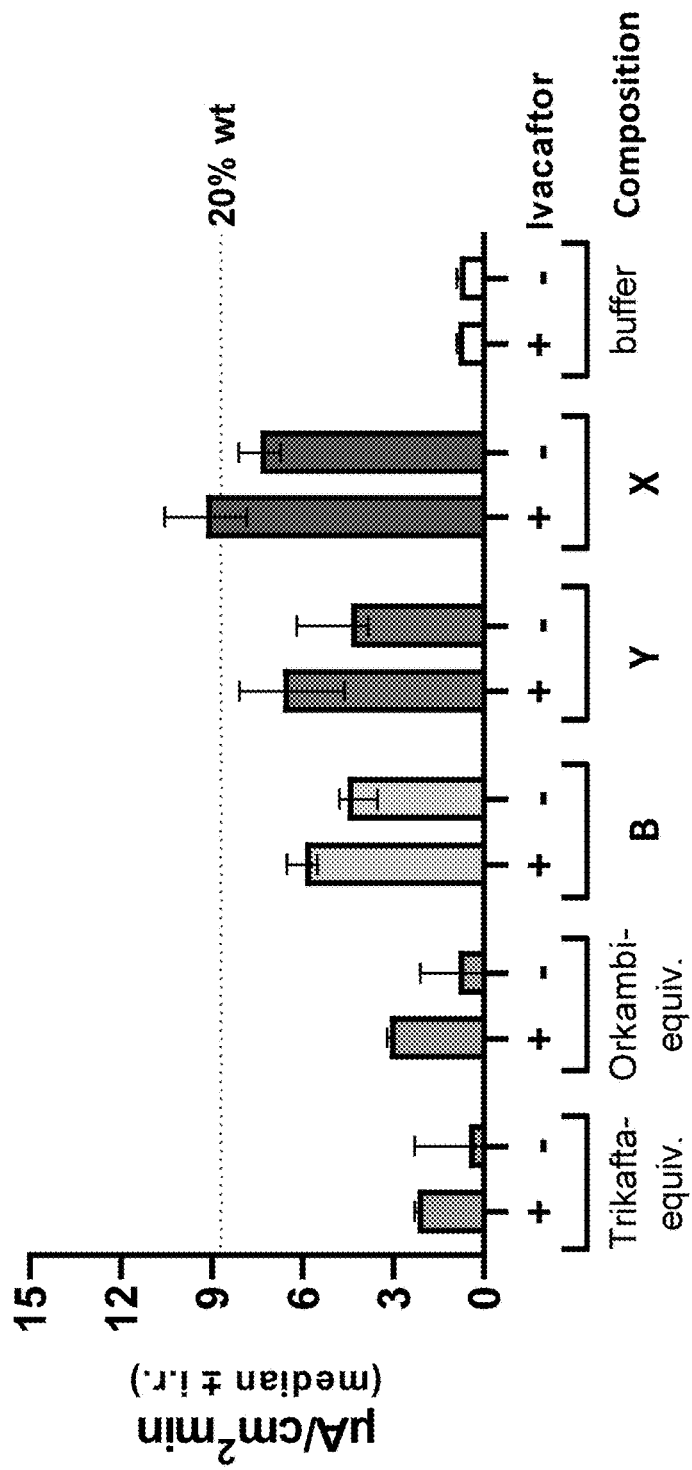
Figure 52B:
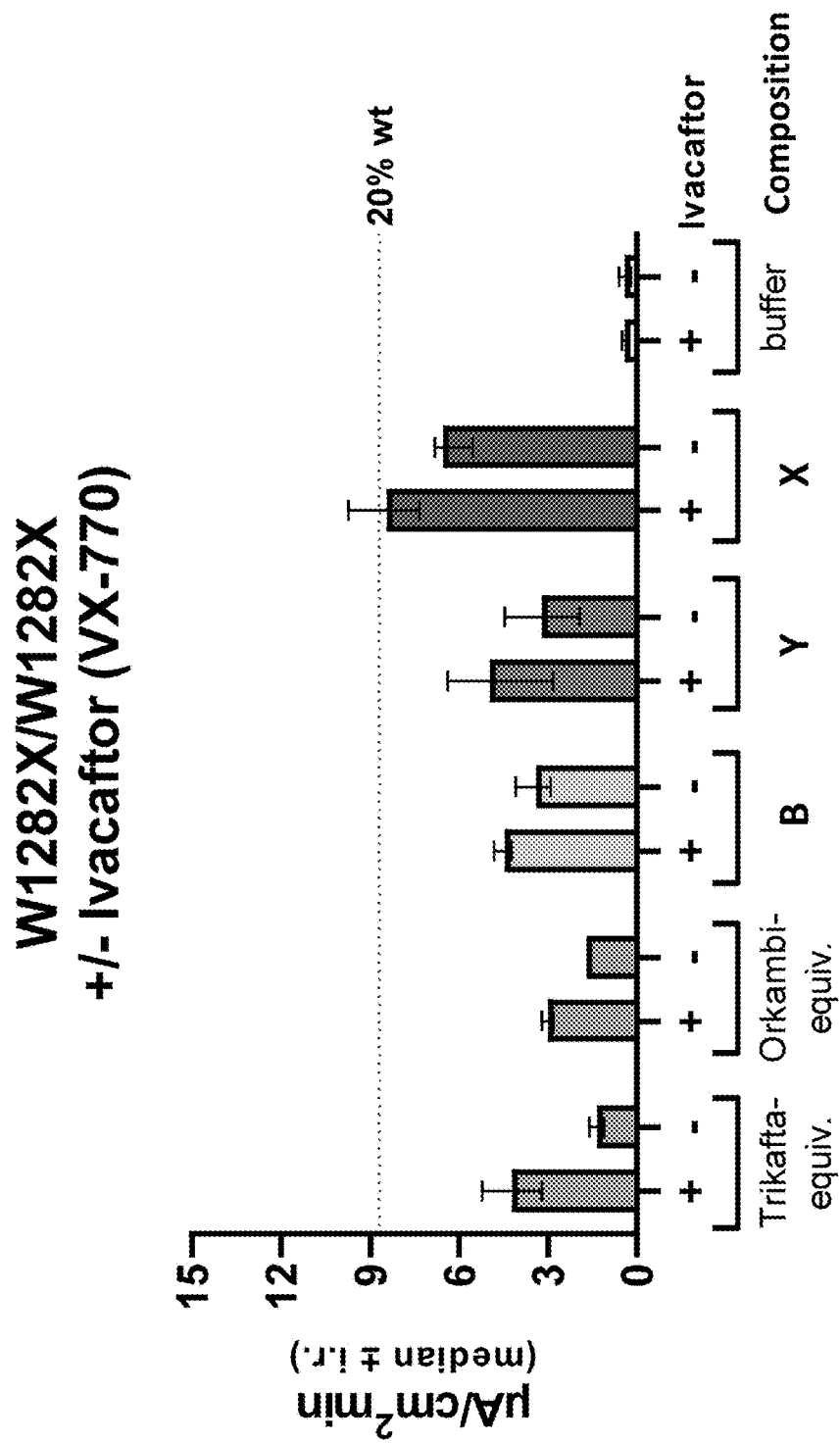

FIGS. 52A-52B show effect of CFTR activator on CFTR function after delivery of lipid nanoparticles. FIG. 52A shows rescue of CFTR function with or without Ivacaftor in R553X/W1282X hBEs. FIG. 52B shows rescue of CFTR function with or without Ivacaftor in W1282X/W1282X hBEs.

Figure 53B:
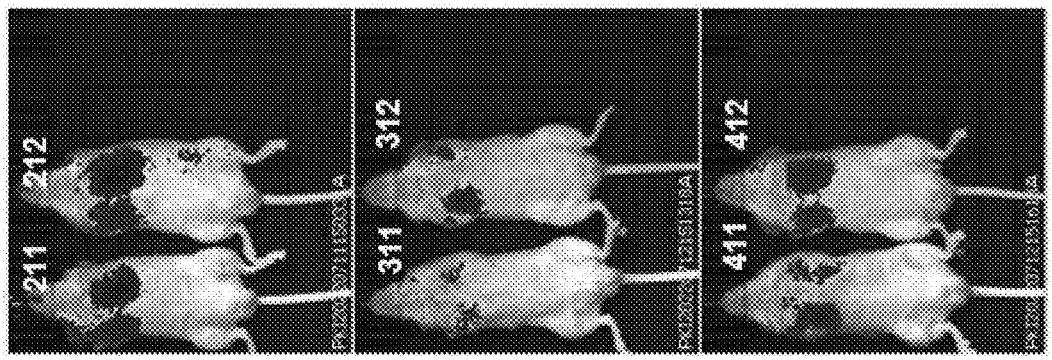
Figure 53A:
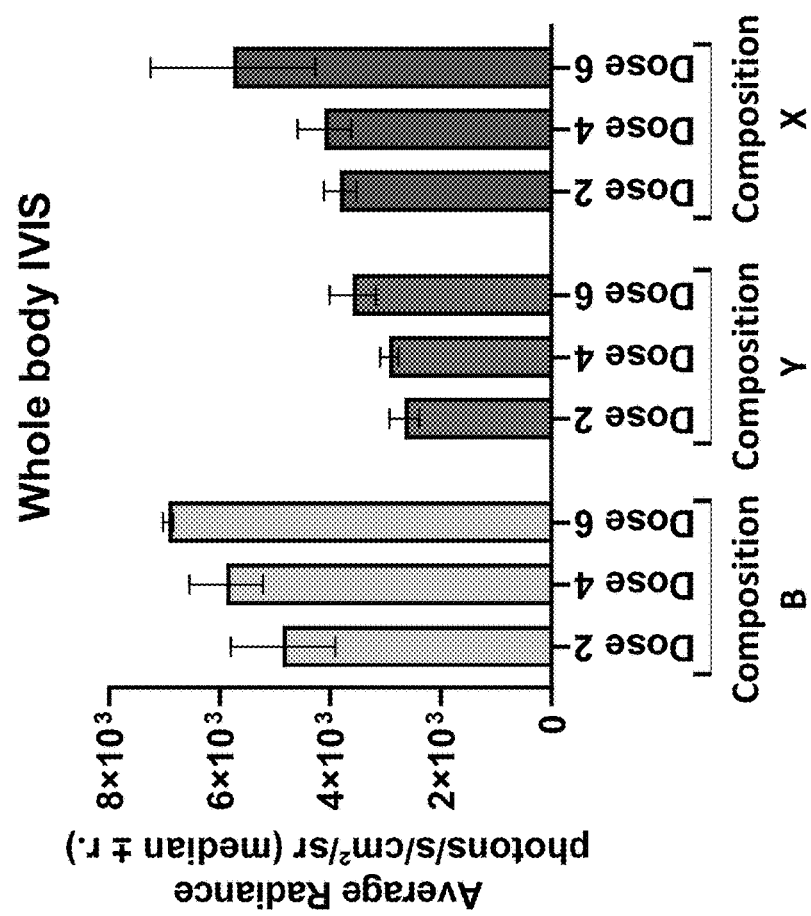

FIGS. 53A-53B show in vivo study of lipid nanoparticles. FIG. 53A shows quantification of luminescence. FIG. 53B shows whole body image IVIS.

Figures 54A, 54B:
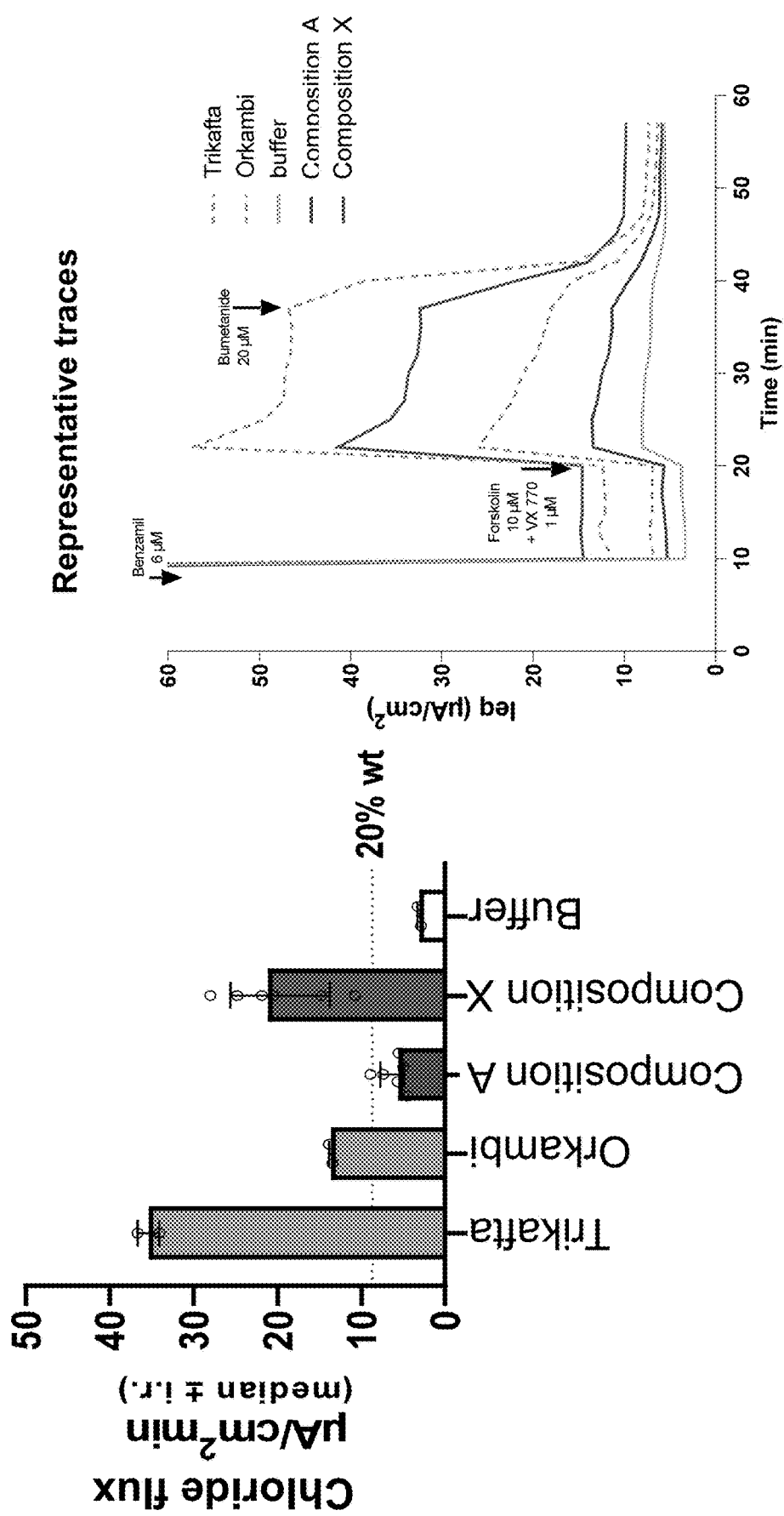
Figure 54C:
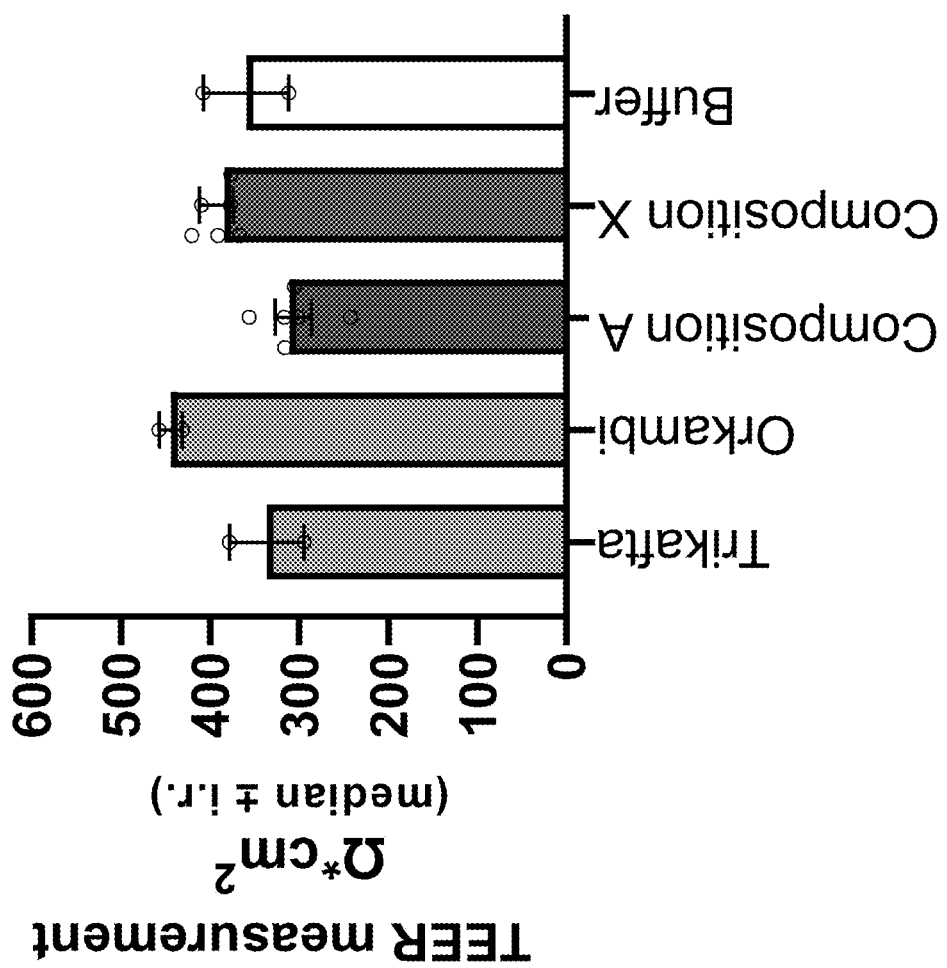

FIGS. 54A-54C show SORT LNP for the PCD program does not rescue CFTR function in ΔF508/ΔF508 hBEs when delivered by aerosol. FIG. 54A shows rescue of CFTR function treated with either Composition A or Composition X. FIG. 54B shows representative traces of chloride flux. FIG. 54C shows measurement of transepithelial resistance (TEER).

Figures 55A, 55B, 55C:
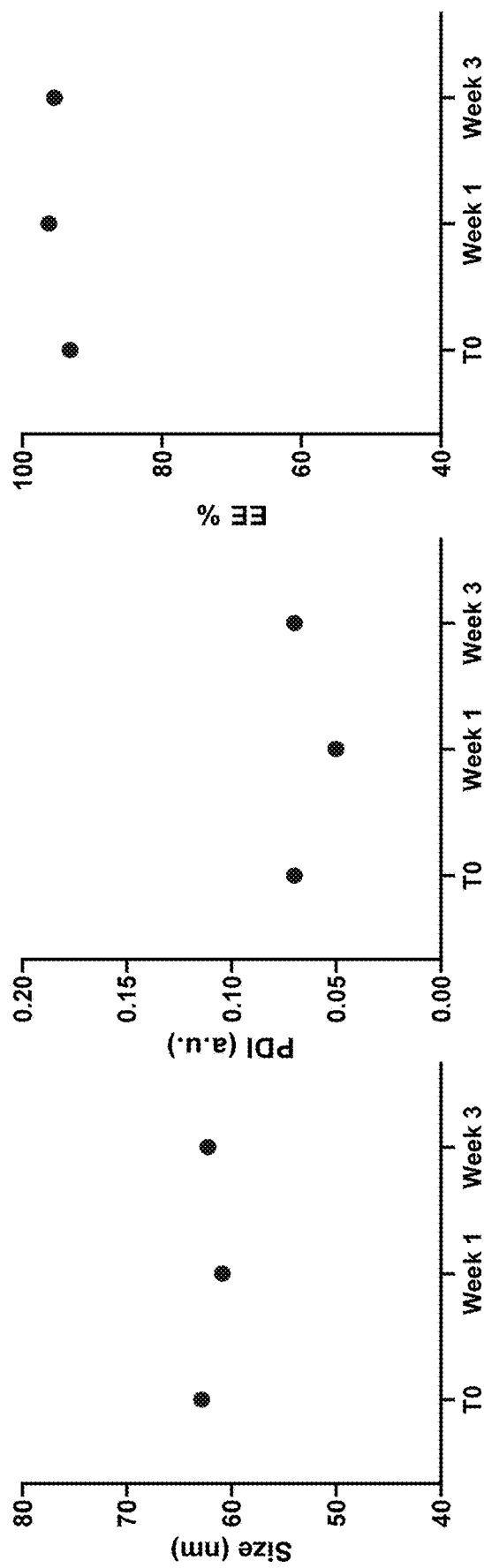

FIGS. 55A-55C show stability study of Composition B over three weeks. FIG. 55A shows size of lipid nanoparticles at week 1 and week 3. FIG. 55B shows polydispersity index of lipid nanoparticles at week 1 and week 3. FIG. 55C shows encapsulation efficiency (%) of lipid nanoparticles at week 1 and week 3.

Figures 56A, 56B, 56C:
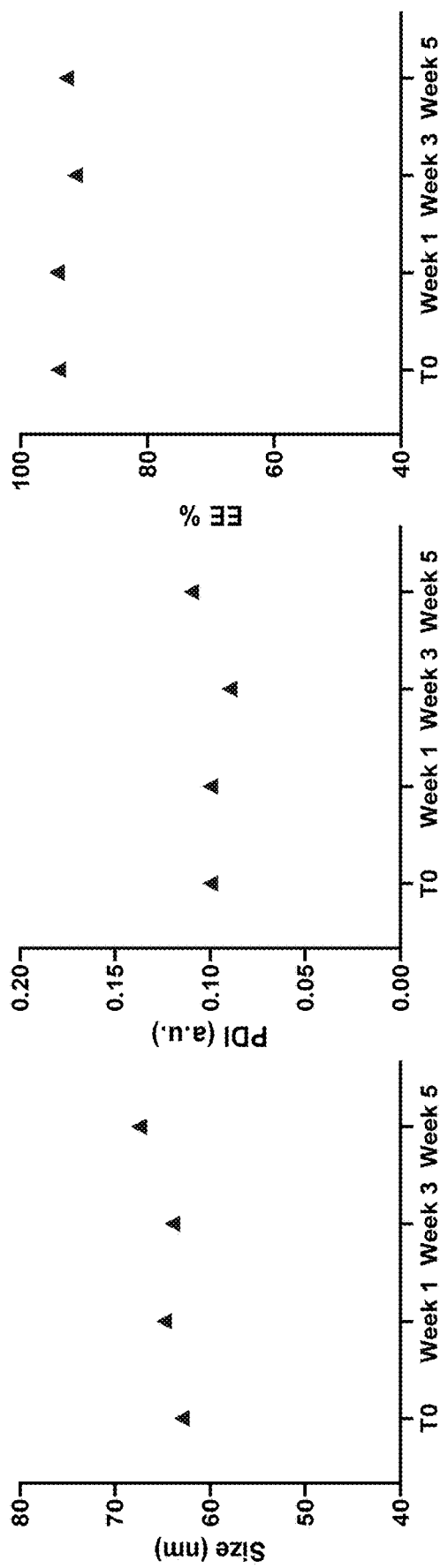

FIGS. 56A-56C show stability study of Composition X over three weeks. FIG. 56A shows size of lipid nanoparticles at week 1 and week 3. FIG. 56B shows polydispersity index of lipid nanoparticles at week 1 and week 3. FIG. 56C shows encapsulation efficiency (%) of lipid nanoparticles at week 1 and week 3.

Figure 57A:
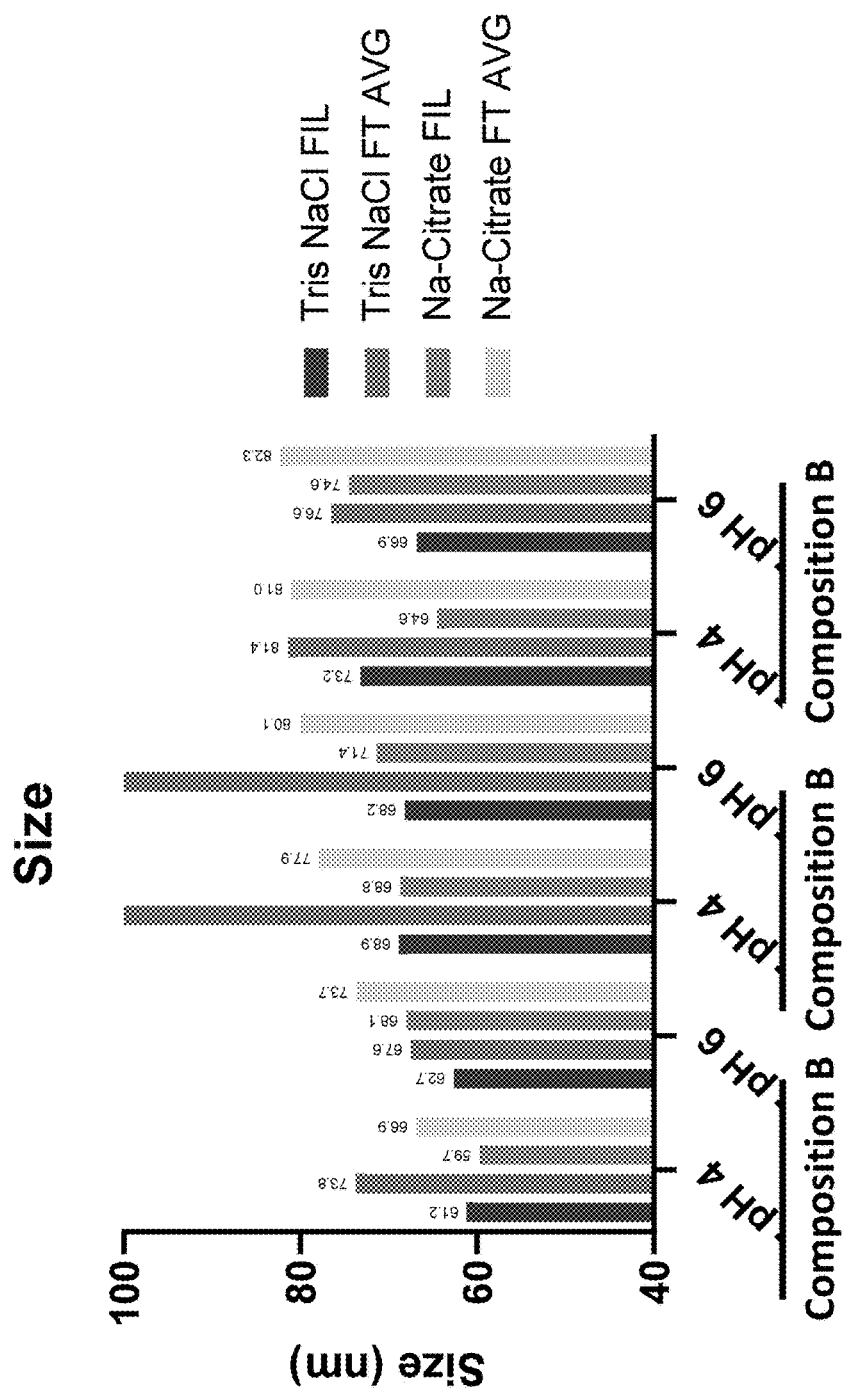
Figure 57B:
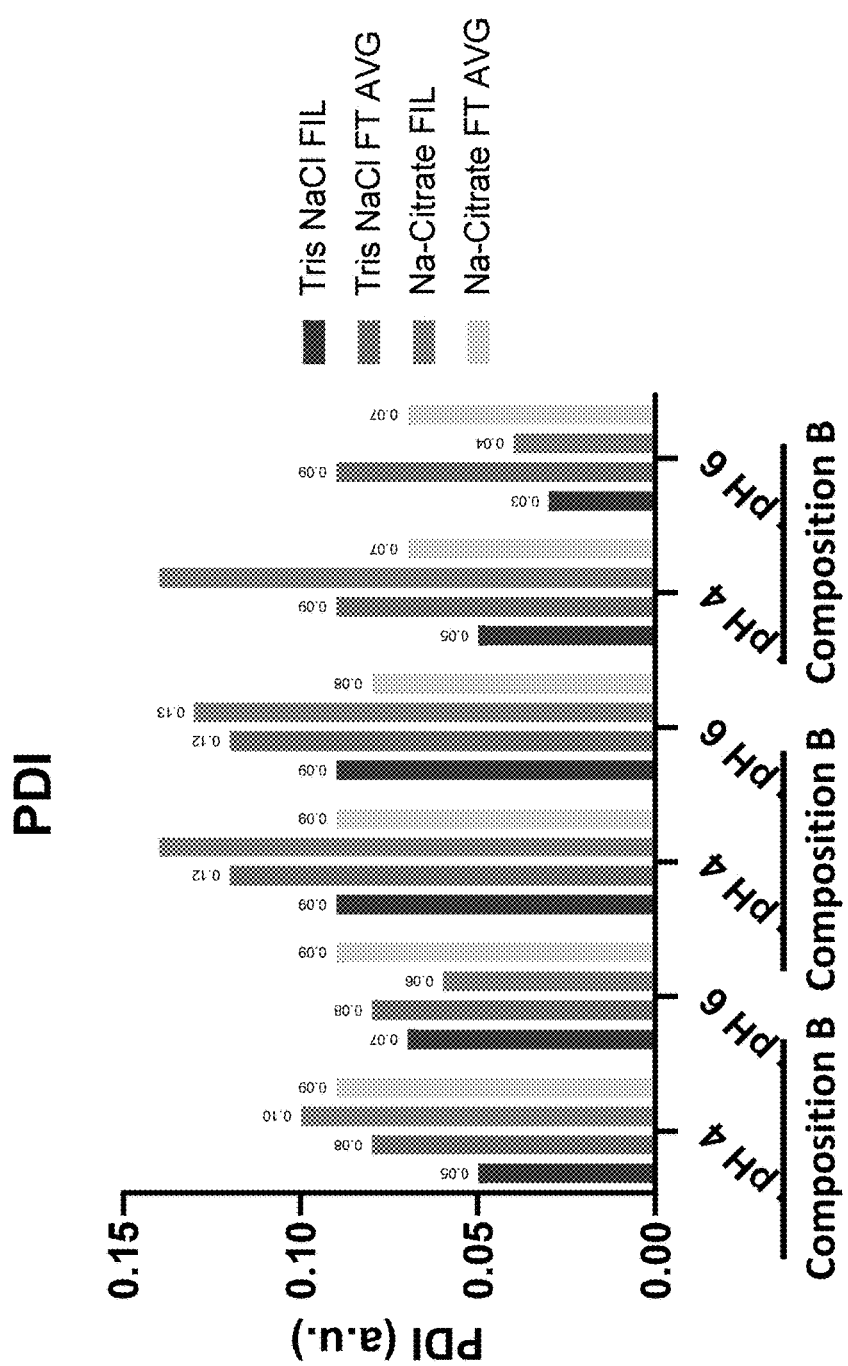
Figure 57C:
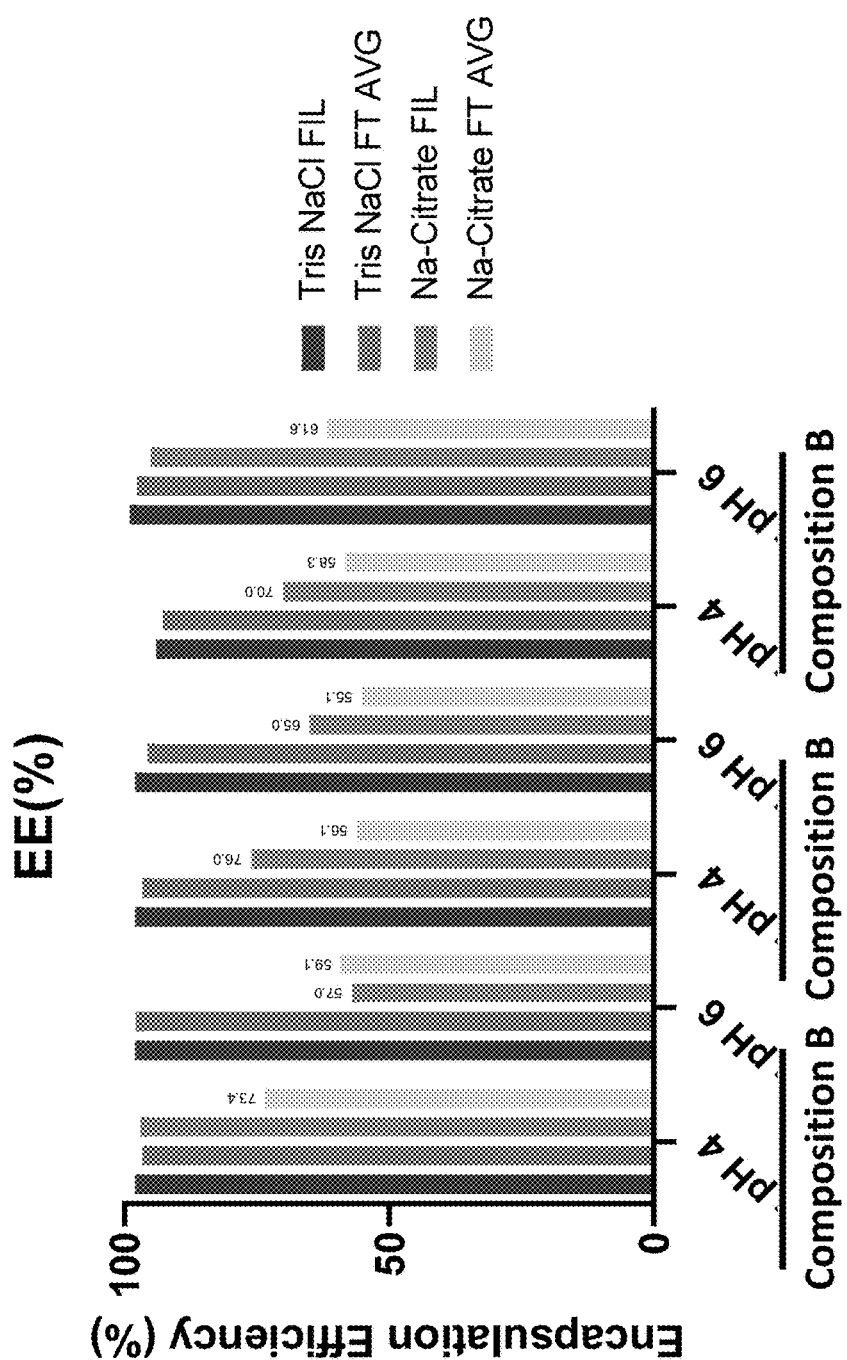

FIGS. 57A-57C show comparison of lipid nanoparticle characterization in both pH 4 and pH 6 Citrate buffer. FIG. 57A shows size of lipid nanoparticles. FIG. 57B shows polydispersity index of lipid nanoparticles. FIG. 57C shows encapsulation efficiency (%) of lipid nanoparticles.

Figure 58A:
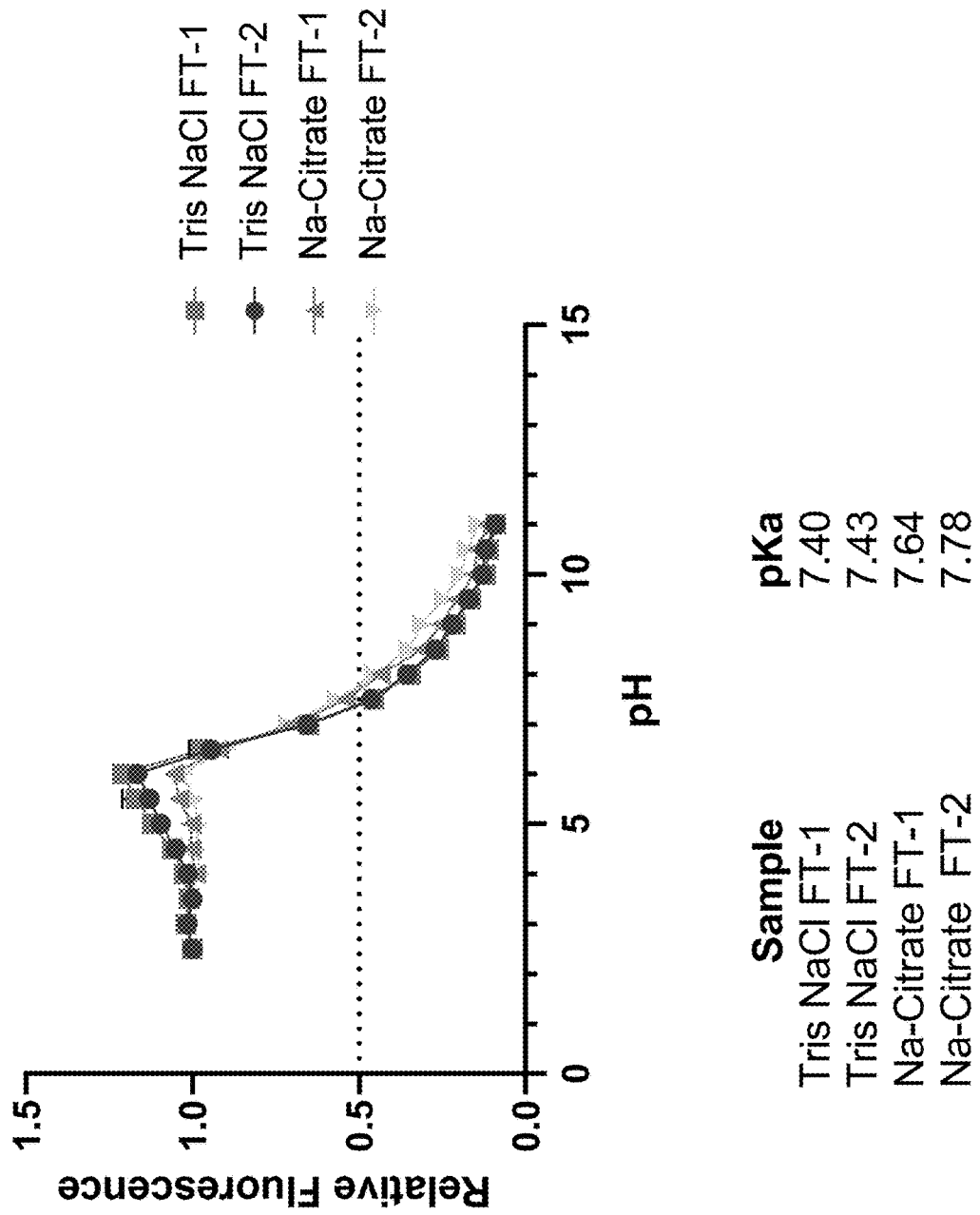
Figure 58B:
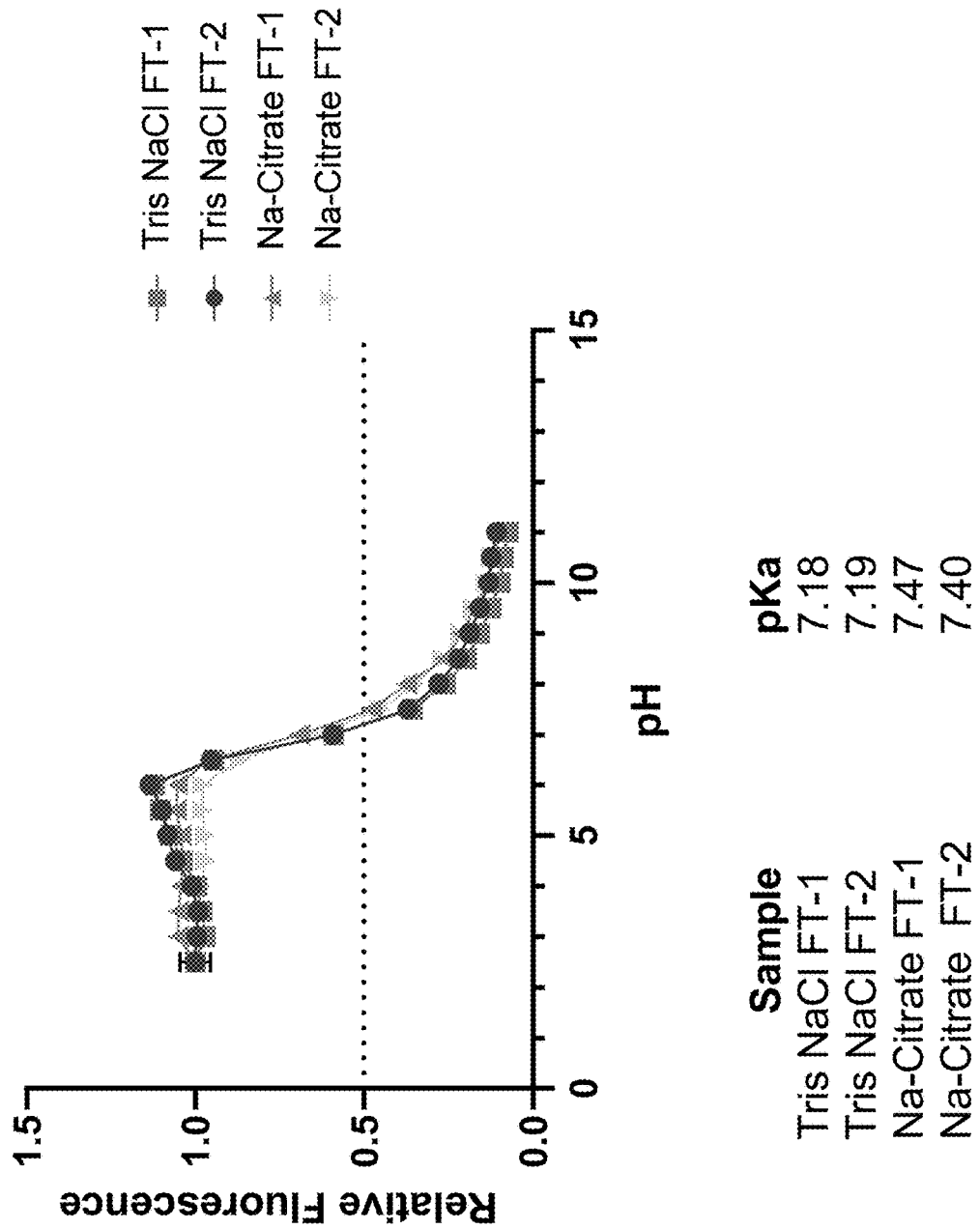
Figure 58C:
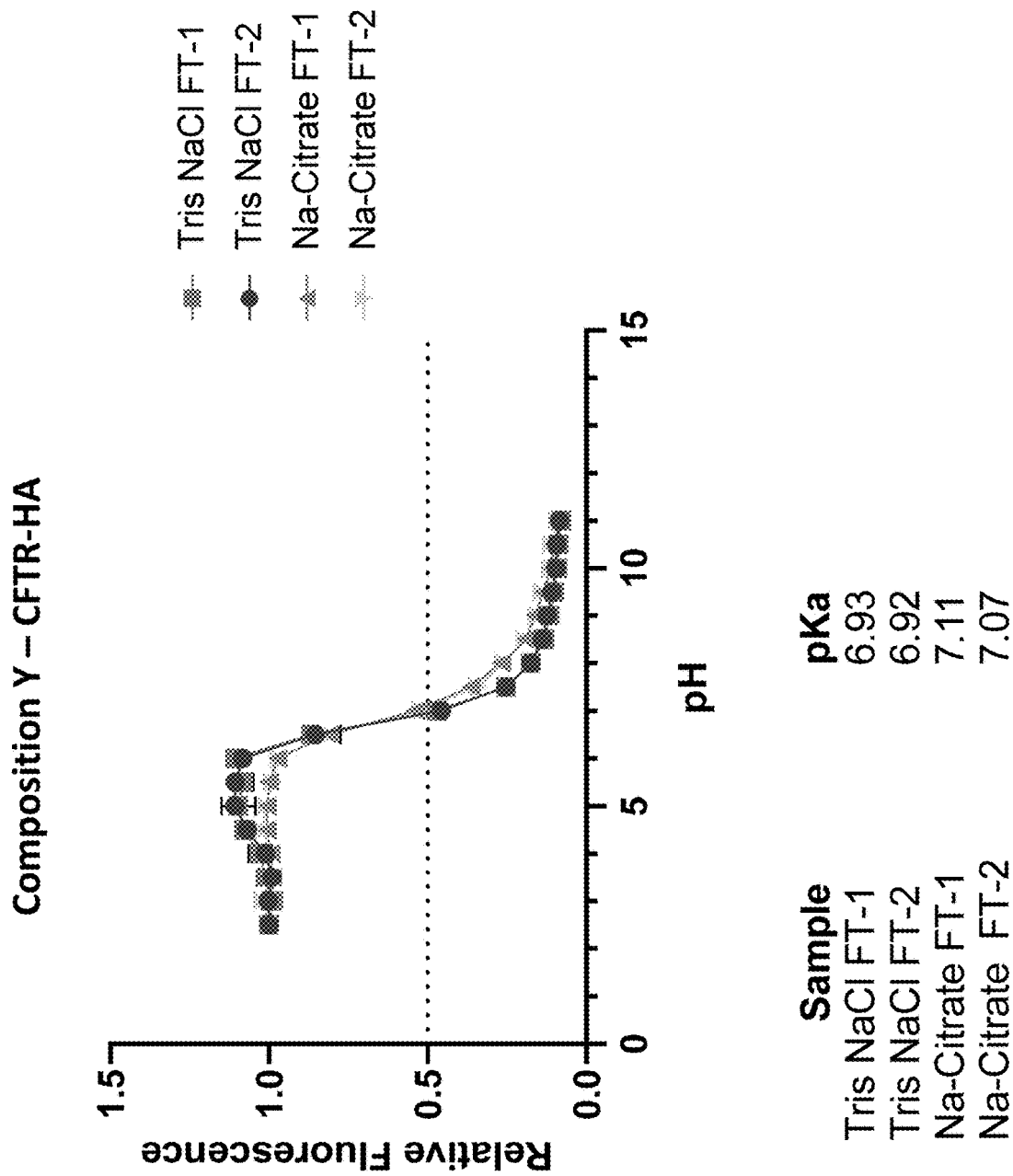

FIGS. 58A-58C show TNS Assay of various lipid nanoparticles in pH 4 Citrate buffer. FIG. 58A shows TNS assay of Composition B in different buffers. FIG. 58B shows TNS assays of Composition X in different buffers. FIG. 58C shows TNS assays of Composition Y in different buffers.

Figure 59A:
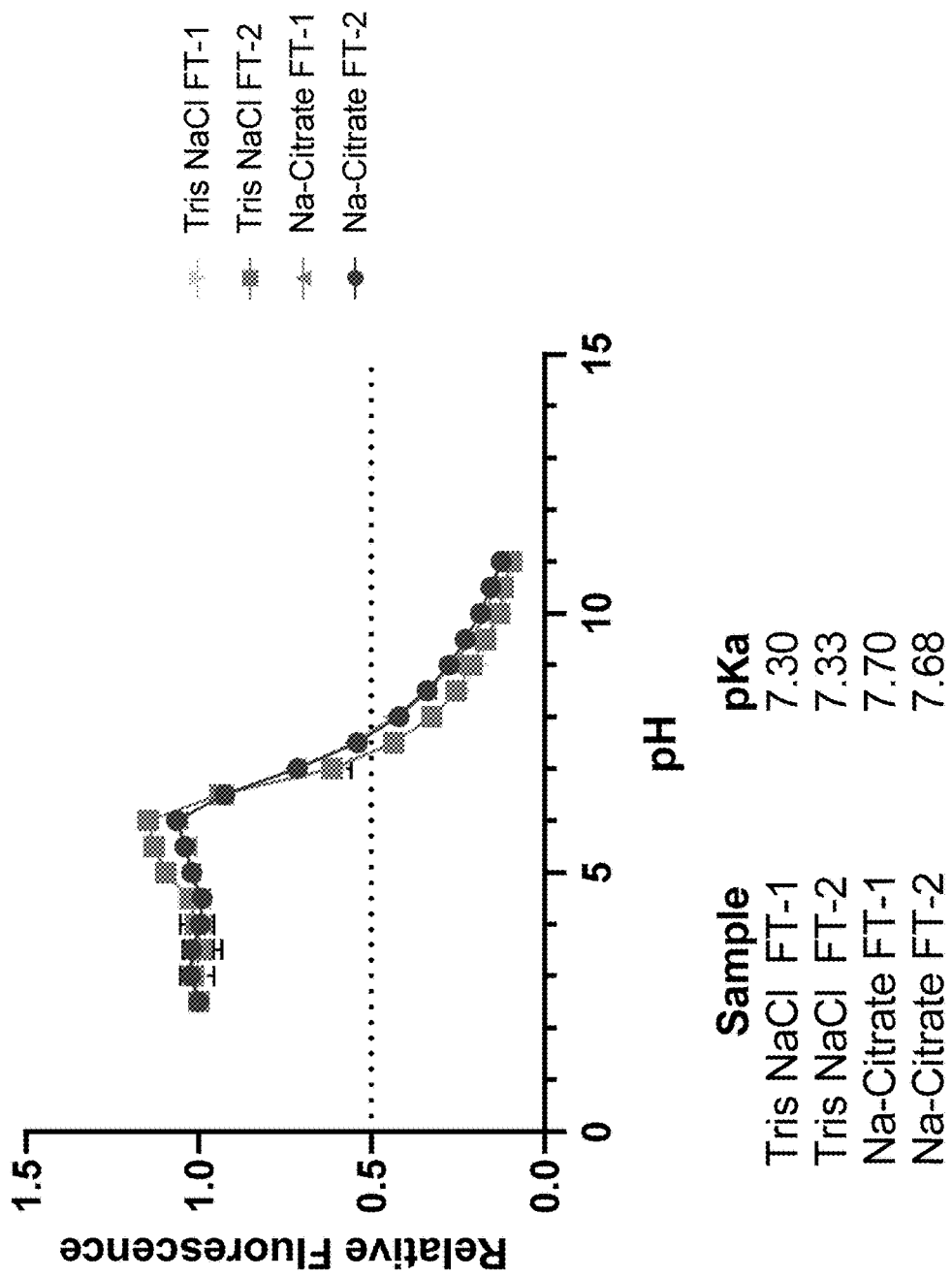
Figure 59B:
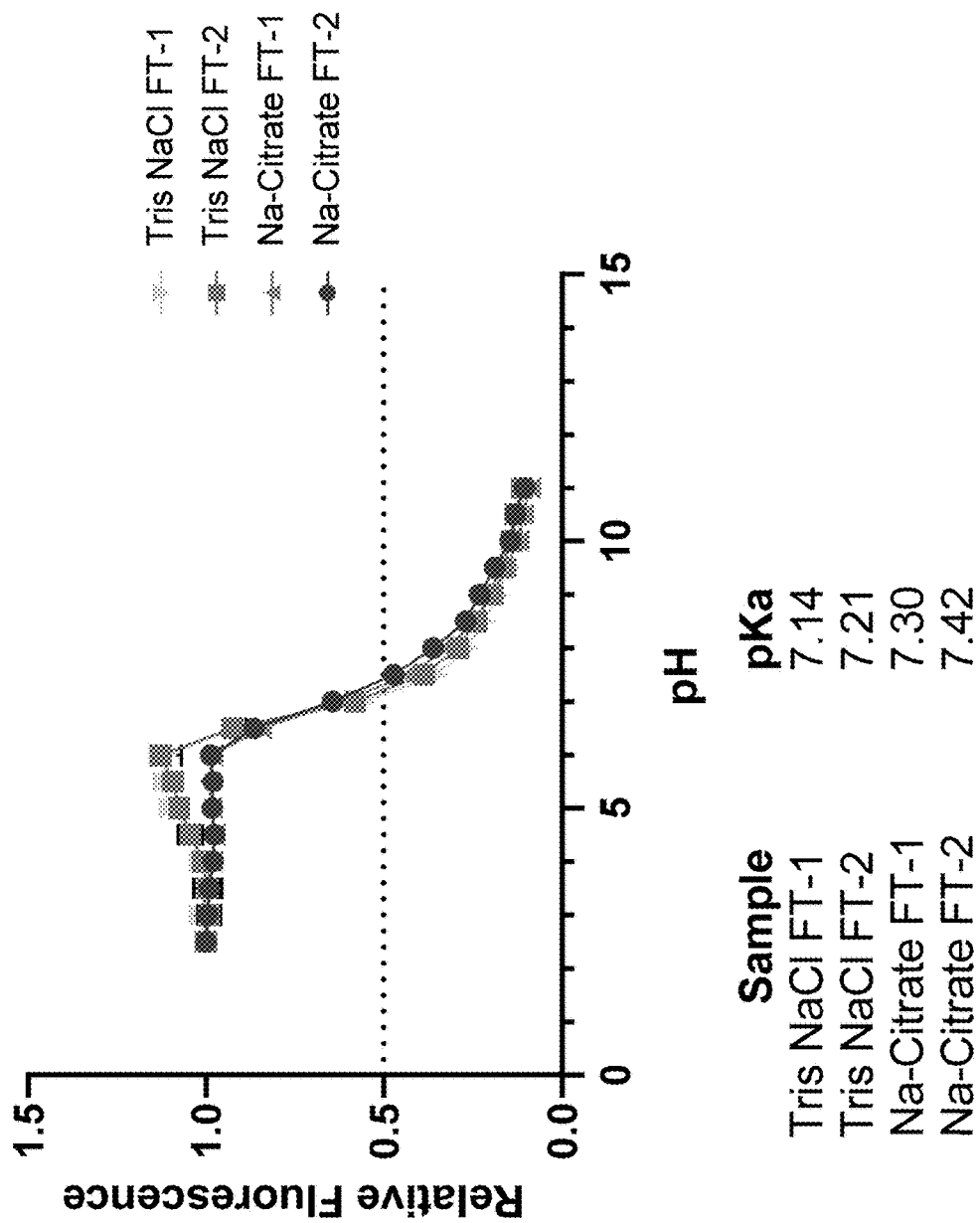
Figure 59C:
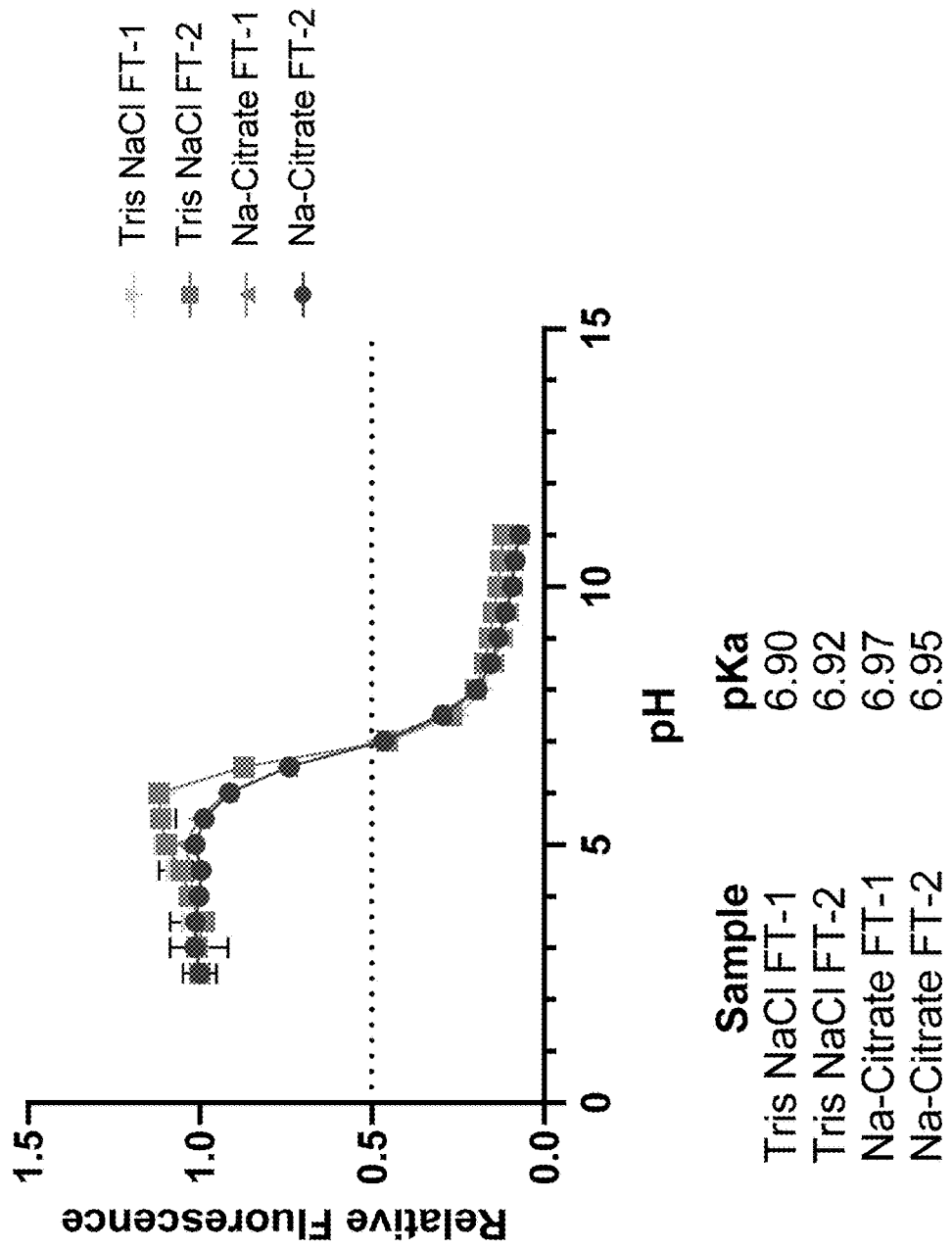

FIGS. 59A-59C show TNS Assay of various lipid nanoparticles in pH 6 Citrate buffer. FIG. 59A shows TNS assays of Composition B in different buffers. FIG. 59B shows TNS assay of Composition X in different buffers. FIG. 59C shows TNS assay of Composition Y in different buffers.

FIG. 60 shows post-nebulization characteristics of Composition B and Composition X in Citrate buffer containing sucrose.

FIG. 61 shows lipid nanoparticle characterization data on free-thaw storage

FIGS. 62A-62G show optimization of Composition X formulation. FIG. 62A shows experimental scheme. FIG. 62B shows buffer conditions for experiments. FIG. 62C shows characterization of lipid nanoparticles (particle size, polydispersity index, and encapsulation efficiency) after freeze-thaw cycle. FIG. 62D shows characterization of lipid nanoparticles (particle size, polydispersity index, and encapsulation efficiency) for longer storage condition.

FIG. 62E shows buffer conditions for experiments. FIG. 62F shows characterization of lipid nanoparticles (particle size, polydispersity index, and encapsulation efficiency) after freeze-thaw cycle. FIG. 62G shows characterization of lipid nanoparticles (particle size, polydispersity index, and encapsulation efficiency) for longer storage condition.

FIG. 63 show pH titration study of Composition X lipid nanoparticle composition.

FIG. 64 shows pH titration study of Composition X lipid nanoparticle composition on Solo.

FIG. 65 shows the CFTR function on Composition X in different pH condition.

FIG. 66 shows reference for the antibodies selected for the immunofluorescence panel.

FIG. 67A shows ΔF508/ΔF508 hBE cell profile. FIG. 67B shows genotype and donor codes of hBE cells. FIG. 67C shows antibody detection for each cell type.

FIG. 68 shows immunofluorescence image of ΔF508/ΔF508 hBE (KKD003K) dosed with Composition B/HA-CFTR.

FIG. 69 shows immunofluorescence image of ΔF508/ΔF508 hBE (KKD003K) dosed with Composition B/HA-CFTR.

FIG. 70 shows immunofluorescence image of ΔF508/ΔF508 hBE (KKD003K) dosed with Composition B/HA-CFTR.

FIG. 71A shows expression level of HA-CFTR in F508del/F508del (TXCF042716) cells. FIG. 71B shows expression level of HA-CFTR in F508del/F508del (20160524CF) cells.

FIG. 72 shows the relationship of CFTR function and its expression.

Figures 77B, 77C:
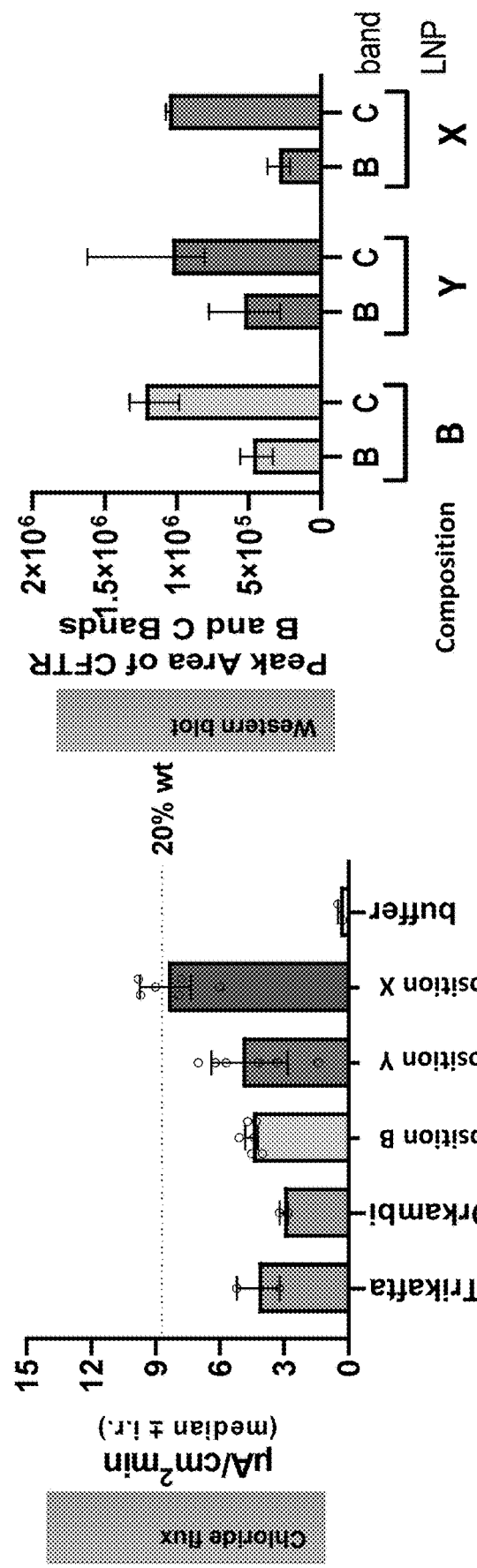

FIG. 73A shows the translocation of HA-CFTR protein to the apical membrane in ΔF508/ΔF508 (TXCF042716) hBE cells. FIG. 73B shows rescue of CFTR function in hBEs.

FIG. 73C shows quantification of CFTR bands by Western blot analysis.

FIG. 74A shows the localization of HA-CFTR protein in ΔF508/ΔF508 (20160524CF). FIG. 74B shows rescue of CFTR function in hBEs. FIG. 74C shows quantification of CFTR bands by Western blot analysis.

FIG. 75 shows the CFTR expression in W1282X/W1282X hBE cells treated with either Composition B or Composition X.

FIG. 76A shows the localization of HA-CFTR protein in W1282X/W1282X (UI0014) cells dosed with Composition X. FIG. 76B shows rescue of CFTR function in hBEs. FIG. 76C shows quantification of CFTR bands by Western blot analysis.

FIG. 77A shows the localization of HA-CFTR protein in W1282X/W1282X (UI0014) cells dosed with Composition B. FIG. 77B shows rescue of CFTR function in hBEs. FIG. 77C shows quantification of CFTR bands by Western blot analysis.

Figure 78:
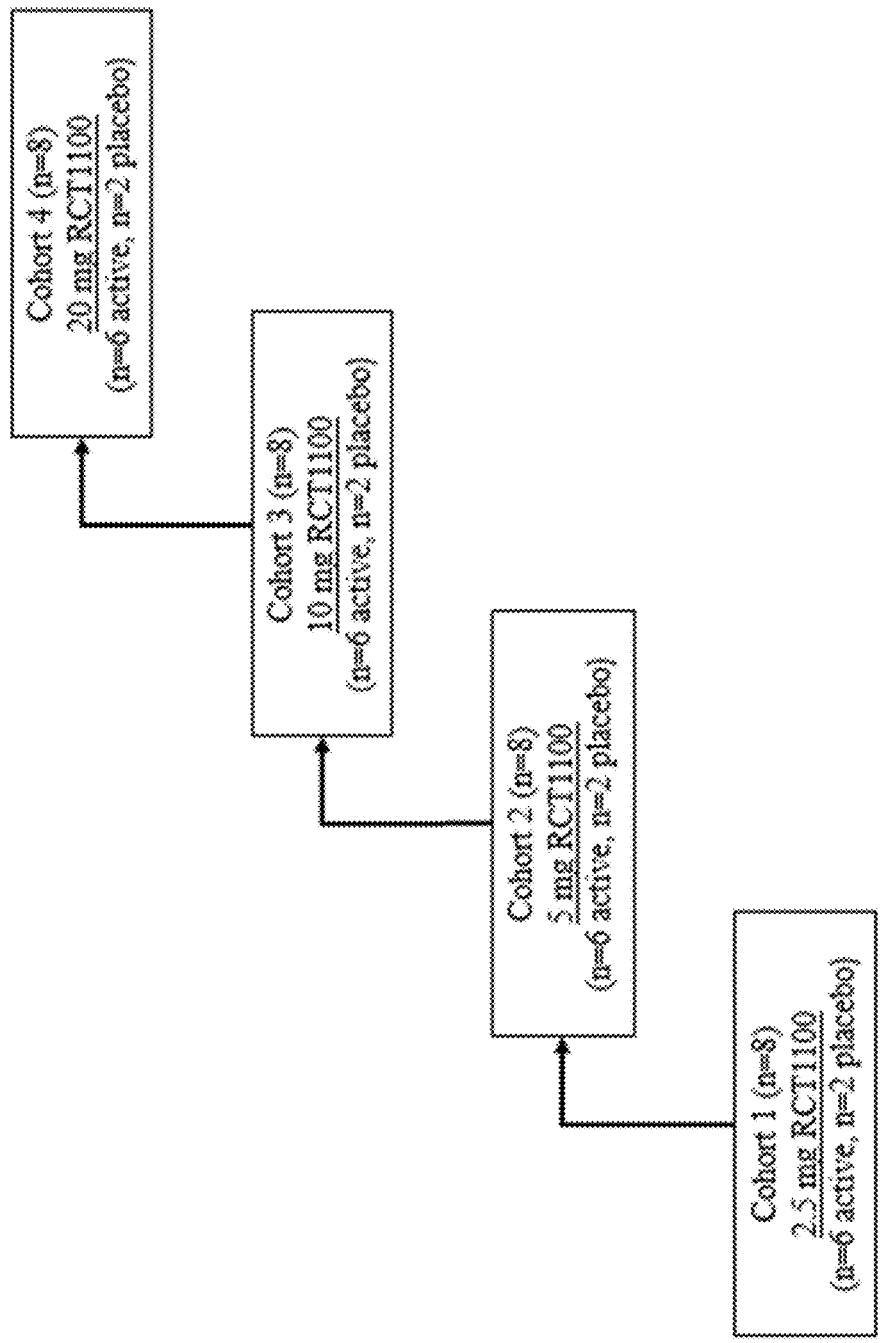

FIG. 78 shows a study schema.

FIG. 79 shows planned dose level of the study.

FIG. 80 shows schedule of event.

FIG. 81 shows cell tropism of Composition B in dF #4 (KKD003K).

Figure 82:
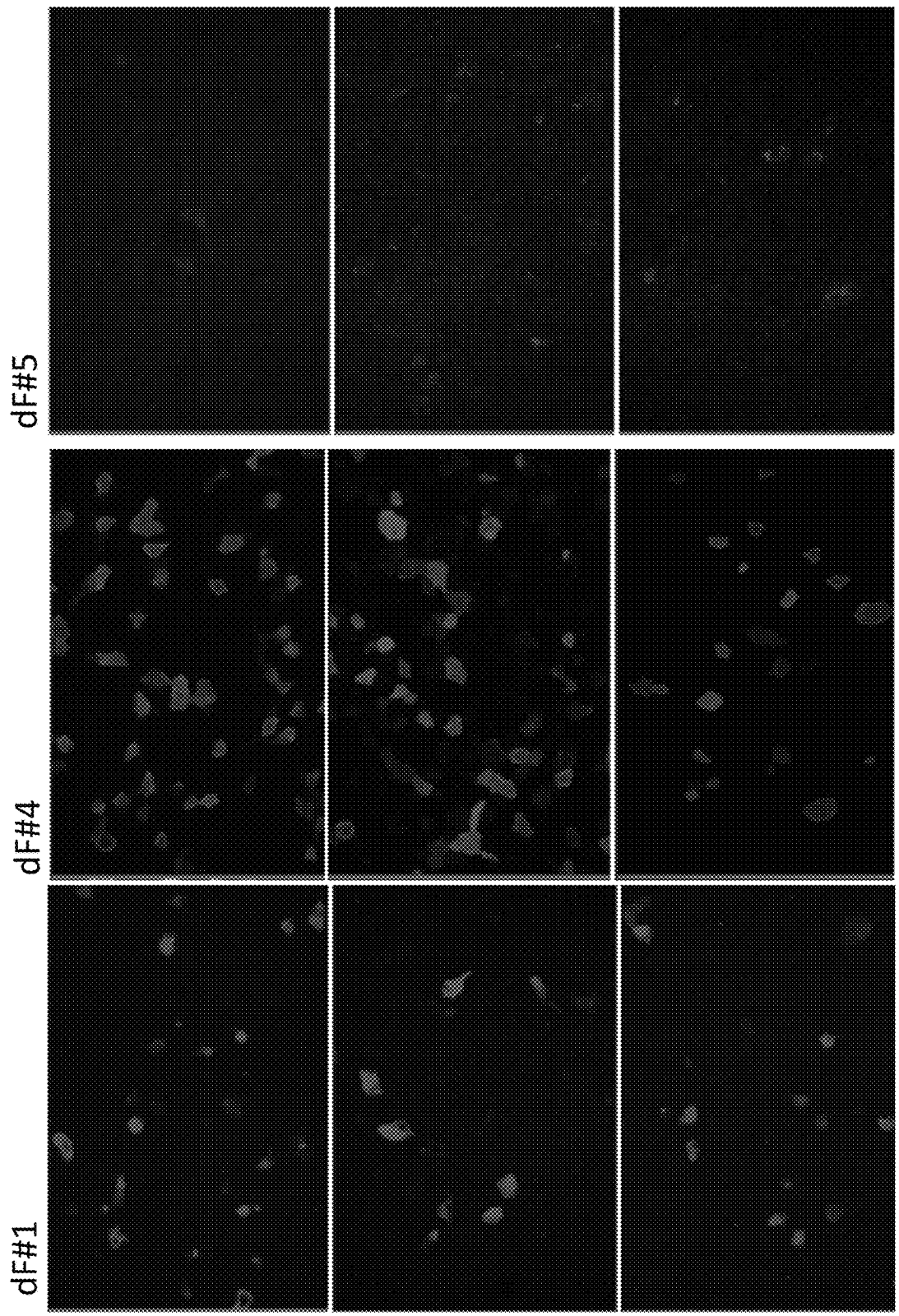

FIG. 82 shows cell-mediated expression of HA-CFTR in dF #1, dF #4, and dF #4.

Figure 83A:
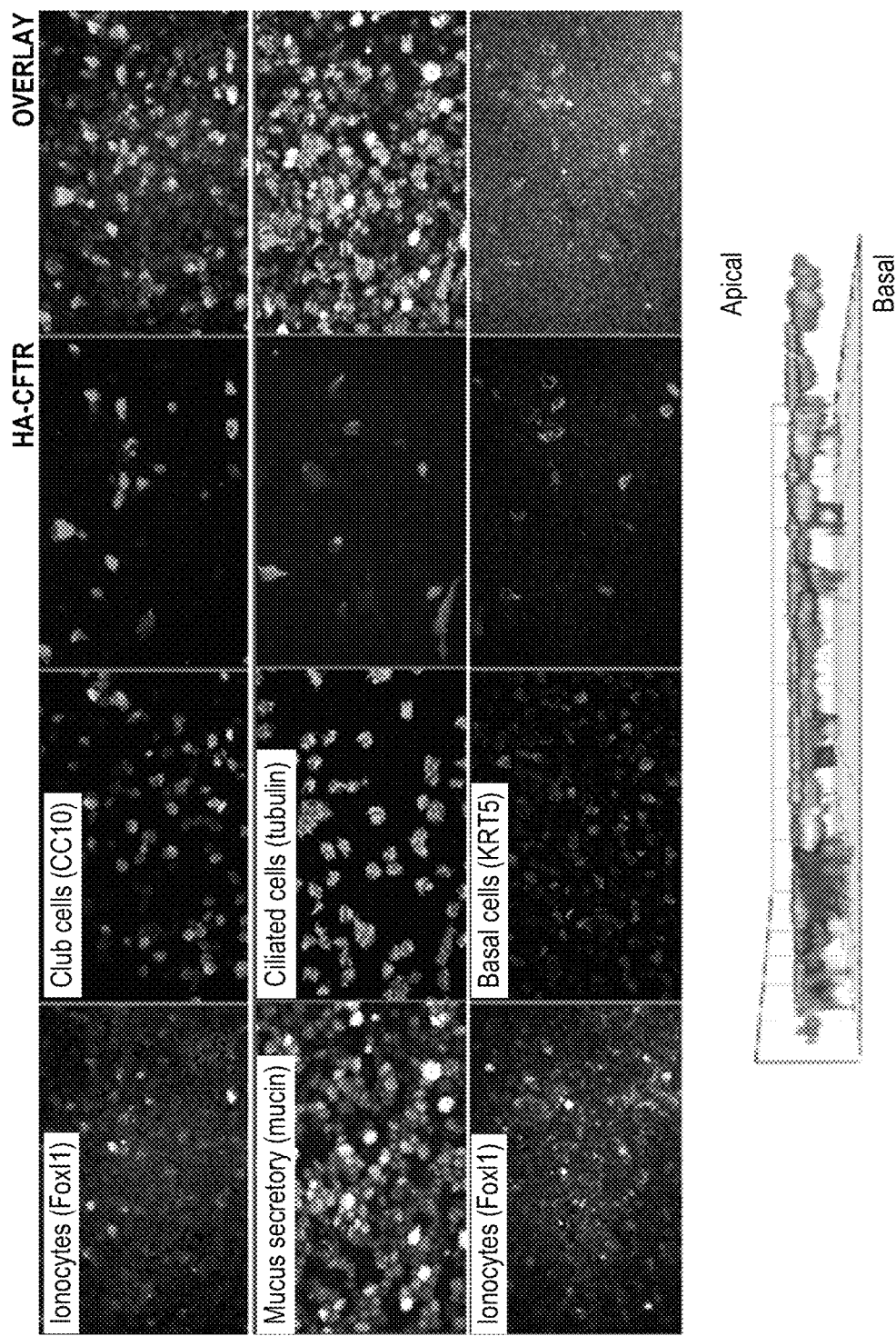
Figures 83B, 83C:
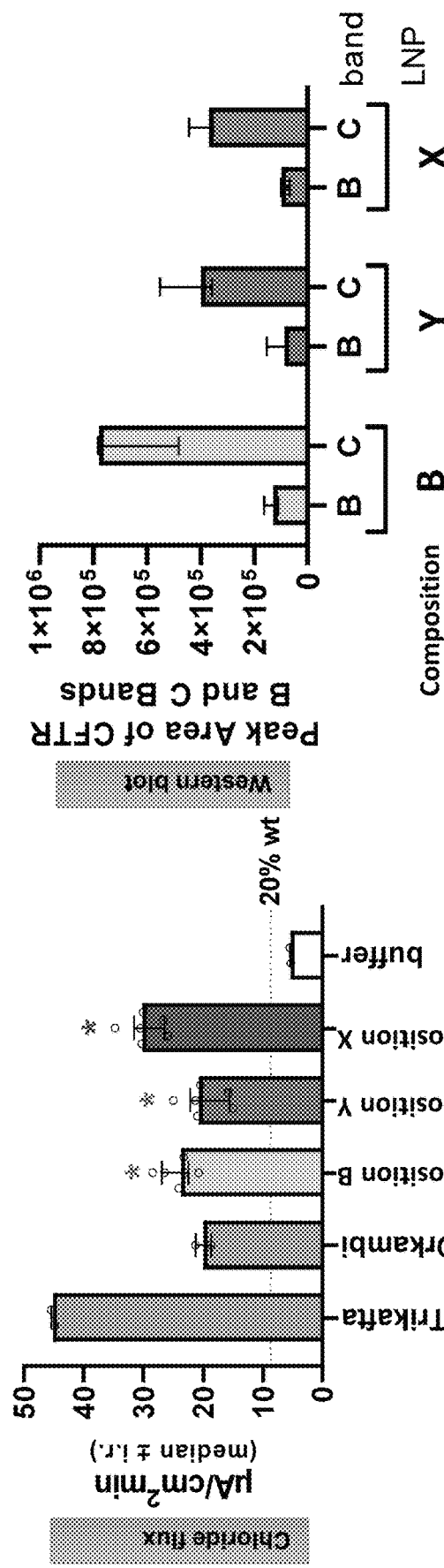

FIG. 83A shows highest expression, apical translocation of HA-CFTR in F508del/F508del hBE (donor TXCF042716) cells dosed with Composition X. FIG. 83B shows rescue of chloride flux in hBEs. FIG. 83C shows quantification of CFTR bands by Western blot analysis.

Figure 84A:
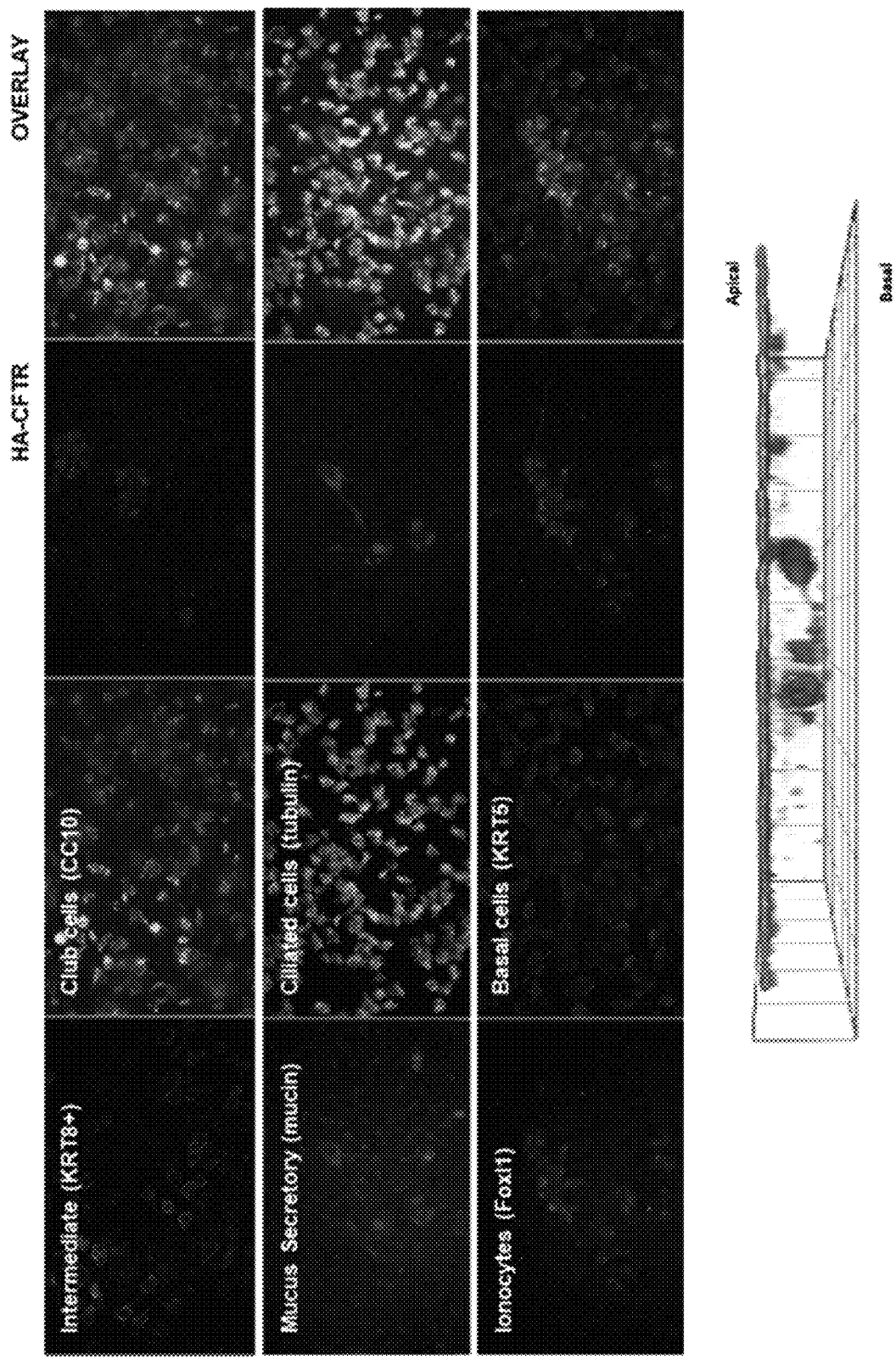
Figures 84B, 84C:
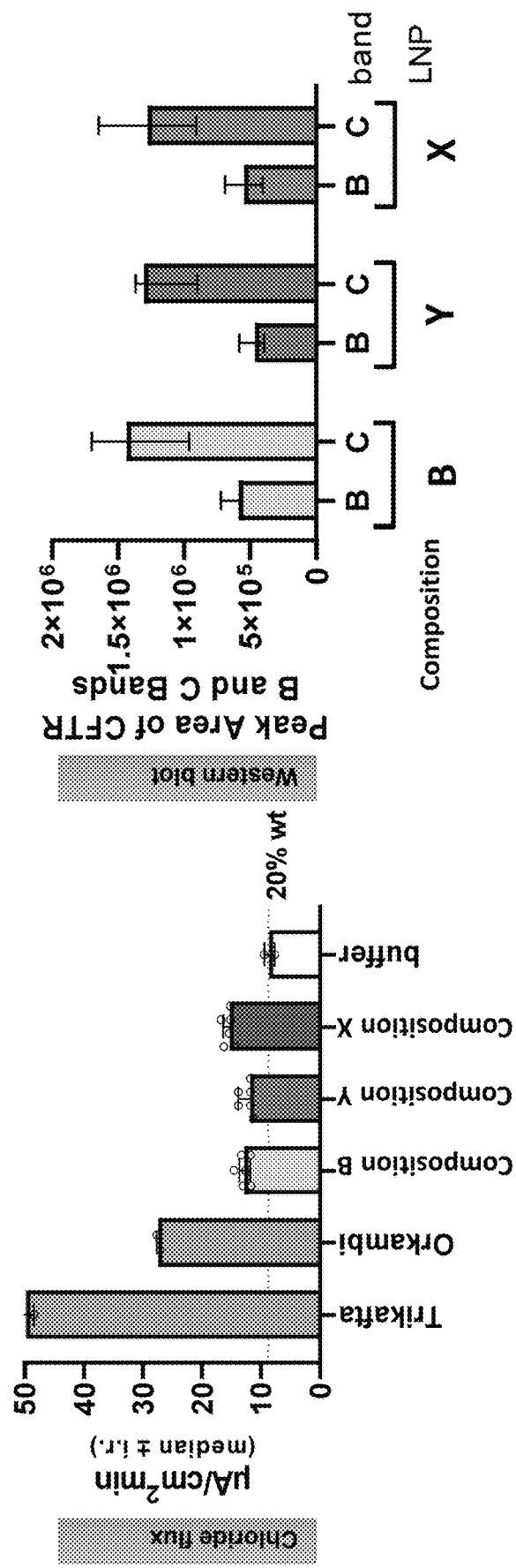

FIG. 84A shows expression of HA-CFTR in F508del/F508del hBE (donor 20160524CF) cells dosed with Composition X. FIG. 84B shows rescue of chloride flux in hBEs.

FIG. 84C shows quantification of CFTR bands by Western blot analysis.

Figure 85A:
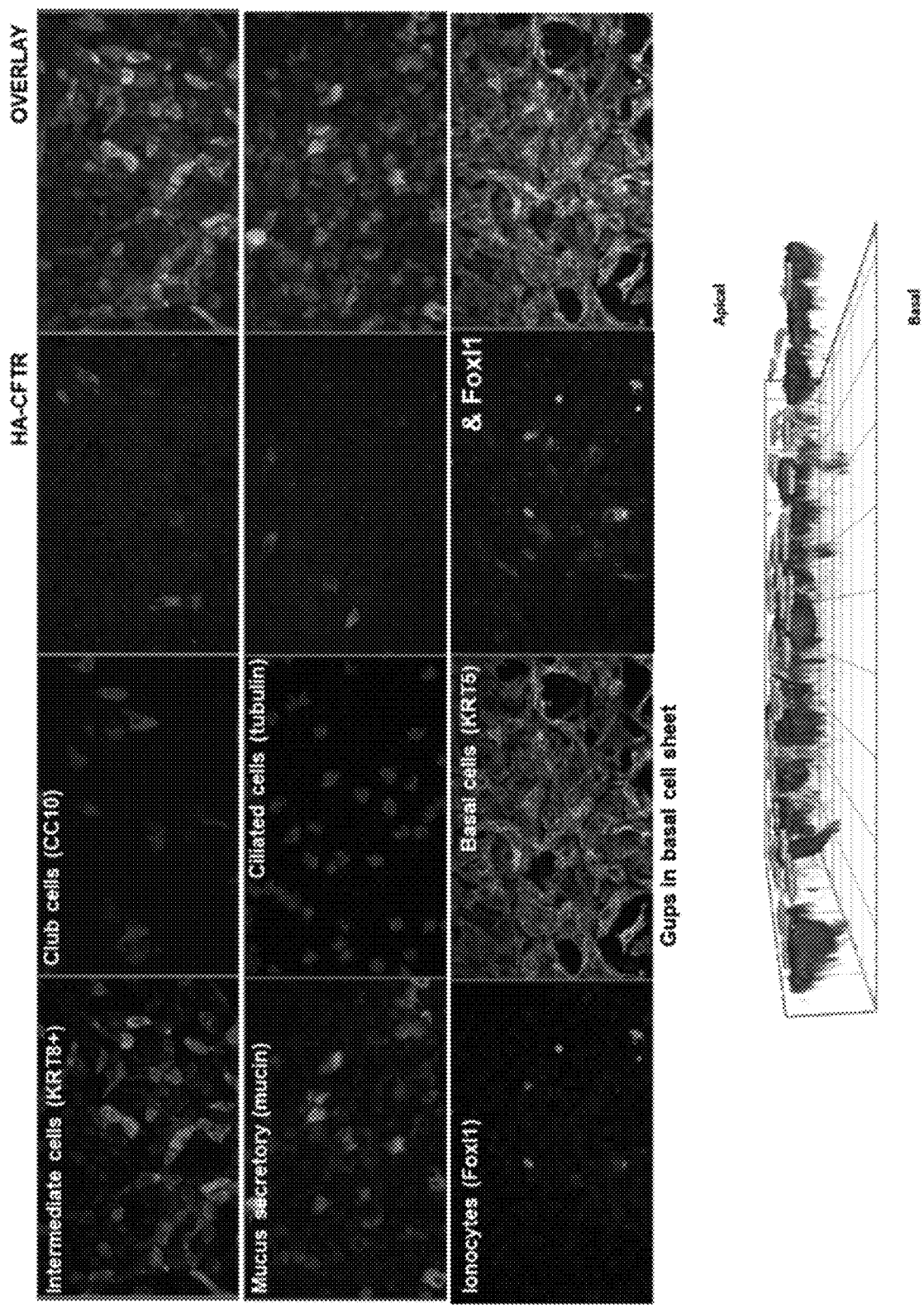
Figure 85B:
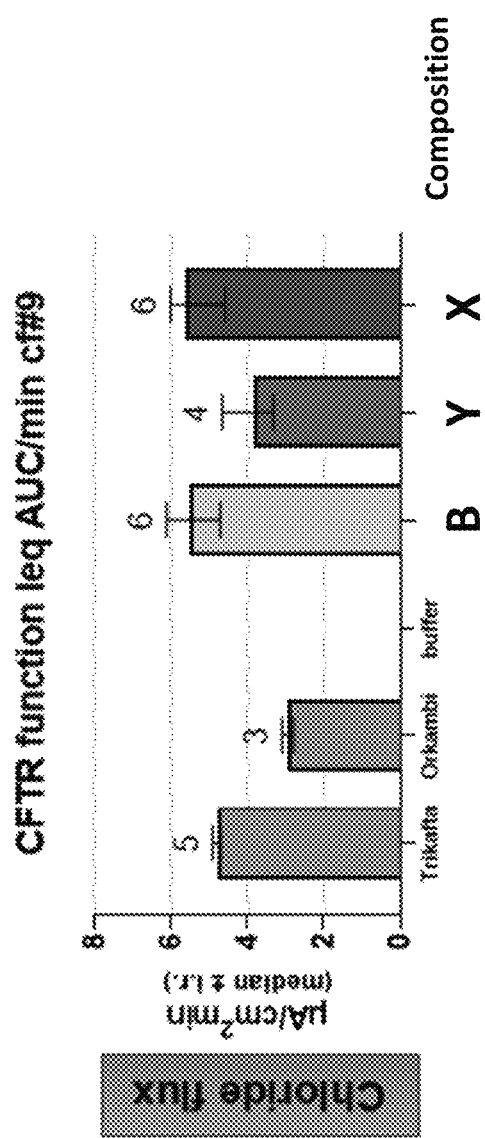

FIG. 85A shows expression and apical translocation of HA-CFTR post exposure to aerosolized Composition B in K710X/L$^{467}$ (ND13816) hBE cells. FIG. 85B shows rescue of chloride flux in hBEs.

Figure 86:
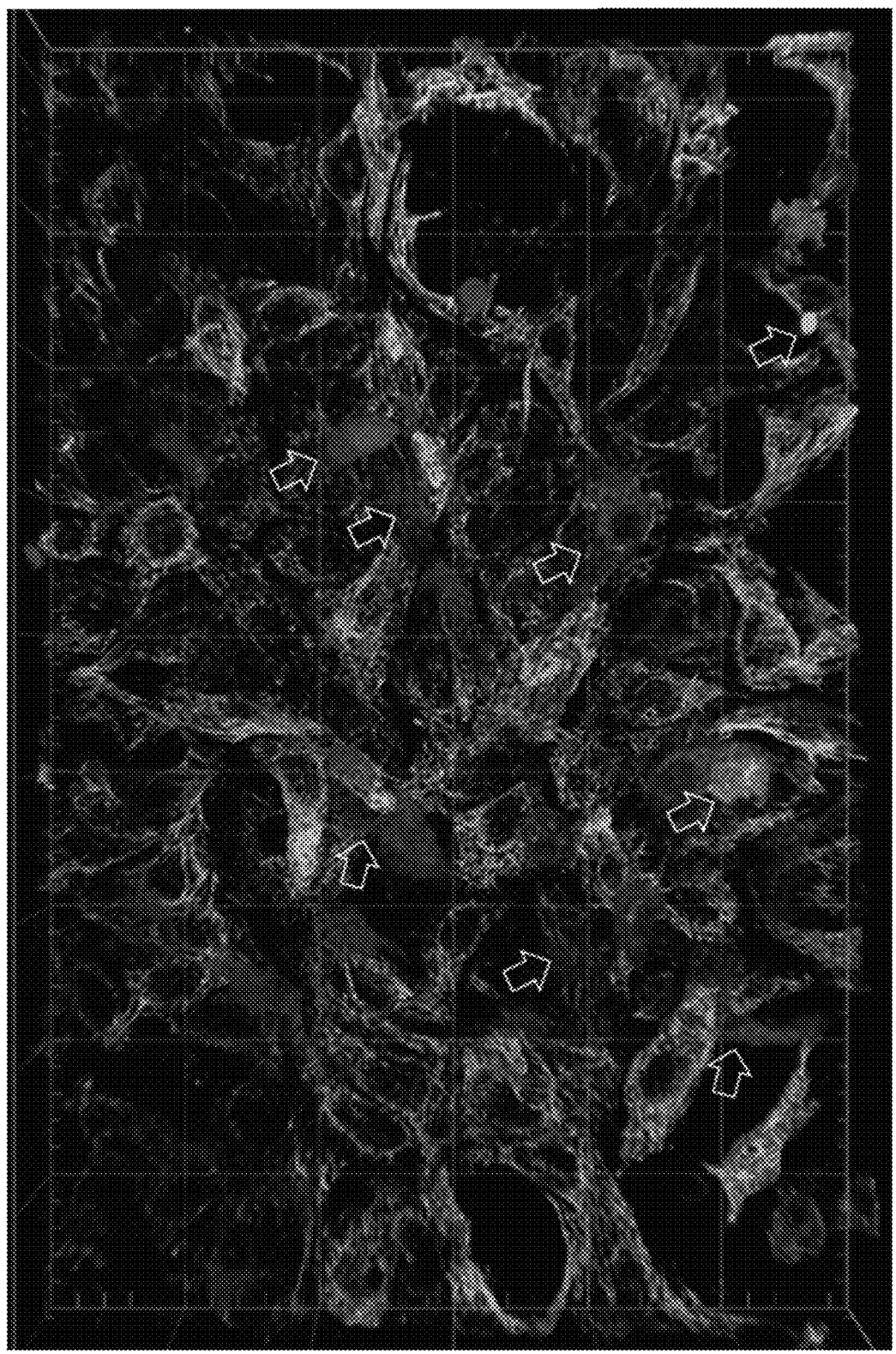

FIG. 86 shows HA-CFTR post exposure to aerosolized Composition B in K710X/L$^{467}$ (ND13816) cultures with significant signs of fibrosis.

Figure 87A:
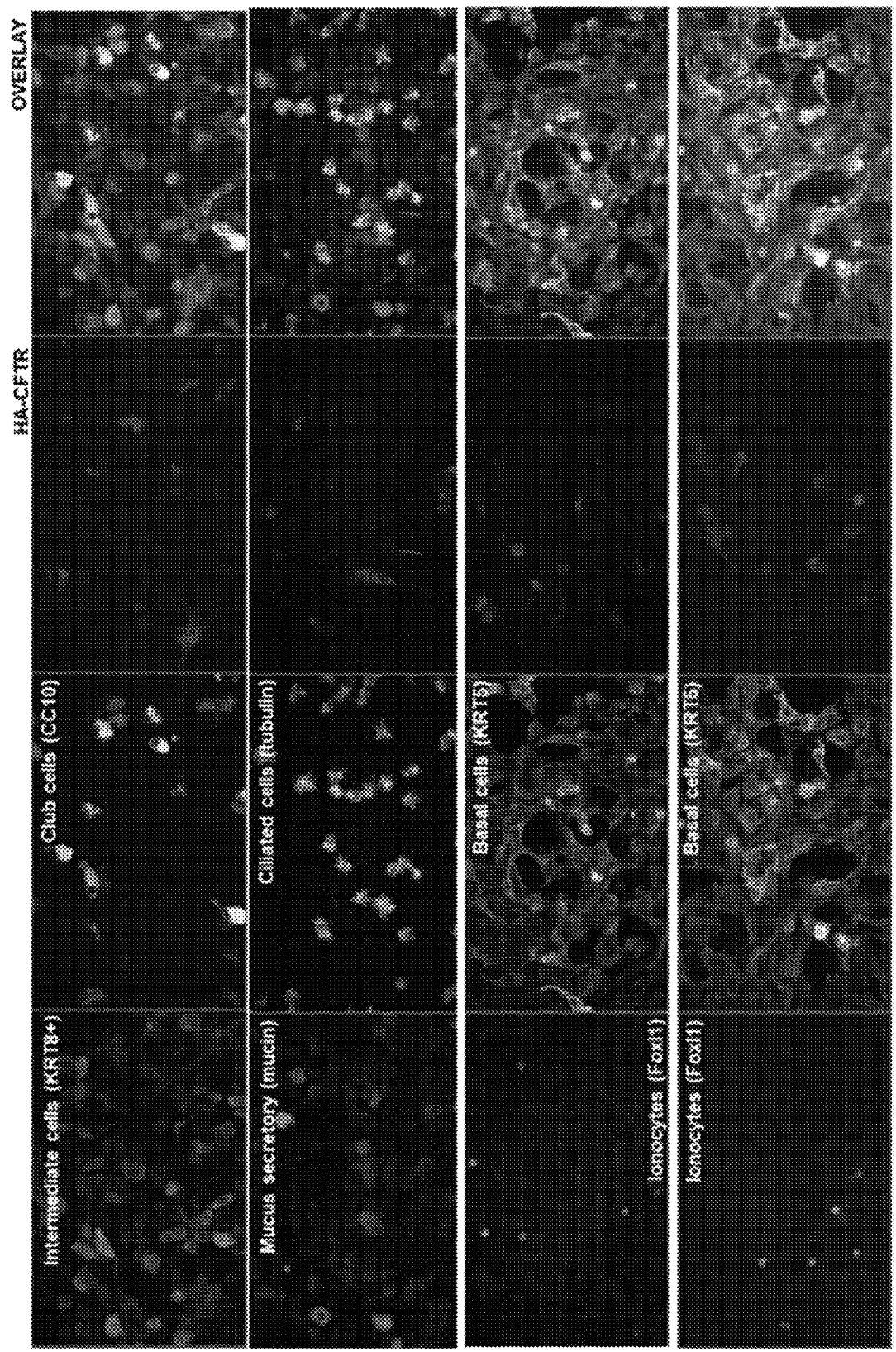
Figure 87B:
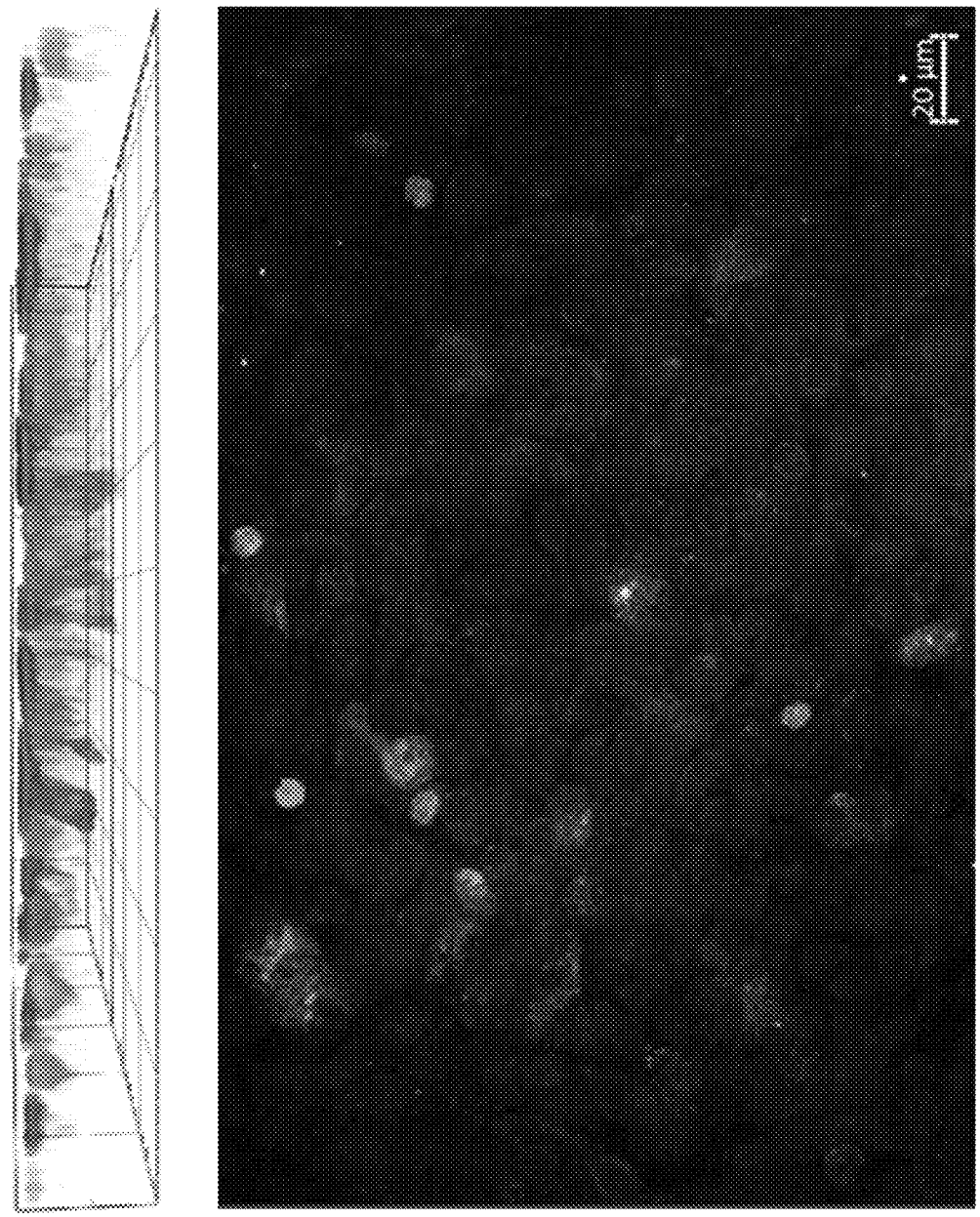

FIG. 87A shows expression and translocation of HA-CFTR post exposure to aerosolized Composition X in K710X/L$^{467}$ (ND13816) hBE cells. FIG. 87B shows merged image.

Figure 88:
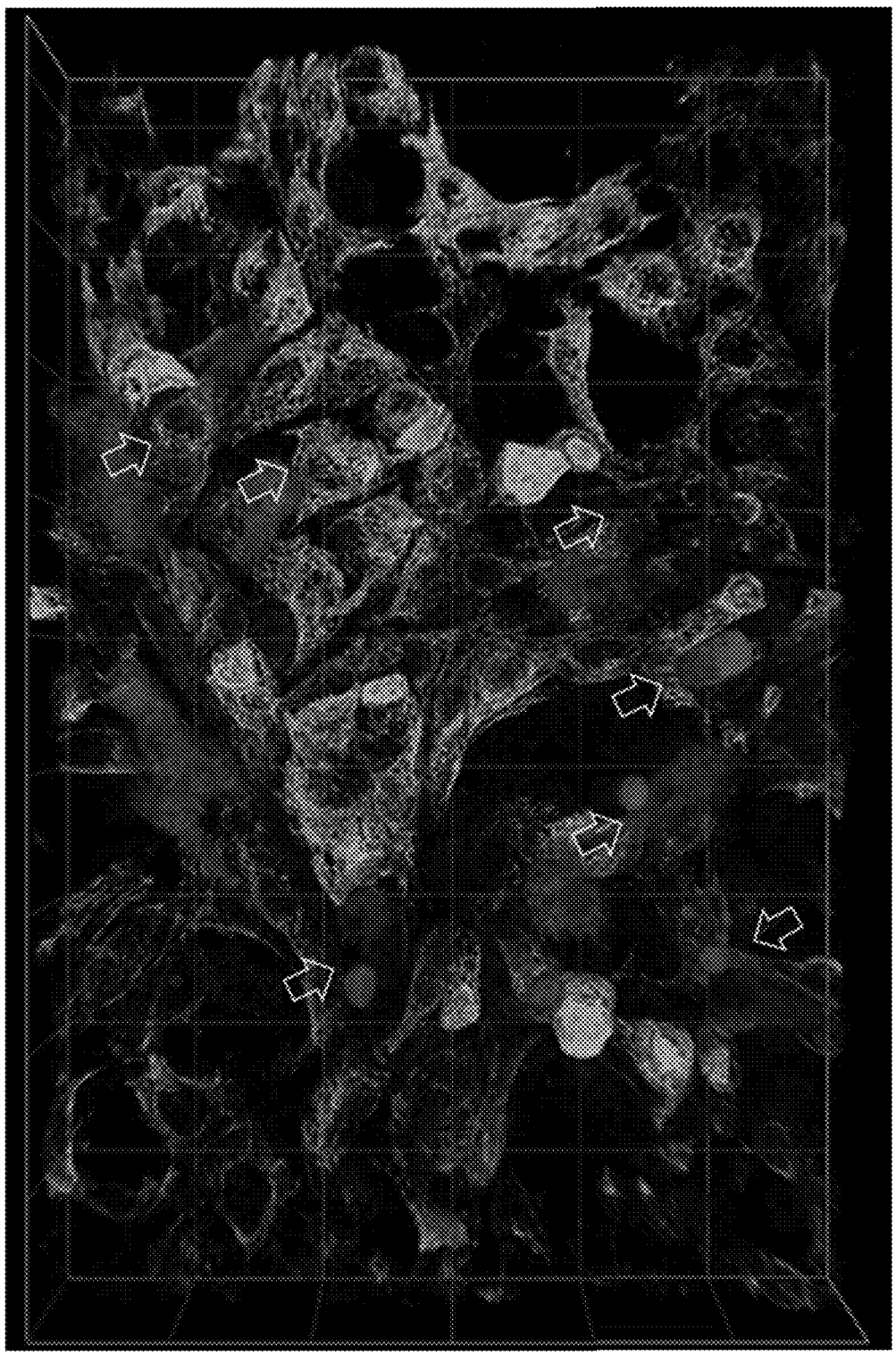

FIG. 88 shows translocation and granulation of HA-CFTR fibrosis post exposure to aerosolized Composition X in K710X/L$^{467}$ (ND13816) cells.

Figure 89:
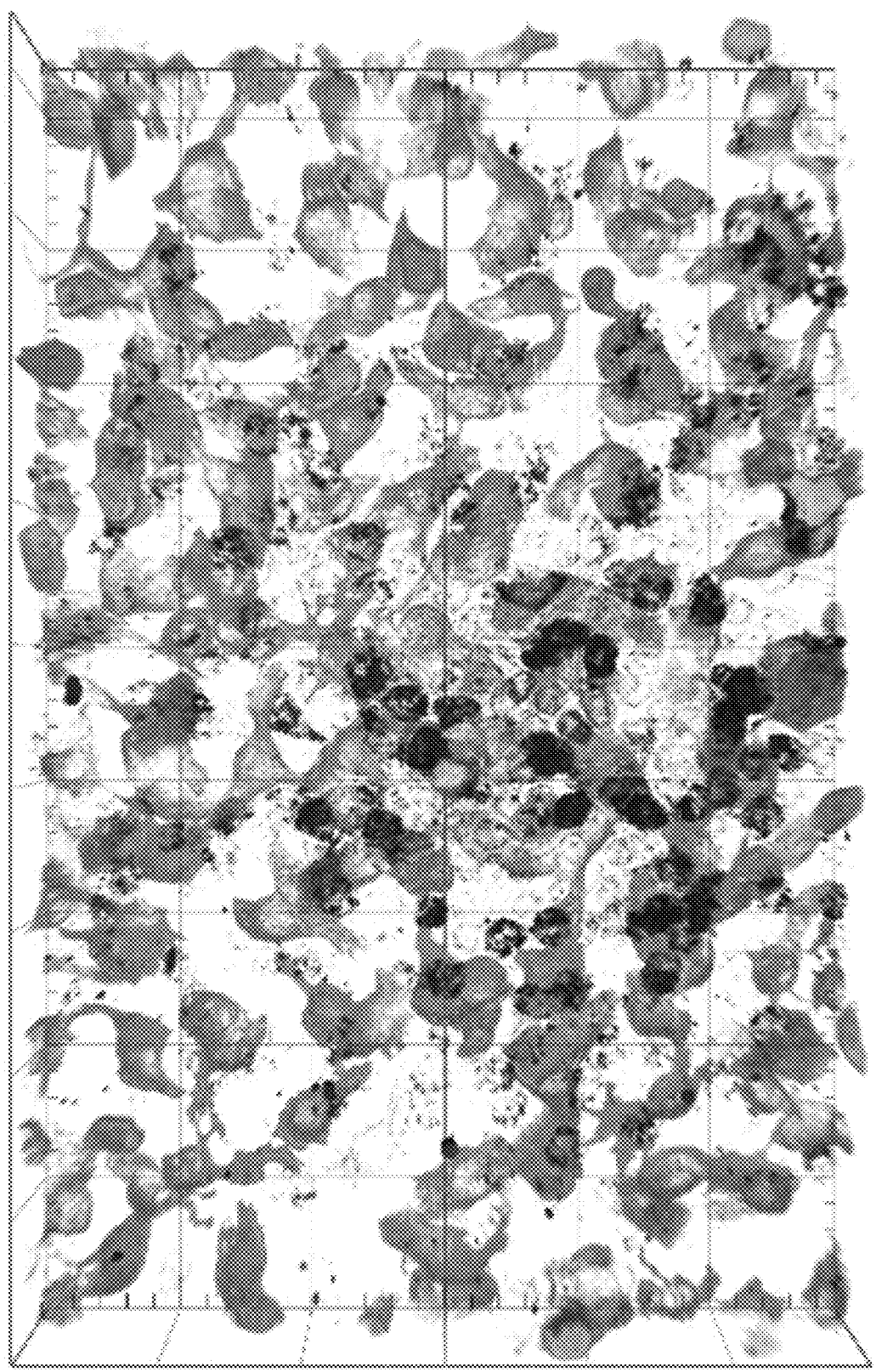

FIG. 89 shows expression and translocation of HA-CFTR post exposure to aerosolized Composition X in F508del/F508del hBE (donor TXCF042716) cells.

Figure 90:
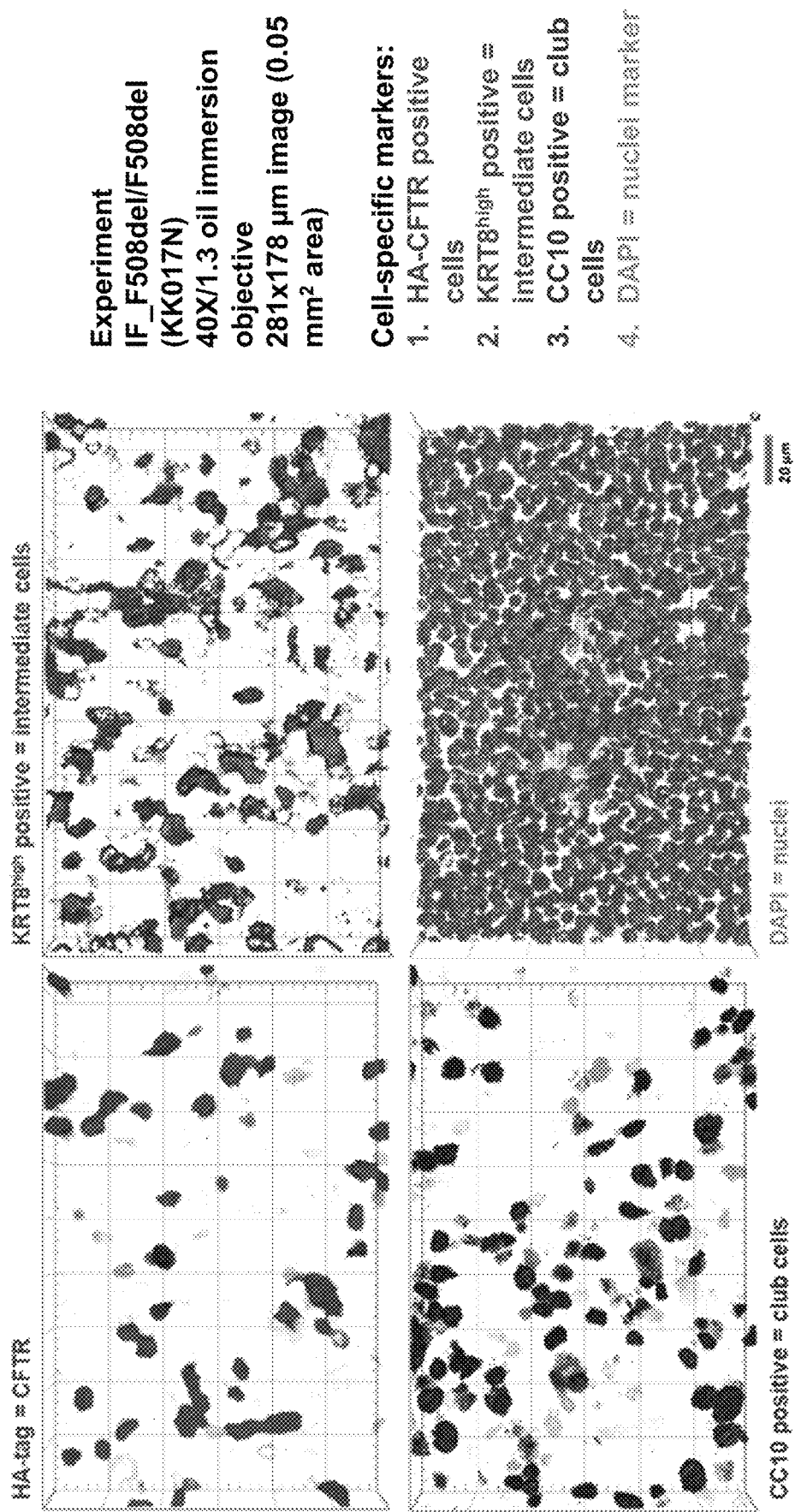

FIG. 90 shows immunofluorescence image of F508del/F508del hBE (KKD017K) dosed with Composition B/HA-CFTR.

Figure 91:
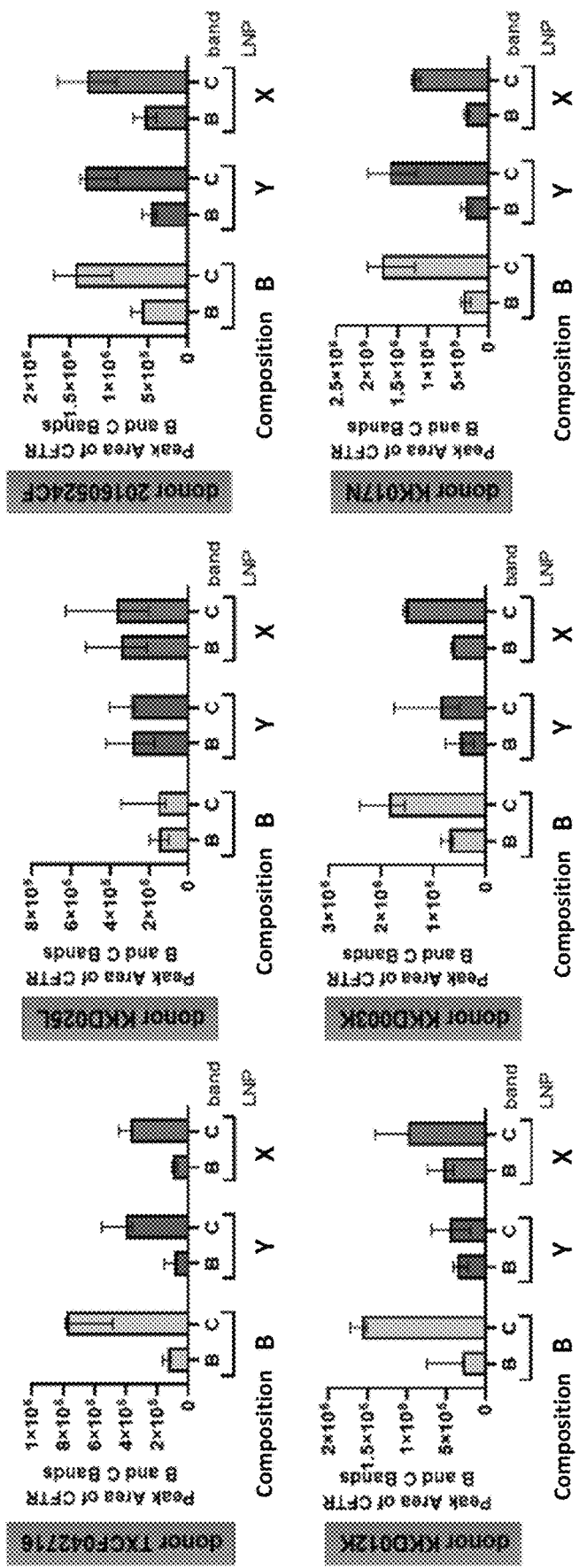

FIG. 91 shows expression level of HA-CFTR after dosing with composition B, Y or X in different F508del/F508del hBE donor cells.

Figure 92:
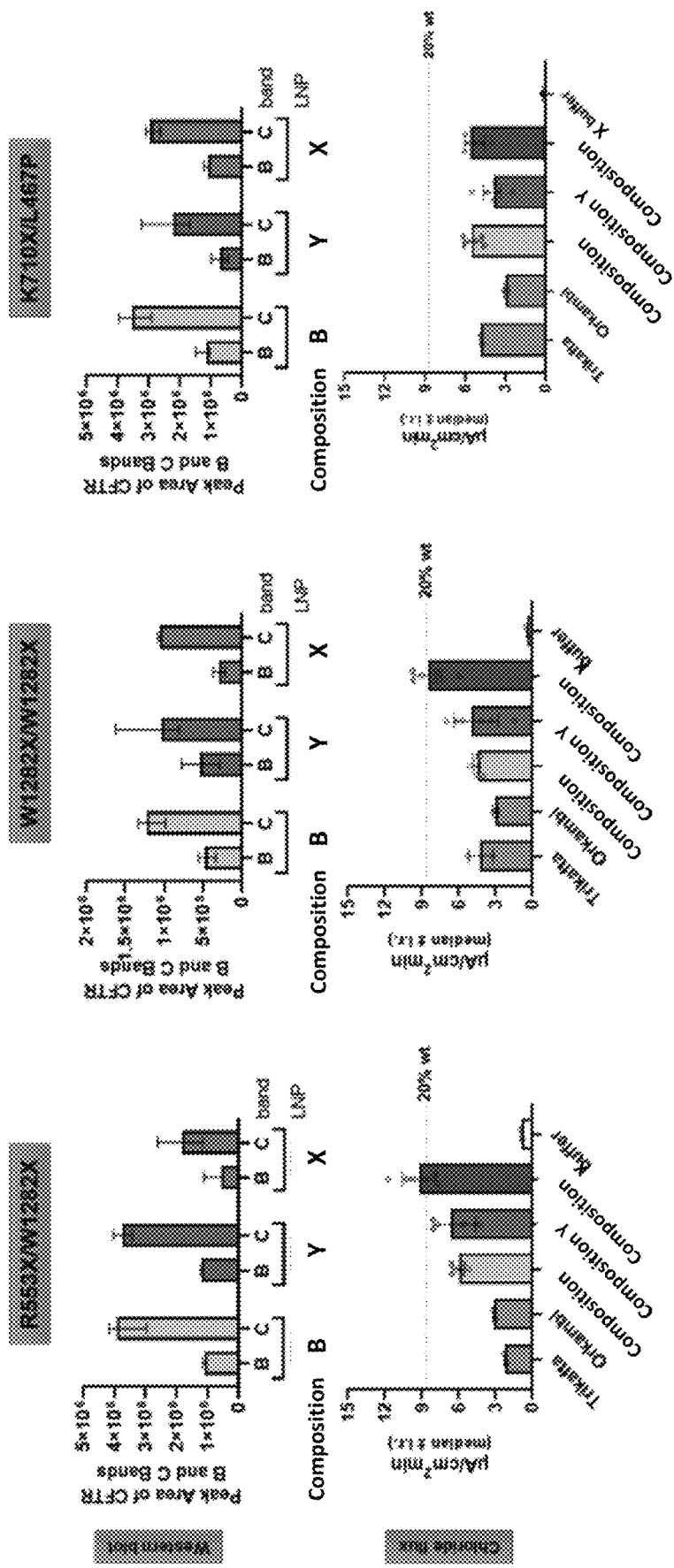

FIG. 92 shows expression level of HA-CFTR and chloride flux after dosing f508. with composition B,Y, or X in nonresponsive genotypes.

Figures 93A, 93B:
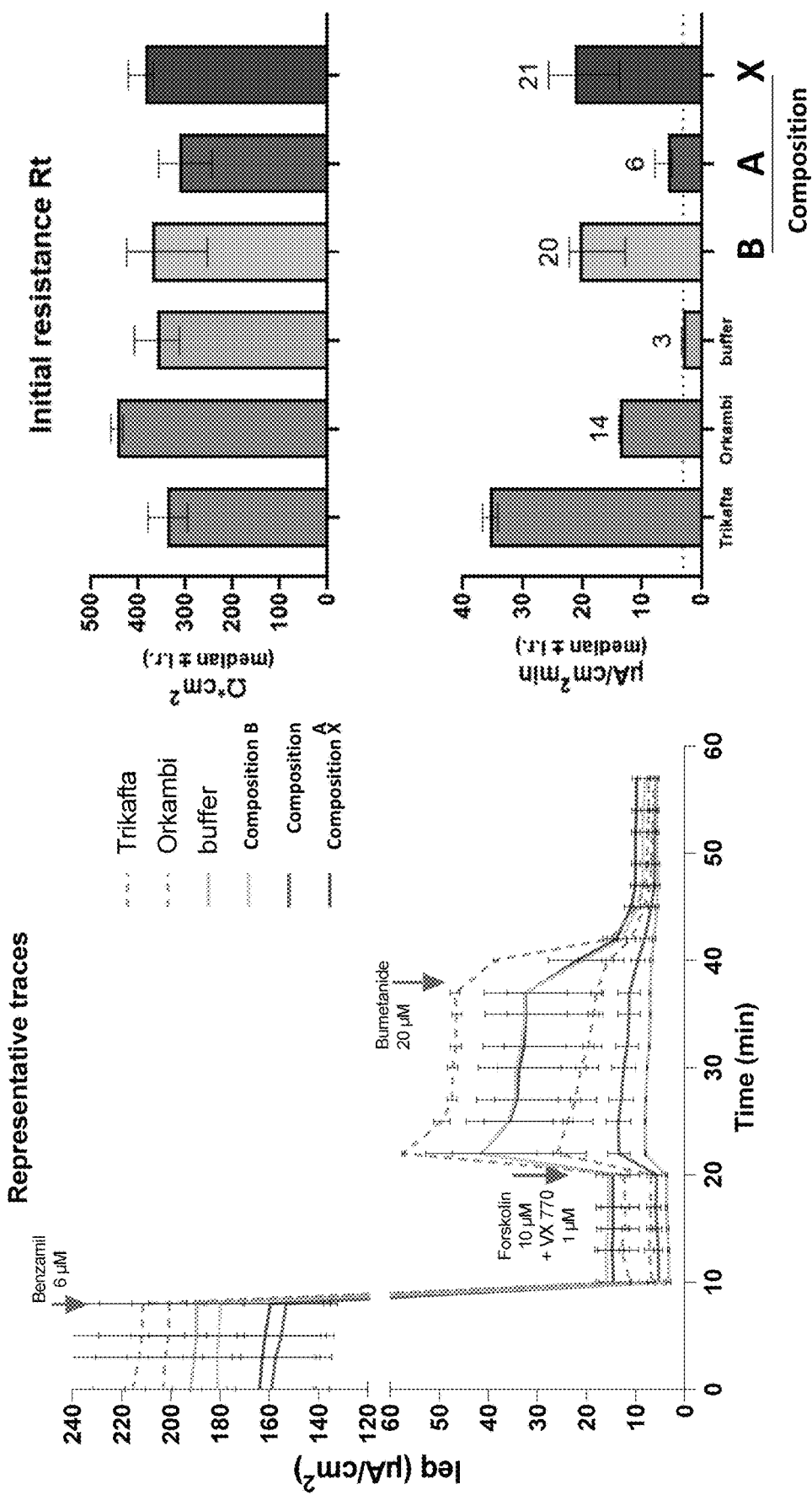

FIGS. 93A-93B show SORT LNP for the PCD program does not rescue CFTR function in F508del/F508del hBEs when delivered by aerosol. FIG. 93A shows representative traces of chloride flux. FIG. 93B shows shows measurement of transepithelial resistance (TEER) (top) and rescue of chloride flux (bottom).

Figure 94:
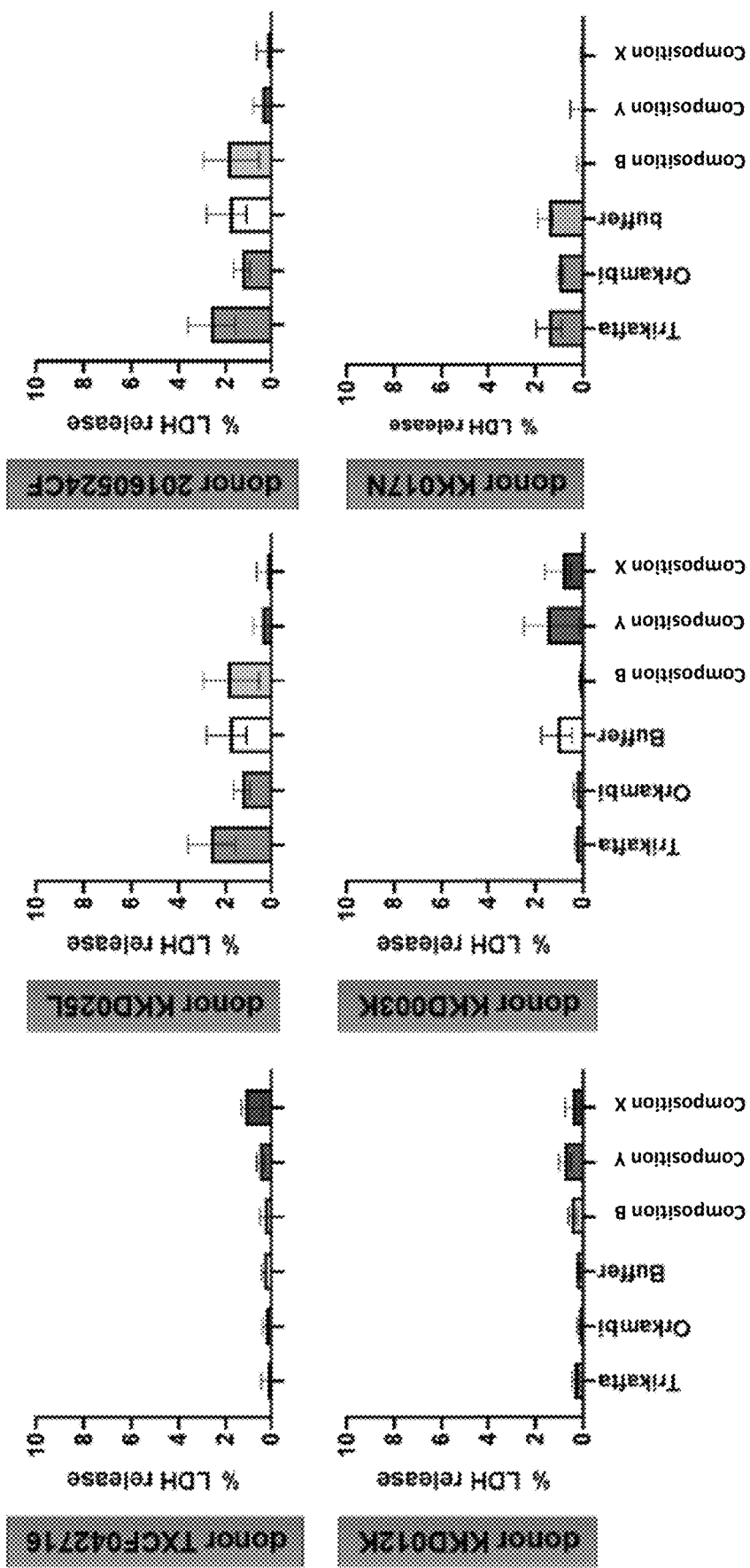

FIG. 94 shows measurement of LDH release to detect cytotoxicity from aerosolized formulations.

Figure 95:
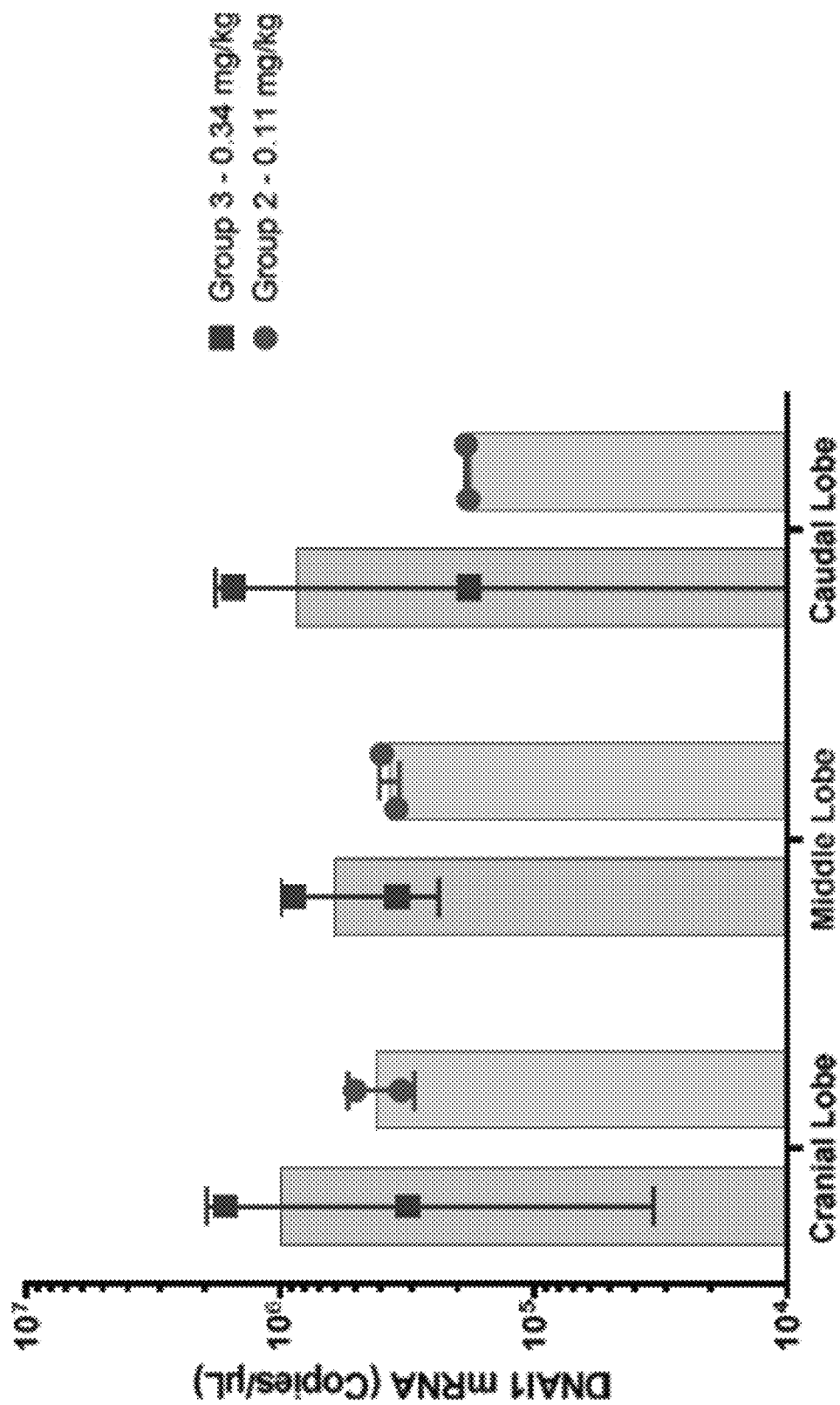

FIG. 95 is a graph illustrating levels of DNAI1-HA mRNA in different lung regions at 6 hour post-administration.

Figure 96:
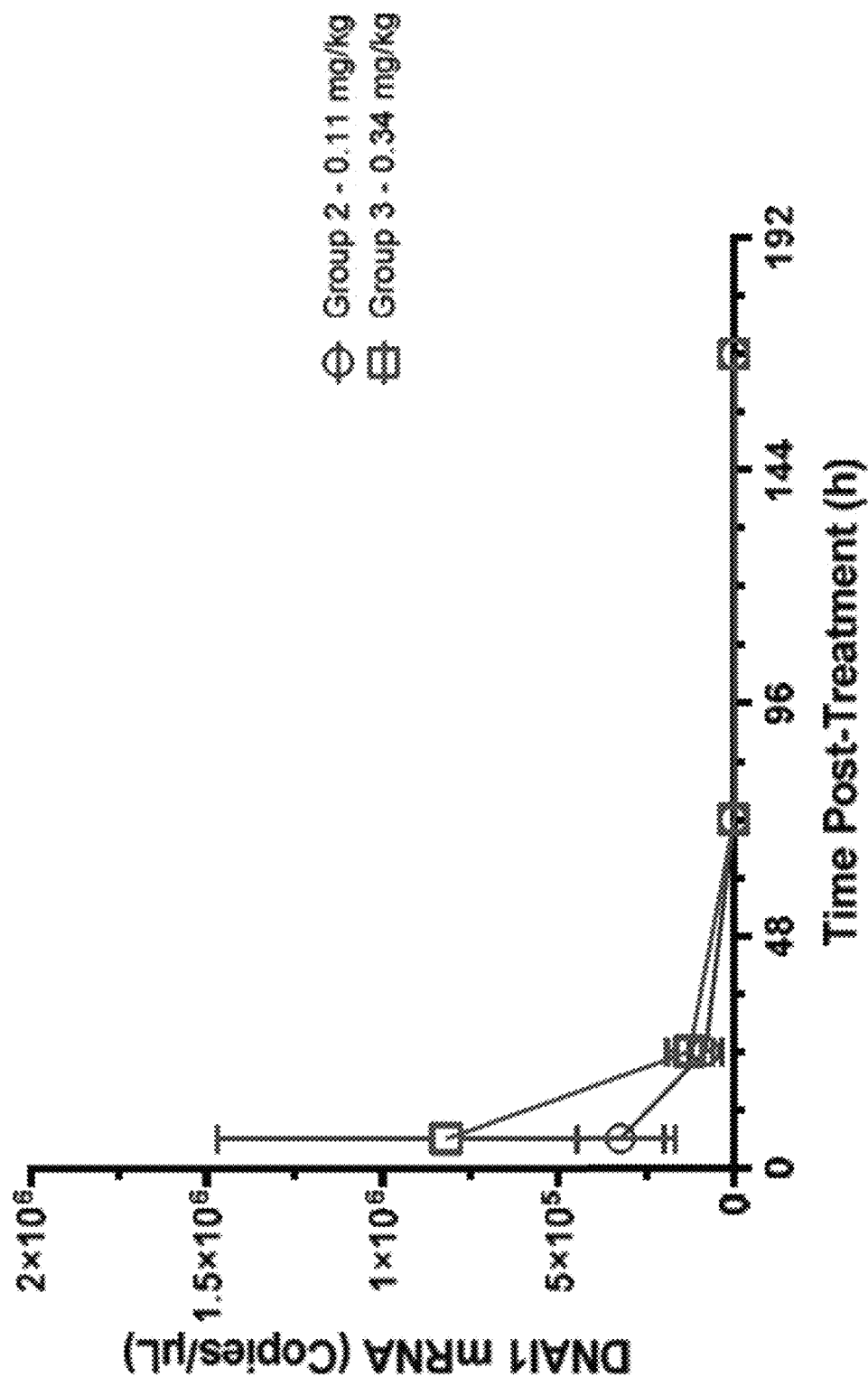

FIG. 96 is a graph illustrating time course of DNAI1-HA mRNA levels in lung tissue following Composition A-DNAI1-HA administration. Plotted is the mean±standard deviation of the values from the three sampled lung regions per animal. N=2 animals per group per time point.

Figure 97:
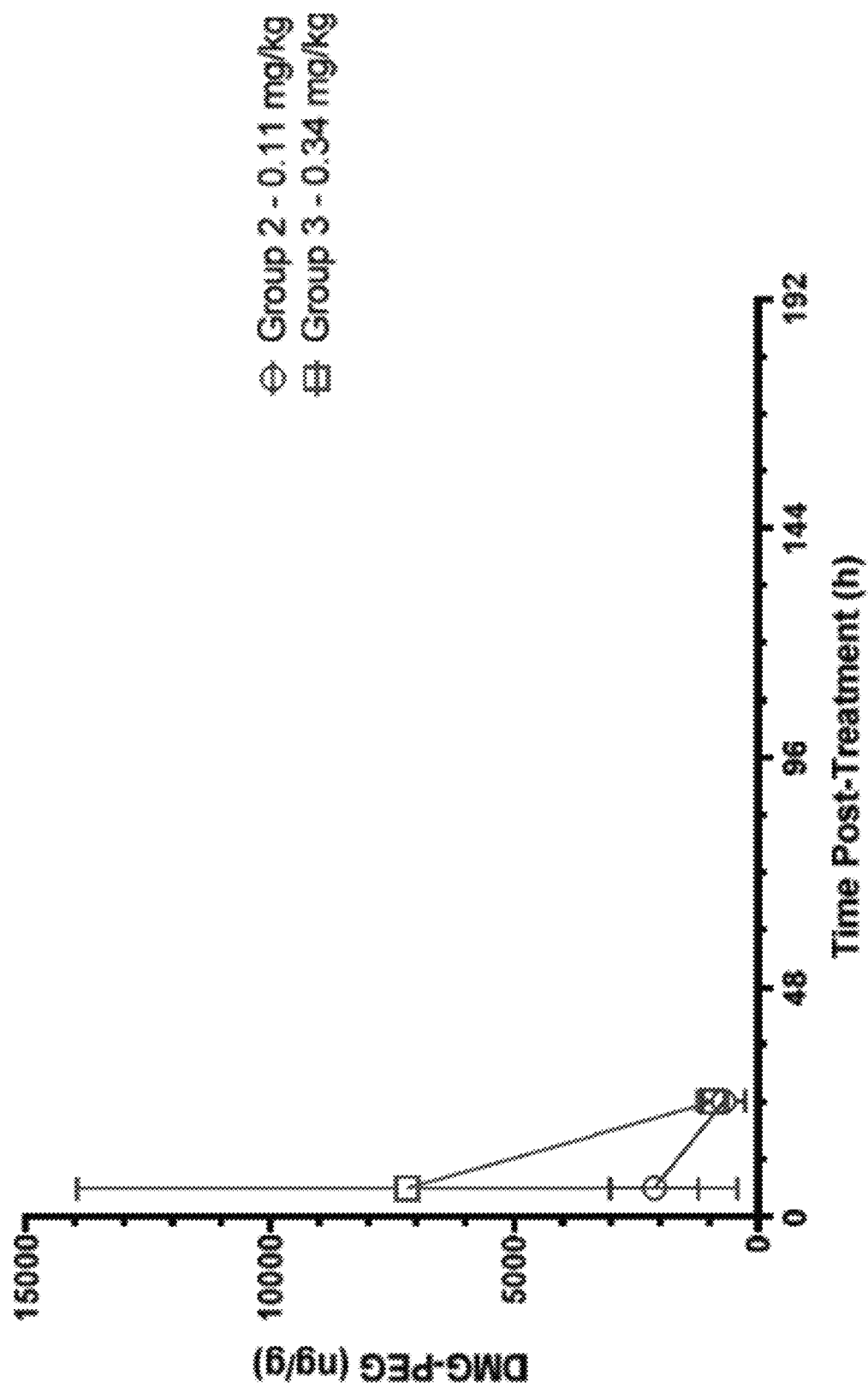

FIG. 97 is a graph illustrating time course of 4A3-SC7 lipid levels in lung tissue following Composition A-DNAI1-HA administration. Plotted is the mean±standard deviation of the values from the three sampled lung regions per animal. N=2 animals per group per time point.

Figure 98:
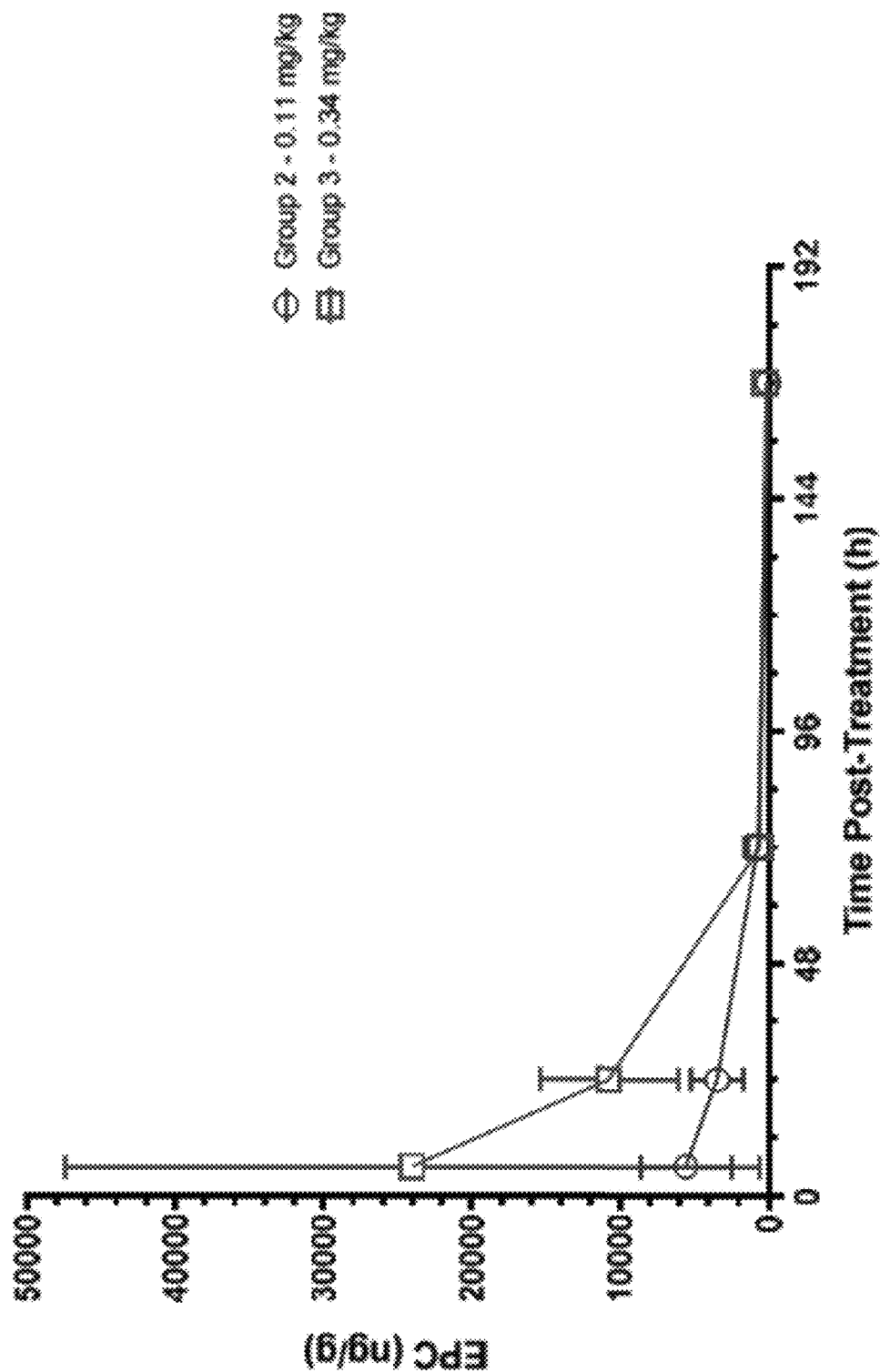

FIG. 98 is a graph illustrating time course of 14:0 EPC lipid levels in lung tissue following Composition A-DNAI1-HA administration. Plotted is the mean±standard deviation of the values from the three sampled lung regions per animal. N=2 animals per group per time point.

Figure 99:
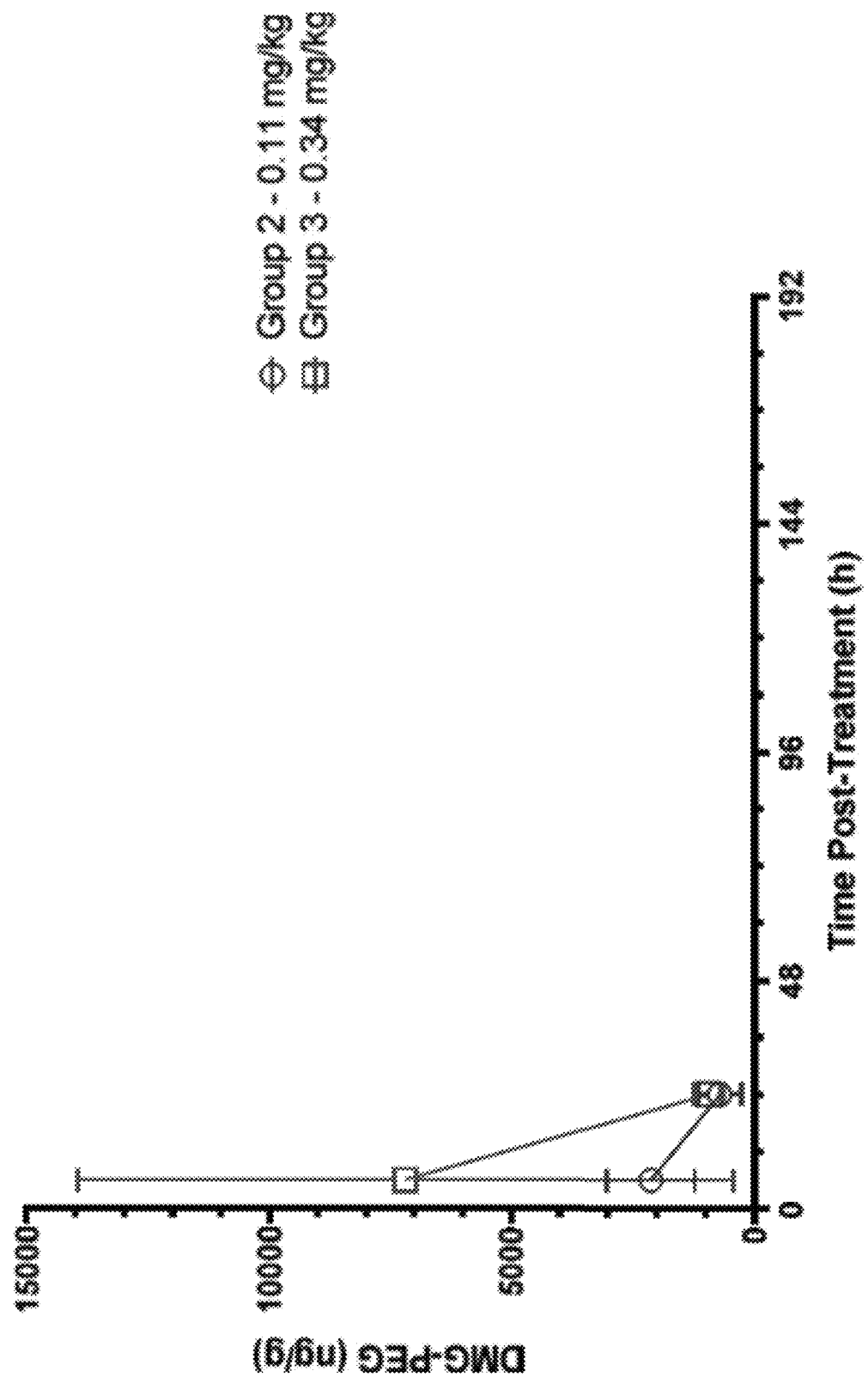

FIG. 99 is a graph illustrating time course of DMG-PEG lipid levels in lung tissue following Composition A-DNAI1-HA administration. Plotted is the mean±standard deviation of the values from the three sampled lung regions per animal. N=2 animals per group per time point.

Figure 100:
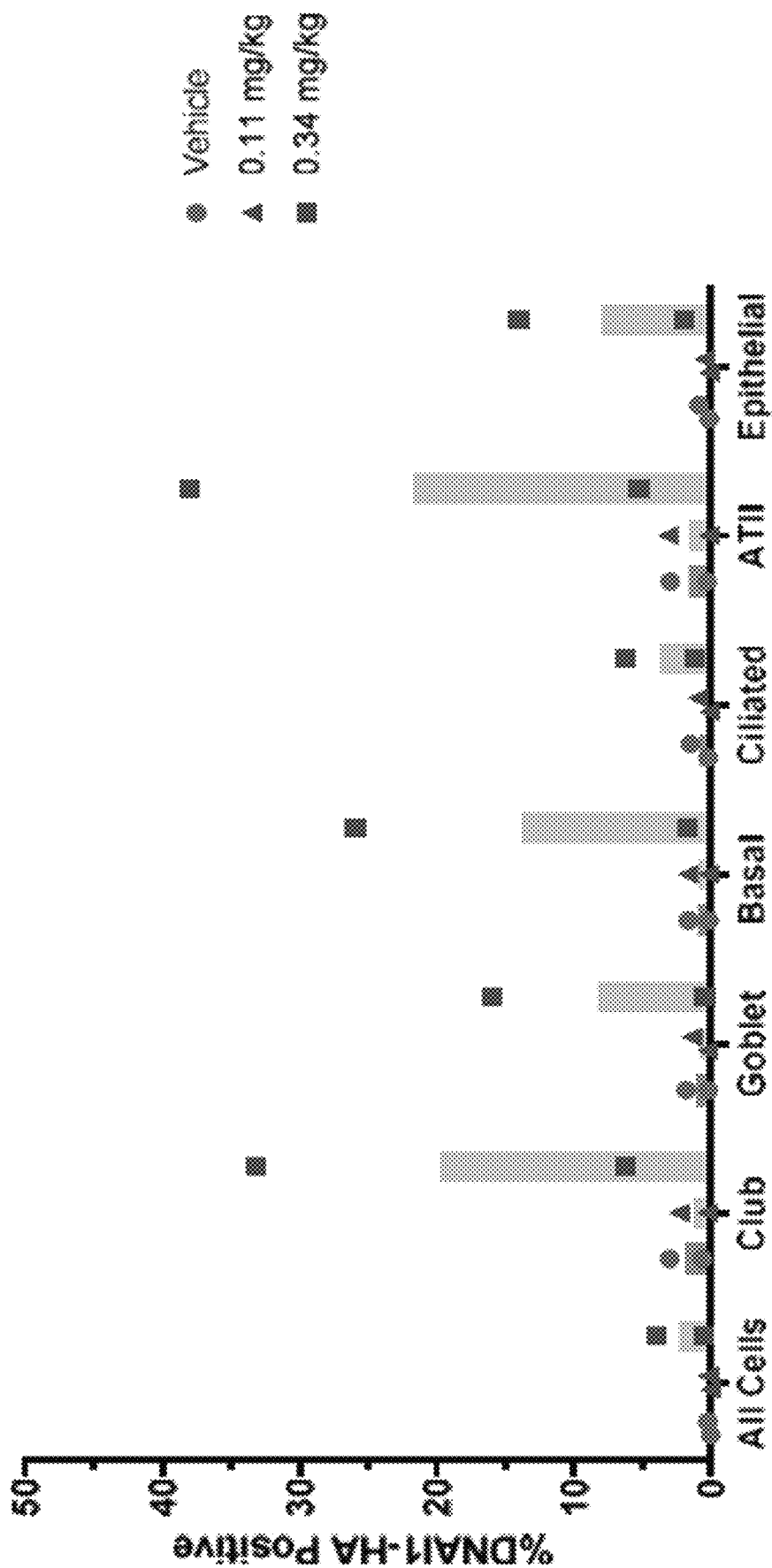

FIG. 100 is a graph illustrating analysis of cell-specific expression of DNAI1-HA protein in lung at 6 hour post-administration by multiplex immunofluorescence. The % DNAI1-HA+ population for each cell type was calculated by combining the cell counts from all four examined lung sections per animal. The total number of cells counted per animal ranged from 225,419 to 319,654. The following markers were used to stain specific airway cell types: Club (SCGB1A1/Uteroglobin), goblet (MUC5B), Basal (cytokeratin 5), ciliated (acetylated tubulin), alveolar type II (ATII) (prosurfactant protein C), epithelial (EpCAM), and DNAI1-HA (HA epitope tag).

Figure 101:
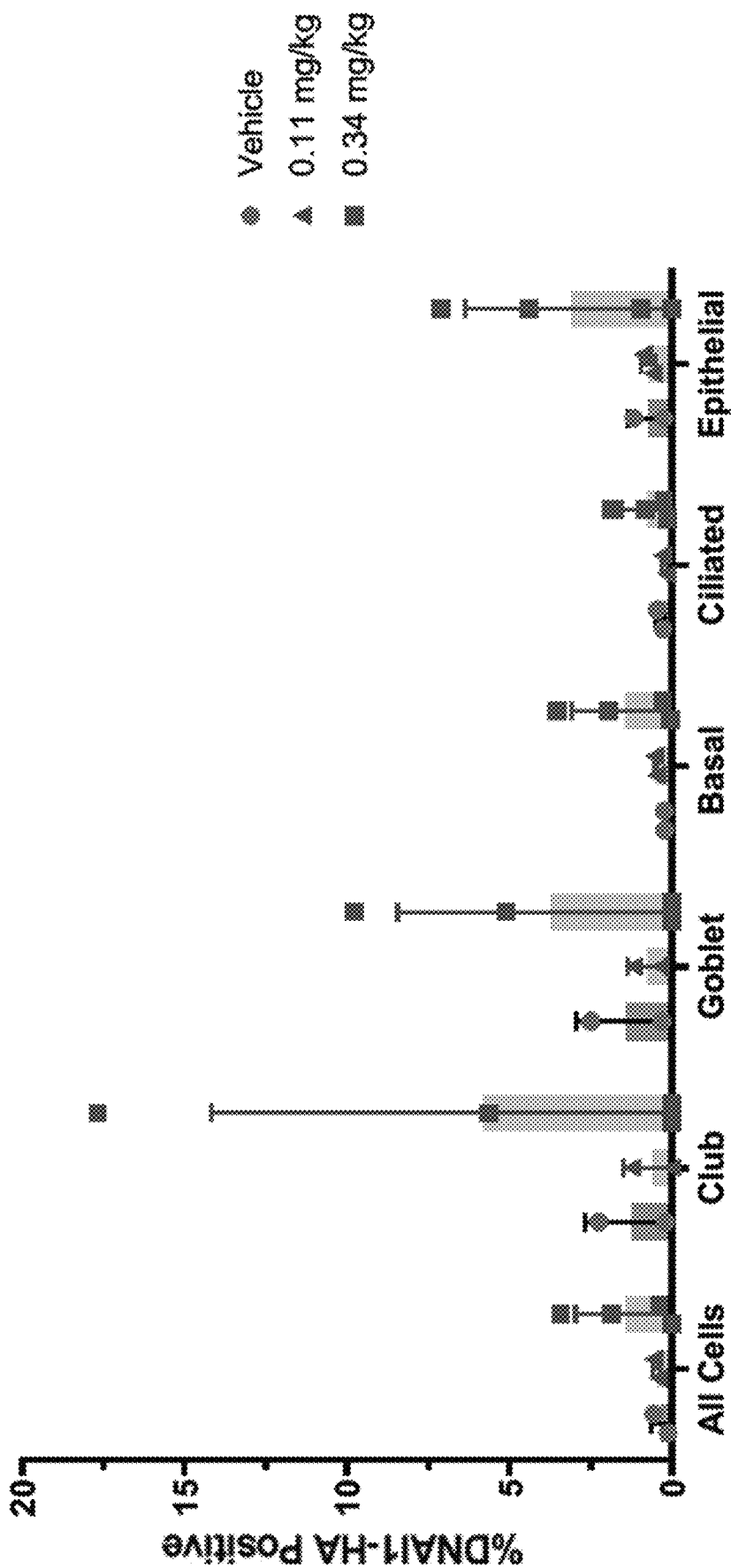

FIG. 101 is a graph illustrating analysis of cell-specific expression of DNAI1-HA protein in lung at 6 hour post-administration by multiplex immunofluorescence. Two trachea sections, proximal and carina, were collected from each animal. For Group 1 (Vehicle) and Group 2 (Low Dose), the carina trachea section from each animal was analyzed. For Group 3 (High Dose), both trachea sections were analyzed. The % DNAI1-HA+ population for each cell type was calculated for each trachea section examined. The total number of cells counted per section ranged from 5,604 to 25,436. Shown are the individual data points for each treated animal and the mean±standard deviation for each group (Groups 1,2 N=2; Group 3 N=4). The following markers were used to stain specific airway cell types: Club (SCGB1A1/Uteroglobin), goblet (MUC5B), basal (cytokeratin 5), ciliated (acetylated tubulin), epithelial (EpCAM), and DNAI1-HA (HA epitope tag).

Figure 102:
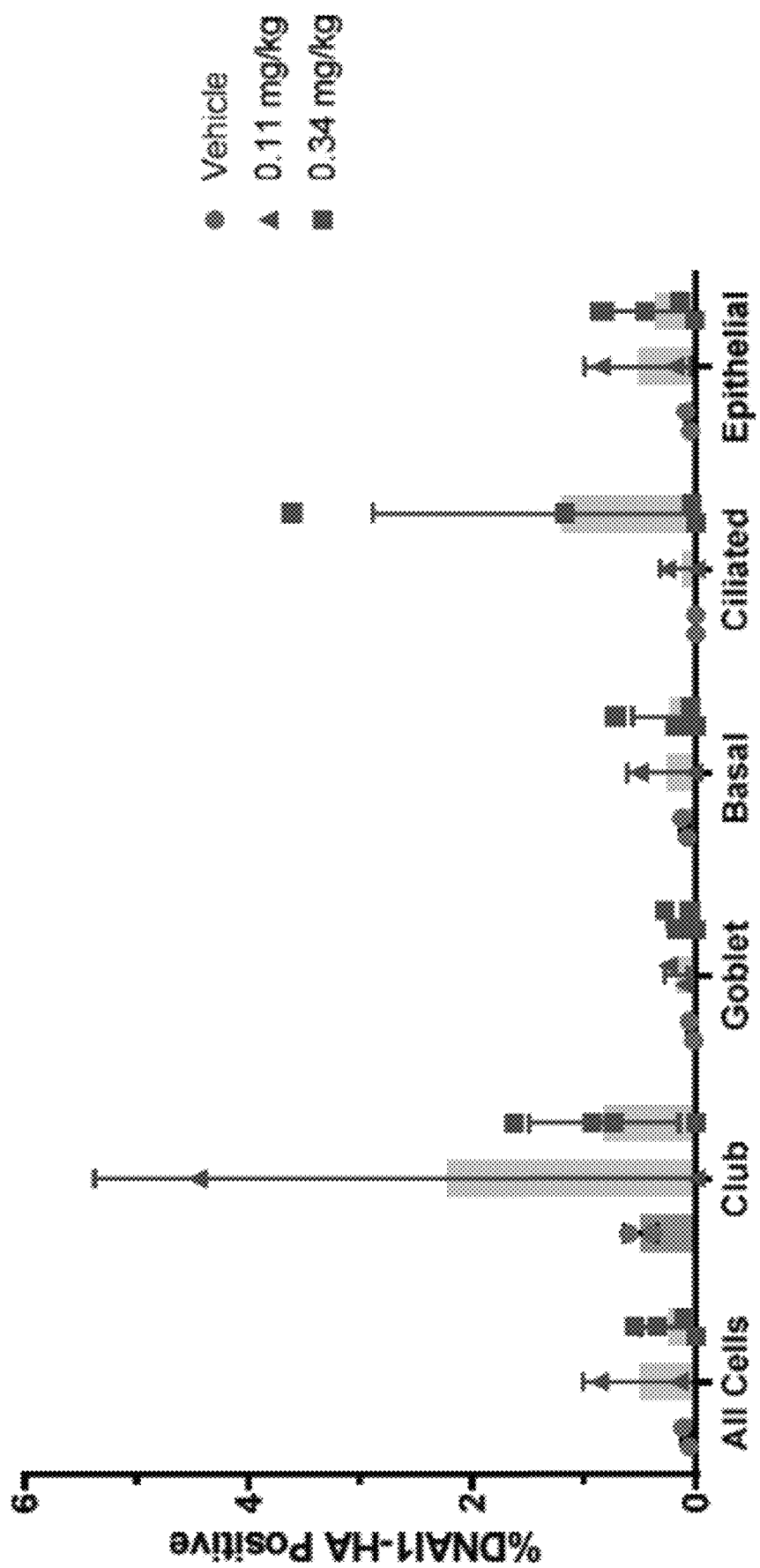

FIG. 102 is a graph illustrating analysis of cell-specific expression of DNAI1-HA protein in nasopharynx and oropharynx at 6 hour post-administration by multiplex immunofluorescence. Two nasopharynx or oropharynx sections were collected from each animal. For Group 1 (Vehicle) and Group 2 (Low Dose), one section from each animal was analyzed. For Group 3 (High Dose), both sections were analyzed. The % DNAI1-HA+ population for each cell type was calculated for each section examined. The total number of cells counted per section ranged from 58,993 to 145,142. Shown are the individual data points for each treated animal and the mean±standard deviation for each group (Groups 1,2 N=2; Group 3 N=4). The following markers were used to stain specific airway cell types: Club (SCGB1A1/Uteroglobin), goblet (MUC5B), basal (cytokeratin 5), ciliated (acetylated tubulin), epithelial (EpCAM), and DNAI1-HA (HA epitope tag).

Figure 103A:
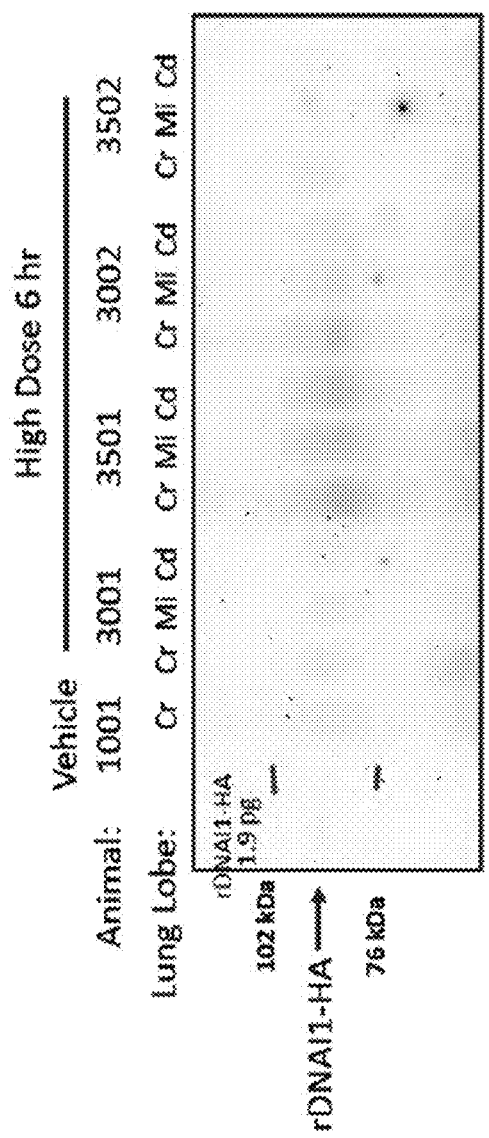

FIG. 103A is a Western blot analysis of lung sample from high dose (0.34 mg/kg, group 3) at 6 hr post-exposure. For each, 50 g total lung lysate protein was separated on an SDS-PAGE gel, transferred to nitrocellulose membranes, and probed for DNAI1-HA expression using a rabbit anti-HA-HRP monoclonal antibody conjugate. Lung samples were taken from the right caudal (Cd), cranial (Cr), and middle (Mi) lobes. As a positive control 1.9 µg recombinant human DNAI1-HA was included on each gel. Location of the DNAI1-HA band is indicated by the arrow.

Figure 103B:
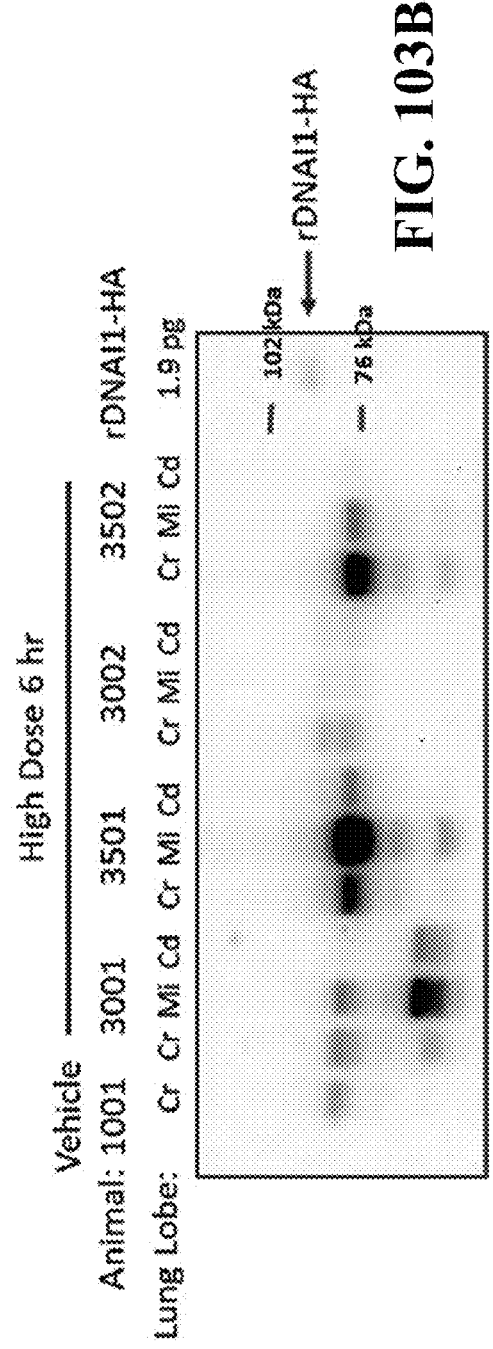

FIG. 103B is a Western blot analysis of lung sample from high dose (0.34 mg/kg, group 3) at 6 hr post-exposure. For each, 50 g total lung lysate protein was separated on an SDS-PAGE gel, transferred to nitrocellulose membranes, and probed for total endogenous monkey DNAI1 using a rabbit anti-DNAI1 polyclonal antibody. Lung samples were taken from the right caudal (Cd), cranial (Cr), and middle (Mi) lobes. As a positive control 1.9 µg recombinant human DNAI1-HA was included on each gel. Location of the DNAI1-HA band is indicated by the arrow.

Figure 104:
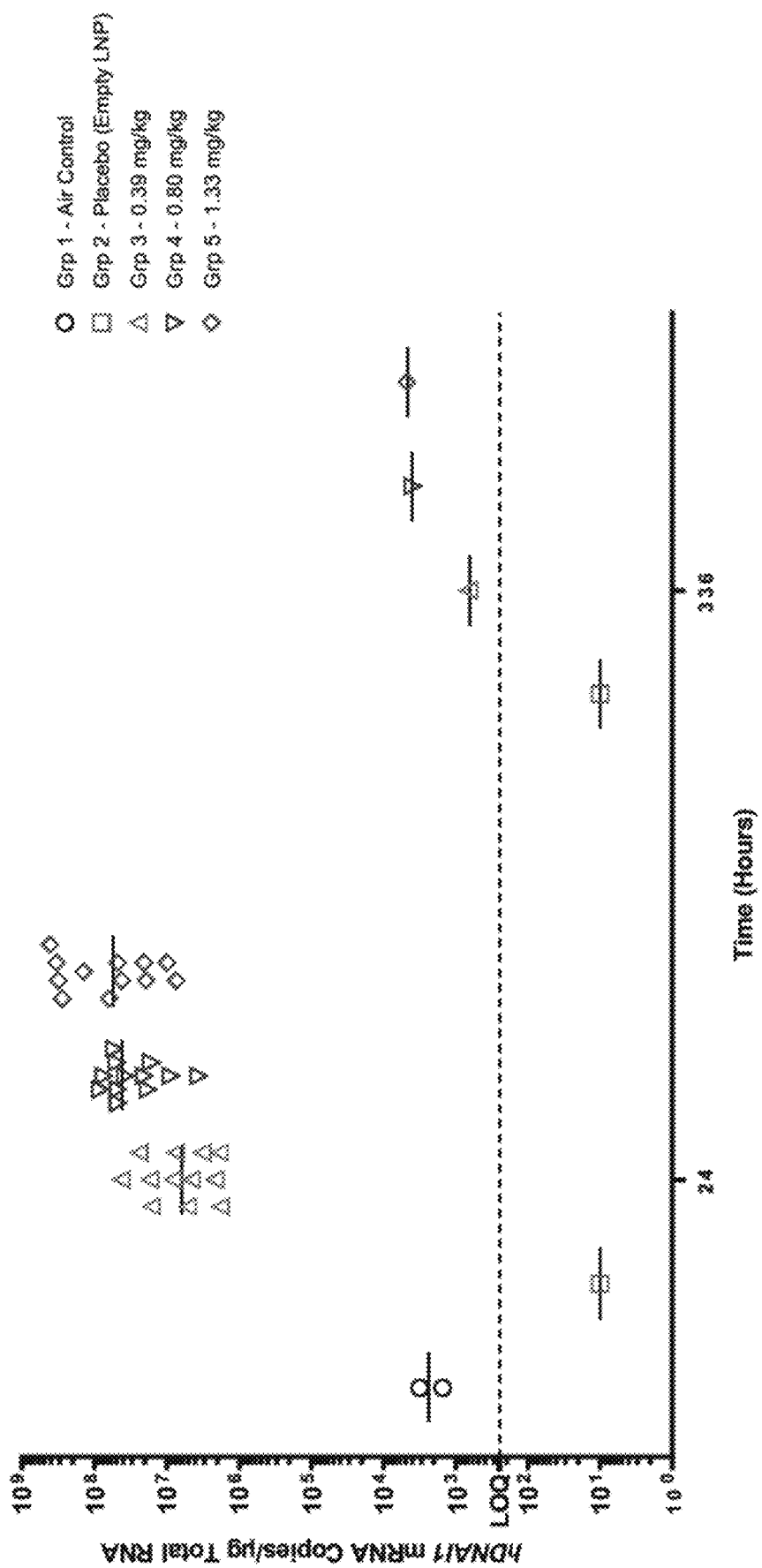

FIG. 104 is a graph illustrating hDNAI1 mRNA level in lung tissue at 24 hr and 336 hr following Composition A-DNAI1 administration. Plotted are the individual values for each sample with levels above the assay LOQ (limit of quantitation). Two samples were tested per animal from six animals per treatment group (N=12). Solid lines indicate median values for each group. Dotted line indicates assay LOQ of 250 copies/µg total RNA. If no samples within a particular group were above the assay LOQ, a single point at 10 copies/µg total RNA is shown on the graph.

Figure 105:
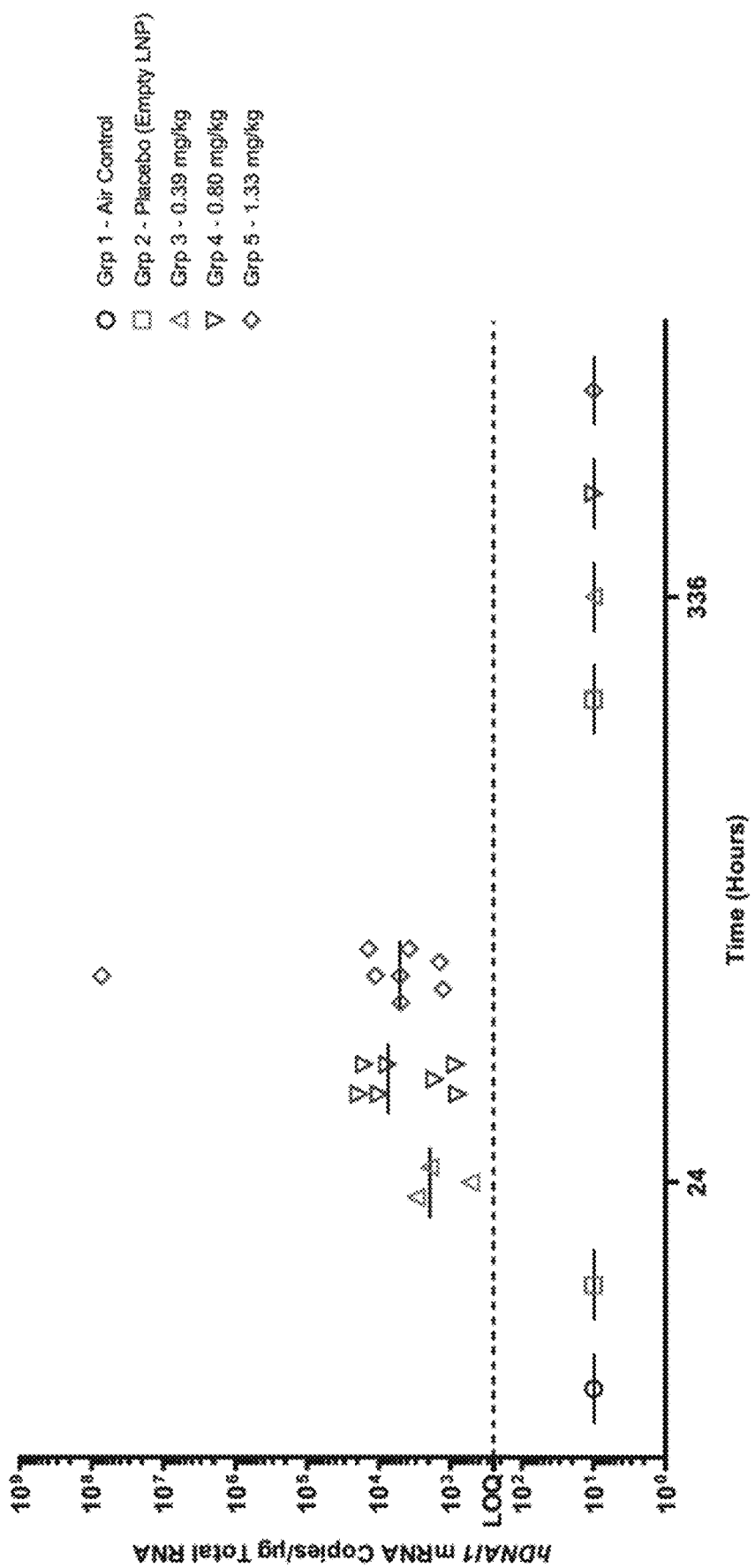

FIG. 105 is a graph illustrating hDNAI1 mRNA level in liver tissue at 24 hr and 336 hr following Composition A-DNAI1 administration. Plotted are the individual values for each sample with levels above the assay LOQ (limit of quantitation). Two samples were tested per animal from six animals per treatment group (N=12). Solid lines indicate median values for each group. Dotted line indicates assay LOQ of 250 copies/µg total RNA. If no samples within a particular group were above the assay LOQ, a single point at 10 copies/µg total RNA is shown on the graph.

Figure 106:
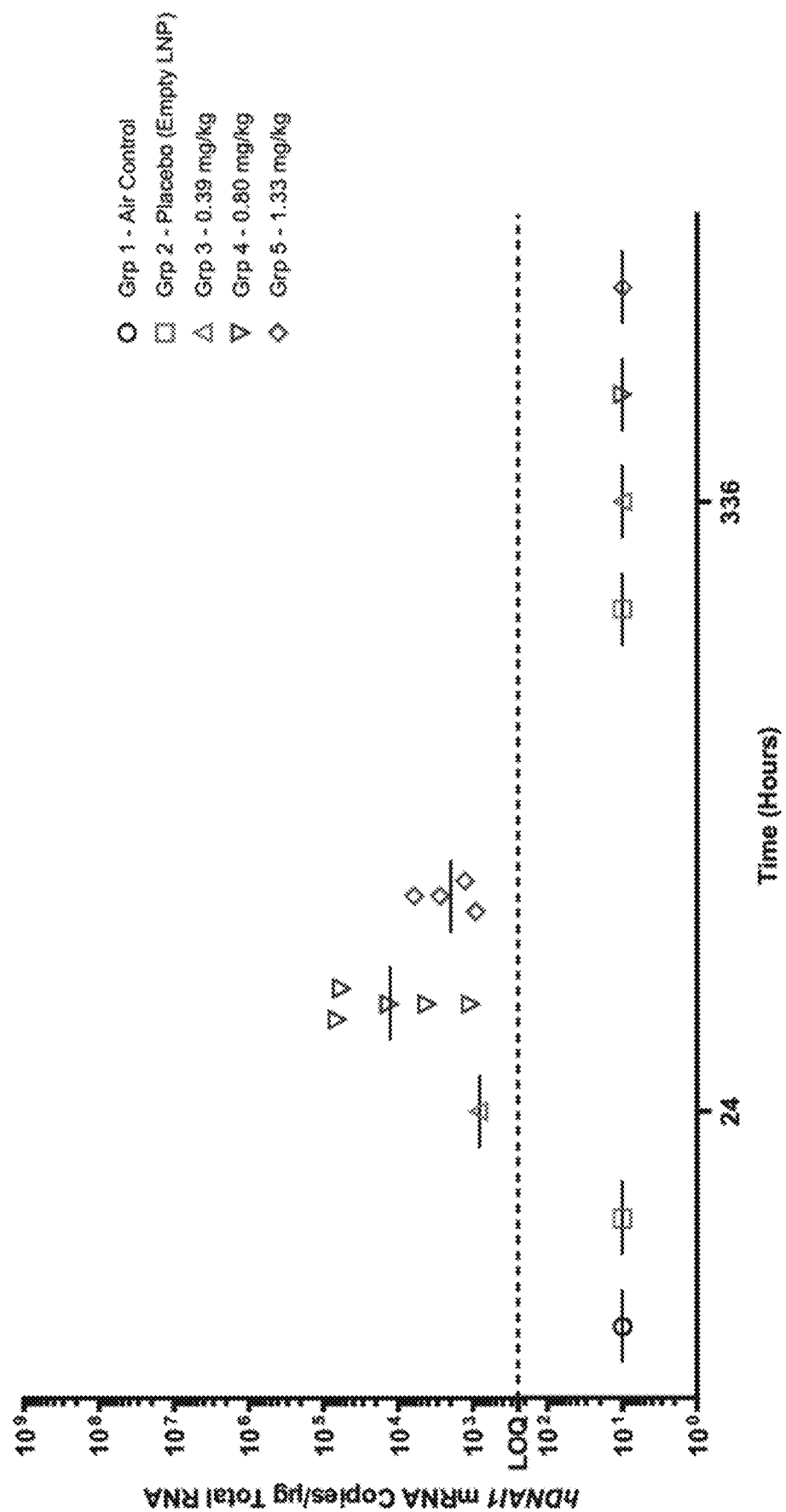

FIG. 106 is a graph illustrating hDNAI1 mRNA level in spleen tissue at 24 hr and 336 hr following Composition A-DNAI1 administration. Plotted are the individual values for each sample with levels above the assay LOQ (limit of quantitation). One sample was tested per animal from six animals per treatment group (N-12). Solid lines indicate median values for each group. Dotted line indicates assay LOQ of 250 copies/µg total RNA. If no samples within a particular group were above the assay LOQ, a single point at 10 copies/µg total RNA is shown on the graph.

Figure 107:
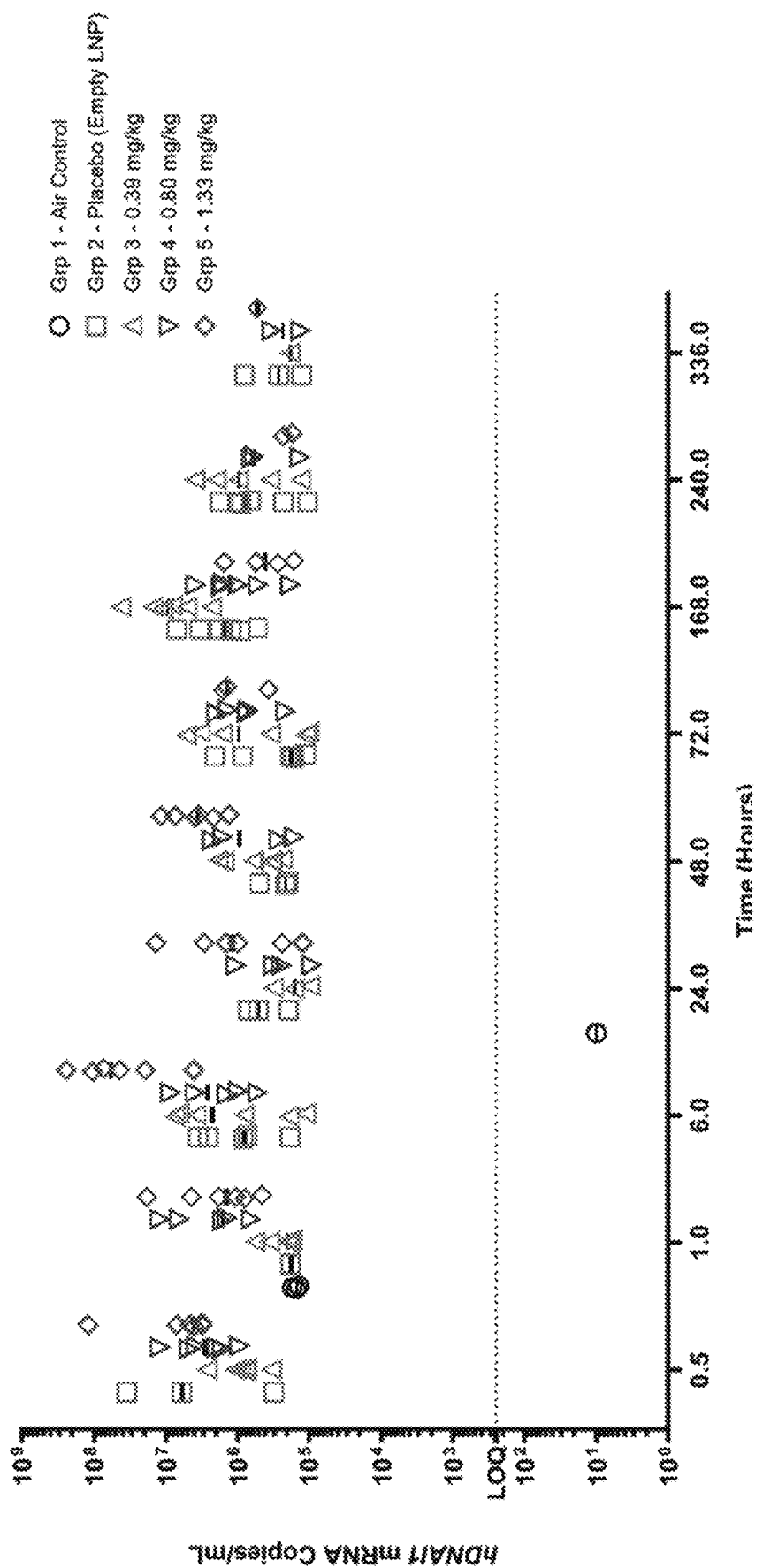

FIG. 107 is a graph illustrating hDNAI1 mRNA level in whole blood at 24 hr and 336 hr following Composition A-DNAI1 administration. Plotted are the individual values for each sample with levels above the assay LOQ. Samples were collected from six animals per treatment group per time point (3 male/3 female; N=6). Solid lines indicate median values for each group. Dotted line indicates assay LOQ of 250 copies/mL. If no samples within a particular group were above the assay LOQ, a single point at 10 copies/mL is shown on the graph.

Figure 108:
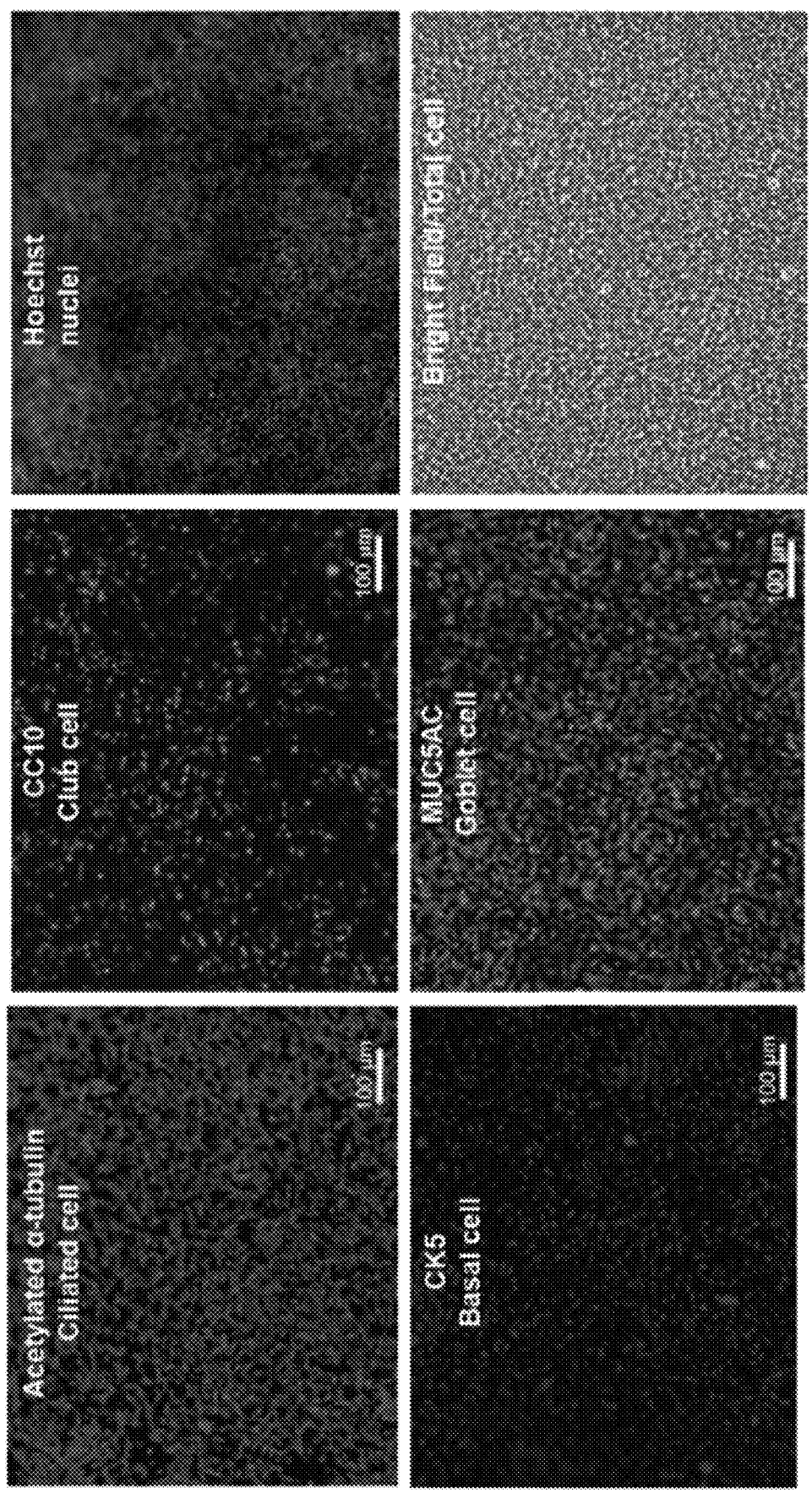

FIG. 108 is immunofluorescence images of well-differentiated wildtype-hBE cultures. Well-differentiated WT-hBE cultures (35 days post ALI) were stained with cell-type specific antibodies for ciliated cells (Acetylated α-tubulin, AT), club cells (club cell 10-kDa protein, CC10 or SCGB1A1), goblet cells (mucin 5AC, MUC5AC), and basal cells (cytokeratin 5 or CK5). Cell nuclei were stained using Hoechst. Each image is a collection of 9 contiguous fields of view (FoV) stitched together. Each FoVs was collected at 40× magnification.

Figure 109:
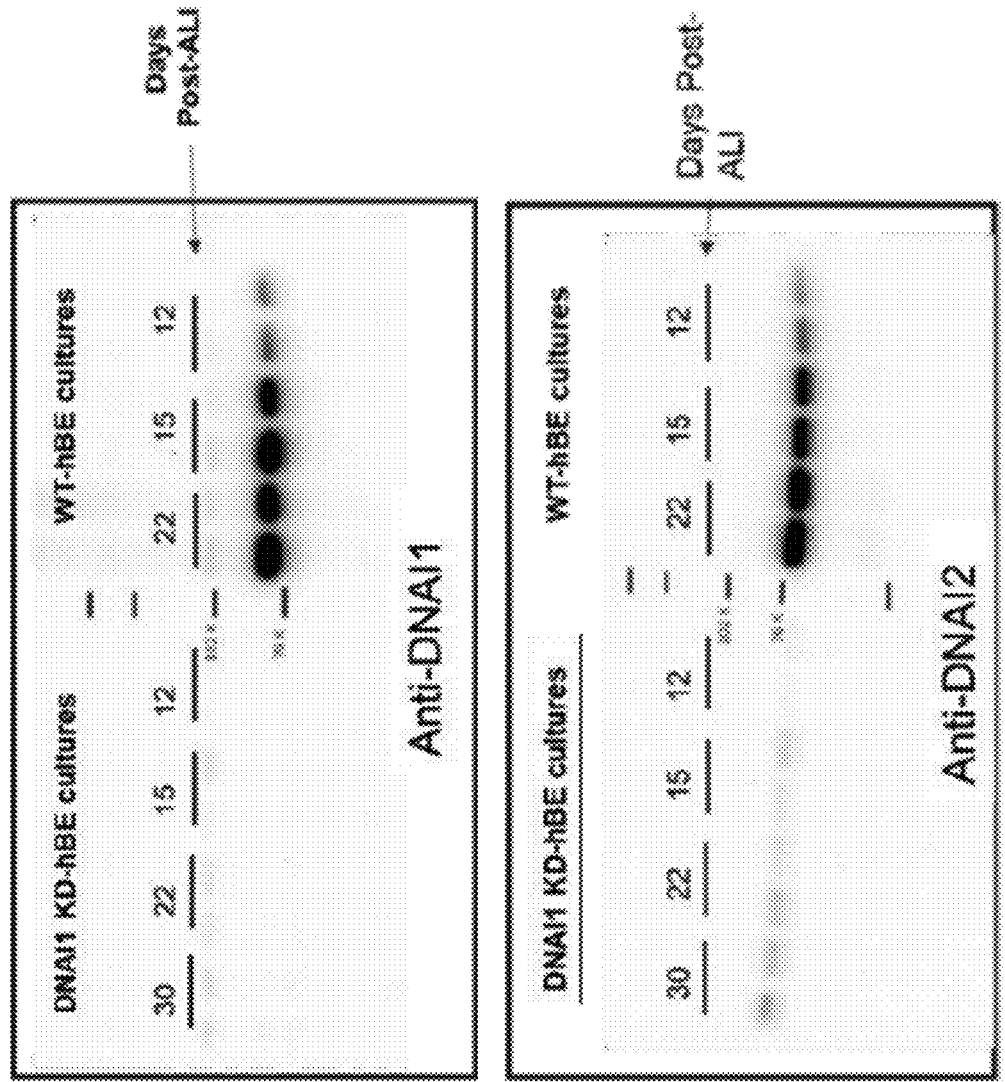

FIG. 109 is Western blot analyses showing DNAI1 (top) and DNAI2 (bottom) levels in WT-hBE and DNAI1-KD hBE cultures 12-, 15-, and 22-days post-ALI (air-liquid interface).

Figure 110:
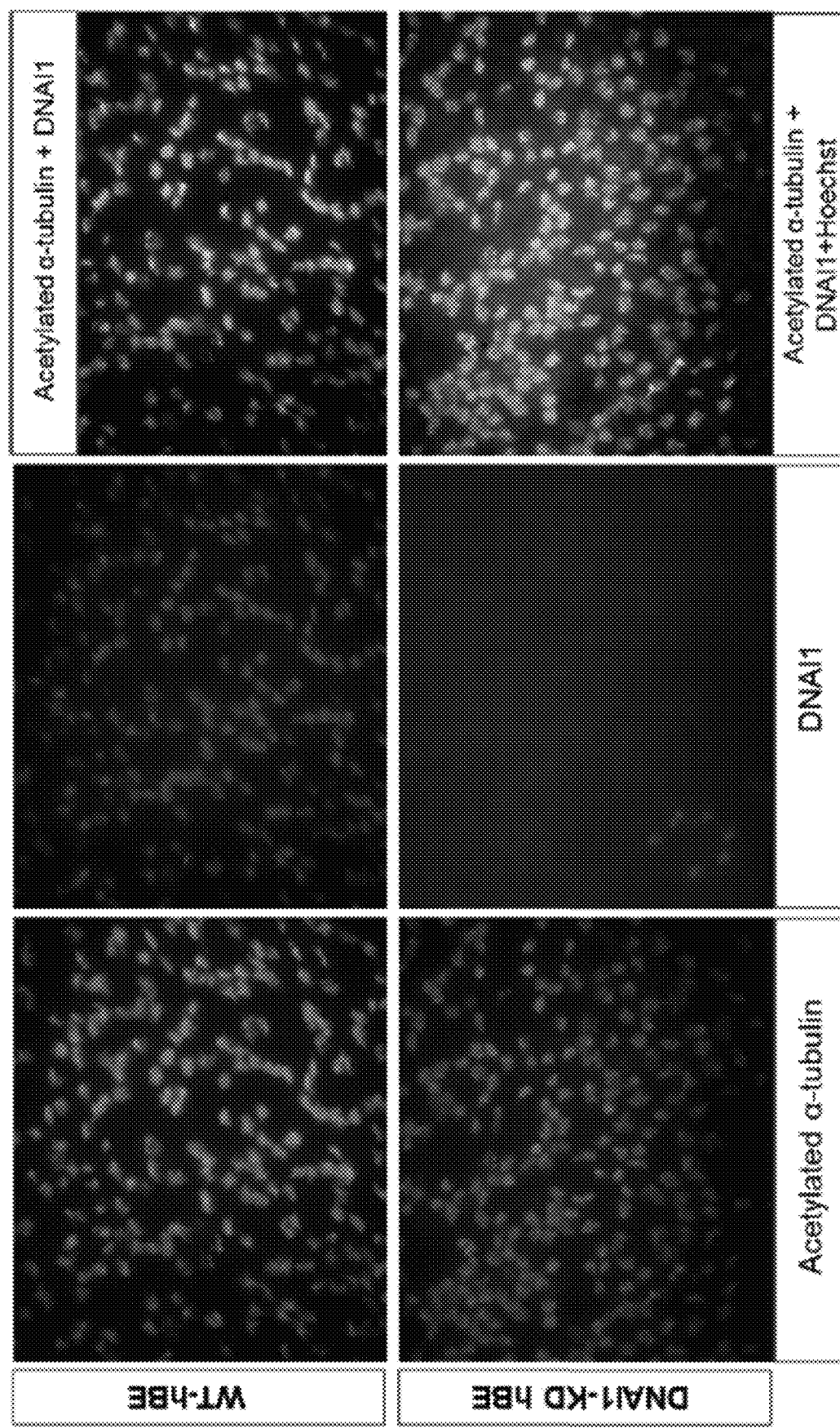

FIG. 110 is immunofluorescence images of WT-hBE and DNAI1-KD hBE cultures using specific markers for ciliated cells (acetylated α-tubulin and DNAI). Ciliated cells in WT-hBE colocalized with DNAI1, while DNAI1 protein was only detected in a few ciliated cells in DNAI1-KD hBEs.

Figure 111:
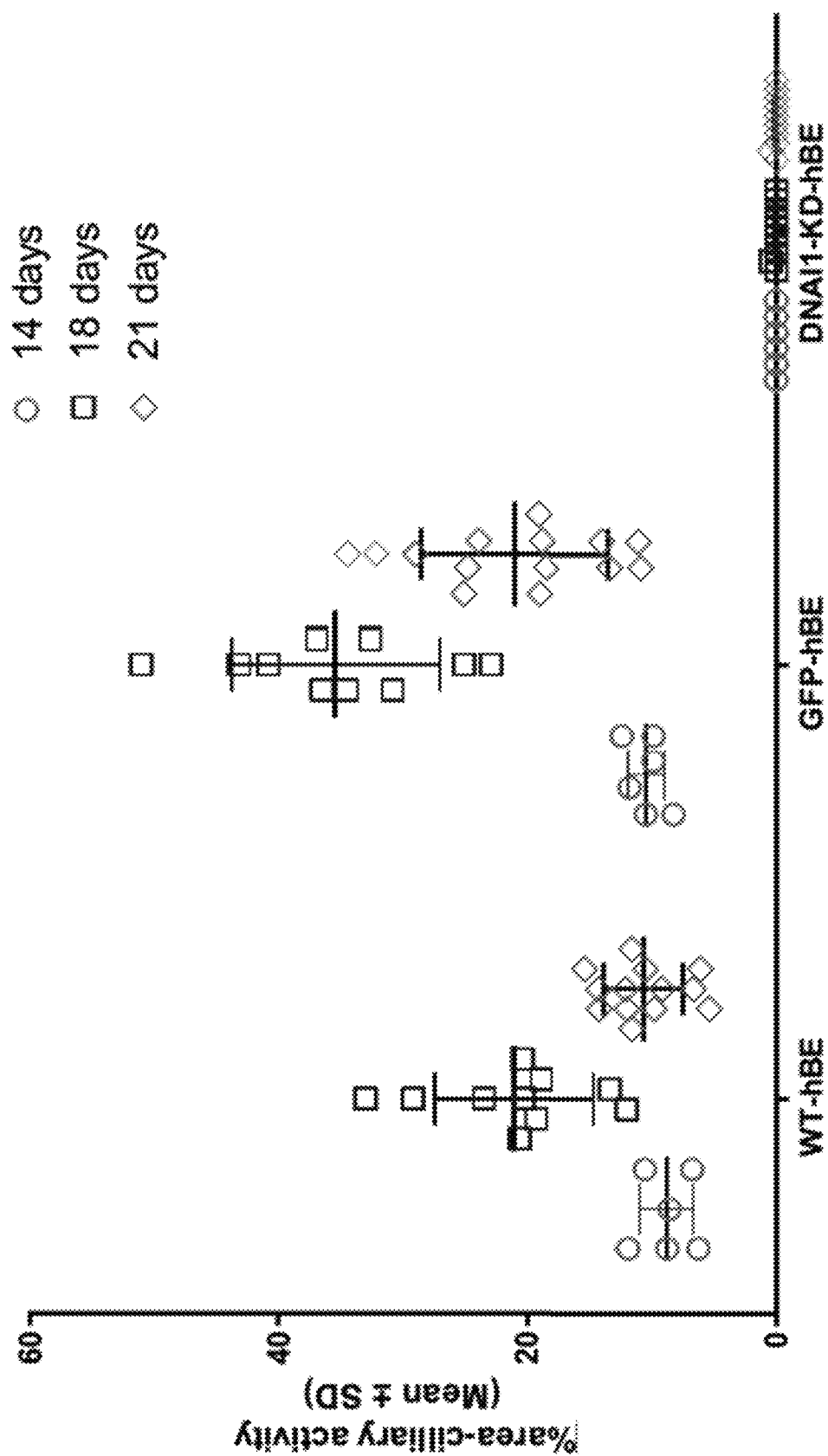

FIG. 111 is a graph illustrating ciliary activity in control and DNAI1-KD hBE cultures 14-, 18-, and 21-days post ALI. WT-hBE controls (untransduced) and WT-hBEs transduced with TurboGFP or shRNA constructs were grown at an ALI under puromycin selection for 21 days. Ciliary activity was measured using high-speed video microscopy and SAVA software (Ammons Engineering). GFP-hBE controls demonstrate that lentiviral transduction alone does not lead to a loss of ciliary activity.

Figure 112:
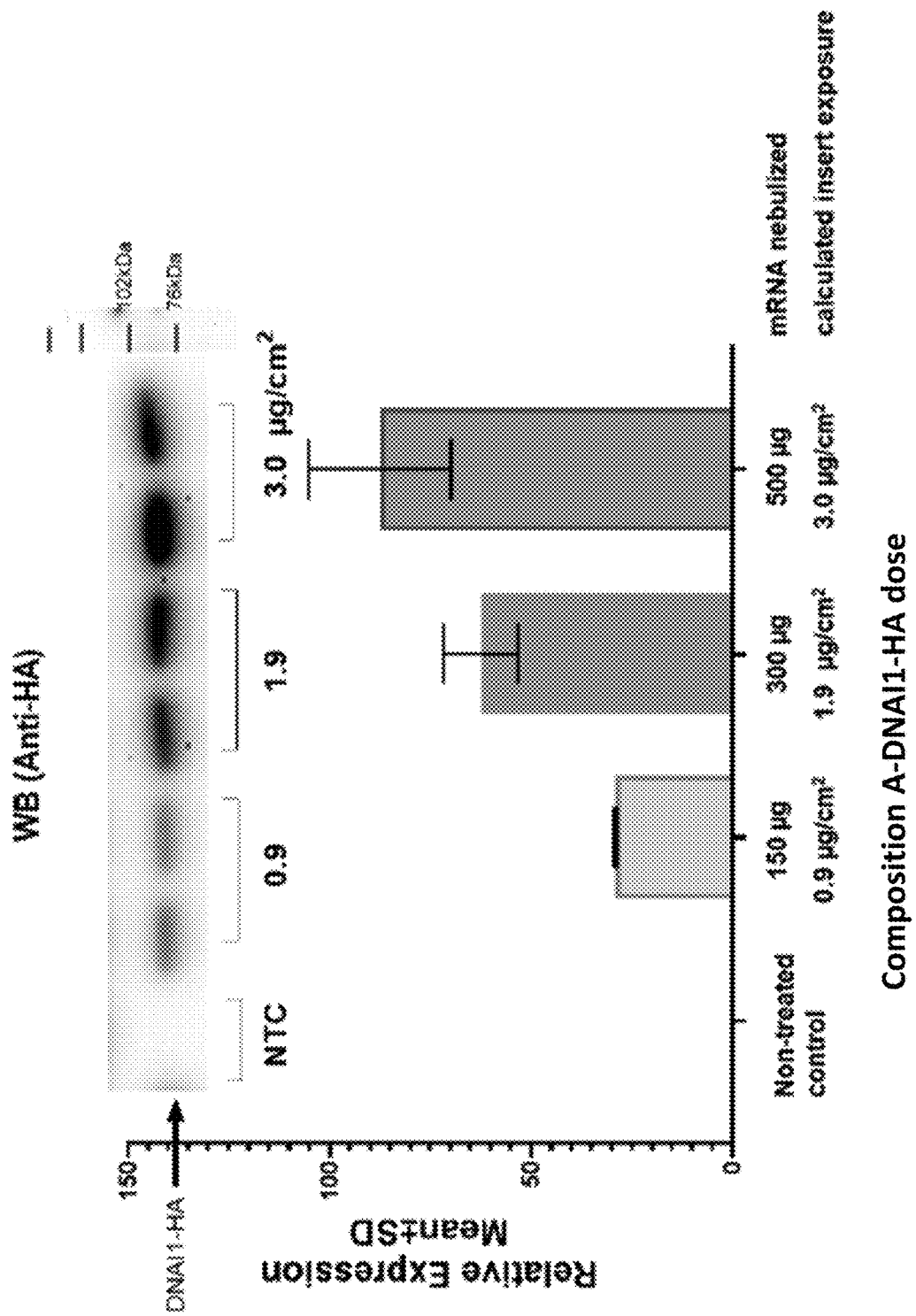

FIG. 112 is a graph illustrating dose-dependent increase in DNAI1-HA protein expression at 24 hr post-treatment (Western blot). Well-differentiated DNAI1-KD hBE cultures (33-days post-ALI) were treated with a single nebulization of 150 µg (0.9 µg/cm$^2$), 300 µg dose (1.9 µg/cm$^2$), or 500 µg (3.0 µg/cm$^2$) of Composition A-DNAI1-HA.

Figure 113:
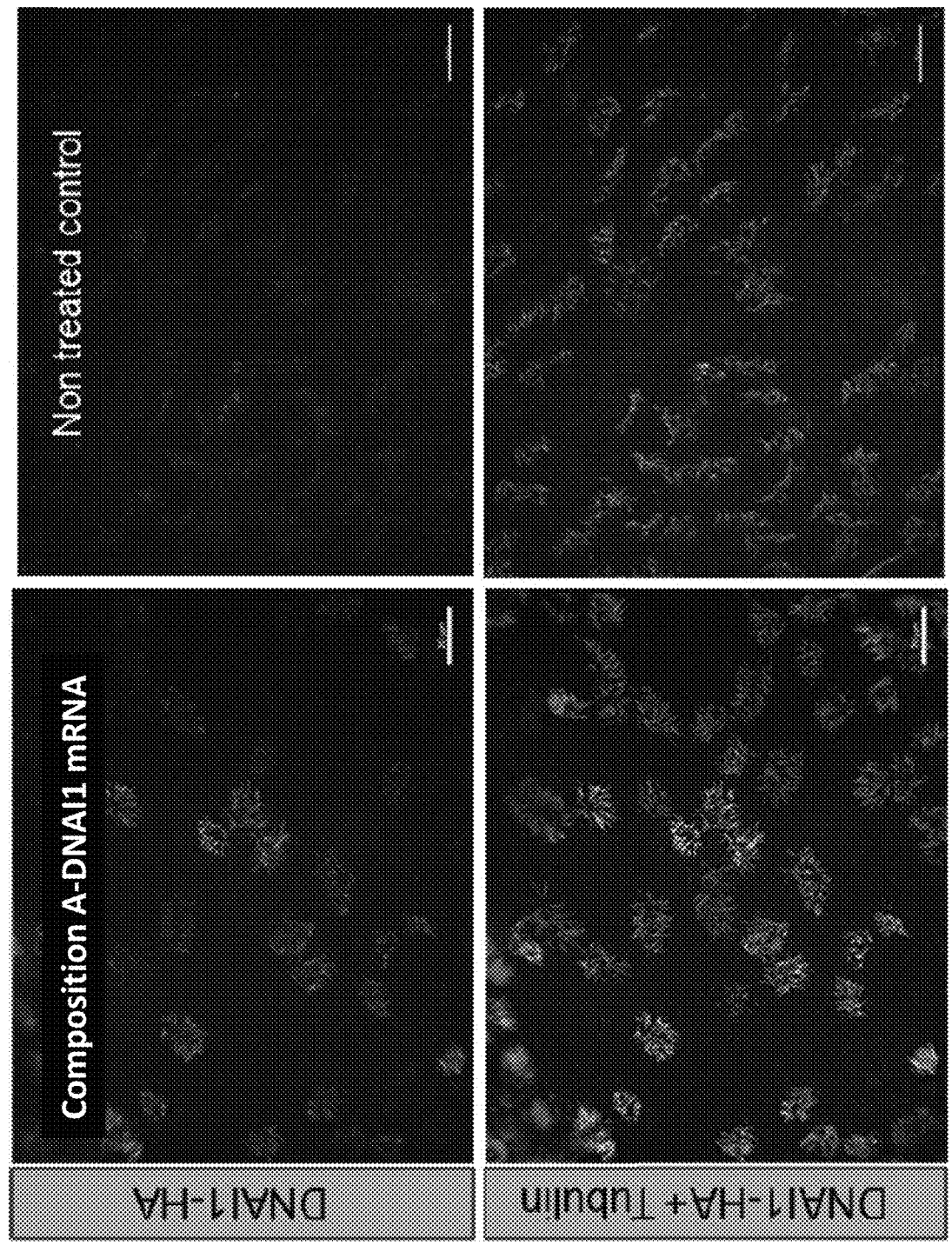

FIG. 113 is immunofluorescence imaging illustrating incorporation of newly translated DNAI1-HA Protein into the ciliary axoneme of DNAI1-KD hBEs by 72 h post-nebulization treatment. Well differentiated KD-hBE (33-days post-ALI) were treated with two nebulization of 300 µg dose (1.9 µg/cm$^2$) of Composition A-DNAI1-HA on two consecutive days. Panels showing DNAI1-HA protein in ciliated cells, acetylated α-tubulin protein in ciliary axonemes and their co-localization. Scale=20 µm binning 1×1; 25 ms exposure, z-stacked, deconvoluted image. Non-treated control staining done as the treated samples.

Figure 114:
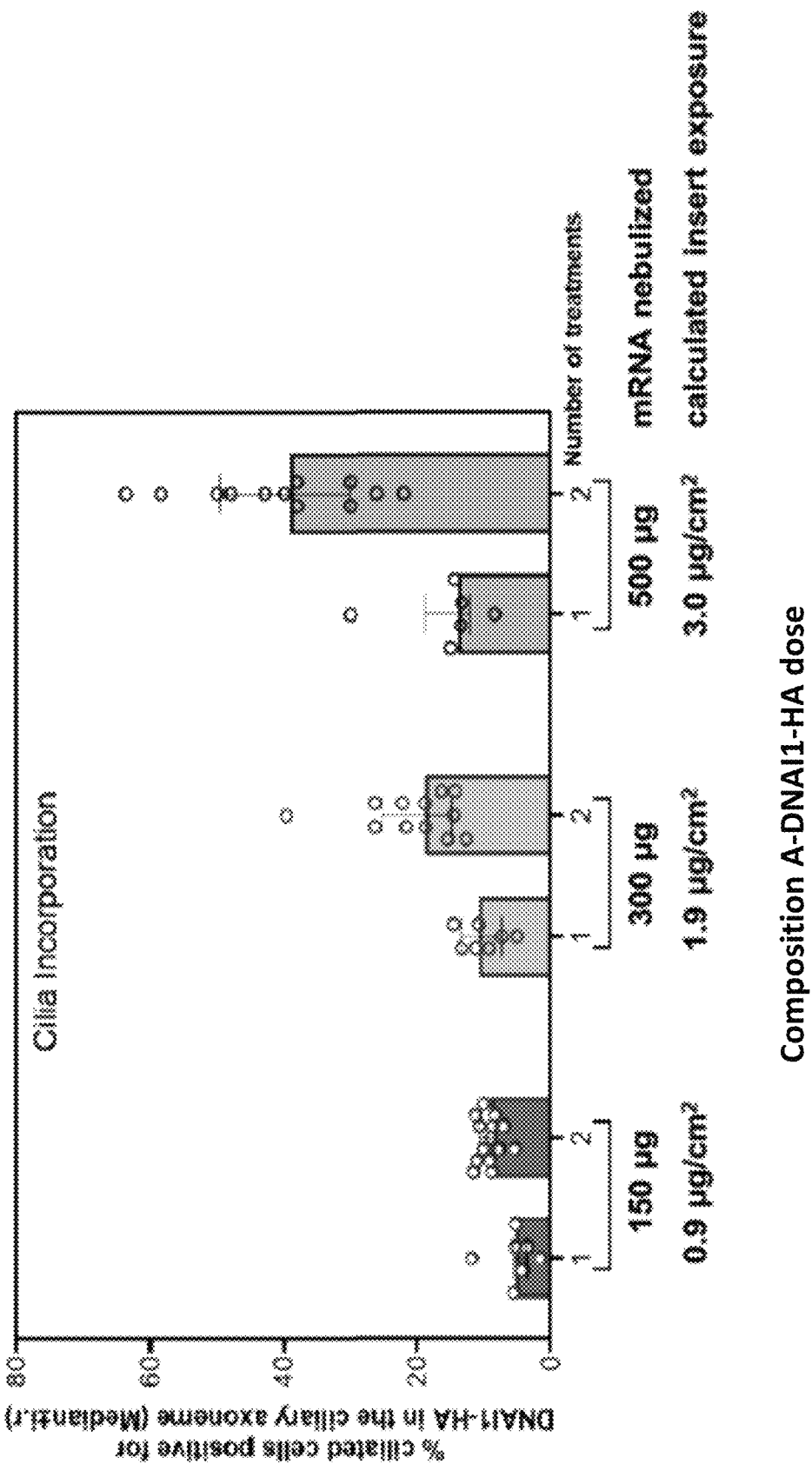

FIG. 114 is a graph illustrating dose response study for ciliary incorporation of DNAI1-HA protein into cilia 72 h post-nebulization. Well differentiated DNAI1-KD hBE (33-days post-ALI) were treated with a single or two nebulization of 150 µg (0.9 µg/cm$^2$) or 300 µg dose (1.9 µg/cm$^2$) or 500 µg dose (3.0 µg/cm$^2$) of Composition A-DNAI1-HA.

Figure 115:
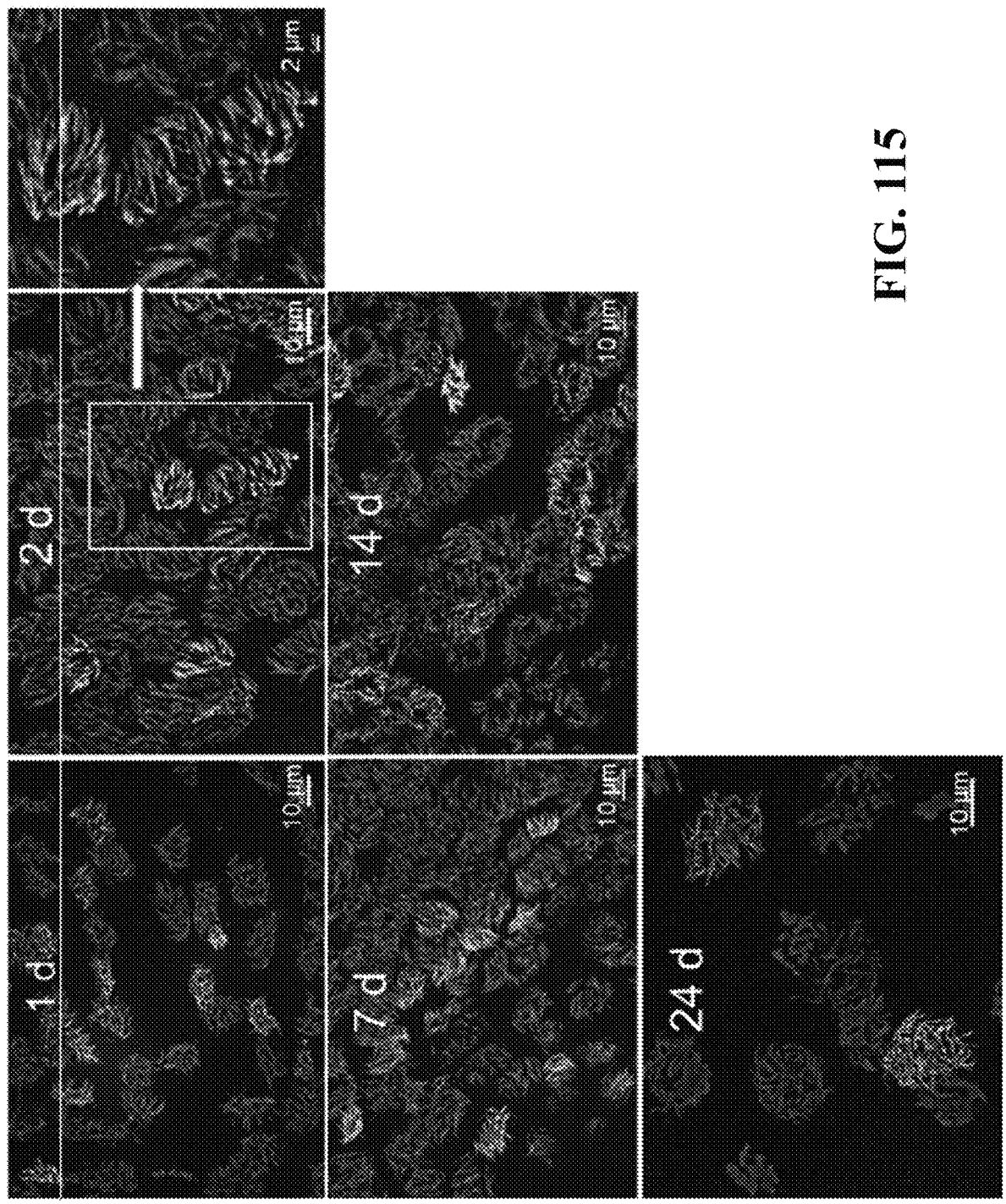

FIG. 115 is immunofluorescence imaging illustrating durable incorporation of DNAI1-HA protein into the axoneme of ciliated cells after a single basolateral administration of Composition A-DNAI1-HA. Differentiated hBEs were treated with Composition A-DNAI1 (10 µg/mL) by addition to the basolateral media. After a single treatment (media containing formulation replaced with fresh media after 5 h), treated inserts were fixed at different timepoints (1 d, 2 d, 7 d, 14 d, and 24 d refer to days after a single basolateral treatment) for immunofluorescence localization. Images show immunofluorescence localization of cilia in red (acetylated α-tubulin), DNAI1-HA in green (HA), and DNAI1-HA protein colocalization with cilia in yellow.

Figure 116:
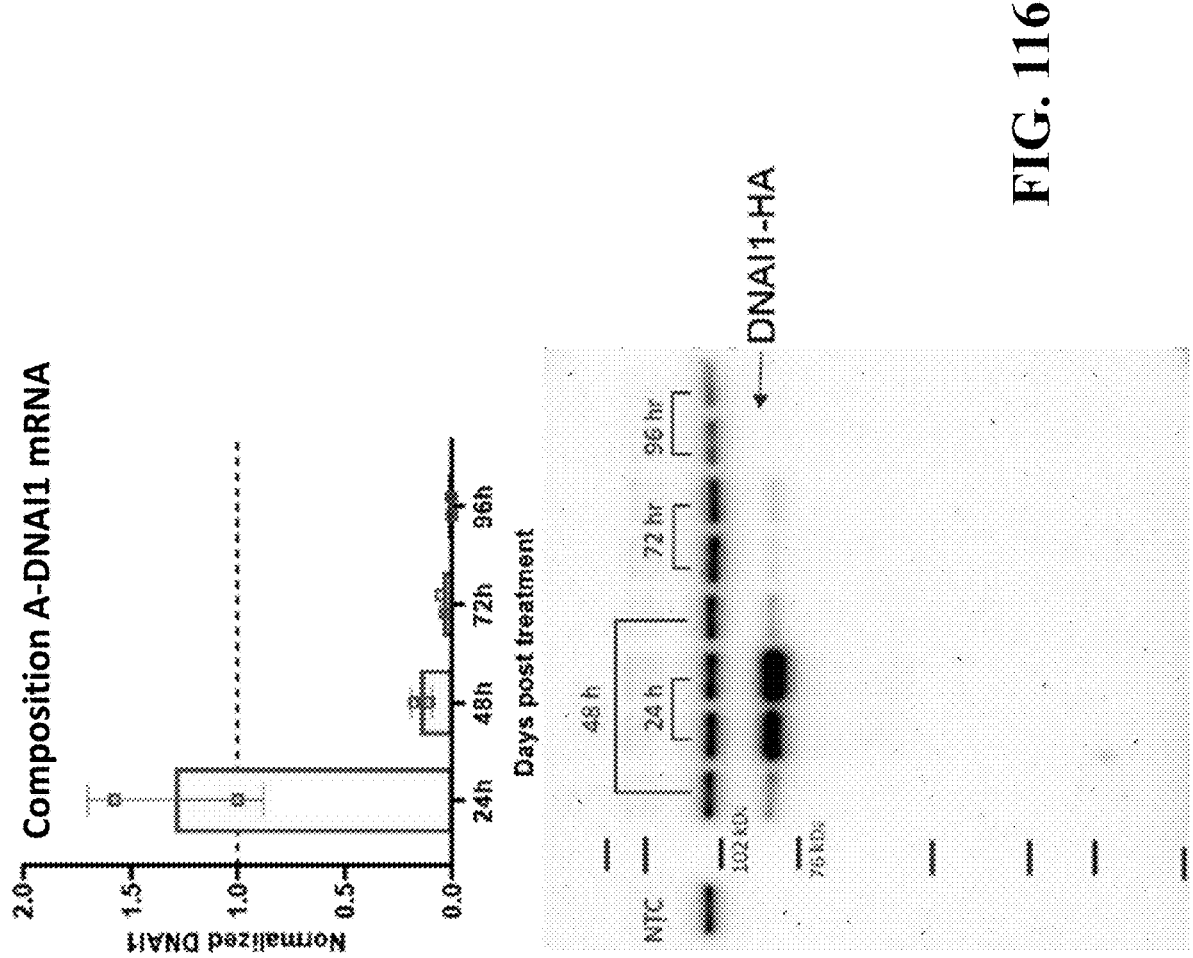

FIG. 116 is a graph and Westernblot illustrating kinetics of newly translated DNAI1-HA protein in WT-hBE after nebulization of Composition A-DNAI1-HA. Well differentiated WT-hBE (36 days post-ALI) were treated with 300 µg (1.9 µg/cm$^2$) of Composition A-DNAI1-HA by nebulization. Inserts were collected at different time points post-treatment and 10 µg of total protein was analyzed on a western blot with anti-HA antibody. NTC refers to non-treated cultures.

Figure 117:
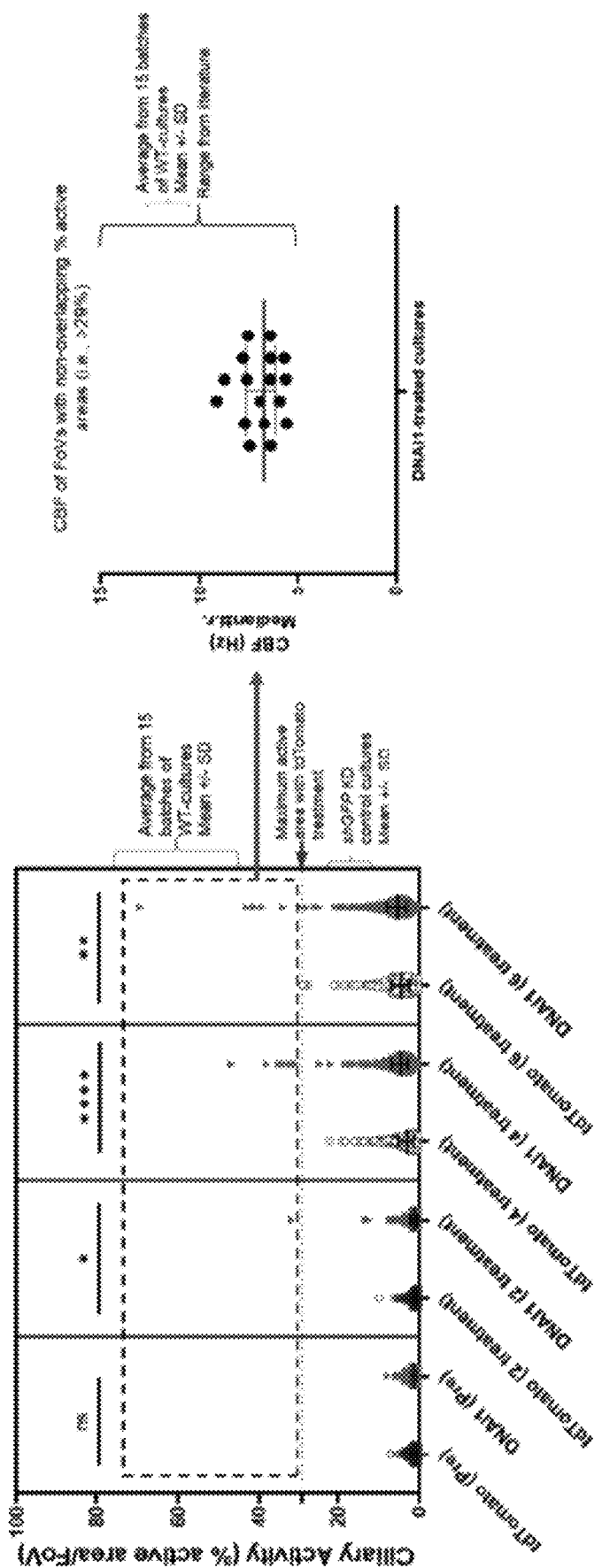

FIG. 117 is graphs illustrating functional rescue of ciliary activity by treatment with nebulized Composition A-DNAI1 in DNAI1-KD hBEs. Ciliary activity in hBEs was recorded and analyzed by Sisson-Ammons Video Analysis (SAVA) software to yield a ciliary % active area score for approximately 700 individual, non-overlapping field of views (FoVs). DNAI1 mRNA treated cultures have higher levels of ciliary activity after 2, 4 and 6 treatments compared to tdTomato mRNA treated cultures. Increased activities were statistically significant as determined by Welch's t-test. *=P≤0.05, =P=0.001, **=P≤0.0001, ns=not significant (P>0.05). Ciliary beat frequencies (right graph) for FoVs with % active areas ≥29% (those with % active areas greater than that observed in any tdTomato treated cultures) fall within the normal range of 5-15 Hz.

Figure 118:
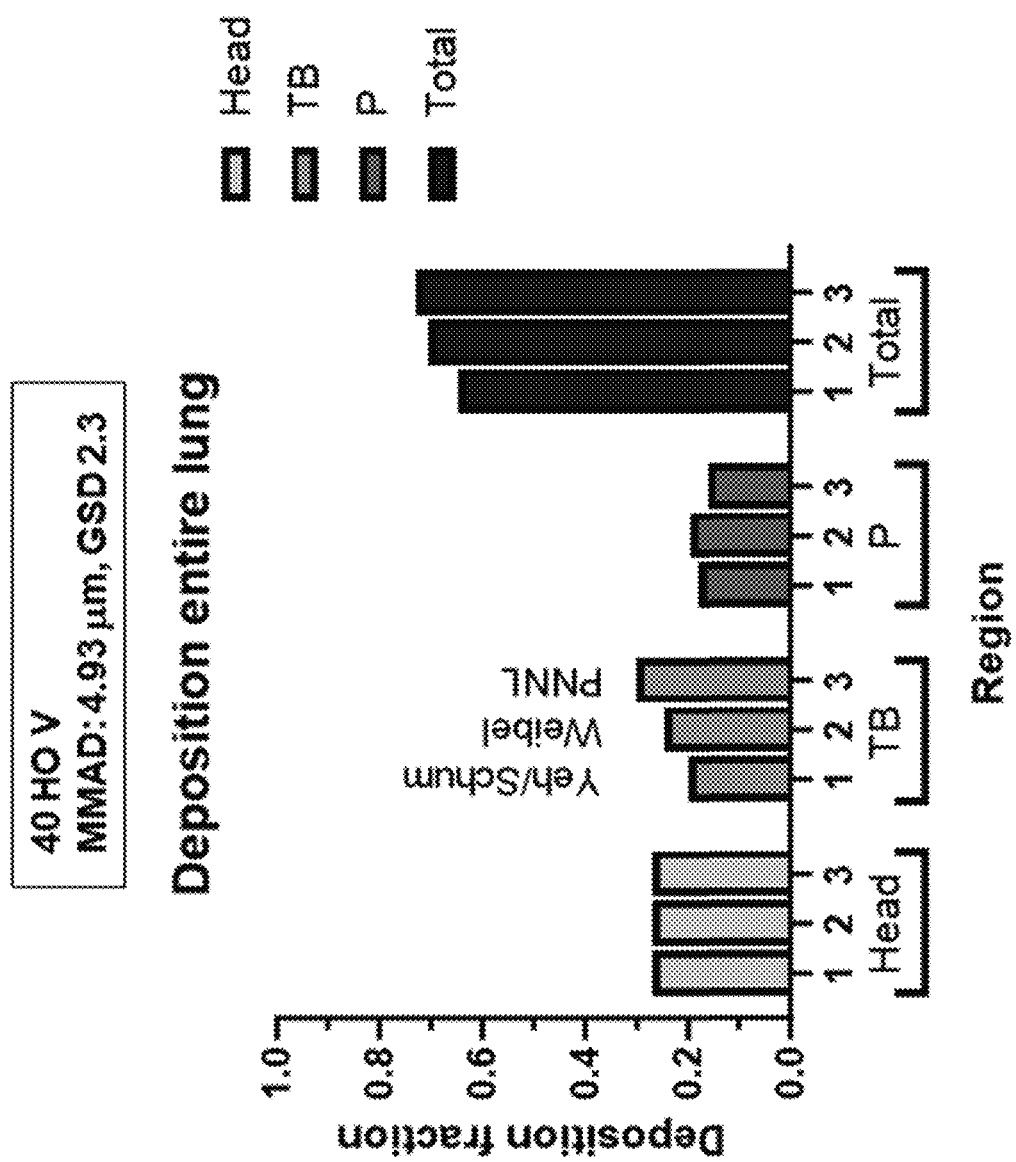

FIG. 118 is a graph illustrating simulated deposition distribution using Yeh/Schum, Weibel, and PNNL airway morphometry models in healthy adults using eFlow Nebulizer aerosol characteristics.

Figure 119:
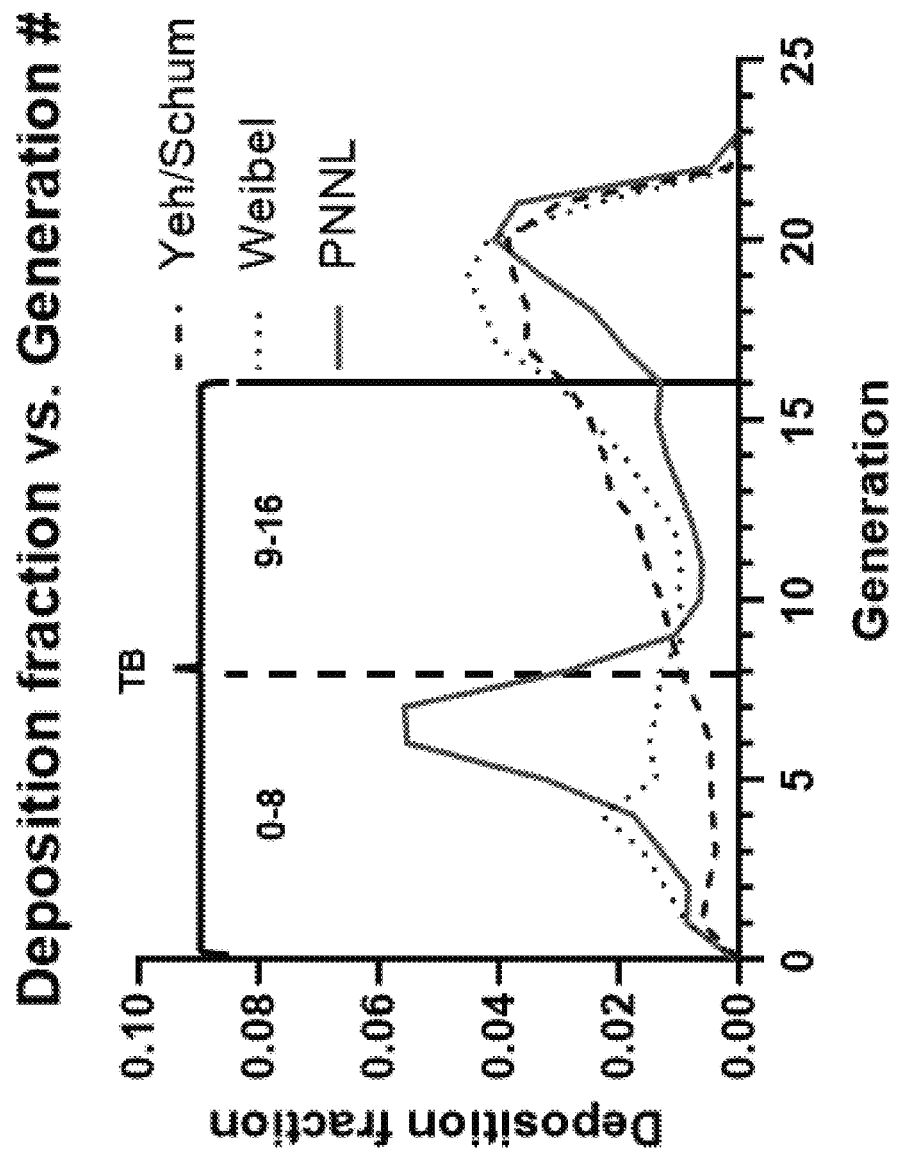

FIG. 119 is a graph illustrating model-dependent and generation-dependent MMPD deposition fraction production.

Figure 120:
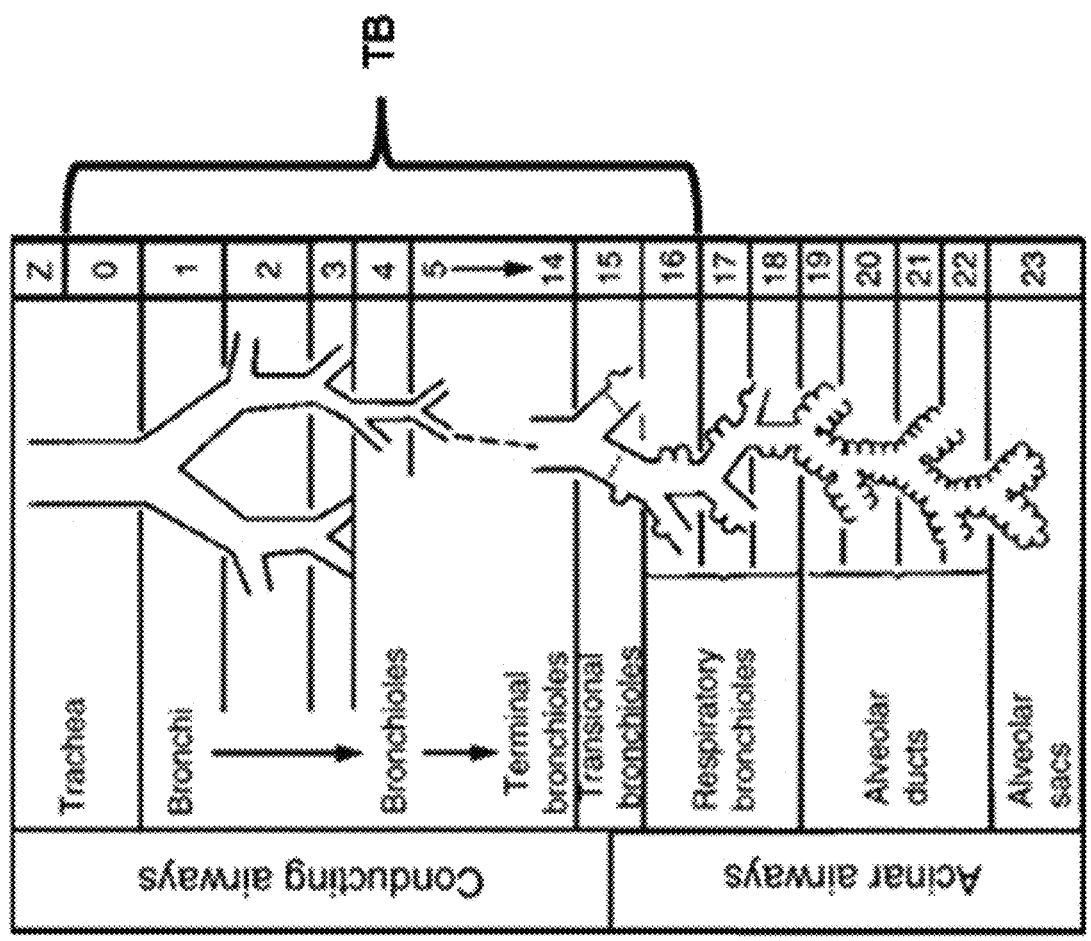

FIG. 120 is a schematic representation of a symmetrical respiratory tract model illustrating conducting (comprised of generations 0-8 representing trachea, bronchi and bronchioles, and 9-16 terminal bronchioles) and acinar or pulmonary airways (generations 17-23).

Figure 121:
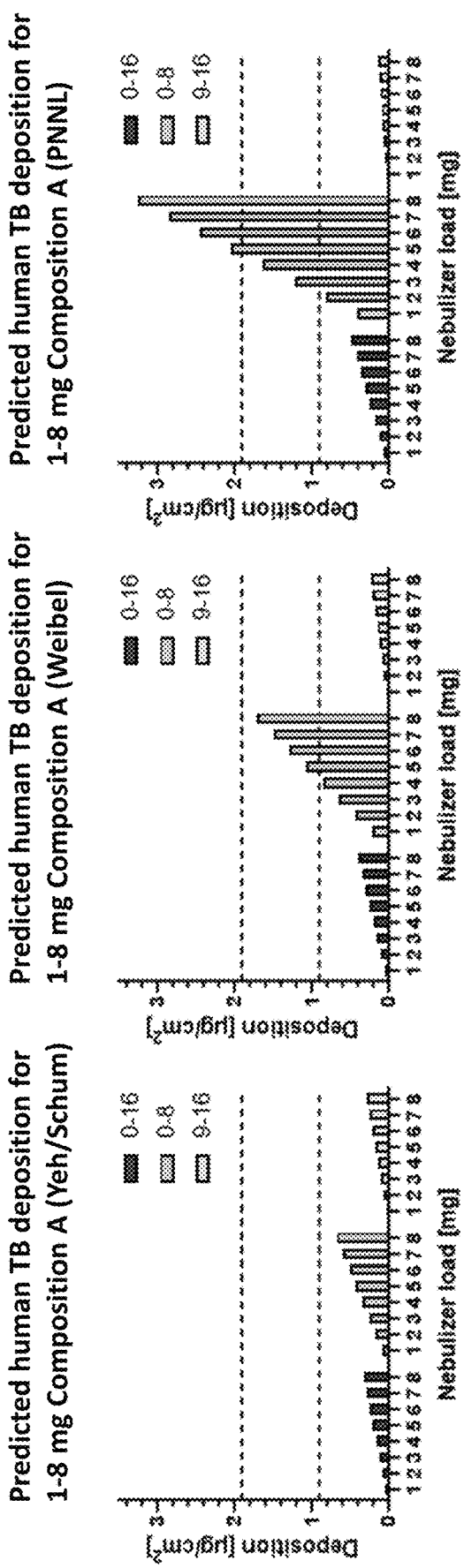

FIG. 121 is graphs illustrating simulated human deposition for generations 0-8 (trachea, bronchi and bronchioles), 9-16 (bronchioles) and 0-16 (entire TB region) as a function of nebulized Composition A and human airway model.

Figure 122:
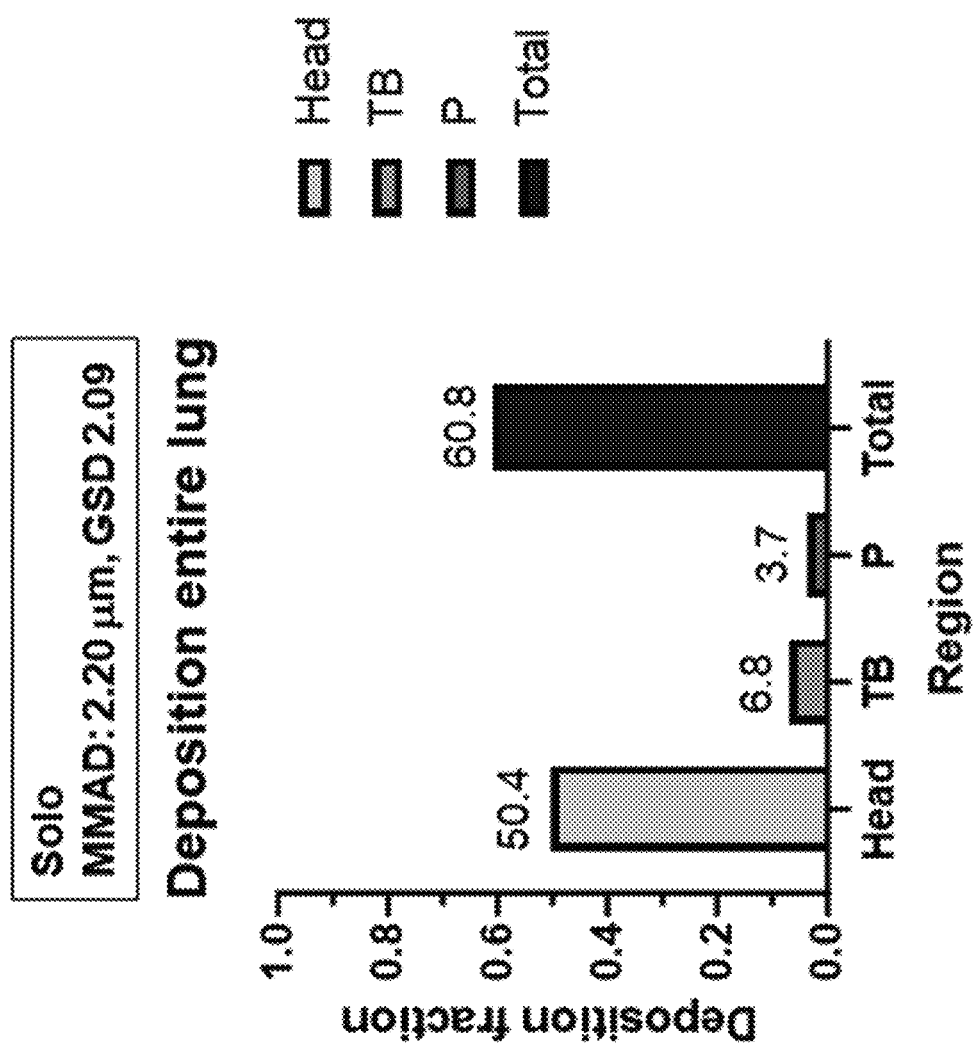

FIG. 122 is a graph illustrating simulated deposition distribution for oronasal mask wearing NHP using experimental aerosol characteristics.

Figure 123:
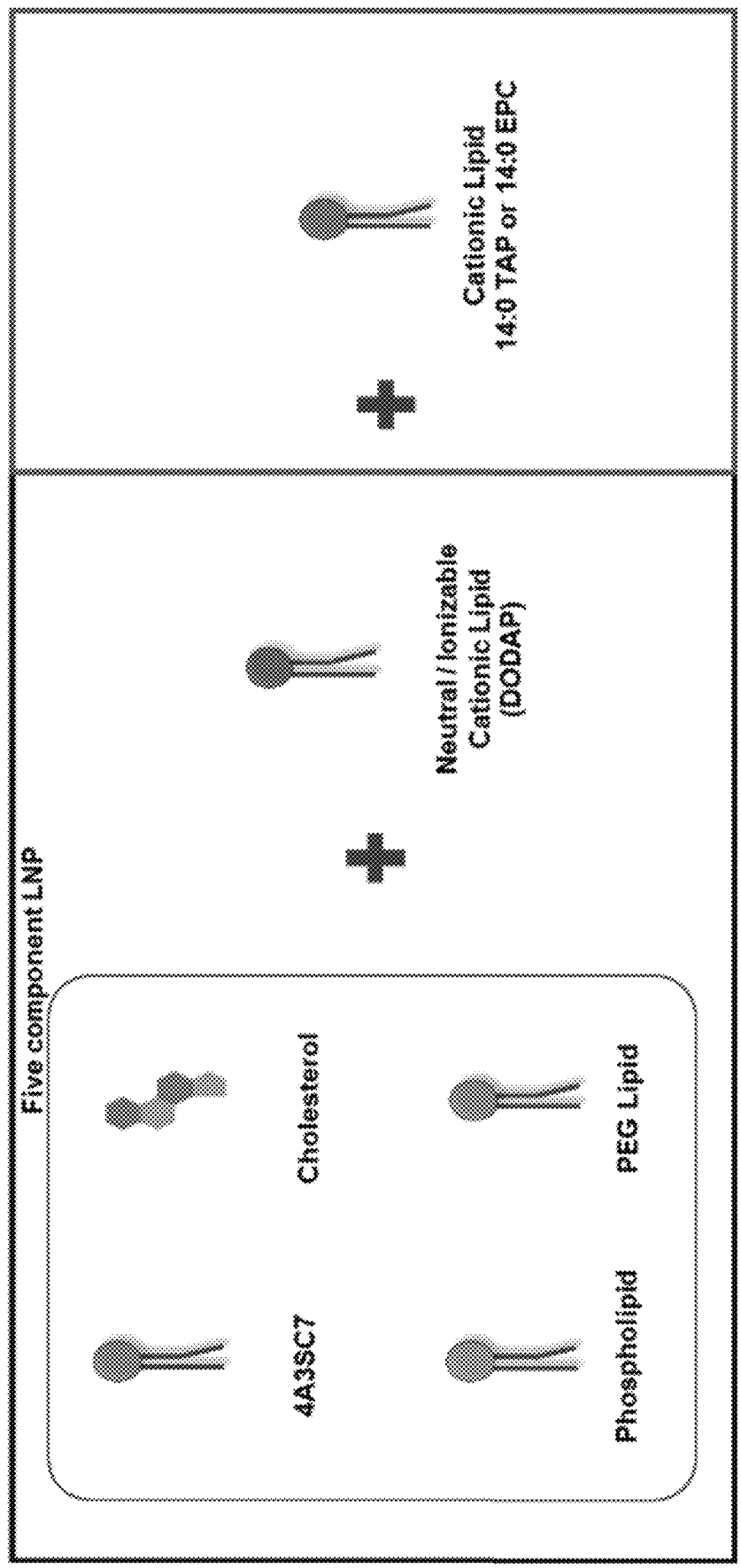

FIG. 123 shows a diagram of exemplary embodiments have six lipid components.

Figure 124:
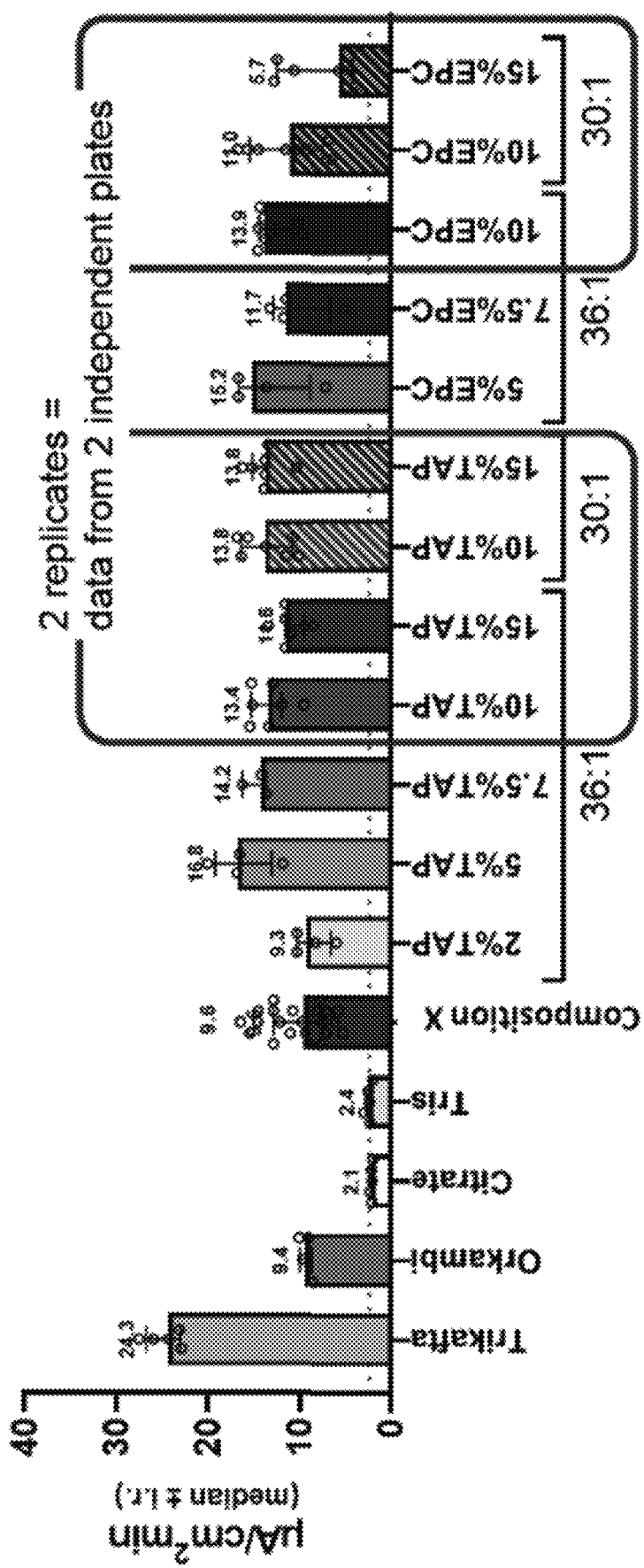

FIG. 124 shows rescue of CFTR function in CF-patient derived hBE cells (G542X/F508del) by various six-component lipid nanoparticles.

Figure 125:
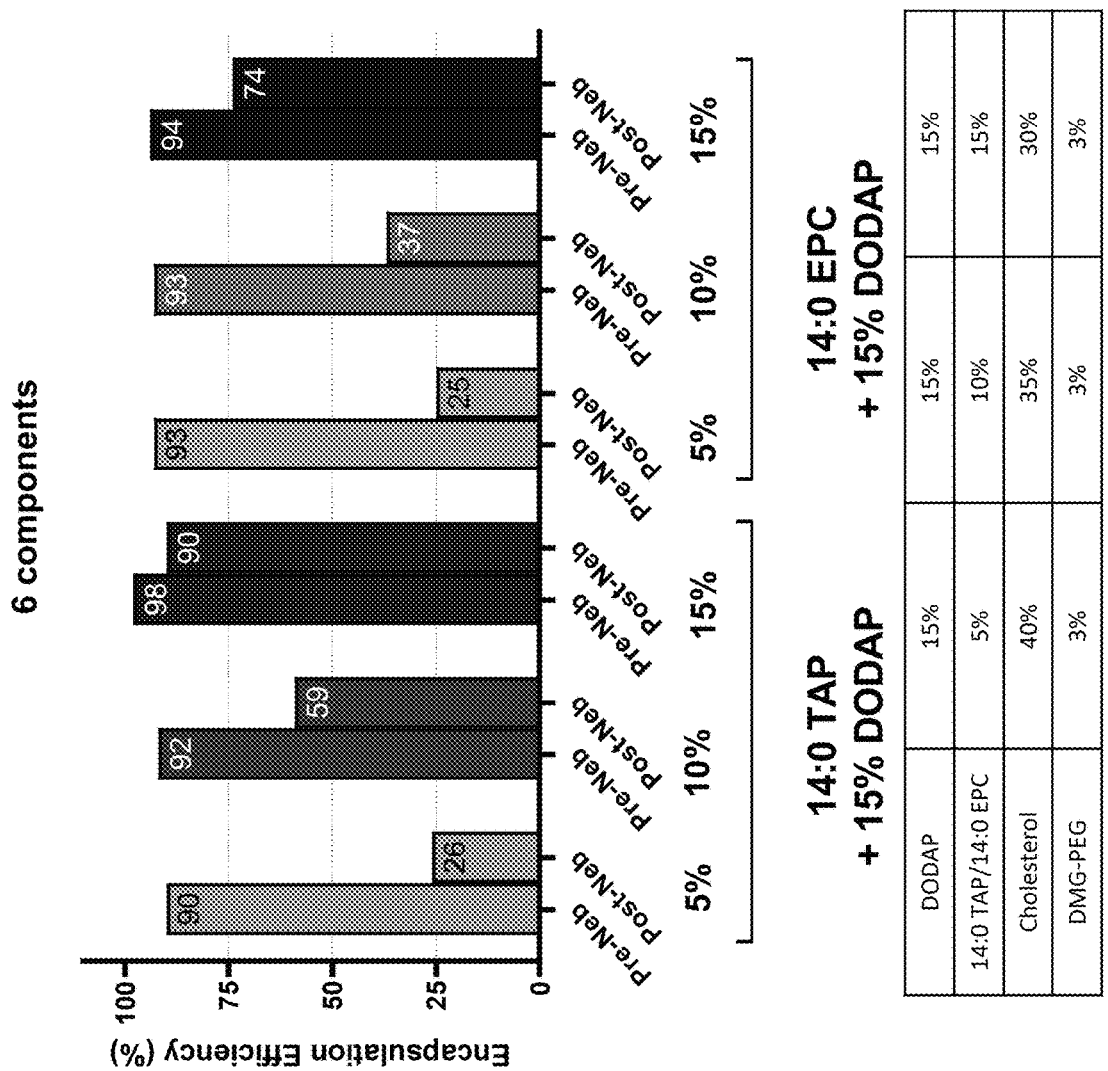

FIG. 125 shows encapsulation efficiency (%) of before and after nebulization of various six-component lipid nanoparticles.

Figure 126A:
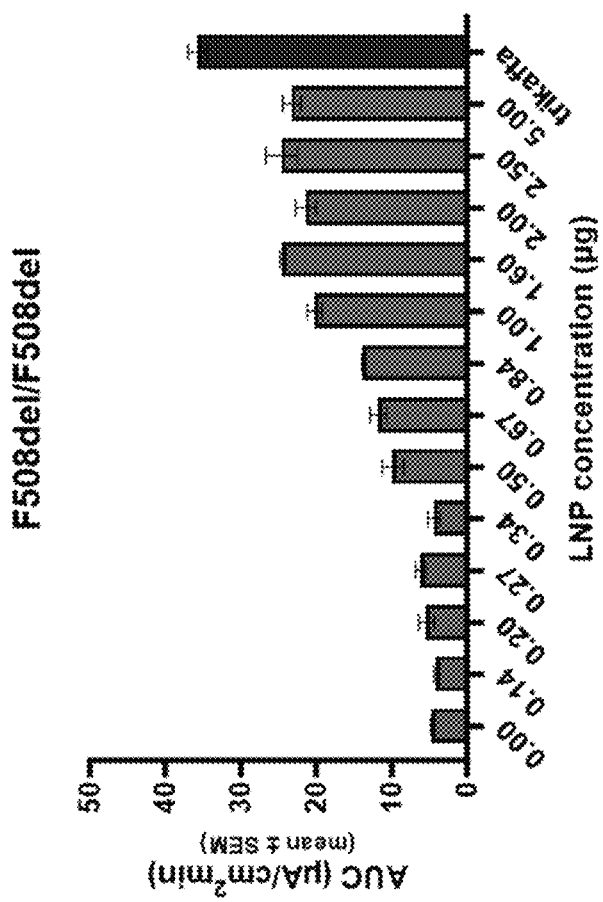

FIG. 126A shows CFTR function of Composition 3D7-treated CF-patient derived hBE cells (F508del/F508del) in a dose-dependent manner.

Figure 126B:
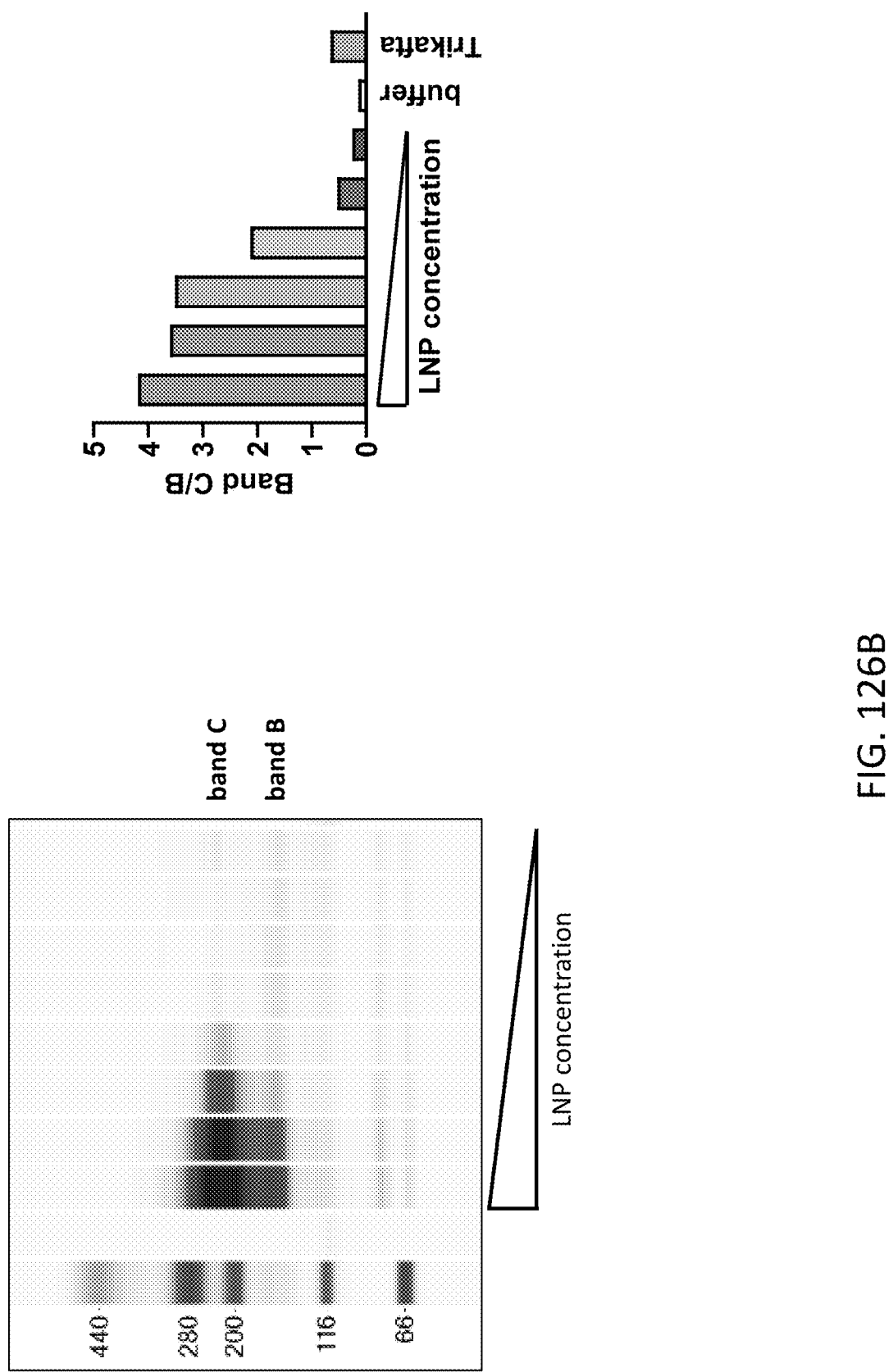

FIG. 126B shows protein expression analysis of Composition 3D7-treated CF-patient derived hBE cells (F508del/F508del) in a dose-dependent manner.

Figure 127A:
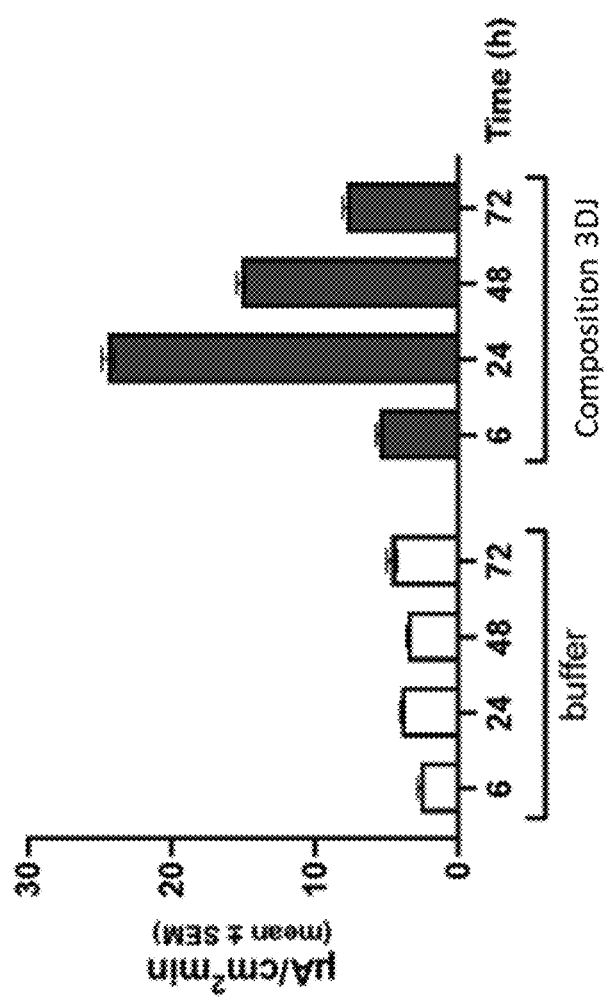

FIG. 127A shows CFTR function of Composition 3D7-treated CF-patient derived hBE cells (F508del/F508del) at different time point.

Figure 127B:
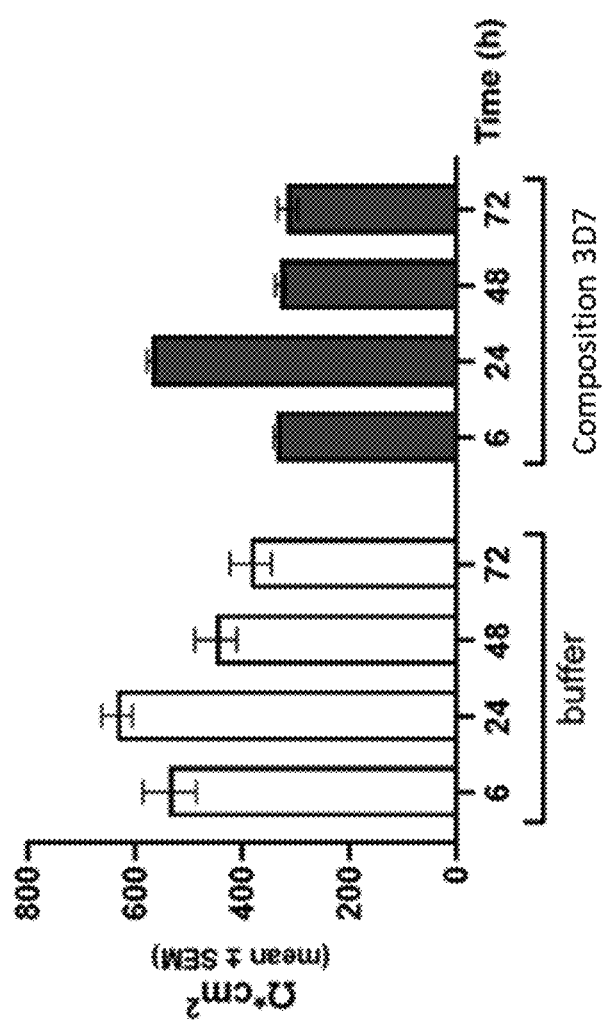

FIG. 127B shows measurement of transepithelial electrical resistance (TEER) of Composition 3D7-treated CF-patient derived hBE cells (F508del/F508del) at different time point.

Figure 127C:
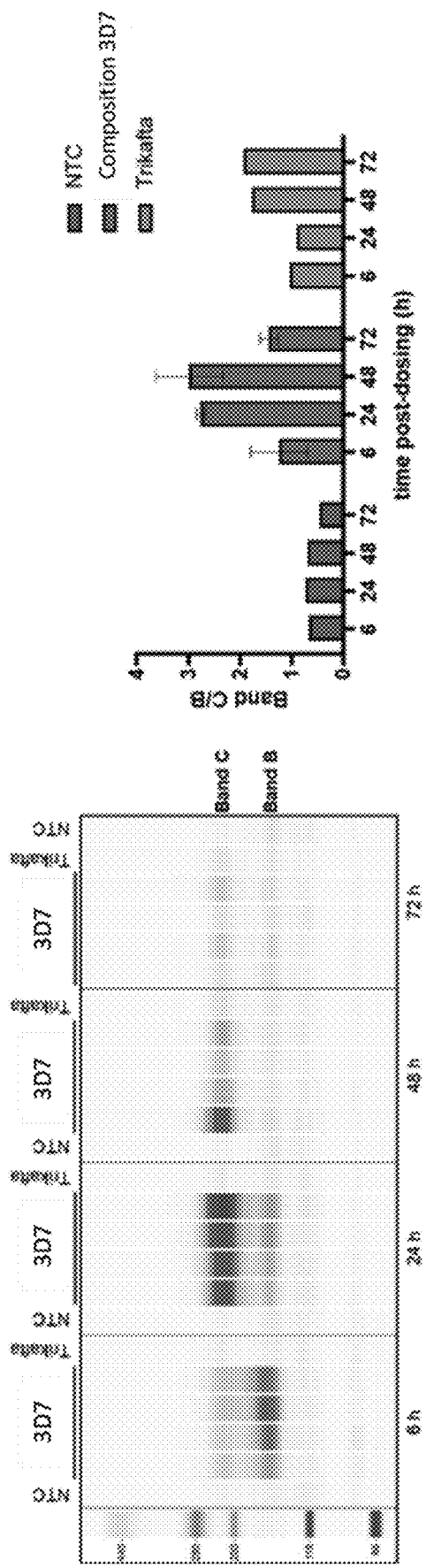

FIG. 127C shows protein expression analysis of Composition 3D7-treated CF-patient derived hBE cells (F508del/F508del) at different time point.

Figure 128A:
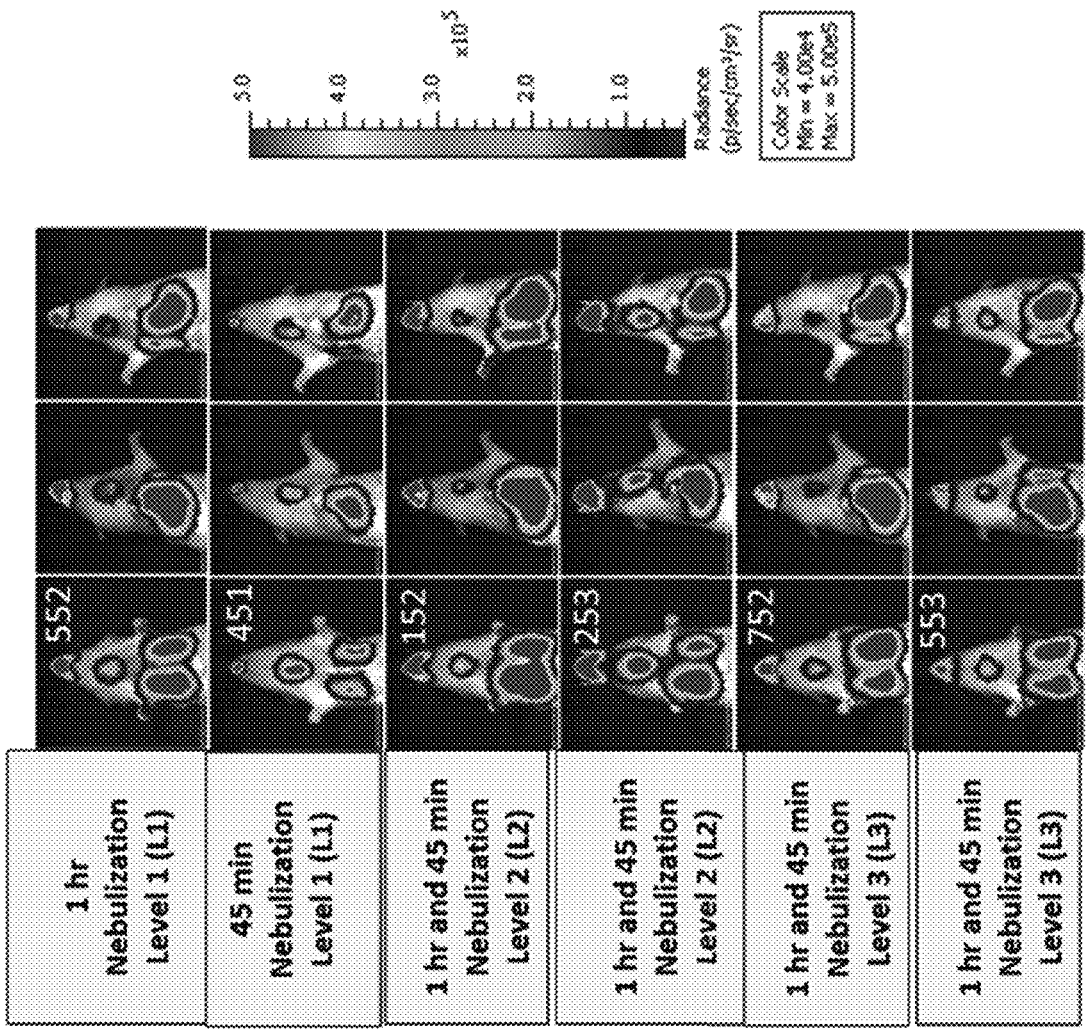

FIG. 128A shows in vivo images of rats nebulized with Composition 3D7.

Figure 128B:
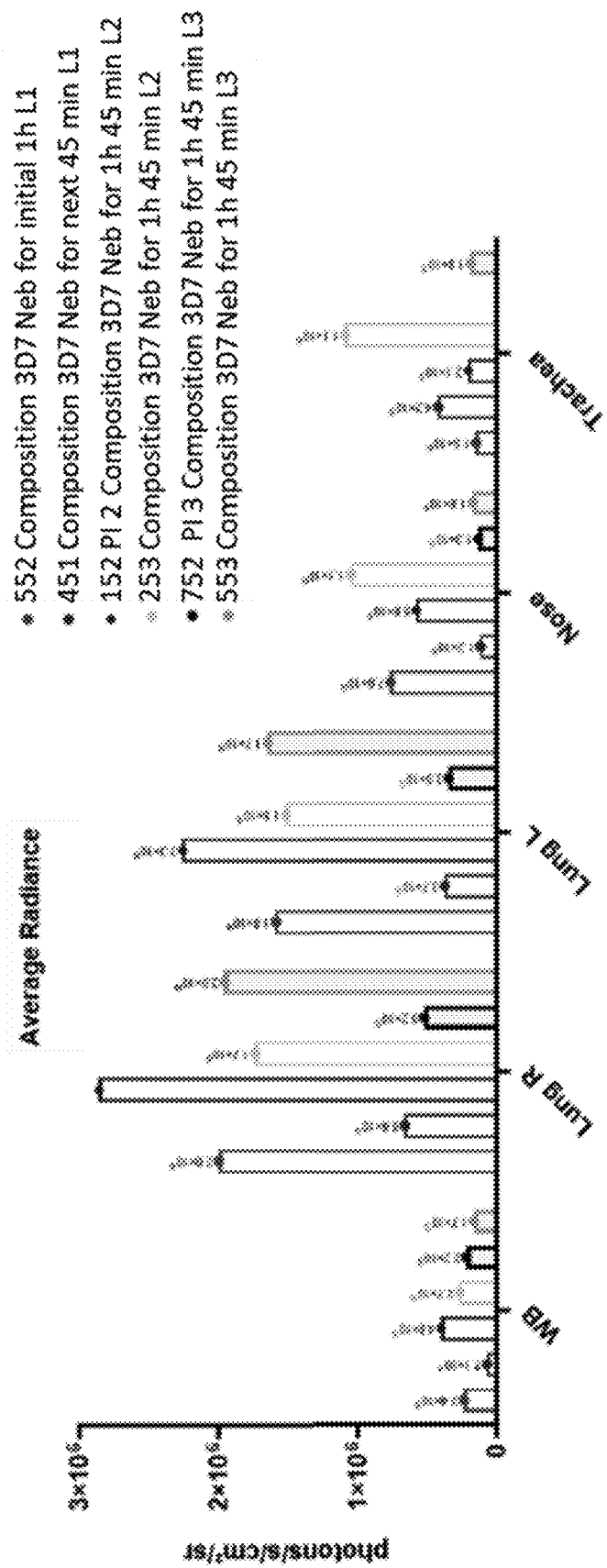

FIG. 128B shows quantification of in vivo images of rats nebulized with Composition 3D7.

Figure 129A:
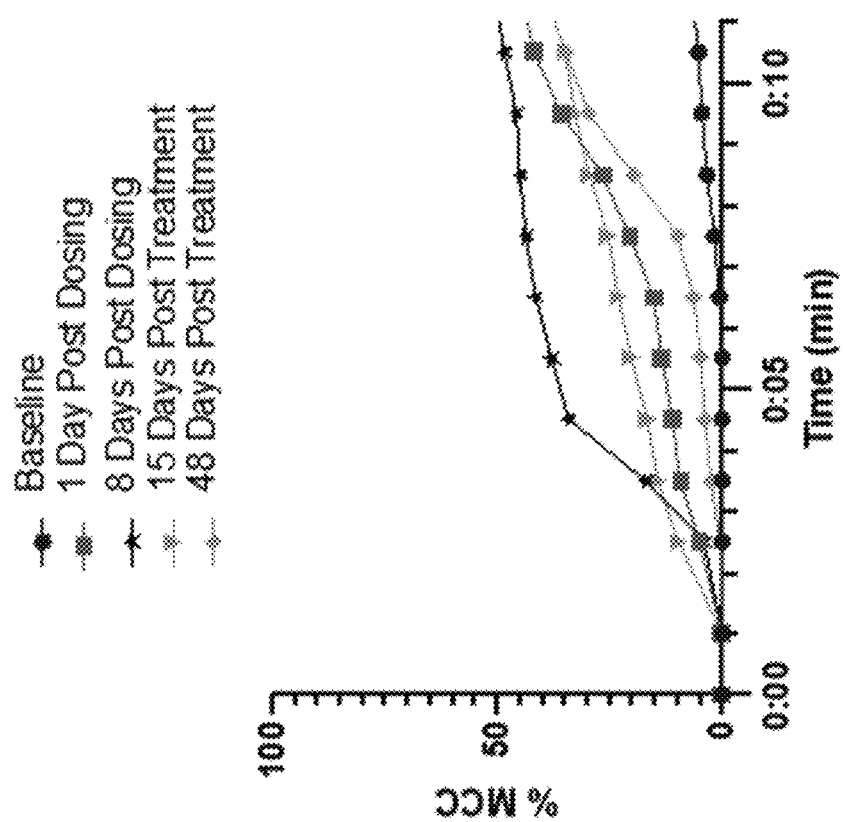

FIG. 129A shows mucociliary clearance of CF transgenic ferret dosed with CFTR mRNA-containing Composition 3D7.

Figure 129B:
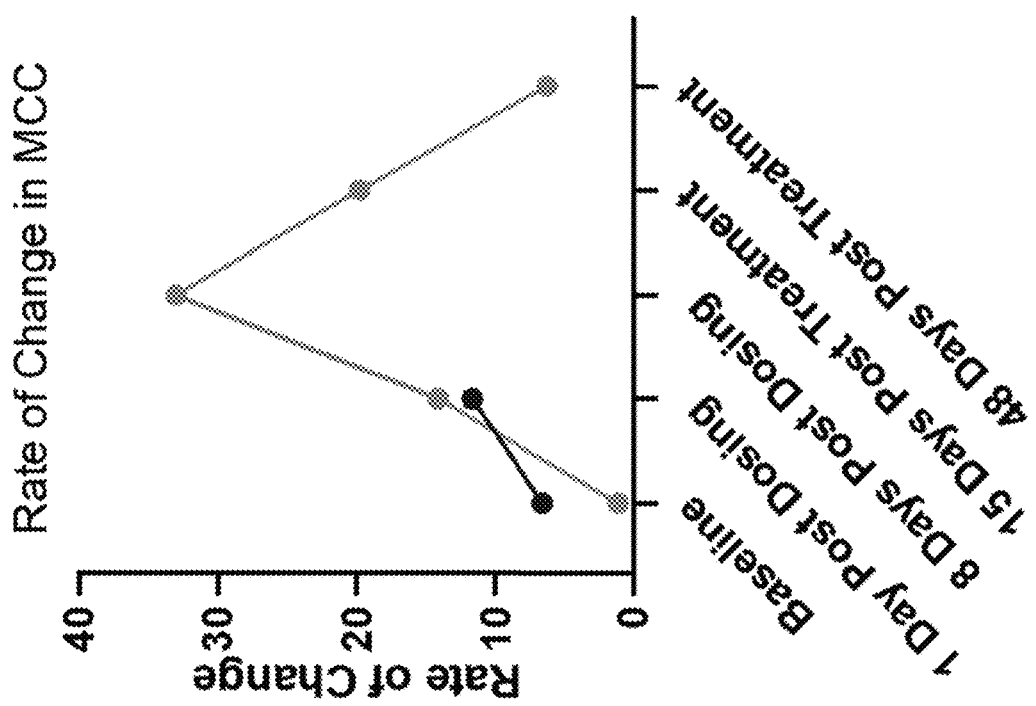

FIG. 129B shows rate of change mucociliary clearance of CF transgenic ferret dosed with CFTR mRNA-containing Composition 3D7.

FIG. 130A shows proliferative growth of ionocytes in apical region of CF transgenic ferret.

Figure 130B:
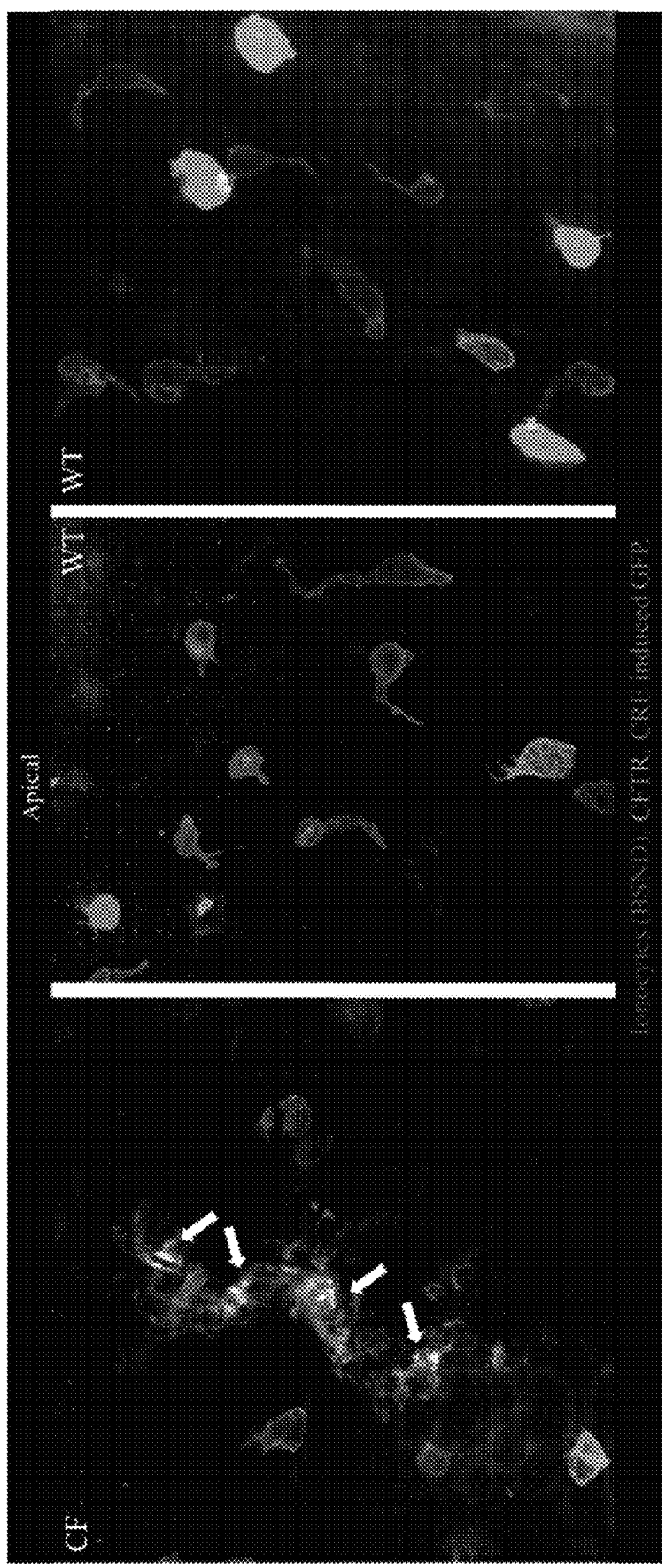

FIG. 130B shows colocalization of cre-induced GFP with ionocytes and CFTR at apical cap in CF transgenic ferret.

Figure 130C:
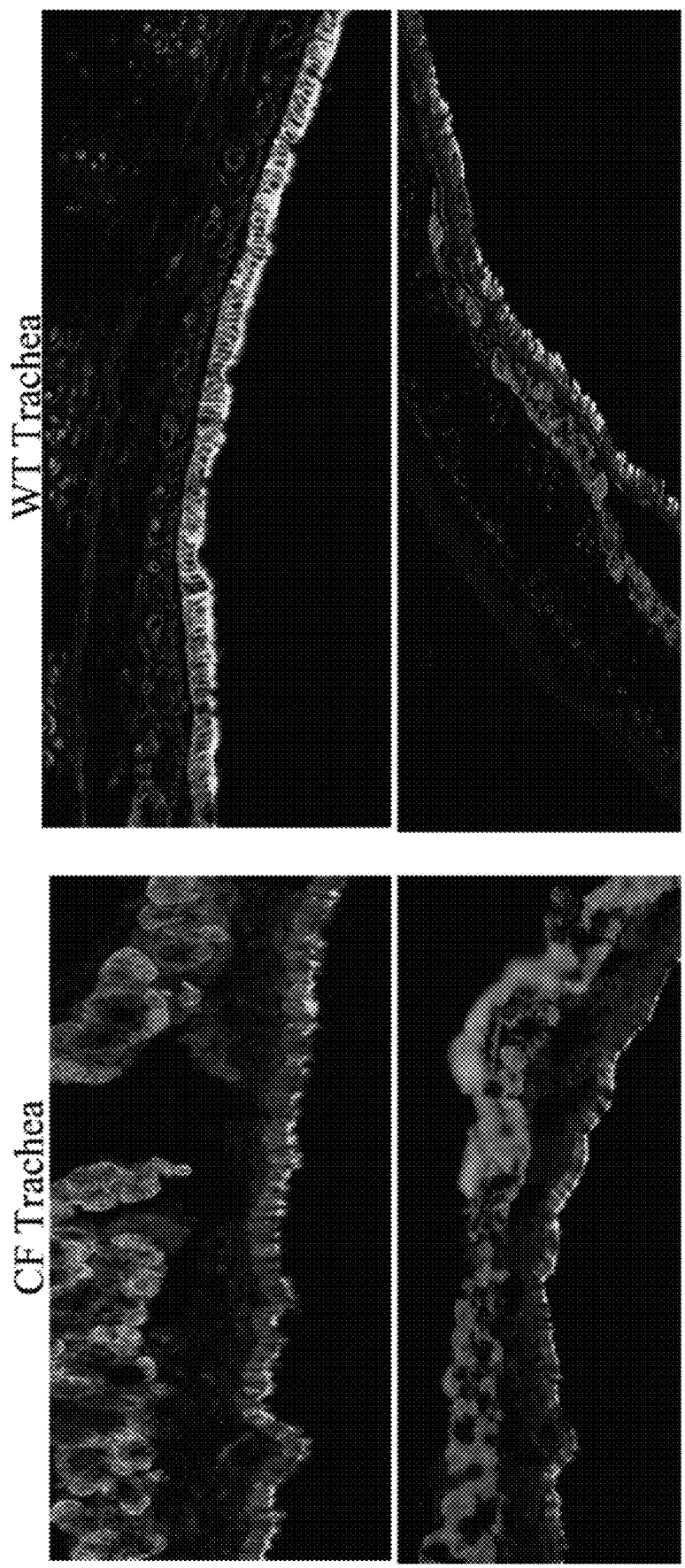

FIG. 130C shows delivers its target gene by Composition 3D7 to ciliated cells in CF ferrets.

Figure 131A:
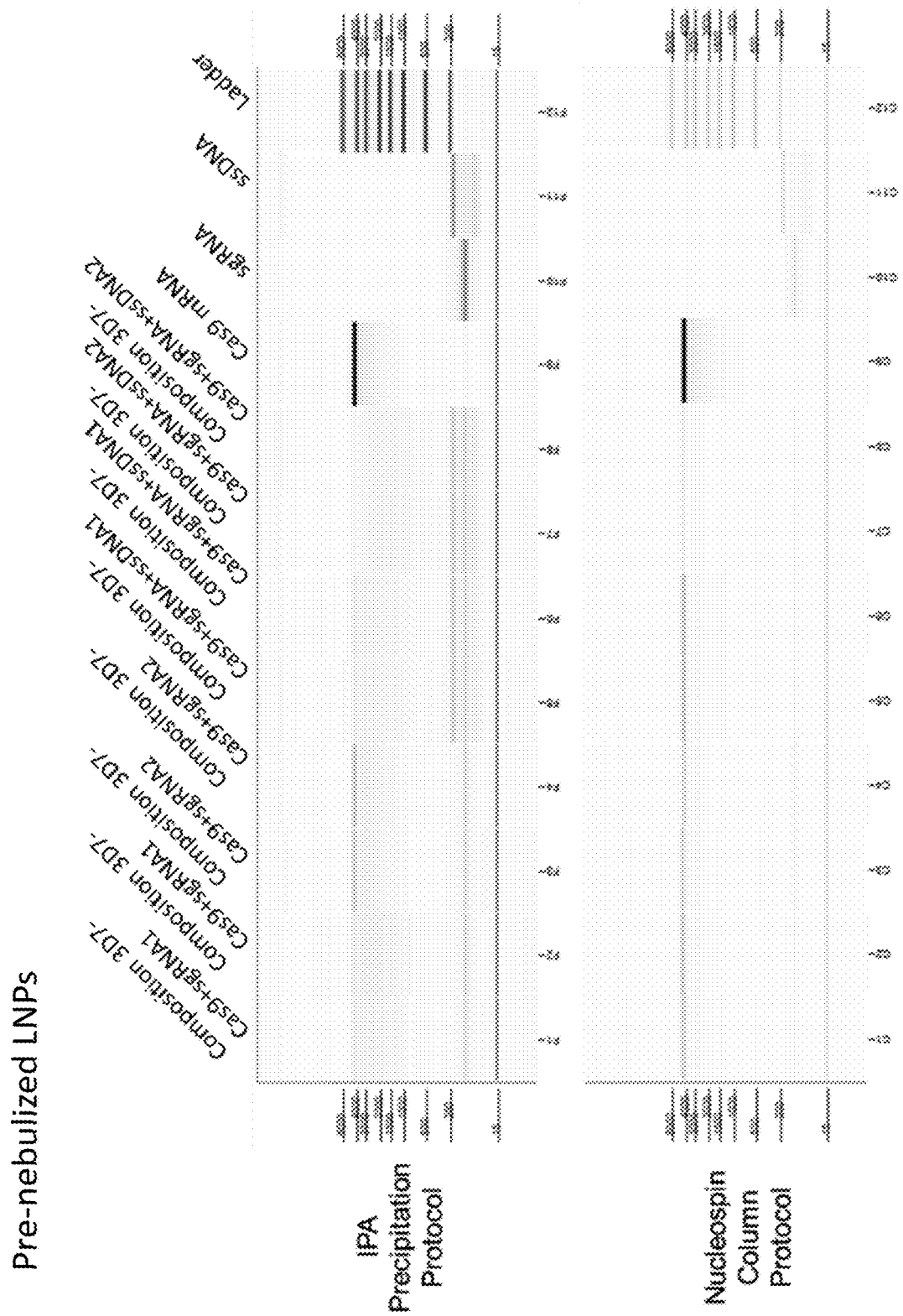
Figure 131B:
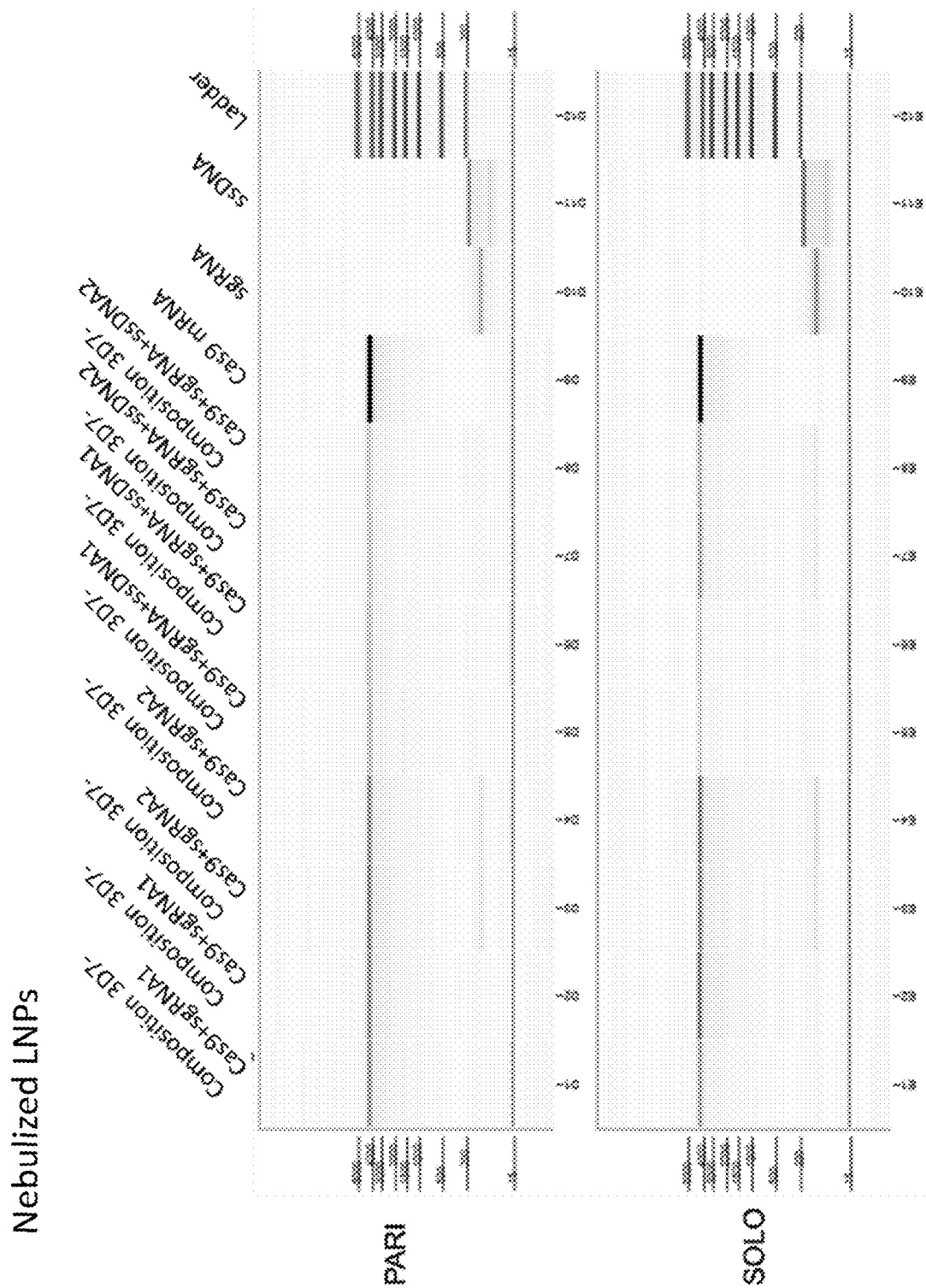

FIG. 131A shows gel images of pre-nebulization fragment analysis. FIG. 131B shows gel images of fragment analysis in nebulized LNP.

FIG. 132A shows % of EGFP-positive cells treated with either Composition 3D7 or cell control formulated with 2- or 3-gene editing component. FIG. 132B shows % of BFP-positive cells treated with either Composition 3D7 or cell control formulated with 2- or 3-gene editing component. FIG. 132C shows LDH levels of cells treated with either Composition 3D7 or cell control formulated with 2- or 3-gene editing component.

DETAILED DESCRIPTION

Provided herein is, inter alia, a lipid nanoparticle (LNP) composition designed to surpass the conventional lipid count in LNPs, raising it from five to six or more. The present disclosure allows LNPs to incorporate a blend of two or more selective organ targeting (SORT) lipids. Noteworthy aspects of these LNPs include reduced toxicity compared to their 5-component counterparts and heightened encapsulation efficiency. In some embodiments, encapsulation efficient is maintained after nebulization of the LNPs to a greater extend than in 5-component LNPs. In some embodiments, the LNP composition comprises at least 3, 4, 5, 6, 7, 8, 9, 10 or more lipids, wherein at least 1, 2, 3, 4, 5, or more of the lipids are SORT lipids.

Accordingly, provided herein is a LNP composition, comprising at least two selective organ targeting (SORT) lipids and/or at least six lipids. In some embodiments, the LNP composition can comprise an ionizable cationic lipid, optionally two or more ionizable lipids; and a permanently cationic lipid, optionally two or more permanently cationic lipids.

I. Definitions

In the Summary and the Detailed Description of the present disclosure, and the claims below, and in the accompanying drawings, reference is made to particular features (including method steps) of the present disclosure. It is to be understood that the present disclosure includes all possible combinations of such particular features. For example, where a particular feature is disclosed in the context of a particular aspect or embodiment of the present disclosure, or a particular claim, that feature can also be used, to the extent possible, in combination with and/or in the context of other particular aspects and embodiments of the present disclosure, and in the present disclosure generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The practice of the present disclosure will employ, unless indicated specifically to the contrary, conventional methods of chemistry, biochemistry, organic chemistry, molecular biology, microbiology, recombinant DNA techniques, genetics, immunology, and/or cell biology that are within the skill of ordinary artisan, many of which are described below for the purpose of illustration. Such techniques are explained fully in the literature. It is to be understood that this disclosure is not limited to any particular methodology, protocols, and reagents described, as these may vary, depending upon the context in which they are used by those of skill in the art.

All publications and patents mentioned herein are hereby incorporated by reference in their entireties as if each individual publication or patent was specifically and individually indicated to be incorporated by reference. In case of conflict, the present disclosure, including any definitions herein, controls. However, mention of any reference, article, publication, patent, patent publication, and patent application cited herein is not, and should not be taken as an acknowledgment, or any form of suggestion, that they constitute valid prior art or form a part of the common general knowledge in any country in the world.

The section headings used herein are for organizational purposes only and are not to be construed as limiting the subject matter described herein. Specifically, features described in one section may be combined with features in any other section of the present disclosure.

While illustrative embodiments are described and depicted, it will be appreciated that various changes can be made to these illustrative embodiments without departing from the spirit and scope of the invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described herein. Accordingly, the terms defined immediately below are more fully described by reference to the specification as a whole.

The singular forms "a", "an", and "the" are intended to include the plural forms as well, unless the context clearly indicates otherwise.

As used herein, the term "about" means a range of values including the specified value, which a person of ordinary skill in the art would consider reasonably similar to the specified value. In embodiments, about means within a standard deviation using measurements generally acceptable in the art. In some embodiments, about means a range extending to +/−10%, +/−5%, +/−3%, or +/−1% of the specified value.

The term "at least" followed by a number is used herein to denote the start of a range beginning with that number (which may be a range having an upper limit or no upper limit, depending on the variable being defined). For example, "at least 1" means 1 or more than 1.

The term "at most" followed by a number is used herein to denote the end of a range ending with that number (which may be a range having, for example, 1 or 0 as its lower limit, or a range having no lower limit, depending upon the variable being defined). For example, "at most 4" means 4 or less than 4, and "at most 40%" means 40% or less than 40%. When, in this present disclosure, a range is given as "(a first number) to (a second number)" or "(a first number)–(a second number)", this means a range whose lower limit is the first number and whose upper limit is the second number. For example, 25 to 100 mm means a range whose lower limit is 25 mm, and whose upper limit is 100 mm.

Throughout this specification, unless the context requires otherwise, the words "comprise", "comprises" and "comprising" will be understood to imply the inclusion of a stated step or element or group of steps or elements but not the exclusion of any other step or element or group of steps or elements. For example, a composition "comprising" (or "which comprises") components A, B, and C can consist of (i.e., contain only) components A, B, and C, or can contain not only components A, B, and C but also one or more other components.

As used herein, the term "consisting of" refers to including, and limited to, whatever follows the phrase "consisting of" Thus, the phrase "consisting of" indicates that the listed elements are required or mandatory and that no other elements may be present. The phrase "consisting essentially of" is meant to include any elements listed after the phrase and limited to other elements that do not interfere with or contribute to the activity or action specified in the present disclosure for the listed elements. Thus, the phrase "consisting essentially of" indicates that the listed elements are required or mandatory, but that no other elements are optional and may or may not be present depending upon whether they affect the activity or action of the listed elements.

As used herein, the terms "specific", "specifically", "specificity", or the like of a composition refers to the composition's ability to cause a particular action, such as, but not limited to, inhibition, to a particular molecular target with minimal or no action to other proteins in the cell.

As used herein, the term "aerosol particle" refers to a liquid or solid particle suspended in gas (e.g., air). Aerosol particles include, but are not limited to, aerosol droplets of liquid. Generally, aerosols have aerosol particles with sizes of e.g., between about 1 micron and about 100 microns, or in some cases between about 1 micron and about 20 microns, or between about 1 micron and about 10 microns.

As used herein, the term "selectively delivered" is used to refer to a composition, upon being delivered, which is delivered to a target organ (e.g., lungs), tissue, or cell at least 25% (e.g., at least 30%, 35%, 40%, 45%, 50%, 55%, 60%, 65%, 70%, or 75%) of the amount administered.

As used herein, the term "contacting" refers to allowing two species to interact, such as by chemical interactions including ionic, non-ionic, polar, hydrophobic, or hydrophilic interactions, or physically touch as accepted in the art, where the two species may be a lipid nanoparticle and a cell, mucus, or lining of tissue. In cell culture, an LNP may be contacted with a cell by mixing an LNP composition with a suitable cell culture media, or by allowing aerosol particles of the LNP composition to come into contact with the cell culture, such that the aerosol particles dissolve into liquid in the cell culture media, or liquid or mucus surrounding the cells, thereby allowing the LNPs to contact the cell.

As used herein, "preventing" or any grammatical variant thereof refers to inhibiting an onset of a disease in a subject or patient which may be at risk and/or predisposed to the disease but does not yet experience or display any or all of the pathology or symptomatology of the disease, and/or slowing the onset of the pathology or symptomatology of the disease in the subject or patient which may be at risk and/or predisposed to the disease but does not yet experience or display any or all of the pathology or symptomatology of the disease. The prevention may be complete (i.e., no detectable symptoms) or partial such that fewer symptoms are observed than would likely to occur absent treatment.

Reference throughout this specification to, for example, "one embodiment", "an embodiment", "another embodiment", "a particular embodiment", "a related embodiment", "a certain embodiment", "an additional embodiment", "a further embodiment", or "some embodiments" or any combination thereof means that a particular feature, structure or characteristic described in connection with the embodiment is included in at least one embodiment of the present disclosure. Thus, the appearances of the foregoing phrases in various places throughout the present disclosure are not necessarily all referring to the same embodiment. Furthermore, any particular feature, structure, or characteristic may be combined in any suitable manner in one or more embodiments.

As used herein, the term "nebulizer" refers to a device that can convert a liquid (e.g., a solution, dispersion, or suspension) into aerosol particles. This process is referred to as "nebulization." The term "nebulizing" refers to the process or state of converting a solution, aqueous dispersion, or suspension, such as a liquid pharmaceutical composition, into an aerosol. The terms "mesh nebulizer" and/or "vibrating mesh nebulizer" refer to nebulizers that achieve nebulization by passing an input substance through a mesh. Using a piezo-element, the mesh may be caused to vibrate, and these vibrating disperses the liquid into the surrounding air. The mesh of a mesh nebulizer may be characterized by the mesh pore size, and/or charge. Mesh nebulizers are driven by a piezo-element and use ultrasonic frequencies to vibrate the mesh. The vibration of the mesh can cause generation of aerosol particles as the liquid passes through it. Ultrasonic nebulizers, by contrast, produce ultrasonic waves directly into the solution causing aerosol particles to be produced at the liquid surface. Other means of generating aerosols include, but are not limited to, pressured metered-dose inhalers, dry-powder inhalers, jet nebulizers, soft mist inhalers, condensation aerosols, and aqueous nasal spray, as described in Chapter 30 of *Remington: The Science and Practice of Pharmacy* ($23^{rd}$ ed., 2021). Nebulizers are also characterized as vented or non-vented. Illustrative mesh nebulizers are described, for example, in U.S. Pat. No. 9,061,303. Illustrative mesh nebulizers useful in the practice of the presently disclosed methods include, but are not limited to, those made and sold by Aerogen®, PARI®, Activaero®, and Omron®.

As used herein, the term "aerosolized" or "aerosol" refer to a suspension of in which fine liquid and/or solid particles are dispersed in a gas, e.g., air. Dispersions in air, or gas of particles containing liquid. The aerosol generated from a nebulizer can refer to a mixture of air and vaporized particles generated from an aerosol-generating material, such as any of the aerosolized pharmaceutical compositions described herein. For example, a nebulizer can convert a liquid phase of any of the presently described pharmaceutical composition into a gaseous phase through e.g., ultrasonic vibrations. In another example, air jet mills can generate dry powder aerosols from dried lipid nanoparticles of the present disclosure. Non-limiting examples of air jet mills include Jet-O-Mizer, Trost jet mill, and the Microjet. In general, the aerosol particles of the present disclosure have low settling velocities and relative airborne stability. In some embodiments, the nebulizer converts a liquid pharmaceutical composition into an aerosolized pharmaceutical composition.

As used herein, the term "output rate" refers to the rate of nebulization of a liquid to an aerosol, generally expressed as the volume of the liquid converted to an aerosol per a given time (e.g., milliliters per minute or mL/min). Ouput rate may be determined by measuring the decrease in the volume of the input liquid over time.

As used herein, the term "apparent pKa" refers to the overall dissociation constant of all titratable groups in the lipid nanoparticles. Apparent pKa is an experimentally determined value of molecules or nanoparticles. Apparent pKa can be expressed as the pH at which the number of ionized (protonated) and deionized groups are equal in a system. The surface charge and ionic interaction of assembled nanomaterials in nanoparticles can be estimated according to apparent pKa. The apparent pKa of a nanoparticle can be the result of the average ratio of all the ionized to deionized groups in the nanoparticles. Thus, apparent pKa is not the intrinsic pKa value of any individual molecule. The apparent pKa of nanoparticles can be measured by various techniques. For example, acid-base titration of 2-(p-toluidino)-6-naphthalene sulfonic acid (TNS) fluorescent methods are widely used in determination of apparent pKa of blank nanoparticles.

The term "therapeutically effective amount," as used herein, refers to an amount of the therapeutic agent sufficient to treat a disease, a disorder, or a condition. For example, with regard to the use of LNPs with mRNA payload to treat e.g., cystic fibrosis (CF) or primary ciliary dyskinesia (PCD), a therapeutically effective amount is the dosage or concentration of the mRNA (e.g., CFTR or PCD mRNA) capable of eradicating, inhibiting, preventing, slowing down the progression of all or part of e.g., CF or PCD respiratory symptoms or some combination thereof. For the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. The "therapeutically effective amount" can vary depending, for example, but not limited to, on the compound, the disease, or the condition and/or symptoms thereof, severity of the disease or the condition and/or symptoms thereof, the age, weight, and/or health of the subject to be treated, and the judgment of the prescribing physician. An appropriate amount in any given instance can be ascertained by those skilled in the art or capable of determination by routine experimentation.

The term "pharmaceutically acceptable" refers to those compounds, materials, compositions, carriers, vehicles, diluents, excipients, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio and/or generally chemically and/or physically compatible with the other ingredients comprising the formulation.

The terms "lung disease," "pulmonary disease," "pulmonary disorder," broadly refer to diseases or disorders of lungs. Lung diseases may be characterized by symptoms including, but not limited to, difficulty breathing, coughing, airway discomfort and inflammation, increased mucus, and/or pulmonary fibrosis. Non-limiting examples of lung diseases include Primary Ciliary Dyskinesia (PCD) (also referred to as Kartageners Syndrome, or Immotile Cilia Syndrome), cystic fibrosis, asthma, lung cancer, Chronic Obstructive Pulmonary Disease (COPD), bronchitis, emphysema, bronchiectasis, pulmonary edema, pulmonary fibrosis, sarcoidosis, pulmonary hypertension, pneumonia, tuberculosis, Interstitial Pulmonary Fibrosis (IPF), Interstitial Lung Disease (ILD), Acute Interstitial Pneumonia (AIP), Respiratory Bronchiolitis-associated Interstitial Lung Disease (RBILD), Desquamative Interstitial Pneumonia (DIP), Non-Specific Interstitial Pneumonia (NSIP), Idiopathic Interstitial Pneumonia (IIP), Bronchiolitis obliterans, with Organizing Pneumonia (BOOP), restrictive lung disease, and pleurisy.

As used herein, the term "lipid nanoparticle" refers to a carrier or vehicle, formed by one or more lipid components, for payload (e.g., nucleic acid, protein, peptide, polypeptide, polynucleotide, or oligonucleotide) delivery in the context of pharmaceutical development. Lipid nanoparticle can have one or more lipids with at least one dimension on the order of nanometers (e.g., 1-1000 nm). Generally, lipid nanoparticle compositions for delivery are composed of one or more lipids, such as, but not limited to, a synthetic ionizable or cationic lipid, a phospholipid, a structural lipid, and a polyethylene glycol (PEG) lipid. These compositions may also include other lipids. In some embodiments, at least one therapeutic agent (e.g., mRNA) can be captured in the lipid portion of the lipid nanoparticle or an aqueous space enveloped by some or all of the lipid portion of the lipid nanoparticle, thereby protecting it from enzymatic degradation of other undesirable effect induced by the biological mechanism of a target subject, tissue, and/or cell, e.g., an adverse immune response. In some embodiments, lipid nanoparticles comprise at least one therapeutic agent (e.g., mRNA) that is either organized within inverse lipid micelles and encased within a lipid monolayer envelop or intercalated between adjacent lipid bilayers. In some embodiments, the morphology of lipid nanoparticles is not like a traditional liposome, which are characterized by a lipid bilayer surrounding an aqueous core. In some embodiments, lipid nanoparticles are substantially non-toxic. In some embodiments, the therapeutic agent (e.g., mRNA) is resistant in aqueous solution to degradation by intracellular or intercellular enzymes.

As used herein, the term "neutral phospholipid" refers to phospholipids that have little or no net charge at physiological pH. In some embodiments, neutral phospholipids are zwitterions, although other types of net neutral phospholipids are known and may be used. In some embodiments, neutral phospholipid can be any vesicle-forming lipid having two hydrocarbon chain moieties which can be effective to produce a stable bilayer formation and a polar head group with no net charge at pH between about 5.5-8.5. Neutral phospholipids having a variety of hydrocarbon chain (e.g., acyl chain) groups of varying chain length and degree of saturation can be readily obtained or can be isolated or synthesized by well-known techniques.

As used herein, the term "PEG-lipid" refers to a lipid modified with a polyethylene glycol unit. In some embodiments, the PEG-lipid comprises dimyristoyl glycerol (DMG). In some embodiments, the PEG-lipid comprises 1,2-distearoyl-sn-glycero-3-phosphorylethanolamine (DSPE).

As used herein, the term "sterol" refers to a subgroup of steroids with a hydroxyl group at the 3-position of the A-ring of a gonane ringsystem. "Cholesterol" is a sterol that has a structure of four fused hydrocarbon rings (gonane ringsystem) with a polar hydroxyl group at one end and an eight-carbon branched aliphatic tail at the other end. Without being bound by theory, the structure of the tetracyclic ring of cholesterol contributes to the fluidity of the cell membrane, as the molecule is in a trans conformation making all but the side chain of cholesterol rigid and planar. Cholesterol influences the fluidity, thickness, compressibility, water penetration and intrinsic curvature of lipid bilayers, for example in LNPs. For example, "sterol" can be cholesterol or sitosterol.

As used herein, the term "messenger RNA" or "mRNA" refers to a polynucleotide that encodes at least one polypeptide. mRNA as used herein encompasses both modified and unmodified RNA. mRNA may contain one or more reading frames or regions.

As used herein, the term "shRNA" or "shor hairpin RNA" refers to a short sequence of RNA, which can make a tight hairpin turn and can be used to silence gene expression.

As used herein, the term "microRNA" refers to noncoding RNA consisting of about 22 ribonucleotides, which can regulate gene expression in the post transcriptional stage by silencing messenger RNA by base-pairing with complementary sequence in its targeted mRNA.

As used herein, the phrase "N/P ratio" refers to a molar ratio of nitrogen in the lipid composition to phosphate in the polynucleotide payload.

As used herein, the phrase "lipid:RNA ratio" refers to milligram of lipid for each milligram of mRNA drug substance which influence the encapsulation efficiency of lipid nanoparticles.

As used herein, the phrase "lung cell" refers to lung airway cells. Examples of lung airway cells that can be targeted by delivering the compositions of the present disclosure include, but are not limited to, basal cell, secretory cell such as goblet cell and club cell, ciliated cell, and any combination thereof.

As used herein, the term "goblet cell" refers to a type of secretory cells. Goblet cells are situated in the epithelium of the conducting airways, often with their apical surfaces protruding into the lumen, a location that fits them for a rapid response to inhaled airway insults.

As used herein, the phrase "ciliated cells" refers to cells with cilia structures on the cell surface. Examples of ciliated cells include, but are not limited to, respiratory tract ciliated cells, oviduct ciliated cell, uterine endometrial ciliated cells, rete testis ciliated cells, ductulus efferent ciliated cells, and/or ciliated ependymal cells. Human respiratory tract ciliated cells can bear 200 to 300 cilia on their surface. Cilia are elongated motile cylindrical projections from the apical cell membrane, approximately 0.25 mm in diameter that contain microtubules and cytoplasm in continuity with that of the cell. Human tracheal cilia can be 5 to 8 mm long, becoming shorter in more distal airways.

The terms "subject" refers to a living organism to which any of the compositions as described herein may be administered. The subject may be suffering from or be at risk for a disease or condition that can be treated by administration of an aerosolized pharmaceutical composition as provided herein. Non-limiting examples of subjects include humans, other mammals, bovines, rats, mice, dogs, monkeys, goat, sheep, cows, deer, and other non-mammalian animals. In some embodiments, the subject is human.

The terms "identity," "identical," and "sequence identity" refer to the extend to which two optimally aligned polynucleotides or polypeptide sequences are invariant throughout a window of alignment of components, e.g., nucleotides or amino acids. "Identity" can readily be calculated by known methods, including, but not limited to, those described in Needleman and Wunsch, *J. Mol. Biol.* 48:443 (1970). as such one polynucleotide or polypeptide sequence has a certain percentage of sequence identity compared to another polynucleotide or polypeptide sequence. The term "percent sequence identity", "percent identity", or "identical to" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence. For sequence comparison, one sequence acts as a reference sequence, to which test sequences are compared. The term "reference sequence" refers to a molecule to which a test sequence is compared. Methods of sequence alignment for comparison and determination of percent sequence identity are well known in the art. Optimal alignment of sequences for comparison can be conducted, e.g., by the homology alignment algorithm of Needleman and Wunsch, (1970) *J. Mol. Biol.* 48:443.

As used herein, the phrase "substantially identical," or "substantial identity" in the context of two nucleic acid molecules, nucleotide sequences or protein sequences, refers to two or more sequences or subsequences that have at least about 80%, 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using one of the following sequence comparison algorithms or by visual inspection. In some embodiments of the present disclosure, the substantial identity exists over a region of consecutive nucleotides of a nucleotide sequence of the disclosure that is about 16 nucleotides to about 30 nucleotides, about 18 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 150 nucleotides to about 200 nucleotides, to about 250 nucleotide to about 400 nucleotides, about 500 nucleotides to about 750 nucleotides, about 700 nucleotides to about 1000 nucleotides, about 1250 nucleotides to about 2500 nucleotides, about 2000 nucleotides to about 4000 nucleotides, or more nucleotides in length, and any range therein, up to the full length of the sequence. In some embodiments, the sequences are substantially identical over the entire length of the coding regions. In some embodiments, substantially identical nucleotide or protein sequences perform substantially the same function (e.g., prenyltransferase activity).

The term "fragment" or "variant" refers to any functional fragment, variant, derivative or analog of a polynucleotide, polypeptide or biomolecule that possesses an in vivo or in vitro activity that is characteristic of the polynucleotide, polypeptide, or therapeutic agent. In some embodiments, the fragment, variant or analog has a length equal to 10%, 20%, 30%, 40%, 50%, 60%, 70%, 80% or 90% or greater of the length of the polynucleotide, polypeptide or biomolecule. Functional expression of the fragment or variant can be easily assayed by the person of ordinary skill in the art by testing enzymatic activity and the ability to manufacture products as described herein.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

As used herein, the phrase "chloride flux" refer to mass of ions incorporated into stimulated cells, or the release of ions from the stimulated cell. Measurement of chloride flux is described, for example, in Moran et al. J. Cystic Fibrosis 7:483-494 (2008).

As used herein, the phrase "transepithelial electrical resistance (TEER)" is a measurement method of electrical resistance across a cellular monolayer to confirm the integrity and permeability of a monolayer. Measurement of TEER is described, for example, in Srinivasan et al. J. Lab. Automation 20:107-126 (2015).

II. Compositions of the Disclosure

Provided herein are compositions and methods related to aerosolized pharmaceutical compositions, such as methods for treating lung diseases or lung disorders, some of which are characterized by difficulty breathing, coughing, airway discomfort and inflammation, increased mucus, and/or pulmonary fibrosis, or other conditions that may be treated by administering agents with aerosolized pharmaceutical compositions. The compositions and methods of the present disclosure provide aerosol particles, where the aerosol particles include lipid nanoparticles (LNPs), and the composition can deliver the LNPs to e.g., a tracheobronchial region of a subject.

The aerosolized pharmaceutical composition comprises LNPs. In some embodiments, the LNPs can selectively deliver to one or more of goblet cells, secretory cells, club cells, basal cells or ionocytes. In some embodiments, the LNPs can selectively deliver to one or more of ciliated cells, club cells, or basal cells.

In one aspect, provided herein is a lipid composition comprising: (i) an ionizable lipid; (ii) a helper lipid; (iii) a PEG-lipid, and (iv) a sterol. In some embodiments, the lipid composition further includes (v) an additional ionizable or a permanently cationic lipid.

In some embodiments, the lipid nanoparticles described herein may be prepared according to any of the methods described in International Publication Nos. WO2016094342, WO2017048789, WO2017201091, WO2017205767, WO201/246203, WO2020051220, WO2022169508, WO2022204053 and WO2022204215; the contents of each of which are incorporated herein by reference in their entireties.

A. Ionizable Lipids

In some embodiments of the lipid composition of the present disclosure, the lipid composition comprises an ionizable lipid. In some embodiments, the ionizable lipid is an ionizable cationic lipid. In some embodiments, the ionizable cationic lipid can contain one or more groups which is protonated at physiological pH but may deprotonate and has no charge at a pH above the pKa of the lipid. The ionizable cationic group may contain one or more protonatable amines, which are able to form a cationic group at physiological pH. The cationic ionizable lipid may also further comprise one or more lipid components, such as two or more fatty acids with $C_6$-$C_{24}$ alkyl or alkenyl carbon groups. The one or more lipid components may be attached to the cationic ionizable lipid through an ester linkage or may be further added through a Michael addition to a sulfur atom. In some embodiments, the one or more lipid components may be a dendrimer, a dendron, a polymer, or a combination thereof.

Ionizable lipid has its ordinary meaning in the art and may refer to a lipid comprising one or more charged moieties. In some embodiments, an ionizable lipid may be positively charged or negatively charged. For instance, an ionizable lipid may be positively charged at lower pHs, in which case it could be referred to as "cationic lipid." In certain embodiments, an ionizable lipid may comprise an amine group and can be referred to as an ionizable amino lipids. A charged moiety is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Non-limiting examples of positively charged moieties include amine groups (e.g., primary, secondary, and/or tertiary amines), ammonium groups, pyridinium group, guanidine groups, and imidazolium groups. In a particular embodiment, the charged moieties comprise amine groups. Non-limiting examples of negatively charged groups or precursors thereof, include carboxylate groups, sulfonate groups, sulfate groups, phosphonate groups, phosphate groups, hydroxyl groups, and the like. The charge of a charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

A lipid nanoparticle composition of the present disclosure may include one or more ionizable (e.g., ionizable amino) lipids (e.g., lipids that may have a positive or partial positive charge at physiological pH). Ionizable lipids may be selected from the non-limiting group consisting of 3-(didodecylamino)-N1,N1,4-tridodecyl-1-piperazineethanamine (KL$^{10}$), N1-[2-(didodecylamino)ethyl]N1,N4,N4-tridodecyl-1,4-piperazinediethanamine (KL$^{22}$), 14,25-ditridecyl-15,18,21,24-tetraaza-octatriacontane (KL$^{25}$), 1,2-dilinoleyloxy-N,N-dimethylaminopropane (Dlin-DMA), 2,2-dilinoleyl-4-dimethylaminomethyl-[1,3]-dioxolane (Dlin-K-DMA), heptatriaconta-6,9,28,31-tetraen-19-yl-4-(dimethylamino)butanoate (Dlin-MC3-DMA), 2,2-dilinoleyl-4-(2 dimethylaminoethyl)-[1,3]-dioxolane (Dlin-KC2-DMA), 1,2-dioleyloxy-N,N dimethylaminopropane (DODMA), 2-({8 [(3(3)-cholest-5-en-3-yloxy]octylIoxy) N,N dimethyl-3-[(9Z,12Z)-octadeca-9,12-dien-1-yloxy]propan-1-amine (Octyl-CLinDMA), (2R)-2-({8-[(3(3)-cholest-5-en-3-yloxy]octylIoxy)-N,N-dimethyl-3-[(9Z,12Z)-octadeca-9,12-dien-1-yloxy]propan-1-amine (Octyl-CLinDMA (2R)), and (2S) 2-({8-[(3(3)-cholest-5-en-3-yloxy]octyl}oxy)-N,N-dimethyl-3-[(9Z,12Z)-octadeca-9,12-di en-1-yloxy]propan-1-amine (Octyl-CLinDMA (2S)), 4-hydroxybutyl) azanediyl)bis(hexane-6,1-diyl)bis(2-hexyldecanoate (ALC-0315), or heptadecan-9-yl 8-((2-hydroxyethyl) (6-oxo-6-(undecyloxy)hexyl)amino)octanoate (SM-102). In addition to these, an ionizable lipid may also be a lipid including a cyclic amine group.

Ionizable lipids can also be the compounds disclosed in International Publication No. WO 2017075531 A1, hereby incorporated by reference in its entirety. Ionizable lipids can also be the compounds disclosed in International Publication No. WO 2015199952 A1, hereby incorporated by reference in its entirety. In one embodiment, the ionizable lipid may be selected from, but not limited to, an ionizable lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466,122 and US Patent Publication No. US20100036115, US20120202871, US20130064894, US20130129785, US20130150625, US20130178541 and S20130225836; the contents of each of which are herein incorporated by reference in their entirety.

As a non-limiting example, a cationic lipid may be selected from (20Z,23Z)-N,N-dimethylnonacosa-20,23-dien-10-amine, (17Z,20Z)-N,N dimemylhexacosa-17,20-dien-9-amine, (1Z,19Z)-N5N-dimethylpentacosa-16, 19-dien-8-amine, (13Z,16Z)-N,N-dimethyldocosa-13,16-dien-5-amine, (12Z,15Z)-N,N dimethylhenicosa-12,15-dien-4-amine, (14Z,17Z)-N,N-dimethyltricosa-14,17-di en-6-amine, (15Z,18Z)-N,N-dimethyltetracosa-15,18-dien-7-amine, (18Z,21Z)-N,N dimethylheptacosa-18,21-dien-10-amine, (15Z,18Z)-N,N-dimethyltetracosa-15,18-dien-5-amine, (14Z,17Z)-N,N-dimethyltricosa-14,17-dien-4-amine, (19Z,22Z)-N,N dimeihyloctacosa-19,22-dien-9-amine, (18Z,21 Z)-N,N-dimethylheptacosa-18,21-dien-8 amine, (17Z,20Z)-N,N-dimethylhexacosa-17,20-dien-7-amine, (16Z,19Z)-N,N dimethylpentacosa-16,19-dien-6-amine, (22Z,25Z)-N,N-dimethylhentriaconta-22,25-dien-10-amine, (21 Z,24Z)-N,N-dimethyltriaconta-21,24-dien-9-amine, (18Z)-N,N dimetylheptacos-18-en-10-amine, (17Z)-N,N-dimethylhexacos-17-en-9-amine, (19Z,22Z)-N,N-dimethyloctacosa-19,22-dien-7-amine, N,N-dimethylheptacosan-10-amine, (20Z,23Z)-N-ethyl-N-methylnonacosa-20,23-dien-10-amine, 1-[(11Z,14Z)-1-nonylicosa-11,14-dien-1-yl]pyrrolidine, (20Z)-N,N-dimethylheptacos-20-en-1 O-amine, (15Z)-N,N-dimethyl eptacos-15-en-1 O-amine, (14Z)-N,N-dimethylnonacosa-14-en-10-amine, (17Z)-N,N-dimethylnonacos-17-en-10-amine, (24Z)-N,N-dimethyltritriacont-24-en-10-amine, (20Z)-N,N-dimethylnonacos-20-en-1 O-amine, (22Z)-N,N dimethylhentriacont-22-en-10-amine, (16Z)-N,N-dimethylpentacos-16-en-8-amine, (12Z,15Z)-N,N-dimethyl-2-nonylhenicosa-12,15-dien-1-amine, (13Z,16Z)-N,N dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N dimethylnonadecan-10-amine, N,N-dimethyl-1-[(1S,2R)-2-oetylcyclopropyl]nonadecan-10-amine, N,N-dimethyl-21-[(1S,2R)-2-octylcyclopropyl] henicosan-10-amine,N,N-dimethyl-1-[(1S,2S)-2-{[(1R, 2R)-2-pentylcy clopropyl]methyl}cyclopropyl]nonadecan-10-amine,N,N-di methyl-1-[(1S,2R)-2-octylcyclopropyl] hexadecan-8-amine, N,N-dimethyl-[(1R,2S)-2 undecylcyclopropyl]tetradecan-5-amine, N,N-dimethyl-3-{7-[(1S,2R)-2-octylcyclopropyl]heptyl dodecan-1-amine, 1-[(1R,2S)-2-heptylcyclopropyl]-N,N dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R-N,N dimethyl-1-[(9Z, 12Z)-octadeca-9,12-dien-1-yloxy]-3-(octyloxy)propan-2-amine, S-N,N dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl] ethylpyrrolidine, (2S)-N,N dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethylazetidin, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yl oxy]propan-2-amine, N,N-di methyl-1-[(9Z)-octadec-9-en-1-yloxy]-3-(octyl oxy)propan-2-amine; (2 S)-N,N-dimethyl-1-[(6Z,9Z,12Z)-octadeca-6, 9,12-tri en-1-yloxy]-3-(octyloxy)propan-2-amine, (2 S)-1-[(11Z,14Z)-icosa-11, 14-dien-1-yloxy]-N,N dimethyl-3-(pentyloxy)propan-2-amine, (2 S)-1-(hexyl oxy)-3-[(11Z,14Z)-i co sa-11,14-di en-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N, N-dimethyl-3-(octyloxy)propan-2-amine, (2 S)-1-[(13Z, 16Z)-docosa-13,16-dien-1-yl oxy]-3-(hexyl oxy)-N,N-dimethylprop an 2-amine, (2 S)-1-[(13Z)-docosa-13-en-1-yl oxy]-3-(hexyloxy)-N,N-dimethylpropan-2-amine, 1-[(13Z)-docos-13-en-1-yloxy]-N,N dimethyl-3-(octyl oxy)propan-2-amine, 1-[(9Z)-hexadec-9-en-1-yloxy]-N,N-dimethyl-3-(octyloxy)propan-2-amine, (2R)-N,N-dimethyl-H(1-methyloctyl)oxy]-3-[(9Z,12Z)-octadeca-9,12-dien-1-yloxy]propan-2-amine, (2R)-1-[(3,7-dimethyloctyl)oxy]-N,N dimethyl-3-[(9Z,12Z)-octadeca-9,12-di en-1-yloxy]propan-2-amine, N,N-dimethyl-1-(octyloxy)-3-({8-[(1 S,2 S)-2-[(1R,2R)-2-pentylcyclopropyl]methylcyclopropyl]octylI-oxy)propan-2-amine, N,N-dimethyl-1-[8-(2-octylcyclopropyl)octyl]oxy}-3-(octyl oxy)propan-2-amine and (11E,20Z,23Z)-N,N dimethylnonacosa-11,20,2-trien-10-amine or a pharmaceutically acceptable salt or stereoisomer thereof.

In some embodiments of the lipid composition of the present application, the ionizable cationic lipids refer to lipid and lipid-like molecules with nitrogen atoms that can acquire a positive charge. The ionizable cationic lipids may be known in the literature as cationic lipids. The ionizable cationic lipids with amino groups typically have between 2 and 6 hydrophobic tails, often alkyl or alkenyl such as $C_6$-$C_{24}$ alkyl or alkenyl groups, but may have at least 1, at least 2, at least 3, at least 4, at least 5, or more than 6 tails.

1. Dendrimers

In some embodiments, the cationic ionizable lipids are dendrimers. Dendrimers are a polymer exhibiting regular dendritic branching, formed by the sequential or generational addition of branched layers to or from a core and are characterized by a core, at least one interior branched layer, and a surface branched layer. (See Petar R. Dvornic and Donald A. Tomalia in *Chem. In Britain,* 641-645, August 1994.) A dendrimer includes, but is not limited to, a molecular architecture with an initiator core, repetitive layers (or generations) of repeating units regularly attached to this initiator core, and an exterior surface of terminal groups attached to the outermost generation. A dendron is a species of dendrimer having branches emanating from a focal point, which is or can be joined to a core, either directly or through a linking moiety to form a larger dendrimer. In some embodiments, a dendrimer structure has radiating repeating groups from a central core, which doubles with each repeating unit for each branch. In some embodiments, the dendrimers described herein may be described as small molecules, medium-sized molecules, lipids, or lipid-like materials. These terms may be used to describe compounds with a dendron like appearance (e.g., molecules which radiate from a single focal point).

While dendrimers are polymers, dendrimers may be preferable over traditional polymers because they have a controllable structure, a single molecular weight, numerous and controllable surface functionalities, and traditionally adopt a globular conformation after reaching a specific generation. Dendrimers can be prepared by sequential reactions of each repeating unit to produce monodisperse, tree-like and/or generational structure polymeric structures. Individual dendrimers consist of a central core molecule, with a dendritic wedge attached to one or more functional sites on that central core. The dendrimeric surface layer can have a variety of functional groups disposed thereon including anionic, cationic, hydrophilic, or lipophilic groups, according to the assembly monomers used during the preparation.

Modifying the functional groups and/or the chemical properties of the core, repeating units, and the surface or terminating groups, their physical properties can be modulated. Some properties which can be varied include, but are not limited to, solubility, toxicity, immunogenicity and bio-attachment capability. Dendrimers are often described by their generation or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible, resulting from only the first condensation reaction with amines and without the second condensation reaction with thiols.

Preparation of dendrimers requires a level of synthetic control achieved through series of stepwise reactions comprising building the dendrimer by each consecutive group. Dendrimer synthesis can be of a convergent or divergent type. During divergent dendrimer synthesis, the molecule is assembled from the core to the periphery in a stepwise process involving attaching one generation to the previous and then changing functional groups for the next stage of reaction. Functional group transformation is necessary to prevent uncontrolled polymerization. Such polymerization can lead to a highly branched molecule that is not monodisperse and is otherwise known as a hyperbranched polymer. Due to steric effects, continuing to react dendrimer repeat units leads to a sphere shaped or globular molecule, until steric overcrowding prevents a complete reaction at a specific generation and destroys the molecule's monodispersity. Thus, in some embodiments, the dendrimers of G1-G10 generation are specifically contemplated. In some embodiments, the dendrimers comprise 1, 2, 3, 4, 5, 6, 7, 8, 9, or 10 repeating units, or any range derivable therein. In some embodiments, the dendrimers used herein are G0, G1, G2, or G3. However, the number of possible generations (such as 11, 12, 13, 14, 15, 20, or 25) may be increased by reducing the spacing units in the branching polymer.

Additionally, dendrimers have two major chemical environments: the environment created by the specific surface groups on the termination generation and the interior of the dendritic structure which due to the higher order structure can be shielded from the bulk media and the surface groups. Because of these different chemical environments, dendrimers have found numerous different potential uses including in therapeutic applications.

In some embodiments of the lipid compositions of the present disclosure, the dendrimers are assembled using a differential reactivity of acrylate and methacrylate groups with amines and thiols. The dendrimers may include secondary or tertiary amines and thioethers formed by a reaction of an acrylate group with a primary or secondary amine and a methacrylate with a mercapto group. Additionally, repeating units of the dendrimers may contain groups degradable under physiological conditions. In some embodiments, the repeating units may contain one or more germinal diethers, esters, amides, or disulfides groups. In some embodiments, the core molecule is a monoamine, which allows dendritic polymerization in only one direction. In other embodiments, the core molecule is a polyamine with multiple different dendritic branches which each may comprise one or more repeating units. The dendrimer may be formed by removing one or more hydrogen atoms from this core. In some embodiments, these hydrogen atoms are on a heteroatom such as a nitrogen atom. In some embodiments, the terminating group is a lipophilic group, such as a long chain alkyl or alkenyl group. In other embodiments, the terminating group is a long chain haloalkyl or haloalkenyl group. In other embodiments, the terminating group is an aliphatic or aromatic group containing an ionizable group, such as an amine (—NH$_2$) or a carboxylic acid (—CO$_2$H). In still other embodiments, the terminating group is an aliphatic or aromatic group containing one or more hydrogen bond donors, such as a hydroxide group, an amide group, or an ester.

The cationic ionizable lipids of the present disclosure may contain one or more asymmetrically substituted carbon or nitrogen atoms and may be isolated in an optically active or racemic form. Thus, all chiral, diastereomeric, racemic form, epimeric form, and all geometric isomeric forms of a chemical formula are intended, unless the specific stereochemistry or isomeric form is specifically indicated. Cationic ionizable lipids may occur as racemates and racemic mixtures, single enantiomers, diastereomeric mixtures and individual diastereomers. In some embodiments, a single diastereomer is obtained. The chiral centers of the cationic ionizable lipids of the present disclosure can have the S or the R configuration. Furthermore, it is contemplated that one or more of the cationic ionizable lipids may be present as constitutional isomers. In some embodiments, the compounds have the same formula but different connectivity to the nitrogen atoms of the core. Without being to be bound by theory, it is believed that such cationic ionizable lipids can exist because the starting monomers react first with primary amines and then statistically with any secondary amines present. Thus, the constitutional isomers may present fully reacted primary amines and then a mixture of reacted secondary amines.

Chemical formulas used to represent cationic ionizable lipids of the present disclosure will typically only show one of possibly several different tautomers. For example, many types of ketone groups are known to exist in equilibrium with corresponding enol groups. Similarly, many types of imine groups can exist in equilibrium with enamine groups. Regardless of which tautomer is depicted for a given formula, and regardless of which one is most prevalent, all tautomers of a given chemical formula are intended herein.

The cationic ionizable lipids of the present disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the cationic ionizable lipids of the present application are intended to include all isotopic forms of such atoms. Isotopes include atoms having the same atomic number but different mass numbers. By way of general example and without limitation, isotopes of hydrogen include tritium and deuterium, and isotopes of carbon include $^{13}$C and $^{14}$C.

It should be recognized that an anion or a cation forming a part of any salt form of cationic ionizable lipids provided herein is not critical, so long as the salt, as a whole, is pharmaceutically acceptable. Additional examples of pharmaceutically acceptable salts and their methods of preparation and use are presented in *Handbook of Pharmaceutical Salts: Properties, and Use* (2002), which is incorporated herein by reference in its entirety.

In some embodiments of the lipid compositions of the present disclosure, an ionizable lipid is a dendrimer or dendron. In some embodiments, an ionizable lipid comprises an ammonium group which is positively charged at physiological pH and contains at least two hydrophobic groups. In some embodiments, the ammonium group is positively charged at a pH from about 6 to about 8. In some embodiments, the ionizable lipid is a dendrimer or dendron. In some embodiments, an ionizable lipid comprises at least two $C_6$-$C_{24}$ alkyl or alkenyl groups.

Modifying the functional groups and/or the chemical properties of the core, repeating units, and the surface or terminating groups, their physical properties can be modulated. Some properties which can be varied include, but are not limited to, solubility, toxicity, immunogenicity and bioattachment capability. Dendrimers are often described by their generations or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible, resulting from only a first condensation reaction with amines and without a second condensation reaction with thiols.

2. Dendrimers of Formula (I)

In some embodiments of the lipid compositions of the present disclosure, the ionizable lipid comprises at least two $C_8$-$C_{24}$ alkyl groups. In some embodiments, the ionizable lipid is a dendrimer further defined by the formula:

Core-(Repeating Unit)$_n$-Terminating Group (*D-I*)

wherein one or more hydrogen atoms of the core are replaced with a repeating unit and wherein:

the core has the formula:

(D-II)

wherein:
X$_1$ is amino or C$_1$-C$_{12}$ alkylamino, C$_1$-C$_{12}$ dialkylamino, C$_3$-C$_{12}$ heterocycloalkyl,
C$_5$-C$_{12}$heteroaryl, or a substituted version thereof;
R$_1$ is amino, hydroxy, mercapto, C$_1$-C$_{12}$ alkylamino, or C$_1$-C$_{12}$ dialkylamino, or a substituted version of either of these groups; and
a is 1, 2, 3, 4, 5, or 6; or
the core has the formula:

(D-III)

wherein:
X$_2$ is N(R$_5$)$_y$;
R$_5$ is hydrogen, C$_1$-C$_{18}$ alkyl, or substituted C$_1$-C$_{18}$ alkyl; and
y is 0, 1, or 2, provided that the sum of y and z is 3;
R$_2$ is amino, hydroxy, mercapto, C$_1$-C$_{12}$ alkylamino, or C$_1$-C$_{12}$ dialkylamino, or a substituted version of either of these groups;
b is 1, 2, 3, 4, 5, or 6; and
z is 1, 2, or 3; provided that the sum of z and y is 3; or
the core has the formula:

(D-IV)

wherein:
X$_3$ is —NR$^6$—, wherein R$_6$ is hydrogen, C$_1$-C$_8$ alkyl, or C$_1$-C$_8$ substituted alkyl, —O—, or C$_1$-C$_8$ alkylaminodiyl, C$_1$-C$_8$ alkoxydiyl, C$_6$-C$_8$ arenediyl, C$_5$-C$_8$heteroarenediyl, C$_3$-C$_8$ heterocycloalkanediyl, or a substituted version of any of these groups;
R$_3$ and R$_4$ are each independently amino, hydroxy, mercapto, C$_1$-C$_{12}$ alkylamino, or C$_1$-C$_{12}$ dialkylamino, or a substituted version of either of these groups; or a group of the formula: —N(R$_f$)$_f$(CH$_2$CH$_2$N(R$_c$))$_e$R$_d$,

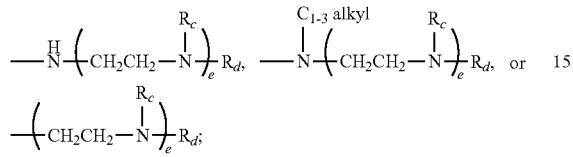

wherein:
e and f are each independently 1, 2, or 3; provided that the sum of e and f is 3;
R$_c$, R$_d$, and R$_f$ are each independently hydrogen, C$_1$-C$_6$ alkyl, or substituted C$_1$-C$_6$ alkyl;
c and d are each independently 1, 2, 3, 4, 5, or 6; or
the core is C$_4$-C$_{18}$ alkylamine, C$_1$-C$_{36}$ dialkylamine, C$_3$-C$_{12}$ heterocycloalkane, or a substituted version of any of these groups;
wherein the repeating unit comprises a degradable diacyl or a degradable diacyl and a linker;
the degradable diacyl group has the formula:

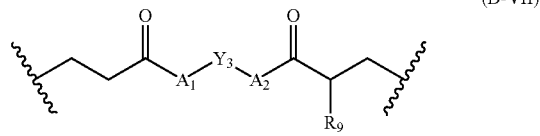 (D-VII)

wherein:
A$_1$ and A$_2$ are each independently —O—, —S—, or —NR$^a$—, wherein:
R$_a$ is hydrogen, C$_1$-C$_6$ alkyl, or substituted C$_1$-C$_6$ alkyl;
Y$_3$ is C$_1$-C$_{12}$ alkanediyl, C$_1$-C$_{12}$ alkenediyl, C$_6$-C$_{12}$ arenediyl, or a substituted version of any of these groups; or a group of the formula:

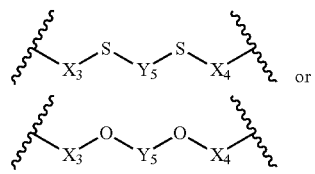

wherein:
X$_3$ and X$_4$ are C$_1$-C$_{12}$ alkanediyl, C$_2$-C$_{12}$ alkenediyl, C$_6$-C$_{12}$ arenediyl, or a substituted version of any of these groups;
Y$_5$ is a covalent bond, C$_1$-C$_{12}$ alkanediyl, C$_1$-C$_{12}$ alkenediyl, C$_6$-C$_{12}$ arenediyl, or a substituted version of any of these groups; and
R$_9$ is C$_1$-C$_8$ alkyl or substituted C$_1$-C$_8$ alkyl;

the linker group has the formula:

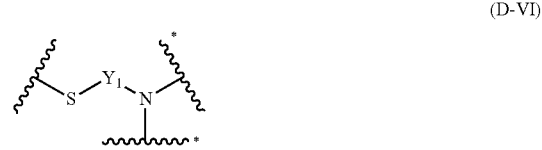 (D-VI)

wherein:
Y$_1$ is C$_1$-C$_{12}$ alkanediyl, C$_1$-C$_{12}$ alkenediyl, C$_6$-C$_{12}$ arenediyl, or a substituted version of any of these groups; and wherein each

independently denotes a point of attachment to another repeating unit or a terminating group; and
the terminating group has the formula:

 (D-VIII)

wherein:
Y$_4$ is alkanediyl or an C$_1$-C$_{18}$ alkanediyl wherein one or more of the hydrogen atoms on the C$_1$-C$_{18}$ alkanediyl has been replaced with —OH, —F, —Cl, —Br, —I, —SH, —OCH$_3$, —OCH$_2$CH$_3$, —SCH$_3$, or —OC(O)CH$_3$;
R$_{10}$ is hydrogen, carboxy, hydroxy, C$_6$-C$_{12}$ aryl, C$_1$-C$_{12}$ alkylamino, C$_1$-C$_{12}$ dialkylamino, C$_3$-C$_{12}$N-heterocycloalkyl, —C(O)N(R$_{11}$)—C$_1$-C$_6$ alkanediyl-C$_3$-C$_{12}$heterocycloalkyl, —C(O)—C$_1$-C$_{12}$ alkylamino, —C(O)—C$_1$-C$_{12}$ dialkylamino, or —C(O)—C$_3$-C$_{12}$N-heterocycloalkyl, wherein:
R$_{11}$ is hydrogen, C$_1$-C$_6$ alkyl, or substituted C$_1$-C$_6$ alkyl;
wherein the final degradable diacyl in the chain is attached to a terminating group;
n is 0, 1, 2, 3, 4, 5, or 6;
or a pharmaceutically acceptable salt thereof.
In some embodiments, the terminating group is further defined by the formula:

 (D-VIII)

wherein:
Y$_4$ is C$_1$-C$_{18}$ alkanediyl; and
R$_{10}$ is hydrogen. In some embodiments, A$_1$ and A$_2$ are each independently —O— or —NR$^a$—.
In some embodiments of the dendrimer of formula (D-I), the terminating group is a structure selected from the structures in Table 3.
In some embodiments of the dendrimer of formula (D-I), the core is further defined by the formula:

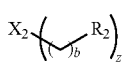 (D-III)

wherein:
X$_2$ is N(R$_5$)$_y$;
R$_5$ is hydrogen or C$_1$-C$_8$ alkyl, or substituted C$_1$-C$_{18}$ alkyl; and
y is 0, 1, or 2, provided that the sum of y and z is 3;
R$_2$ is amino, hydroxy, or mercapto, or C$_4$-C$_{12}$ alkylamino, C$_1$-C$_{12}$ dialkylamino, or a substituted version of either of these groups;
b is 1, 2, 3, 4, 5, or 6; and
z is 1, 2, 3; provided that the sum of z and y is 3.

In some embodiments of the dendrimer of formula (D-I), the core is further defined by the formula:

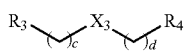 (D-IV)

wherein:
X$_3$ is —NR$^6$—, wherein R$_6$ is hydrogen, C$_1$-C$_8$ alkyl, or substituted C$_1$-C$_8$ alkyl, —O—, or C$_1$-C$_8$ alkylaminodiyl, C$_1$-C$_8$ alkoxydiyl, C$_1$-C$_8$ arenediyl, C$_1$-C$_8$ heteroarenediyl, C$_1$-C$_8$ heterocycloalkanediyl, or a substituted version of any of these groups;
R$_3$ and R$_4$ are each independently amino, hydroxy, or mercapto, or C$_1$-C$_{12}$ alkylamino, dialkylamino, or a substituted version of either of these groups; or a group of the formula:

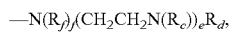

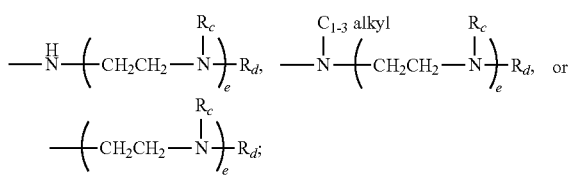

wherein:
e and f are each independently 1, 2, or 3; provided that the sum of e and f is 3;
R$_c$, R$_d$, and R$_f$ are each independently hydrogen, C$_1$-C$_6$ alkyl, or substituted C$_1$-C$_6$ alkyl;
c and d are each independently 1, 2, 3, 4, 5, or 6.

In some embodiments of the dendrimer of formula (I), the terminating group is represented by the formula:

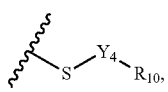 (D-VIII)

wherein:
Y$_4$ is alkanediyl(C≤18); and
R$_{10}$ is hydrogen.

In some embodiments of the dendrimer of formula (D-I), a core of the structure of formula (D-IV) is:

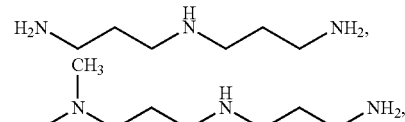

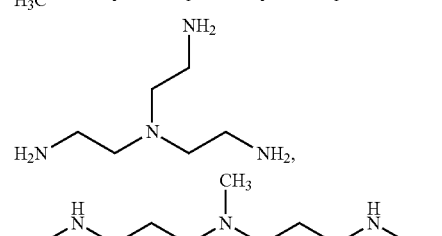

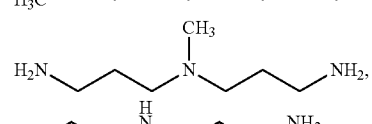

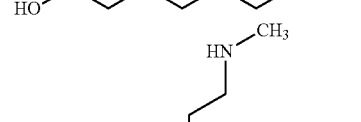

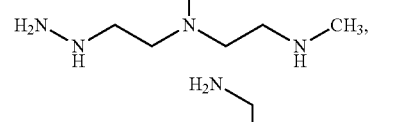

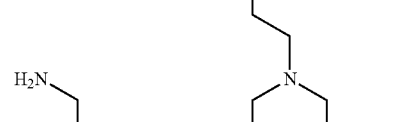

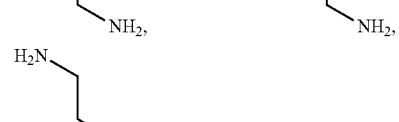

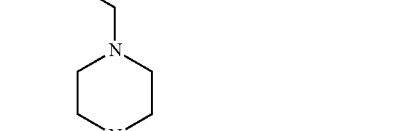

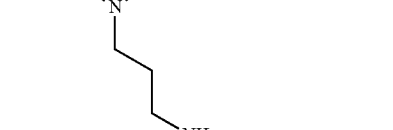

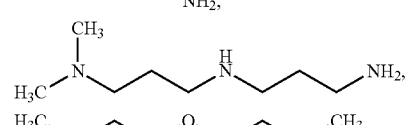

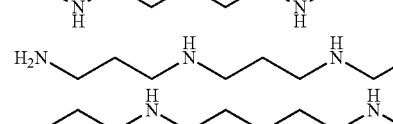

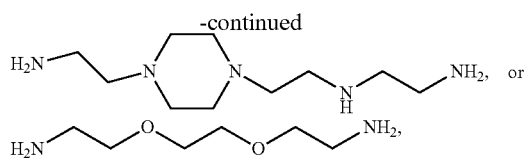 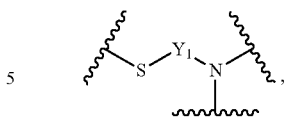

or a pharmaceutically acceptable salt thereof.

In some embodiments of the dendrimer of formula (D-I), the core comprises a structural formula set forth in Table 2 and pharmaceutically acceptable salts thereof, wherein * indicates a point of attachment of the core to a repeating unit (i.e., where a hydrogen of the core is replaced with a repeating unit).

In some embodiments of the dendrimer of formula (D-I), the degradable diacyl is further defined as:

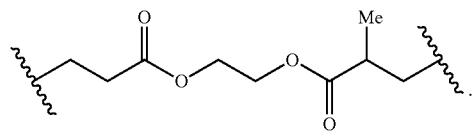 [SMILES: *CCC(=O)OCCOC(=O)C(C)C*]

In some embodiments of the dendrimer of formula (D-I), the linker is further defined as wherein $Y_1$ is $C_1$-$C_8$ alkanediyl or substituted $C_1$-$C_{12}$ alkanediyl.

In some embodiments, in the core of formula (D-IV), $R_6$ is H. In some embodiments, in the core of formula (D-IV), $R_6$ is $C_1$-$C_8$ alkyl. In some embodiments, in the core of formula (D-IV), $R_6$ is substituted alkyl (e.g., alkyl substituted with —$NH_2$, alkyl substituted with —$NHCH_3$, or alkyl substituted with —$NHCH_2CH_3$).

In some embodiments, one or two hydrogen atoms of the core are replaced with a repeating unit. In some embodiments, three or four hydrogen atoms of the core are replaced with a repeating unit. In some embodiments, five hydrogen atoms of the core are replaced with a repeating unit. In some embodiments, six hydrogen atoms of the core are replaced with a repeating unit.

In some embodiments of the dendrimer of formula (D-I), the dendrimer is selected from the group consisting of:

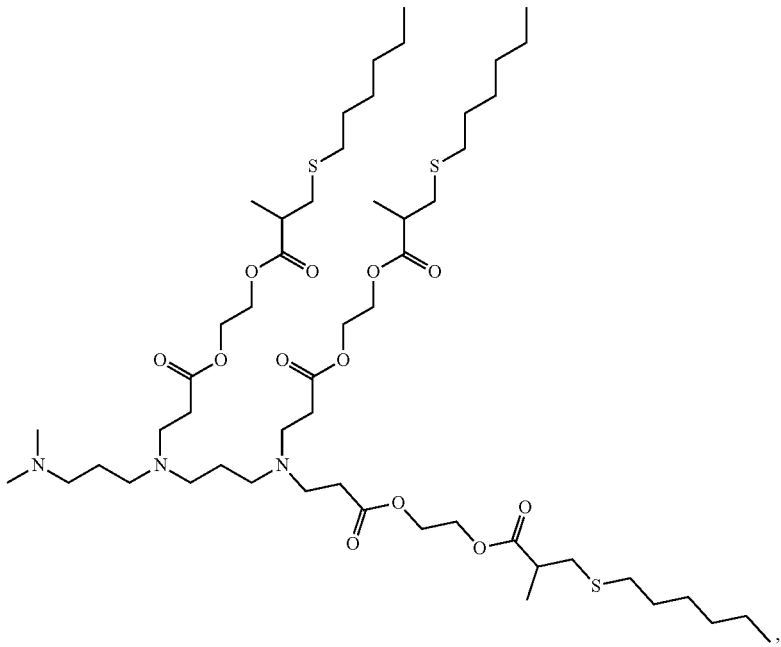

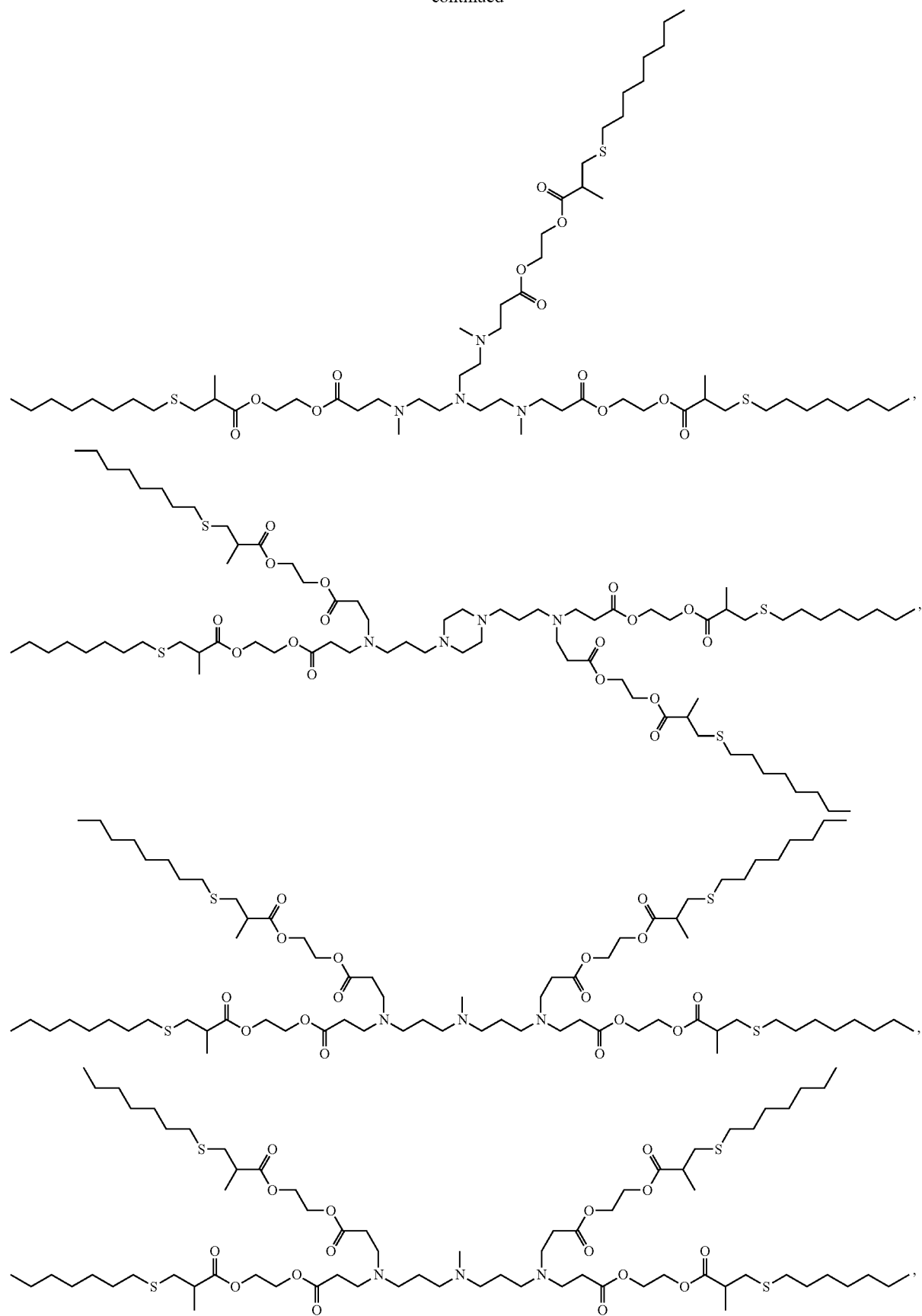

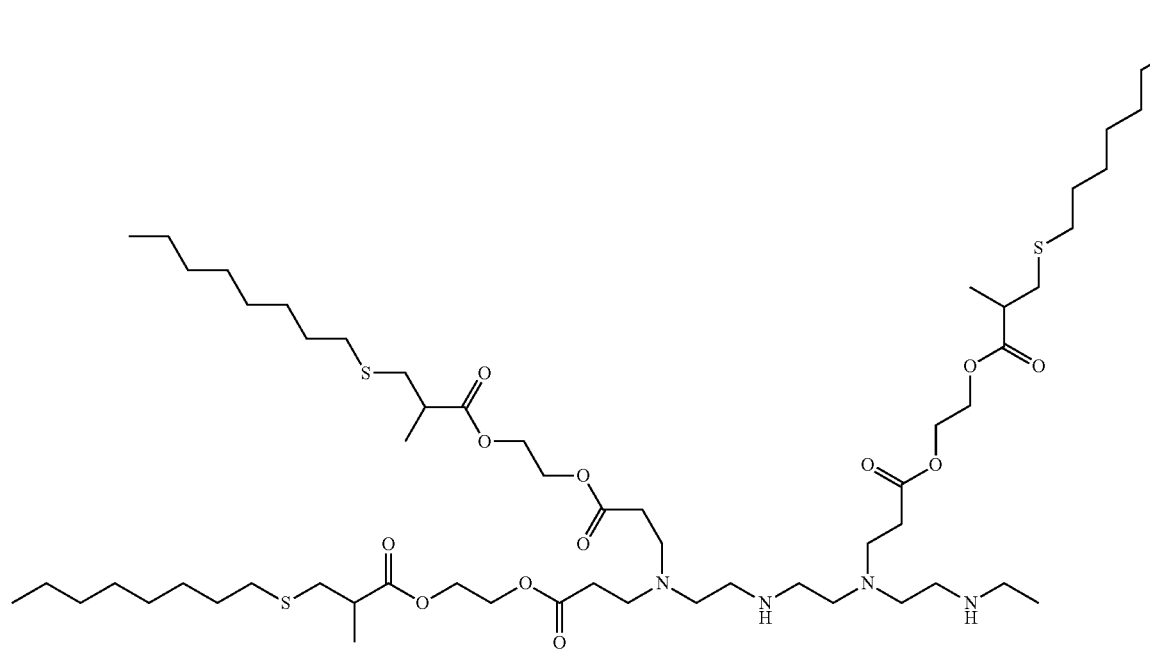
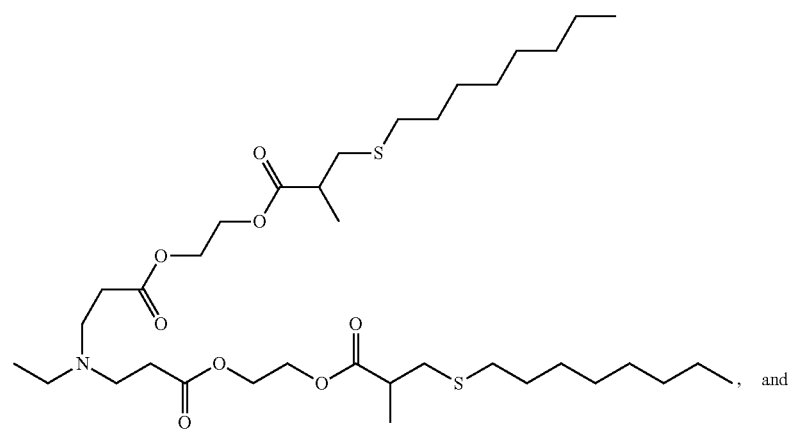

-continued

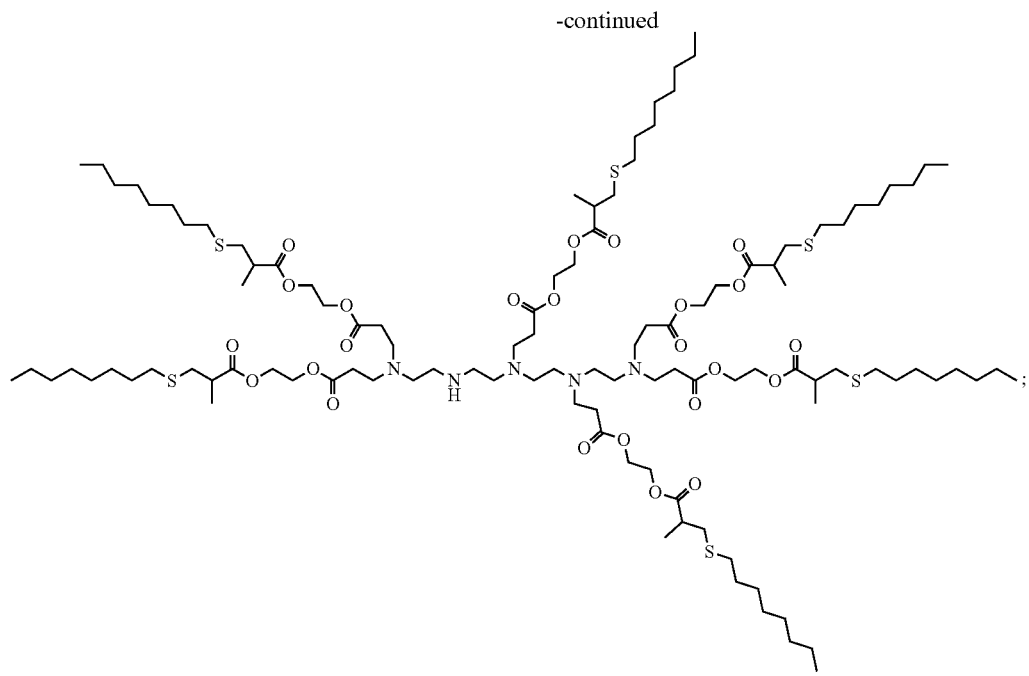

and pharmaceutically acceptable salts thereof.

1. Dendrimers of Formula (X)

In some embodiments of the lipid composition, the ionizable lipid is a dendrimer of the formula Core—(Branch)$_N$.

In some embodiments, the ionizable lipid is a dendrimer of the formula

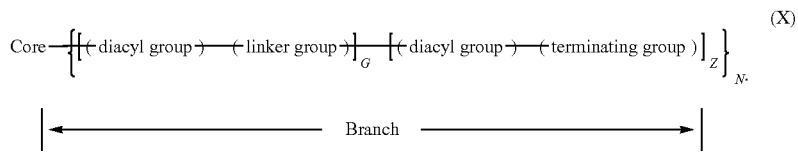

In some embodiments of the lipid composition, the ionizable lipid is a dendrimer of a generation (g) having a structural formula:

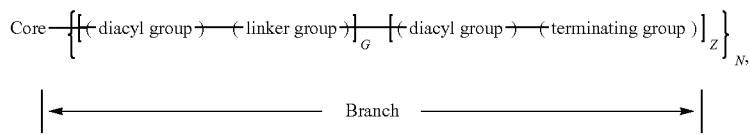

or a pharmaceutically acceptable salt thereof, wherein: (VI) the core comprises a structural formula ($X_{Core}$):

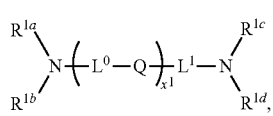

wherein:

Q is independently at each occurrence a covalent bond, —O—, —S—, —NR$^2$—, or —CR$^{3a}$R$^{3b}$—;

R$^2$ is independently at each occurrence R$^{1g}$ or —L$^2$—NR$^{1e}$R$^{1f}$;

R$^{3a}$ and R$^{3b}$ are each independently at each occurrence hydrogen or an optionally substituted (e.g., C$_1$-C$_6$, such as C$_1$-C$_3$)alkyl;

R$^{1a}$, R$^{1b}$, R$^{1c}$, R$^{1d}$, R$^{1e}$, R$^{1f}$, and R$^{1g}$ (if present) are each independently at each occurrence a point of connection to a branch, hydrogen, or an optionally substituted (e.g., C$_1$-C$_{12}$)alkyl;

L$^0$, L$^1$, and L$^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or, alternatively, part of $L^1$ form a (e.g., $C_4$-$C_6$) heterocycloalkyl (e.g., containing one or two nitrogen atoms and, optionally, an additional heteroatom selected from oxygen and sulfur) with one of $R^{1c}$ and $R^{1d}$; and
$x^1$ is 0, 1, 2, 3, 4, 5, or 6; and
(b) each branch of the plurality (N) of branches independently comprises a structural formula ($X_{Branch}$):

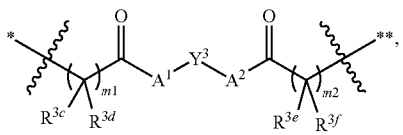
($X_{Branch}$)

wherein:
* indicates a point of attachment of the branch to the core;
g is 1, 2, 3, or 4;
$Z=2^{(g-1)}$;
$G=0$, when $g=1$; or $G=\Sigma_{i=0}^{i=g-2} 2^i$, when $g\ne 1$;
each diacyl group independently comprises a structural formula

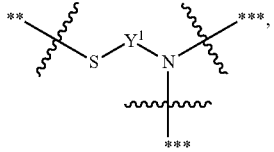

wherein:
* indicates a point of attachment of the diacyl group at the proximal end thereof;
** indicates a point of attachment of the diacyl group at the distal end thereof;
$Y^3$ is independently at each occurrence an optionally substituted (e.g., $C_1$-$C_{12}$); alkylene, an optionally substituted (e.g., $C_1$-$C_{12}$)alkenylene, or an optionally substituted (e.g., $C_1$-$C_{12}$) arenylene;
$A^1$ and $A^2$ are each independently at each occurrence —O—, —S—, or —$NR^4$—,
wherein:
$R^4$ is hydrogen or optionally substituted (e.g., $C_1$-$C_6$) alkyl;
$m^1$ and $m^2$ are each independently at each occurrence 1, 2, or 3; and
$R^{3c}$, $R^{3d}$, $R^{3e}$, and $R^{3f}$ are each independently at each occurrence hydrogen
or an optionally substituted (e.g., $C_1$-$C_8$)alkyl; and
(d) each linker group independently comprises a structural formula wherein:
** indicates a point of attachment of the linker to a proximal diacyl group;
*** indicates a point of attachment of the linker to a distal diacyl group; and
$Y_1$ is independently at each occurrence an optionally substituted (e.g., $C_1$-$C_{12}$)alkylene, an optionally substituted (e.g., $C_1$-$C_{12}$)alkenylene, or an optionally substituted (e.g., $C_1$-$C_{12}$) arenylene; and
each terminating group is independently selected from optionally substituted (e.g., $C_1$-$C_{18}$, such as $C_4$-$C_{18}$) alkylthiol, and optionally substituted (e.g., $C_1$-$C_{18}$, such as $C_4$-$C_{18}$)alkenylthiol.

In some embodiments of $X_{Core}$, Q is independently at each occurrence a covalent bond, —O—, —S—, —$NR^2$—, or —$CR^{3a}R^{3b}$. In some embodiments of $X_{Core}$, Q is independently at each occurrence a covalent bond. In some embodiments of $X_{Core}$, Q is independently at each occurrence an —O—. In some embodiments of $X_{Core}$, Q is independently at each occurrence a —S—. In some embodiments of $X_{Core}$, Q is independently at each occurrence a —$NR^2$ and $R^2$ is independently at each occurrence $R^{1g}$ or —$L^2$—$NR^{1e}R^{1f}$. In some embodiments of $X_{Core}$ Q, is independently at each occurrence a —$CR^{3a}R^{3b}R^{3a}$, and $R^{3a}$ and $R^{3b}$ are each independently at each occurrence hydrogen or an optionally substituted alkyl (e.g., $C_1$-$C_6$, such as $C_1$-$C_3$).

In some embodiments of $X_{Core}$, $R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen, or an optionally substituted alkyl. In some embodiments of $X_{Core}$, $R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen. In some embodiments of $X_{Core}$, $R^{1a}$, $R^{1b}$, $R^{1c}$, $R^{1d}$, $R^{1e}$, $R^{1f}$, and $R^{1g}$ (if present) are each independently at each occurrence a point of connection to a branch an optionally substituted alkyl (e.g., $C_1$-$C_{12}$).

In some embodiments of $X_{Core}$, $L^0$, $L^1$, and $L^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or,
alternatively, part of $L^1$ form a heterocycloalkyl (e.g., $C_4$-$C_6$ and containing one or two nitrogen atoms and, optionally, an additional heteroatom selected from oxygen and sulfur) with one of $R^{1c}$ and $R^{1d}$. In some embodiments of $X_{Core}$, $L^0$, $L^1$, and $L^2$ are each independently at each occurrence can be a covalent bond. In some embodiments of $X_{Core}$, $L^0$, $L^1$, and $L^2$ are each independently at each occurrence can be a hydrogen. In some embodiments of $X_{Core}$, $L^0$, $L^1$, and $L^2$ are each independently at each occurrence can be an alkylene (e.g., $C_1$-$C_{12}$, such as $C_1$-$C_6$ or $C_1$-$C_3$). In some embodiments of $X_{Core}$, $L^0$, $L^1$, and $L^2$ are each independently at each occurrence can be a heteroalkylene (e.g., $C_1$-$C_{12}$, such as $C_1$-$C_8$ or $C_1$-$C_6$). In some embodiments of $X_{Core}$, $L^0$, $L^1$, and $L^2$ are each independently at each occurrence can be a heteroalkylene (e.g., $C_2$-$C_8$ alkyleneoxide, such as oligo(ethyleneoxide)). In some embodiments of $X_{Core}$, $L^0$, $L^1$, and $L^2$ are each independently at each occurrence can be a [alkylene]-[heterocycloalkyl]-[alkylene][(e.g., $C_1$-$C_6$)alkylene]-[(e.g., $C_4$-$C_6$) heterocycloalkyl]-[(e.g., $C_1$-$C_6$) alkylene]. In some embodiments of $X_{Core}$, $L^0$, $L^1$, and $L^2$ are each independently at each occurrence can be a [alkylene]-(arylene)-[alkylene][(e.g., $C_1$-$C_6$)alkylene]-(arylene)-[(e.g., $C_1$-$C_6$)alkylene]. In some embodiments of $X_{Core}$, $L^0$, $L^1$, and $L^2$ are each independently at each occurrence can be a [alkylene]-(arylene)-[alkylene](e.g., [(e.g., $C_1$-$C_6$)alkylene]-phenylene-[(e.g., $C_1$-$C_6$)alkylene]). In some embodiments of $X_{Core}$, $L^0$, $L^1$, and $L^2$ are each independently at each occurrence can be a heterocycloalkyl (e.g., $C_4$-$C_6$heterocycloalkyl). In some embodiments of $X_{Core}$, $L^0$, $L^1$, and $L^2$ are each independently at each occurrence can be an arylene (e.g., phenylene). In some embodiments of $X_{Core}$, part of $L^1$ form a heterocycloalkyl with one of $R^{1c}$ and $R^{1d}$. In some embodiments of $X_{Core}$, part of $L^1$ form a heterocycloalkyl (e.g., $C_4$-$C_6$ heterocycloalkyl) with one of $R^{1c}$ and $R^{1d}$ and the heterocycloalkyl can contain one or two nitrogen atoms and, optionally, an additional heteroatom selected from oxygen and sulfur.

In some embodiments of $X_{Core}$, $L^0$, $L^1$, and $L^2$ are each independently at each occurrence selected from a covalent bond, $C_1$-$C_6$ alkylene (e.g., $C_1$-$C_3$ alkylene), $C_2$-$C_{12}$ (e.g., $C_2$-$C_8$)alkyleneoxide (e.g., oligo(ethyleneoxide), such as —$(CH_2CH_2O)_{1-4}$—$(CH_2CH_2)$—), [($C_1$-$C_4$)alkylene]-[($C_4$-$C_6$) heterocycloalkyl]-[($C_1$-$C_4$)alkylene](e.g.,

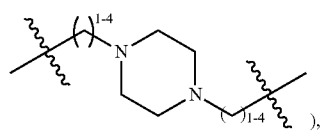

and [($C_1$-$C_4$)alkylene]-phenylene-[($C_1$-$C_4$)alkylene](e.g.,

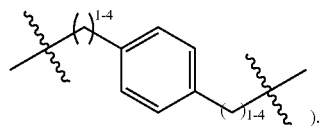

In some embodiments of $X_{Core}$, $L^0$, $L^1$, and $L^2$ are each independently at each occurrence selected from $C_1$-$C_6$ alkylene (e.g., $C_1$-$C_3$ alkylene), —($C_1$-$C_3$ alkylene-O)$_{1-4}$—($C_1$-$C_3$ alkylene), —($C_1$-$C_3$ alkylene)-phenylene-($C_1$-$C_3$ alkylene)-, and —($C_1$-$C_3$ alkylene)-piperazinyl-($C_1$-$C_3$ alkylene)-. In some embodiments of $X_{Core}$, $L^0$, $L^1$, and $L^2$ are each independently at each occurrence $C_1$-$C_6$ alkylene (e.g., $C_1$-$C_3$ alkylene). In some embodiments, $L^0$, $L^1$, and $L^2$ are each independently at each occurrence $C_2$-$C_{12}$ (e.g., $C_2$-$C_8$)alkyleneoxide (e.g., —($C_1$-$C_3$ alkylene-O)$_{1-4}$—($C_1$-$C_3$ alkylene)). In some embodiments of $X_{Core}$, $L^0$, $L^1$, and $L^2$ are each independently at each occurrence selected from [($C_1$-$C_4$)alkylene]-[($C_4$-$C_6$) heterocycloalkyl]-[($C_1$-$C_4$)alkylene](e.g., —($C_1$-$C_3$ alkylene)-phenylene-($C_1$-$C_3$ alkylene)-) and [($C_1$-$C_4$)alkylene]-[($C_4$-$C_6$) heterocycloalkyl]-[($C_1$-$C_4$)alkylene](e.g., —($C_1$-$C_3$ alkylene)-piperazinyl-($C_1$-$C_3$ alkylene)-).

In some embodiments of $X_{Core}$, $x^1$ is 0, 1, 2, 3, 4, 5, or 6. In some embodiments of $X_{Core}$, $x^1$ is 0. In some embodiments of $X_{Core}$, $x^1$ is 1. In some embodiments of $X_{Core}$, $x^1$ is 2. In some embodiments of $X_{Core}$, $x^1$ is 0, 3. In some embodiments of $X_{Core}$ $x^1$ is 4. In some embodiments of $X_{Core}$ $x^1$ is 5. In some embodiments of $X_{Core}$, $x^1$ is 6.

In some embodiments of $X_{Core}$, the core comprises a structural formula:

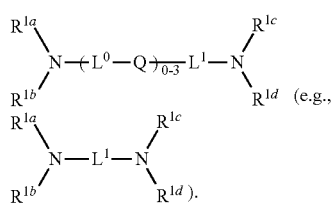

In some embodiments of $X_{Core}$, the core comprises a structural formula:

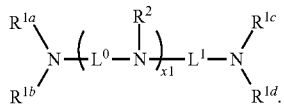

In some embodiments of $X_{Core}$, the core comprises a structural formula:

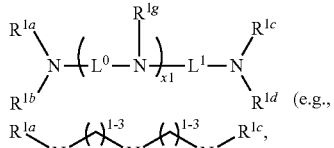

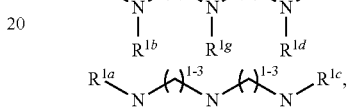

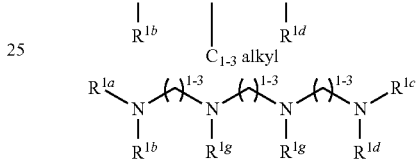

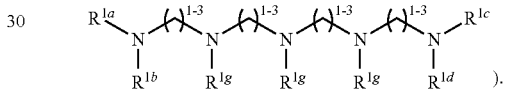

In some embodiments of $X_{Core}$, the core comprises a structural formula:

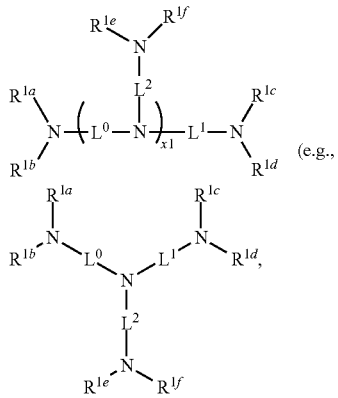

such as

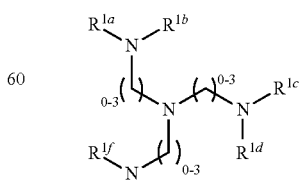 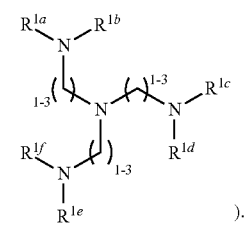

In some embodiments of $X_{Core}$, the core comprises a structural formula:

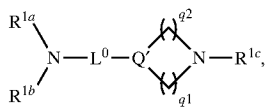

wherein Q' is —NR²— or —CR³ᵃR³ᵇ—; q¹ and q² are each independently 1 or 2. In some embodiments of $X_{Core}$, the core comprises a structural formula:

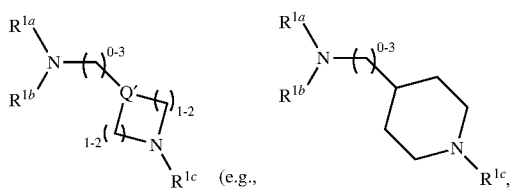

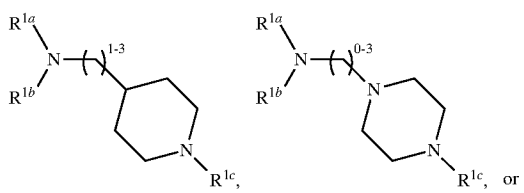

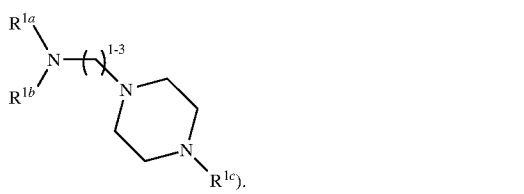

In some embodiments of $X_{Core}$, the core comprises a structural formula

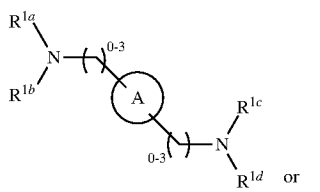

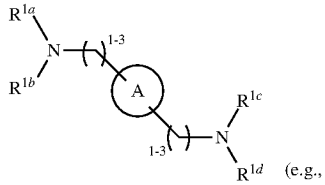

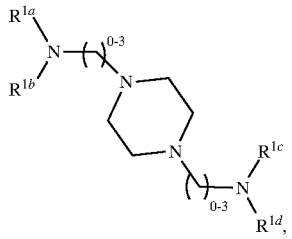

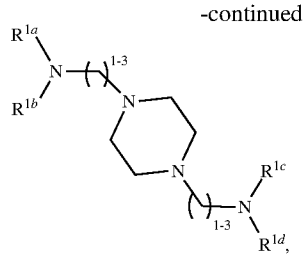

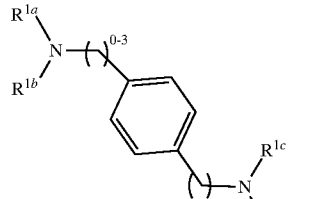

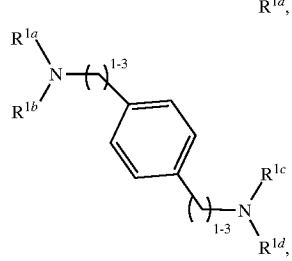

wherein ring A is an optionally substituted aryl or an optionally substituted (e.g., $C_3$-$C_{12}$, such as $C_3$-$C_5$) heteroaryl. In some embodiments of $X_{Core}$, the core comprises has a structural formula

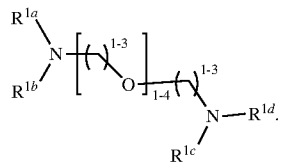

In some embodiments of $X_{Core}$, the core comprises a structural formula set forth in Table 2 and pharmaceutically acceptable salts thereof, wherein * indicates a point of attachment of the core to a branch of the plurality of branches.

In some embodiments, the plurality (N) of branches comprises at least 3 branches, at least 4 branches, at least 5 branches. In some embodiments, the plurality (N) of branches comprises at least 3 branches. In some embodiments, the plurality (N) of branches comprises at least 4 branches. In some embodiments, the plurality (N) of branches comprises at least 5 branches.

In some embodiments of $X_{Branch}$, g is 1, 2, 3, or 4. In some embodiments of $X_{Branch}$, g is 1. In some embodiments of $X_{Branch}$, g is 2. In some embodiments of $X_{Branch}$, g is 3. In some embodiments of $X_{Branch}$, g is 4.

In some embodiments of $X_{Branch}$, $Z=2^{(g-1)}$ and when g=1, G=0. In some embodiments of $X_{Branch}$, $Z=2^{(g-1)}$ and $$G = \sum_{i=0}^{i=g-2} 2^i,$$

when g≠1.

In some embodiments of $X_{Branch}$, g=1, G=0, Z=1, and each branch of the plurality of branches comprises a structural formula each branch of the plurality of branches comprises a structural formula

*—(diacyl group)—(terminating group).

In some embodiments of $X_{Branch}$, g=2, G=1, Z=2, and each branch of the plurality of branches comprises a structural formula

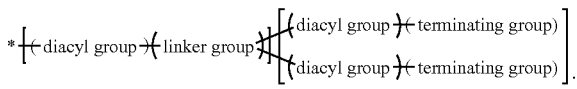

In some embodiments of $X_{Branch}$, g=3, G=3, Z=4, and each branch of the plurality of branches comprises a structural formula

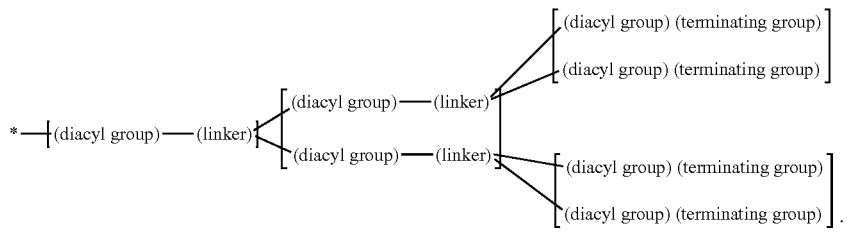

In some embodiments of $X_{Branch}$, g=4, G=7, Z=8, and each branch of the plurality of branches comprises a structural formula

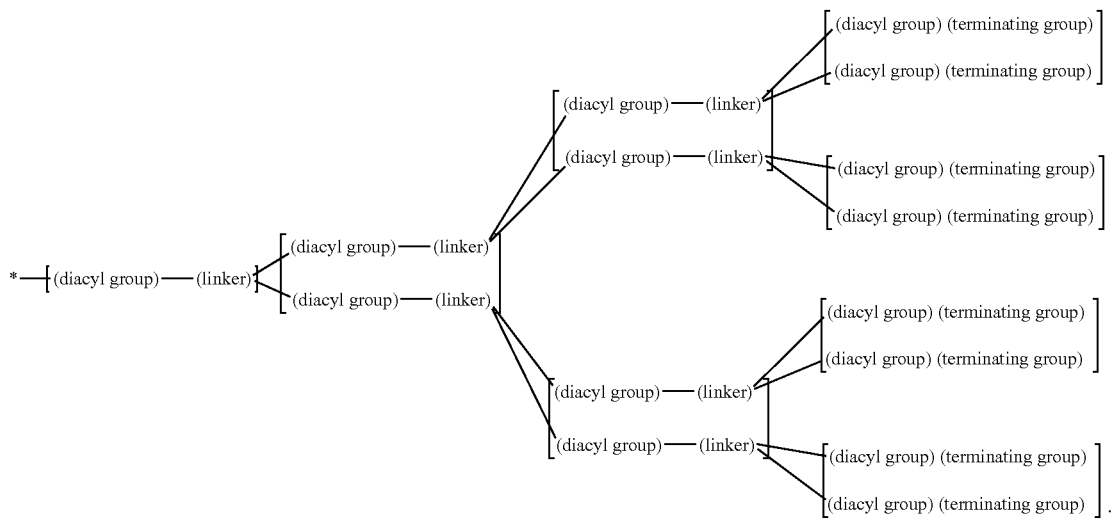

In some embodiments, the dendrimers described herein with a generation (g)=1 has the structure:

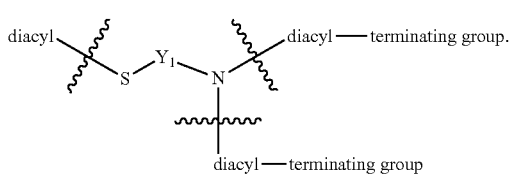

In some embodiments, the dendrimers described herein with a generation (g)=1 has the structure:

GEN "g-2"    GEN "g-1"    GEN "g"

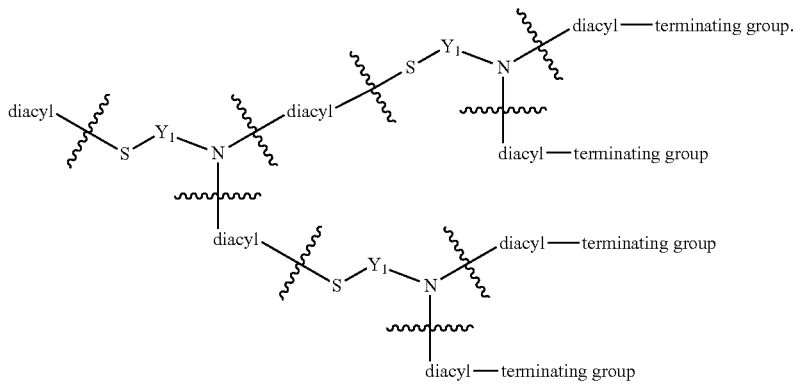

An example formulation of the dendrimers described herein for generations 1-4 is shown in Table 1. The number of diacyl groups, linker groups, and terminating groups can be calculated based on g.

TABLE 1

Formulation of Dendrimer Groups Based on Generation (g)

| | g = 1 | g = 2 | g = 3 | g = 4 | |
|---|---|---|---|---|---|
| # of diacyl grp | 1 | 1 + 2 = 3 | $1 + 2 + 2^2 = 7$ | $1 + 2 + 2^2 + 2^3 = 15$ | $1 + 2 + \ldots + 2^{g-1}$ |
| # of linker grp | 0 | 1 | 1 + 2 | $1 + 2 + 2^2$ | $1 + 2 + \ldots + 2^{g-2}$ |
| # of terminating grp | 1 | 2 | $2^2$ | $2^3$ | $2^{(g-1)}$ |

In some embodiments, the diacyl group independently comprises a structural formula

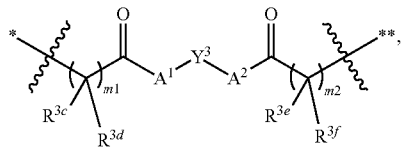

* indicates a point of attachment of the diacyl group at the proximal end thereof, and ** indicates a point of attachment of the diacyl group at the distal end thereof.

In some embodiments of the diacyl group of $X_{Branch}$, $Y^3$ is independently at each occurrence an optionally substituted; alkylene, an optionally substituted alkenylene, or an optionally substituted arenylene. In some embodiments of the diacyl group of $X_{Branch}$, $Y^3$ is independently at each occurrence an optionally substituted alkylene (e.g., $C_1$-$C_{12}$). In some embodiments of the diacyl group of $X_{Branch}$, $Y^3$ is independently at each occurrence an optionally substituted alkenylene (e.g., $C_1$-$C_{12}$). In some embodiments of the diacyl group of $X_{Branch}$, $Y^3$ is independently at each occurrence an optionally substituted arenylene (e.g., $C_1$-$C_{12}$).

In some embodiments of the diacyl group of $X_{Branch}$, $A^1$ and $A^2$ are each independently at each occurrence —O—, —S—, or —NR$^4$—. In some embodiments of the diacyl group of $X_{Branch}$, $A^1$ and $A^2$ are each independently at each occurrence —O—. In some embodiments of the diacyl group of $X_{Branch}$, $A^1$ and $A^2$ are each independently at each occurrence —S—. In some embodiments of the diacyl group of $X_{Branch}$, $A^1$ and $A^2$ are each independently at each occurrence —NR$^4$—and R$^4$ is hydrogen or optionally substituted alkyl (e.g., $C_1$-$C_6$). In some embodiments of the diacyl group of $X_{Branch}$, $m^1$ and $m^2$ are each independently at each occurrence 1, 2, or 3. In some embodiments of the diacyl group of $X_{Branch}$, $m^1$ and $m^2$ are each independently at each occurrence 1. In some embodiments of the diacyl group of $X_{Branch}$, $m^1$ and $m^2$ are each independently at each occurrence 2. In some embodiments of the diacyl group of $X_{Branch}$, $m^1$ and $m^2$ are each independently at each occurrence 3. In some embodiments of the diacyl group of $X_{Branch}$, $R^{3c}$, $R^{3d}$, $R^{3e}$, and $R^{3f}$ are each independently at each occurrence hydrogen or an optionally substituted alkyl. In some embodiments of the diacyl group of $X_{Branch}$, $R^{3c}$, $R^{3d}$, $R^{3e}$, and $R^{3f}$ are each independently at each occurrence hydrogen. In some embodiments of the diacyl group of $X_{Branch}$, $R^{3c}$, $R^{3d}$, $R^{3e}$, and $R^{3f}$ are each independently at each occurrence an optionally substituted (e.g., $C_1$-$C_8$)alkyl.

In some embodiments of the diacyl group, $A^1$ is —O— or —NH—. In some embodiments of the diacyl group, $A^1$ is —O—. In some embodiments of the diacyl group, $A^2$ is —O— or —NH—. In some embodiments of the diacyl group, $A^2$ is —O—. In some embodiments of the diacyl group, $Y^3$ is $C_1$-$C_{12}$ (e.g., $C_1$-$C_6$, such as $C_1$-$C_3$)alkylene.

In some embodiments of the diacyl group, the diacyl group independently at each occurrence comprises a structural formula

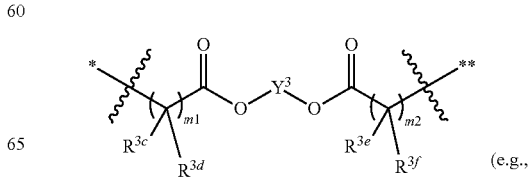

(e.g.,

-continued

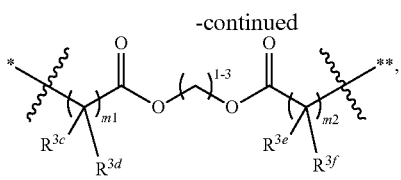

such as

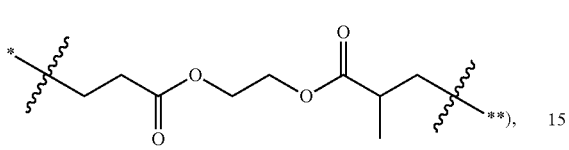

and optionally $R^{3c}$, $R^{3d}$, $R^{3e}$, and $R^{3f}$ are each independently at each occurrence hydrogen or $C_1$-$C_3$ alkyl.

In some embodiments, linker group independently comprises a structural formula

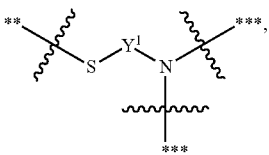

indicates a point of attachment of the linker to a proximal diacyl group, and * indicates a point of attachment of the linker to a distal diacyl group.

In some embodiments of the linker group of $X_{Branch}$ if present, $Y_1$ is independently at each occurrence an optionally substituted alkylene, an optionally substituted alkenylene, or an optionally substituted arenylene. In some embodiments of the linker group of $X_{Branch}$ if present, $Y_1$ is independently at each occurrence an optionally substituted alkylene (e.g., $C_1$-$C_{12}$). In some embodiments of the linker group of $X_{Branch}$ if present, $Y_1$ is independently at each occurrence an optionally substituted alkenylene (e.g., $C_1$-$C_{12}$). In some embodiments of the linker group of $X_{Branch}$ if present, $Y_1$ is independently at each occurrence an optionally substituted arenylene (e.g., $C_1$-$C_{12}$).

In some embodiments of the terminating group of $X_{Branch}$, each terminating group is independently selected from optionally substituted alkylthiol and optionally substituted alkenylthiol. In some embodiments of the terminating group of $X_{Branch}$, each terminating group is an optionally substituted alkylthiol (e.g., $C_1$-$C_{18}$, such as $C_4$-$C_{18}$). In some embodiments of the terminating group of $X_{Branch}$, each terminating group is optionally substituted alkenylthiol (e.g., $C_1$-$C_{18}$, such as $C_4$-$C_{18}$).

In some embodiments of the terminating group of $X_{Branch}$, each terminating group is independently $C_1$-$C_{18}$ alkenylthiol or $C_1$-$C_{18}$ alkylthiol, and the alkyl or alkenyl moiety is optionally substituted with one or more substituents each independently selected from halogen, $C_6$-$C_{12}$ aryl, $C_1$-$C_{12}$ alkylamino, $C_4$-$C_6$ N-heterocycloalkyl, —OH, —C(O)OH, —C(O)N($C_1$-$C_3$ alkyl)-($C_1$-$C_6$ alkylene)-($C_1$-$C_{12}$ alkylamino), —C(O)N($C_1$-$C_3$ alkyl)-($C_1$-$C_6$ alkylene)-($C_4$-$C_6$ N-heterocycloalkyl), —C(O)—($C_1$-$C_{12}$ alkylamino), and —C(O)—($C_4$-$C_6$ N-heterocycloalkyl), and the $C_4$-$C_6$ N-heterocycloalkyl moiety of any of the preceding substituents is optionally substituted with $C_1$-$C_3$ alkyl or $C_1$-$C_3$ hydroxyalkyl.

In some embodiments of the terminating group of $X_{Branch}$, each terminating group is independently $C_1$-$C_{18}$ (e.g., $C_4$-$C_{18}$)alkenylthiol or $C_1$-$C_{18}$ (e.g., $C_4$-$C_{18}$)alkylthiol, wherein the alkyl or alkenyl moiety is optionally substituted with one or more substituents each independently selected from halogen, $C_6$-$C_{12}$ aryl (e.g., phenyl), $C_1$-$C_{12}$ (e.g., $C_1$-$C_8$)alkylamino (e.g., $C_1$-$C_6$ mono-alkylamino (such as —NHCH$_2$CH$_2$CH$_2$CH$_3$) or $C_1$-$C_8$ di-alkylamino (such as

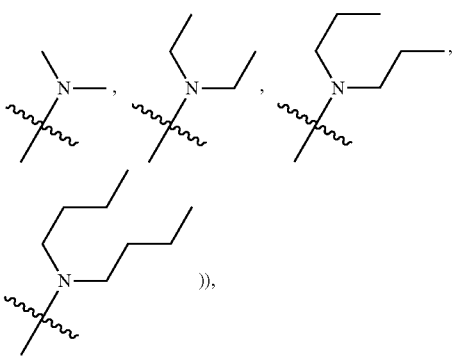

)), $C_4$-$C_6$ N-heterocycloalkyl (e.g., N-pyrrolidinyl (

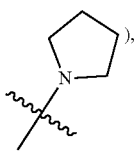 [SMILES: *N1CCCC1]

),

N-piperidinyl

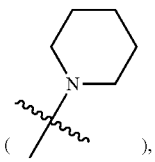 [SMILES: *N1CCCCC1]

( ),

N-azepanyl

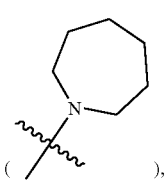

( ),

—OH, —C(O)OH, —C(O)N($C_1$-$C_3$ alkyl)-($C_1$-$C_6$ alkylene)-($C_1$-$C_{12}$ alkylamino (e.g., mono- or di-alkylamino)) (e.g.,

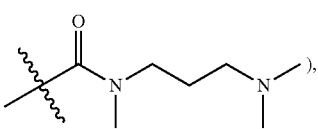 [SMILES: *C(=O)N(C)CCCN(C)C]

),

—C(O)N(C$_1$-C$_3$ alkyl)-(C$_1$-C$_6$ alkylene)-(C$_4$-C$_6$ N-heterocycloalkyl) (e.g.,

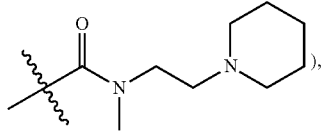 [SMILES: *C(=O)N(C)CCN1CCCCC1]),

—C(O)—(C$_1$-C$_{12}$ alkylamino (e.g., mono- or di-alkylamino)), and —C(O)—(C$_4$-C$_6$ N-heterocycloalkyl) (e.g.,

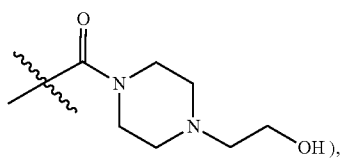), wherein the C$_4$-C$_6$ N-heterocycloalkyl moiety of any of the preceding substituents is optionally substituted with C$_1$-C$_3$ alkyl or C$_1$-C$_3$ hydroxyalkyl. In some embodiments of the terminating group of X$_{Branch}$, each terminating group is independently C$_1$-C$_{18}$ (e.g., C$_4$-C$_{18}$)alkylthiol, wherein the alkyl moiety is optionally substituted with one substituent —OH. In some embodiments of the terminating group of X$_{Branch}$, each terminating group is independently C$_1$-C$_{18}$ (e.g., C$_4$-C$_{18}$)alkylthiol, wherein the alkyl moiety is optionally substituted with one substituent selected from C$_1$-C$_{12}$ (e.g., C$_1$-C$_8$)alkylamino (e.g., C$_1$-C$_6$ mono-alkylamino (such as —NHCH$_2$CH$_2$CH$_2$CH$_3$) or C$_1$-C$_8$ di-alkylamino (such as

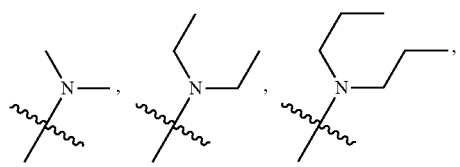,

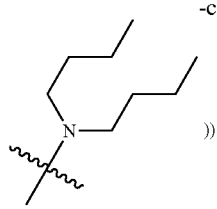))

and C$_4$-C$_6$ N-heterocycloalkyl (e.g., N-pyrrolidinyl

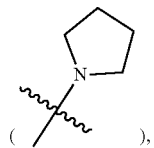),

N-piperidinyl

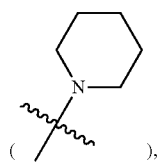),

N-azepanyl

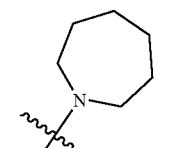)).

In some embodiments of the terminating group of X$_{Branch}$, each terminating group is independently C$_1$-C$_{18}$ (e.g., C$_4$-C$_{18}$)alkenylthiol or C$_1$-C$_{18}$ (e.g., C$_4$-C$_{18}$)alkylthiol. In some embodiments of the terminating group of X$_{Branch}$, each terminating group is independently C$_1$-C$_{18}$ (e.g., C$_4$-C$_{18}$)alkylthiol.

TABLE 2

Example core structures

| ID # | Structure |
|---|---|
| 1A1 | 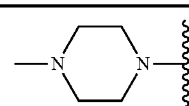 |
| 1A2 | 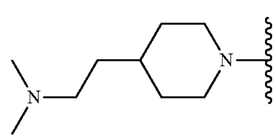 [SMILES: *N1CCC(CCN(C)C)CC1] |
| 1A3 | 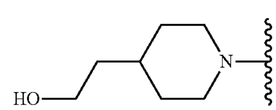 [SMILES: *N1CCC(CCO)CC1] |

TABLE 2-continued
Example core structures
| ID # | Structure |
|---|---|
| 1A4 | 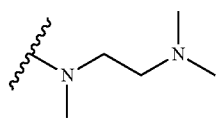 [SMILES: *N(C)CCN(C)C] |
| 1A5 | 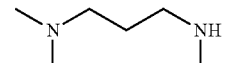 |
| 2A1 | 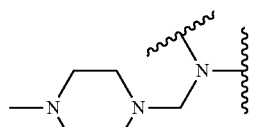 |
| 2A2 | 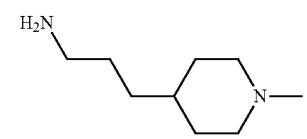 |
| 2A3 | 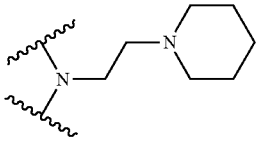 [SMILES: *N(*)CCN1CCCCC1] |
| 2A4 | 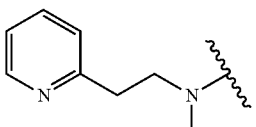 |
| 2A5 | 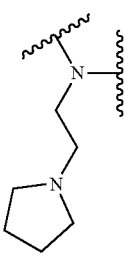 [SMILES: *N(*)CCN1CCCC1] |
| 2A6 | 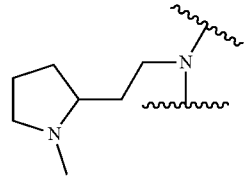 [SMILES: *N(*)CCC1CCCN1C] |
| 2A7 | 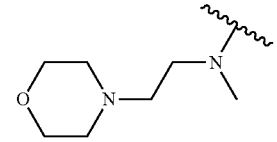 [SMILES: *N(C)CCN1CCOCC1] |

TABLE 2-continued
| Example core structures | |
|---|---|
| ID # | Structure |
| 2A8 | 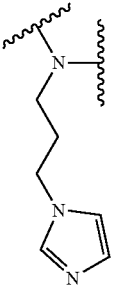 [SMILES: *N(*)CCCn1ccnc1] |
| 2A9 | 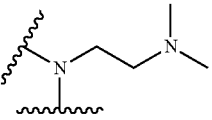 [SMILES: *N(*)CCN(C)C] |
| 2A10 | 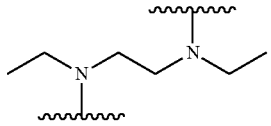 [SMILES: *N(CC)CCN(*)CC] |
| 2A11 | 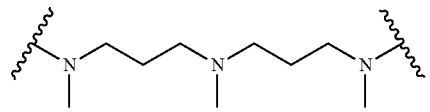 [SMILES: *N(C)CCCN(C)CCCN(*)C] |
| 2A12 | 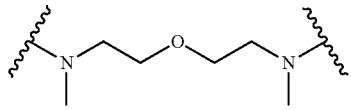 [SMILES: *N(C)CCOCCN(*)C] |
| 3A1 | 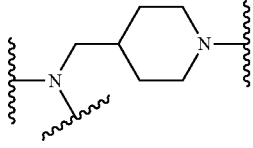 [SMILES: *N(*)CC1CCN(*)CC1] |
| 3A2 | 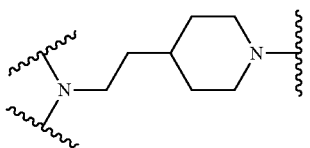 [SMILES: *N(*)CCC1CCN(*)CC1] |
| 3A3 | 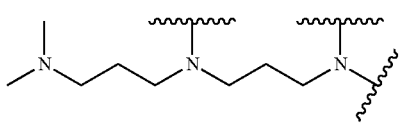 [SMILES: *N(*)CCCN(*)CCCN(C)C] |
| 3A4 | 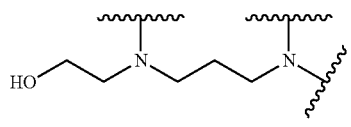 [SMILES: *N(*)CCCN(*)CCO] |

TABLE 2-continued
Example core structures
| ID # | Structure |
|---|---|
| 3A5 | 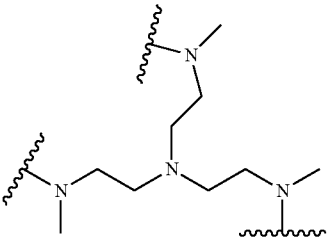 [SMILES: *N(C)CCN(CCN(*)C)CCN(*)C] |
| 4A1 | 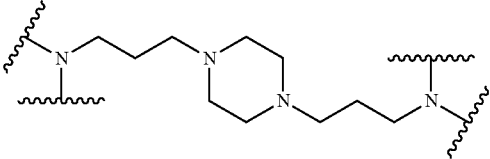 [SMILES: *N(*)CCCN1CCN(CCCN(*)*)CC1] |
| 4A2 | 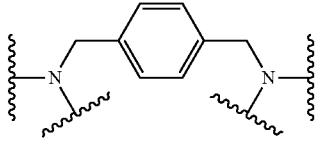 [SMILES: *N(*)Cc1ccc(CN(*)*)cc1] |
| 4A3 | 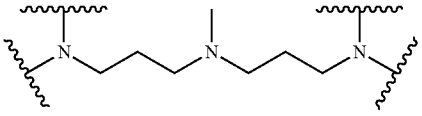 [SMILES: *N(*)CCCN(C)CCCN(*)*] |
| 4A4 | 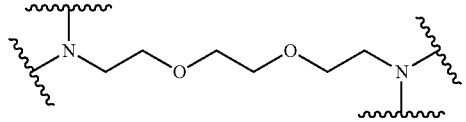 [SMILES: *N(*)CCOCCOCCN(*)*] |
| 5A1 | 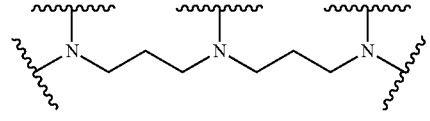 [SMILES: *N(*)CCCN(*)CCCN(*)*] |
| 5A2 | 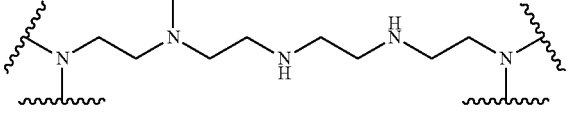 |
| 5A3 | 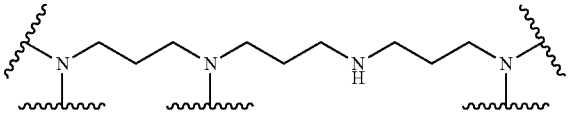 [SMILES: *N(*)CCCNCCCN(*)CCCN(*)*] |
| 5A4 | 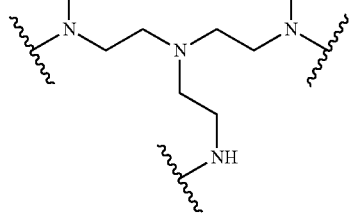 |

TABLE 2-continued

Example core structures

| ID # | Structure |
|------|-----------|
| 5A5 | (structure) |
| 6A1 | (structure) |
| 6A2 | (structure) |
| 6A3 | (structure) |
| 6A4 | (structure) |
| 1H1 | (structure) |
| 1H2 | (structure) |
| 1H3 | (structure) |
| 2H1 | (structure) |
| 2H2 | (structure) |
| 2H3 | (structure) |

TABLE 2-continued
Example core structures
| ID # | Structure |
|---|---|
| 2H4 | 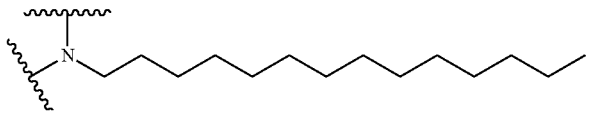 [SMILES: *N(*)CCCCCCCCCCCCCC] |
| 2H5 | 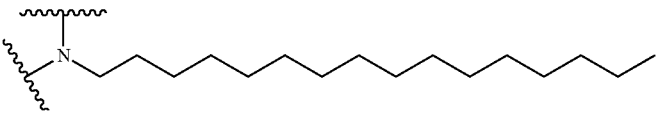 [SMILES: *N(*)CCCCCCCCCCCCCCCC] |
| 2H6 | 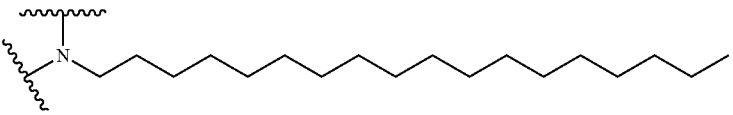 [SMILES: *N(*)CCCCCCCCCCCCCCCCCC] |
In some embodiments of $X_{Core}$, the core comprises a structural formula selected from the group consisting of:
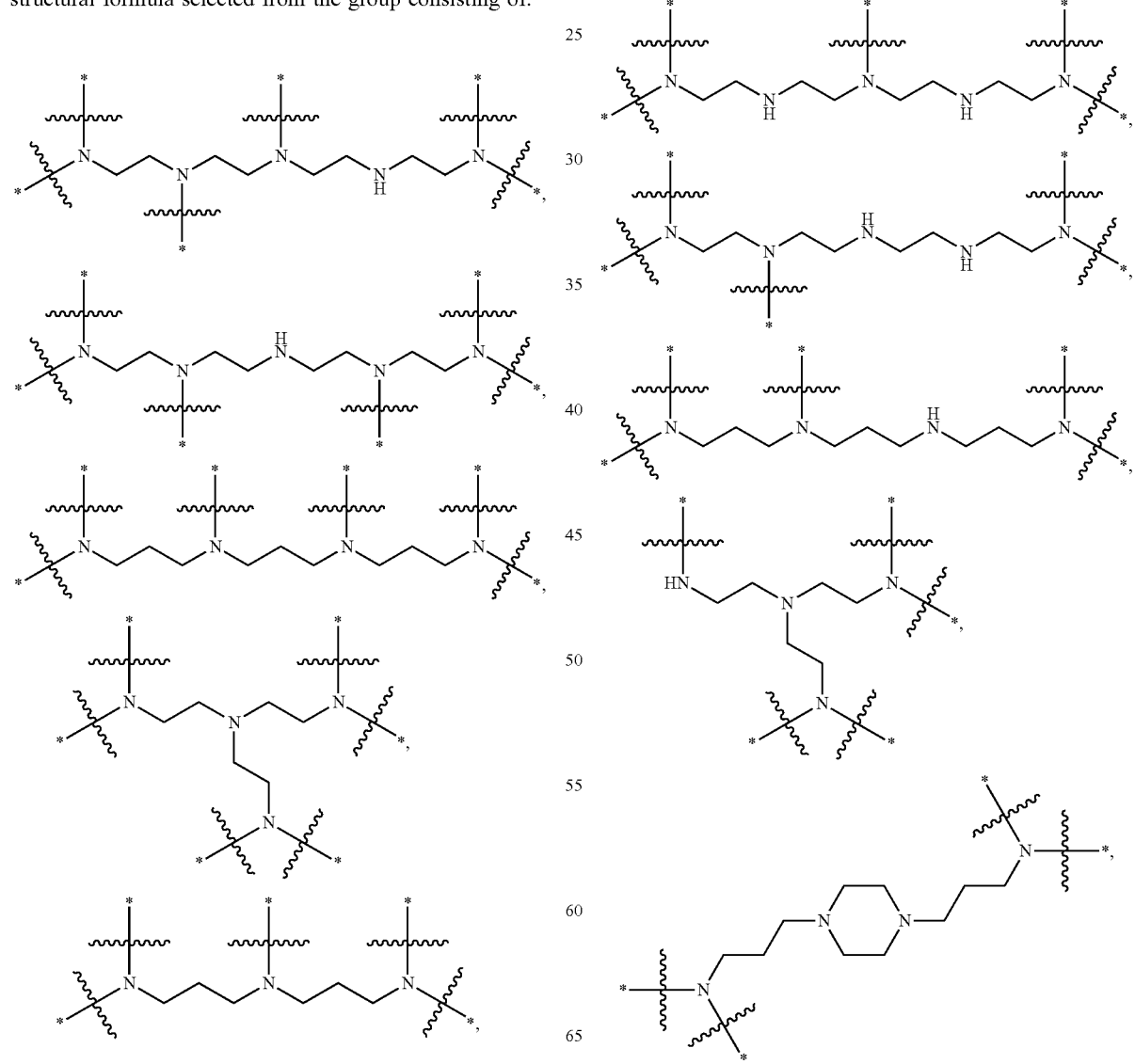

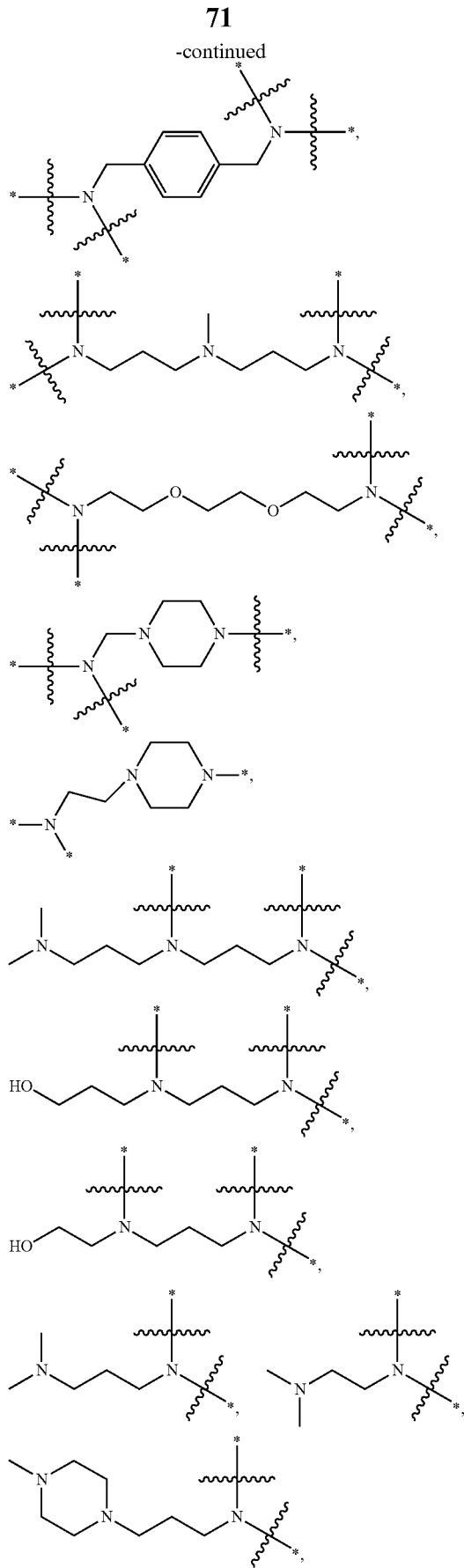

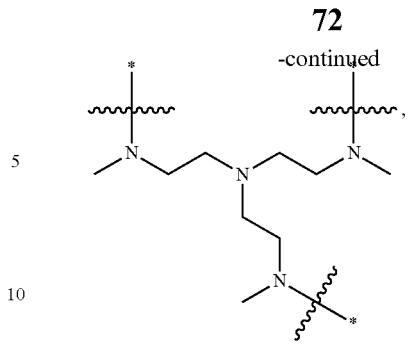

and pharmaceutically acceptable salts thereof, wherein * indicates a point of attachment of the core to a branch of the plurality of branches.

In some embodiments of the terminating group of $X_{Branch}$, each terminating group is independently a structure selected from the structures in Table 3. In some embodiments, the dendrimers described herein can comprise a terminating group or pharmaceutically acceptable salt, or thereof selected in Table 3.

TABLE 3

Example terminating group/peripheries structures

| ID # | Structure |
|---|---|
| SC1 | 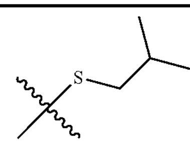 |
| SC2 | 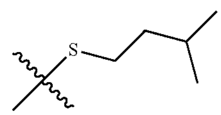 [SMILES: *SCCC(C)C] |
| SC3 | 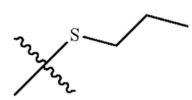 [SMILES: *SCCC] |
| SC4 | 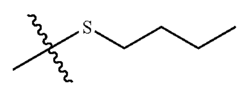 [SMILES: *SCCCC] |
| SC5 | 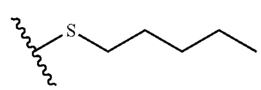 [SMILES: *SCCCCC] |
| SC6 | 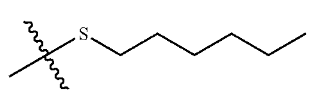 [SMILES: *SCCCCCC] |
| SC7 | 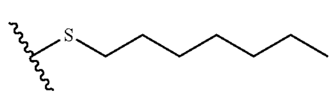 [SMILES: *SCCCCCCC] |
| SC8 | 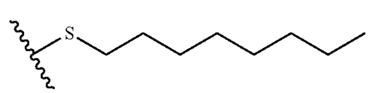 [SMILES: *SCCCCCCCC] |
| SC9 | 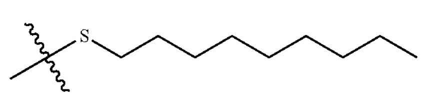 [SMILES: *SCCCCCCCCC] |

TABLE 3-continued

Example terminating group/peripheries structures

| ID # | Structure |
|---|---|
| SC10 | 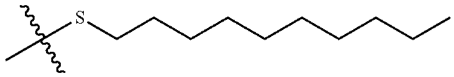 [SMILES: *SCCCCCCCCCC] |
| SC11 | 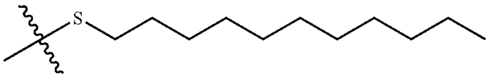 [SMILES: *SCCCCCCCCCCC] |
| SC12 | 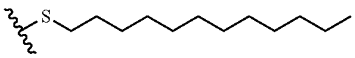 [SMILES: *SCCCCCCCCCCCC] |
| SC14 | 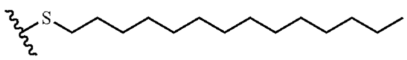 [SMILES: *SCCCCCCCCCCCCCC] |
| SC16 | 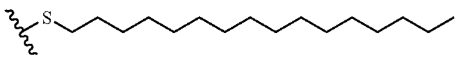 [SMILES: *SCCCCCCCCCCCCCCCC] |
| SC18 | 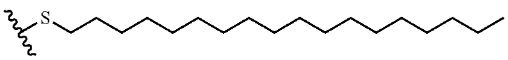 [SMILES: *SCCCCCCCCCCCCCCCCCC] |
| SC19 | 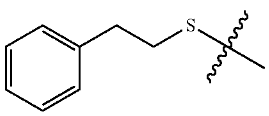 [SMILES: *SCCc1ccccc1] |
| SO1 | 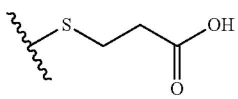 [SMILES: *SCCC(=O)O] |
| SO2 | 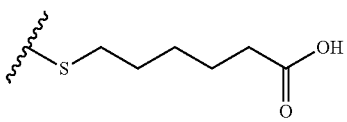 [SMILES: *SCCCCCC(=O)O] |
| SO3 | 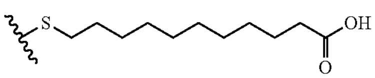 [SMILES: *SCCCCCCCCCCC(=O)O] |
| SO4 | 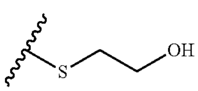 [SMILES: *SCCO] |
| SO5 | 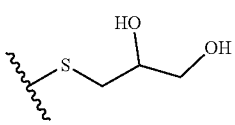 [SMILES: *SCC(O)CO] |
| SO6 | 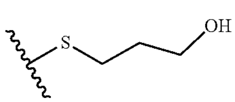 [SMILES: *SCCCO] |
| SO7 | 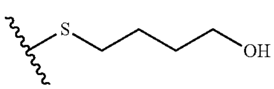 [SMILES: *SCCCCO] |
| SO8 | 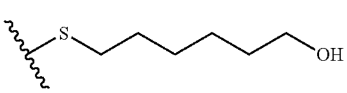 [SMILES: *SCCCCCCO] |
| SO9 | 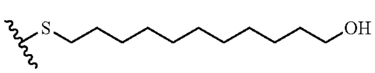 [SMILES: *SCCCCCCCCCCCO] |
| SN1 | |
| SN2 | |
| SN3 | |
| SN4 | |
| SN5 | |
| SN6 | |
| SN7 | |
| SN8 | |
| SN9 | |
| SN10 | |

TABLE 3-continued

Example terminating group/peripheries structures

| ID # | Structure |
|---|---|
| SN11 | *(structure: thioether-CH2CH2CH2-C(=O)-N(CH3)-CH2CH2-piperidine)* |

In some embodiments, the dendrimer of Formula (X) is selected from those set forth in Table 4 and pharmaceutically acceptable salts thereof.

TABLE 4
Example ionizable cationic lipo-dendrimers
| ID # | Structure |
|---|---|
| 2A2-SC14 | 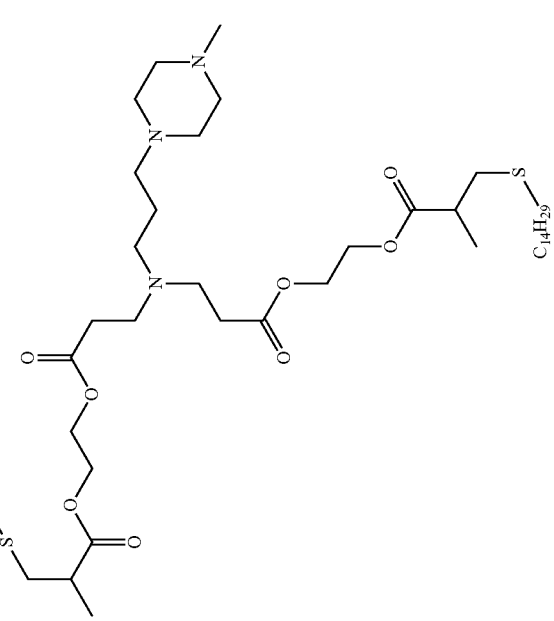 |
| 2A6-SC14 | 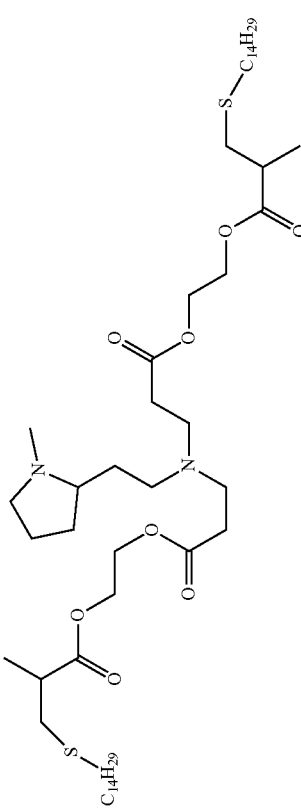 |

TABLE 4-continued
Example ionizable cationic lipo-dendrimers
| ID # | Structure |
|---|---|
| 2A9-SC14 | 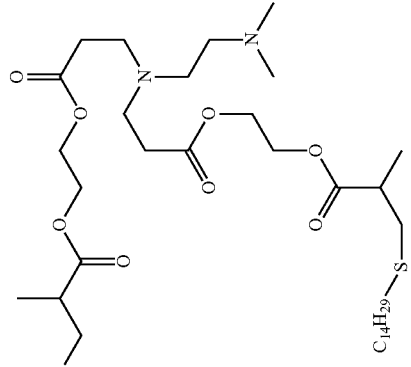 |

TABLE 4-continued

Example ionizable cationic lipo-dendrimers

| ID # | Structure |
|---|---|
| 3A3-SC10 | 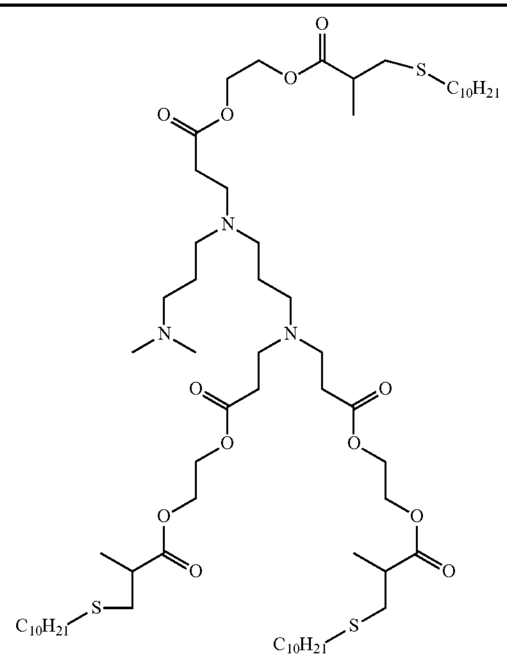 |

TABLE 4-continued
Example ionizable cationic lipo-dendrimers
| ID # | Structure |
|---|---|
| 3A3-SC14 | 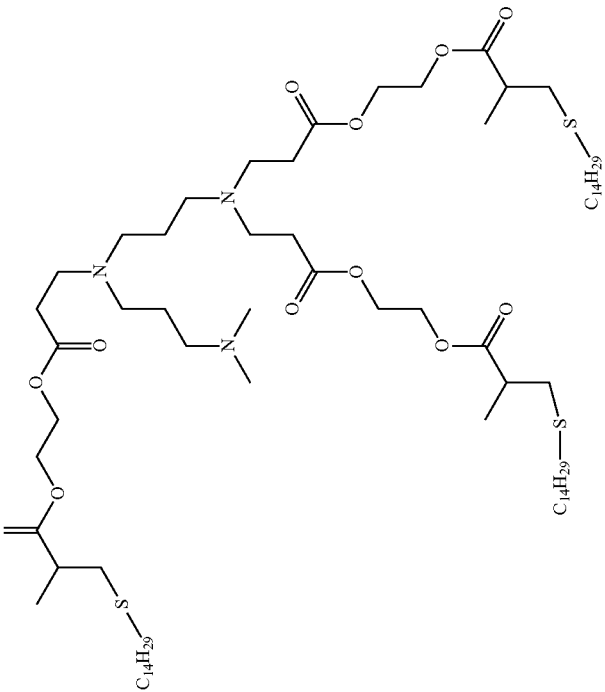 |

TABLE 4-continued
Example ionizable cationic lipo-dendrimers
| ID # | Structure |
|---|---|
| 3A5-SC10 | 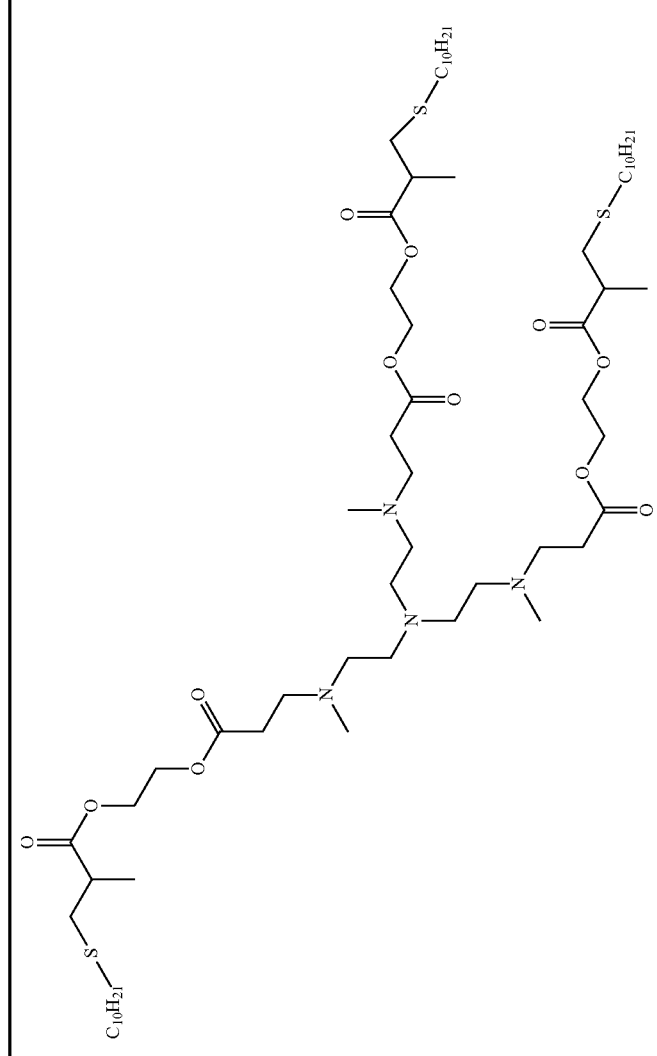 |

TABLE 4-continued
Example ionizable cationic lipo-dendrimers
| ID # | Structure |
|---|---|
| 3A5-SC14 | 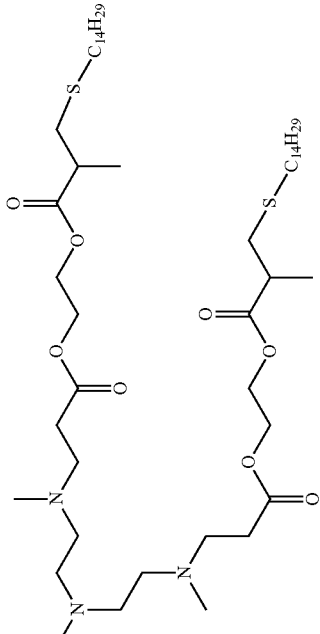 |

TABLE 4-continued

Example ionizable cationic lipo-dendrimers

| ID # | Structure |
|---|---|
| 4A1-SC12 | 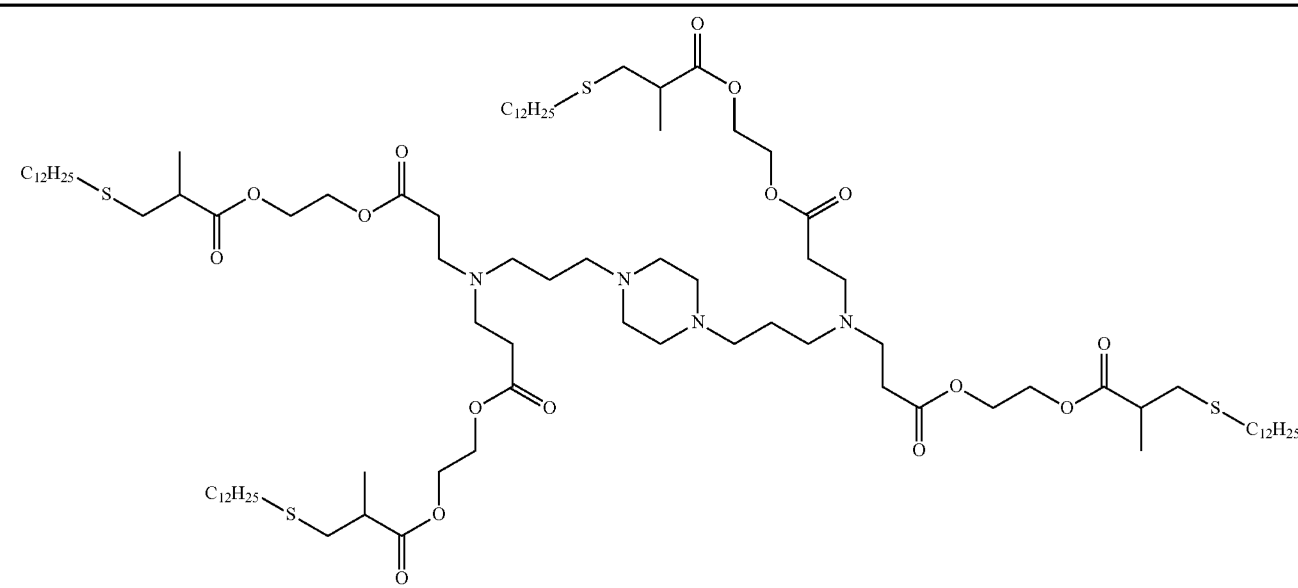 |

TABLE 4-continued

Example ionizable cationic lipo-dendrimers

| ID # | Structure |
|---|---|
| 4A3-SC12 | 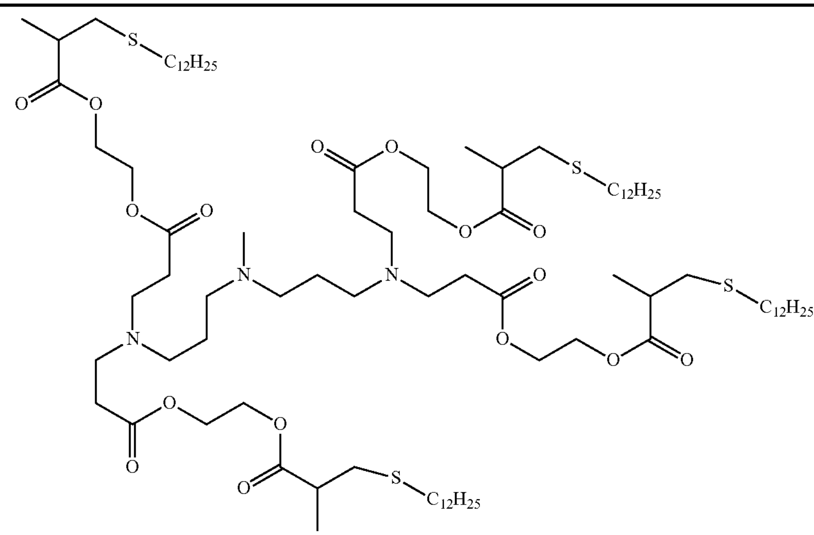 |
| 5A1-SC12 | 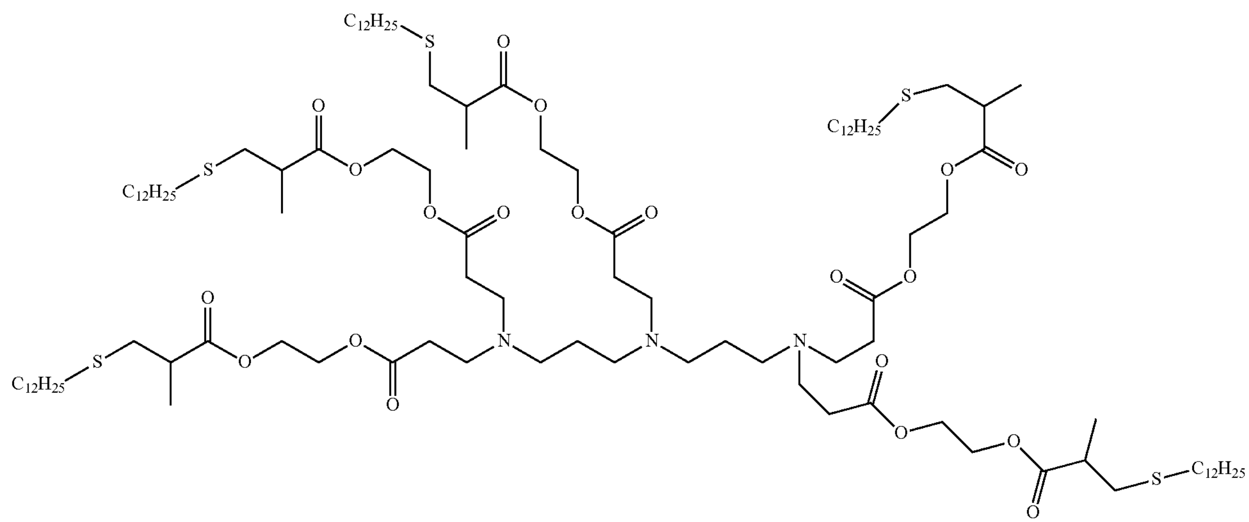 |

TABLE 4-continued

Example ionizable cationic lipo-dendrimers

| ID # | Structure |
|---|---|
| 5A1-SC8 | 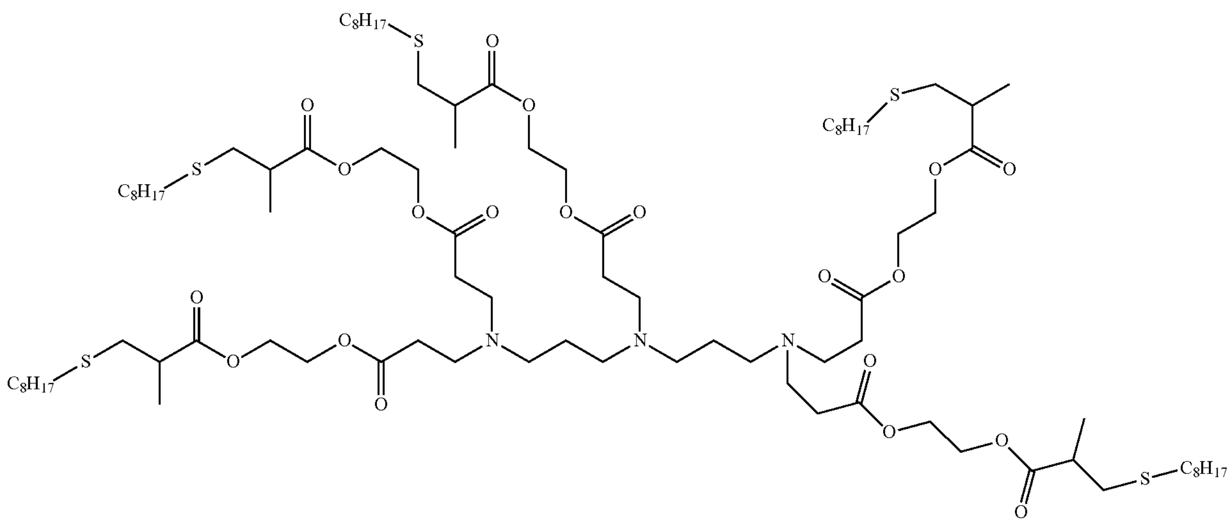 |

TABLE 4-continued

Example ionizable cationic lipo-dendrimers

| ID # | Structure |
|---|---|
| 5A2-2-SC12 (5-arm) | 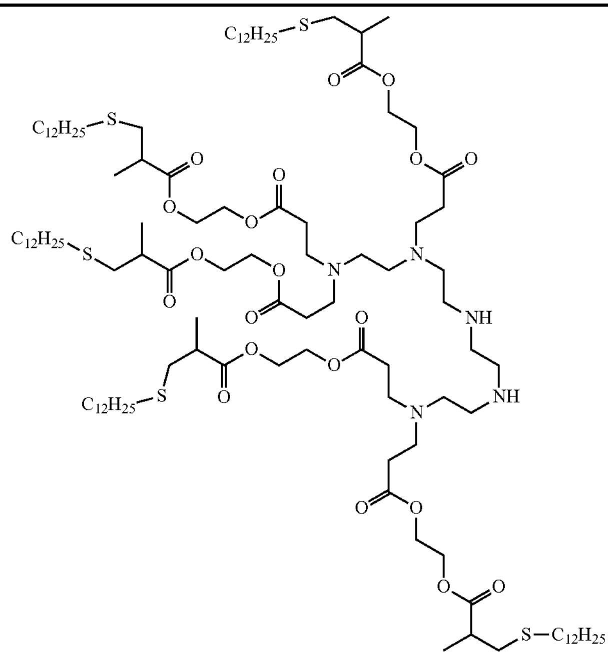 |

TABLE 4-continued

Example ionizable cationic lipo-dendrimers

| ID # | Structure |
|---|---|
| 5A3-1-SC12 (5 arm) | 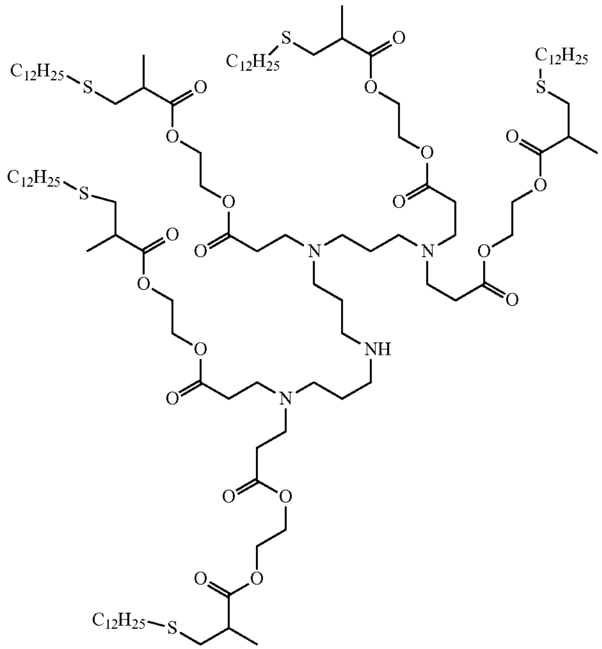 |

TABLE 4-continued

Example ionizable cationic lipo-dendrimers

| ID # | Structure |
|---|---|
| 5A3-1-SC8 (5-arm) | 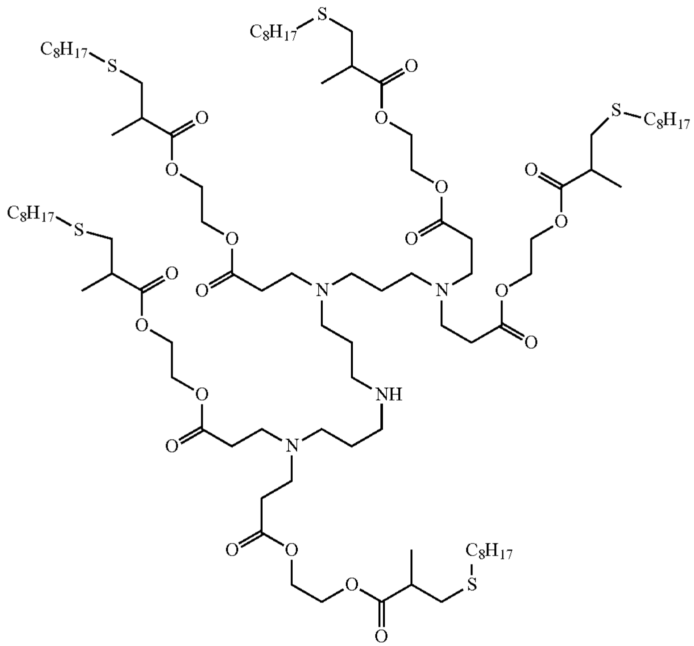 |

TABLE 4-continued

Example ionizable cationic lipo-dendrimers

| ID # | Structure |
|---|---|
| 5A4-1-SC12 (5-arm) | (structure image) |

TABLE 4-continued

Example ionizable cationic lipo-dendrimers

| ID # | Structure |
|---|---|
| 5A4-1-SC8 (5-arm) | 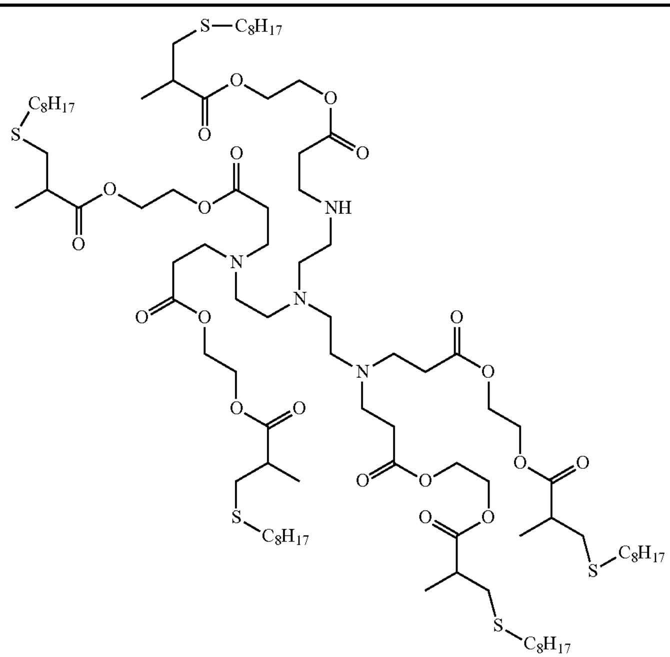 |

TABLE 4-continued
Example ionizable cationic lipo-dendrimers
| ID # | Structure |
|---|---|
| 5A5-SC8 | 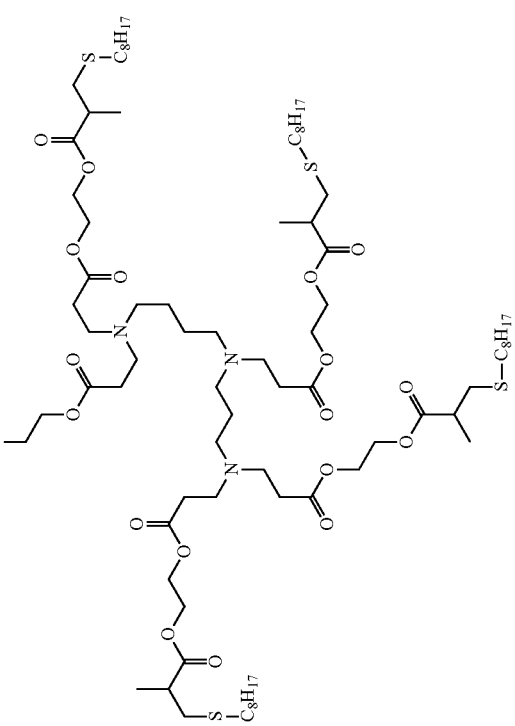 |

TABLE 4-continued
Example ionizable cationic lipo-dendrimers
| ID # | Structure |
|---|---|
| 5A5-SC12 | 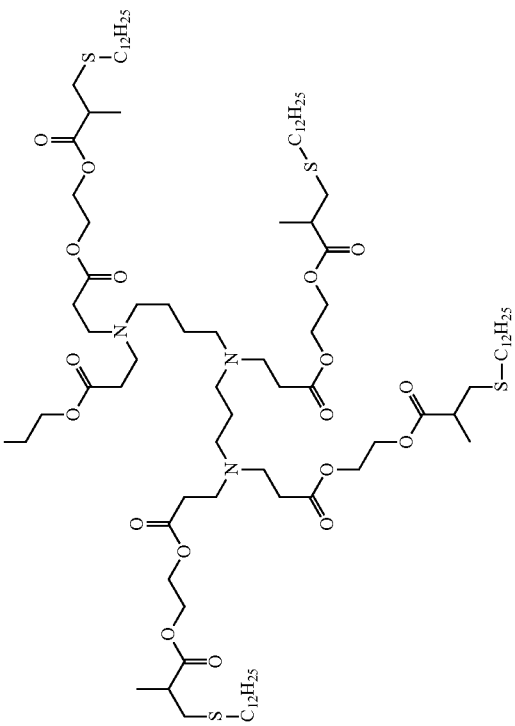 |

TABLE 4-continued
Example ionizable cationic lipo-dendrimers
| ID # | Structure |
|---|---|
| 5A2-4 SC12 (6-arm) | 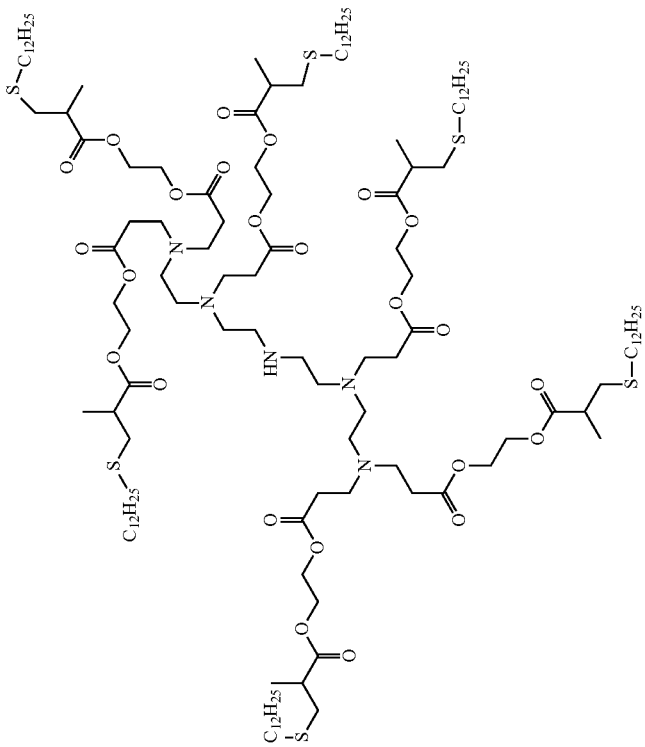 |

TABLE 4-continued
Example ionizable cationic lipo-dendrimers
| ID # | Structure |
|---|---|
| 5A2-4 SC10 (6-arm) | 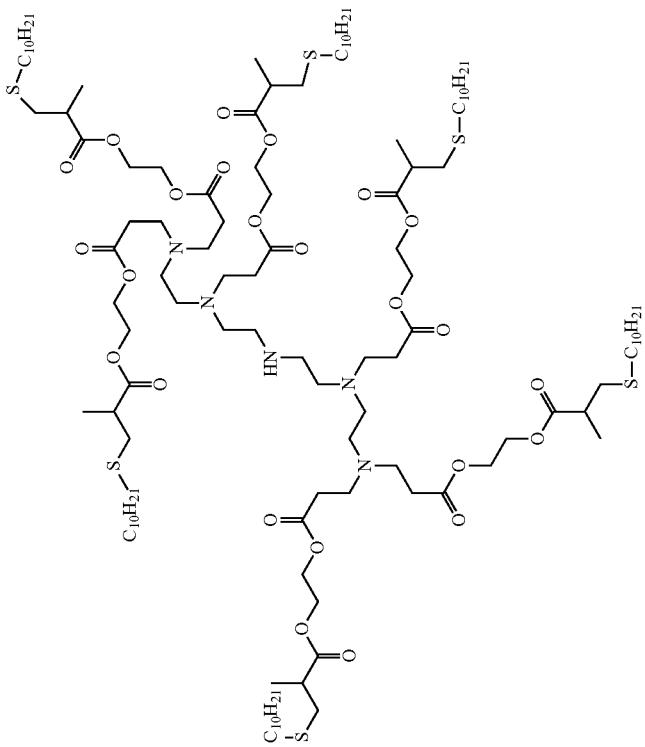 |

TABLE 4-continued
Example ionizable cationic lipo-dendrimers
| ID # | Structure |
|---|---|
| 5A3-2-SC8 (6-arm) | 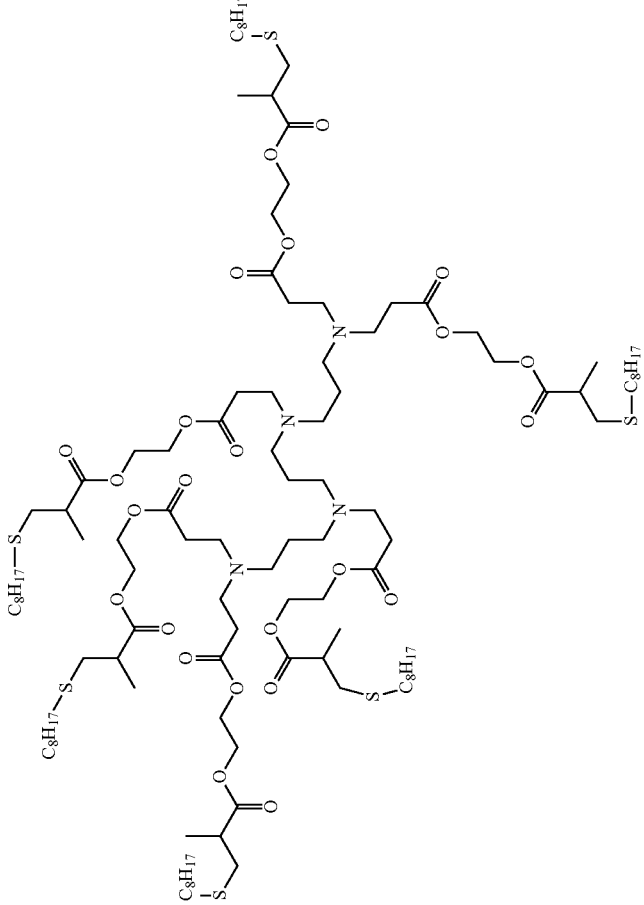 |

TABLE 4-continued
Example ionizable cationic lipo-dendrimers
| ID # | Structure |
|---|---|
| 5A3-2-SC12 (6-arm) | 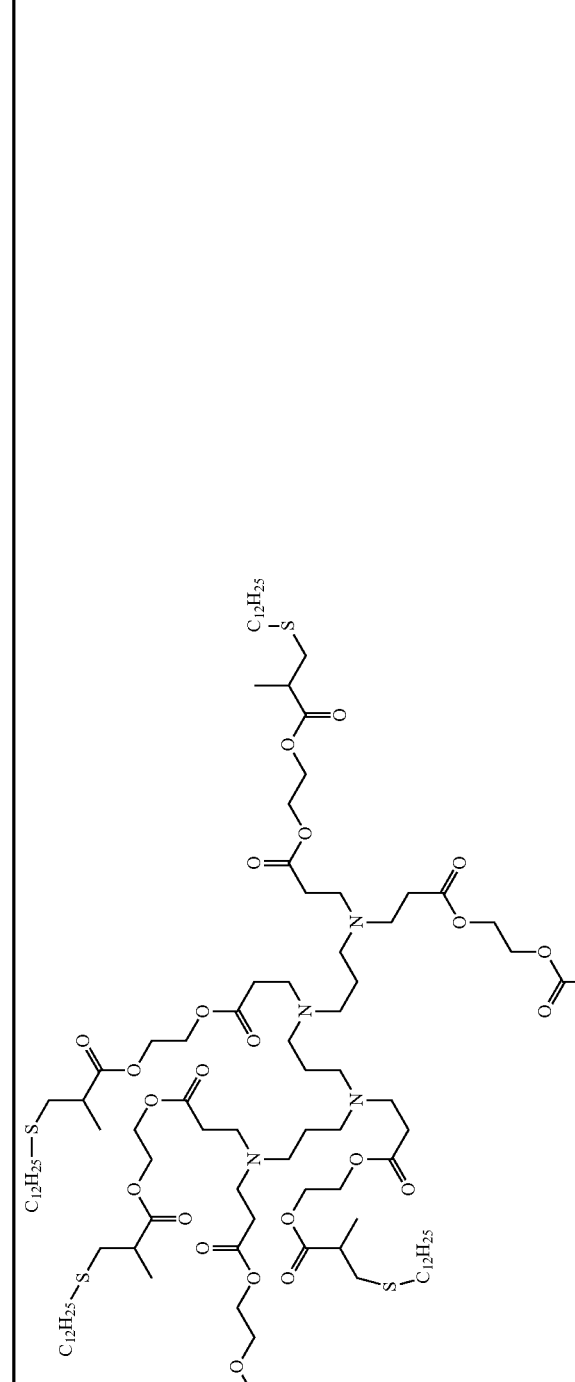 |

TABLE 4-continued
Example ionizable cationic lipo-dendrimers
| ID # | Structure |
|---|---|
| 5A4-2-SC8 (6-arm) | 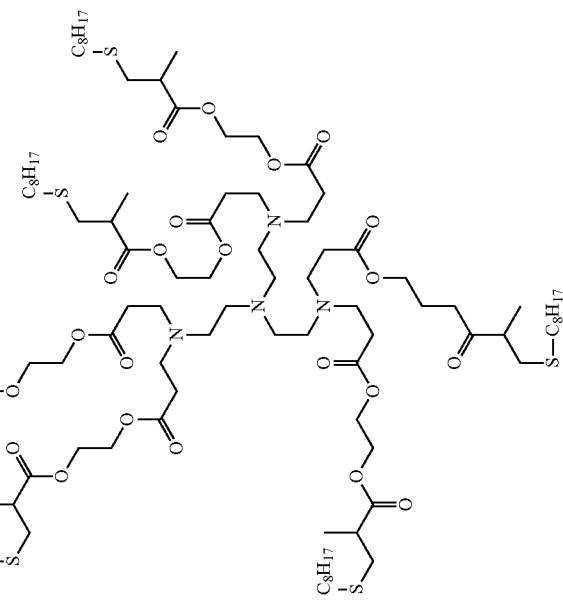 |

TABLE 4-continued
Example ionizable cationic lipo-dendrimers
| ID # | Structure |
|---|---|
| 5A4-2-SC12 (6-arm) | 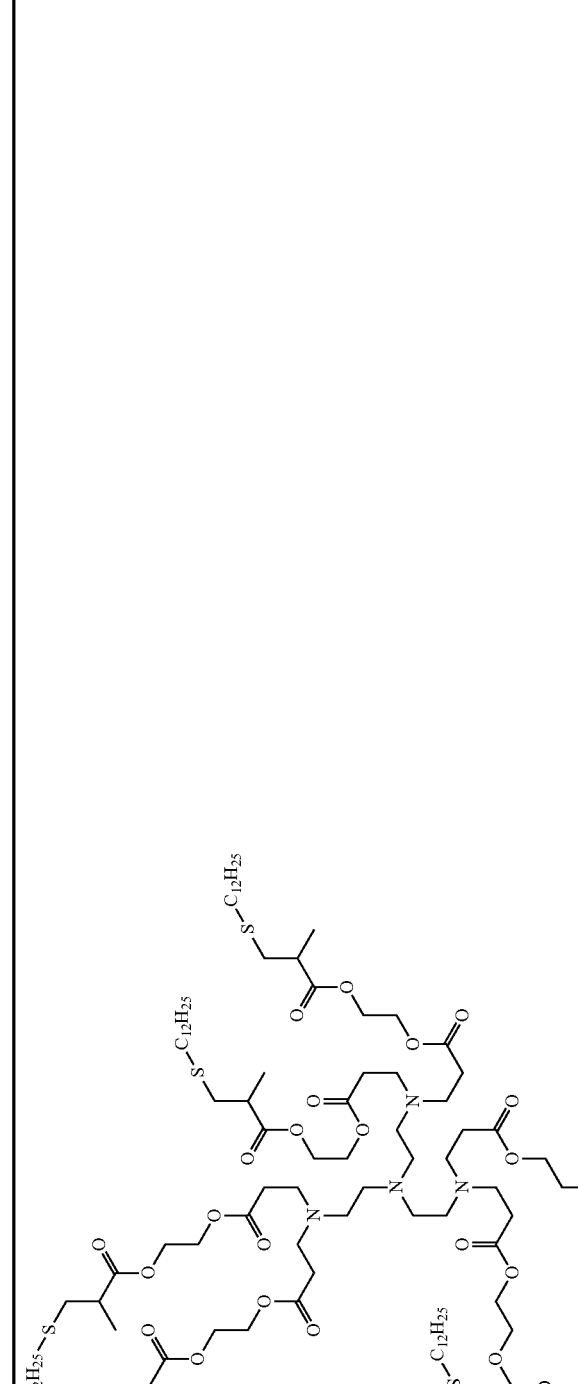 |

TABLE 4-continued
Example ionizable cationic lipo-dendrimers
| ID # | Structure |
|---|---|
| 6A4-SC8 | 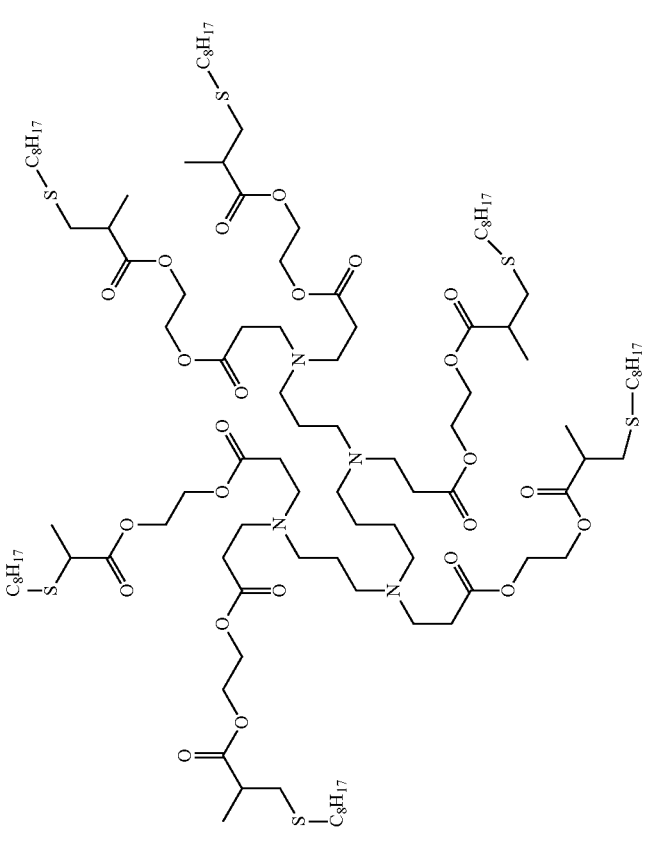 |

TABLE 4-continued
Example ionizable cationic lipo-dendrimers
| ID # | Structure |
|---|---|
| 6A4-SC12 | 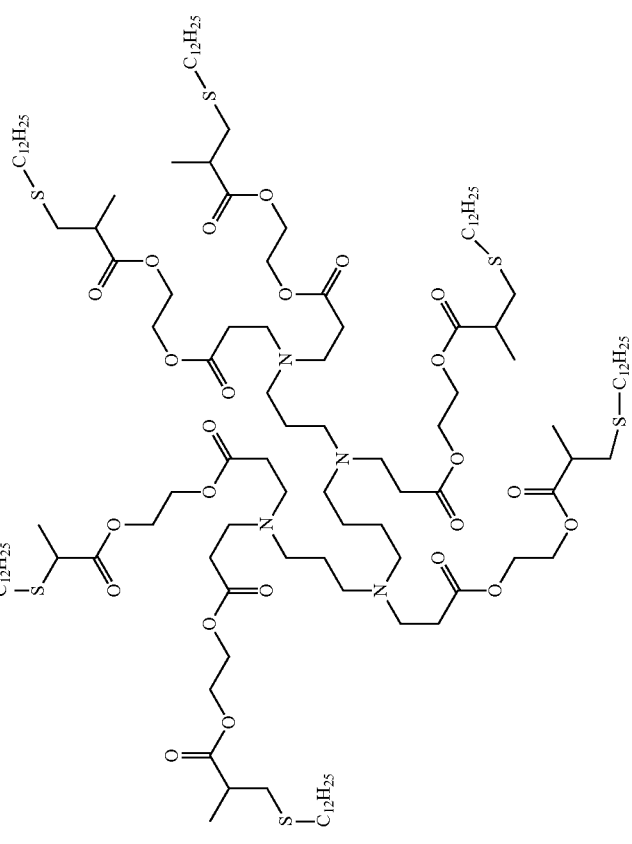 |

TABLE 4-continued
Example ionizable cationic lipo-dendrimers
| ID # | Structure |
|---|---|
| 2A2-g2-SC12 | 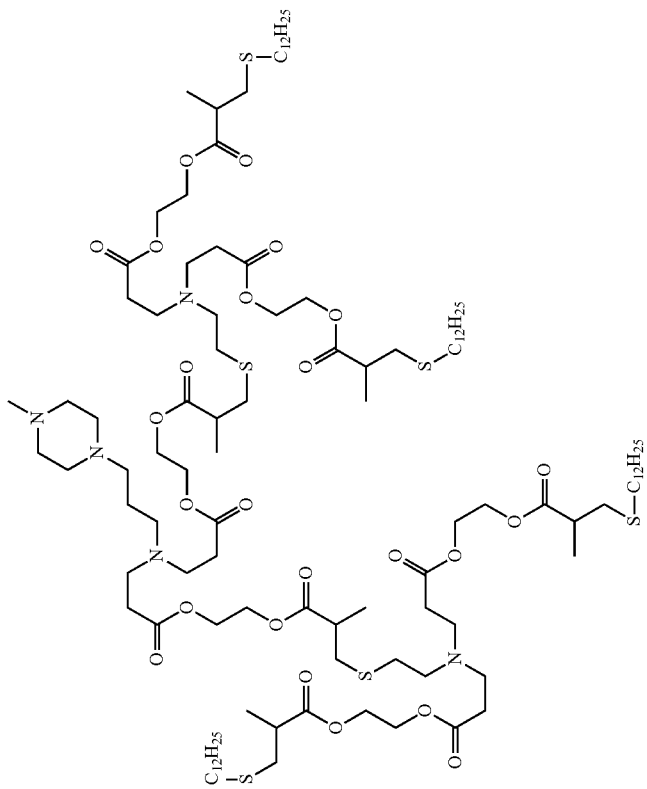 |

TABLE 4-continued

Example ionizable cationic lipo-dendrimers

| ID # | Structure |
|---|---|
| 2A2-g2-SC8 | 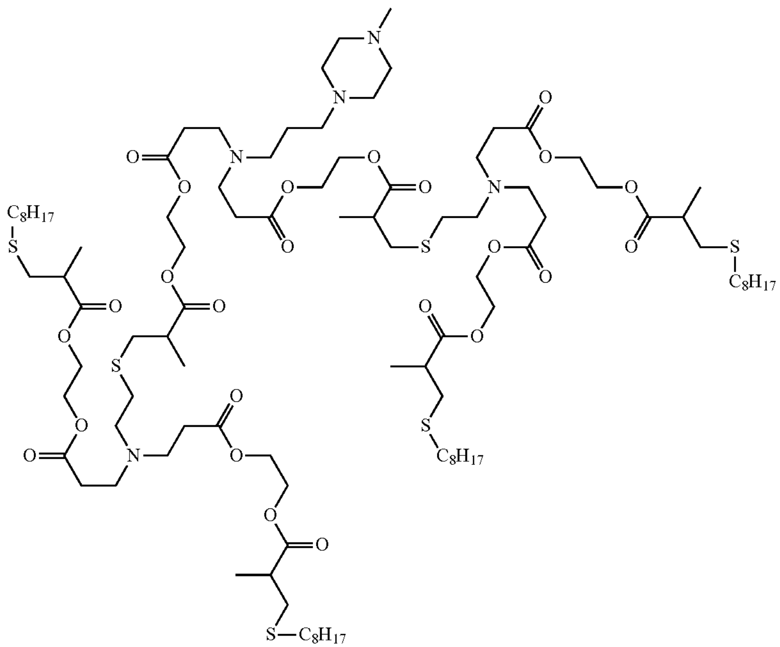 |

TABLE 4-continued
Example ionizable cationic lipo-dendrimers
| ID # | Structure |
|---|---|
| 2A11-g2-SC12 | 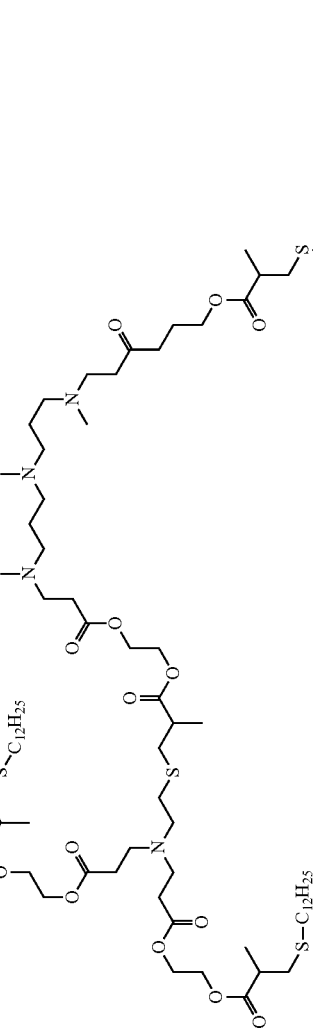 |

TABLE 4-continued
Example ionizable cationic lipo-dendrimers
| ID # | Structure |
|---|---|
| 2A11-g2-SC8 | 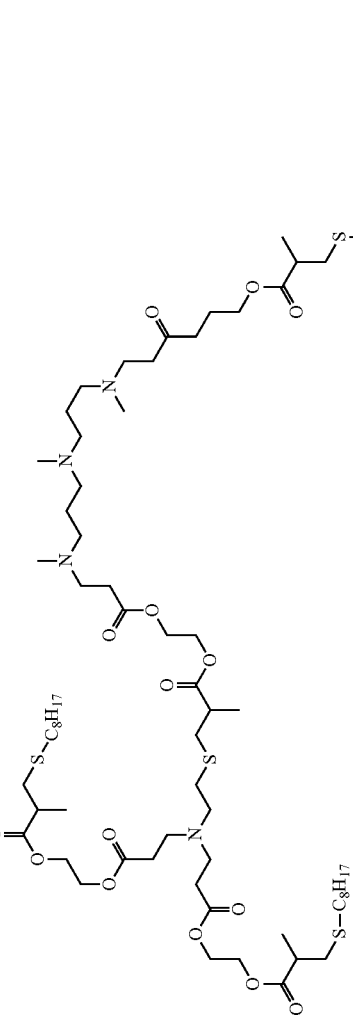 |

TABLE 4-continued
Example ionizable cationic lipo-dendrimers
| ID # | Structure |
|---|---|
| 3A3-g2-SC12 | 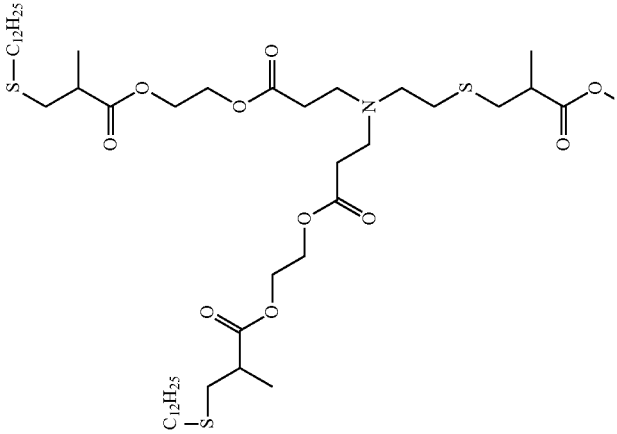 |

TABLE 4-continued
Example ionizable cationic lipo-dendrimers
| ID # | Structure |
|---|---|
| | 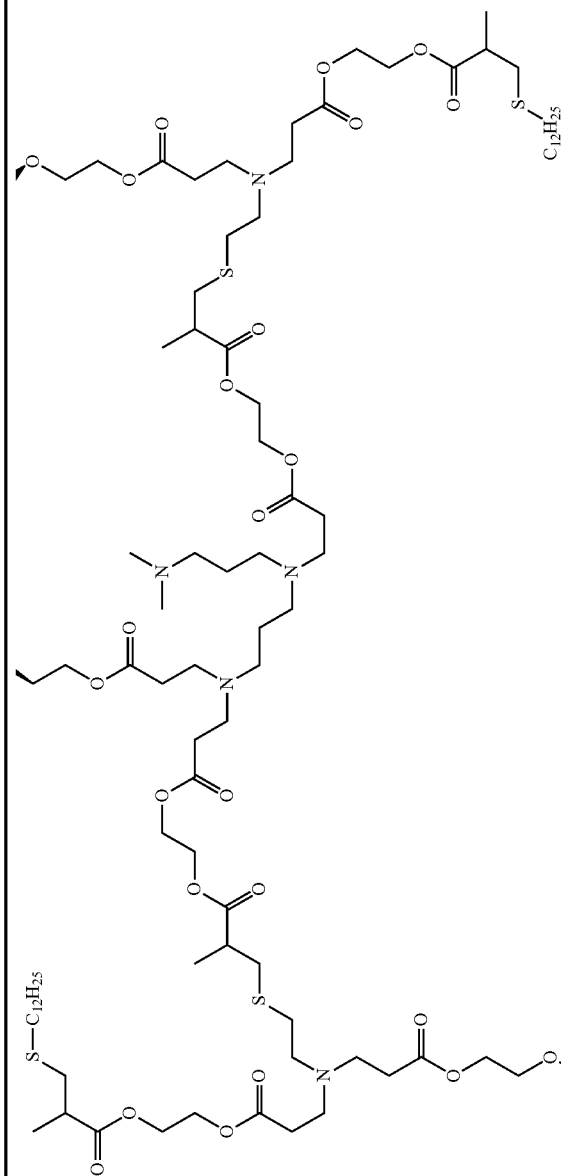 |

TABLE 4-continued
Example ionizable cationic lipo-dendrimers
| ID # | Structure |
|---|---|
| 3A3-g2-SC8 | 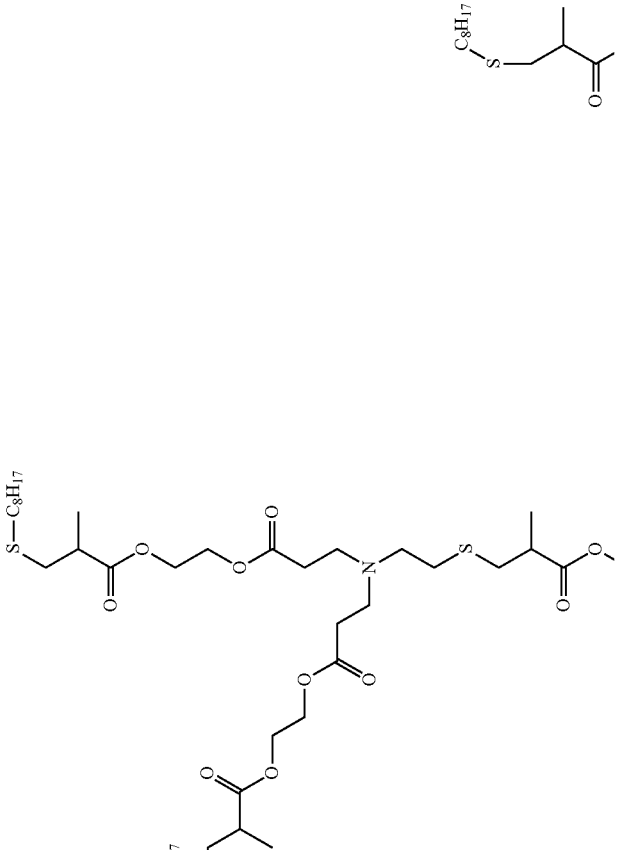 |

TABLE 4-continued
Example ionizable cationic lipo-dendrimers
| ID # | Structure |
|---|---|
| | 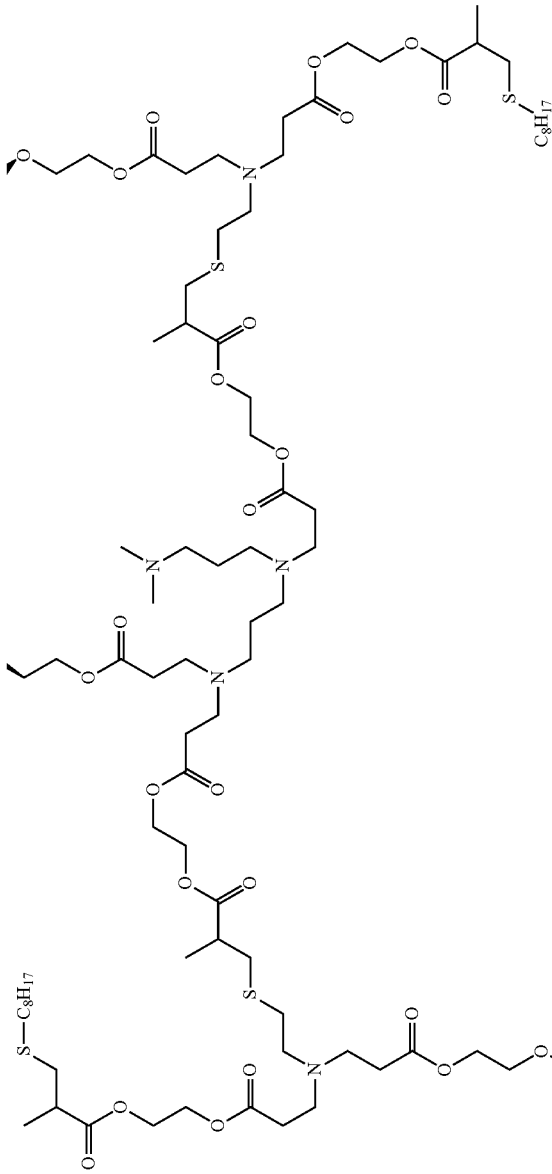 |

TABLE 4-continued
Example ionizable cationic lipo-dendrimers
| ID # | Structure |
|---|---|
| 3A5-g2-SC12 | 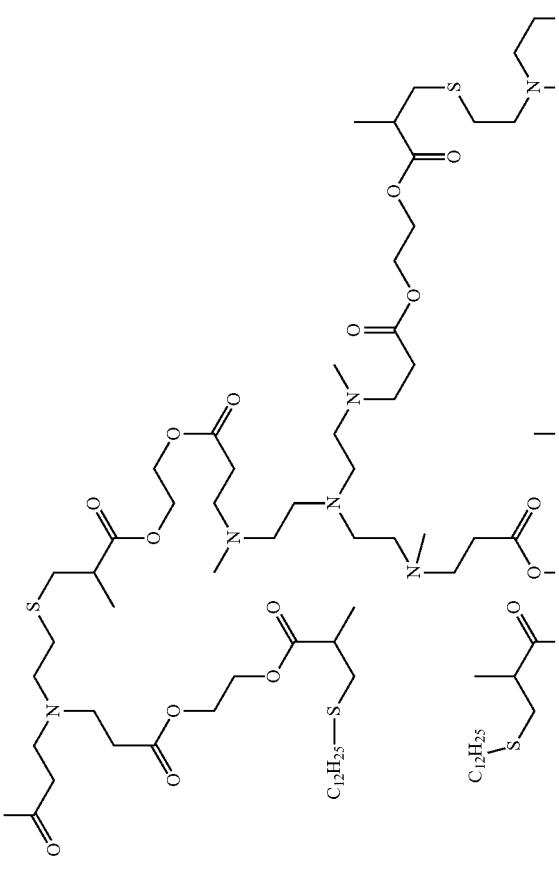 |

TABLE 4-continued
Example ionizable cationic lipo-dendrimers
| ID # | Structure |
|---|---|
| 2A11-g3-SC12 | 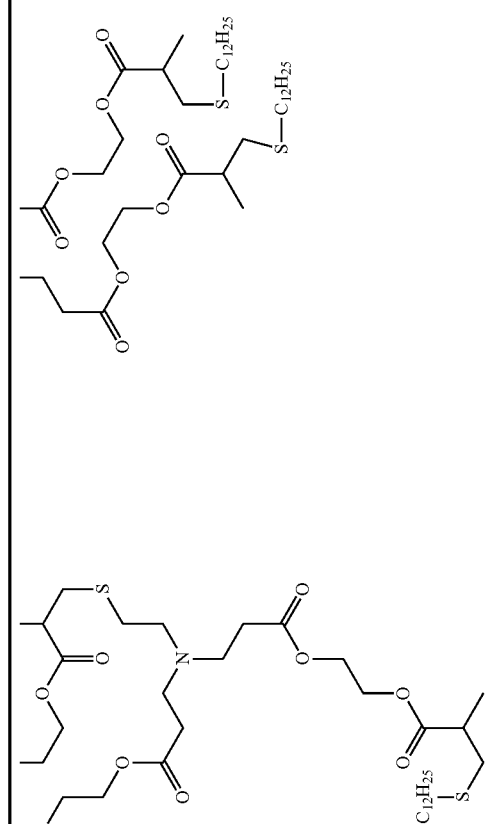 |

TABLE 4-continued

Example ionizable cationic lipo-dendrimers

| ID # | Structure |
|---|---|

TABLE 4-continued

Example ionizable cationic lipo-dendrimers

| ID # | Structure |
|---|---|

TABLE 4-continued

Example ionizable cationic lipo-dendrimers

| ID # | Structure |
|---|---|
| 2A11-g3-SC8 | 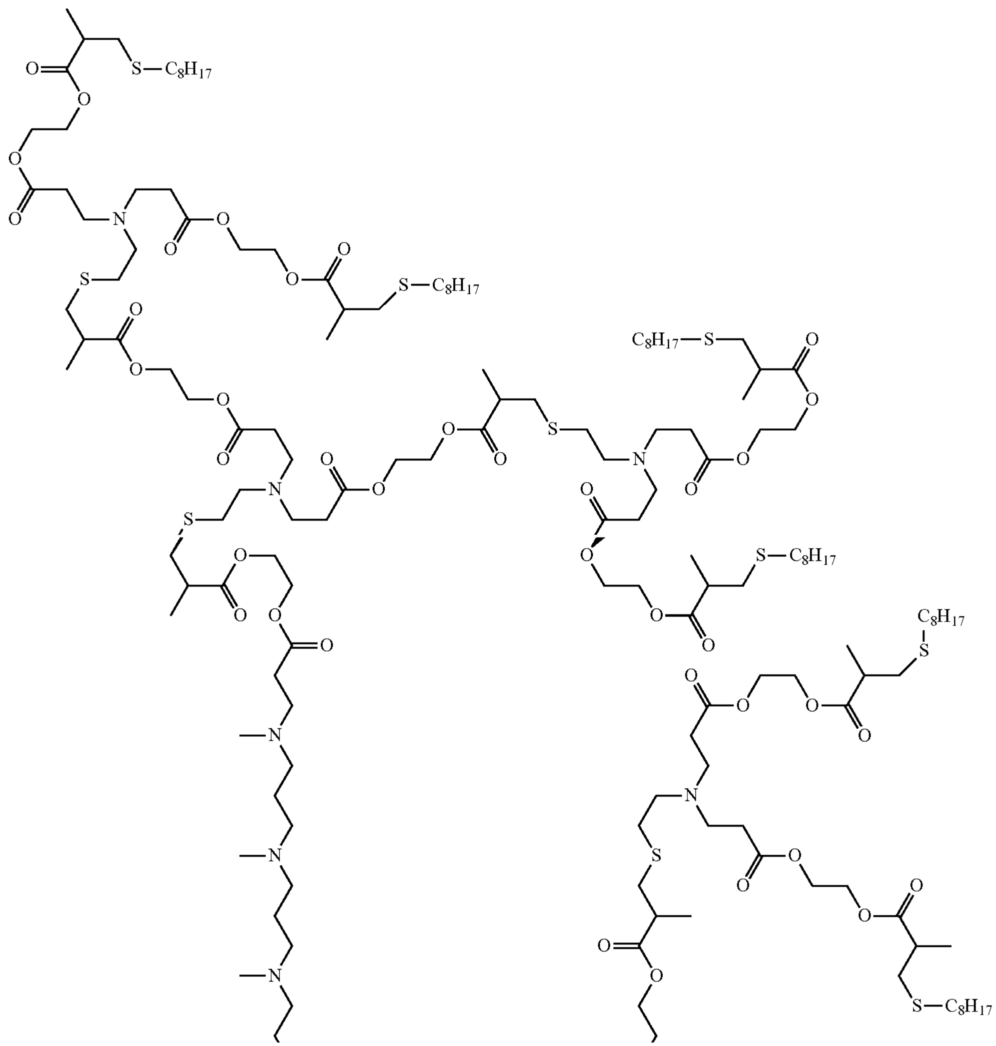 |

TABLE 4-continued
Example ionizable cationic lipo-dendrimers
| ID # | Structure |
|---|---|
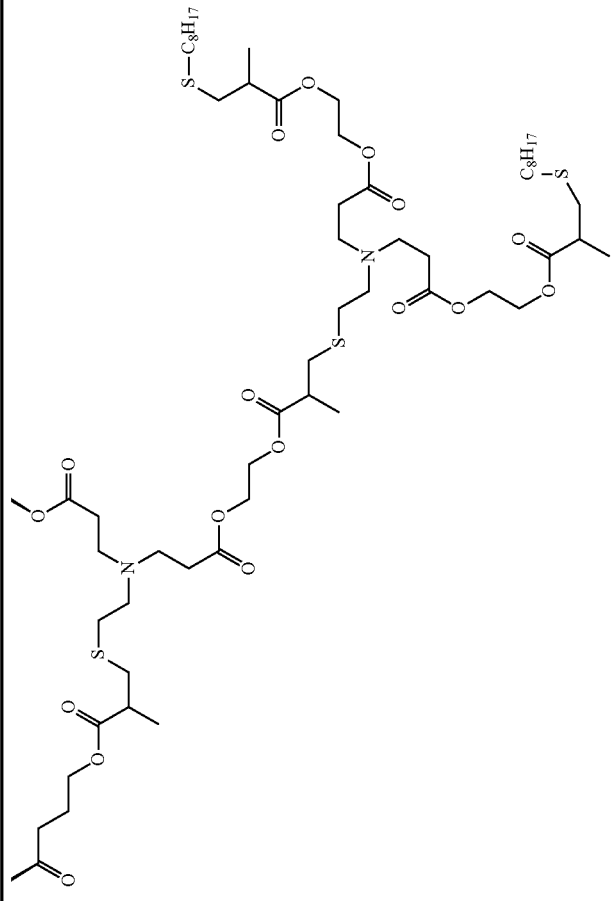

TABLE 4-continued

Example ionizable cationic lipo-dendrimers

| ID # | Structure |
|---|---|
| 1A2-g4-SC12 | 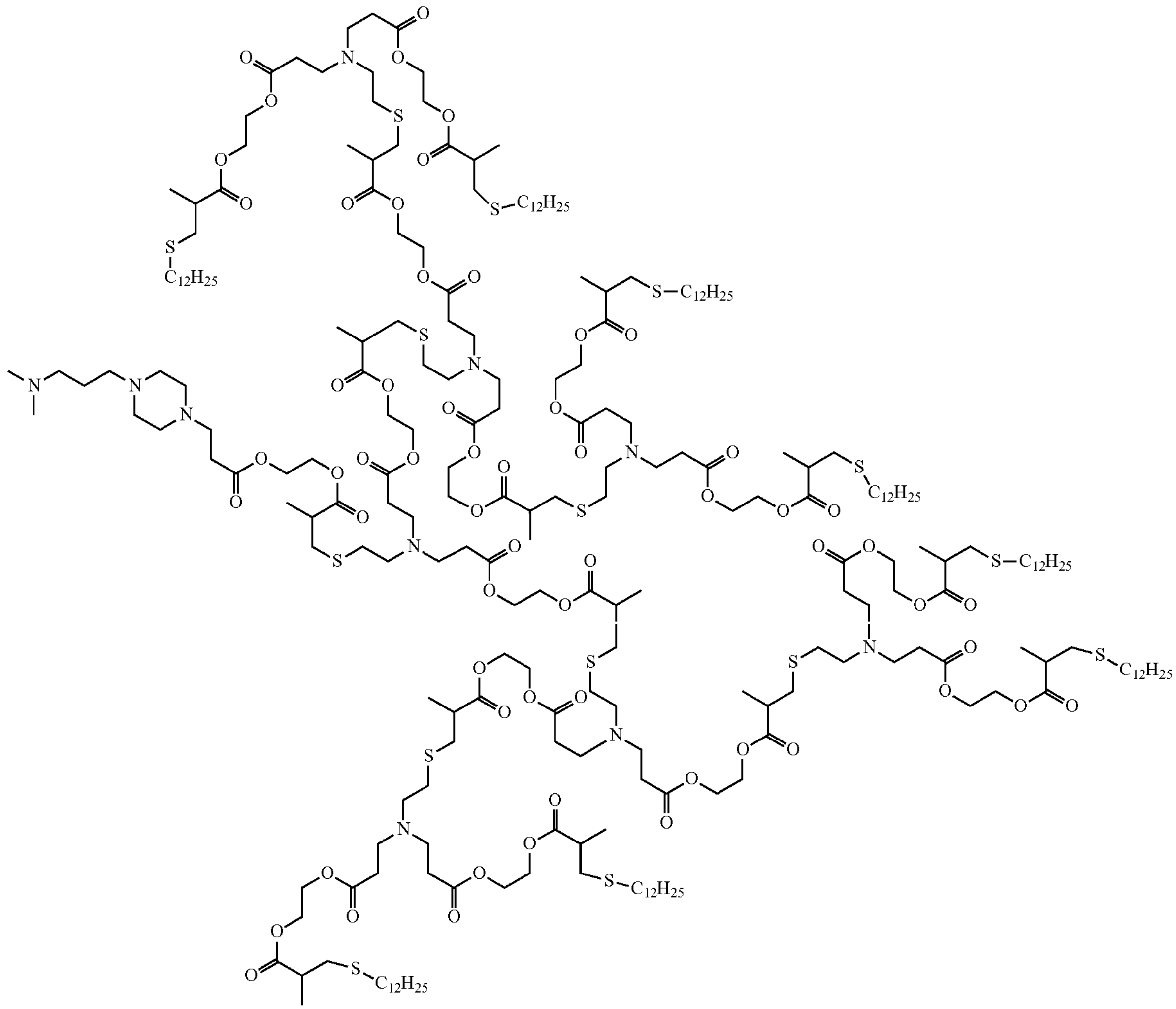 |

TABLE 4-continued
Example ionizable cationic lipo-dendrimers
| ID # | Structure |
|---|---|
| 4A1-g2-SC12 | 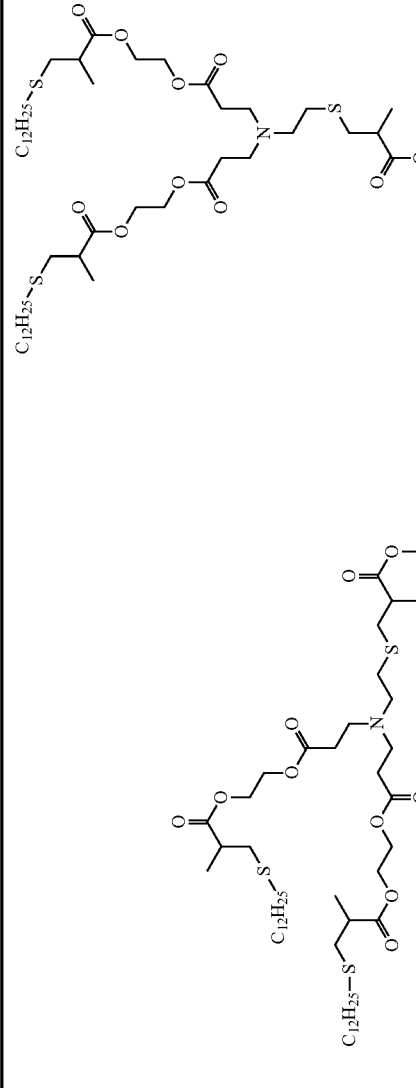 |

TABLE 4-continued
Example ionizable cationic lipo-dendrimers
| ID # | Structure |
|---|---|
| 1A2-g4-SC8 | 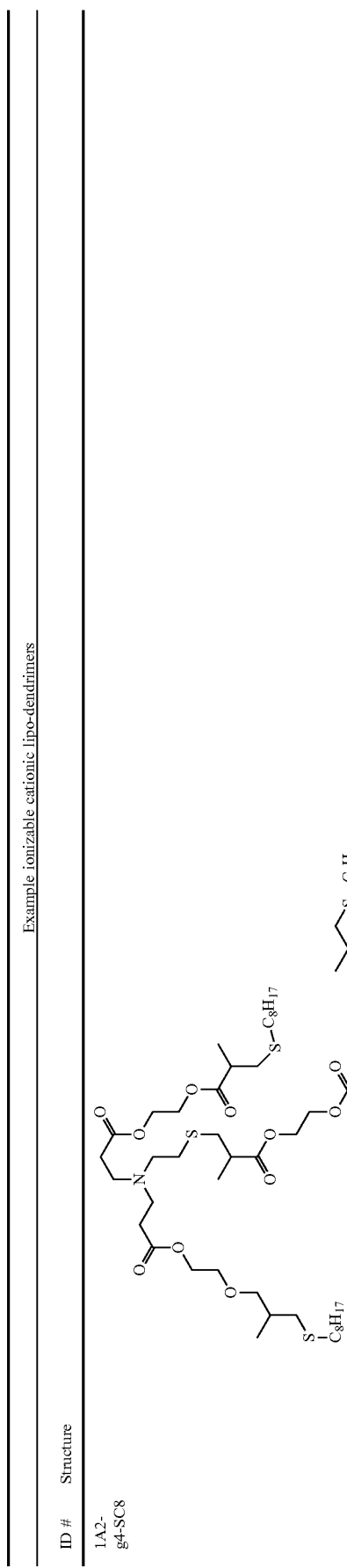 |

TABLE 4-continued
Example ionizable cationic lipo-dendrimers
| ID # | Structure |
|---|---|
| 4A1-g2-SC8 | 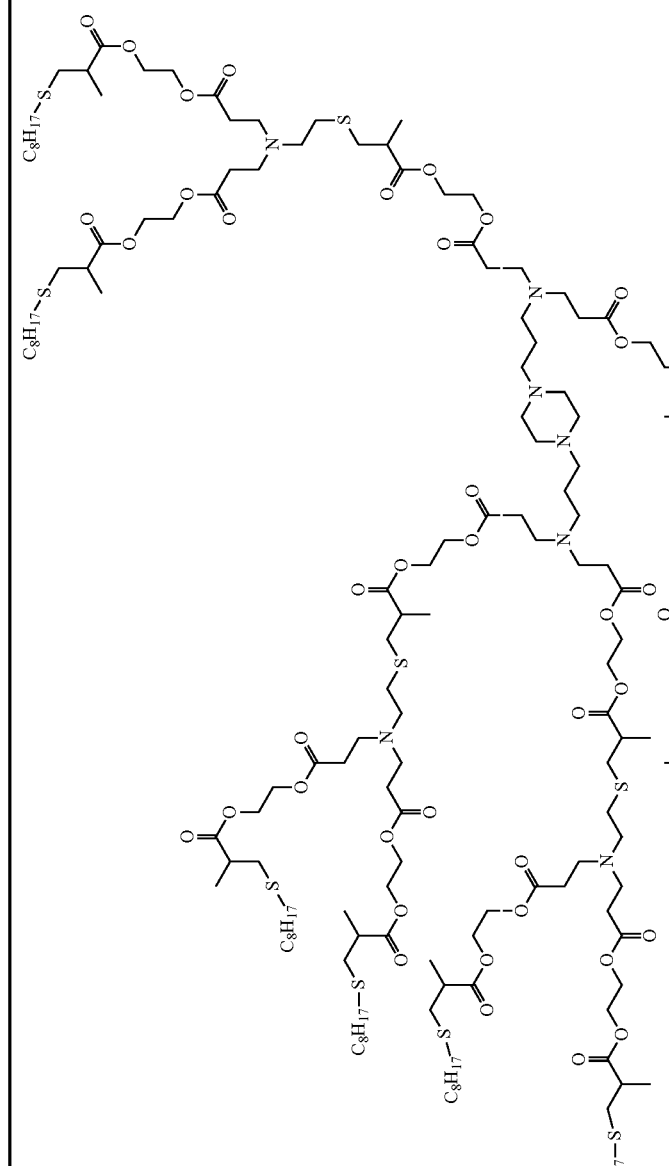 |

TABLE 4-continued
Example ionizable cationic lipo-dendrimers
| ID # | Structure |
|---|---|
| 4A3-g2-SC12 | 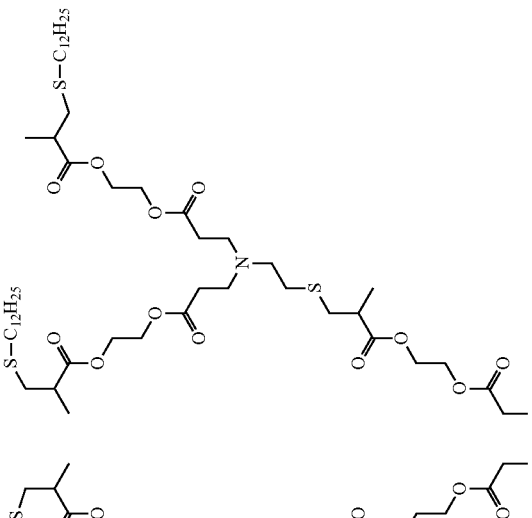 |

TABLE 4-continued
Example ionizable cationic lipo-dendrimers
| ID # | Structure |
|---|---|
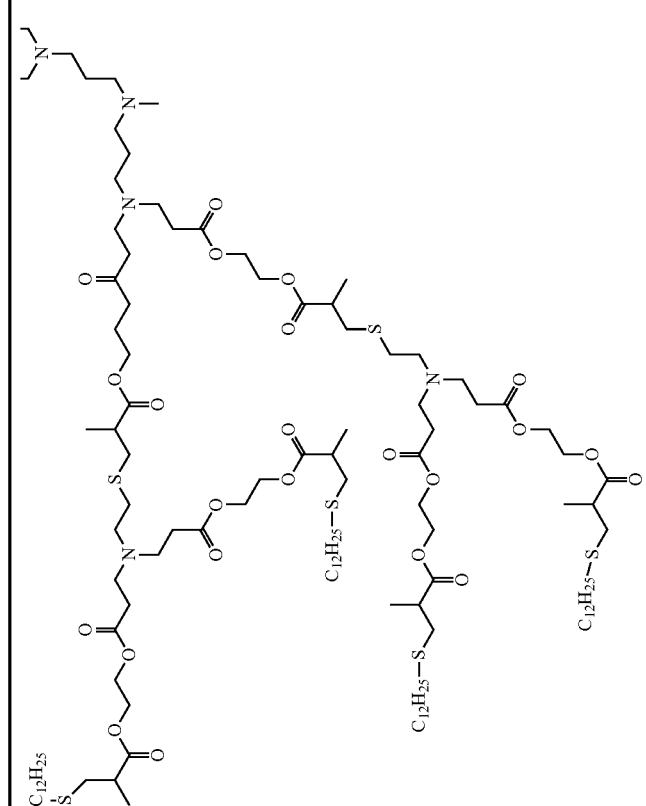

TABLE 4-continued
Example ionizable cationic lipo-dendrimers
| ID # | Structure |
|---|---|
| 4A3-g2-SC8 | 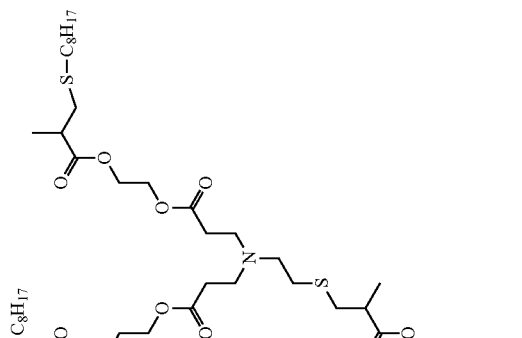 |

TABLE 4-continued

Example ionizable cationic lipo-dendrimers

| ID # | Structure |
|------|-----------|
|      |           |

TABLE 4-continued

Example ionizable cationic lipo-dendrimers

| ID # | Structure |
|---|---|
| 1A2-g3-SC12 | (structure) |

TABLE 4-continued
Example ionizable cationic lipo-dendrimers
| ID # | Structure |
|---|---|
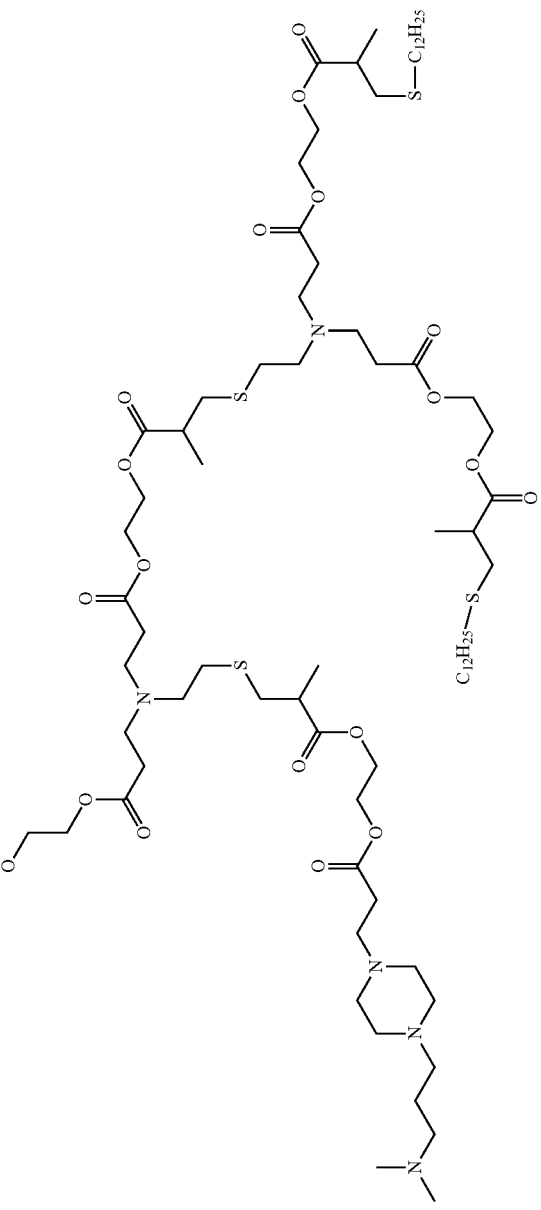

TABLE 4-continued

Example ionizable cationic lipo-dendrimers

| ID # | Structure |
|---|---|
| 1A2-g3-SC8 | 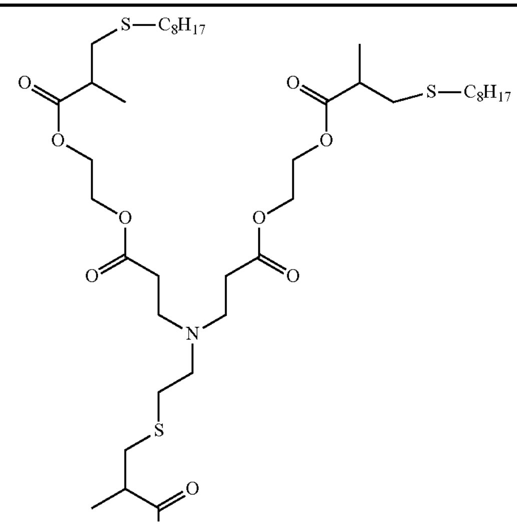 |

TABLE 4-continued
Example ionizable cationic lipo-dendrimers
| ID # | Structure |
|---|---|
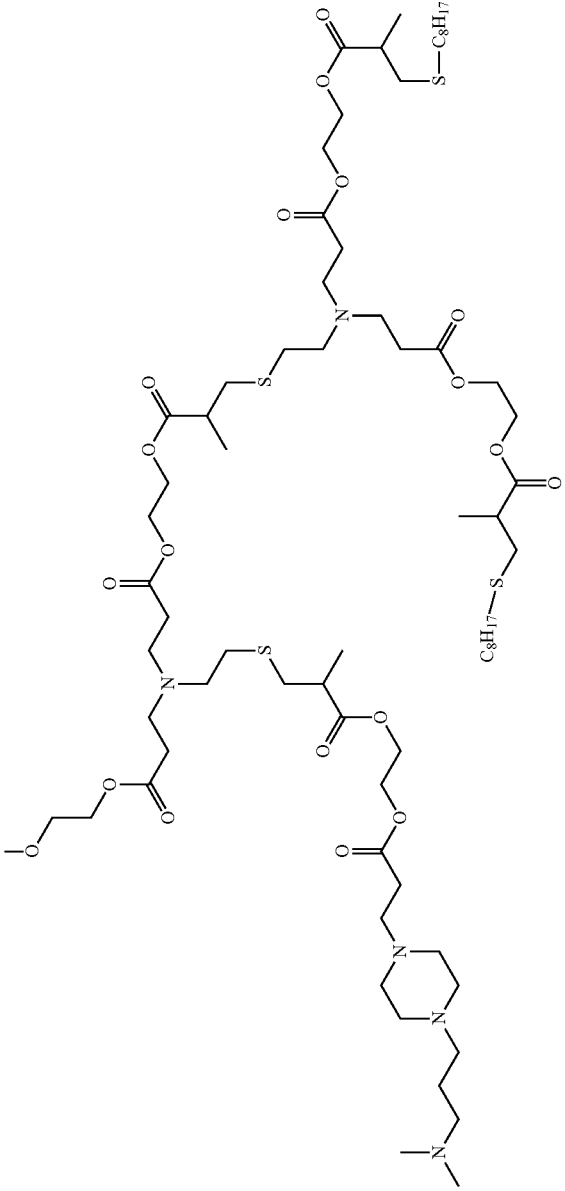

TABLE 4-continued
Example ionizable cationic lipo-dendrimers
| ID # | Structure |
|---|---|
| 2A2-g3-SC12 | 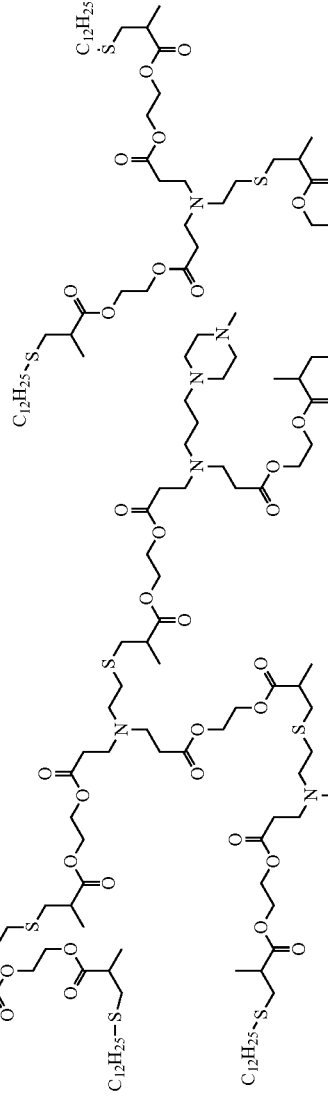 |

TABLE 4-continued
Example ionizable cationic lipo-dendrimers
| ID # | Structure |
|---|---|
| 2A2-g3-SC8 | 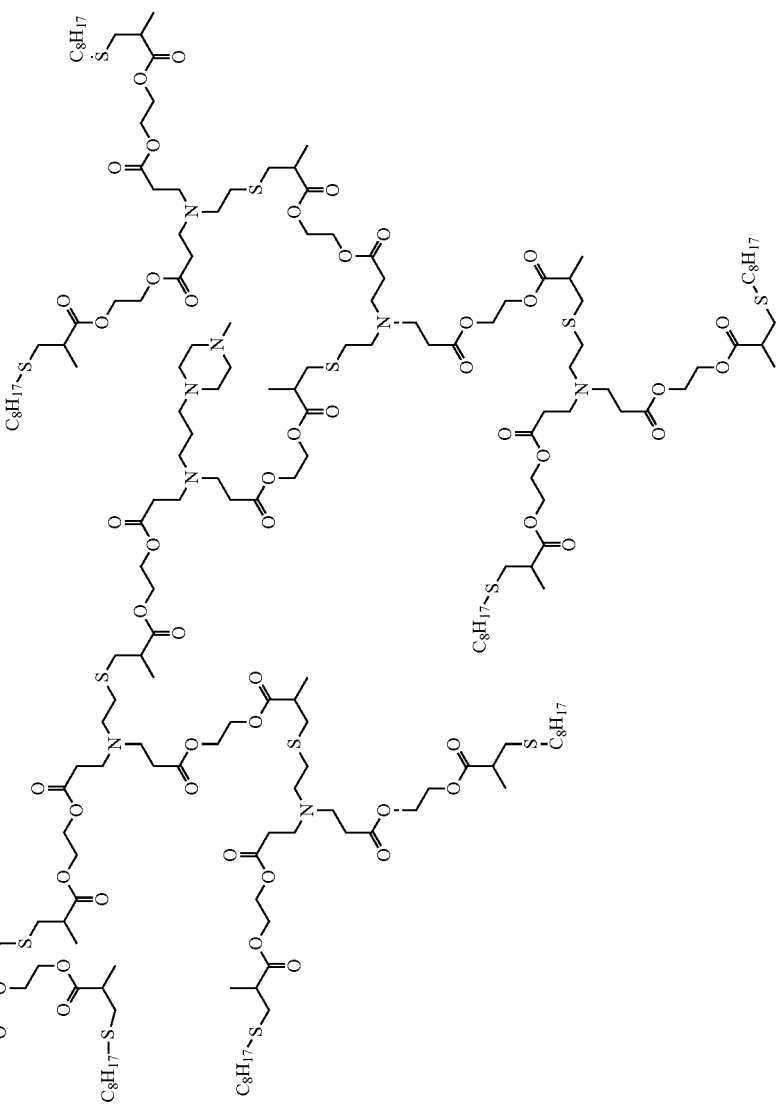 |

TABLE 4-continued
Example ionizable cationic lipo-dendrimers
| ID # | Structure |
|---|---|
| 5A2-4 SC8 (6-arm) | 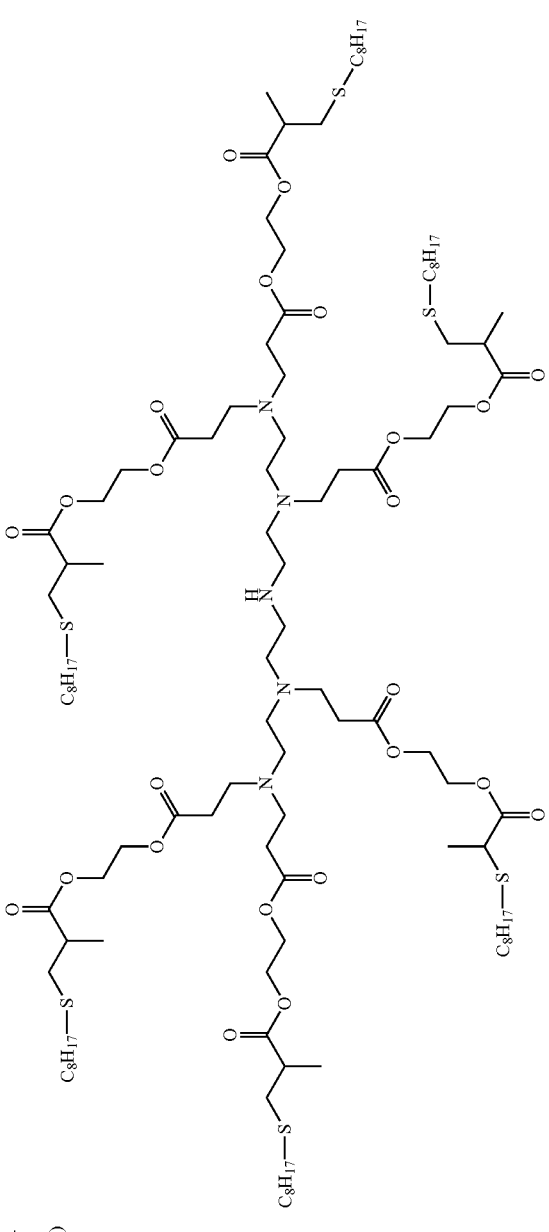 |
| 5A-5 SC8 (6 arm) | 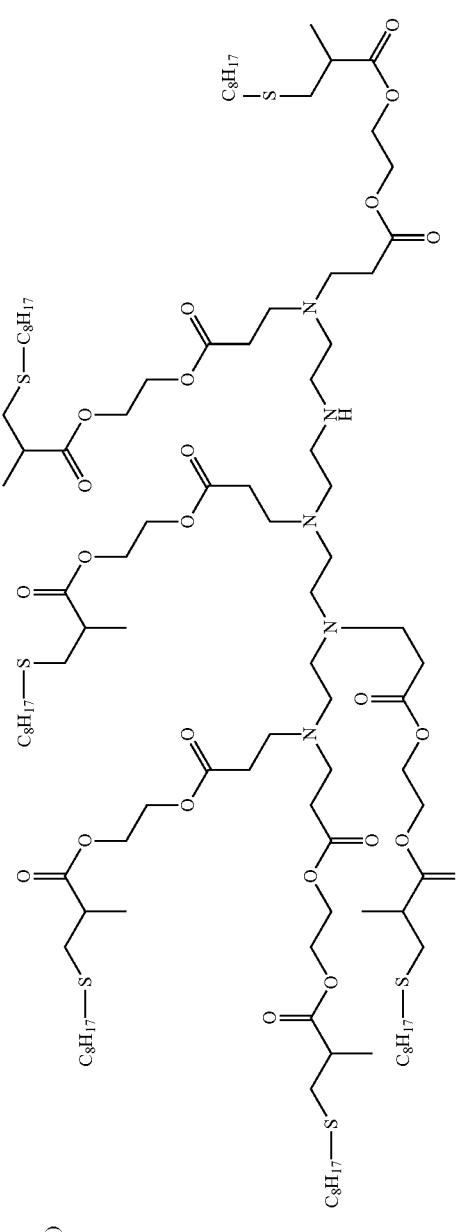 |

TABLE 4-continued

Example ionizable cationic lipo-dendrimers

| ID # | Structure |
|---|---|
| 5A2-6-SC8 (6 arm) | 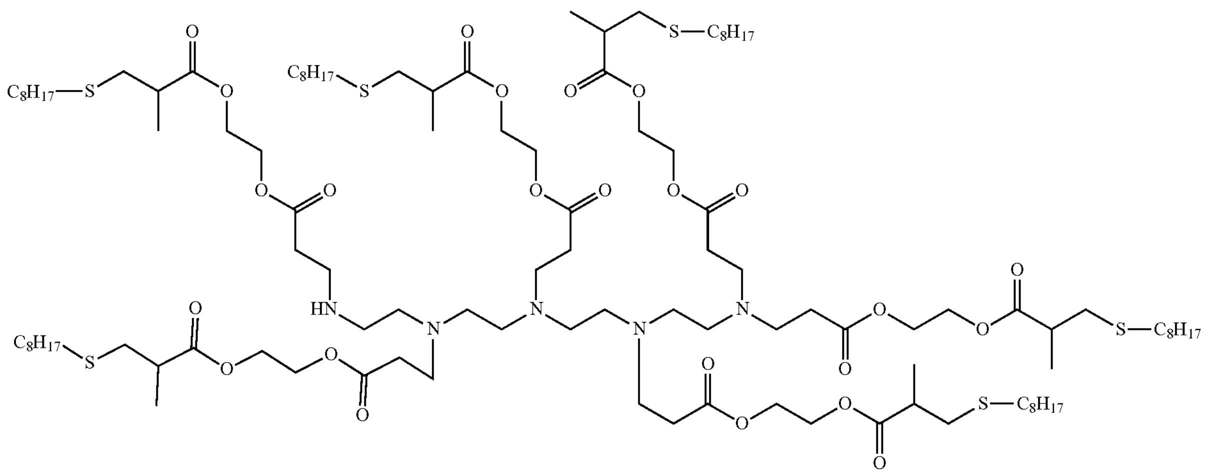 |
| 5A2-1-SC8 (5-arm) | 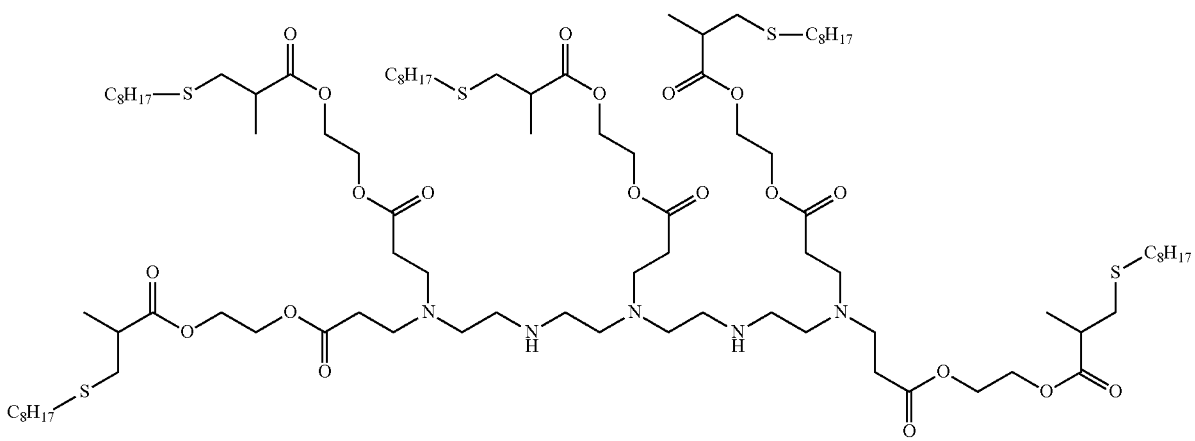 |

TABLE 4-continued

Example ionizable cationic lipo-dendrimers

| ID # | Structure |
|---|---|
| 5A2-2-SC8 | 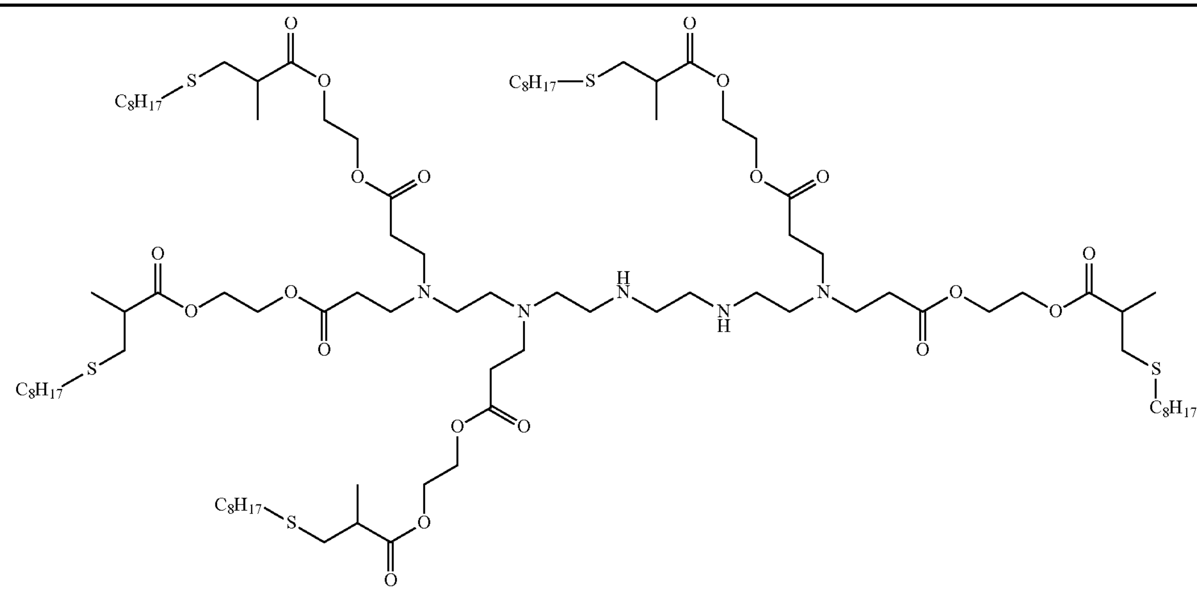 |

TABLE 4-continued

Example ionizable cationic lipo-dendrimers

| ID # | Structure |
|---|---|
| 4A1-SC5 | 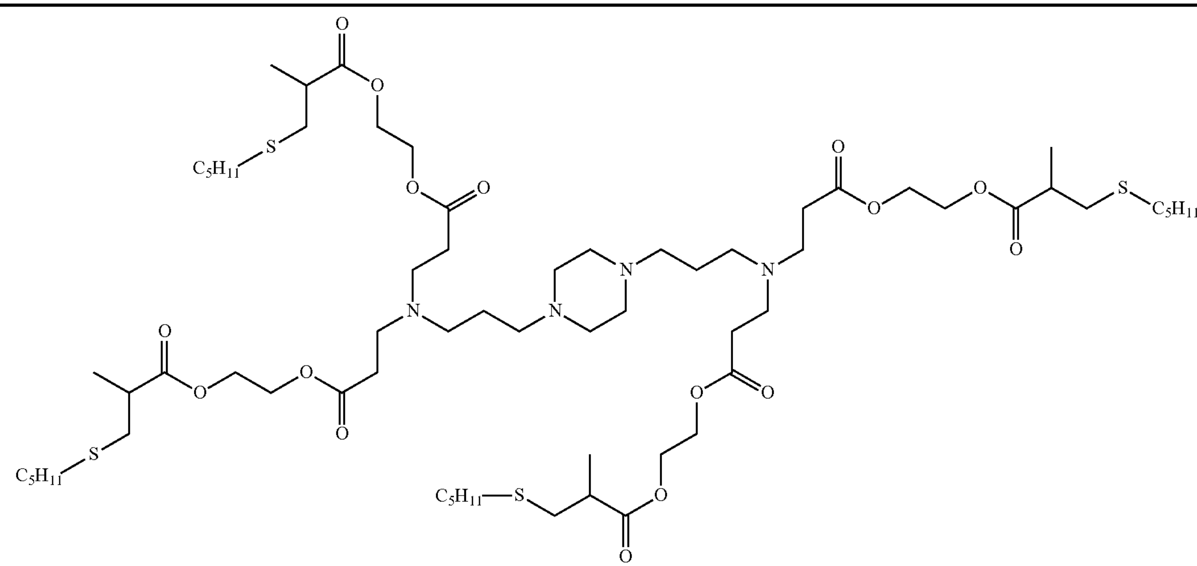 |

TABLE 4-continued

Example ionizable cationic lipo-dendrimers

| ID # | Structure |
|------|-----------|
| 4A1-SC8 | 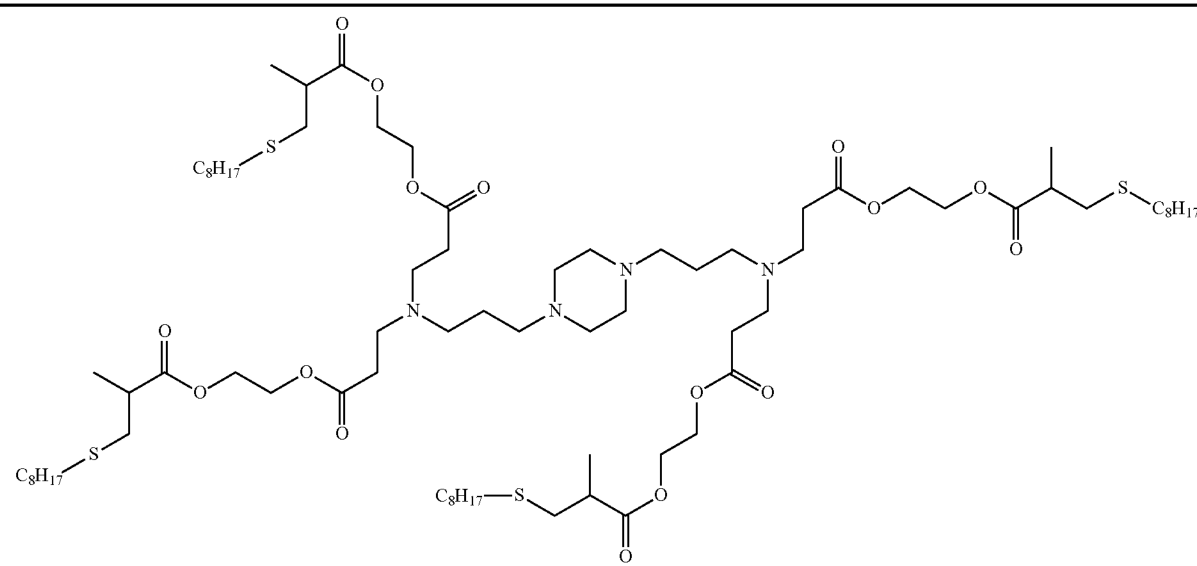 |
| 4A3-SC6 | 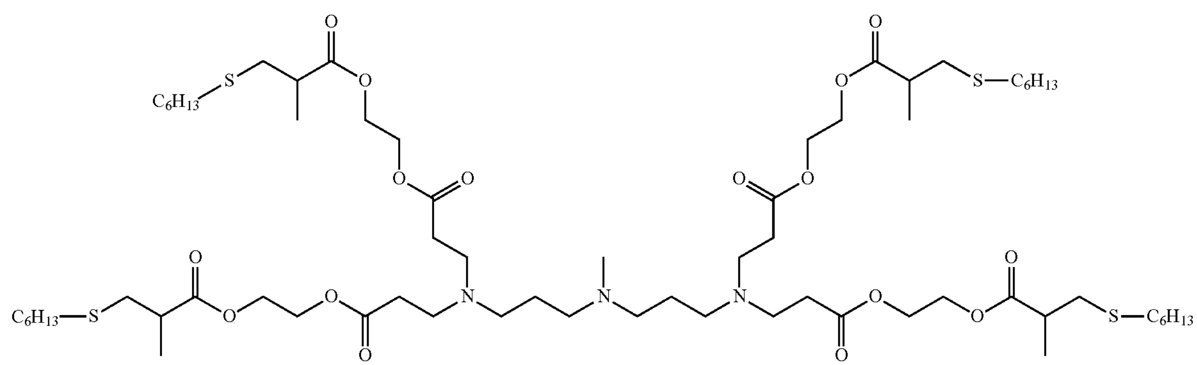 |

TABLE 4-continued

Example ionizable cationic lipo-dendrimers

| ID # | Structure |
|---|---|
| 4A3-SC7 | 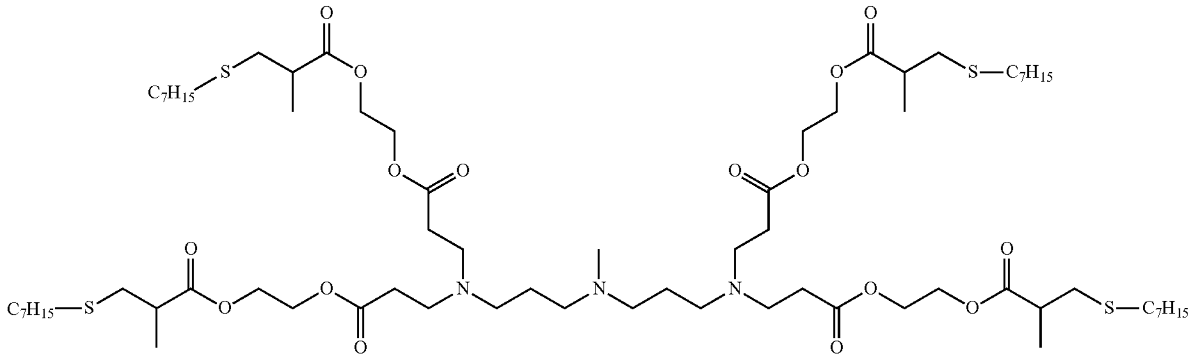 |
| 4A3-SC8 | 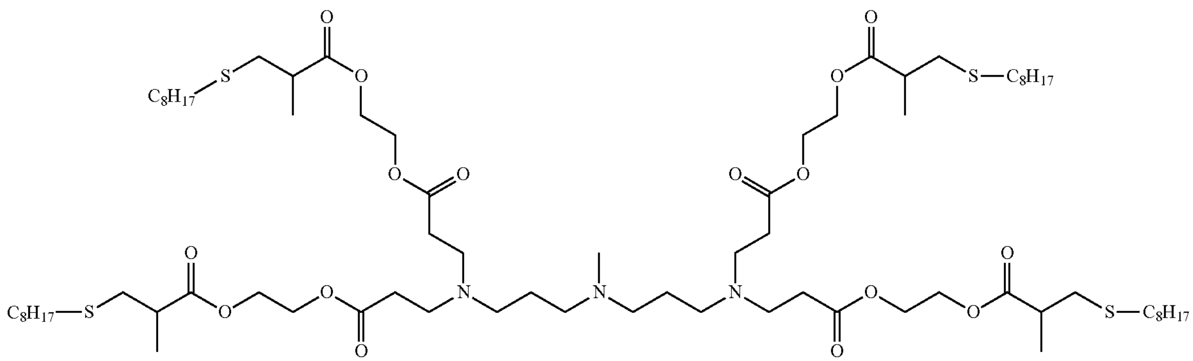 |

TABLE 4-continued

Example ionizable cationic lipo-dendrimers

| ID # | Structure |
|---|---|
| 5A4-2-SC5 (6 arm) | 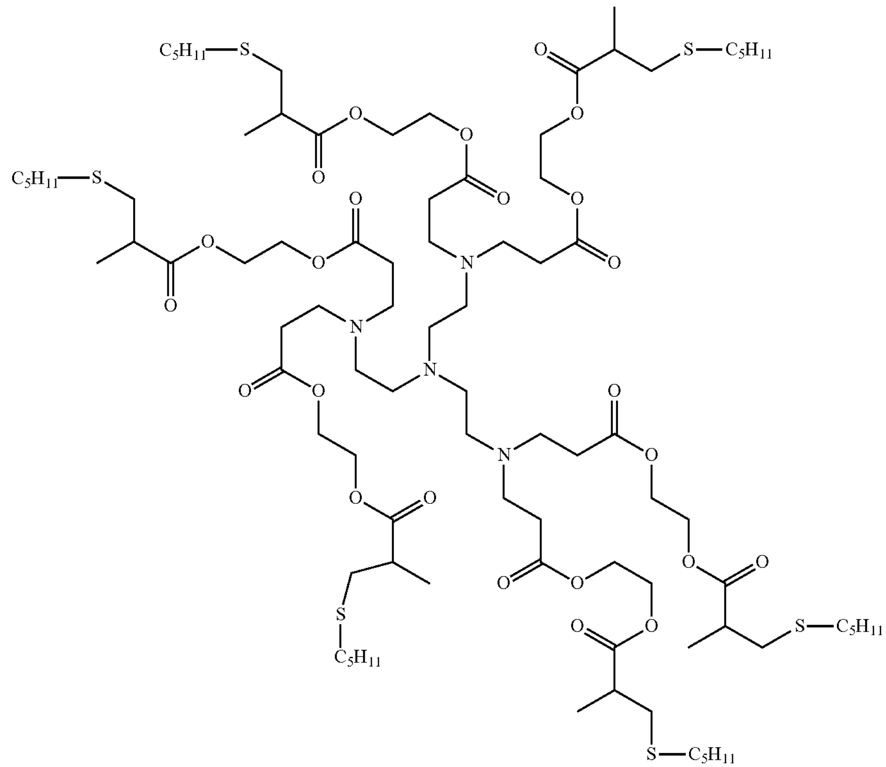 |

TABLE 4-continued
Example ionizable cationic lipo-dendrimers
| ID # | Structure |
|---|---|
| 5A4-2-SC6 (6 arm) | 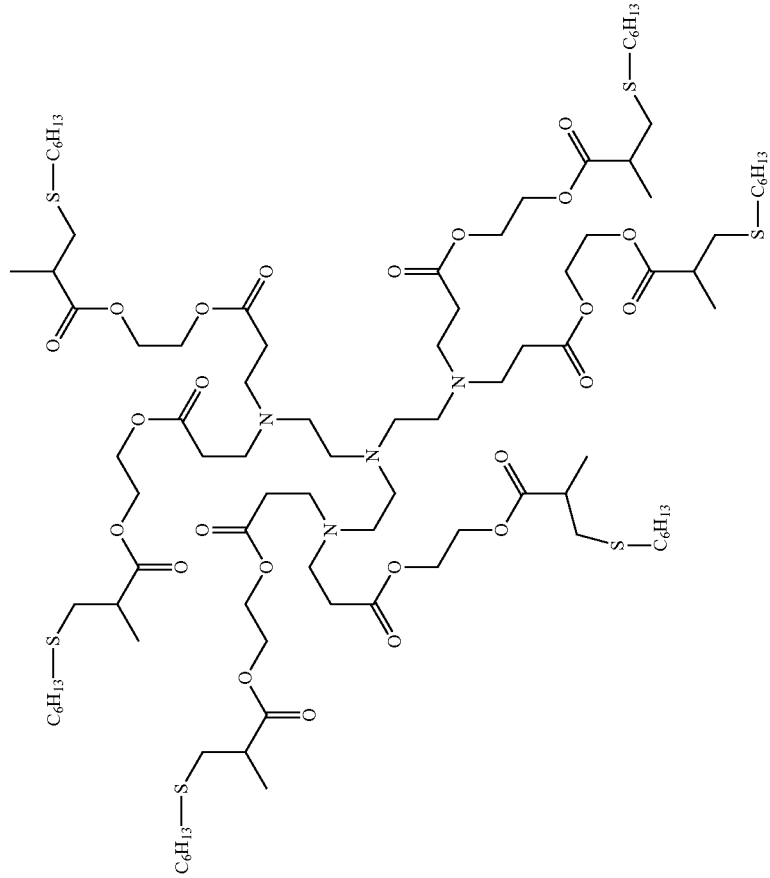 |

TABLE 4-continued
Example ionizable cationic lipo-dendrimers
| ID # | Structure |
|---|---|
| 5A2-4-SC8 (5-arm) | 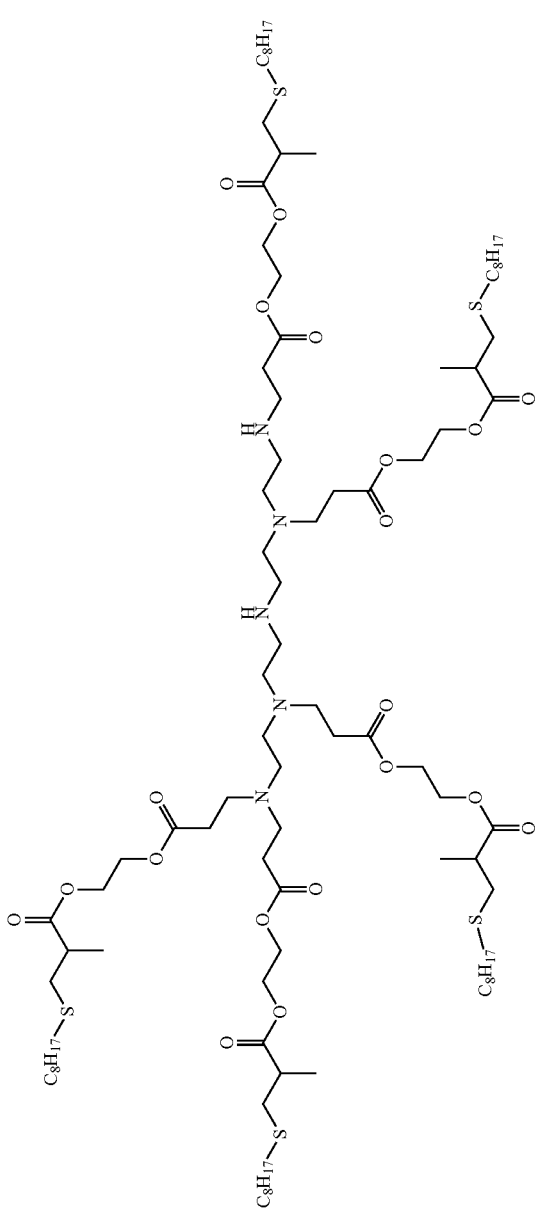 |

TABLE 4-continued
Example ionizable cationic lipo-dendrimers
| ID # | Structure |
|---|---|
| 3A5-g2-SC8 | 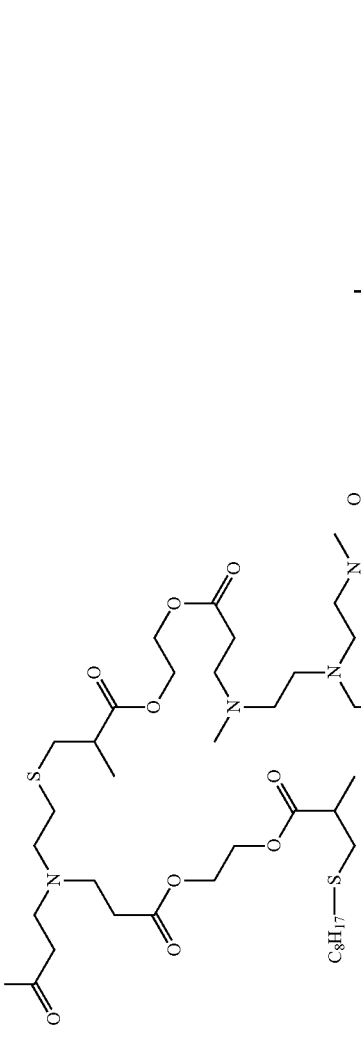 |

TABLE 4-continued

Example ionizable cationic lipo-dendrimers

| ID # | Structure |
|---|---|
| 5A2-SC8 | 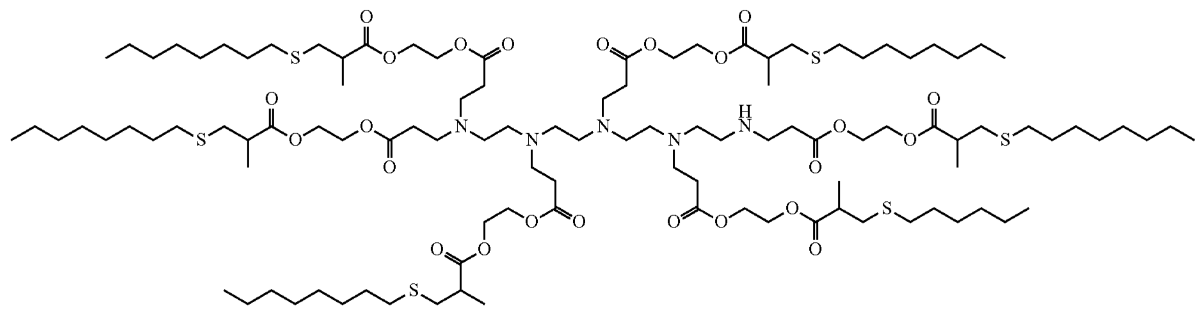 [SMILES: CCCCCCCCSCC(C)C(=O)OCCOC(=O)CCNCCN(CCC(=O)OCCOC(=O)C(C)CSCCCCCC)CCN(CCC(=O)OCCOC(=O)C(C)CSCCCCCCCC)CCN(CCC(=O)OCCOC(=O)C(C)CSCCCCCCCC)CCN(CCC(=O)OCCOC(=O)C(C)CSCCCCCCCC)CCC(=O)OCCOC(=O)C(C)CSCCCCCCCC] |

In some embodiments, the dendrimer is 2A2-SC14. In some embodiments, the dendrimer is 2A6-SC 14. In some embodiments, the dendrimer is 2A9-SC 14. In some embodiments, the dendrimer is 3A3-SC10. In some embodiments, the dendrimer is 3A3-SC14. In some embodiments, the dendrimer is 4A5-SC10. In some embodiments, the dendrimer is 3A5-SC14. In some embodiments, the dendrimer is 4A1-SC12. In some embodiments, the dendrimer is 4A3-SC12. In some embodiments, the dendrimer is 5A1-SC12. In some embodiments, the dendrimer is 5A1-SC8. In some embodiments, the dendrimer is 5A2-2-SC12. In some embodiments, the dendrimer is 5A3-1-SC12. In some embodiments, the dendrimer is 5A3-1-SC8. In some embodiments, the dendrimer is 5A4-1-SC12. In some embodiments, the dendrimer is 5A4-1-SC8. In some embodiments, the dendrimer is 5A5-SC8. In some embodiments, the dendrimer is 5A5-SC 12. In some embodiments, the dendrimer is 5A2-4-SC 12. In some embodiments, the dendrimer is 5A2-4-SC10. In some embodiments, the dendrimer is 5A3-2-SC8. In some embodiments, the dendrimer is 5A3-2-SC12. In some embodiments, the dendrimer is 5A4-2-SC8. In some embodiments, the dendrimer is 5A4-2-SC12. In some embodiments, the dendrimer is 6A4-SC8. In some embodiments, the dendrimer is 6A4-SC12. In some embodiments, the dendrimer is 2A2-g2-SC12. In some embodiments, the dendrimer is 2A2-g2-SC8. In some embodiments, the dendrimer is 2A11-g2-SC12. In some embodiments, the dendrimer is 2A11-g2-SC8. In some embodiments, the dendrimer is 3A3-g2-SC12. In some embodiments, the dendrimer is 3A3-g2-SC8. In some embodiments, the dendrimer is 3A5-g2-SC12. In some embodiments, the dendrimer is 2A11-g3-SC12. In some embodiments, the dendrimer is 2A11-g3-SC8. In some embodiments, the dendrimer is 1A2-g4-SC12. In some embodiments, the dendrimer is 4A1-g2-SC12. In some embodiments, the dendrimer is 1A2-g4-SC8. In some embodiments, the dendrimer is 4A1-g2-SC8. In some embodiments, the dendrimer is 4A3-g2-SC12. In some embodiments, the dendrimer is 4A3-g2-SC8. In some embodiments, the dendrimer is 1A2-g3-SC12. In some embodiments, the dendrimer is 1A2-g3-SC8. In some embodiments, the dendrimer is 2A2-g3-SC12. In some embodiments, the dendrimer is 2A2-g3-SC8. In some embodiments, the dendrimer is 5A2-4-SC8. In some embodiments, the dendrimer is 5A5-SC8. In some embodiments, the dendrimer is 5A2-6-SC8. In some embodiments, the dendrimer is 5A2-1-SC8. In some embodiments, the dendrimer is 5A2-2-SC8. In some embodiments, the dendrimer is 4A1-SC5. In some embodiments, the dendrimer is 4A1-SC8. In some embodiments, the dendrimer is 4A3-SC6. In some embodiments, the dendrimer is 4A3-SC7. In some embodiments, the dendrimer is 4A3-SC8. In some embodiments, the dendrimer is 5A4-2-SC5. In some embodiments, the dendrimer is 5A4-2-SC6. In some embodiments, the dendrimer is 5A2-4-SC8. In some embodiments, the dendrimer is 3A5-g2-SC8. In some embodiments, the dendrimer is 5A2-SC8.

1. Other Ionizable Lipids

In some embodiments of the lipid composition, the cationic lipid comprises a structural formula (D-I'):

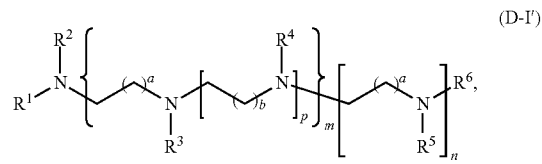

wherein:
a is 1 and b is 2, 3, or 4; or, alternatively, b is 1 and a is 2, 3, or 4;
m is 1 and n is 1; or, alternatively, m is 2 and n is 0; or, alternatively, m is 2 and n is 1; and
$R^1$, $R^2$, $R^3$, $R^4$, $R^5$, and $R^6$ are each independently selected from the group consisting of H, —$CH_2CH(OH)R^7$, —$CH(R^7)CH_2OH$, —$CH_2CH_2C(=O)OR^7$, —$CH_2CH_2C(=O)NHR^7$, and —$CH_2R^7$, wherein $R^7$ is independently selected from $C_3$-$C_{18}$ alkyl, $C_3$-$C_{18}$ alkenyl having one C=C double bond, a protecting group for an amino group, —$C(=NH)NH_2$, a poly(ethylene glycol) chain, and a receptor ligand;
provided that at least two moieties among $R^1$ to $R^6$ are independently selected from —$CH_2CH(OH)R^7$, —$CH(R^7)CH_2OH$, —$CH_2CH_2C(=O)OR^7$, —$CH_2CH_2C(=O)NHR^7$, or —$CH_2R^7$, wherein $R^7$ is independently selected from $C_3$-$C_{18}$ alkyl or $C_3$-$C_{18}$ alkenyl having one C=C double bond; and
wherein one or more of the nitrogen atoms indicated in formula (D-I') may be protonated to provide a cationic lipid.

In some embodiments of the cationic lipid of formula (D-I'), a is 1. In some embodiments of the cationic lipid of formula (D-I'), b is 2. In some embodiments of the cationic lipid of formula (D-I'), m is 1. In some embodiments of the cationic lipid of formula (D-I'), n is 1. In some embodiments of the cationic lipid of formula (D-I'), $R^1$, $R^2$, $R^3$, $R^4$, $R^5$, and $R^6$ are each independently H or —$CH_2CH(OH)R^7$. In some embodiments of the cationic lipid of formula (D-I'), $R^1$, $R^2$, $R^3$, $R^4$, $R^5$, and $R^6$ are each independently H or

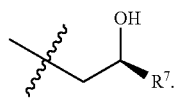

In some embodiments of the cationic lipid of formula (D-I'), $R^1$, $R^2$, $R^3$, $R^4$, $R^5$, and $R^6$ are each independently H or

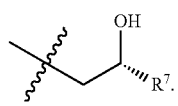

In some embodiments of the cationic lipid of formula (D-I'), $R^7$ is $C_3$-$C_{18}$ alkyl (e.g., $C_6$-$C_{12}$ alkyl).

In some embodiments, the cationic lipid of formula (D-I') is 13,16,20-tris(2-hydroxydodecyl)-13,16,20,23-tetraazapentatricontane-11,25-diol:

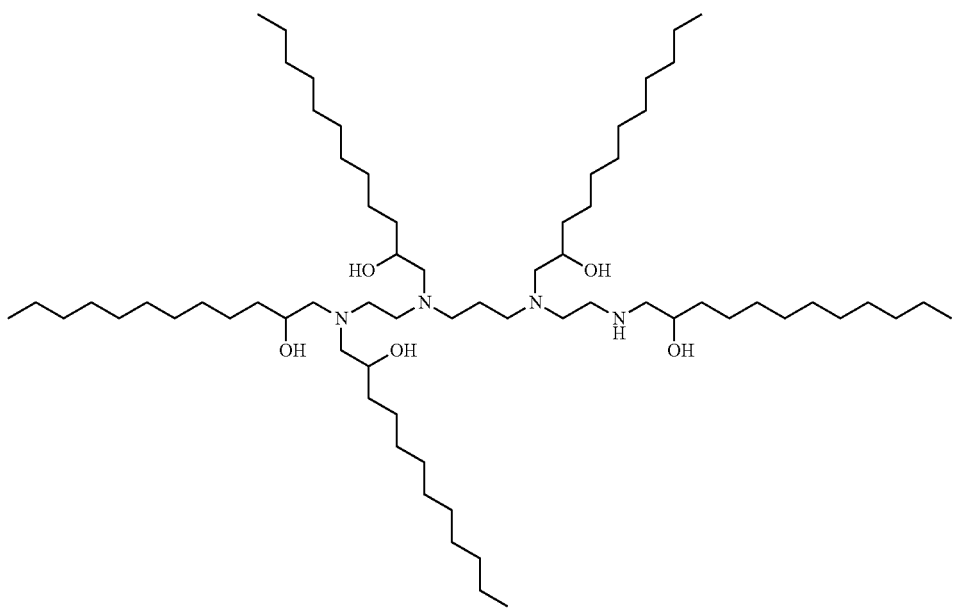 [SMILES: CCCCCCCCCCC(O)CNCCN(CCCN(CCN(CC(O)CCCCCCCCCC)CC(O)CCCCCCCCCC)CC(O)CCCCCCCCCC)CC(O)CCCCCCCCCC]

In some embodiments, the cationic lipid of formula (D-I') is (11R,25R)-13,16,20-tris(1-2-hydroxydodecyl)-13,16,20,23-tetraazapentatricontane-11,25-diol:

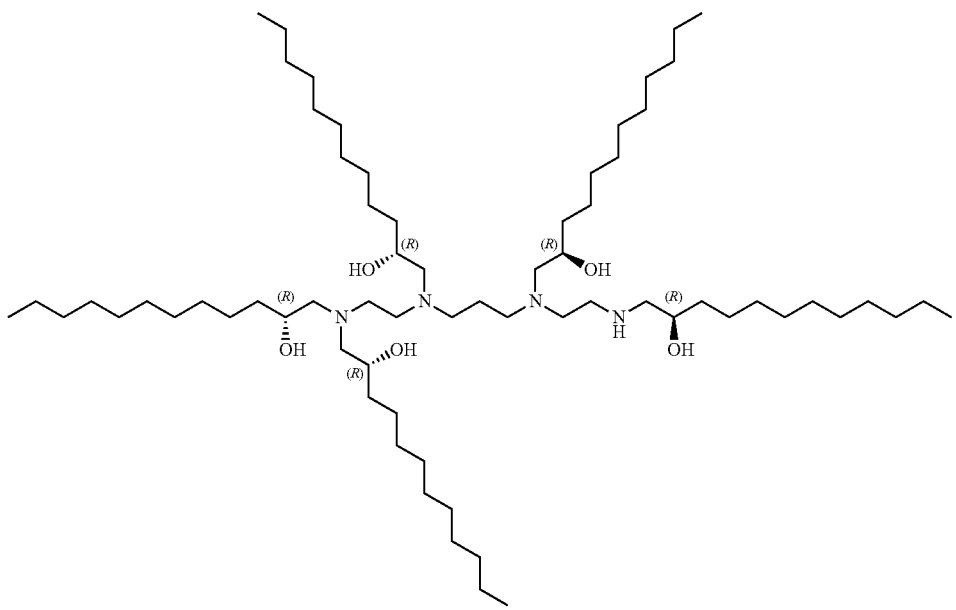

Additional cationic lipids that can be used in the compositions and methods of the present application include those cationic lipids as described in J. McClellan, M. C. King, Cell 2010, 141, 210-217, and International Patent Publication WO2010144740, WO2013149140, WO2016118725, WO2016118724, WO2013063468, WO2016205691, WO2015184256, WO2016004202, WO2015199952, WO2017004143, WO2017075531, WO2017117528, WO2017049245, WO2017173054 and WO2015095340, which are incorporated herein by reference for all purposes. Examples of those ionizable cationic lipids include but are not limited to those as shown in Table 5.

TABLE 5
Example Ionizable Cationic Lipids
| # | Structure of example ionizable cationic lipid |
|---|---|
| 1 | 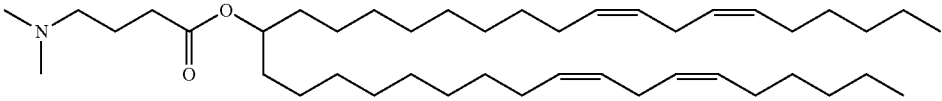 [SMILES: CCCCC/C=C\C/C=C\CCCCCCCCC(CCCCCCCC/C=C\C/C=C\CCCCC)OC(=O)CCCN(C)C] |
| 2 | 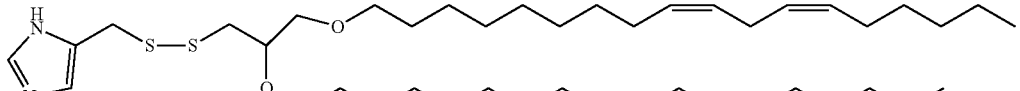 |
| 3 | 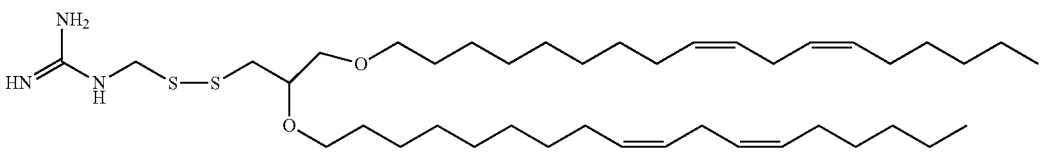 |
| 4 | 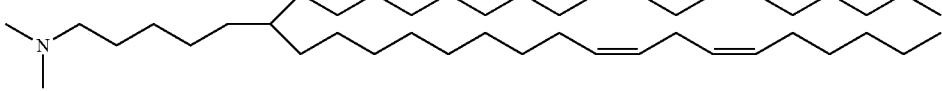 |
| 5 | 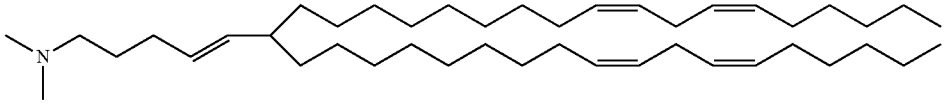 [SMILES: CCCCC/C=C\C/C=C\CCCCCCCCC(/C=C/CCCN(C)C)CCCCCCCC/C=C\C/C=C\CCCCC] |
| 6 | 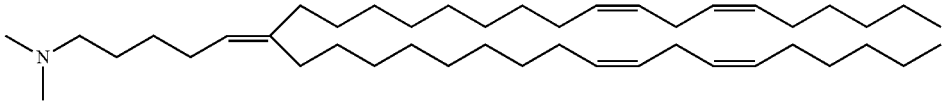 [SMILES: CCCCC/C=C\C/C=C\CCCCCCCCC(=CCCCCN(C)C)CCCCCCCC/C=C\C/C=C\CCCCC] |
| 7 | 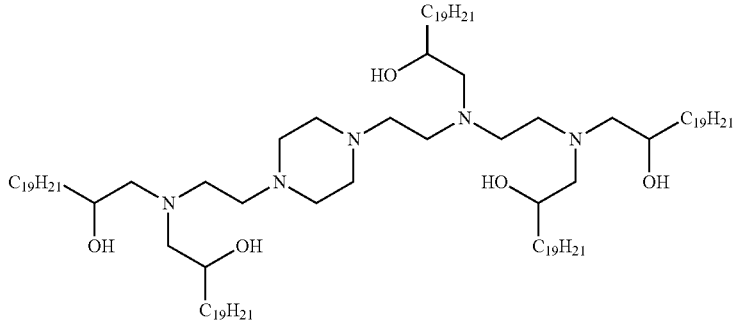 |
| 8 | 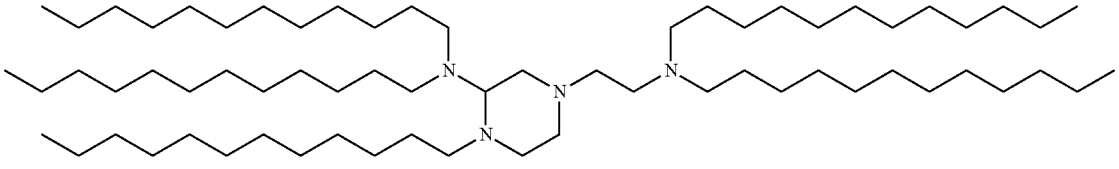 [SMILES: CCCCCCCCCCCCN(CCCCCCCCCCCC)CCN1CCN(CCCCCCCCCCCC)C(N(CCCCCCCCCCCC)CCCCCCCCCCCC)C1] |
| 9 | 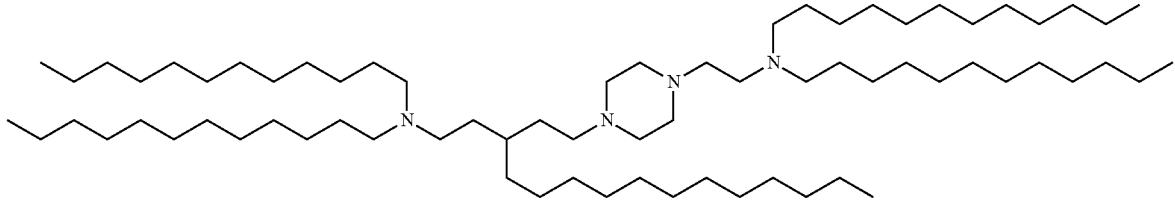 [SMILES: CCCCCCCCCCCCC(CCN(CCCCCCCCCCCC)CCCCCCCCCCCC)CCN1CCN(CCN(CCCCCCCCCCCC)CCCCCCCCCCCC)CC1] |

TABLE 5-continued
Example Ionizable Cationic Lipids
| # | Structure of example ionizable cationic lipid |
|---|---|
| 10 | 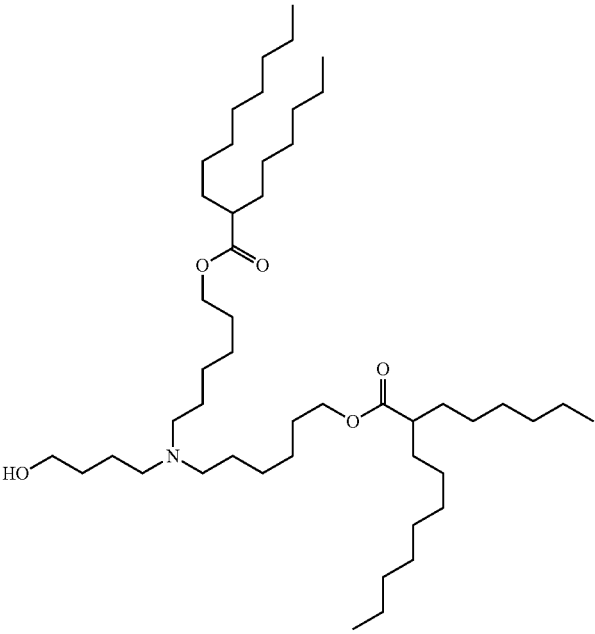 [SMILES: CCCCCCCCC(CCCCCC)C(=O)OCCCCCCN(CCCCO)CCCCCCOC(=O)C(CCCCCC)CCCCCCCC] |
| 11 | 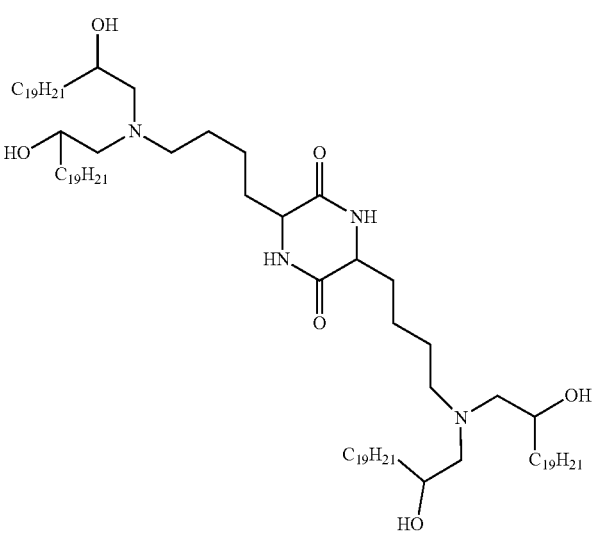 |

TABLE 5-continued
Example Ionizable Cationic Lipids
| # | Structure of example ionizable cationic lipid |
|---|---|
| 12 | 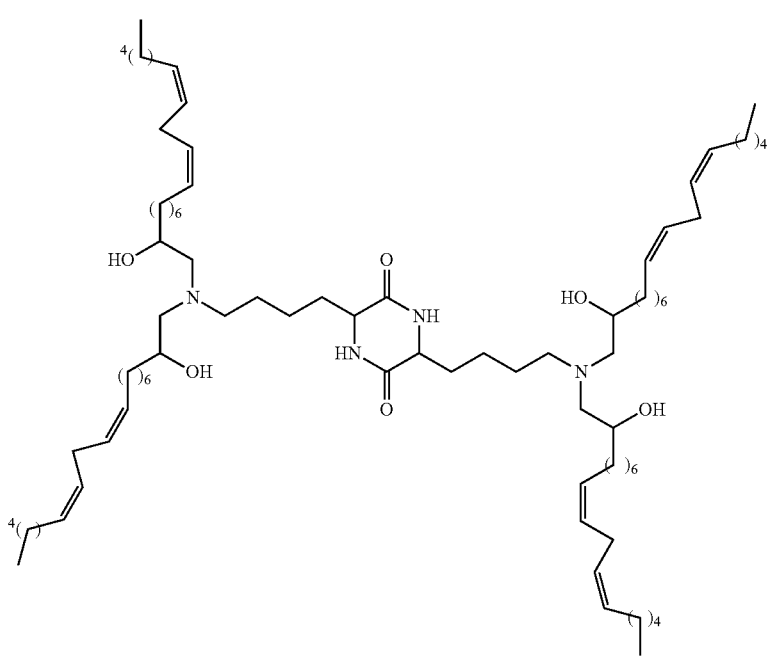 |
| 13 | 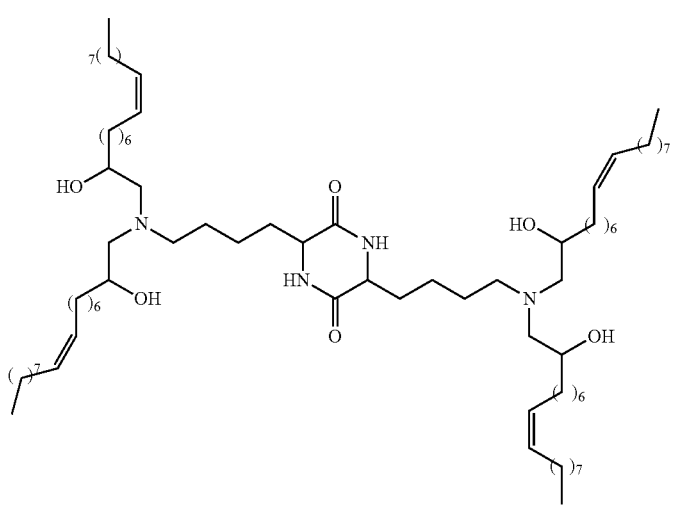 |

TABLE 5-continued
Example Ionizable Cationic Lipids
| # | Structure of example ionizable cationic lipid |
|---|---|
| 14 | 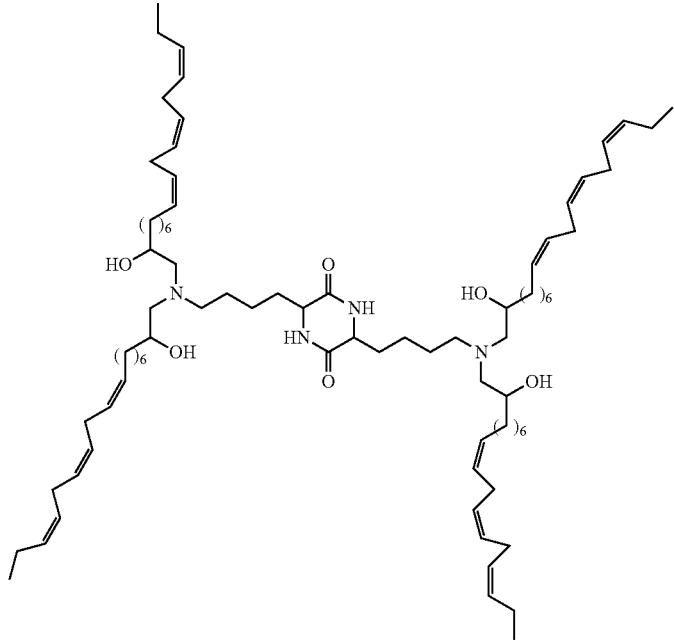 |
| 15 | 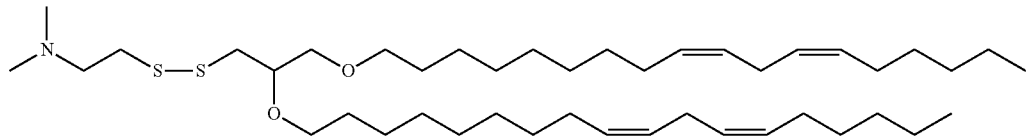 [SMILES: CCCCC/C=C\C/C=C\CCCCCCCCOCC(CSSCCN(C)C)OCCCCCCCC/C=C\C/C=C\CCCCC]<br>(HGT4003) |
| 16 | 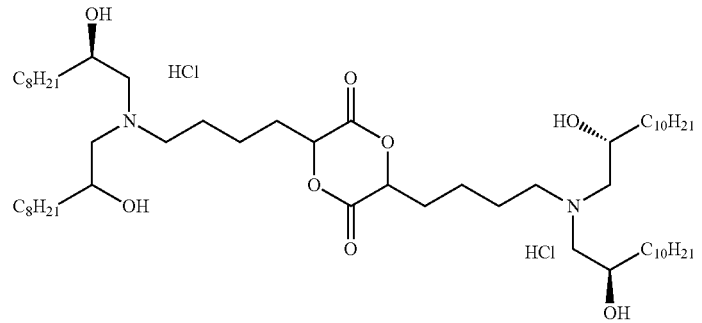 |
| 17 | 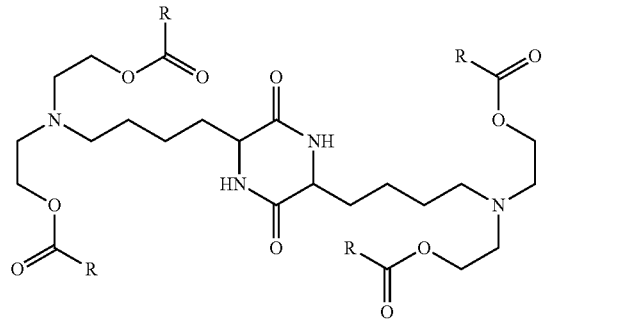<br>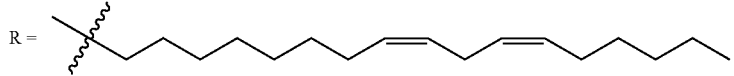 |

TABLE 5-continued
Example Ionizable Cationic Lipids
| # | Structure of example ionizable cationic lipid |
|---|---|
| 18 | 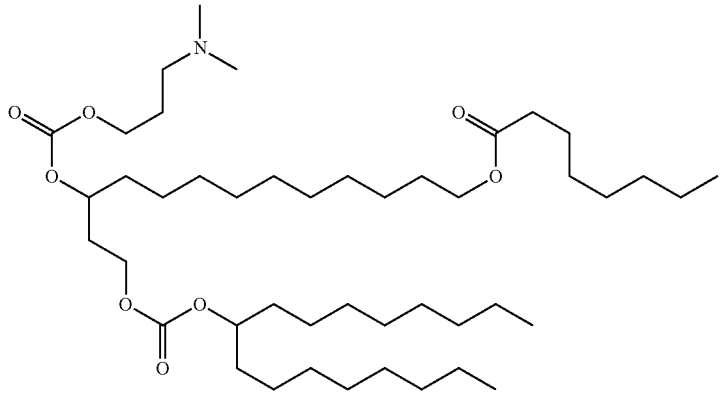 [SMILES: CCCCCCCCC(CCCCCCCC)OC(=O)OCCC(CCCCCCCCCCOC(=O)CCCCCCC)OC(=O)OCCCN(C)C] |
| 19 | 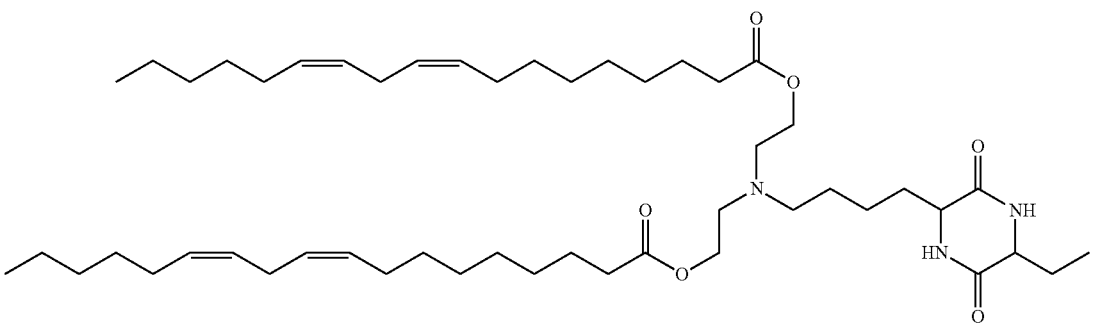 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC] |
| 20 | 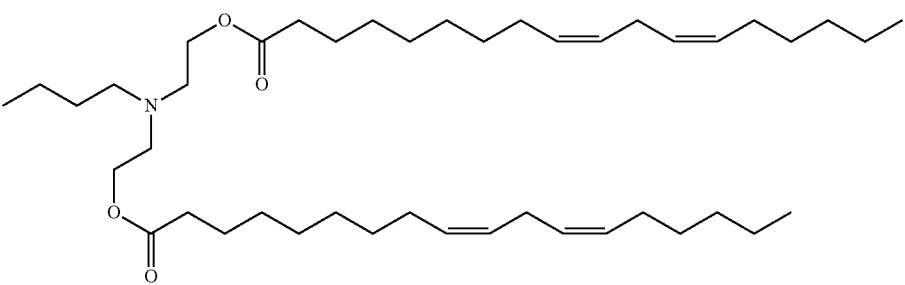 [SMILES: CCCCC/C=C\C/C=C\CCCCCCCC(=O)OCCN(CCCC)CCOC(=O)CCCCCCC/C=C\C/C=C\CCCCC] |
| 21 | 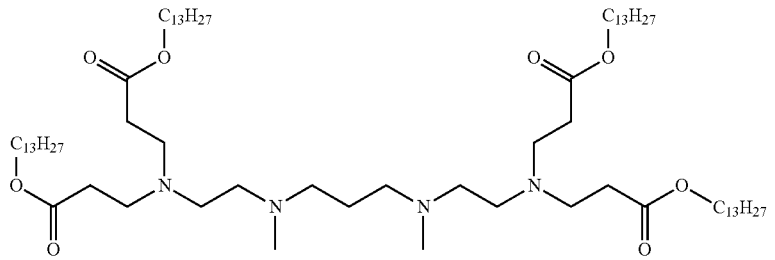 |

TABLE 5-continued
Example Ionizable Cationic Lipids
| # | Structure of example ionizable cationic lipid |
|---|---|
| 22 | 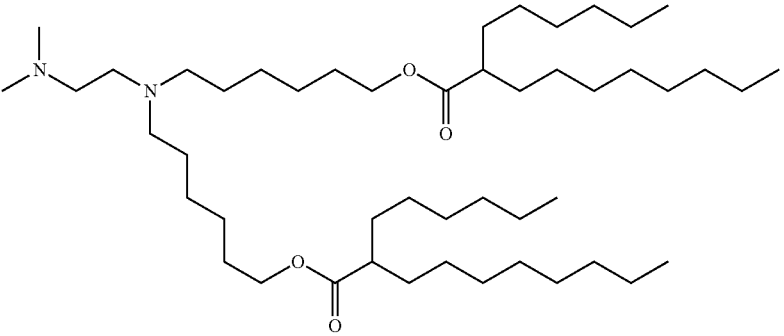 [SMILES: CCCCCCCCC(CCCCCC)C(=O)OCCCCCCN(CCCCCCOC(=O)C(CCCCCC)CCCCCCCC)CCN(C)C] |
| 23 | 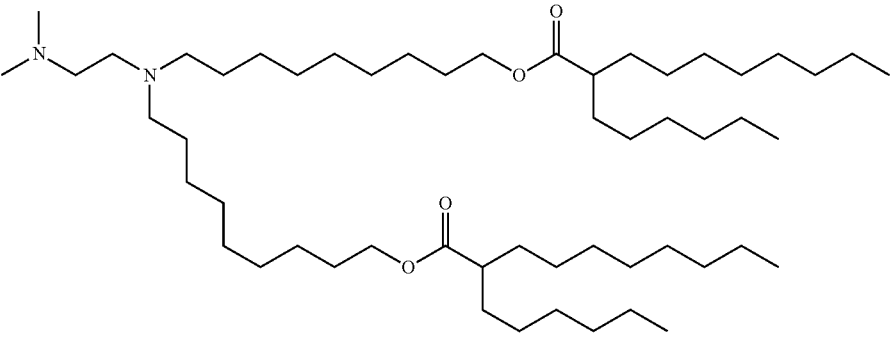 [SMILES: CCCCCCCCC(CCCCCC)C(=O)OCCCCCCCCCN(CCCCCCCCCOC(=O)C(CCCCCC)CCCCCCCC)CCN(C)C] |
| 24 | 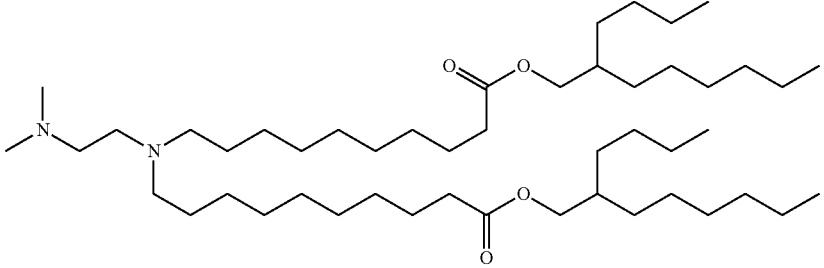 [SMILES: CCCCCCC(CCCC)COC(=O)CCCCCCCCCN(CCCCCCCCCC(=O)OCC(CCCC)CCCCCC)CCN(C)C] |
| 25 | 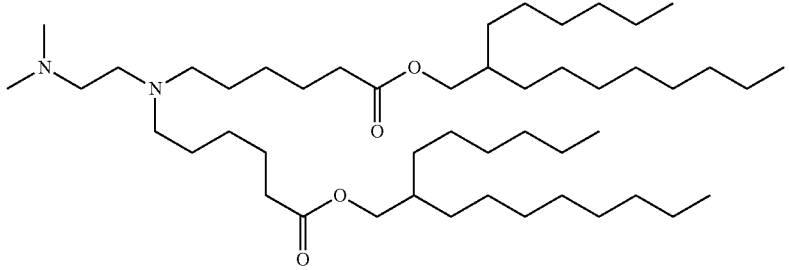 [SMILES: CCCCCCCCC(CCCCCC)COC(=O)CCCCCN(CCCCCC(=O)OCC(CCCCCC)CCCCCCCC)CCN(C)C] |
| 26 | 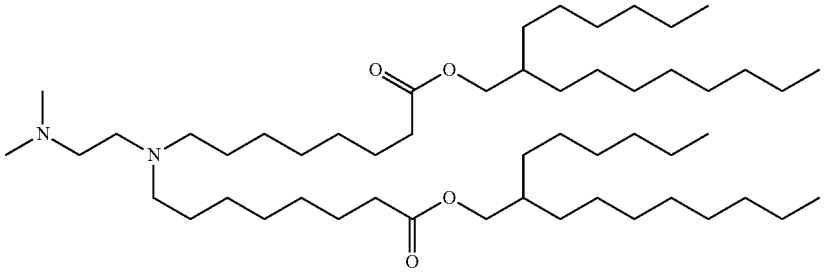 [SMILES: CCCCCCCCC(CCCCCC)COC(=O)CCCCCCCN(CCCCCCCC(=O)OCC(CCCCCC)CCCCCCCC)CCN(C)C] |

TABLE 5-continued

Example Ionizable Cationic Lipids

| # | Structure of example ionizable cationic lipid |
|---|---|
| 27 | |
| 28 | |
| 29 | |
| 30 | |
| 31 | |

TABLE 5-continued
Example Ionizable Cationic Lipids
| # | Structure of example ionizable cationic lipid |
|---|---|
| 32 | 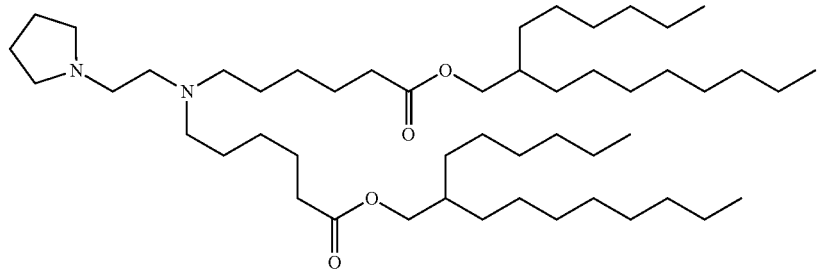 [SMILES: CCCCCCCCC(CCCCCC)COC(=O)CCCCCN(CCCCCC(=O)OCC(CCCCCC)CCCCCCCC)CCN1CCCC1] |
| 33 | 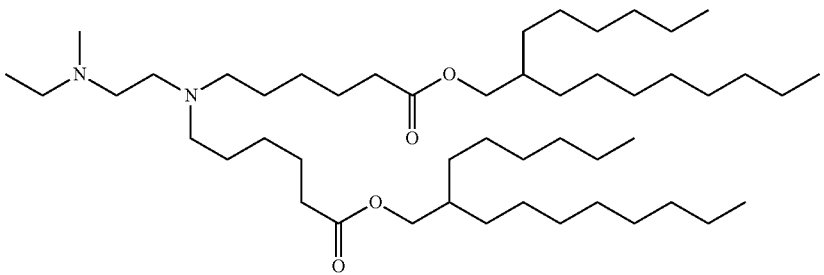 [SMILES: CCCCCCCCC(CCCCCC)COC(=O)CCCCCN(CCCCCC(=O)OCC(CCCCCC)CCCCCCCC)CCN(C)CC] |
| 34 | 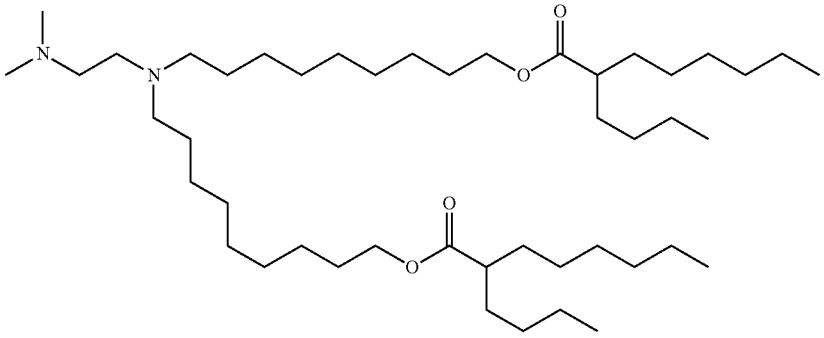 [SMILES: CCCCCCC(CCCC)C(=O)OCCCCCCCCCN(CCCCCCCCCOC(=O)C(CCCC)CCCCCC)CCN(C)C] |
| 35 | 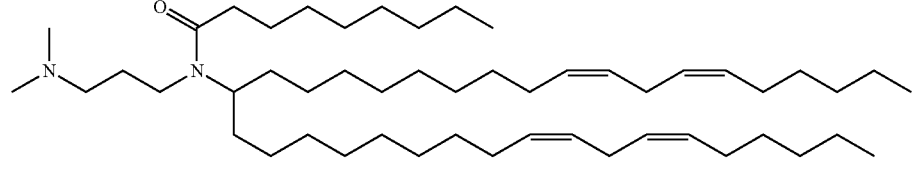 [SMILES: CCCCC/C=C\C/C=C\CCCCCCCCC(CCCCCCCC/C=C\C/C=C\CCCCC)N(CCCN(C)C)C(=O)CCCCCCCC] |
| 36 | 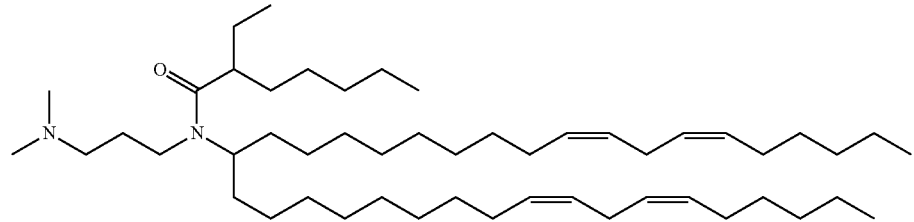 [SMILES: CCCCC/C=C\C/C=C\CCCCCCCCC(CCCCCCCC/C=C\C/C=C\CCCCC)N(CCCN(C)C)C(=O)C(CC)CCCCC] |

TABLE 5-continued

Example Ionizable Cationic Lipids

| # | Structure of example ionizable cationic lipid |
|---|---|
| 37 | |
| 38 | |
| 39 | |
| 40 | |
| 41 | |

US 12,364,773 B2
225 226
TABLE 5-continued
Example Ionizable Cationic Lipids
| # | Structure of example ionizable cationic lipid |
|---|---|
| 42 | 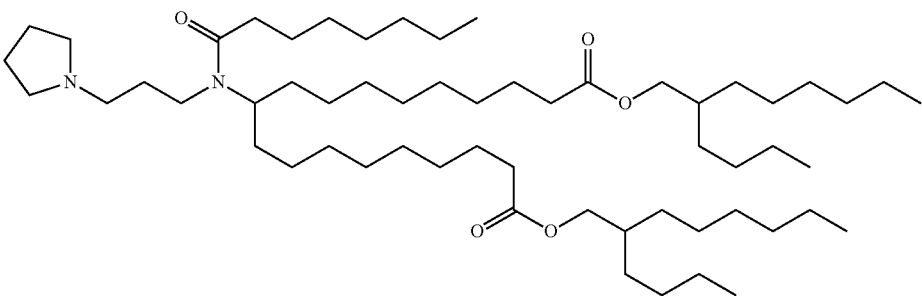 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] |
| 43 | 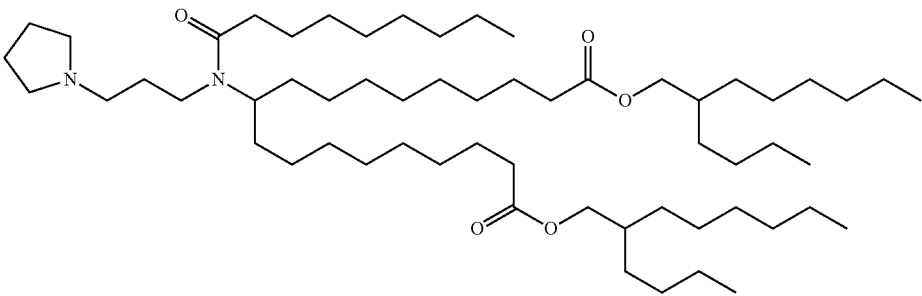 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] |
| 44 | 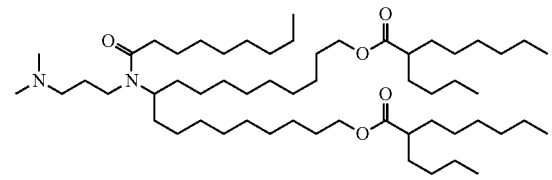 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC] |
| 45 | 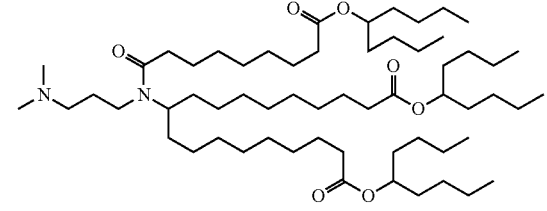 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] |
| 46 | 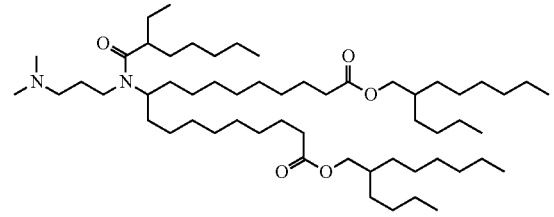 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC] |

TABLE 5-continued
Example Ionizable Cationic Lipids
| # | Structure of example ionizable cationic lipid |
|---|---|
| 47 | 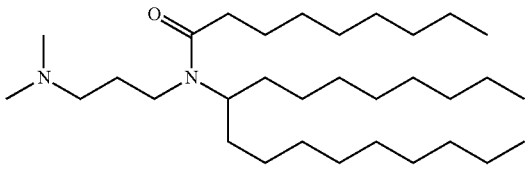 |
| 48 | 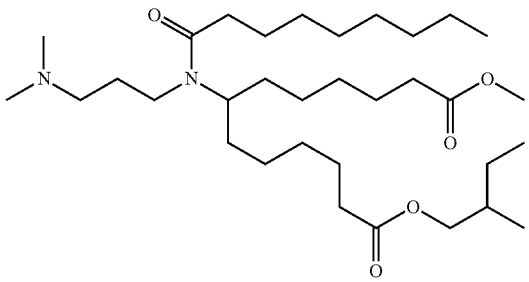 |
| 49 | 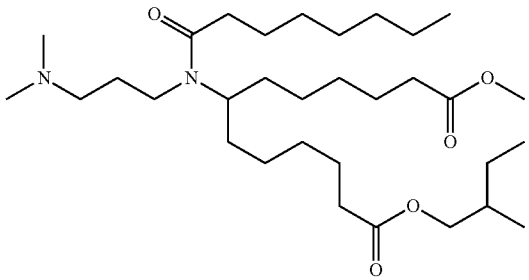 |

TABLE 5-continued
Example Ionizable Cationic Lipids
| # | Structure of example ionizable cationic lipid |
|---|---|
| 50 | 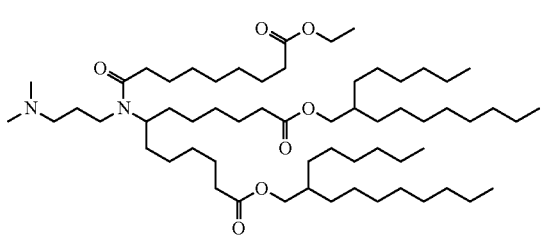 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC] |
| 51 | 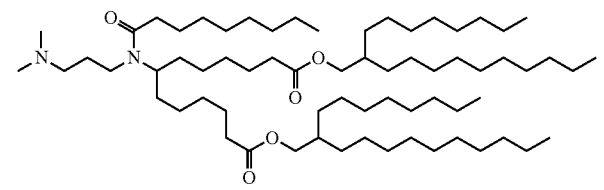 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC] |
| 52 | 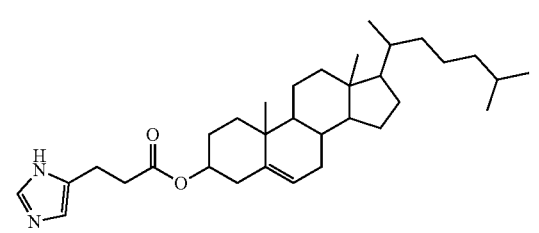 [SMILES: CC(C)CCCC(C)C1CCC2C3CC=C4CC(OC(=O)CCc5cnc[nH]5)CCC4(C)C3CCC12C] |
| 53 | 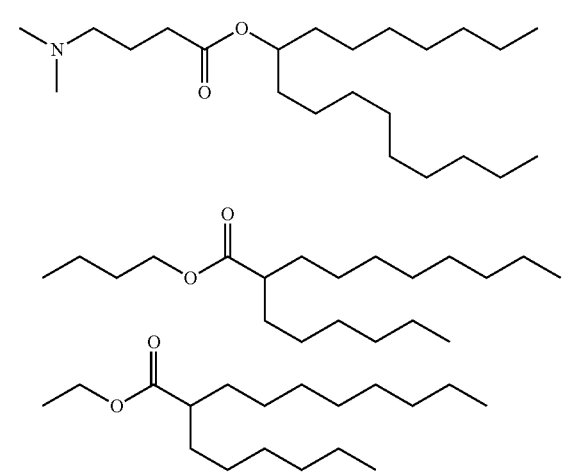 |

TABLE 5-continued
Example Ionizable Cationic Lipids
| # | Structure of example ionizable cationic lipid |
|---|---|
| 54 | 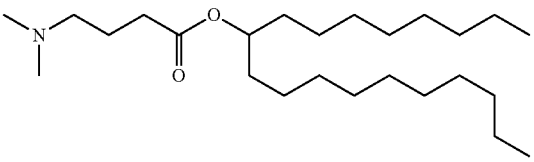 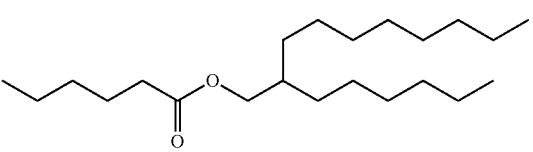 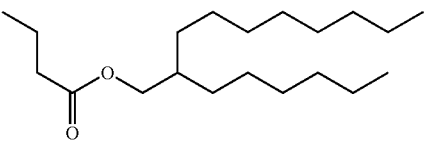 |
| 55 | 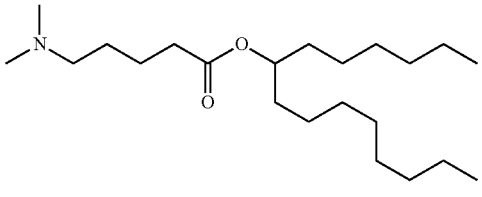 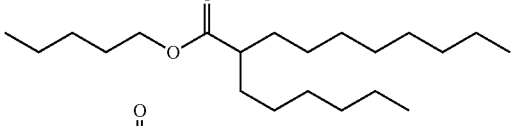 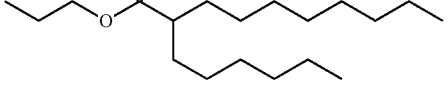 |
| 56 | 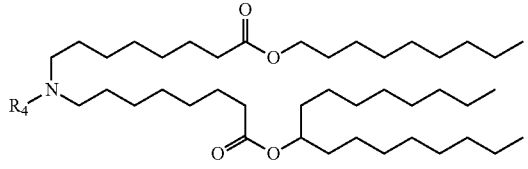
$R_4 =$ —$(CH_2)_2OH$, —$(CH_2)_3OH$, —$(CH_2)_4OH$; |
| 57 | 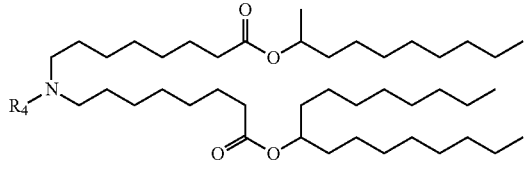
$R_4 =$ —$(CH_2)_2OH$, —$(CH_2)_3OH$, —$(CH_2)_4OH$; |

TABLE 5-continued
Example Ionizable Cationic Lipids
| # | Structure of example ionizable cationic lipid |
|---|---|
| 58 | 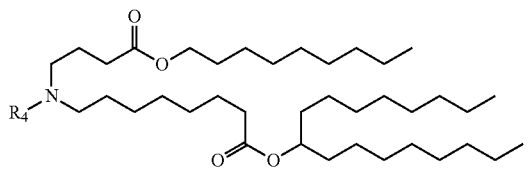
$R_4 =$ —$(CH_2)_2OH$, —$(CH_2)_3OH$, —$(CH_2)_4OH$; |
| 59 | 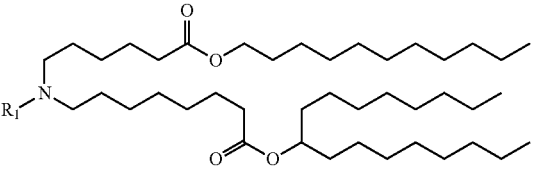
$R_4 =$ —$(CH_2)_2OH$, —$(CH_2)_3OH$, —$(CH_2)_4OH$; |
| 60 | 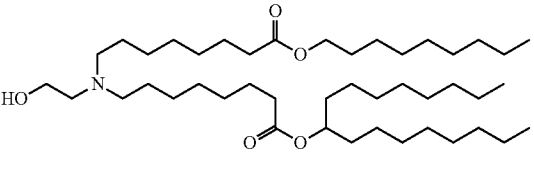 [SMILES: CCCCCCCCCOC(=O)CCCCCCCN(CCO)CCCCCCCC(=O)OC(CCCCCCCC)CCCCCCCC] |
| 61 | 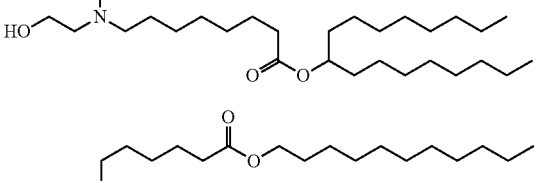 |
| 62 | 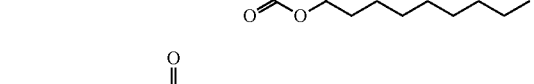 |
| 63 | 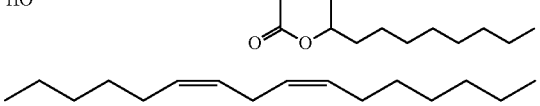 |
| 64 | 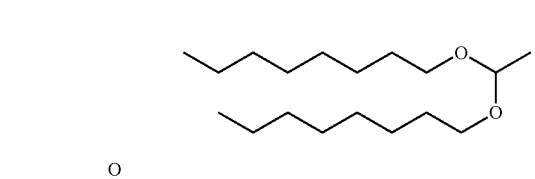 |

TABLE 5-continued

Example Ionizable Cationic Lipids

| # | Structure of example ionizable cationic lipid |
|---|---|
| 65 | |
| 66 | |
| 67 | |
| 68 | |

In some embodiments of the lipid composition of the present disclosure, the ionizable lipid is present in an amount of from about from about 20 mol % to about 23 mol %. In some embodiments, the ionizable lipid is present in an amount of about 20 mol %, about 20.5 mol %, about 21 mol %, about 21.5 mol %, about 22 mol %, about 22.5 mol %, or about 23 mol %. In other embodiments, the ionizable lipid is present in an amount of from about 7.5 mol % to about 20 mol %. In some embodiments, the ionizable lipid is present in an amount of about 7.5 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, or about 20 mol %.

In some embodiments of the lipid composition of the present disclosure, the lipid composition comprises the ionizable lipid in an amount of from about 5 mol % to about 30 mol %. In some embodiments of the lipid composition of the present disclosure, the lipid composition comprises the ionizable lipid in an amount of from about 10 mol % to about 25 mol %. In some embodiments of the lipid composition of the present disclosure, the lipid composition comprises the ionizable lipid in an amount of from about 15 mol % to about 20 mol %. In some embodiments of the lipid composition of the present disclosure, the lipid composition comprises the ionizable lipid in an amount of from about 10 mol % to about 20 mol %. In some embodiments of the lipid composition of the present disclosure, the lipid composition comprises the ionizable lipid in an amount of from about 20 mol % to about 30 mol %. In some embodiments of the lipid composition of the present disclosure, the lipid composition comprises the ionizable lipid in an amount of of at least (about) 5 mol %, at least (about) 10 mol %, at least (about) 15 mol %, at least (about) 20 mol %, at least (about) 25 mol %, or at least (about) 30 mol %. In some embodiments of the lipid composition of the present disclosure, the lipid composition comprises the ionizable lipid in an amount of of at most (about) 5 mol %, at most (about) 10 mol %, at most (about) 15 mol %, at most (about) 20 mol %, at most (about) 25 mol %, or at most (about) 30 mol %.

B. Helper Lipids

In some embodiments, helper lipids are phospholipids. Phospholipids, as defined herein, are any lipids that comprise a phosphate group. The lipid component of a lipid nanoparticles may include one or more phospholipids, such as one or more (poly) unsaturated lipids. Phospholipids may assemble into one or more lipid bilayers. In general, phospholipids may include a phospholipid moiety and one or more fatty acid moieties. A phospholipid moiety may be selected from the non-limiting group of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing nanoparticles to facilitate membrane permeation or cellular recognition or in conjugating nanoparticles to an additional component, such as a targeting or imaging moiety (e.g., a dye).

In some embodiments, the LNPs described herein comprises about 5 mol % to about 30 mol % of phospholipid. In some embodiments, the LNPs comprises about 10 mol % to about 30 mol %, or about 12 mol % to about 30 mol %, or about 14 mol % to about 30 mol %, or about 16 mol % to about 30 mol %, or about 18 mol % to about 30 mol %, or about 20 mol % to about 30 mol %, or about 22 mol % to about 30 mol %, or about 24 mol % to about 30 mol %, or about 26 mol % to about 30 mol %, or about 28 mol % to about 30 mol %. In some embodiments, the LNPs comprises about 10 mol %, or about 11 mol %, or about 12 mol %, or about 13 mol %, or about 14 mol %, or about 15 mol %, or about 16 mol %, or about 17 mol %, or about 18 mol %, or about 19 mol %, or about 20 mol %, or about 21 mol %, or about 22 mol %, or about 23 mol %, or about 24 mol %, or about 25 mol %, or about 26 mol %, or about 27 mol %, or about 28 mol %, or about 29 mol %, or about 30 mol %.

In some embodiments, the LNPs comprises about 5% to about 30% weight of phoshpolipid. In some embodiments, the LNPs comprises about 5% weight, or 10%, or 12%, or 15%, or 18%, or 20%, or 25%, or 30% weight of phospholipid.

In some embodiments of the lipid components of the present disclosure, the lipid components may further comprise a molar percentage of the phospholipid to the total lipid composition from about 20 to about 23. In some embodiments, the molar percentage is from about 20, 20.5, 21, 21.5, 22, 22.5, to about 23 or any range derivable therein. In other embodiments, the molar percentage is from about 7.5 to about 60. In some embodiments, the molar percentage is from about 7.5, 8, 9, 10, 11, 12, 13, 14, 15, 16, 17, 18, 19, to about 20 or any range derivable therein.

In some embodiments of the lipid components of the present disclosure, the lipid components comprise the phospholipid at a molar percentage from about 8% to about 23%. In some embodiments of the lipid components of the present disclosure, the lipid components comprise the phospholipid at a molar percentage from about 10% to about 20%. In some embodiments of the lipid components of the present application, the lipid components comprise the phospholipid at a molar percentage from about 15% to about 20%. In some embodiments of the lipid components of the present disclosure, the lipid components comprise the phospholipid at a molar percentage from about 8% to about 15%. In some embodiments of the lipid components of the present disclosure, the lipid comp components position comprises the phospholipid at a molar percentage from about 10% to about 15%. In some embodiments of the lipid components of the present disclosure, the lipid components comprise the phospholipid at a molar percentage from about 12% to about 18%. In some embodiments of the lipid components of the present disclosure, the lipid composition comprises the phospholipid at a molar percentage of at least (about) 8%, at least (about) 10%, at least (about) 12%, at least (about) 15%, at least (about) 18%, at least (about) 20%, or at least (about) 23%. In some embodiments of the lipid components of the present disclosure, the lipid components comprise the phospholipid at a molar percentage of at most (about) 8%, at most (about) 10%, at most (about) 12%, at most (about) 15%, at most (about) 18%, at most (about) 20%, or at most (about) 23%.

Phospholipids useful or potentially useful in the presently described compositions and methods may be selected from: 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OchemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-diphytanoyl-sn-glycero-3-phosphocholine (4ME 16:0 PC), 1,2-diphytanoyl-sn-glycero-3-phospho-(1'-rac-glycerol) (sodium salt) (4ME 16:0 PG), 1,2-diphytanoyl-sn-glycero-3-phospho-L-serine (sodium salt) (4ME 16:0 PS), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, and 1,2-dioleoyl-sn-glycero-3-phospho-rac-(1-glycerol) sodium salt (DOPG), and sphingomyelin.

In some embodiments, the phospholipid may contain one or two long chain (e.g., $C_6$-$C_{24}$)alkyl or alkenyl groups, a glycerol or a sphingosine, one or two phosphate groups, and, optionally, a small organic molecule. The small organic molecule may be an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine. In some embodiments, other zwitterionic lipids are used, where zwitterionic lipid defines lipid and lipid-like molecules with both a positive charge and a negative charge.

In some embodiments of the lipid components of the present disclosure, the phospholipid is not an ethylphosphocholine.

C. Polymer-Conjugated Lipids

The lipid components of the present disclosure may include lipids conjugated to polymers, such as lipids conjugated to polyethylene glycol (PEG-lipid). Illustrative methods for making and using PEG-lipids are described, for example, in International Patent Publication No. WO2012099755 and U.S. Patent Publication No. 2014/0200257.

In one embodiment, PEG-lipids useful in the present disclosure can be PEG-lipids described in International Patent Publication No. WO 2012/099755, the contents of which is herein incorporated by reference in its entirety. Any of these exemplary PEG-lipids described herein may be modified to comprise a hydroxyl group on the PEG chain. In certain embodiments, the PEG-lipid is a PEG-OH lipid. PEG-OH lipid is a PEG-lipid having one or more hydroxyl (—OH) groups on the lipid. In certain embodiments, the PEG-OH lipid includes one or more hydroxyl groups on the PEG chain. In certain embodiments, a PEG-OH or hydroxy-PEG-lipid comprises an —OH group at the terminus of the PEG chain. Each possibility represents a separate embodiment of the present disclosure.

In some embodiments of the lipid component of the present disclosure, the lipid component further comprises a polymer conjugated lipid. In some embodiments, the polymer conjugated lipid is a PEG-lipid. In some embodiments, the PEG-lipid is a diglyceride, which also comprises a PEG chain attached to the glycerol group. In other embodiments, the PEG-lipid is a compound, which contains one or more $C_6$-$C_{24}$ long chain alkyl or alkenyl group or a $C_6$-$C_{24}$ fatty acid group attached to a linker group with a PEG chain. Some non-limiting examples of a PEG-lipid includes a PEG modified phosphatidylethanolamine, a PEG-modified phosphatidic acid, a PEG-modified ceramide, PEG-modified dialkylamines, and PEG-modified 1,2-diacyloxypropan-3-amines, PEG-modified diacylglycerols, PEG-modified dialkylglycerols, and mixtures thereof. For example, a PEG-lipid may be PEG-c-DOMG, PEG-DMG, PEG-DLPE, PEG-DMPE, PEG-DPPC, or PEG-DSPE. In some embodiments, PEG modified diastearoylphosphatidylethanolamine or PEG-modified dimyristoyl-sn-glycerol. In some embodiments, the PEG modification is measured by the molecular weight of PEG component of the lipid. In some embodiments, the PEG modification has a molecular weight from about 100 Da to about 15,000 Da. In some embodiments, the molecular weight is from about 200 Da to about 500 Da, from about 400 Da to about 5,000 Da, from about 500 Da to about 3,000 Da, or from about 1,200 Da to about 3,000 Da. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000 Da. Some non-limiting examples of lipids that may be used in the present disclosure are taught in U.S. Pat. No. 5,820,873, International Patent Publication No. WO 2010/141069, or U.S. Pat. No. 8,450,298, which are incorporated herein by reference in their entireties.

In some embodiments of the lipid composition of the present application, the PEG-lipid has a structural formula:

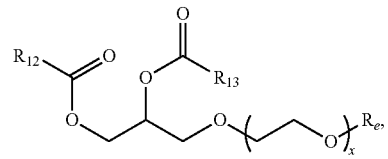

wherein: $R_{12}$ and $R_{13}$ are each independently alkyl($C_{\leq 24}$), alkenyl($C_{\leq 24}$), or a substituted version of either of these groups; $R_e$ is hydrogen, alkyl($C_{\leq 8}$), or substituted alkyl ($C_{\leq 8}$); and x is 1-250. In some embodiments, $R_e$ is alkyl ($C_{\leq 8}$) such as methyl. $R^{12}$ and $R_{13}$ are each independently alkyl($C_{\leq 4-20}$). In some embodiments, x is 5-250. In one embodiment, x is 5-125 or x is 100-250. In some embodiments, the PEG-lipid is 1,2-dimyristoyl-sn-glycerol, methoxypolyethylene glycol.

In some embodiments of the lipid component of the present disclosure, the PEG-lipid has a structural formula:

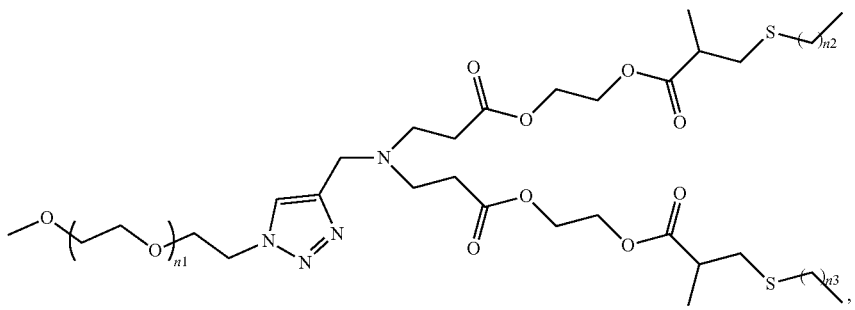

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments of the lipid component of the present disclosure, the component may further comprise a molar percentage of the PEG-lipid to the total lipid composition from about 4.0% to about 4.6%. In some embodiments, the molar percentage is from about 4.0%, 4.1%, 4.2%, 4.3%, 4.4%, 4.5%, to about 4.6% or any range derivable therein. In other embodiments, the molar percentage is from about 1.5% to about 4.0%. In some embodiments, the molar percentage is from about 1.5%, 1.75%, 2%, 2.25%, 2.5%, 2.75%, 3%, 3.25%, 3.5%, 3.75%, to about 4.0% or any range derivable therein.

In some embodiments of the lipid component of the present disclosure, the lipid component comprises the polymer-conjugated lipid at a molar percentage from about 0.5% to about 10%. In some embodiments of the lipid component of the present disclosure, the lipid composition comprises the polymer-conjugated lipid at a molar percentage from about 1% to about 8%. In some embodiments of the lipid component of the present disclosure, the lipid composition comprises the polymer-conjugated lipid at a molar percentage from about 2% to about 7%. In some embodiments of the lipid component of the present application, the lipid component comprises the polymer-conjugated lipid at a molar percentage from about 3% to about 5%. In some embodiments of the lipid component of the present disclosure, the lipid component comprises the polymer-conjugated lipid at a molar percentage from about 5% to about 10%. In some embodiments of the lipid component of the present disclosure, the lipid component comprises the polymer-conjugated lipid at a molar percentage of at least (about) 0.5%, at least (about) 1%, at least (about) 1.5%, at least (about) 2%, at least (about) 2.5%, at least (about) 3%, at least (about) 3.5%, at least (about) 4%, at least (about) 4.5%, at least (about) 5%, at least (about) 5.5%, at least (about) 6%, at least (about) 6.5%, at least (about) 7%, at least (about) 7.5%, at least (about) 8%, at least (about) 8.5%, at least (about) 9%, at least (about) 9.5%, or at least (about) 10%. In some embodiments of the lipid component of the present disclosure, the lipid component comprises the polymer-conjugated lipid at a molar percentage of at most (about) 0.5%, at most (about) 1%, at most (about) 1.5%, at most (about) 2%, at most (about) 2.5%, at most (about) 3%, at most (about) 3.5%, at most (about) 4%, at most (about) 4.5%, at most (about) 5%, at most (about) 5.5%, at most (about) 6%, at most (about) 6.5%, at most (about) 7%, at most (about) 7.5%, at most (about) 8%, at most (about) 8.5%, at most (about) 9%, at most (about) 9.5%, or at most (about) 10%.

D. Structural Lipids

The lipid nanoparticle may include one or more structural lipids. A structural lipid can be a steroid or a steroid derivative. In some embodiments of the lipid component of the present disclosure, the lipid component further comprises a steroid or steroid derivative. In some embodiments, the steroid or steroid derivative comprises any steroid or steroid derivative. Steroids is a class of compounds with a four ring 17 carbon cyclic structure, which can further comprise one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula:

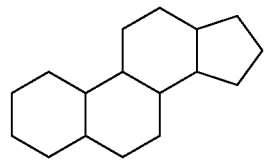

In some embodiments, a steroid derivative comprises the ring structure above with one or more non-alkyl substitutions. In some embodiments, the steroid or steroid derivative is a sterol wherein the formula is further defined as:

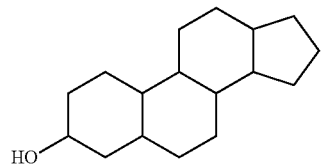

In some embodiments of the present disclosure, the steroid or steroid derivative is a cholestane or cholestane derivative. In a cholestane, the ring structure is further defined by the formula:

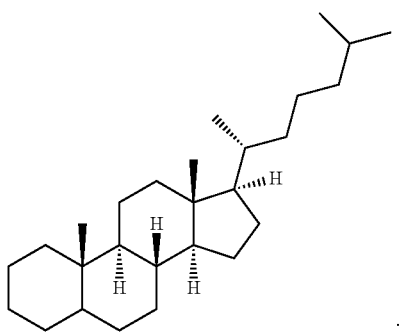

As described above, a cholestane derivative includes one or more non-alkyl substitution of the above ring system. In some embodiments, the cholestane or cholestane derivative is a cholestene or cholestene derivative. In some embodiments, the steroid or steroid derivative is a secosteroid or a secosteroid derivative. In some embodiments, the steroid or steroid derivative is a cardenolide or a cardenolide derivative. In some embodiments, the steroid or steroid derivative is a sapogenin or a sapogenin derivative. In some embodiments, the steroid or steroid derivative is a saponin or a saponin derivative. In some embodiments, the steroid or steroid derivative is an eicosanoid or an eicosanoid derivative. In some embodiments, the steroid or steroid derivative is an alkaloid or an alkaloid derivative. In some embodiments, the steroid or steroid derivative is a sterol or a sterol derivative.

A sterol useful in the compositions and methods described herein may be selected from, but are not limited to: cholesterol, fecosterol, sitosterol, ergosterol, campesterol, stigmasterol, brassicasterol, tomatidine, ursolic acid, and alpha-tocopherol.

In some embodiments of the lipid components, the components may further comprise a molar percentage of the steroid to the total lipid composition from about 40% to about 46%. In some embodiments, the molar percentage is from about 40%, 41%, 42%, 43%, 44%, 45%, to about 46% or any range derivable therein. In other embodiments, the molar percentage of the steroid relative to the total lipid composition is from about 15% to about 40%. In some embodiments, the molar percentage is 15%, 16%, 18%, 20%, 22%, 24%, 26%, 28%, 30%, 32%, 34%, 36%, 38%, or 40%, or any range derivable therein.

In some embodiments, the lipid components comprise a steroid or steroid derivative at a molar percentage from about 15% to about 60%. In some embodiments, the lipid components comprise a steroid or steroid derivative at a molar percentage from about 15% to about 55%. In some embodiments, the lipid composition comprises a steroid or steroid derivative at a molar percentage from about 15% to about 50%. In some embodiments, the lipid components comprise a steroid or steroid derivative at a molar percentage from about 15% to about 46%. In some embodiments, the lipid components comprise a steroid or steroid derivative at a molar percentage from about 20% to about 40%. In some embodiments, the lipid components comprise a steroid or steroid derivative at a molar percentage from about 25% to about 35%. In some embodiments, the lipid components comprise a steroid or steroid derivative at a molar percentage from about 30% to about 40%. In some embodiments, the lipid components comprise a steroid or steroid derivative at a molar percentage from about 20% to about 30%. In some embodiments, the lipid components comprise a steroid or steroid derivative at a molar percentage of at least (about) 15%, of at least (about) 20%, of at least (about) 25%, of at least (about) 30%, of at least (about) 35%, of at least (about) 40%, of at least (about) 45%, or of at least (about) 46%. In some embodiments, the lipid components comprise a steroid or steroid derivative at a molar percentage of at most (about) 15%, of at most (about) 20%, of at most (about) 25%, of at most (about) 30%, of at most (about) 35%, of at most (about) 40%, of at most (about) 45%, or of at most (about) 46%.

In some embodiments, a cationic lipid is a sterol amine. A sterol amine has, for its hydrophobic portion, a sterol, and for its hydrophilic portion, an amine group. The sterol portion is selected from, but not limited to, cholesterol, sitosterol, campesterol, stigmasterol or derivatives thereof. The amine group can comprise one to five primary, secondary, tertiary amines, or mixtures thereof. At least one of the amines has a pKa of 8 or greater and is charged at physiological pH. The primary, secondary, or tertiary amines can be part of a larger amine containing functional group selected from, but not limited to —C(=N—)—N—, —C=C—N—, —C=N—, or —N—C(=N—)—N—. The amine group can be contained in a three to eight membered heteroalkyl or heteroaryl ring.

E. Additional Lipids

The lipid composition may include an additional anionic lipid, ionizable cationic lipid, or permanently cationic lipid. In some, the lipid nanoparticles are preferentially delivered to a target organ. In some embodiments, the target organ is lungs, a lung tissue or lung cells. "Preferentially delivered" means a composition is delivered to the target organ (e.g., lungs), tissue, or cell at least 25% (e.g., at least 30%, 35%, 40%, 45%, 50%, 55%, 60%, 65%, 70%, or 75%) of the amount administered. An additional lipid can support selective delivery of the composition of the present disclosure to a particular organ. In some embodiments, the additional lipid can be a selective organ targeting (SORT) lipid. In some embodiments, SORT lipids can allow LNPs to be delivered into the target organ, tissue, or cells.

SORT lipid refers to a lipid that when included in an LNP composition enables the LNPs to selectively and predictably target an organ, a cell type, or a tissue (for example, as described in Cheng et al. Nature 15:313-320 (2020); Wang et al. Nat. Protoc. 18(1):265-291; and U.S. Patent Publication No. US 2022/0071916 A1 and US 2021/0259980 A1, the entire contents of which are incorporated herein for their entireties). For example, addition of a specific SORT lipid to LNPs may re-target the LNPs from liver to lungs. SORT lipids include, but are not limited to, permanently cationic lipids, anionic lipids, zwitterionic lipids, and ionizable cationic lipids. Without being bound by theory, anionic SORT lipids generally favor delivery to spleen, at least when administered intravenously; ionizable cationic SORT lipids generally favor delivery to liver; permanently cationic SORT lipids generally favor delivery to lungs; and zwitterionic SORT lipids favor delivery to spleen.

In some embodiments, the additional lipid comprises a permanently positively charged moiety (i.e., is a permanently cationic lipid). The permanently positively charged moiety may be positively charged at a physiological pH such that the additional lipid (e.g., SORT lipid) comprises a positive charge upon delivery of a payload (e.g., polynucleotide) to a cell. In some embodiments the positively charged moiety is quaternary amine or quaternary ammonium ion. In some embodiments, the additional lipid (e.g., SORT lipid)) comprises, or is otherwise complexed to or interacting with, a counterion.

In some embodiments, the additional lipid is a permanently cationic lipid (i.e., comprising one or more hydrophobic components and a permanently cationic group). The permanently cationic lipid may contain a group which has a positive charge regardless of the pH. One permanently cationic group that may be used in the permanently cationic lipid is a quaternary ammonium group. The permanently cationic lipid may comprise a structural formula:

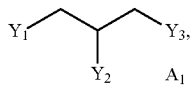
(S-I)

wherein:
Y$_1$, Y$_2$, or Y$_3$ are each independently X$_1$C(O)R$_1$ or X$_2$N$^+$R$_3$R$_4$R$_5$; provided at least one of Y$_1$, Y$_2$, and Y$_3$ is X$_2$N$^+$R$_3$R$_4$R$_5$;
R$_1$ is C$_1$-C$_{24}$ alkyl, C$_1$-C$_{24}$ substituted alkyl, C$_1$-C$_{24}$ alkenyl, C$_1$-C$_{24}$ substituted alkenyl;
X$_1$ is O or NR$^a$, wherein R$_a$ is hydrogen, C$_1$-C$_4$ alkyl, or C$_1$-C$_4$ substituted alkyl;
X$_2$ is C$_1$-C$_6$ alkanediyl or C$_1$-C$_6$ substituted alkanediyl;
R$_3$, R$_4$, and R$_5$ are each independently C$_1$-C$_{24}$ alkyl, C$_1$-C$_{24}$ substituted alkyl, C$_1$-C$_{24}$ alkenyl, C$_1$-C$_{24}$ substituted alkenyl; and
A$_1$ is an anion with a charge equal to the number of X$_2$N$^+$R$_3$R$_4$R$_5$ groups in the compound.

In some embodiments, the permanently cationic additional lipid (e.g., SORT lipid) has a structural formula:

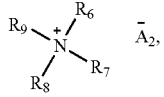
(S-II)

wherein:
R$_6$-R$_9$ are each independently C$_1$-C$_{24}$ alkyl, C$_1$-C$_{24}$ substituted alkyl, C$_1$-C$_{24}$ alkenyl, C$_1$-C$_{24}$ substituted alkenyl; provided at least one of R$_6$-R$_9$ is a group of C$_8$-C$_{24}$; and
A$_2$ is a monovalent anion.

In some embodiments, the permanently cationic lipids is 1,2-dilauroyl-sn-glycero-3-ethylphosphocholine (12:0 EPC), 1,2-dimyristoyl-sn-glycero-3-ethylphosphocholine (14:0 EPC), 1,2-dipalmitoyl-sn-glycero-3-ethylphospho-choline (16:0 EPC), 1,2-distearoyl-sn-glycero-3-ethylphosphocholine (18:0 EPC), 1,2-dioleoyl-sn-glycero-3-ethylphosphocholine (18:1 EPC), 1-palmitoyl-2-oleoyl-sn-glycero-3-ethylphosphocholine (16:0-18:0 EPC), 1,2-dimyristoleoyl-sn-glycero-3-ethylphosphocholine (14:1 EPC), dimethyldioctadecylammonium (18:0 DDAB), 1,2-dimyristoyl-3-trimethylammonium-propane(14:0 TAP), 1,2-dipalmitoyl-3-trimethylammonium-propane (16:0 TAP), 1,2-stearoyl-3-trimethylammonium-propane (18:0 TAP), 1,2-dioleoyl-3-trimethylammonium-propane (18:1 TAP, DOTAP), or 1,2-di-O-octadecenyl-3-trimethylammonium propane (DOTMA).

In some embodiments, the SORT lipid is an ionizable cationic lipid (i.e., comprising one or more hydrophobic components and an ionizable cationic group, e.g., a tertiary amino group). An ionizable cationic group may be positively charged at a physiological pH. One ionizable cationic group that may be used in the ionizable lipid is a tertiary ammine group. In some embodiments, the additional lipid (e.g., SORT lipid) has a structural formula:

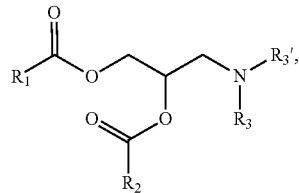
(S-I'a)

wherein:
R$_1$ and R$_2$ are each independently C$_8$-C$_{24}$ alkyl, C$_8$-C$_{24}$ alkenyl, or a substituted version of either group; and
R$_3$ and R$_3$' are each independently C$_1$-C$_6$ alkyl or substituted C$_1$-C$_6$ alkyl.

In some embodiments of formula (S-I'a), R$_1$ and R$_2$ are each independently C$_8$-C$_{24}$ alkenyl(e.g., hexadecane, heptadecene, or octadecene). In some embodiments of formula (S-I'a), R$_3$ and R$_3$' are each independently C$_1$-C$_6$ alkyl (e.g., methyl or ethyl). In some embodiments of formula (S-I'a), R$_1$ and R$_2$ are each independently C$_8$-C$_{24}$ alkenyl, (e.g., hexadecane, heptadecene, or octadecene) and R$_3$ and R$_3$' are each independently C$_1$-C$_6$ alkyl (e.g., methyl or ethyl).

In some embodiments, the ionizable cationic lipids is 1,2-distearoyl-3-dimethylammonium-propane (18:0 DAP), 1,2-dipalmitoyl-3-dimethylammonium-propane (16:0 DAP), 1,2-dimyristoyl-3-dimethylammonium-propane (14:0 DAP), 1,2-dioleoyl-3-dimethylammonium-propane (18:1 DAP, DODAP), or 1,2-dioleyloxy-3-dimethylamino-propane (DODMA).

In some embodiments of the lipid compositions, the additional ionizable lipid or permanently cationic lipid comprises a head group of a particular structure. In some embodiments, the additional lipid (e.g., SORT lipid) comprises a headgroup having a structural formula:

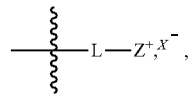

wherein L is a linker; Z$^+$ is positively charged moiety and X$^-$ is a counterion. In some embodiment, the linker is a biodegradable linker. The biodegradable linker may be degradable under physiological pH and temperature. The biodegradable linker may be degraded by proteins or enzymes from a subject. In some embodiments, the positively charged moiety is a quaternary ammonium ion or quaternary amine.

In some embodiments, the SORT (additional ionizable lipid or permanently cationic) lipid has a structural formula:

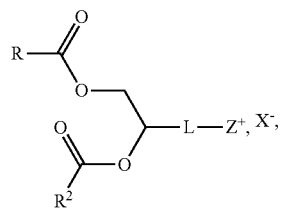

wherein $R^1$ and $R^2$ are each independently an optionally substituted $C_6$-$C_{24}$ alkyl, or an optionally substituted $C_6$-$C_{24}$ alkenyl.

In some embodiments, the additional lipid (e.g., SORT lipid) has a structural formula:

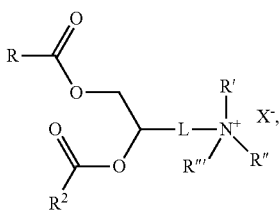

In some embodiments, the additional lipid (e.g., SORT lipid) comprises a Linker (L). In some embodiments, L is

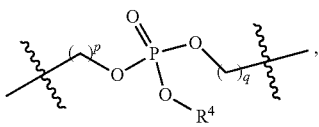

wherein:
p and q are each independently 1, 2, or 3; and
$R^4$ is an optionally substituted $C_1$-$C_6$ alkyl.

In some embodiments, the additional lipid (e.g., SORT lipid) has a structural formula:

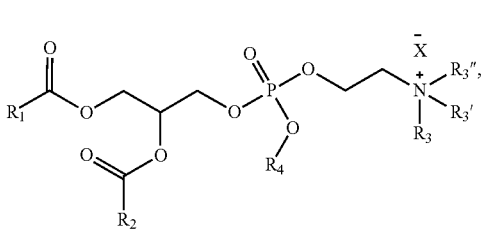

(IA)

wherein:
$R_1$ and $R_2$ are each independently $C_8$-$C_{24}$ alkyl, $C_8$-$C_{24}$ alkenyl, or a substituted version of either group;
$R_3$, $R_3$', and $R_3$" are each independently $C_1$-$C_6$ alkyl or substituted $C_1$-$C_6$ alkyl;
$R_4$ is $C_1$-$C_6$ alkyl or substituted $C_1$-$C_6$ alkyl; and
$X^-$ is a monovalent anion.

In some embodiments, the additional lipid (e.g., SORT lipid) is a phosphatidylcholine (e.g., 14:0 EPC). In some embodiments, the phosphatidylcholine compound is further defined as:

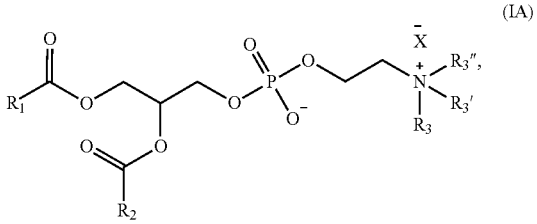

(IA)

wherein:
$R_1$ and $R_2$ are each independently $C_8$-$C_{24}$ alkyl, $C_8$-$C_{24}$ alkenyl, or a substituted version of either group;
$R_3$, $R_3$', and $R_3$" are each independently $C_1$-$C_6$ alkyl or substituted $C_1$-$C_6$ alkyl; and
$X^-$ is a monovalent anion.

In some embodiments, the additional lipid (e.g., SORT lipid) is a phosphocholine lipid. In some embodiments, the additional lipid (e.g., SORT lipid) is an ethylphosphocholine. The ethylphosphocholine may be, by way of example, without being limited to, 1,2-dimyristoleoyl-sn-glycero-3-ethylphosphocholine (14:1 EPC), 1,2-dioleoyl-sn-glycero-3-ethylphosphocholine (18:1 EPC), 1,2-distearoyl-sn-glycero-3-ethylphosphocholine (18:0 EPC), 1,2-dipalmitoyl-sn-glycero-3-ethylphosphocholine (16:0 EPC), 1,2-dimyristoyl-sn-glycero-3-ethylphosphocholine (14:0 EPC), 1,2-dilauroyl-sn-glycero-3-ethylphosphocholine (12:0 EPC), 1-palmitoyl-2-oleoyl-sn-glycero-3-ethylphosphocholine (16:0-18:0 EPC).

In some embodiments, the SORT lipid has a structural formula:

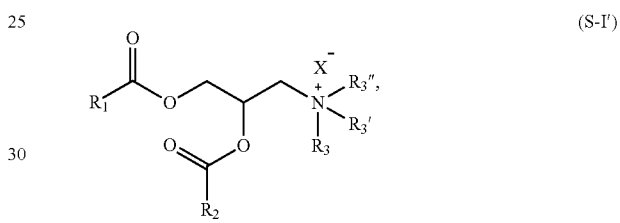

(S-I')

wherein:
$R_1$ and $R_2$ are each independently $C_8$-$C_{24}$ alkyl, $C_8$-$C_{24}$ alkenyl, or a substituted version of either group;
$R_3$, $R_3$', and $R_3$" are each independently $C_1$-$C_6$ alkyl or substituted $C_1$-$C_6$ alkyl; $X^-$ is a monovalent anion.

By way of example, and without being limited thereto, an additional lipid (e.g., SORT lipid) of the structural formula of the immediately preceding paragraph is 1,2-dioleoyl-3-trimethylammonium-propane (18:1 DOTAP) (e.g., chloride salt).

In some embodiments, the additional lipid (e.g., SORT lipid) has a structural formula:

(S-II')

wherein:
$R_4$ and $R_4$' are each independently alkyl($C_6$-$C_{24}$), alkenyl($C_6$-$C_{24}$), or a substituted version of either group;
$R_4$" is alkyl($C \leq 24$), alkenyl($C \leq 24$), or a substituted version of either group;
$R_4$''' is alkyl($C_1$-$C_8$), alkenyl($C_2$-$C_8$), or a substituted version of either group; and
$X_2$ is a monovalent anion.

By way of example, and without being limited thereto, an additional lipid (e.g., SORT lipid) of the structural formula of the immediately preceding paragraph is dimethyldioctadecylammonium (DDAB).

In some embodiments, the additional lipid (e.g., SORT lipid) is

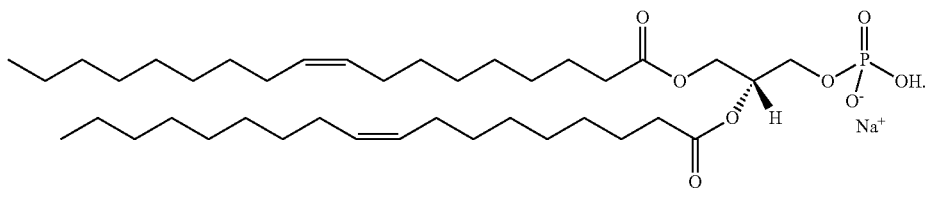

1,2-dioleoyl-sn-glycero-3-phosphate (18:1 PA)

In some embodiments of the lipid compositions, the additional lipid is selected from the lipids set forth in Table 6.

TABLE 6

Example additonal lipid (e.g., SORT lipids)

| Lipid Name | Structure |
| --- | --- |
| 1,2-dioleoyl-3-dimethyl-ammonium-propane (18:1 DODAP) | 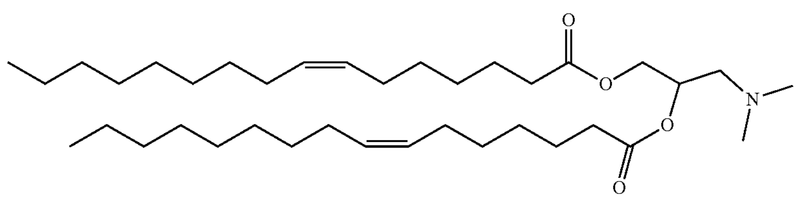 [SMILES: CCCCCCCC/C=C\CCCCCC(=O)OCC(CN(C)C)OC(=O)CCCCC/C=C\CCCCCCCC] |
| 1,2-dimyristoyl-3-trimethyl-ammonium-propane (14:0 TAP) | 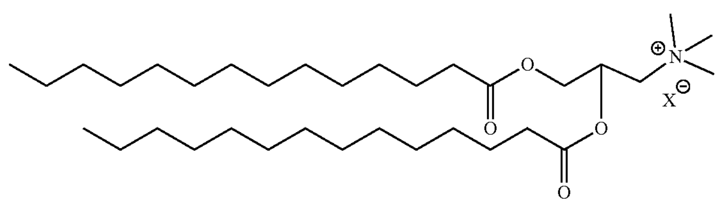 |
| 1,2-dipalmitoyl-3-trimethyl-ammonium-propane (16:0 TAP) | 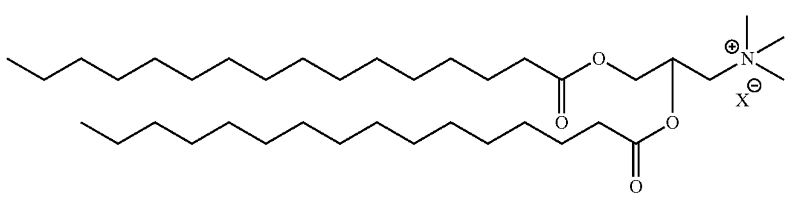 |
| 1,2-stearoyl-3-trimethyl-ammonium-propane (18:0 TAP) | 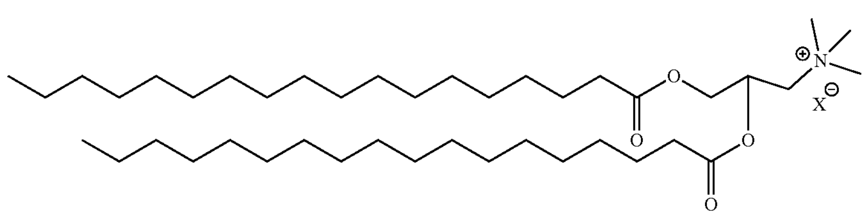 |
| 1,2-dioleoyl-3-trimethyl-ammonium-propane (18:0 DOTAP) | 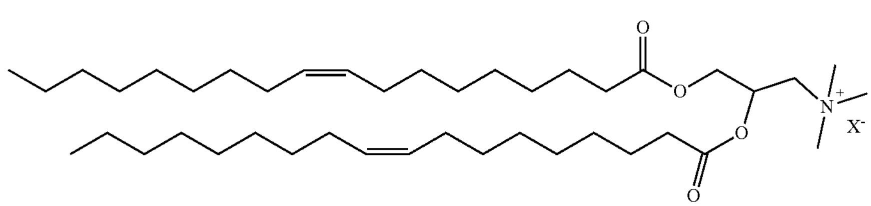 |

TABLE 6-continued

Example additonal lipid (e.g., SORT lipids)

| Lipid Name | Structure |
|---|---|
| 1,2-di-O-octadecenyl-3-trimethyl-ammonium propane (DOTMA) | 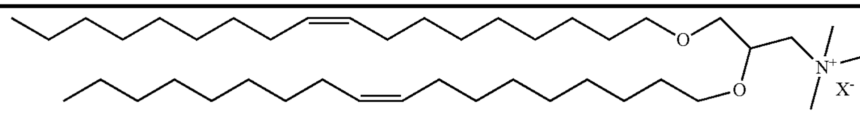 |
| Dimethyl-dioctadecyl-ammonium (DDAB) | 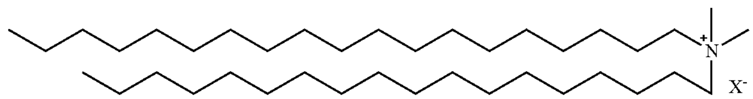 |
| 1,2-dilauroyl-sn-glycero-3-ethyl-phosphocholine (12:0 EPC) | 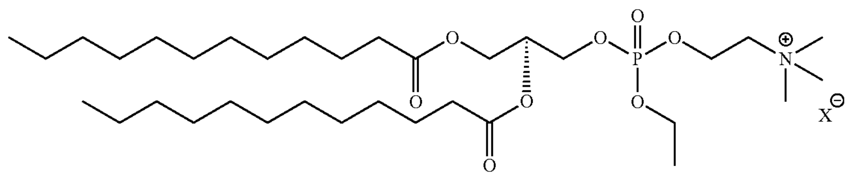 |
| 1,2-dioleoyl-sn-glycero-3-ethyl-phosphocholine (14:0 EPC) | 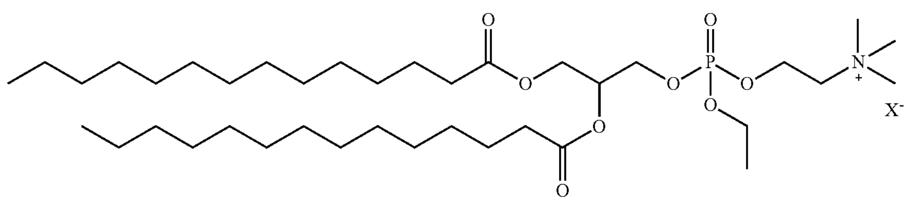 |
| 1,2-dimyristoleoyl-sn-glycero-3-ethyl-phosphocholine (14:1 EPC) | 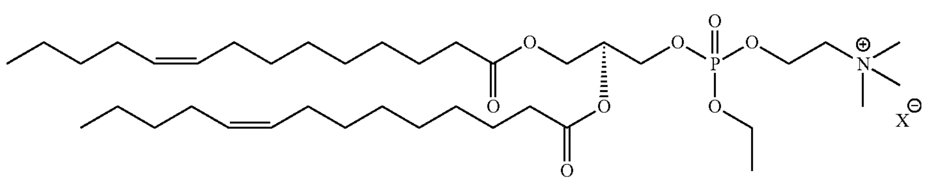 |
| 1,2-dipalmitoyl-sn-glycero-3-ethyl-phosphocholine (16:0 EPC) | 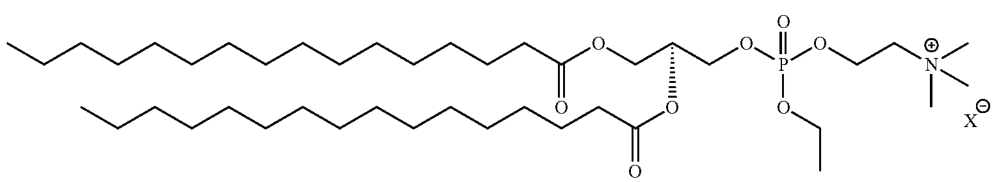 |
| 1,2-distearoyl-sn-glycero-3-ethyl-phosphocholine (18:0 EPC) | 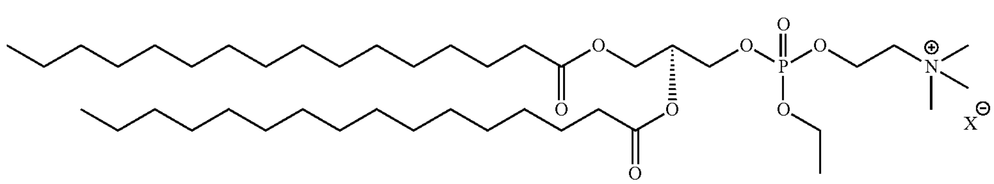 |
| 1,2-dioleoyl-sn-glycero-3-ethyl-phosphocholine (18:1 EPC) | 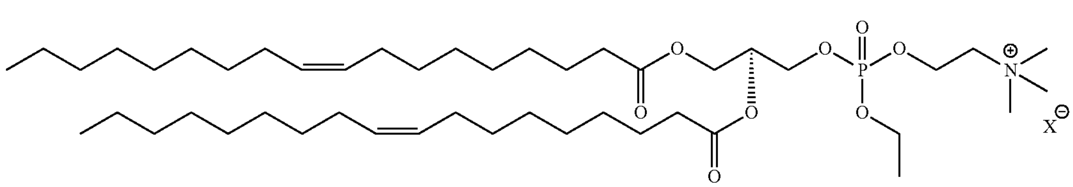 |
| 1-palmitoyl-2-oleoyl-sn-glycero-3-ethyl-phosphocholine (16:0-18:1 EPC) | 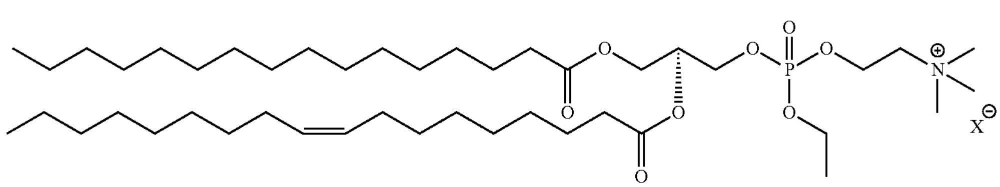 |

TABLE 6-continued

Example additional lipid (e.g., SORT lipids)

| Lipid Name | Structure |
|---|---|
| 1,2-di-O-octadecenyl-3-trimethyl-ammonium propane (18:1 DOTMA) | 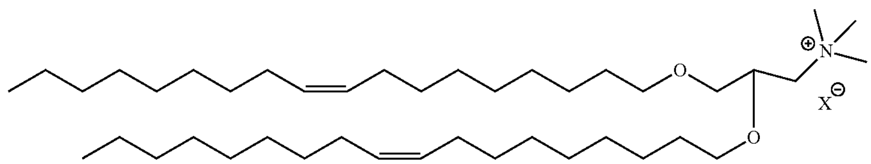 |
| 1,2-dioleoyl-sn-glycero-3-phosphate (18:1 PA) | 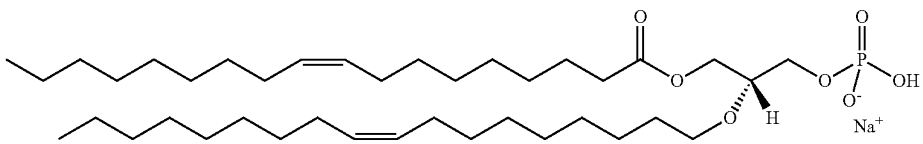 [SMILES: CCCCCCCC/C=C\CCCCCCCCO[C@H](COC(=O)CCCCCCC/C=C\CCCCCCCC)COP(=O)([O-])O ; [Na+]] |
| 1,2-distearoyl-sn-glycero-3-phosphate (18:0 PA) | 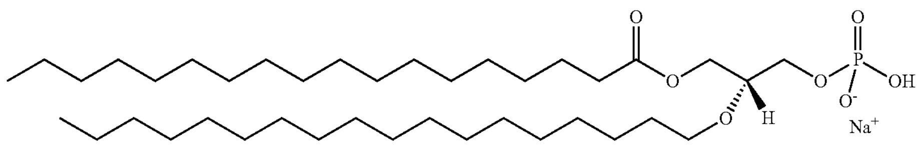 [SMILES: CCCCCCCCCCCCCCCCCCO[C@H](COC(=O)CCCCCCCCCCCCCCCCC)COP(=O)([O-])O ; [Na+]] |
| 1,2-dipalmitoyl-sn-glycero-3-phosphate (16:0 PA) | 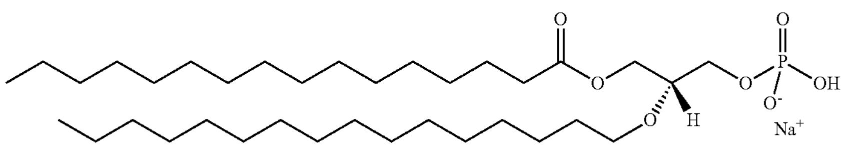 [SMILES: CCCCCCCCCCCCCCCCO[C@H](COC(=O)CCCCCCCCCCCCCCC)COP(=O)([O-])O ; [Na+]] |
| 1,2-dimyristoyl-sn-glycero-3-phosphate (14:0 PA) | 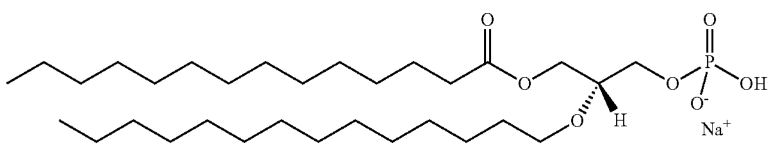 [SMILES: CCCCCCCCCCCCCCO[C@H](COC(=O)CCCCCCCCCCCCC)COP(=O)([O-])O ; [Na+]] |
| 1,2-dilauroyl-sn-glycero-3-phosphate (12:0 PA) | 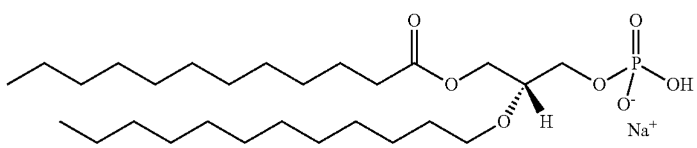 [SMILES: CCCCCCCCCCCCO[C@H](COC(=O)CCCCCCCCCCC)COP(=O)([O-])O ; [Na+]] |

$X^-$ is a counterion (e.g., Cl—, Br—etc.)

In some embodiments, the lipid component comprises the additional lipid (e.g., SORT lipid) at a molar percentage from about 20% to about 65%. In some embodiments, the lipid component comprises the additional lipid (e.g., SORT lipid) at a molar percentage from about 25% to about 60%. In some, the lipid component comprises the additional lipid (e.g., SORT lipid) at a molar percentage from about 30% to about 55%. In some embodiments, the lipid component comprises the additional lipid (e.g., SORT lipid) at a molar percentage from about 20% to about 50%. In some embodiments, the lipid component comprises the additional lipid (e.g., SORT lipid) at a molar percentage from about 30% to about 60%. In some embodiments, the lipid component comprises the additional lipid (e.g., SORT lipid) at a molar percentage from about 25% to about 60%. In some embodiments, the lipid component comprises the additional lipid (e.g., SORT lipid) at a molar percentage of at least (about) 25%, at least (about) 30%, at least (about) 35%, at least (about) 40%, at least (about) 45%, at least (about) 50%, at least (about) 55%, at least (about) 60%, or at least (about) 65%. In some embodiments, the lipid component comprises the additional lipid (e.g., SORT lipid) at a molar percentage of at most (about) 25%, at most (about) 30%, at most (about) 35%, at most (about) 40%, at least (about) 45%, at most (about) 50%, at most (about) 55%, at most (about) 60%, or at most (about) 65%. In some embodiments, the lipid component comprises the additional lipid (e.g., SORT lipid) at a molar percentage of about 20%, 25%, 30%, 35%, 40%, 45%, 50%, 55%, 60%, or 65%, or of a range between (inclusive) any two of the foregoing values.

Non-limiting illustrative LNP compositions are provided in Table 7.

TABLE 7

Non-limiting illustrative LNP compositions

| Dendrimer SORT Helper Chol PEG | Mol % | Wt % | Lipid:RNA (wt/wt) |
|---|---|---|---|
| 4A3-SC7 | 19.05 | 34.33 | 40 |
| DODAP | 20 | 16.54 | |
| DOPE | 19.05 | 18.1 | |
| Chol | 38.09 | 18.81 | |

TABLE 7-continued

Non-limiting illustrative LNP compositions

| Dendrimer<br>SORT<br>Helper<br>Chol<br>PEG | Mol % | Wt % | Lipid:RNA<br>(wt/wt) |
|---|---|---|---|
| DMG-PEG | 3.81 | 12.21 | |
| 5A2-SC8 | 23.81 | 51.83 | 40 |
| DOPE | 23.81 | 17.75 | |
| Chol | 47.62 | 18.45 | |
| DMG-PEG | 4.76 | 11.97 | |
| 5A2-SC8 | 11.9 | 30.5 | 40 |
| DOTAP | 50 | 41.15 | |
| DOPE | 11.9 | 10.45 | |
| Chol | 23.82 | 10.86 | |
| DMG-PEG | 2.38 | 7.05 | |
| 5A2-SC8 | 19.05 | 44.59 | 40 |
| DODAP | 20 | 15.27 | |
| DOPE | 19.05 | 15.87 | |
| Chol | 38.09 | 10.3 | |
| DMG-PEG | 3.81 | 13.96 | |
| 4A3-SC7 | 19.05 | 33.53 | 30 |
| 14:0 EPC | 20 | 18.5 | |
| DOPE | 19.05 | 17.68 | |
| Chol | 38.09 | 18.37 | |
| DMG-PEG | 3.81 | 11.92 | |
| 4A3-SC7 | 19.05 | 34.85 | 30 |
| 14:0 TAP | 20 | 15.28 | |
| DOPE | 19.05 | 18.38 | |
| Chol | 38.09 | 19.1 | |
| DMG-PEG | 3.81 | 12.39 | |
| 5A2-SC8 | 22.62 | 49.93 | 40 |
| 18:1 PA | 5 | 3.67 | |
| DOPE | 22.62 | 17.1 | |
| Chol | 45.24 | 17.77 | |
| DMG-PEG | 4.52 | 11.52 | |
| 5A2-SC8 | 14.29 | 37.19 | 40 |
| 14:0 TAP | 40 | 28.25 | |
| DOPE | 14.29 | 12.74 | |
| Chol | 28.57 | 13.23 | |
| DMG-PEG | 2.86 | 8.6 | |

1. Six-Component Lipid Nanoparticle

In one aspect, the present disclosure provides a lipid nanoparticle (LNP) composition, comprising at least two selective organ targeting (SORT) lipids and/or at least six lipids.

In some embodiments, the LNP composition comprises an ionizable cationic lipid, optionally two or more ionizable lipids; and a permanently cationic lipid, optionally two or more permanently cationic lipids.

In some embodiments, the LNP composition comprises an ionizable cationic lipid, a permanently cationic lipid, optionally a phospholipid, optionally a polyethylene-glycol (PEG)-lipid, and/or optionally a sterol.

In some embodiments, the LNP composition comprises at least six lipids.

In some embodiments, the LNP composition comprises an ionizable cationic lipid, a permanently cationic lipid, optionally a phospholipid, optionally a polyethylene-glycol (PEG)-lipid, and/or optionally a sterol.

In some embodiments, the LNP composition comprises at least two selective organ targeting (SORT) lipids. In some embodiments, the ionizable cationic lipid is a dendrimeric lipid, optionally 4A3-SC7 or 5A2-SC8. In some embodiments, the ionizable cationic lipid is a SORT lipid; and/or the permanently cationic lipid is a SORT lipid. In some embodiments, the ionizable cationic lipid is 1,2-dioleoyl-3-dimethylammonium-propane (DODAP). In some embodiments, the permanently cationic lipid is trimethylammonium-propane, optionally 1,2-dimyristoyl-3-trimethylammonium-propane(14:0 TAP), 1,2-dipalmitoyl-3-trimethylammonium-propane (16:0 TAP), 1,2-stearoyl-3-trimethylammonium-propane (18:0 TAP), 1,2-dioleoyl-3-trimethylammonium-propane (DOTAP). In some embodiments, the permanently cationic lipid is ethylphosphocholine (EPC), optionally 1,2-dilauroyl-sn-glycero-3-ethylphosphocholine (12:0 EPC), 1,2-dimyristoyl-sn-glycero-3-ethylphosphocholine (14:0 EPC), 1,2-dipalmitoyl-sn-glycero-3-ethylphosphocholine (16:0 EPC), 1,2-distearoyl-sn-glycero-3-ethylphosphocholine (18:0 EPC).

In some embodiments, the LNP specifically transduces a lung cell; and/or the LNP delivers mRNA to a lung cell in an amount effective to increase expression and/or function of a protein encoded by the mRNA. In some embodiments, the lung cell is ionocyte. In some embodiments, the lung cell is ciliated cell. In some embodiments, the lung cell is secretory cell.

In some embodiments, the LNP comprises the ionizable cationic lipid at a molar percentage greater than 15%. In some embodiments, the ionizable cationic lipid is the dendrimeric lipid at a molar percentage between 10% and 30%. In some embodiments, the LNP comprises DODAP at a molar percentage between 5% and 40%. In some embodiments, the LNP comprises permanently cationic lipids at a molar percentage less than 40%. In some embodiments, the permanently cationic lipids at a molar percentage between 5% and 25%, between 5% and 20%, between 5% and 15%, between 5% and 10%, between 10% and 20%, between 15% and 20%. In some embodiments, the permanently cationic lipid is trimethylammonium-propane (TAP). In some embodiments, the TAP is 1,2-dimyristoyl-3-trimethylammonium-propane(14:0 TAP). In some embodiments, the permanently cationic lipid is 14:0 TAP at a molar percentage between 10% and 15%. In some embodiments, the permanently cationic lipid is ethylphosphocholine (EPC). In some embodiments, the TAP is 1,2-dimyristoyl-sn-glycero-3-ethylphosphocholine (14:0 EPC). In some embodiments, the permanently cationic lipid is 14:0 EPC at a molar percentage between 10% and 15%.

In some embodiments, the LNP comprises phospholipid at a molar percentage between 10% and 30%. In some embodiments, the LNP comprises cholesterol at a molar percentage greater than 25%. In some embodiments, the cholesterol at a molar percentage between 25% and 50%, between 30% and 50%, between 30% and 45%, between 30% and 40%, or between 30% and 35%. In some embodiments, the LNP comprises polyethylene-glycol (PEG)-lipid at a molar percentage between 0.5% and 10% or between 1% and 4%.

In some embodiments, the LNP comprises messenger RNA (mRNA). In some embodiments, the LNP comprises mRNA at a lipid:mRNA ratio less than 40:1. In some embodiments, the lipid:mRNA ratio is 36:1. In some embodiments, the lipid:mRNA ratio is 33:1. In some embodiments, the lipid:mRNA ratio is 30:1.

In some embodiments, the LNP comprises gene editing payload. In some embodiments, the gene editing payload comprises a nuclease, and/or one or more guide RNAs, and optionally a repair template. In some embodiments, the LNP comprises polypeptide, or protein.

In some embodiments, the LNP comprising the cationic ionizable lipid is 5A2-SC8 or 4A3-SC7, the cationic ionizable SORT lipid is DODAP, the permanently cationic lipid is 14:0 TAP or 14:0 EPC, phospholipid is 1,2-dioleoyl-sn-glycero-3-phosphoethanolamine (DOPE) or 1,2-distearoyl-sn-glycero-3-phosphocholine (DSPC), the sterol is cholesterol or sitosterol, and/or the polyethylene-glycol (PEG)-lipid is DMG-PEG, optionally DMG-PEG2000.

In some embodiments, the LNP comprising the cationic ionizable lipid is 4A3-SC7, the cationic ionizable SORT lipid is DODAP, the permanently cationic lipid is 14:0 TAP, the phospholipid is DOPE, the sterol is cholesterol, and/or the polyethylene-glycol (PEG)-lipid is DMG-PEG.

In some embodiments, the LNP comprising the cationic ionizable lipid is 4A3-SC7, the cationic ionizable SORT lipid is DODAP, the permanently cationic lipid is 14:0 EPC, the phospholipid is DOPE, the sterol is cholesterol, and/or the polyethylene-glycol (PEG)-lipid is DMG-PEG.

In some embodiments, the cationic ionizable lipid is 4A3-SC7 and the LNP comprises 4A3-SC7 at a molar percentage between about 10% and about 30%. In some embodiments, the cationic ionizable SORT lipid is DODAP and the LNP comprises DODAP at a molar percentage between about 5% and about 40%. In some embodiments, the permanently cationic lipid is 14:0 TAP and the LNP comprises 14:0 TAP at a molar percentage between about 5% and about 25%. In some embodiments, the permanently cationic lipid is 14:0 EPC and the LNP comprises 14:0 EPC at a molar percentage between about 5% and about 25%.

In some embodiments, the LNP comprises 4A3-SC7 at a molar percentage between about 10% and about 30%, DODAP at a molar percentage between about 5% and about 40%, 14:0 TAP at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises 4A3-SC7 at a molar percentage between about 10% and about 15%, (DODAP at a molar percentage between about 5% and about 20%, 14:0 TAP at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises 4A3-SC7 at a molar percentage between about 10% and about 30%, DODAP at a molar percentage between about 5% and about 40%, 14:0 EPC at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises 4A3-SC7 at a molar percentage between about 10% and about 15%, DODAP at a molar percentage between about 5% and about 20%, 14:0 EPC at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about about 30%, and DMG-PEG at a molar percentage of about about 3%.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about about 3%.

In some embodiments, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%.

In some embodiments, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and
DMG-PEG at a molar percentage of about 3%.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises a payload. In some embodiments, the payload is a messenger RNA (mRNA). In some embodiments, the mRNA comprises between 100 bases and 8 kilobases (kb). In some embodiments, the mRNA comprises between 1 kb and 8 kb, or between 2 kb and 8 kb, between 3 kb and 8 kb, or between 4 kb and 8 kb. In some embodiments, the mRNA comprises (about) 2 kb. In some embodiments, the mRNA comprises (about) 4.6 kb. In some embodiments, the mRNA encodes a cystic fibrosis transmembrane conductance regulator (CFTR) protein. In some embodiments, the mRNA encodes a Dynein axonemal intermediate chain 1 (DNAI1) protein. In some embodiments, the mRNA encodes a gene-editing system or components thereof. In some embodiments, wherein the payload is an shRNA or a polynucleotide encoding an shRNA. In some embodiments, the payload is a microRNA or a polynucleotide encoding a microRNA. In some embodiments, the payload is polypeptide. In some embodiments, the payload is protein.

In some embodiments, the composition is a pharmaceutical composition. In some embodiments, the composition is an aerosolized composition.

In some embodiments, wherein the LNP has an encapsulation efficiency of between 50% and 99%, between 60% and 99%, between 70% and 99%, or between 80% and 99%. In some embodiments, the LNP has an encapsulation efficiency of between 50% and 95%, between 60% and 95%, between 70% and 95%, or between 80% and 95%. In some embodiments, the LNP composition is a liquid. In some embodiments, the LNP composition is an aerosol.

In some embodiments, the lipid nanoparticle comprises six lipid compositions.

In some embodiments of the six component lipid nanoparticle, the LNP comprises DODAP at a molar percentage between 12.5% and 17.5%, the permanently cationic lipid at a molar percentage between 2% and 12.5%, cholesterol at a molar percentage between 30% and 40%, and polyethylene-glycol (PEG)-lipid at a molar percentage between 1.5% and 3.5%.

Critical benchmarks for lipid nanoparticle delivery include maximizing cellular uptake and facilitating the efficient release of mRNA from the endosome. In one embodiment, the lipid nanoparticles (LNPs) disclosed herein exhibit enhancements in either cellular uptake or endosomal release. Each component of LNPs play a crucial role in ensuring effective payload delivery and particle stability. For example, cholesterol and the PEG-lipid can contribute to stability, while the phospholipid can enhance fusogenicity, aiding in endosomal escape and making the nucleic acid bioavailable in the cell cytosol.

While LNPs offer several advantages in terms of improving drug stability, enhancing bioavailability, and facilitating targeted delivery, their safety profile is a critical consideration. Understanding the relationship between LNP composition, dose, administration route, and potential side effects can be crucial for the development of safe and effective LNP-based therapies. Choosing biocompatible lipids can be crucial. For example, coating LNPs with polyethylene glycol (PEG) or other polymers can improve their stability, reduce aggregation, and minimize interactions with the immune system. PEGylation can also extend the circulation time of LNPs in the bloodstream, potentially reducing immune system activation. The size of nanoparticles can also play a role in their toxicity. Controlling particle size within a specific range can influence biodistribution, cellular uptake, and potential adverse effects. Smaller particles may be more prone to clearance by the kidneys, while larger particles may have increased uptake by the liver. Moreover, surface charge of LNPs can impact their interactions with biological systems. Neutral or slightly negatively charged LNPs can be generally considered less toxic than highly positively charged ones. Charge modification can also affect cellular uptake and stability. Ensuring high encapsulation efficiency of the therapeutic payload within LNPs can reduce the amount of free, unencapsulated drug or nucleic acid, which can contribute to toxicity. Furthermore, careful consideration of the administered dose can be critical. This can involve determining the maximum tolerated dose through dose-escalation studies.

F. Payload

Payload can encompass bioactive molecules, including small molecules, biomolecules, nucleic acids (e.g., DNA, RNA, siRNA, shRNA), proteins, or peptides that are part of the LNP composition. The payload can be attached to the LNP through covalent or non-covalent bonds, enclosed within the LNP, linked to the LNP, or combined with the LNP within the LNP composition. In some embodiments, the LNP comprises a payload. In some embodiments, the payload includes a polynucleotide, a protein, or an antibody. In some embodiments, the payload includes a polynucleotide, wherein the polynucleotide is mRNA.

In some embodiments, the mRNA molecule is greater than 2000 nucleotides, greater than 2500 nucleotides, greater than 3000 nucleotides, greater than 3500 nucleotides, greater than 4000 nucleotides, greater than 4500 nucleotides, or greater than 5000 nucleotides in length. In some embodiments, the mRNA molecule is about 2000 nucleotides in length. In some embodiments, the mRNA molecule is about 2500 nucleotides in length. In some embodiments, the mRNA molecule is about 3000 nucleotides in length. In some embodiments, the mRNA molecule is about 3500 nucleotides in length. In some embodiments, the mRNA molecule is about 4000 nucleotides in length. In some embodiments, the mRNA molecule is about 4500 nucleotides in length. In some embodiments, the mRNA molecule is about 5000 nucleotides in length.

In some embodiments, the polynucleotide is from 2000 nucleotides to 5000 nucleotides in length. In some embodiments, the polynucleotide is from 2500 to 5000 nucleotides in length. In some embodiments, the polynucleotide is from 3000 to 5000 nucleotides in length. In some embodiments, the polynucleotide is from 3500 to 5000 nucleotides in length. In some embodiments, the polynucleotide is from 4000 to 5000 nucleotides in length. In some embodiments, the polynucleotide is from 4500 to 5000 nucleotides in length.

In some embodiments, the polynucleotide has a concentration of 0.5-3.0 mg/mL, 1.0-3.0 mg/mL, or 2.0-3.0 mg/mL of 1.0 mg/mL. In some embodiments, the polynucleotide has a concentration of 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, or 1.5 mg/mL. In some embodiments, the polynucleotide has a concentration of 1.0 mg/mL.

In some embodiments, the polynucleotide is from 2000 to 5000 nucleotides in length and at a concentration of 1.0 mg/mL. In some embodiments, the polynucleotide is from 2500 to 5000 nucleotides in length and at a concentration of 1.0 mg/mL. In some embodiments, the polynucleotide is from 3000 to 5000 nucleotides in length and at a concentration of 1.0 mg/mL. In some embodiments, the polynucleotide is from 3500 to 5000 nucleotides in length and at a concentration of 1.0 mg/mL. In some embodiments, the polynucleotide is from 4000 to 5000 nucleotides in length and at a concentration of 1.0 mg/mL. In some embodiments, the polynucleotide is from 4500 to 5000 nucleotides in length and at a concentration of 1.0 mg/mL.

In some embodiments, the polynucleotide is from 2000 to 5000 nucleotides in length and at a concentration of 0.9 mg/mL. In some embodiments, the polynucleotide is from 2500 to 5000 nucleotides in length and at a concentration of 0.9 mg/mL. In some embodiments, the polynucleotide is from 3000 to 5000 nucleotides in length and at a concentration of 0.9 mg/mL. In some embodiments, the polynucleotide is from 3500 to 5000 nucleotides in length and at a concentration of 0.9 mg/mL. In some embodiments, the polynucleotide is from 4000 to 5000 nucleotides in length and at a concentration of 0.9 mg/mL. In some embodiments, the polynucleotide is from 4500 to 5000 nucleotides in length and at a concentration of 0.9 mg/mL.

In some embodiments, the polynucleotide is from 2000 to 5000 nucleotides in length and at a concentration of 0.8 mg/mL. In some embodiments, the polynucleotide is from 2500 to 5000 nucleotides in length and at a concentration of 0.8 mg/mL. In some embodiments, the polynucleotide is from 3000 to 5000 nucleotides in length and at a concentration of 0.8 mg/mL. In some embodiments, the polynucleotide is from 3500 to 5000 nucleotides in length and at a concentration of 0.8 mg/mL. In some embodiments, the polynucleotide is from 4000 to 5000 nucleotides in length and at a concentration of 0.8 mg/mL. In some embodiments, the polynucleotide is from 4500 to 5000 nucleotides in length and at a concentration of 0.8 mg/mL.

In some embodiments, the polynucleotide is from 2000 to 5000 nucleotides in length and at a concentration of 0.7 mg/mL. In some embodiments, the polynucleotide is from 2500 to 5000 nucleotides in length and at a concentration of 0.7 mg/mL. In some embodiments, the polynucleotide is from 3000 to 5000 nucleotides in length and at a concentration of 0.7 mg/mL. In some embodiments, the polynucleotide is from 3500 to 5000 nucleotides in length and at a concentration of 0.7 mg/mL. In some embodiments, the polynucleotide is from 4000 to 5000 nucleotides in length and at a concentration of 0.7 mg/mL. In some embodiments, the polynucleotide is from 4500 to 5000 nucleotides in length and at a concentration of 0.7 mg/mL.

In some embodiments, the polynucleotide is from 2000 to 5000 nucleotides in length and at a concentration of 0.6 mg/mL. In some embodiments, the polynucleotide is from 2500 to 5000 nucleotides in length and at a concentration of 0.6 mg/mL. In some embodiments, the polynucleotide is from 3000 to 5000 nucleotides in length and at a concentration of 0.6 mg/mL. In some embodiments, the polynucleotide is from 3500 to 5000 nucleotides in length and at a concentration of 0.6 mg/mL. In some embodiments, the polynucleotide is from 4000 to 5000 nucleotides in length and at a concentration of 0.6 mg/mL. In some embodiments, the polynucleotide is from 4500 to 5000 nucleotides in length and at a concentration of 0.6 mg/mL.

In some embodiments, the mRNA encodes dynein axonemal intermediate chain 1 (DNAI1) protein. In other embodiments, the mRNA encodes cystic fibrosis transmembrane conductance regulator (CFTR).

In some embodiments, the mRNA comprises a polynucleotide sequence of SEQ ID NO: 1. In some embodiments, the mRNA encoding the CFTR protein comprises a polynucleotide sequence at least 80% identical to SEQ ID NO: 1. In some embodiments, the mRNA encoding the CFTR protein comprises a polynucleotide sequence at least 85% identical to SEQ ID NO: 1. In some embodiments, the mRNA encoding the CFTR protein comprises a polynucleotide sequence at least 90% identical to SEQ ID NO: 1. In some embodiments, the mRNA encoding the CFTR protein comprises a polynucleotide sequence at least 95% identical to SEQ ID NO: 1. In some embodiments, the mRNA encoding the CFTR protein comprises a polynucleotide sequence at least 99% identical to SEQ ID NO: 1. In some embodiments, the mRNA encoding the CFTR protein comprises a polynucleotide sequence identical to SEQ ID NO: 1.

In some embodiments, the mRNA comprises the sequence of SEQ ID NO: 4. In some embodiments, the mRNA encoding the DNAI1 protein comprises a polynucleotide sequence at least 80% identical to SEQ ID NO: 4. In some embodiments, the mRNA encoding the DNAI1 protein comprises a polynucleotide sequence at least 85% identical to SEQ ID NO: 4. In some embodiments, the mRNA encoding the DNAI1 protein comprises a polynucleotide sequence at least 90% identical to SEQ ID NO: 4. In some embodiments, the mRNA encoding the DNAI1 protein comprises a polynucleotide sequence at least 95% identical to SEQ ID NO: 4. In some embodiments, the mRNA encoding the DNAI1 protein comprises a polynucleotide sequence at least 99% identical to SEQ ID NO: 4. In some embodiments, the mRNA encoding the DNAI1 protein comprises a polynucleotide sequence identical to SEQ ID NO: 4.

In some embodiments, the payload has an average molecular weight of up to 20,000,000 Da. In some embodiments, the payload can have an average molecular weight of up to 2,000,000 Da. In some embodiments, the payload may have an average molecular weight of up to 150,000 Da. In further implementations, the payload has an average molecular weight of up to 15,000 Da, 5,000 Da or 1,000 Da.

In one aspect, the present disclosure provides a lipid nanoparticle (LNP) composition, comprising an LNP, wherein the LNP comprises 1,2-dioleoyl-3-dimethylammonium propane (DODAP) at a molar percentage less then 25% or less then 20%; cholesterol at a molar percentage greater than 40%; and/or messenger RNA (mRNA) at a lipid:mRNA ratio less than 40:1.

In another aspect, the present disclosure provides a lipid nanoparticle (LNP) composition, comprising an LNP, wherein the LNP specifically transduces secretory cells and/or ionocytes; and/or the LNP delivers mRNA to lung cells in an amount effective to increase expression and/or function of a polypeptide or polynucleotide encoded by the mRNA.

In some embodiments, the LNP specifically transduces secretory cells and/or ionocytes; and/or wherein the LNP delivers mRNA to lung cells in an amount effective to increase expression and/or function of a polypeptide or polynucleotide encoded by the mRNA.

In some embodiments, the LNP comprises an ionizable cationic lipid; a neutral phospholipid; a polyethylene-glycol (PEG)-lipid; and/or a/the cholesterol. In some embodiments, the LNP comprises a second ionizable cationic lipid. In some embodiments, the LNP comprises an anionic lipid. In some embodiments, the LNP comprises a permanently cationic lipid.

In some embodiments, the LNP comprises DODAP at a molar percentage less than 25% or less then 20%. In some embodiments, the LNP comprises a DODAP at a molar percentage of less than 5%, less than 10%, less than 15%, less than 16%, than 17%, than 18%, than 19%, than 20%, than 21%, than 22%, than 22%, than 23%, than 24% or of less than 25%.

In some embodiments, the LNP comprises DODAP at a molar percentage between 5% and 25%, between 7.5% and 25%, between 10% and 25%, between 15% and 25%, between 20% and 25%, between 5% and 20%, between 7.5% and 20%, between 10% and 20%, between 15% and 20%, between 5% and 15%, between 7.5% and 15%, between 10% and 15%, between 5% and 10%, or between 7.5% and 10%.

In some embodiments, the LNP comprises DODAP at a molar percentage between 17.5% and 20%, between 17.5% and 22.5%, between 17.5% and 25%, between 5% and 17.5%, between 7.5% and 17.5%, between 10% and 17.5%, between 12.5% and 17.5% or between 15% and 17.5%.

In some embodiments, the LNP comprises DODAP at a molar percentage of 16%.

In some embodiments, the LNP comprises cholesterol at a molar percentage greater than 40%, greater than 45%, greater than 50%, greater than 55%, greater than 60%, greater than 65%, greater than 70%, greater than 75%, greater than 80%, greater than 85%, greater than 90%, greater than 95% or greater than 99%.

In some embodiments, the LNP comprises cholesterol at a molar percentage between 40% and 60%, between 45% and 60%, between 50% and 60%, between 55% and 60%, between 40% and 55%, between 40% and 50%, between 40% and 45%, between 45% and 55%, between 45% and 50% or between 50% and 55%. In some embodiments, the LNP comprises cholesterol at a molar percentage of 50%.

TABLE 8

Exemplary formulations

| | Ionizable Lipid | SORT Lipid | Helper Lipid | Sterol | PEGylated lipid | Lipid:RNA ratio |
|---|---|---|---|---|---|---|
| 1 | 4A3-SC7 13%-15% | DODAP 15%-25% | DOPE 10%-25% | Cholesterol 40%-60% | DMG-PEG 2%-6% | 20:1-40:1 |
| 2 | 4A3-SC7 13.5%-15% | DODAP 15%-25% | DOPE 10%-25% | Cholesterol 40%-55% | DMG-PEG 2%-4% | 25:1-40:1 |

TABLE 8-continued

Exemplary formulations

| | Ionizable Lipid | SORT Lipid | Helper Lipid | Sterol | PEGylated lipid | Lipid:RNA ratio |
|---|---|---|---|---|---|---|
| 3 | 4A3-SC7 14%-15% | DODAP 10%-20% | DOPE 15%-25% | Cholesterol 40%-50% | DMG-PEG 2.5%-3% | 30:1-40:1 |
| 4 | 4A3-SC8 14%-15% | DODAP 15%-20% | DOPE 15%-25% | Cholesterol 40%-45% | DMG-PEG 2%-3% | 30:1-40:1 |
| 5 | 4A3-SC7 14.5%-15% | DODAP 7.5%-17.5% | DOPE 15%-25% | Cholesterol 40%-45% | DMG-PEG 2.5%-3% | 30:1-40:1 |
| 6 | 4A3-SC7 14.5%-15% | DODAP 10%-17.5% | DOPE 20%-25% | Cholesterol 40%-50% | DMG-PEG 2%-3% | 35:1-40:1 |
| 7 | 4A3-SC7 14%-15% | DODAP 12.5%-17.5% | DOPE 20%-25% | Cholesterol 40%-50% | DMG-PEG 2.5%-3% | 35:1-40:1 |
| 8 | 4A3-SC7 14.5%-15% | DODAP 15%-17.5% | DOPE 20%-25% | Cholesterol 40%-45% | DMG-PEG 2%-3% | 35:1-40:1 |
| 9 | 4A3-SC7 13%-14.5% | DODAP 20%-25% | DOPE 10%-20% | Cholesterol 45%-60% | DMG-PEG 2.5%-3.5% | 20:1-35:1 |
| 10 | 4A3-SC7 13.5%-14.5% | DODAP 20%-25% | DOPE 10%-20% | Cholesterol 50%-60% | DMG-PEG 3%-3.5% | 25:1-35:1 |
| 11 | 4A3-SC7 13%-14% | DODAP 17.5%-22.5% | DOPE 10%-20% | Cholesterol 45%-50% | DMG-PEG 2.5%-3.5% | 25:1-30:0 |
| 12 | 4A3-SC7 13.5%-14% | DODAP 17.5%-22.5% | DOPE 10%-12.5% | Cholesterol 45%-50% | DMG-PEG 3%-3.5% | 20:0-30:0 |
| 13 | 4A3-SC7 13.5%-14% | DODAP 17.5%-25% | DOPE 10%-12.5% | Cholesterol 50%-60% | DMG-PEG 2.5%-3.5% | 20:0-30:0 |
| 14 | 4A3-SC7 13%-14% | DODAP 17.5%-25% | DOPE 10%-12.5% | Cholesterol 45%-60% | DMG-PEG 3%-4% | 20:1-35:1 |
| 15 | 5A2-SC8 13%-15% | DODAP 15%-25% | DOPE 10%-25% | Cholesterol 40%-60% | DMG-PEG 2%-6% | 25:1-40:1 |
| 16 | 5A2-SC8 13.5%-15% | DODAP 15%-25% | DOPE 10%-25% | Cholesterol 40%-55% | DMG-PEG 2%-4% | 25:1-40:1 |
| 17 | 4A3-SC7 13.5%-15% | DODAP 15%-25% | DOPE 10%-25% | Sitosterol 40%-60% | DMG-PEG 2%-4% | 25:1-40:1 |
| 18 | 4A3-SC7 13%-15% | DOTMA 15%-25% | DOPE 10%-25% | Cholesterol 40%-60% | DMG-PEG 2%-6% | 20:1-40:1 |
| 19 | 5A2-SC8 13.5%-15% | DOTMA 15%-25% | DOPE 10%-25% | Cholesterol 40%-55% | DMG-PEG 2%-4% | 25:1-40:1 |
| 20 | 4A3-SC7 13%-15% | DODAP 15%-25% | DSPC 10%-25% | Cholesterol 40%-60% | DMG-PEG 2%-6% | 25:1-40:1 |
| 21 | 5A2-SC8 13.5%-15% | DODAP 15%-25%c | DSPC 10%-25% | Cholesterol 40%-55% | DMG-PEG 2%-4% | 20:1-40:1 |
| 22 | 4A3-SC7 13.5%-15% | DODAP 15%-25% | DSPC 10%-25% | Cholesterol 40%-55% | DMG-PEG2000 2%-4% | 20:1-40:1 |
| 23 | 4A3-SC7 13%-15% | 14:0 TAP 15%-25% | DOPE 10%-25% | Cholesterol 40%-60% | DMG-PEG2000 2%-4% | 20:1-40:1 |
| 24 | 5A2-SC8 13%-15% | 14:0 EPC 15%-25% | DOPE 10%-25% | Sitosterol 40%-60% | DMG-PEG2000 2%-6% | 20:1-40:1 |
| 25 | 5A2-SC8 13%-15% | DOTMA 15%-25% | DOPE 10%-25% | Sitosterol 40%-55% | DMG-PEG2000 2%-6% | 20:1-40:1 |

In some embodiments, the LNP comprises messenger RNA (mRNA).

In some embodiments, the LNP comprises mRNA at a lipid:mRNA ratio less than 40:1.

In some embodiments, the lipid:mRNA ratio is between 20:1 and 40:1, between 25:1 and 40:1, between 30:1 and 40:1, between 35:1 and 40:1, between 20:1 and 35:1, between 25:1 and 35:1, between 30:1 and 35:1, between 20:1 and 30:1, between 25:1 and 30:1, between 20:1 and 25:1, between 25:1 and 30:1, between 25:1 and 35:1, between 20:1 and 36:1, or between 25:1 and 36:1.

In some embodiments, the lipid:mRNA ratio is 36:1.

In some embodiments, the lipid:mRNA ratio is 25:1.

In some embodiments, the ionizable cationic lipid is 5A2-SC8 or 4A3-SC7; the neutral phospholipid is 1,2-dioleoyl-sn-glycero-3-phosphoethanolamine (DOPE) or 1,2-distearoyl-sn-glycero-3-phosphocholine (DSPC); and/or the polyethylene-glycol (PEG)-lipid is DMG-PEG, optionally DMG-PEG2000. In some embodiments, the ionizable cationic lipid is 4A3-SC7; the neutral phospholipid is DOPE; and the polyethylene-glycol (PEG)-lipid is DMG-PEG.

In some embodiments, the LNP comprises a second cationic lipid, and the second cationic lipid is DODAP.

In some embodiments, the LNP comprises a second cationic lipid, and the second cationic lipid is 1,2-di-O-octadecenyl-3-trimethylammonium propane (DOTMA).

In some embodiments, the ionizable cationic lipid is 4A3-SC7, and the LNP comprises 4A3-SC7 at a molar percentage between 13% and 15%, between 13.5% and 15%, between 14% and 15%, between 14.5 and 15%, between 13% and 14.5%, between 13.5% and 14.5%, between 14% and 14.5%, between 13% and 14%, between 13.5% and 14% or between 13% and 13.5%.

In some embodiments, the LNP comprises PEG-lipid at a molar percentage between 2% and 8%, between 4% and 8%, between 6% and 8%, between 2% and 6%, between 4% and 6%, between 2% and 4%, between 2% and 3%, between 3% and 4%, between 2.5% and 3.5%, between 2.5% and 3% or between 3% and 3.5%.

In some embodiments, the PEG-lipid at a molar percentage of (about) 3%.

In some embodiments, the LNP comprises a neutral phospholipid and the neutral phospholipid is DOPE.

In some embodiments, the LNP comprises DOPE at a molar percentage between 10% and 25%, between 10% and 20%, between 10% and 15%, between 10% and 12.5%, between 15% and 25, between 15% and 20% or between 20% and 25%.

In some embodiments, the LNP comprises DOPE at a molar percentage of 11% or 22%.

In some embodiments, the LNP comprises a payload.

In some embodiments, the payload is a messenger RNA (mRNA).

In some embodiments, the mRNA comprises between 100 bases and 8 kilobases (kb).

In some embodiments, the mRNA comprises between 1 lkb and 8 kb, between 2 kb and 8 kb, between 3 kb and 8 kb, between 4 kb and 8 kb, between 5 kb and 8 kb, between 6 kb and 8 kb, between 7 kb and 8 kb, between 1 kb and 7 kb, between 2 kb and 7 kb, between 3 kb and 7 kb, between 4 kb and 7 kb, between 5 kb and 7 kb, or between 6 kb and 7 kb, between 1 kb and 6 kb, between 2 kb and 6 kb, between 3 kb and 6 kb, between 4 kb and 6 kb, or between 5 kb and 6 kb.

In some embodiments, the mRNA comprises (about) 2 kb.

In some embodiments, the mRNA comprises (about) 4.6 kb.

In some embodiments, the mRNA encodes a cystic fibrosis transmembrane conductance regulator (CFTR) protein.

In some embodiments, the mRNA encodes a dynein axonemal intermediate chain 1 (DNAI1) protein.

In some embodiments, the mRNA encodes a gene-editing system or components thereof.

In some embodiments, the mRNA encodes an shRNA or a microRNA.

In some embodiments, the LNP composition is a pharmaceutical composition.

In some embodiments, the LNP composition is an aerosolized composition.

In some embodiments, the LNP composition has an encapsulation efficiency of between 50% and 99%, between 60% and 99%, between 70% and 99%, between 80% and 99%, between 90% and 99%, between 95% and 99%, between 50% and 95%, between 60% and 95%, between 70% and 95%, between 80% and 95%, between 85% and 95%, or between 90% and 95%.

In some embodiments, the LNP is composition is substantively free of any anionic lipid, of any permanently cationic lipid, or of any anionic lipid and any any permanently cationic lipid. In some embodiments, the LNP is composition is substantively free of any ionizable cationic lipid.

1. Gene Editing Payload

The LNPs of the present disclosure can comprise one or more components for gene editing, such as, but not limited to, a guide RNA, a tracr RNA, a sgRNA, an mRNA encoding a gene or base editing protein, a zinc-finger nuclease (ZFN), a transcription activator-like effector nuclease (TALEN), a clustered regularly interspaced short palindromic repeats (CRISPR) nuclease (e.g., Cas9), a DNA template for gene editing, or a combination thereof. In some embodiments, the payload of the LNPs can be suitable for a genome editing technique. In some embodiments, the genome editing technique can be CRISPR or TALEN. In some embodiments, the LNPs can comprise one or more mRNAs, which can encode a gene editing or base editing protein. In some embodiments, the LNPs can comprises both a gene- or base-editing protein encoding mRNA and one or more guide RNAs. In some embodiments, the LNPs can comprise at least one nucleic acid suitable for a genome editing technique, such as a CRISPR RNA (crRNA), a trans-activating crRNA (tracrRNA), a guide RNA (gRNA), and a DNA repair template. In some embodiments, CRISPR nucleases can have altered activity, for example, modifying the nuclease so that it can be a nickase instead of making double-strand cuts or so that it can bind the sequence specified by the guide RNA but has no enzymatic activity. In some embodiments, the base editing protein can be a fusion protein comprising a deaminase domain and a sequence-specific DNA binding domain, such as an inactive CRISPR nuclease.

(a) Gene Editing Methods

The presently described LNPs or pharmaceutical composition can comprise a payload of any conventional gene editing methods. In some embodiments, gene editing components can be selectively delivered to the cells of target organ. In some embodiments, the target organ can be lungs. In some embodiments, the cells of target organ can be lung cells. In some embodiments, the cells can be ciliated cells, goblet cells, secretory cells, club cells, basal cells or ionocytes.

In some embodiments, the gene editing can be targeted editing. Targeted editing can be achieved either through a nuclease-independent approach or through a nuclease-dependent approach.

The nuclease-independent targeted editing, such as base-editing and/or prime editing, can involve precise modifications to DNA sequences without creating double-strand breaks. Homologous recombination can be guided by homologous sequences flanking an exogenous polynucleotide to be introduced into an endogenous sequence through the enzymatic machinery of the cells of target organ.

Base editing can allow for the conversion of one DNA base pair into another at a specific target site. In some embodiments, the nuclease can be a fusion of a deaminase enzyme to a modified Cas9 protein (dCas9) or other engineered Cas variants. In some embodiments, base editing can change C (cytosine) to T (thymine) or A (adenine) to G (guanine) in the endogenous DNA. A guide RNA can be designed to target the specific genomic location of interest in the cells of target organ.

Prime editing can allow for more complex and precise DNA modifications, including insertions, deletions, and all 12 possible base-to-base conversions (A, C, G, T) without double-strand breaks. A prime editing guide RNA, which can consist of a guide sequence and a template for the desired edit, can be designed. The prime editor protein (PE2), which can combine a reverse transcriptase and a Cas9 variant, can be guided to the target site by the prime editing guide RNA. The Cas9 variant can generate a single-strand break (nick) in the DNA. The reverse transcriptase then can use the prime editing guide RNA's template sequence to copy the desired changes into the nicked strand of DNA. Subsequently, the cellular repair machinery of the cells of target organ can repair the nick, incorporating the edited sequence, via homology-directed repair (HDR).

The nuclease-dependent approach can achieve targeted editing with higher frequency through the specific introduction of double strand breaks (DSBs) by specific rare-cutting nucleases (e.g., endonucleases). Such nuclease-dependent targeted editing can also utilize DNA repair mechanisms, for example, non-homologous end joining (NHEJ), which can occur in response to DSBs. In some embodiments, DNA repair by NHEJ can lead to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which can result in targeted integration of the exogenous genetic material. In some embodiments, a nuclease of the nuclease-dependent targeted editing can include, but not limited to, CRISPR-Cas9, CRISPR-Cas12 (Cpf1), CRISPR-Cas13, C2c2, C2c6, NgAgo, and/or TALEN.

Methods of using CRISPR-Cas gene editing technology to create a genomic deletion in a cell (e.g., to knock out a gene in a cell) are well-known techniques. See for example, Bauer et al., *J Vis Exp.* 95:e52118 (2015). Available endonucleases capable of introducing specific and targeted DSBs can include, but not limited to, ZFN, TALEN, and CRISPR/Cas9.

In some embodiments, targeted gene editing can be achieved via dual integrase cassette exchange (DICE) system utilizing phiC$_{31}$ and Bxb1 integrases.

i. (i) CRISPR-Cas9 Gene Editing System

The CRISPR-Cas9 system is a naturally occurring defense mechanism in prokaryotes that has been repurposed as an RNA-guided DNA-targeting platform used for gene editing. It can rely on the DNA nuclease Cas9, and two noncoding RNAs, crisprRNA (crRNA) and transactivating RNA (tracrRNA), to target the cleavage of DNA. CRISPR is a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA can be used by the prokaryote to detect and destroy similar foreign DNA upon re-introduction, for example, from similar viruses during subsequent attacks. Transcription of the CRISPR locus can result in the formation of an RNA molecule comprising the spacer sequence, which can associate with and target Cas (CRISPR-associated) proteins able to recognize and cut the foreign, exogenous DNA. Numerous types and classes of CRISPR/Cas systems have been described in e.g., Koonin et al., *Curr Opin Microbiol* 37:67-78 (2017).

crRNA can drive sequence recognition and specificity of the CRISPR-Cas9 complex through Watson-Crick base pairing typically with about 20 nucleotide sequence in the target DNA. Changing the sequence of the 5' 20 nucleotides in the crRNA can allow targeting of the CRISPR-Cas9 complex to specific loci. The CRISPR-Cas9 complex can only bind DNA sequences that contain a sequence match to the first 20 nucleotides of the crRNA, if the target sequence is followed by a specific short DNA motif (with the sequence NGG) referred to as a protospacer adjacent motif (PAM).

tracrRNA can hybridize with the 3' end of crRNA to form an RNA-duplex structure that can be bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, cells can use two main DNA repair pathways to repair the DSB: non-homologous end joining (NHEJ) and homology-directed repair (HDR). NHEJ is a repair mechanism that is highly active in the majority of cell types, including non-dividing cells. NHEJ can be error-prone and can often result in the removal or addition of between one and several hundred nucleotides at the site of the DSB, though such modifications can typically be less than 20 nucleotides. The resulting insertions and deletions (indels) can disrupt coding or noncoding regions of genes. Alternatively, HDR can use a long stretch of homologous donor DNA, provided endogenously or exogenously, to repair the DSB with high fidelity. HDR is active only in dividing cells and can occur at a relatively low frequency in most cell types.

ii. CRISPR Endonuclease

In some embodiments, Cas9 endonuclease can be used in a CRISPR method for genetically engineering cells of the target organ of the LNPs described herein. In some embodiments, Cas9 enzyme can be from *Streptococcus pyogenes*, although other Cas9 homologs can also be used. In some embodiments, the Cas9 enzyme can be wild-type Cas9. In some embodiments, the Cas9 enzyme can be a modified version of Cas9 (e.g., evolved versions of Cas9, or Cas9 orthologues or variants). In some embodiments, Cas9 can be substituted with another RNA-guided endonuclease, such as Cpf1 (class II CRISPR/Cas system).

In some embodiments, the CRISPR/Cas system can comprise components derived from a Type-I, Type-II, or Type-III system. In some embodiments, the CRISPR/Cas system can comprise components derived from Class 1 and Class 2 CRISPR/Cas systems, having Types I to V or Types II, V, and VI, respectively (Makarova et al., *Nat Rev Microbiol* 13(11):722-36 (2015); Shmakov et al., *Mol Cell* 60:385-397 (2015)).

Class 2 CRISPR/Cas systems can have single protein effectors. Cas proteins of Types II, V, and VI can be single-protein, RNA-guided endonucleases, herein called Class 2 Cas nucleases. Class 2 Cas nucleases can include, for example, but not limited to, Cas9, Cpf1, C2c1, C2c2, and C2c3 proteins. The Cpf1 nuclease is homologous to Cas9 and contains a RuvC-like nuclease domain.

In some embodiments, the Cas nuclease can be from a Type-II CRISPR/Cas system (e.g., a Cas9 protein from a CRISPR/Cas9 system). In some embodiments, the Cas nuclease can be from a Class 2 CRISPR/Cas system (a single-protein Cas nuclease, such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, which is further explained infra.

In some embodiments, a Cas nuclease can comprise more than one nuclease domain. In some embodiments, a Cas9 nuclease can comprise at least one RuvC-like nuclease domain (e.g., Cpf1) and at least one HNH-like nuclease domain (e.g., Cas9). In some embodiments, the Cas9 nuclease can introduce a DSB in the target sequence. In some embodiments, the Cas9 nuclease can be modified to contain only one functional nuclease domain. For example, the Cas9 nuclease can be modified such that one of the nuclease domains can be mutated or fully or partially deleted to reduce its nucleic acid cleavage activity. In some embodiments, the Cas9 nuclease can be modified to contain no functional RuvC-like nuclease domain. In other embodiments, the Cas9 nuclease can be modified to contain no functional HNH-like nuclease domain. In some embodiments in which only one of the nuclease domains can be functional, the Cas9 nuclease can be a nickase that can introduce a single-stranded break (nick) into the target sequence. In some embodiments, a conserved amino acid within a Cas9 nuclease domain can be substituted to reduce or alter a nuclease activity. In some embodiments, the Cas nuclease nickase can comprise an amino acid substitution in the RuvC-like nuclease domain. Exemplary amino acid substitutions in the RuvC-like nuclease domain can include D10A (based on the *S. pyogenes* Cas9 nuclease). In some embodiments, the nickase can comprise an amino acid substitution in the HNH-like nuclease domain. Exemplary amino acid substitutions in the HNH-like nuclease domain can include, but not limited to, E762A, H840A, N863A, H983A, and D986A (based on the *S. pyogenes* Cas9 nuclease).

In some embodiments, the Cas nuclease can be from a Type-I CRISPR/Cas system. In some embodiments, the Cas nuclease can be a component of the Cascade complex of a Type-I CRISPR/Cas system. For example, the Cas nuclease can be a Cas3 nuclease. In some embodiments, the Cas nuclease can be derived from a Type-III CRISPR/Cas system. In some embodiments, the Cas nuclease can be derived from Type-IV CRISPR/Cas system. In some embodiments, the Cas nuclease can be derived from a Type-V CRISPR/Cas system. In some embodiments, the Cas nuclease can be derived from a Type-VI CRISPR/Cas system.

A Type I CRISPR/Cas system can utilize a large effector complex known as Cascade (CRISPR-associated complex for antiviral defense) for target binding and interference. The Cascade complex can contain multiple Cas proteins, including Cas3, which can be responsible for the destruction of the target DNA. A Type II CRISPR/Cas system, particularly the CRISPR-Cas9 system, can utilize a single Cas9 protein, guided by a synthetic guide RNA (sgRNA), to introduce double-strand breaks in target DNA for subsequent repair or modification. A Type III CRISPR/Cas system can utilize a Csm (CRISPR-Cas subtype multiprotein) or Cmr (CRISPR-Cas subtype ribonucleoprotein) complex for interference. Type III CRISPR/Cas system can target RNA molecules in addition to DNA. A Type V CRISPR/Cas system, including Cpf1 (also known as Cas12) and C2c2 (also known as Cas13), can utilize a single effector protein to perform interference. A Type VI CRISPR/Cas system can utilize a single Cas protein, such as C2c2 (also known as Cas13), to target and cleave RNA molecules, making it useful for RNA editing and manipulation.

iii. Guide RNAs (gRNAs)

The CRISPR technology can involves the use of a genome-targeting nucleic acid that can direct one or more endonucleases to a specific target sequence within a target gene for gene editing at the specific target sequence. The genome-targeting nucleic acid can be an RNA. A genome-targeting RNA is referred to as a "guide RNA" or "gRNA" herein. A guide RNA can comprise at least one spacer sequence that can hybridize to a target nucleic acid sequence within a target gene for editing, and a CRISPR repeat sequence.

In Type II systems, the gRNA can also comprise a second RNA called the tracrRNA sequence. In the Type II gRNA, the CRISPR repeat sequence and tracrRNA sequence can hybridize to each other to form a duplex. In the Type V gRNA, the crRNA can form a duplex. In both systems, the duplex can bind a site-directed polypeptide, such that the guide RNA and site-direct polypeptide can form a complex. In some embodiments, the genome-targeting nucleic acid can provide target specificity to the complex by virtue of its association with the site-directed polypeptide. The genome-targeting nucleic acid can thus direct the activity of the site-directed polypeptide.

As is understood by the person of ordinary skill in the art, each guide RNA can be designed to include a spacer sequence complementary to its genomic target sequence.

See Jinek et al., Science 337:816-821 (2012); Deltcheva et al., Nature 471:602-607 (2011).

In some embodiments, the genome-targeting nucleic acid (e.g., gRNA) can be a double-stranded guide RNA, comprising two strands of RNA molecules. The first strand can comprise in the 5' to 3' direction, an optional spacer extension sequence, a spacer sequence, and a minimum CRISPR repeat sequence. The second strand can comprise a minimum tracrRNA sequence (complementary to the minimum CRISPR repeat sequence), a 3' tracrRNA sequence, and an optional tracrRNA extension sequence.

In some embodiments, the genome-targeting nucleic acid (e.g., gRNA) can be a single-molecule guide RNA (sgRNA). sgRNA in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence, and an optional tracrRNA extension sequence. The optional tracrRNA extension can comprise elements that can contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins. A single-molecule guide RNA in a Type V system can comprise, in the 5' to 3' direction, a minimum CRISPR repeat sequence and a spacer sequence.

A spacer sequence in a gRNA is a sequence (e.g., a 20-nucleotide sequence) that can define the target sequence (e.g., a DNA target sequences, such as a genomic target sequence) of a target gene of interest (e.g., DNAI1 or CFTR). In some embodiments, the spacer sequence can range from 15 to 30 nucleotides. For example, the spacer sequence can contain 15, 16, 17, 18, 19, 29, 21, 22, 23, 24, 25, 26, 27, 28, 29, or 30 nucleotides. In some embodiments, a spacer sequence can contain 20 nucleotides.

The target sequence is in a target gene (e.g., DNAI1 or CFTR) that can be adjacent to a PAM sequence and can be the sequence to be modified by an RNA-guided nuclease (e.g., Cas9). The target sequence is on the PAM strand in a target nucleic acid, which is a double-stranded molecule containing the PAM strand and a complementary non-PAM strand. One of skill in the art recognizes that the gRNA spacer sequence can hybridize to the complementary sequence located in the non-PAM strand of the target nucleic acid of interest. Thus, the gRNA spacer sequence can be the RNA equivalent of the target sequence. The spacer of a gRNA can interact with a target nucleic acid of interest in a sequence-specific manner via hybridization (i.e., base pairing). The nucleotide sequence of the spacer thus can vary depending on the target sequence of the target nucleic acid of interest.

In a CRISPR/Cas system, the spacer sequence can be designed to hybridize to a region of the target nucleic acid that is located 5' of a PAM recognizable by a Cas9 enzyme used in the system. The spacer can perfectly match the target sequence or can have mismatches. Each Cas9 enzyme can have a particular PAM sequence that it can recognize in a target DNA. For example, *S. pyogenes* can recognize in a target nucleic acid a PAM that comprises the sequence 5'—NRG-3', where R can comprise either A or G, where N can be any nucleotide and N can be immediately 3' of the target nucleic acid sequence targeted by the spacer sequence.

In some embodiments, the target nucleic acid sequence can have about 20 nucleotides in length. In some embodiments, the target nucleic acid can have less than about 20 nucleotides in length. In some embodiments, the target nucleic acid can have more than about 20 nucleotides in length. In some embodiments, the target nucleic acid can have at least 5, 10, 15, 16, 17, 18, 19, 20, 21, 22, 23, 24, 25, 30 or more nucleotides in length. In some embodiments, the target nucleic acid can have at most 5, 10, 15, 16, 17, 18, 19, 20, 21, 22, 23, 24, 25, 30 or more nucleotides in length. In some embodiments, the target nucleic acid sequence can have 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence can be the S. pyogenes PAM.

The guide RNA can target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene can be 100% complementary. In other embodiments, the spacer sequence of the guide RNA and the target sequence in the target gene can contain up to 10 mismatches, e.g., up to 9, up to 8, up to 7, up to 6, up to 5, up to 4, up to 3, up to 2, or up to 1 mismatch.

The length of the spacer sequence in gRNAs can depend on the CRISPR/Cas9 system and components used for editing any of the target genes (e.g., DNAI1 or CFTR). For example, different Cas9 proteins from different bacterial species can have varying optimal spacer sequence lengths. Accordingly, the spacer sequence can have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence can have 18-24 nucleotides in length. In some embodiments, the targeting sequence can have 19-21 nucleotides in length. In some embodiments, the spacer sequence can comprise 20 nucleotides in length.

In some embodiments, the gRNA can be an sgRNA, which can comprise a 20-nucleotide spacer sequence at the 5' end of the sgRNA sequence. In some embodiments, the sgRNA can comprise a less than 20 nucleotide spacer sequence at the 5' end of the sgRNA sequence. In some embodiments, the sgRNA can comprise a more than 20 nucleotide spacer sequence at the 5' end of the sgRNA sequence. In some embodiments, the sgRNA can comprise a variable length spacer sequence with about 17-30 nucleotides at the 5' end of the sgRNA sequence.

In some embodiments, the gRNAs can comprise unmodified ribonucleic acid. In some embodiments, the gRNAs can comprise modified ribonucleic acid. Various types of RNA modifications can be introduced during or after chemical synthesis and/or enzymatic generation of RNAs, e.g., modifications that can enhance stability, reduce the likelihood or degree of innate immune response, and/or enhance other attributes, as described in the art. In some embodiments, non-natural modified nucleobases can be introduced into any of the gRNAs during synthesis or post-synthesis. In some embodiments, modifications can be on internucleoside linkages, purine or pyrimidine bases, or sugar. In some embodiments, a modification can be introduced at the terminal of a gRNA with chemical synthesis or with a polymerase enzyme.

In some embodiments, more than one guide RNAs can be used with a CRISPR/Cas nuclease system. Each guide RNA can contain a different targeting sequence, such that the CRISPR/Cas system can cleave more than one target nucleic acid. In some embodiments, one or more guide RNAs can have the same or differing properties, such as activity or stability within the Cas9 RNP complex. Where more than one guide RNA can be used, each guide RNA can be encoded on the same or on different vectors. The promoters used to drive expression of the more than one guide RNA can be the same or different.

In some embodiments, enzymatic or chemical ligation methods can be used to conjugate polynucleotides or their regions with different functional moieties, such as targeting or delivery agents, fluorescent labels, liquids, nanoparticles, and the like.

In some embodiments, the CRISPR/Cas nuclease system can contain multiple gRNAs, for example, 2, 3, or 4 gRNAs. Such multiple gRNAs can target different sites in a same target gene. Alternatively, the multiple gRNAs can target different genes. In some embodiments, the guide RNA(s) and the Cas protein can form a ribonucleoprotein (RNP), e.g., a CRISPR/Cas complex. The guide RNAs can guide the Cas protein to a target sequence(s) on one or more target genes (e.g., DNAI1 and CFTR), where the Cas protein can cleave the target gene at the target site. In some embodiments, the CRISPR/Cas complex can be a Cpf1/guide RNA complex. In some embodiments, the CRISPR complex can be a Type-II CRISPR/Cas9 complex. In some embodiments, the Cas protein can be a Cas9 protein. In some embodiments, the CRISPR/Cas9 complex can be a Cas9/guide RNA complex.

In some embodiments, the indel frequency (editing frequency) of a particular CRISPR/Cas nuclease system, comprising one or more specific gRNAs, can be determined using a TIDE analysis, which can be used to identify highly efficient gRNA molecules for editing a target gene. In some embodiments, a highly efficient gRNA can yield a gene editing frequency of higher than 80%. For example, a gRNA can be considered to be highly efficient if it can yield a gene editing frequency of at least 80%, at least 85%, at least 90%, at least 95%, or 100%.

iv. Other Gene Editing Methods

Besides the CRISPR system disclosed herein, additional gene editing systems as known in the art can also be used as a payload of the LNPs described herein. In some embodiments, the additional gene editing system can comprise zinc finger nuclease (ZFN), transcription activator-like effector nucleases (TALEN), restriction endonucleases, meganucleases homing endonucleases, or the like.

ZFNs are targeted nucleases comprising a nuclease fused to a zinc finger DNA binding domain (ZFBD), which can be a polypeptide domain that can bind DNA in a sequence-specific manner through one or more zinc fingers. A zinc finger can be a domain of about 30 amino acids within the zinc finger binding domain whose structure can be stabilized through coordination of a zinc ion. Examples of zinc fingers include, but not limited to, $C_2H2$ zinc fingers, $C_3H$ zinc fingers, and $C_4$ zinc fingers. A designed zinc finger domain can be a domain not occurring in nature whose design/composition results principally from rational criteria, e.g., application of substitution rules and computerized algorithms for processing information in a database storing information of existing ZFP designs and binding data. A selected zinc finger domain can be a domain not found in nature whose production can result primarily from an empirical process such as phage display, interaction trap or hybrid selection. In some embodiments, a ZFN can be a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins can be secreted by plant pathogens of the genus *Xanthomonas* during infection. These proteins can enter the nucleus of the plant cell, bind effector-specific DNA sequences via their DNA binding domain, and activate gene transcription at these sequences via their transactivation domains. TAL effector DNA binding domain specificity can depend on an effector-variable number of imperfect 34 amino acid repeats, which can comprise polymorphisms at select repeat positions called repeat variable-diresidues (RVD). In some embodiments, a TALEN can be a fusion polypeptide of the FokI nuclease to a TAL effector DNA binding domain.

Additional examples of targeted nucleases suitable for use can include, but not limited to, Bxb1, phiC$_{31}$, PhiBT1, and Wβ/SPBc/TP901-1, whether used individually or in combination. The Bxb1 nuclease, also known as the Bxb1 integrase, is a site-specific recombinase enzyme derived from the mycobacteriophage Bxb1. The Bxb1 integrase can catalyze site-specific recombination between two specific DNA sequences, referred to as attachment (att) sites. The Bxb1 integrase can recognize a specific 48 base-pair sequence within the attachment sites. The phiC$_{31}$ nuclease, also known as the phiC$_{31}$ integrase, is derived from the bacteriophage phiC$_{31}$. The phiC$_{31}$ nuclease can catalyze site-specific recombination between two specific DNA sequences, referred to as attB (attachment site in bacteriophage) and attP (attachment site in the phage). The phiC$_{31}$ nuclease can promote integration of a DNA fragment flanked by attB and attP into the genome in cells of target organ. The phiBTI nuclease can integrate into a different attachment site than phiC$_{31}$. The Wβ/SPBc/TP901-1 nuclease, also known as bacteriophage P2 Bxb1 Cre nuclease, is a site-specific recombination enzyme derived from the temperate bacteriophage P2.

G. Physical Properties and Characteristics of LNPs

The present disclosure relates, in part, aerosolized pharmaceutical compositions having aerosol particles of lipid nanoparticles (LNPs). In some embodiments, the LNPs can be delivered to a tracheobronchial region of a subject. In some embodiments, the LNPs have one or more of the following: an encapsulation efficiency (EE) greater than 50%; an mRNA integrity of greater than 50%; a diameter from 20 nm to 600 nm; and a polydispersity of less than 0.6.

1. Encapsulation Efficiency

Encapsulation efficiency (EE) refers the fraction of a payload that is encapsulated within or otherwise incorporated into a lipid nanoparticle composition when LNPs are formed. Encapsulation efficiency may be determined by comparing the amount of input payload to the amount of payload encapsulated in a sample of LNPs, or by comparing the amount of payload in the LNPs to the free excess payload not encapsulated in the sample. In some embodiments, a fluorescence detection assay (e.g., RiboGreen™) is used to determine encapsulation efficiency by measuring the free RNA in a sample with intact LNPs with the total RNA is a sample treated to disrupt the LNPs.

Encapsulation refers to the process of confining a payload within an LNP. In some embodiments, encapsulation refers to confining one or more mRNA molecules within an LNP. In some embodiments, the payload can be captured in the lipid portion of the LNP or an aqueous space enveloped by some or all of the lipid component of the LNP. In some embodiments, the payload can be encased within a lipid mono- or bi-layer envelop. In some embodiments, the payload can be intercalated in-between lipid components. In some embodiments, the payload can be encased within an aqueous core of the LNP.

In some embodiments, the LNPs are formed with an average encapsulation efficiency ranging from about 50% to about 100%. In some embodiments, the LNPs are formed with an average encapsulation efficiency ranging from about 50% to about 70%. In some embodiments, the LNPs are formed with an average encapsulation efficiency ranging from about 70% to about 90%. In some embodiments, the LNPs are formed with an average encapsulation efficiency ranging from about 90% to about 100%. In some embodiments, the LNPs are formed with an average encapsulation efficiency ranging from about 75% to about 95%.

In various embodiments, the LNPs have an encapsulation efficiency of greater than 50%. For example, the EE of the LNPs is greater than 50%, 55%, 60%, 65%, 70%, 75%, 80%, 85%, 90%, 95%, 96%, 97%, 98%, 99%, or 100%. In other embodiments, the LNPs have an EE of 50-95%, of 60-95%, of 70-95%, of 80-95%, or of 90-95%. In some embodiments, the LNPs have an EE of 91%, 92%, 93%, 94% or 95%. In some embodiments, the LNPs have an EE of 95%.

In various embodiments, the present disclosure provides a composition having a polynucleotide (e.g., an mRNA molecule) incorporated into the LNPs described herein. In some embodiments, mRNA molecules are incorporated into the majority of the LNPs. In some embodiments, greater than about 50%, 55%, 60%, 65%, 70%, 75%, 80%, 85%, 90%, or 95%, of the mRNA molecules are incorporated into the LNPs. In some embodiments, at least 70% of total mRNA molecules encoding CFTR are incorporated into the composition. In various embodiments, at least 70% of total mRNA molecules encoding DNAI1 are incorporated into the LNP composition.

2. mRNA Integrity mRNA integrity can refer to the quality of mRNA. In some embodiments, mRNA integrity refers to the percentage of mRNA that is not degraded after e.g., a purification process. In some embodiments, mRNA integrity refers to the quality of the mRNAs within the LNPs after nebulization.

mRNA integrity may be determined by any of the methods well known in the art, for example, by RNA agarose gel electrophoresis (e.g., Ausubel et al., John Wiley & Sons, Inc., 1997, Current Protocols in Molecular Biology). The gels can be analyzed to determine whether the banding pattern and apparent nucleotide length is consistent with an analytical reference standard. Additional methods to assess RNA integrity include, for example, assessment of the purified mRNA using capillary gel electrophoresis (CGE).

In some embodiments, mRNA integrity is measured via a multiplexed capillary electrophoresis (CE), e.g., using an Agilent Advanced Analytical 5200 Fragment Analyzer. The electropherograms can be analyzed with e.g., ProSize Data Analysis software using smear analysis to quantify mRNA transcript integrity.

In some embodiments, at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% of the mRNA products are full-length.

In various embodiments, the LNPs described herein have an mRNA integrity greater than 50%, 55%, 60%, 70%, 75%, 80%, 85%, 90%, 91%, 92%, 93%, 94%, 95%, 96%, 97%, 98%, or 99%. In other embodiments, the LNPs have an mRNA integrity of 75-99%, of 80-95%, of 85-90%, or of 90-95%.

3. LNP Diameter

In various embodiments, the LNPs have a diameter of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, the LNPs have a diameter of about 80 to 150 nm. In some embodiments, the LNPs have a diameter of about 20 to 600 nm, about 40 to 600 nm, about 60 to 600 nm, about 80 to 600 nm, about 100 to 600 nm, or 150 to 600 nm, or 200 to 600 nm, or 250 to 600 nm, or 300 to 600 nm, or 350 to 600 nm.

In various embodiments, the LNPs have a diameter of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, the LNPs have a diameter of about 80 to 150 nm. In some embodiments, the LNPs have a diameter of about 20 to 400 nm, about 40 to 400 nm, about 60 to 400 nm, about 80 to 400 nm, about 100 to 400 nm, or 150 to 400 nm, or 200 to 400 nm, or 250 to 400 nm, or 300 to 400 nm, or 350 to 400 nm.

In some embodiments, the LNPs have a size distribution in which the mean size (e.g., diameter) is about 70 nm to about 200 nm, and more typically the mean size is about 100 nm or less. In some embodiments, the LNPs have a diameter of 50-90 nm.

In various embodiments, the LNPs have a diameter of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, the LNPs have a size distribution in which the mean size (e.g., diameter) is about 70 nm to about 200 nm, and more typically the mean size is about 100 nm or less.

In some embodiments, the LNPs have a diameter of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, the LNPs have an average size of about 150 nm or less, e.g., between 75 nm and 150 nm, in particular between 100 nm and 150 nm.

In various embodiments, the LNPs have a diameter of 20 to 180 nm, 30 to 180 nm, 40 to 180 nm, 50 to 180 nm, 60 to 180 nm, 70 to 180 nm, 80 to 180 nm, 90 to 180 nm, 100 to 180 nm, or 50 nm, 60 nm, 70 nm, 80 nm, 90 nm, 100 nm, 120 nm, 140 nm, 160 nm, or 180 nm, post-nebulization.

In some embodiments, the LNPs have a diameter of 100 to 400 nm, 120 to 400 nm, 140 to 400 nm, 160 to 400 nm, 180 to 400 nm, 200 to 400 nm, 220 to 400 nm, 240 to 400 nm, 260 to 400 nm, 280 to 400 nm, 300 to 400 nm, 320 to 400 nm, 340 to 400 nm, 360 to 400, or 380 to 400 nm.

In various embodiments, the diameter of the LNPs is determined by various techniques known in the art, including, but not limited to, dynamic light scattering (DLS).

4. Polydispersity Index (PDI)

In some embodiments, the LNPs are characterized as having a polydispersity (or polydispersity index) of less than 0.5. In various embodiments, the LNPs have a polydispersity of less than 0.5. The polydispersity index (PDI) is the standard deviation of the LNP diameter distribution divided by the mean LNP diameter. The PDI is often used as an indication of the quality of the LNP with respect to the size distribution.

In various embodiments, dynamic light scattering (DLS) can be used to characterize the polydispersity index and size of the LNPs of the present disclosure. DLS measures the scattering of light that results from subjecting a sample to a light source. PDI, as determined from DLS measurements, represents the distribution of LNP size (at or around the mean LNP diameter) in a population, with a perfectly uniform population of LNPs having a PDI of zero.

In various embodiments, the LNPs have a polydispersity of less than 0.5, less than 0.4, less than 0.3, less than 0.2, or less than 0.1. In some embodiments, the LNPs have a polydispersity of 0.5. In some embodiments, the LNPs have a polydispersity of 0.4. In some embodiments, the LNPs have a polydispersity of 0.3. In some embodiments, the LNPs have a polydispersity of 0.2. In some embodiments, the LNPs have a polydispersity of 0.1.

H. Physical Properties and Characteristics of Aerosol Particles

The present disclosure relates, in part, aerosolized pharmaceutical compositions having aerosol particles of lipid nanoparticles (LNPs). In some embodiments, the LNPs can be delivered to a tracheobronchial region of a subject. In some embodiments, the aerosol particles of the present disclosure have one or more of following characteristics: a mass median aerodynamic diameter (MMAD) between 1 μm to 10 μm, a geometric standard deviation (GSD) from 1 to 5, and a fine particle fraction (FPF) percent of at least 50%.

1. Mass Median Aerodynamic Diameter (MMAD)

The size distribution of aerosol particles in an aerosol can be measured by determining the mass median aerodynamic diameter (MMAD) thereof. The MMAD of an aerosol is the median of the diameter of the aerosol particles in the aerosol. In some embodiments, the MMAD is measured usign a next generation impactor (NGI). As described herein, the MMAD of an aerosol may affect where in the lung the aerosol is deposited when administered to a subject.

Without being bound by theory, aerosols having a mass median aerodynamic diameter (MMAD) of 5-10 μm may be deposited mainly in the large conducting airways and oropharyngeal region. Aerosol particles with a 1-5 μm MMAD range may be deposited mainly in the small pulmonary airways and alveoli, whereas more than 50% of the aerosol particles with 3 μm MMAD may be deposited in the alveolar region. In the case of employing the pulmonary route for systemic drug delivery, aerosols with a small average particle size are required to ensure peripheral penetration of the drug.

In some embodiments, the calculation of MMAD is in accordance with USP chapter <601>. In some embodiments, the diameter at which 50% of the aerosol particles by mass are larger and 50% are smaller. In some embodiments, an intercept of the line drawn on the lognormal distribution plot, and the line is determined by using the entire distribution focusing more on points with majority of the mass.

Upon nebulization, the aerosolized pharmaceutical composition comprises aerosol particles of the pharmaceutical composition. Aerosol particles refer to particles of a solution (or solid) that has been nebulized. Each aerosol particle may comprise a quantity of LNPs suspended in a solution (or solid). The size of an LNP is substantially smaller than the size of an aerosol particle. The aerosolized pharmaceutical composition can be characterized by a number of parameters, including the particle size of the aerosol (e.g., diameter), for example, by measuring the mass median aerodynamic diameter or fine particle fraction associated with the aerosol particles of the aerosolized pharmaceutical composition. MMAD may be determined by impactor measurements, e.g., the Anderson Cascade Impactor (ACI) or the Next Generation Impactor (NGI).

In some embodiments, the aerosol particles have an MMAD from 1 μm to 9 μm, from 1 μm to 8 μm, from 1 μm to 7 μm, from 1 μm to 6 μm, from 1 μm to 5 μm, from 1 μm to 4 μm, from 1 μm to 3 μm, from 1 μm to 2 μm, or from 3 μm to 5 μm. In various embodiments, the aerosol particles have an MMAD from 1 μm to 9 μm, or from 1 μm to 8 μm, or from 1 μm to 7 μm, or from 1 μm to 6 μm, or from 1 μm to 5 μm, or from 1 μm to 4 μm, or from 1 μm to 3 μm, or from 1 μm to 2 μm, or from 3 μm to 5 μm post nebulization.

2. Geometric Standard Deviation (GSD)

The uniformity of a particle size distribution of an aerosol (such as the aerosolized pharmaceutical compositions of the present disclosure) can be quantified as the geometric standard deviation (GSD) of the particle size of the aerosol particles. GSD is a measure of the variability of the aerosol particle diameters. The GSD of an aerosol can be calculated as the square root of the ratio of the observed droplet size at the $84^{th}$ percentile divided by the observed droplet size at the $16^{th}$ percentile on a cumulative percent mass undersize distribution. Low GSDs reflect a narrow droplet size distribution (i.e., homogeneously sized droplets), which may be advantageous for targeting aerosol to the respiratory system.

Monodispersity and polydispersity relate to the uniformity of the particle size distribution of the aerosol. The lower the GSD of an aerosol, the more monodispersed the particle size distribution is. Similarly, the higher the GSD is of an aerosol, the more polydispersed the particle size distribution is. For example, monodispersed particle size distributions typically include aerosols having a GSD of about 2 or less, and polydispersed particle size distributions typically include aerosols having a GSD of about 3 or more.

In various embodiments, the aerosol particles have a GSD from 1 to 4, from 1 to 3, or from 1 to 2, or 1, 1.5, 2, 2.5, or 3. In various embodiments, the aerosol particles have a GSD from 1 to 4, or from 1 to 3, or from 1 to 2, or 1, 1.5, 2, 2.5, or 3 after nebulization.

In other embodiments, the GSD is determined by the formula provided below:

$$GSD = \sqrt{\frac{D_{84}}{D_{16}}}$$

In some embodiments, $D_{16}$ (Probit=−1) is the diameter at which 84% of the particles by mass are larger and 16% are smaller. In some embodiments, $D_{84}$ (Probit=1) is the diameter at which 16% of the particles by mass are larger and 84% are smaller. An intercept of the line drawn on the log-normal distribution plot and the line is determined using the entire distribution flanking the Probit=1.

The average droplet size of the aerosolized pharmaceutical compositions provided herein, may be less than about 5 m, or about 1 m to about 5 m. Aerosolized pharmaceutical composition may have a GSD in a range of 1.0 to 2.2, or about 1.0 to about 2.2, or 1.5 to 2.2, or about 1.5 to about 2.2.

3. Fine Particle Fraction

The fine particle fraction (FPF) represents the mass percentage of aerosol particles with an aerodynamic diameter below 5 m and is used for in vitro assessment of the aerodynamic properties of aerosols. In some embodiments, FPF represents the mass percentage of LNPs with an aerodynamic diameter below 5 m. In some embodiments, the FPF is used for an in vitro assessment of the aerodynamic properties of aerosols.

In some embodiments, a fine particle dose (FPD) is determined as the collective mass of the drug (e.g., polynucleotide payload) that is ≤5.0 μm in size, by measuring the amount of the drug (e.g., polynucleotide payload) collected on all stages with an equivalent circular diameter (ECD) of ≤5.0 μm.

In various embodiments, the aerosol particles of the present disclosure have a fine particle fraction of 55%, of 60%, of 70%, of 75%, of 80%, of 85%, or of 90%. In various embodiments, the aerosol particles of the disclosure have a fine particle fraction of 55%, of 60%, of 70%, of 75%, of 80%, of 85%, or of 90% after nebulization.

III. Methods of the Disclosure

In one aspect, the present disclosure provides a method of treating a lung disease or lung disorder in a subject the method comprising administering the aerosolized pharmaceutical composition described herein. The present disclosure provides, among other things, methods and compositions of treating cystic fibrosis comprising administering to a subject an aerosolized LNP composition comprising an mRNA encoding a Cystic Fibrosis Transmembrane conductance Regulator (CFTR) protein. In other embodiments, the present disclosure provides methods and compositions for treating primary ciliary dyskinesia (PCD) comprising administering to a subject an aerosolized LNP composition comprising an mRNA encoding dynein axonemal intermediate chain 1 (DNAI1) protein.

Cystic fibrosis, also known as mucoviscidosis, is an autosomal recessive genetic disorder that affects most critically the lungs, and also the pancreas, liver, and intestine (Gibson et al., Am J Respir Crit Care Med. (2003) 168(8): 918-951; Ratjen et al., Lancet Lond Engl. (2003) 361(9358): 681-689; O'Sullivan et al., Lancet Lond Engl. (2009) 373 (9678):1891-1904). Cystic fibrosis is caused by mutations in the gene encoding for the Cystic Fibrosis Transmembrane conductance Regulator (CFTR) protein. This protein functions as a channel that transports chloride ions across the membrane of cells and is required to regulate the components of mucus, sweat, saliva, tears, and digestive enzymes. Disease-causing mutations in the CFTR protein cause dysfunction of its channel activity resulting in abnormal transport of chloride and sodium ions across the epithelium, leading to the thick, viscous secretions in the lung, pancreas, and other organs (O'Sulliven et al., Lancet Lond Engl. (2009) 373(9678):1891-1904; Rowe et al., N Engl J Med. (2005) 352(19):1992-2001). Most CF patients develop severe, chronic lung disease related to airway obstruction partly due to increased levels of sulfated mucins, inflammation, and recurrent infections that are eventually lethal; the median predicted survival age in the US is 40.7 years. Cystic fibrosis is the most frequent lethal genetic disease in the white population.

The lungs of individuals with CF are colonized and infected by bacteria from an early age. This leads to chronic airway infection and inflammation, progressing to bronchiectasis, gas trapping, hypoxemia, and hypercarbia. Pulmonary insufficiency is responsible for 68.1% of CF-related deaths in the US. In the initial stage, common bacteria such as *Staphylococcus aureus* and *Hemophilus influenzae* colonize and infect the lungs. Eventually, *Pseudomonas aeruginosa* (and sometimes *Burkholderia cepacia*) dominates. By 18 years of age, 80% of patients with classic CF harbor *P.*

*aeruginosa*, and 3.5% harbor *B. cepacia*. Once within the lungs, these bacteria adapt to the environment and develop resistance to commonly used antibiotics.

Primary ciliary dyskinesia (PCD) is an auto recessive disorder characterized by abnormal cilia and flagella that are found in the linings of the airway, the reproductive system, and other organs and tissues. PCD occurs in approximately 1 in 16,000. Symptoms are present as early as at birth, with breathing problems, and the affected individuals develop frequent respiratory tract infections beginning in early childhood. People with PCD also have year-round nasal congestion and chronic cough. Chronic respiratory tract infections can result in condition called bronchiectasis, which damages the passages, called bronchi, and can cause life-threatening breathing problems. Some individuals with PCD also have infertility, recurrent ear infections, abnormally placed organs within their chest and abdomen.

Among several genes confirmed to be directly involved in PCD pathogenesis, a significant number of mutations are found in two genes: DNAI1 and DNAH5, encoding intermediate and heavy chains of the axonemal dynein, respectively. Mutations in other genes, coding for proteins involved in the axonemal ultrastructure (DNAH11, DNAI2, TXNDC3, RSPH9, RSPH4A) or assembly (KTU, CRRC50), also have been reported, as well as mutations in the RPGR gene in certain cases of PCD. Mutations in DNAI1 and DNAH5, both associated with a ciliary outer dynein arm (ODA) defect phenotype, are collectively estimated to account for almost 40% of PCD cases.

A. Treatment Methods

In some embodiments, a patient in need of treatment is a male or female of 2 years or older, of 3 years or older, of 6 years or older, of 7 years or older, of 12 years or older, of 13 years or older, of 18 years or older, of 19 years or older, of 25 years or older, of 25 years or older, of 30 years or older, of 35 years or older, of 40 years or older, of 45 years or older, or of 50 years or older. In some embodiments, a patient in need of treatment is less than 50 years old, less than 45 years old, less than 40 years old, less than 35 years old, less than 30 years old, less than 25 years old, less than 20 years old, less than 19 years old, less than 18 years old, less than 13 years old, less than 12 years old, less than 7 years old, less than 6 years old, less than 3 years old, or less than 2 years old. In some embodiments, a patient in need of treatment is a male or female from 2 to 18 years old, from 2 to 12 years old, from 2 to 6 years old, from 6 to 12 years old, from 6 to 18 years old, from 12 to 16 years old, from 2 to 50 years old, from 6 to 50 years old, from 12 to 50 years old, or from 18 to 50 years old. In some embodiments, a patient in need of treatment is a female who is pregnant or who may become pregnant.

Patients with CF have more chloride in their sweat than people who do not have CF. For a child who has CF, the sweat chloride test results will confirm the diagnosis by showing a high chloride level. A baby must sweat enough to do the test. Full-term babies usually produce enough sweat by 2 weeks of age. Thus, In some embodiments, a patient in need of treatment has a sweat chloride value of ≥60 mmol/L, ≥65 mmol/L, ≥70 mmol/L, ≥75 mmol/L, ≥80 mmol/L, ≥85 mmol/L, ≥90 mmol/L, ≥95 mmol/L, ≥100 mmol/L, ≥110 mmol/L, ≥120 mmol/L, ≥130 mmol/L, ≥140 mmol/L or ≥150 mmol/L by quantitative pilocarpine iontophoresis (documented in the subject's medical record). In some embodiments, a patient in need of treatment has chronic sinopulmonary disease and/or gastrointestinal/nutritional abnormalities consistent with CF disease.

In some embodiments, forced expiratory volume in 1 second ($FEV_1$) is an established marker of cystic fibrosis (CF) disease progression that is used to capture clinical course and evaluate therapeutic efficacy. Thus, in various embodiments a patient in need of treatment has $FEV_1 \geq 50\%$ and ≤90% (e.g., ≤85%, ≤80%, ≤75%, ≤70%, ≤65%, ≤60%, or ≤55%) of the predicted normal (i.e., the average FEV of non-CF patients) based on the patient's age, gender, and height. In some embodiments, a patient in need of treatment has resting oxygen saturation ≥92% on room air (pulse oximetry). In some embodiments, a patient in need of treatment has a body mass index ≥17.5 kg/m² and weight ≥40 kg.

In some embodiments, any of the CF treatment methods disclosed herein results in the production of CFTR protein in the subject. In some embodiments, any of the PCD treatment methods disclosed herein results in the production of DNAI1 protein in the subject. In some embodiments, any of the treatment methods disclosed herein results in an increase of CFTR protein or DNAI1 protein in the subject of at least about 2-fold, at least about 3-fold, at least about 4-fold, at least about 5-fold, at least about 10-fold, at least about 15-fold, at least about 20-fold, or at least about 25-fold compared to baseline.

In some embodiments, the increase in CFTR protein or DNAI1 protein is detectable within about 6 hours, 8 hours, 12 hours, 24 hours, 36 hours, or 48 hours of administration of the pharmaceutical composition. In some embodiments, the increase in the CFTR protein is detectable by qPCR on RNA purified from tissue samples. In some embodiments, the increase in the DNAI1 protein is detectable by qPCR on RNA purified from tissue samples.

In some embodiments, a patient in need of treatment has received or is concurrently receiving other lung disease medications. For example, a patient in need of treatment may be receiving lumacaftor/ivacaftor combination drug (ORKAMBI®) or may have been on this treatment for at least 28 days prior to commencement of the treatment according to the present disclosure. The structures of lumacaftor and ivacaftor are provided below:

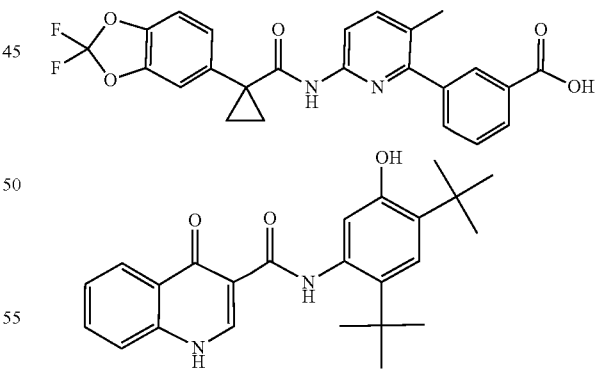

Other CF medications may include, but are not limited to, routine inhaled therapies directed at airway clearance and management of respiratory infections, such as bronchodilators, rhDNase (PULMOZYME® (Dornase alfa)), hypertonic saline, antibiotics, and steroids; and other routine CF-related therapies such as systemic antibiotics, pancreatic enzymes, multivitamins, and diabetes and liver medications.

Specifically, a method of treatment consists of (1) providing: a) a nebulizer, and b) a container including the LNP formulation for aerosolization in a pharmaceutically acceptable carrier, and (2) administering the LNP formulation using the nebulizer. In some embodiments, the volume of the LNP formulation in the container has a volume of (about) 10 mL, 9 mL, 8 mL, 7 mL, 6 mL, 5 mL, 4 mL, 3 mL, 2 mL, or 1 mL. In some embodiments, formulations and compositions generally include a pharmaceutically acceptable carrier. The carrier is preferably a liquid carrier. Further, the carrier preferably includes water and may include other components. In some embodiments, the composition including the LNP formulation is stored in an ampule, a vial, or a single-use vial prior to administrating. In some embodiments, the composition is stored in a single-use vial prior to administering.

In some embodiments, the administration of the aerosolized pharmaceutical composition of the present disclosure results in the expression of a protein (e.g., CFTR or DNAI1) in a lung of the subject. In still other embodiments, administration of the aerosolized pharmaceutical composition of the present disclosure results in detection of a protein (e.g., CFTR or DNAI1) in a lung of the subject between 6 and 12 hours after delivery to the subject. In some embodiments, detection of the protein in the lung is at 6 hours, 7 hours, 8 hours, 9 hours, 10 hours, 11 hours or 12 hours. In various embodiments, the protein (e.g., CFTR or DNAI1) may be detected using any of the known techniques in the art, including but not limited to Western blot analysis.

In some embodiments, an mRNA delivered according to the present disclosure results in increased protein level or activity an upper airway, a central airway, or peripheral airway of a lung of the subject by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the disclosure, or a historical reference level).

In some embodiments, a CFTR mRNA delivered according to the present disclosure results in increased CFTR protein level or activity an upper airway, a central airway, or peripheral airway of a lung of the subject by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the disclosure, or a historical reference level).

In some embodiments, a DNAI mRNA delivered according to the present disclosure results in increased DNAI protein level or activity an upper airway, a central airway, or peripheral airway of a lung of the subject by, e.g., at least approximately 10%, 20%, 30%, 40%, 50%, 60%, 70%, 80%, 90%, 1-fold, 2-fold, 3-fold, 4-fold, 5-fold, 10-fold, 20-fold, 30-fold, 40-fold, 50-fold, 100-fold, 500-fold, 1000-fold, or 1500-fold as compared to a control (e.g., endogenous level of protein or activity without or before the treatment according to the disclosure, or a historical reference level).

In various embodiments, mRNA expression may be detected or quantified by qPCR on RNA purified from tissue samples. The protein expression (e.g., CFTR or DNAI1) may be determined by measuring immune responses to the protein. Qualitative assessment of the protein may also be performed by e.g., Western blot analysis. The protein activity may be measured by an appropriate activity assay. Various other methods are known in the art and may be used to determine the protein expression or activity.

The CFTR mRNA expression may be detected or quantified by qPCR on RNA purified from tissue samples. In some embodiments, the DNAI mRNA expression may be detected or quantified by qPCR on RNA purified from tissue samples. The CFTR protein expression may be determined by measuring immune responses to CFTR protein. In some embodiments, IgG antibody to CFTR protein is measured by an enzyme-linked immunosorbent assay in collected serum samples. In some embodiments, CFTR-specific T cell responses are assessed using collected peripheral blood mononuclear cells. In some embodiments, T cell responses to CFTR protein are measured by a human interferon-7 enzyme-linked immunospot assay as described by Calcedo et al. (Calcedo et al., Hum Gene Ther Clin Dev. (2013) 24:108-15). Qualitative assessment of CFTR protein or DNAI may also be performed by e.g., Western blot analysis. The CFTR protein activity may be measured by CFTR chloride channel activity in appropriate tissue cells. A stable potential with the mean value of a 10 second scoring interval after perfusion of solution is recorded. CFTR activity is estimated by the change in potential difference following perfusion with chloride-free isoproterenol. Various other methods are known in the art and may be used to determine the CFTR mRNA and CFTR protein expression or activity.

In another aspect, the disclosure provides methods of delivering a payload to a cell, comprises contacting the cell with an LNP composition of the present disclosure.

In another aspect, the disclosure provides methods of delivering expressing a protein or an RNA in a cell, comprises contacting the cell with an LNP composition of the present disclosure.

In another aspect, the disclosure provides methods of increasing chloride flux in a cell, comprising contacting the cell with a LNP composition of the present disclosure, wherein optionally the cell comprises homozygous inactivating mutations in the CFTR gene.

In another aspect, the disclosure provides methods of maintaining transepithelial electrical resistance (TEER) or reducing TEER by at most 10%, at most 20%, or at most 30%.

In some embodiments, the cell is a lung cell. In some embodiments, the lung cell is a secretory cell and/or ionocyte.

In some embodiments, the methods specifically transduce secretory cells and/or ionocytes compared to other lung cells.

In some embodiments, the lung cell is a ciliated cell.

In some embodiments, the methods specifically transduce ciliated cells compared to other lung cell.

In some embodiments, any of the treatment methods disclosed herein comprises nebulizing the composition to generate an aerosolized composition, then contacting the aerosolized composition with the cell.

In some embodiments, the composition of the present disclosure is an aerosolized composition, and any of the treatment methods disclosed herein comprises contacting the aerosolized composition with the cell.

In another aspect, the present disclosure provides a method of delivering a payload to the lungs of a subject, comprising administering to the subject a composition of the present disclosure.

In one aspect, the present disclosure provides a method of treating or preventing lung disease in a subject, comprising administering to the subject a composition of the present disclosure.

In some embodiments, any of the treatment method disclosed herein comprises nebulizing the composition of the present disclosure prior to the administering step.

In some embodiments, the composition of the present disclosure is administered, as an aerosolized composition, by inhalation.

In some embodiments, any of the treatment methods disclosed herein delivers to the lung an effective amount of the composition.

In some embodiments, any of the treatment methods disclosed herein delivers to the lung an amount effective to treat the lung disease.

In some embodiments, any of the treatment methods disclosed herein is more effective than contacting the cell with or administering to the subject elexacaftor, tezacaftor, lumacaftor, ivacaftor, or any combination thereof. In some embodiments, any of the treatment methods disclosed herein is at least 10%, at least 20%, at least 30%, at least 40%, at least 50%, or at least 60% more effective than administering elexacaftor, tezacaftor, lumacaftor, ivacaftor, or any combination thereof. In some embodiments, any of the methods disclosed herein is 10%-70%, 20%-70%, 30%-70%, 40%-70%, 50%-70%, or 60%-70% more effective than administering elexacaftor, tezacaftor, lumacaftor, ivacaftor, or any combination thereof. The structure of ivacaftor is:

The structure of lumacaftor is:

In one aspect, the present disclosure provides use of the presently disclosed compositions for treatment of a lung disease.

In another aspect, the present disclosure provides various LNP compositions for treatment of a lung disease, which are described in greater depth *supra*.

In another aspect, the disclosure provides a method of treating or preventing lung disease in a subject, comprising administering to the subject a composition disclosed herein.

In some embodiments, the method comprising nebulizing the composition prior to the administering step. In some embodiments of the method, the LNP composition is administered, as an aerosolized composition, by inhalation.

In another aspect, the disclosure provides use of a composition described herein for treatment of a lung disease. In another aspect, the disclosure provides a composition described herein for treatment of a lung disease.

In another aspect, the disclosure provides a method for treating a lung disease in a subject, the method comprising administering the aerosolized pharmaceutical composition described herein to the subject.

B. Nebulization and Pulmonary Delivery

The compositions of the present disclosure, either alone or in combination with other suitable components, can be made into aerosol formulations (i.e., they can be nebulized). In various embodiments, the compositions of the present disclosure can be formulated to be administered via inhalation (e.g., intranasally or intratracheally) (see, Brigham et al., Am. J. Sci., 298:278 (1989)). In some embodiments, delivery is pulmonary delivery, e.g., comprising nebulization.

A payload (such as a CFTR mRNA or a DNAI mRNA) may be incorporated into a lipid nanoparticle for delivery via different administration routes. In some embodiments, a CFTR mRNA or DNAI mRNA is incorporated into an LNP for pulmonary delivery. As used herein, pulmonary delivery refers to delivery to lungs via, e.g., nasal cavity, trachea, bronchi, bronchioles, and/or other pulmonary system. In some embodiments, a CFTR mRNA is incorporated into an LNP for nebulization. In a particular embodiment, a DNAI1 mRNA is incorporated into an LNP for nebulization. In these embodiments, the delivery vehicle may be in an aerosolized pharmaceutical composition which can be inhaled.

In some embodiments, the composition of the present disclosure is nebulized prior to inhalation.

In some embodiments, aerosol formulations can be placed into pressurized acceptable propellants, such as dichlorodifluoromethane, propane, nitrogen, and the like.

In various embodiments, provided herein is a method for targeting the aerosolized pharmaceutical compositions to a lung cell of a subject comprising administering the aerosolized pharmaceutical composition to the subject. For example, the method includes delivering a polynucleotide to a lung cell of a subject, comprising administering the aerosolized pharmaceutical compositions described herein. In other examples, the present disclosure provides for expressing a protein in the lung of a subject, comprising administering the aerosolized pharmaceutical composition described herein to the subject. In some embodiments, provided herein are methods for expressing a protein in the lungs of a subject, comprising administering the aerosolized pharmaceutical composition to the subject.

In various embodiments, the aerosolized pharmaceutical composition is administered to the subject using a nebulizer.

In some embodiments, the nebulizer is administered at an output rate from 0.1 to 1.0 mL/min. In other embodiments, the nebulizer is administered at an output rate of 0.5 mL/min.

In some embodiments, the aerosolized pharmaceutical composition is administered for less than 60 minutes, 50 minutes, 40 minutes, 30 minutes, 20 minutes, 15 minutes, 10 minutes or 5 minutes. In some embodiments, the aerosolized pharmaceutical composition is administered for less than 60 minutes, 50 minutes, 40 minutes, 30 minutes, 20 minutes, 15 minutes, 10 minutes or 5 minutes. In some embodiments, the aerosolized pharmaceutical composition is administered for less than 5 minutes, 4 minutes, 3 minutes, 2 minutes or 1 minute. In some embodiments, the aerosolized pharmaceutical composition is administered for less than 1 minute.

In some embodiments, the duration of nebulization ranges from 1 minute to 60 minutes. In some embodiments, the duration of nebulization is less than or equal to 1 minute. In some embodiments, the duration of nebulization is less than or equal to 2 minutes. In some embodiments, the duration of nebulization is less than or equal to 3 minutes. In some embodiments, the duration of nebulization is less than or equal to 6 minutes. In some embodiments, the duration of nebulization is less than or equal to 9 minutes. In some embodiments, the duration of nebulization is less than or equal to 12 minutes. In some embodiments, the duration of nebulization is less than or equal to 15 minutes. In some embodiments, the duration of nebulization is less than or equal to 18 minutes. In some embodiments, the duration of nebulization is less than or equal to 21 minutes. In some embodiments, the duration of nebulization is less than or equal to 24 minutes. In some embodiments, the duration of nebulization is less than or equal to 27 minutes. In some embodiments, the duration of nebulization is less than or equal to 30 minutes. In some embodiments, the duration of nebulization is less than or equal to 33 minutes. In some embodiments, the duration of nebulization is less than or equal to 36 minutes. In some embodiments, the duration of nebulization is less than or equal to 40 minutes. In some embodiments, the duration of nebulization is less than or equal to 45 minutes. In some embodiments, the duration of nebulization is less than or equal to 50 minutes. In some embodiments, the duration of nebulization is less than or equal to 55 minutes. In some embodiments, the duration of nebulization is less than or equal to 60 minutes.

In various embodiments, the volume of the composition administered by nebulization is 1 mL to 10 mL. In some embodiments, the volume of the composition administered by nebulization is at most about 1 mL. In some embodiments, the volume of the composition administered by nebulization is at most about 4 mL. In some embodiments, the volume of the composition administered by nebulization is at most about 8 mL.

In another aspect, the disclosure provides a method of delivering a payload to a cell, comprising contacting a cell with the LNP composition disclosed herein. In another aspect, the disclosure provides a method of delivering expressing a protein or an RNA in a cell, comprises contacting a cell with an LNP composition disclosed herein. In some embodiments, the cell is a lung cell. In some embodiments, the lung cell is a secretory cell. In some embodiments, the lung cell is an ionocyte. In some embodiments, the lung cell is a ciliated cell. In some embodiments, the method specifically transduces the secretory cells compared to other lung cells. In some embodiments, the method specifically transduces the ionocyte compared to other lung cells. In some embodiments, the method specifically transduces the ciliated cell compared to other lung cells. In some embodiments, the method comprises nebulizing the LNP composition to generate an aerosolized composition, then contacting the aerosolized composition with the cell. In some embodiments, the LNP composition is an aerosolized composition, and the method comprises contacting the aerosolized composition with the cell. In another aspect, the disclosure provides a method of delivering a payload to lungs of a subject, comprising administering to the subject a composition disclosed herein.

In some embodiments, the method delivers an effective amount of the LNP composition to the lungs. In some embodiments, the method delivers an effective amount of the LNP composition to the lungs to treat the lung disease.

In another aspect, the disclosure provides a method for delivering lipid nanoparticles (LNPs) to a lung cell of a subject, the method comprising nebulizing the liquid pharmaceutical composition described herein to generate an aerosolized pharmaceutical composition, and administering the aerosolized pharmaceutical composition to the subject.

In another aspect, the disclosure provides a method of delivering a payload to a lung cell of a subject, the method comprising administering the aerosolized pharmaceutical composition described herein to the subject, wherein optionally the payload is a polynucleotide.

In another aspect, the disclosure provides a method for expressing a protein in the lung of a subject, the method comprising administering the aerosolized pharmaceutical composition described herein to the subject.

In some embodiments, lipid nanoparticle is nebulized. In some embodiments, lipid nanoparticle is administered by inhalation. In some embodiment, the nebulized lipid nanoparticle delivers nose, trachea, and lungs of the subject.

C. Formulation of Pharmaceutical Compositions

The disclosure also provides pharmaceutical compositions (e.g, in liquid form prior to aerosolization) comprising the LNPs described herein. Such compositions can be used for the treatment of a lung disease in a patient or subject. The pharmaceutical compositions of the disclosure may include a pharmaceutically acceptable carrier, and a thorough discussion of such carriers is available in Chapter 30 of *Remington: The Science and Practice of Pharmacy* ($23^{rd}$ed., 2021).

In some embodiments, the composition of the present disclosure comprises LNPs for selective delivery to one or more of goblet cells, secretory cells, club cells, basal cells or ionocytes. In other embodiments, the aerosolized pharmaceutical composition comprises LNPs for selective delivery to one or more of ciliated cells, club cells, or basal cells.

In some embodiments, the pharmaceutical compositions of the present disclosure include one or more of a poloxamer (e.g., Poloxamer 188) polyethylene glycol ("PEG"), sucrose, and a buffer, wherein the buffer comprises a citrate buffer, an acetate buffer, or a Tris buffer.

In some embodiments, the LNPs of the present disclosure comprises a PEG with a concentration ranging from 1% to 4% (w/v). In other embodiments, the PEG has a concentration from 1% to 5%, or 2 to 4%.

In some embodiments, the pharmaceutical compositions of the present disclosure include Poloxamer 188 at a concentration of between about 0.001% w/v and 0.5% v/w.

In some embodiments, the pharmaceutical compositions of the present disclosure include sucrose. In some embodiments, the sucrose is at a concentration from 1% to 15% w/v, 5% to 15% w/v, 1% to 10% w/v, or 5% to 10% w/v.

In some embodiments, the pharmaceutical compositions of the present disclosure includes a citrate buffer. For example, the citrate buffer is at a pH from 4 to 8. In various examples, the buffer is an acetate buffer and has a pH from 4 to 8. In still other embodiments, the composition includes a Tris buffer, and the Tris buffer has a pH from 4 to 8.

In some embodiments, the pharmaceutical composition has a pH of 7.0, 7.1, 7.2, 7.3, 7.4, 7.5, 7.6, 7.7, 7.8, 7.9, or 8.0. In some embodiments, the pharmaceutical composition has apparent pKa 4 to 7.

In some embodiments, the pharmaceutical compositions comprising the LNPs described herein have at least one pharmaceutically acceptable excipient or carrier. In some embodiments, the pharmaceutically acceptable excipient or carrier is for nebulization of the presently described compositions.

In some embodiments, the pharmaceutical compositions can also include excipients and/or additives. Non-limiting examples of the excipients and/or additives are surfactants, stabilizers, complexing agents, antioxidants, or preservatives which prolong the duration of use of the finished pharmaceutical formulation, flavorings, vitamins, or other additives known in the art. The complexing agents include, but are not limited to, ethylenediaminetetraacetic acid (EDTA) or a salt thereof, such as the disodium salt, citric acid, nitrilotriacetic acid and the salts thereof. In some embodiments, the preservatives include, but are not limited to, those that protect a solution from contamination with pathogenic particles, including benzalkonium chloride or benzoic acid, or benzoates such as sodium benzoate. The antioxidants include, but are not limited to, vitamins, provitamins, ascorbic acid, vitamin E, salts or esters thereof.

In some embodiments, one or more tonicity agents may be added to the presently described pharmaceutical composition to provide the desired ionic strength. The tonicity agents for use herein include those which display no or only negligible pharmacological activity after administration. Both inorganic and organic tonicity adjusting agents may be used.

In some embodiments, the presently described methods comprise nebulizing the the presently disclosed compositions to generate an aerosolized LNP composition.

In another aspect, the disclosure provides a method of making an LNP composition described herein, comprising mixing the lipid components and the payload in conditions effective to assemble the LNPs comprising the payload. In some embodiments, the method comprising nebulizing the composition to generate an aerosolized LNP composition.

In another aspect, the disclosure provides an aerosolized pharmaceutical composition comprising the LNP composition described herein. In some embodiments of the aerosolized pharmaceutical composition comprises at least two selective organ targeting (SORT) lipids and/or at least six lipids. In some embodiments of the aerosolized pharmaceutical composition, the LNP composition comprises an ionizable cationic lipid, optionally two or more ionizable lipids; and a permanently cationic lipid, optionally two or more permanently cationic lipids.

In some embodiments of the aerosolized pharmaceutical composition, the LNP composition comprises an ionizable cationic lipid, a permanently cationic lipid, optionally a phospholipid, optionally a polyethylene-glycol (PEG)-lipid, and/or optionally a sterol.

In some embodiments of the aerosolized pharmaceutical composition, the LNP composition comprises at least six lipids.

In some embodiments of the aerosolized pharmaceutical composition, the LNP composition comprises an ionizable cationic lipid, a permanently cationic lipid, optionally a phospholipid, optionally a polyethylene-glycol (PEG)-lipid, and/or optionally a sterol.

In some embodiments of the aerosolized pharmaceutical composition, the LNP composition comprises at least two selective organ targeting (SORT) lipids.

In some embodiments, the ionizable cationic lipid is a dendrimeric lipid, optionally 4A3-SC7 or 5A2-SC8. In some embodiments of the aerosolized pharmaceutical composition, the ionizable cationic lipid is a SORT lipid; and/or the permanently cationic lipid is a SORT lipid. In some embodiments of the aerosolized pharmaceutical composition, the ionizable cationic lipid is 1,2-dioleoyl-3-dimethylammonium-propane (DODAP). In some embodiments of the aerosolized pharmaceutical composition, the permanently cationic lipid is trimethylammonium-propane, optionally 1,2-dimyristoyl-3-trimethylammonium-propane(14:0 TAP), 1,2-dipalmitoyl-3-trimethylammonium-propane (16:0 TAP), 1,2-stearoyl-3-trimethylammonium-propane (18:0 TAP), 1,2-dioleoyl-3-trimethylammonium-propane (DOTAP). In some embodiments of the aerosolized pharmaceutical composition, the permanently cationic lipid is ethylphosphocholine (EPC), optionally 1,2-dilauroyl-sn-glycero-3-ethylphosphocholine (12:0 EPC), 1,2-dimyristoyl-sn-glycero-3-ethylphosphocholine (14:0 EPC), 1,2-dipalmitoyl-sn-glycero-3-ethylphosphocholine (16:0 EPC), 1,2-distearoyl-sn-glycero-3-ethylphosphocholine (18:0 EPC).

In some embodiments of the aerosolized pharmaceutical composition, the LNP specifically transduces a lung cell; and/or the LNP delivers mRNA to a lung cell in an amount effective to increase expression and/or function of a protein encoded by the mRNA. In some embodiments of the aerosolized pharmaceutical composition, the lung cell is ionocyte. In some embodiments of the aerosolized pharmaceutical composition, the lung cell is ciliated cell. In some embodiments of the aerosolized pharmaceutical composition, the lung cell is secretory cell.

In some embodiments of the aerosolized pharmaceutical composition, the LNP comprises the ionizable cationic lipid at a molar percentage greater than 15%. In some embodiments of the aerosolized pharmaceutical composition, the the ionizable cationic lipid is the dendrimeric lipid at a molar percentage between 10% and 30%. In some embodiments of the aerosolized pharmaceutical composition, the LNP comprises DODAP at a molar percentage between 5% and 40%. In some embodiments of the aerosolized pharmaceutical composition, the LNP comprises permanently cationic lipids at a molar percentage less than 40%. In some embodiments of the aerosolized pharmaceutical composition, the permanently cationic lipids at a molar percentage between 5% and 25%, between 5% and 20%, between 5% and 15%, between 5% and 10%, between 10% and 20%, between 15% and 20%. In some embodiments of the aerosolized pharmaceutical composition, the permanently cationic lipid is trimethylammonium-propane (TAP). In some embodiments of the aerosolized pharmaceutical composition, the TAP is 1,2-dimyristoyl-3-trimethylammonium-propane(14:0 TAP). In some embodiments of the aerosolized pharmaceutical composition, the permanently cationic lipid is 14:0 TAP at a molar percentage between 10% and 15%. In some embodiments of the aerosolized pharmaceutical composition, the permanently cationic lipid is ethylphosphocholine (EPC). In some embodiments of the aerosolized pharmaceutical composition, the EPC is 1,2-dimyristoyl-sn-glycero-3-ethylphosphocholine (14:0 EPC). In some embodiments of the aerosolized pharmaceutical composition, the permanently cationic lipid is 14:0 EPC at a molar percentage between 10% and 15%. In some embodiments of the aerosolized pharmaceutical composition, the LNP comprises phospholipid at a molar percentage between 10% and 30%. In some embodiments of the aerosolized pharmaceutical composition, the LNP comprises cholesterol at a molar percentage greater than 25%. In some embodiments of the aerosolized pharmaceutical composition, the cholesterol at a molar percentage between 25% and 50%, between 30% and 50%, between 30% and 45%, between 30% and 40%, or between 30% and 35%. In some embodiments of the aerosolized pharmaceutical composition, the LNP comprises polyethylene-glycol (PEG)-lipid at a molar percentage between 0.5% and 10% or between 1% and 4%.

In some embodiments of the aerosolized pharmaceutical composition, the LNP comprises messenger RNA (mRNA). In some embodiments of the aerosolized pharmaceutical composition, the LNP comprises mRNA at a lipid:mRNA ratio less than 40:1. In some embodiments of the aerosolized pharmaceutical composition, the lipid:mRNA ratio is 36:1. In some embodiments of the aerosolized pharmaceutical composition, the lipid:mRNA ratio is 33:1. In some embodiments of the aerosolized pharmaceutical composition, the lipid:mRNA ratio is 30:1.

In some embodiments of the aerosolized pharmaceutical composition, the LNP comprises gene editing payload. In some embodiments of the aerosolized pharmaceutical composition, the gene editing payload comprises Cas9, sgRNA, and/or ss DNA.

In some embodiments of the aerosolized pharmaceutical composition, the LNP comprise the cationic ionizable lipid is 5A2-SC8 or 4A3-SC7, the cationic ionizable SORT lipid is DODAP, the permanently cationic lipid is 14:0 TAP or 14:0 EPC, phospholipid is 1,2-dioleoyl-sn-glycero-3-phosphoethanolamine (DOPE) or 1,2-distearoyl-sn-glycero-3-phosphocholine (DSPC), the sterol is cholesterol or sitosterol, and/or the polyethylene-glycol (PEG)-lipid is DMG-PEG, optionally DMG-PEG2000.

In some embodiments of the aerosolized pharmaceutical composition, the LNP comprise the cationic ionizable lipid is 4A3-SC7, the cationic ionizable SORT lipid is DODAP, the permanently cationic lipid is 14:0 TAP, the phospholipid is DOPE, the sterol is cholesterol, and/or the polyethylene-glycol (PEG)-lipid is DMG-PEG.

In some embodiments of the aerosolized pharmaceutical composition, the LNP comprise the cationic ionizable lipid is 4A3-SC7, the cationic ionizable SORT lipid is DODAP, the permanently cationic lipid is 14:0 EPC, the phospholipid is DOPE, the sterol is cholesterol, and/or the polyethylene-glycol (PEG)-lipid is DMG-PEG.

In some embodiments of the aerosolized pharmaceutical composition, the cationic ionizable lipid is 4A3-SC7 and the LNP comprises 4A3-SC7 at a molar percentage between about 10% and about 30%. In some embodiments of the aerosolized pharmaceutical composition, the cationic ionizable SORT lipid is DODAP and the LNP comprises DODAP at a molar percentage between about 5% and about 40%. In some embodiments of the aerosolized pharmaceutical composition, the permanently cationic lipid is 14:0 TAP and the LNP comprises 14:0 TAP at a molar percentage between about 5% and about 25%. In some embodiments of the aerosolized pharmaceutical composition, the permanently cationic lipid is 14:0 EPC and the LNP comprises 14:0 EPC at a molar percentage between about 5% and about 25%.

In some embodiments of the aerosolized pharmaceutical composition, the LNP comprises 4A3-SC7 at a molar percentage between about 10% and about 30%, DODAP at a molar percentage between about 5% and about 40%, 14:0 TAP at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments of the aerosolized pharmaceutical composition, the LNP comprises 4A3-SC7 at a molar percentage between about 10% and about 15%, DODAP at a molar percentage between about 5% and about 20%, 14:0 TAP at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments of the aerosolized pharmaceutical composition, the LNP comprises 4A3-SC7 at a molar percentage between about 10% and about 30%, DODAP at a molar percentage between about 5% and about 40%, 14:0 EPC at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments of the aerosolized pharmaceutical composition, the LNP comprises 4A3-SC7 at a molar percentage between about 10% and about 15%, DODAP at a molar percentage between about 5% and about 20%, 14:0 EPC at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments of the aerosolized pharmaceutical composition, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%.

In some embodiments of the aerosolized pharmaceutical composition, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments of the aerosolized pharmaceutical composition, the LNP comprises a payload. In some embodiments of the aerosolized pharmaceutical composition, the payload is a messenger RNA (mRNA). In some embodiments of the aerosolized pharmaceutical composition, the mRNA encodes a gene-editing system or components thereof. In some embodiments of the aerosolized pharmaceutical composition, the payload is an shRNA or a polynucleotide encoding an shRNA. In some embodiments of the aerosolized pharmaceutical composition, the payload is a microRNA or a polynucleotide encoding a microRNA. In some embodiments of the aerosolized pharmaceutical composition, the composition is a pharmaceutical composition.

In another aspect, the disclosure provides a liquid pharmaceutical composition for use in making the aerosolized pharmaceutical compositions described herein.

In some embodiments of the nebulized lipid nanoparticle, the particle size is between 223 and 290 (nm). In some embodiments of the nebulized lipid nanoparticle, the encapsulation efficiency is between 12.5% and 91%. In some embodiments of the nebulized lipid nanoparticle, the output rate is between 405 and 659 (μL/min). In some embodiments of the nebulized lipid nanoparticle, the PDI is between 0.419-0.652. In some embodiments of the nebulized lipid nanoparticle, the total output rate (TOR) is between 195-789 (L/min). In some embodiments of the nebulized lipid nanoparticle, the mass median diameter (MMD) is between 3.88-4.28 (μm). In some embodiments of the nebulized lipid nanoparticle, the geometric standard deviation (GSD) is between 1.62-1.77. In some embodiments of the nebulized lipid nanoparticle, the % of fine particle fraction smaller than 5 μm (FPF<5 μm) is 61.7-70.81 (%).

IV. Devices

In various aspects of the present disclosure, pulmonary drug delivery involves inhalation of the drug (e.g., for nasal, tracheal, or bronchial delivery). In some embodiments, an aerosol is a stable suspension of fine liquid particles (droplets) dispersed in a gas or vapor. In some embodiments, an LNP composition of the present disclosure having a payload is nebulized prior to inhalation by a subject. In other embodiments, an LNP composition of the present disclosure having a polynucleotide as a payload is nebulized prior to inhalation by a subject. In various embodiments, an LNP composition of the present disclosure having an mRNA molecule as a payload is nebulized prior to inhalation by a subject. In some embodiments, the LNP composition comprising CFTR mRNA is nebulized prior to inhalation. In some embodiments, the LNP composition comprising DNAI mRNA is nebulized prior to inhalation.

A nebulizer is a device used to produce an aerosolized pharmaceutical composition for pulmonary drug delivery. A nebulizer transforms a liquid to a mist so that it can be inhaled more easily into the lungs. Nebulizers are effective for infants, children, and adults. Nebulizers can nebulize large doses of inhaled medications. One type of nebulizer is a jet nebulizer, which comprises tubing connected to a compressor, which causes compressed air or oxygen to flow at a high velocity through a liquid medicine to turn it into an aerosol, which is then inhaled by a patient.

In other embodiments, the nebulizer is an ultrasonic wave nebulizer, which comprises an electronic oscillator that generates a high frequency ultrasonic wave, which causes the mechanical vibration of a piezoelectric element, which is in contact with a liquid reservoir. The high frequency vibration of the liquid is sufficient to produce a vapor mist. Non-limiting exemplary ultrasonic wave nebulizers include the Omron NE-U17 and the Beurer Nebulizer IH30.

In various embodiments, a nebulizer comprises a vibrating mesh technology (VMT). The VMT comprises mesh/membrane with 1000-7000 holes that vibrate at the top of a liquid reservoir and thereby pressures out a mist of very fine droplets through the holes in the mesh/membrane. Non-limiting exemplary VMT nebulizers include PARI® eFlow®, Respironics i-Neb, Beurer Nebulizer IH50, Aerogen Aeroneb, HC Med deepro™, Pulmotree Kolibri Mesh-Nebulizer, and Philips InnoSpire Go.

Nebulizers described herein includes a nebulizer providing an increased amount of aerosol during inhalation while minimizing both aerosol losses during exhalation and the residual drug in the nebulizer reservoir (see, U.S. Pat. No. 9,061,303, the contents of which is incorporated herein by reference in its entirety). The nebulizer includes an aerosol generator that atomizes the liquid through a vibrating diaphragm into particle sizes that are efficiently delivered to the lungs. This nebulizer is currently commercialized under the trade name eFlow®. U.S. Patent Application Nos. US 2005/0006359; US 2008/0311648; US 2008/0060640 and U.S. Pat. No. 5,518,179 disclose further aspects of the eFlow® technology and are incorporated herein by reference in their entireties.

Nebulization principles generally involve a solution, such as an aqueous solution, being exposed to shear stresses, which may negatively affect the delicate nature of polynucleotides such as mRNA. However, the present disclosure provides that the eFlow® nebulizer can retain the integrity of the mRNA and LNP, and thus is suited for pulmonary administration of the LNP composition.

In an aspect, a device suitable for pulmonary delivery can contain and be used to deliver a single dose of the LNP composition of the present disclosure. In another aspect, a device suitable for pulmonary delivery can contain and be used to deliver multi-doses of the LNP composition of the present disclosure.

A nebulizer type inhalation delivery device can contain the LNP compositions of the present disclosure as a solution, usually aqueous, a suspension, or a micellar suspension. For example, various embodiments of the presently described LNP compositions can be suspended in saline or buffer and loaded into the inhalation delivery device. In generating the nebulized spray of the LNP compositions for inhalation, the nebulizer delivery device may be driven ultrasonically, by compressed air, by other gases, electronically or mechanically (e.g., vibrating mesh or aperture plate). Vibrating mesh nebulizers generate fine particle, low velocity aerosols, and nebulize therapeutic solutions and suspensions at a faster rate than conventional jet or ultrasonic nebulizers. Vibrating mesh nebulizers amenable for use with the methods described herein include the Philips Respironics I-Neb®, the Omron MicroAir, the Nektar Aeroneb®, the PARI® eFlow®, or the Aerogen® Solo.

The nebulizer may be portable and handheld in design and may be equipped with a self-contained electrical unit. The nebulizer device may comprise a nozzle that has two coincident outlet channels of defined aperture size through which the liquid formulation can be accelerated. This results in impaction of the two streams and atomization of the formulation (e.g., any of the presently described LNP compositions). The nebulizer may use a mechanical actuator to force the liquid formulation through a multiorifice nozzle of defined aperture size(s) to produce an aerosol of the formulation for inhalation.

V. Kits

The present disclosure provides a variety of kits for conveniently and/or effectively performing the presently described methods or using the presently described compositions. Typically, the kits will comprise sufficient amounts and/or numbers of components to allow a user to perform multiple treatments of a subject and/or perform multiple experiments. In some embodiments, the kits include one or more containers comprising any of the presently described LNP compositions or a pharmaceutical composition thereof.

In one aspect, the present disclosure provides kits comprising the LNPs of the present disclosure. The disclosure further provides kits, which may be used to prepare the aerosolized pharmaceutical compositions. In some embodiment, a kit includes a lipid nanoparticle composition comprising one or more of a phospholipid, an ionizable lipid, a PEG-lipid, cholesterol, and a mesh. In some embodiments, the kit can further comprise packaging and instructions and/or a delivery agent to form, prior to nebulization, a liquid formulation comprising any of the presently described LNP compositions. The delivery agent can comprise sucrose, a saline, a buffer, such as, but not limited to a citrate buffer, an acetate buffer, or a Tris buffer, or any other well known delivery agent for nebulization. In some embodiments, the delivery agent can be in a lyophilized form. The included instructions can comprise a description of administering the presently described LNP compositions to treat, delay the onset, or alleviate a target disease (e.g., CF and/or PCD). In some embodiments, the instruction can comprise a description of administering the presently described LNP compositions to a subject at risk of the target disease (e.g., CF and/or PCD). In some embodiments, the kits provide articles of manufacture comprising the contents of the kits described herein.

In some embodiments, the instructions comprise dosage information, dosing schedule, and route of administration. In some embodiments, the kits comprise one or more the containers that are unit doses, bulk packages (e.g., multi-dose packages) or sub-unit doses. In some embodiments, the instructions are written instructions on a label or package insert (e.g., a paper sheet included in the kit). In some embodiments, the instructions are machine-readable instructions (e.g., instructions carried on a magnetic or optical storage disk).

In some embodiments, the label or package insert of the kits indicates that the LNPs or any of the pharmaceutical compositions disclosed herein are used for treating, delaying the onset, and/or alleviating a disease or disorder associated with lungs (e.g., CF and/or PCD). Instructions may be provided for practicing any of the treatment methods described herein.

In some embodiments, the kits described herein are in suitable packaging. In some embodiments, suitable packing comprises vials, bottles, jars, flexible packaging (e.g., seal Mylar® or plastic bags), or combinations thereof. In some embodiments, the packaging comprises packages for use in combination with a specific device such as a nebulizer, an inhaler, and/or nasal administration device (e.g., an atomizer).

In another aspect, the disclosure provides a kit comprising a composition and a nebulizer mask and/or a mesh suitable for use in a nebulizer.

In another aspect, the disclosure provides a kit comprising a lipid nanoparticle composition comprising at least two selective organ targeting (SORT) lipids and/or at least six lipids, optionally comprising a polynucleotide.

VI. Embodiments

In some embodiments, the lipid nanoparticle (LNP) composition comprises at least two selective organ targeting (SORT) lipids and/or at least six lipids.

In some embodiments, the LNP composition comprises an ionizable cationic lipid, optionally two or more ionizable lipids; and a permanently cationic lipid, optionally two or more permanently cationic lipids.

In some embodiments, the LNP composition comprises at least six lipids.

In some embodiments, the LNP composition comprises at least two selective organ targeting (SORT) lipids.

In some embodiments, the LNP specifically transduces a lung cell; and/or the LNP delivers mRNA to a lung cell in an amount effective to increase expression and/or function of a protein encoded by the mRNA. In some embodiments, the lung cell is ionocyte. In some embodiments, the lung cell is ciliated cell. In some embodiments, the lung cell is secretory cell.

In some embodiments, the LNP comprising the cationic ionizable lipid is 4A3-SC7, the cationic ionizable SORT lipid is DODAP, the permanently cationic lipid is 14:0 EPC, phospholipid is 1,2-dioleoyl-sn-glycero-3-phosphoethanolamine (DOPE), the cholesterol, and/or the DMG-PEG.

In some embodiments, the LNP comprising the cationic ionizable lipid is 4A3-SC7, the cationic ionizable SORT lipid is DODAP, the permanently cationic lipid is 14:0 EPC, 1,2-distearoyl-sn-glycero-3-phosphocholine (DSPC), the cholesterol, and/or the DMG-PEG.

In some embodiments, the LNP comprising the cationic ionizable lipid is 4A3-SC7, the cationic ionizable SORT lipid is DODAP, the permanently cationic lipid is 14:0 TAP, phospholipid is 1,2-dioleoyl-sn-glycero-3-phosphoethanolamine (DOPE), the cholesterol, and/or the DMG-PEG.

In some embodiments, the LNP comprising the cationic ionizable lipid is 4A3-SC7, the cationic ionizable SORT lipid is DODAP, the permanently cationic lipid is 14:0 TAP, 1,2-distearoyl-sn-glycero-3-phosphocholine (DSPC), the cholesterol, and/or the DMG-PEG.

In some embodiments, the LNP comprising the cationic ionizable lipid is 5A2-SC8, the cationic ionizable SORT lipid is DODAP, the permanently cationic lipid is 14:0 EPC, phospholipid is 1,2-dioleoyl-sn-glycero-3-phosphoethanolamine (DOPE), the cholesterol, and/or the DMG-PEG.

In some embodiments, the LNP comprising the cationic ionizable lipid is 5A2-SC8, the cationic ionizable SORT lipid is DODAP, the permanently cationic lipid is 14:0 EPC, 1,2-distearoyl-sn-glycero-3-phosphocholine (DSPC), the cholesterol, and/or the DMG-PEG.

In some embodiments, the LNP comprising the cationic ionizable lipid is 5A2-SC8, the cationic ionizable SORT lipid is DODAP, the permanently cationic lipid is 14:0 TAP, phospholipid is 1,2-dioleoyl-sn-glycero-3-phosphoethanolamine (DOPE), the cholesterol, and/or the DMG-PEG.

In some embodiments, the LNP comprising the cationic ionizable lipid is 5A2-SC8, the cationic ionizable SORT lipid is DODAP, the permanently cationic lipid is 14:0 TAP, 1,2-distearoyl-sn-glycero-3-phosphocholine (DSPC), the cholesterol, and/or the DMG-PEG.

In some embodiments, the LNP comprises 4A3-SC7 at a molar percentage between about 10% and about 30%, DODAP at a molar percentage between about 5% and about 40%, 14:0 TAP at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises 4A3-SC7 at a molar percentage between about 10% and about 15%, DODAP at a molar percentage between about 5% and about 20%, 14:0 TAP at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises 4A3-SC7 at a molar percentage between about 10% and about 30%, DODAP at a molar percentage between about 5% and about 40%, 14:0 EPC at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises 4A3-SC7 at a molar percentage between about 10% and about 15%, DODAP at a molar percentage between about 5% and about 20%, 14:0 EPC at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about about 30%, and DMG-PEG at a molar percentage of about about 3%.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about about 32%, and DMG-PEG at a molar percentage of about about 3%.

In some embodiments, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%.

In some embodiments, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%, wherein the lipid:mRNA ratio is 36:1.

In some embodiments, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%, wherein the lipid:mRNA ratio is 33:1.

In some embodiments, the LNP comprises 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%, wherein the lipid:mRNA ratio is 30:1.

In some embodiments, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%, wherein the lipid:mRNA ratio is 36:1.

In some embodiments, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%, wherein the lipid:mRNA ratio is 30:1.

In some embodiments, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%, wherein the lipid:mRNA ratio is 36:1.

In some embodiments, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%, wherein the lipid:mRNA ratio is 33:1.

In some embodiments, the LNP comprises 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%, wherein the lipid:mRNA ratio is 30:1.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 36:1.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 30:1.

In some embodiments of the nebulized lipid nanoparticle, the particle size is between 223 and 290 (nm). In some embodiments of the nebulized lipid nanoparticle, the particle size is between 200 and 300 (nm). In some embodiments of the nebulized lipid nanoparticle, the particle size is between 220 and 280 (nm). In some embodiments of the nebulized lipid nanoparticle, the particle size is between 250 and 270 (nm). In some embodiments of the nebulized lipid nanoparticle, the particle size is between 240 and 280 (nm). In some embodiments of the nebulized lipid nanoparticle, the particle size is about 220 (nm). In some embodiments of the nebulized lipid nanoparticle, the particle size is about 230 (nm). In some embodiments of the nebulized lipid nanoparticle, the particle size is about 240 (nm). In some embodiments of the nebulized lipid nanoparticle, the particle size is about 250 (nm). In some embodiments of the nebulized lipid nanoparticle, the particle size is about 260 (nm). In some embodiments of the nebulized lipid nanoparticle, the particle size is about 270 (nm). In some embodiments of the nebulized lipid nanoparticle, the particle size is about 280 (nm). In some embodiments of the nebulized lipid nanoparticle, the particle size is about 290 (nm).

In some embodiments of the nebulized lipid nanoparticle, the encapsulation efficiency is between 12.5% and 91%. In some embodiments of the nebulized lipid nanoparticle, the encapsulation efficiency is between 20% and 90%. In some embodiments of the nebulized lipid nanoparticle, the encapsulation efficiency is between 30% and 90%. In some embodiments of the nebulized lipid nanoparticle, the encapsulation efficiency is between 40% and 90%. In some embodiments of the nebulized lipid nanoparticle, the encapsulation efficiency is between 50% and 90%. In some embodiments of the nebulized lipid nanoparticle, the encapsulation efficiency is between 60% and 90%. In some embodiments of the nebulized lipid nanoparticle, the encapsulation efficiency is between 70% and 90%. In some embodiments of the nebulized lipid nanoparticle, the encapsulation efficiency is between 80% and 90%. In some embodiments of the nebulized lipid nanoparticle, the encapsulation efficiency is about 10%. In some embodiments of the nebulized lipid nanoparticle, the encapsulation efficiency is about 15%. In some embodiments of the nebulized lipid nanoparticle, the encapsulation efficiency is about 20%. In some embodiments of the nebulized lipid nanoparticle, the encapsulation efficiency is about 25%. In some embodiments of the nebulized lipid nanoparticle, the encapsulation efficiency is about 30%. In some embodiments of the nebulized lipid nanoparticle, the encapsulation efficiency is about 35%. In some embodiments of the nebulized lipid nanoparticle, the encapsulation efficiency is about 40%. In some embodiments of the nebulized lipid nanoparticle, the encapsulation efficiency is about 45%. In some embodiments of the nebulized lipid nanoparticle, the encapsulation efficiency is about 50%. In some embodiments of the nebulized lipid nanoparticle, the encapsulation efficiency is about 55%. In some embodiments of the nebulized lipid nanoparticle, the encapsulation efficiency is about 60%. In some embodiments of the nebulized lipid nanoparticle, the encapsulation efficiency is about 65%. In some embodiments of the nebulized lipid nanoparticle, the encapsulation efficiency is about 70%. In some embodiments of the nebulized lipid nanoparticle, the encapsulation efficiency is about 75%. In some embodiments of the nebulized lipid nanoparticle, the encapsulation efficiency is about 80%. In some embodiments of the nebulized lipid nanoparticle, the encapsulation efficiency is about 85%. In some embodiments of the nebulized lipid nanoparticle, the encapsulation efficiency is about 90%, about 91, about 92, about 93, about 94, about 95, about 96, about 97, about 98, about 99%.

In some embodiments of the nebulized lipid nanoparticle, the PDI is between 0.419-0.652. In some embodiments of the nebulized lipid nanoparticle, the PDI is between 0.4-0.6. In some embodiments of the nebulized lipid nanoparticle, the PDI is between 0.4-0.5. In some embodiments of the nebulized lipid nanoparticle, the PDI is between 0.5-0.6.

In some embodiments of the nebulized lipid nanoparticle, the total output rate (TOR) is between 195-789 (µL/min). In some embodiments of the nebulized lipid nanoparticle, the total output rate (TOR) is between 195-750 (L/min). In some embodiments of the nebulized lipid nanoparticle, the total output rate (TOR) is between 195-700 (L/min). In some embodiments of the nebulized lipid nanoparticle, the total output rate (TOR) is between 195-650 (L/min). In some embodiments of the nebulized lipid nanoparticle, the total output rate (TOR) is between 195-600 (µL/min). In some embodiments of the nebulized lipid nanoparticle, the total output rate (TOR) is between 195-500 (µL/min). In some embodiments of the nebulized lipid nanoparticle, the total output rate (TOR) is between 195-400 (µL/min). In some embodiments of the nebulized lipid nanoparticle, the total output rate (TOR) is between 195-300 (µL/min). In some embodiments of the nebulized lipid nanoparticle, the total output rate (TOR) is about 200 (µL/min). In some embodiments of the nebulized lipid nanoparticle, the total output rate (TOR) is about 205 (µL/min). In some embodiments of the nebulized lipid nanoparticle, the total output rate (TOR) is about 195 (µL/min). In some embodiments of the nebulized lipid nanoparticle, the total output rate (TOR) is about 730 (µL/min). In some embodiments of the nebulized lipid nanoparticle, the total output rate (TOR) is about 790 (µL/min). In some embodiments of the nebulized lipid nanoparticle, the total output rate (TOR) is about 780 (µL/min).

In some embodiments of the nebulized lipid nanoparticle, the mass median diameter (MMD) is between 3.88-4.28 (µm). In some embodiments of the nebulized lipid nanoparticle, the mass median diameter (MMD) is between 3.88-4 (µm). In some embodiments of the nebulized lipid nanoparticle, the mass median diameter (MMD) is between 4-4.28 (µm). In some embodiments of the nebulized lipid nanoparticle, the mass median diameter (MMD) is about 3.7 (µm). In some embodiments of the nebulized lipid nanoparticle, the mass median diameter (MMD) is about 3.8 (µm). In some embodiments of the nebulized lipid nanoparticle, the mass median diameter (MMD) is about 3.9 (µm). In some embodiments of the nebulized lipid nanoparticle, the mass median diameter (MMD) is about 4.0 (µm). In some embodiments of the nebulized lipid nanoparticle, the mass median diameter (MMD) is about 4.1 (µm). In some embodiments of the nebulized lipid nanoparticle, the mass median diameter (MMD) is about 4.2 (µm).

In some embodiments of the nebulized lipid nanoparticle, the geometric standard deviation (GSD) is between 1.62-1.77. In some embodiments of the nebulized lipid nanoparticle, the geometric standard deviation (GSD) is between 1.7-1.8. In some embodiments of the nebulized lipid nanoparticle, the geometric standard deviation (GSD) is 1.6. In some embodiments of the nebulized lipid nanoparticle, the geometric standard deviation (GSD) is 1.65. In some embodiments of the nebulized lipid nanoparticle, the geometric standard deviation (GSD) is 1.7.

In some embodiments of the nebulized lipid nanoparticle, the % of fine particle fraction smaller than 5 µm (FPF<5 µm) is 61.7-70.81(%). In some embodiments of the nebulized lipid nanoparticle, the % of fine particle fraction smaller than 5 µm (FPF<5 µm) is 61-63(%). In some embodiments of the nebulized lipid nanoparticle, the % of fine particle fraction smaller than 5 µm (FPF<5 µm) is 63-65(%). In some embodiments of the nebulized lipid nanoparticle, the % of fine particle fraction smaller than 5 µm (FPF<5 µm) is 65-67(%). In some embodiments of the nebulized lipid nanoparticle, the % of fine particle fraction smaller than 5

μm (FPF<5 μm) is 67-69(%). In some embodiments of the nebulized lipid nanoparticle, the % of fine particle fraction smaller than 5 μm (FPF<5 μm) is 69-71(%). In some embodiments of the nebulized lipid nanoparticle, the % of fine particle fraction smaller than 5 μm (FPF<5 μm) is about 61(%). In some embodiments of the nebulized lipid nanoparticle, the % of fine particle fraction smaller than 5 μm (FPF<5 μm) is about 62 (%). In some embodiments of the nebulized lipid nanoparticle, the % of fine particle fraction smaller than 5 μm (FPF<5 μm) is about 63 (%). In some embodiments of the nebulized lipid nanoparticle, the % of fine particle fraction smaller than 5p m (FPF<5 μm) is about 64 (%). In some embodiments of the nebulized lipid nanoparticle, the % of fine particle fraction smaller than 5 μm (FPF<5 μm) is about 65 (%). In some embodiments of the nebulized lipid nanoparticle, the % of fine particle fraction smaller than 5 μm (FPF<5 μm) is about 66 (%). In some embodiments of the nebulized lipid nanoparticle, the % of fine particle fraction smaller than 5 μm (FPF<5 μm) is about 67 (%). In some embodiments of the nebulized lipid nanoparticle, the % of fine particle fraction smaller than 5 μm (FPF<5 μm) is about 68 (%). In some embodiments of the nebulized lipid nanoparticle, the % of fine particle fraction smaller than 5 μm (FPF<5 μm) is about 69 (%). In some embodiments of the nebulized lipid nanoparticle, the % of fine particle fraction smaller than 5 μm (FPF<5 μm) is about 70 (%). In some embodiments of the nebulized lipid nanoparticle, the % of fine particle fraction smaller than 5 μm (FPF<5 μm) is about 71 (%).

In some embodiments, the LNP comprises one or more components for gene editing, the cationic ionizable lipid is 4A3-SC7, the cationic ionizable SORT lipid is DODAP, the permanently cationic lipid is 14:0 EPC, phospholipid is 1,2-dioleoyl-sn-glycero-3-phosphoethanolamine (DOPE), the cholesterol, and/or the DMG-PEG.

In some embodiments, the LNP comprises one or more components for gene editing, the cationic ionizable lipid is 4A3-SC7, the cationic ionizable SORT lipid is DODAP, the permanently cationic lipid is 14:0 EPC, 1,2-distearoyl-sn-glycero-3-phosphocholine (DSPC), the cholesterol, and/or the DMG-PEG.

In some embodiments, the LNP comprises one or more components for gene editing, the cationic ionizable lipid is 4A3-SC7, the cationic ionizable SORT lipid is DODAP, the permanently cationic lipid is 14:0 TAP, phospholipid is 1,2-dioleoyl-sn-glycero-3-phosphoethanolamine (DOPE), the cholesterol, and/or the DMG-PEG.

In some embodiments, the LNP comprises one or more components for gene editing, the cationic ionizable lipid is 4A3-SC7, the cationic ionizable SORT lipid is DODAP, the permanently cationic lipid is 14:0 TAP, 1,2-distearoyl-sn-glycero-3-phosphocholine (DSPC), the cholesterol, and/or the DMG-PEG.

In some embodiments, the LNP c comprises one or more components for gene editing, the cationic ionizable lipid is 5A2-SC8, the cationic ionizable SORT lipid is DODAP, the permanently cationic lipid is 14:0 EPC, phospholipid is 1,2-dioleoyl-sn-glycero-3-phosphoethanolamine (DOPE), the cholesterol, and/or the DMG-PEG.

In some embodiments, the LNP comprises one or more components for gene editing, the cationic ionizable lipid is 5A2-SC8, the cationic ionizable SORT lipid is DODAP, the permanently cationic lipid is 14:0 EPC, 1,2-distearoyl-sn-glycero-3-phosphocholine (DSPC), the cholesterol, and/or the DMG-PEG.

In some embodiments, the LNP comprises one or more components for gene editing, the cationic ionizable lipid is 5A2-SC8, the cationic ionizable SORT lipid is DODAP, the permanently cationic lipid is 14:0 TAP, phospholipid is 1,2-dioleoyl-sn-glycero-3-phosphoethanolamine (DOPE), the cholesterol, and/or the DMG-PEG.

In some embodiments, the LNP comprises one or more components for gene editing, the cationic ionizable lipid is 5A2-SC8, the cationic ionizable SORT lipid is DODAP, the permanently cationic lipid is 14:0 TAP, 1,2-distearoyl-sn-glycero-3-phosphocholine (DSPC), the cholesterol, and/or the DMG-PEG.

In some embodiments, the LNP comprises one or more components for gene editing, 4A3-SC7 at a molar percentage between about 10% and about 30%, DODAP at a molar percentage between about 5% and about 40%, 14:0 TAP at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises one or more components for gene editing, 4A3-SC7 at a molar percentage between about 10% and about 15%, DODAP at a molar percentage between about 5% and about 20%, 14:0 TAP at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises one or more components for gene editing, 4A3-SC7 at a molar percentage between about 10% and about 30%, DODAP at a molar percentage between about 5% and about 40%, 14:0 EPC at a molar percentage between about 5% and about 25%, DOPE at a molar percentage between about 10% and about 30%, cholesterol at a molar percentage between about 30% and about 50%, and DMG-PEG at a molar percentage between about 0.5% and about 10%.

In some embodiments, the LNP comprises one or more components for gene editing, 4A3-SC7 at a molar percentage between about 10% and about 15%, DODAP at a molar percentage between about 5% and about 20%, 14:0 EPC at a molar percentage between about 10% and about 20%, DOPE at a molar percentage between about 15% and about 25%, cholesterol at a molar percentage between about 30% and about 40%, and DMG-PEG at a molar percentage between about 1% and about 5%.

In some embodiments, the LNP comprises one or more components for gene editing, 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about about 30%, and DMG-PEG at a molar percentage of about about 3%.

In some embodiments, the LNP comprises one or more components for gene editing, 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about about 32%, and DMG-PEG at a molar percentage of about about 3%.

In some embodiments, the LNP comprises one or more components for gene editing, 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%.

In some embodiments, the LNP comprises one or more components for gene editing, 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%.

In some embodiments, the LNP comprises one or more components for gene editing, 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises one or more components for gene editing, 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%, wherein the lipid:mRNA ratio is 36:1.

In some embodiments, the LNP comprises one or more components for gene editing, 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%, wherein the lipid:mRNA ratio is 33:1.

In some embodiments, the LNP comprises one or more components for gene editing, s 4A3-SC7 at a molar percentage of about 15%, DODAP at a molar percentage of about 15%, 14:0 EPC at a molar percentage of about 15%, DOPE at a molar percentage of about 22%, cholesterol at a molar percentage of about 30%, and DMG-PEG at a molar percentage of about 3%, wherein the lipid:mRNA ratio is 30:1.

In some embodiments, the LNP comprises one or more components for gene editing, 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%, wherein the lipid:mRNA ratio is 36:1.

In some embodiments, the LNP comprises one or more components for gene editing, 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises one or more components for gene editing, 4A3-SC7 at a molar percentage of about 15%, DODAP at a molar percentage of about 15%, 14:0 EPC at a molar percentage of about 12%, DOPE at a molar percentage of about 22%, cholesterol at a molar percentage of about 32%, and DMG-PEG at a molar percentage of about 3%, wherein the lipid:mRNA ratio is 30:1.

In some embodiments, the LNP comprises one or more components for gene editing, 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%, wherein the lipid:mRNA ratio is 36:1.

In some embodiments, the LNP comprises one or more components for gene editing, 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%, wherein the lipid:mRNA ratio is 33:1.

In some embodiments, the LNP comprises one or more components for gene editing, 4A3-SC7 at a molar percentage of about 15%, DODAP at a molar percentage of about 15%, 14:0 TAP at a molar percentage of about 15%, DOPE at a molar percentage of about 22%, cholesterol at a molar percentage of about 30%, and DMG-PEG at a molar percentage of about 3%, wherein the lipid:mRNA ratio is 30:1.

In some embodiments, the LNP comprises one or more components for gene editing, 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 36:1.

In some embodiments, the LNP comprises one or more components for gene editing, 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 33:1.

In some embodiments, the LNP comprises one or more components for gene editing, 4A3-SC7 at a molar percentage of about 15%, DODAP at a molar percentage of about 15%, 14:0 TAP at a molar percentage of about 12%, DOPE at a molar percentage of about 22%, cholesterol at a molar percentage of about 32%, and DMG-PEG at a molar percentage of about 3%, wherein the lipid:mRNA ratio is 30:1.

A. Gene-Editing Payload

In some embodiments, the LNP composition comprises one or more components for gene editing, 4A3-SC7 at a molar percentage of about 19%, DODAP at a molar percentage of about 20%, DOPE at a molar percentage of about 19%, cholesterol at a molar percentage of about 38%, DMG-PEG at a molar percentage of about 4%, wherein the LNPs comprise a total lipid to RNA (weight/weight) ratio of about 40, and/or wherein a N/P ratio is about 13.

In some embodiments, the LNP composition comprises one or more components for gene editing, 4A3-SC7 at a molar percentage of about 19%, DODAP at a molar percentage of about 20%, DOPE at a molar percentage of about 19%, cholesterol at a molar percentage of about 38%, DMG-PEG at a molar percentage of about 4%, wherein the LNPs comprise a total lipid to RNA (weight/weight) ratio of about 30, and/or wherein a N/P ratio is about 10.

In some embodiments, the LNP composition comprises one or more components for gene editing, 4A3-SC7 at a molar percentage of about 19%, DODAP at a molar percentage of about 28%, DOPE at a molar percentage of about 17%, cholesterol at a molar percentage of about 33%, DMG-PEG at a molar percentage of about 3%, wherein the LNPs comprise a total lipid to RNA (weight/weight) ratio of about 30, and/or wherein a N/P ratio is about 11.

In some embodiments, the LNP composition comprises one or more components for gene editing, 4A3-SC7 at a molar percentage of about 19%, DODAP at a molar percentage of about 28%, DOPE at a molar percentage of about 17%, cholesterol at a molar percentage of about 33%, DMG-PEG at a molar percentage of about 3%, and/or wherein the LNPs comprise a total lipid to RNA (weight/weight) ratio of about 25, and/or wherein a N/P ratio is about 9.

In some embodiments, the LNP composition comprises one or more components for gene editing, 4A3-SC7 at a molar percentage of about 19%, DODAP at a molar percentage of about 37%, DOPE at a molar percentage of about 14%, cholesterol at a molar percentage of about 28%, DMG-PEG at a molar percentage of about 3%, wherein the LNPs comprise a total lipid to RNA (weight/weight) ratio of about 30, and/or wherein a N/P ratio is about 12.

In some embodiments, the LNP composition comprises one or more components for gene editing, 4A3-SC7 at a molar percentage of about 24%, DODAP at a molar percentage of about 19%, DOPE at a molar percentage of about 18%, cholesterol at a molar percentage of about 36%, DMG-PEG at a molar percentage of about 4%, wherein the LNPs comprise a total lipid to RNA (weight/weight) ratio of about 30, and/or wherein a N/P ratio is about 11.

In some embodiments, the LNP composition comprises one or more components for gene editing, 4A3-SC7 at a molar percentage of about 19%, DODAP at a molar percentage of about 20%, DOPE at a molar percentage of about 19%, cholesterol at a molar percentage of about 38%, DMG-PEG at a molar percentage of about 4%, and/or wherein the LNPs comprise a total lipid to RNA (weight/weight) ratio of about 40.

In some embodiments, the LNP composition comprises one or more components for gene editing, 4A3-SC7 at a molar percentage of about 19%, DODAP at a molar percentage of about 20%, DOPE at a molar percentage of about 19%, cholesterol at a molar percentage of about 36%, DMG-PEG at a molar percentage of about 6%, and/or wherein the LNPs comprise a total lipid to RNA (weight/weight) ratio of about 40.

In some embodiments, the LNP composition comprises one or more components for gene editing, 4A3-SC7 at a molar percentage of about 19%, DODAP at a molar percentage of about 20%, DOPE at a molar percentage of about 19%, cholesterol at a molar percentage of about 34%, DMG-PEG at a molar percentage of about 8%, and/or wherein the LNPs comprise a total lipid to RNA (weight/weight) ratio of about 40.

In some embodiments, the LNP composition comprises one or more components for gene editing, 4A3-SC7 at a molar percentage of about 19%, DODAP at a molar percentage of about 20%, DOPE at a molar percentage of about 19%, cholesterol at a molar percentage of about 32%, DMG-PEG at a molar percentage of about 10%, and/or wherein the LNPs comprise a total lipid to RNA (weight/weight) ratio of about 40.

In some embodiments, the LNP composition comprises one or more components for gene editing, 4A3-SC7 at a molar percentage of about 16%, DODAP at a molar percentage of about 16%, DOPE at a molar percentage of about 16%, cholesterol at a molar percentage of about 50%, DMG-PEG at a molar percentage of about 4%, and/or wherein the LNPs comprise a total lipid to RNA (weight/weight) ratio of about 40.

In some embodiments, the LNP composition comprises one or more components for gene editing, 4A3-SC7 at a molar percentage of about 14%, DODAP at a molar percentage of about 22%, DOPE at a molar percentage of about 11%, cholesterol at a molar percentage of about 50%, DMG-PEG at a molar percentage of about 3%, and/or wherein the LNPs comprise a total lipid to RNA (weight/weight) ratio of about 25.

In some embodiments, the LNP composition comprises one or more components for gene editing, 4A3-SC7 at a molar percentage of about 15%, DODAP at a molar percentage of about 16%, DOPE at a molar percentage of about 22%, cholesterol at a molar percentage of about 44%, DMG-PEG at a molar percentage of about 3%, and/or wherein the LNPs comprise a total lipid to RNA (weight/weight) ratio of about 36.

In some embodiments, the LNP composition comprises one or more components for gene editing, 4A3-SC7 at a molar percentage from about 13% to about 15%, DODAP at a molar percentage from about 15% to about 25%, DOPE at a molar percentage from about 10% to about 25%, cholesterol at a molar percentage from about 40% to about 60%, DMG-PEG at a molar percentage from about 2% to about 6%, wherein the LNPs comprise a total lipid to RNA (weight/weight) ratio from about 20:1 to about 40:1.

In some embodiments, the LNP composition comprises one or more components for gene editing, 4A3-SC7 at a molar percentage from about 10% to about 20%, DODAP at a molar percentage from about 15% to about 25%, DOPE at a molar percentage from about 10% to about 25%, cholesterol at a molar percentage from about 30% to about 60%, DMG-PEG at a molar percentage from about 2% to about 6%, wherein the LNPs comprise a total lipid to RNA (weight/weight) ratio from about 20:1 to about 40:1.

EXAMPLES

Example 1

Figure 1:
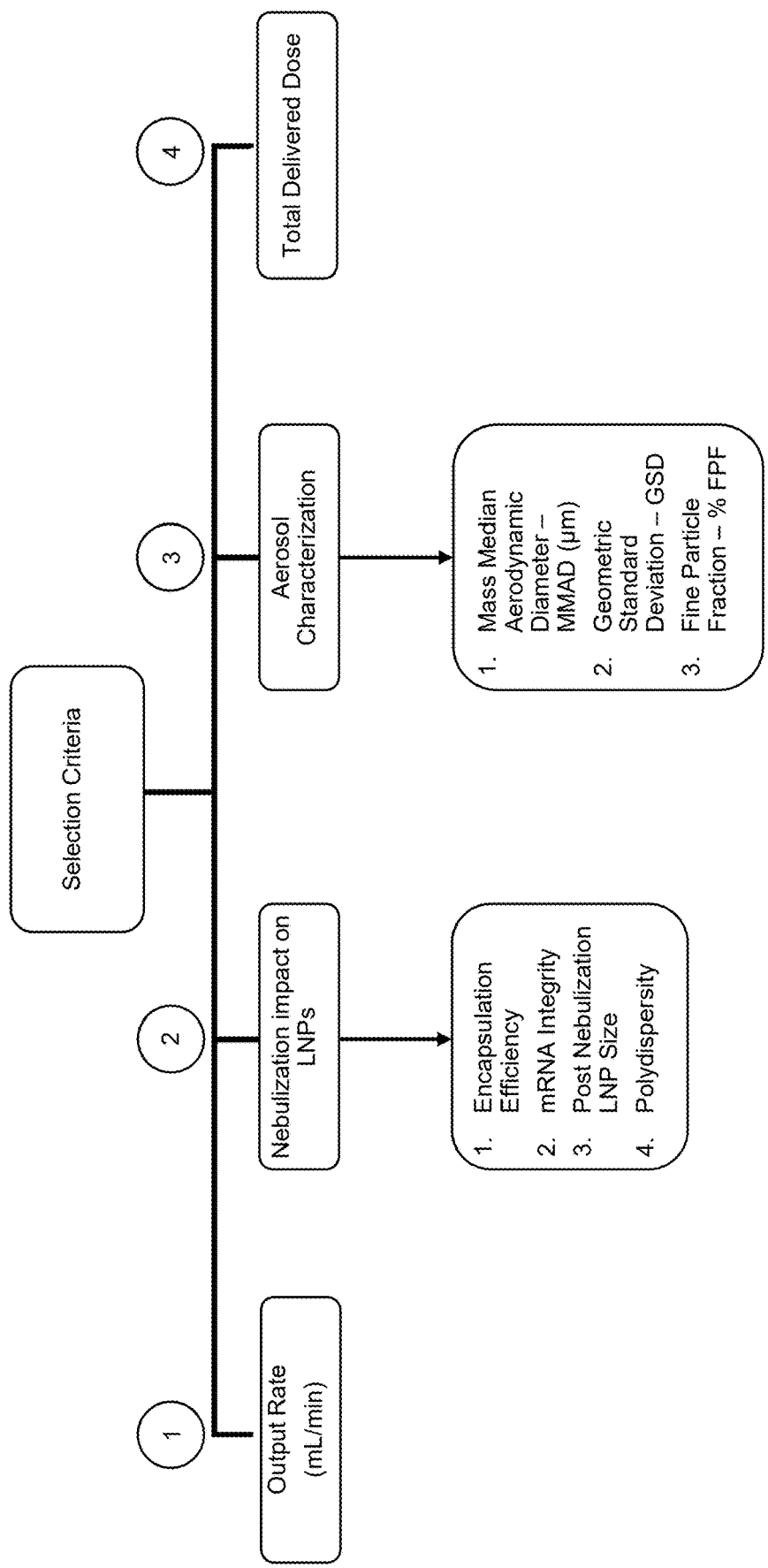

This example describes experiments to show nebulization of a liquid pharmaceutical compositions containing mRNA-containing LNPs prepared using the lipid composition termed "Composition A." FIG. 1 shows a schematic of criteria used to evaluate aerosolized pharmaceutical compositions. Composition A includes 4A3-SC7, 14:0 EPC, DOPE, cholesterol, and DMG-PEG at molar percentages of about 19%, about 20%, about 19%, about 39%, and about 3.8%, respectively; and its lipid to RNA (weight/weight) ratio is about 30. This formulation is used to deliver mRNA encoding DNAI1 for treatment of PCD.

TABLE 9

| Criteria for assessing LNP compositions | |
|---|---|
| Nebulization Rate (mL/min) | Treatment times ≤20 min (as short as possible) |
| Impact on LNPs | Encapsulation Efficiency (>70%) |
| | mRNA Integrity (D <10%) |
| | Post-Nebulization LNP Size (nm) |
| | Polydispersity |
| | Minimal changes in percent encapsulation efficiency (% EE) |
| | RNA integrity |
| Aerosol characteristics | Mass Median Aerodynamic Diameter—MMAD (μm) |
| | Geometric Standard Deviation—GSD |
| | Fine Particle Fraction—% FPF (<5.3 μm) |
| | Predicted Lung deposition patterns (% Tracheobronchial target region) |

Figure 2:
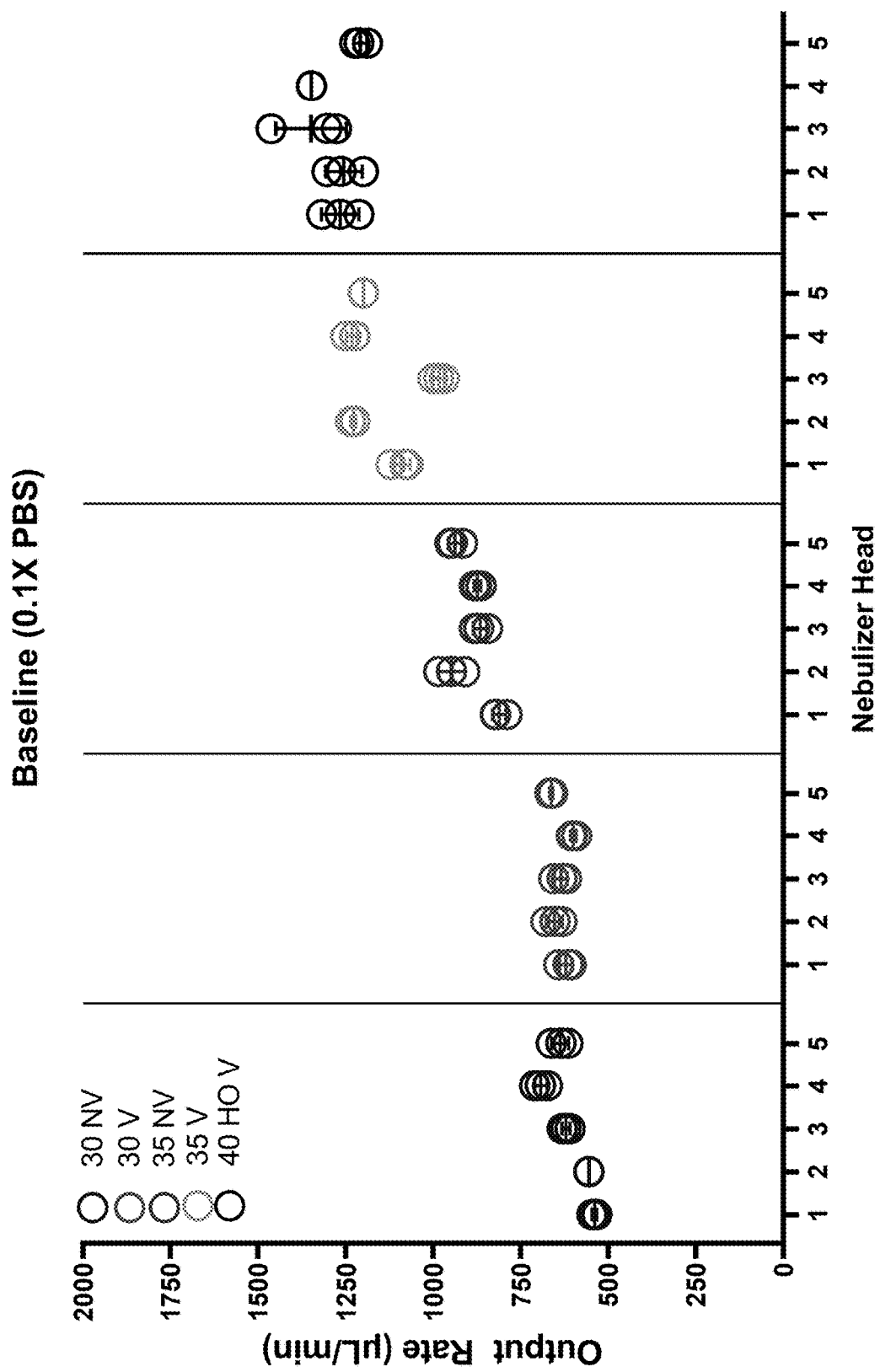

To establish a baseline, the PARI® eFlow® nebulizer device was operated using 0.1× phosphate buffered saline (PBS) as the input solution. Nebulization rates are shown in FIG. 2. The device was timed to deliver 1 mL of input material. The observed nebulization rate increased with increasing mesh size (40 HO V>35 V>35 NV>30 V>30 NV; V=vented, NV=not vented), with moderate variation between trials with different versions of the same head (#1-5).

Figure 3:
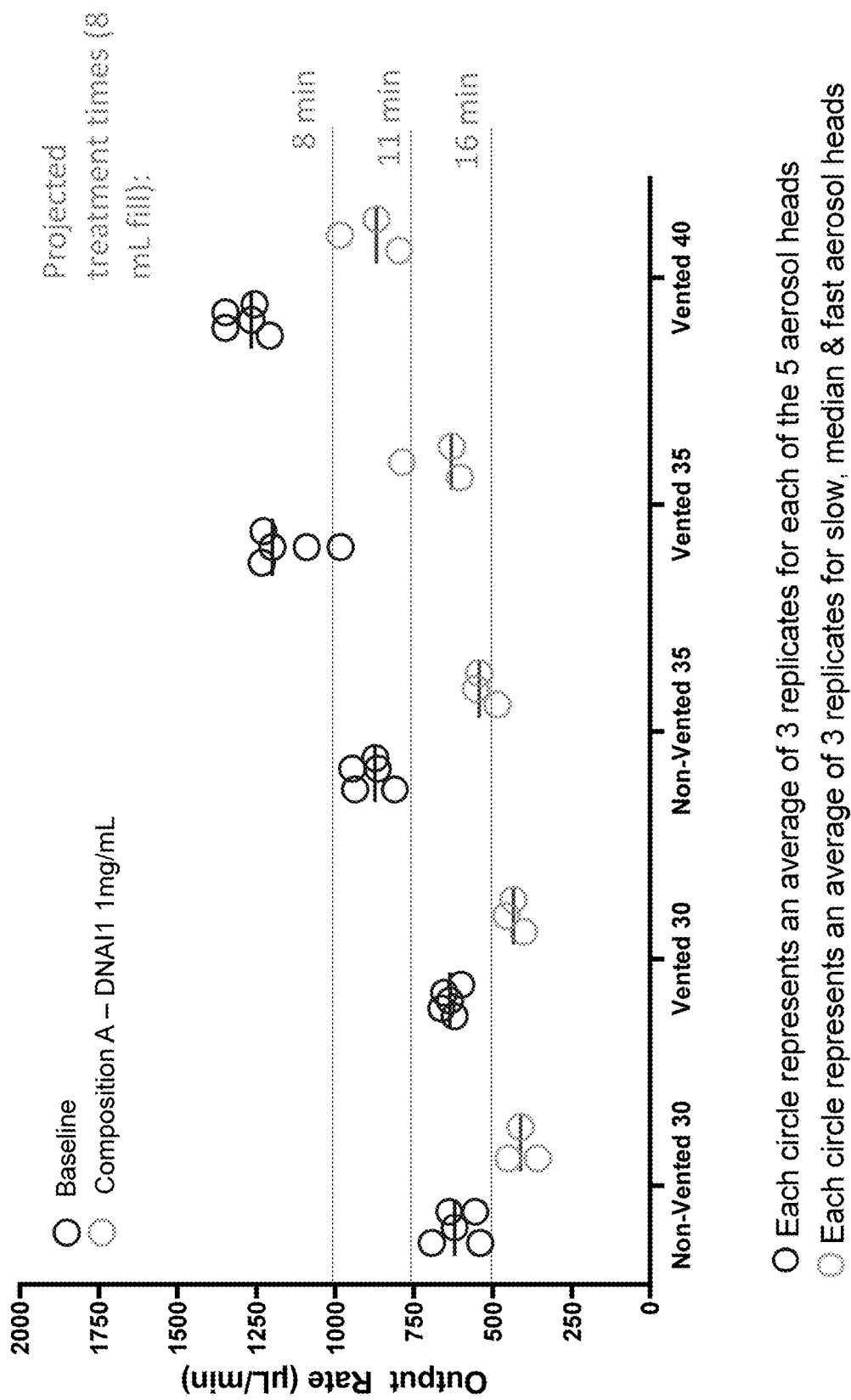

Composition A/DNAI1 at 1.0 mg/ml in 15 mM Tris pH 7.5 containing 10% sucrose or 2 mL of 0.1× PBS (Baseline) were nebulized to establish PARI® eFlow® nebulization rate. Output rates are shown in FIG. 3. Left circles on each column indicate baseline, while right circles on each column indicate Composition A 1 mg/mL. Nebulization rate of Composition A showed similar rate in 30 NV and 30 V, while the output rate was increased with increasing mesh size (0 HO V>35 V>35 NV>30 V=30 NV; V=vented, NV=not vented).

Figure 4A:
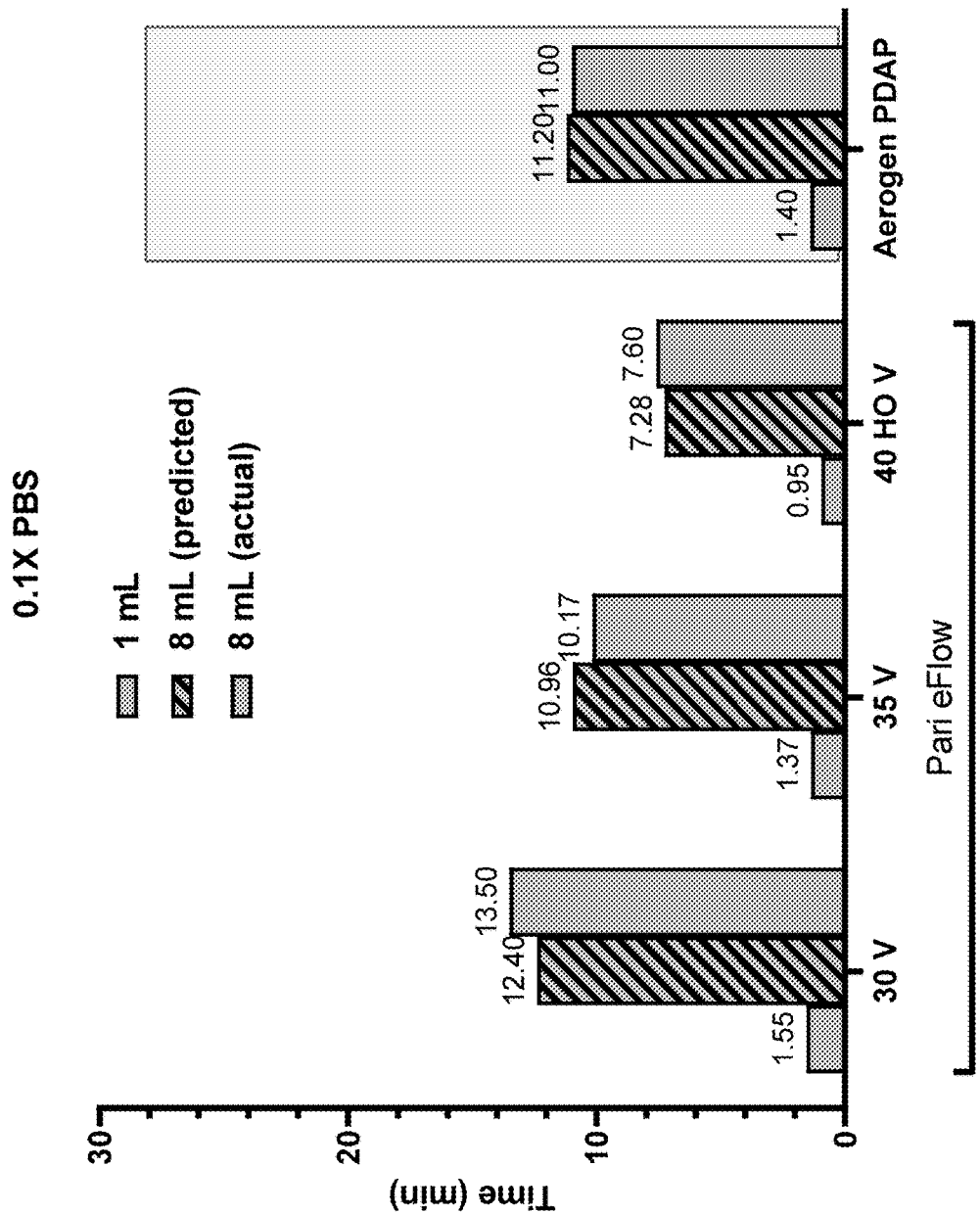
Figure 4B:
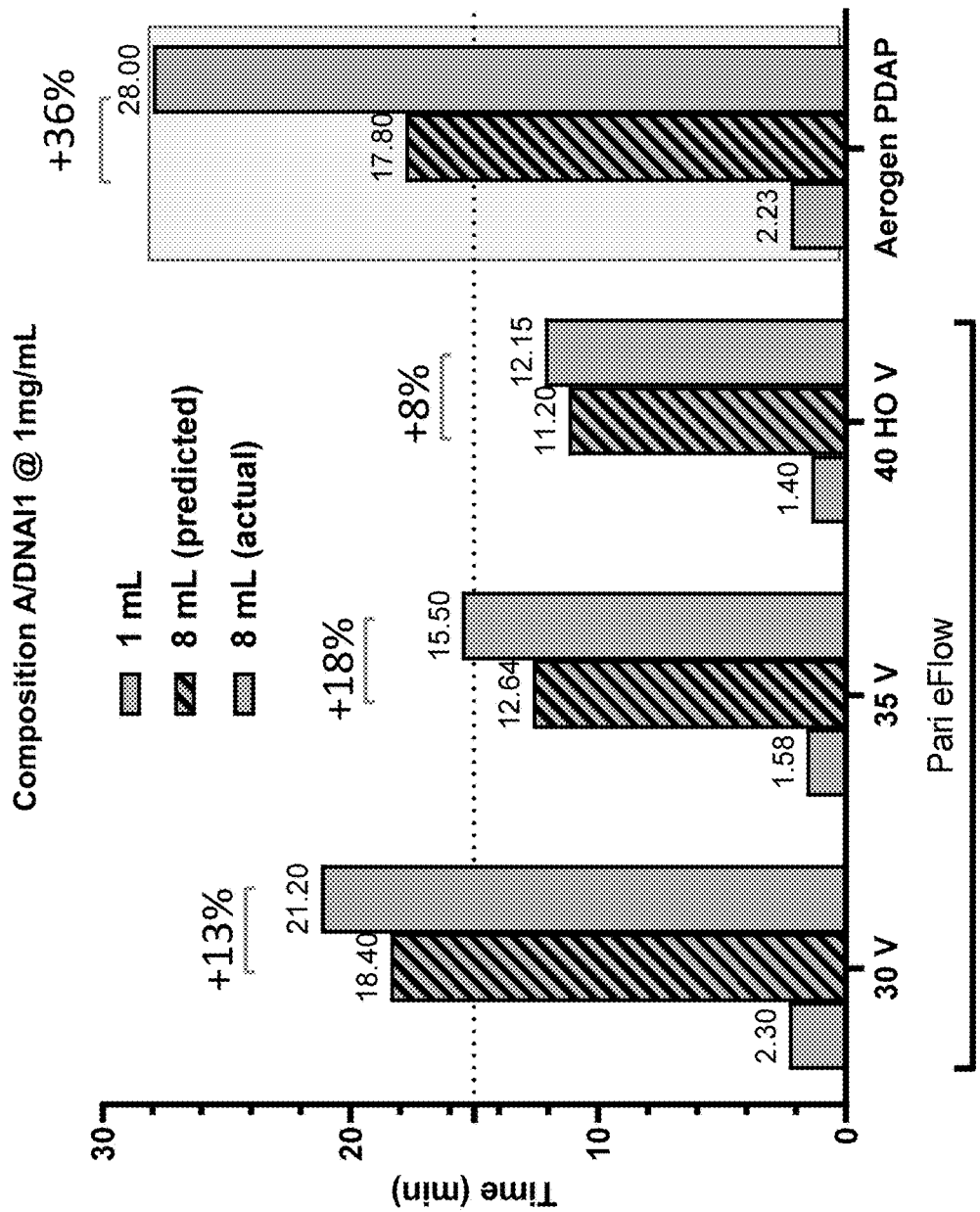

Predicted and actual nebulization times were compared for baseline (FIG. 4A) or Composition A/DNAI1 lipid nanoparticles at 1 mg/mL (FIG. 41B) in PARI® eFlow® device and Aerogen PDAP. In baseline experience, non-existent changes in actual nebulization times were observed in three PARI® eFlow® configurations and Aerogen PDAP. However, there were moderate increases of actual Composition A nebulization times (between 8 and 18%) using three eFlow® configurations (30 V, 35 V, and 40 HO V). Also, more drastic increase of actual Composition A nebulization time (36%) was observed when using Aerogen PDAP.

Figure 5:
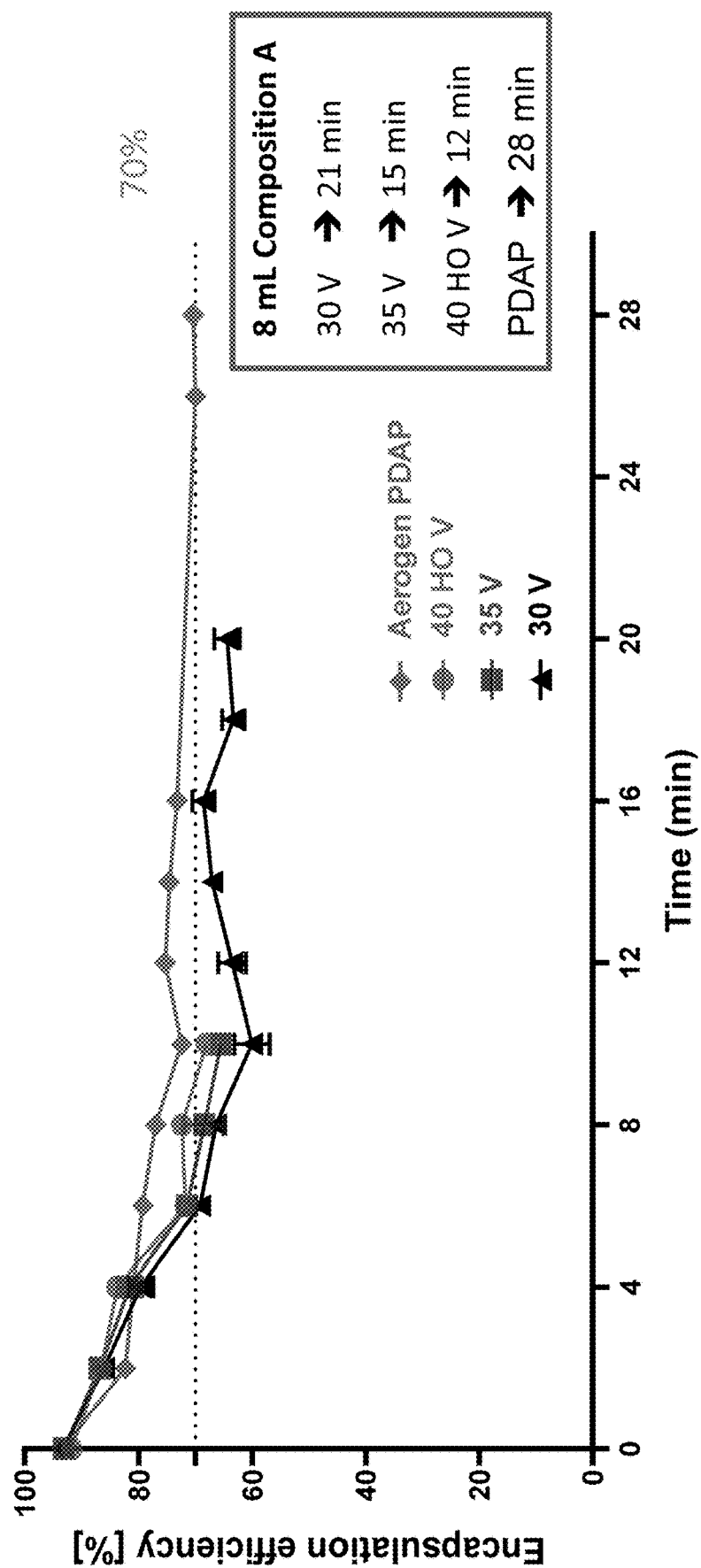
Figure 6:
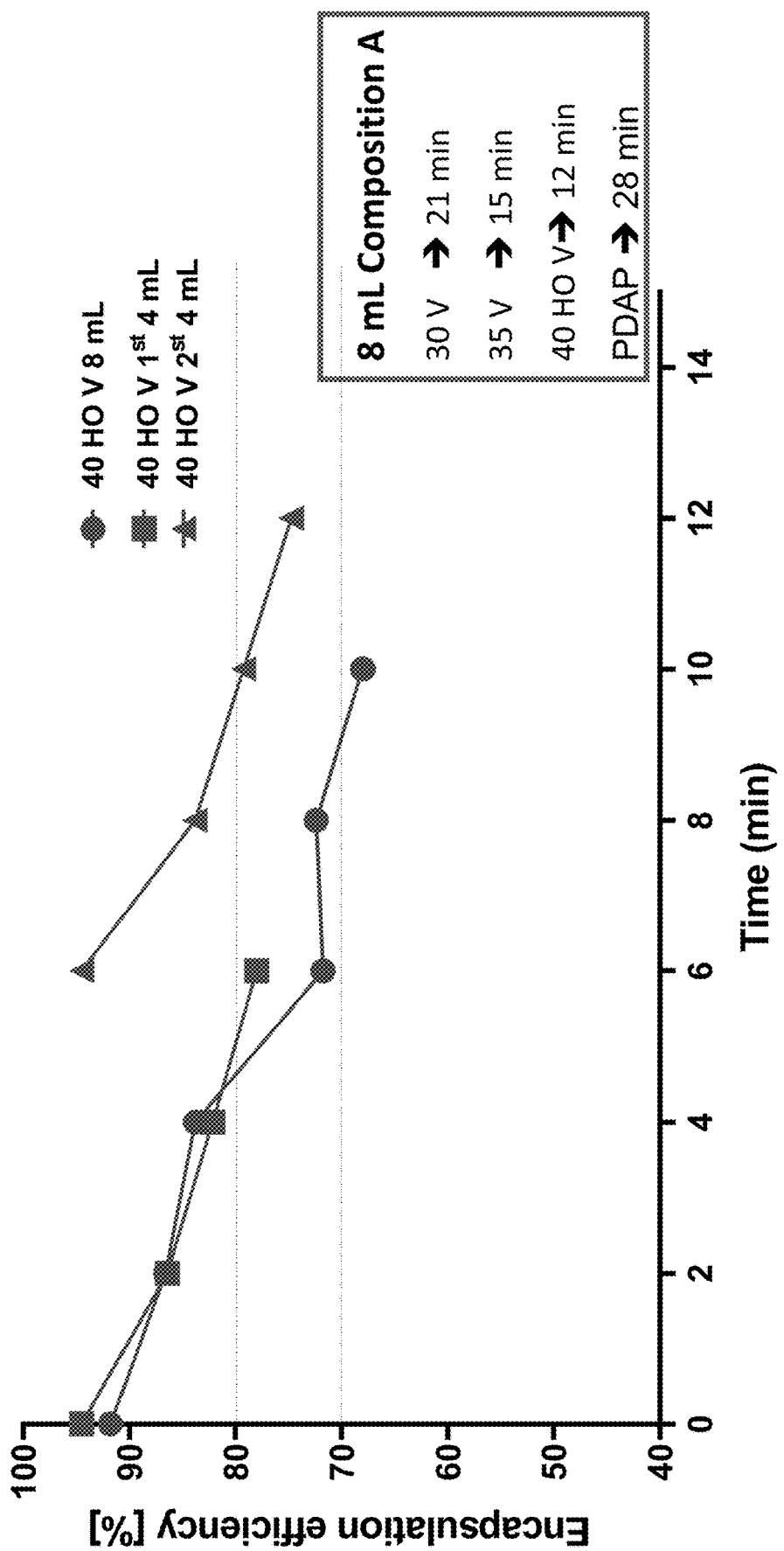
Figure 7:
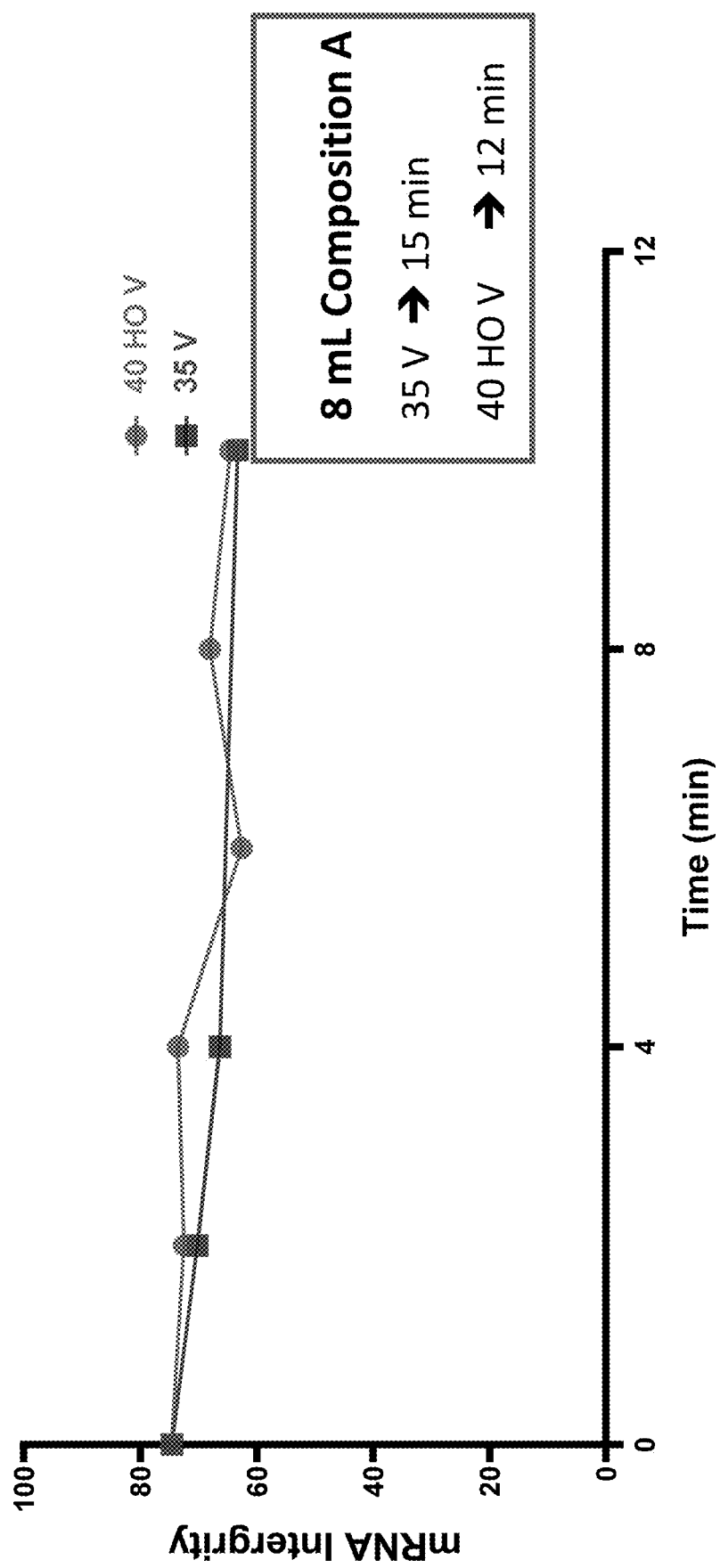

Encapsulation efficiency (%) and mRNA integrity were selected to determine nebulization impact on lipid nanoparticles. Encapsulation efficiency (%) was measured using Composition A/DNAI1 at 1.0 mg/ml in 15 mM Tris pH 7.5 containing 10% sucrose. Aerosols were collected and analyzed every 2 min over duration of 8 mL full reservoir nebulization in various PARI® eFlow® configurations and Aerogen PDAP (FIG. 5). At 10 minutes, the encapsulation efficiency of 40 HO V and 35 V were dropped slightly below 70% (68% and 65% respectively). The average encapsulation efficiently over the course of nebulization was >80% for both 40 HO V and 35 V. Aerogen PDAP remained >70% of encapsulation efficiency for the entire duration of nebulization. The encapsulation efficiently of 30 V decreased to 60% over 10 minutes before plateauing for the remaining time between 10 and 20 minutes. Additional encapsulation efficiently data for 40 HO V are shown in FIG. 6. The encapsulation efficiency of 40 HO V $1^{st}$ 4 mL was slightly below 80% while 40 HO V$2^{nd}$ 4 mL was about 75%.

mRNA integrity was also tested to measure the impact of nebulization (FIG. 7). Composition A/DNAI1 at 1.0 mg/ml in 15 mM Tris pH 7.5 containing 10% sucrose was subjected and its aerosols were collected and analyzed every 2 min over duration of 8 mL full reservoir nebulization. mRNA integrity was calculated by $\Delta(\text{RNA integrity}=\text{RNAi}_{post-neb}-\text{RNAi}_{pre-neb})$. At final time points (10 minutes), only the mRNA integrity of 40 HO V and 35 V were slightly exceeded 10% (10.2% and 11.3%, respectively).

Mesh nebulizer device were compared by Mass Median Aerodynamic Diameter (MMAD; μm), Geometric Standard Deviation (GSD), and Fine Particle Fraction (FPF; ≤5.3 μm) (data shown in Table 10 below).

TABLE 10

Comparison of mesh nebulizer device

| Formulation | Aerogen SOLO | Aerogen PDAP | Pari 30 V | Pari 35 V | Pari 35 HO V | Pari 40 HO V |
|---|---|---|---|---|---|---|
| MMAD (μm) | 3.58 μm | 4.11 μm | 3.47 (3.33) | 4.3 (3.78) | 4.23 | 4.93 (4.24) |
| GSD | 2.198 | 1.781 | 1.76 (1.57) | 1.9 (1.53) | 2.06 | 2.3 (1.63) |
| FPF % | 61 | 60 | 73.5 (84.0) | 58.0 (76.0) | 59.4 | 50.8 (64.1) |
| Nebulization Rate [μL/min] | 212 | 531 | 435 | 630 | 740 | 885 |
| Nebulization time 8 mL fill | 38 min | 28 min | 21 min | 15 min | N/A | 12 min |

Aerosol data were obtained using Phase I formulation (Composition A/DNAI1 at 1 mg/ml in 15 mM Tris pH 7.5 containing 10% sucrose). Values ill brackets were obtained under Study No.: WUO10 "Feasibility study for the nebulization of an mRNA in lipid nanoparticles inhalation formulation by ReCode Therapeutics with eFlow Technology" using a Laser diffraction analyzer, Helos BR, Sympatec GmbH at PARI® eFlow® using Composition A/DNAI1 at 0.5 mg/ml in 15 mM HEPES/Na-phosphate pH 7.4 containing 10% sucrose.

To predict deposition pattern, multiple-path particle dosimetry (MPPD) Yeh/Schum symmetric airway morphometry model was used as defaults for healthy human adult oral breathing scenario. Table 11 below shows percentage of lipid nanoparticles in each target region (Head; TB=tracheobronchial; P=peripheral airway), using both a model device and a predictive algorithm. Measured by $\mu g/cm^2$, most of lipid nanoparticles were targeted to TB.

TABLE 11

Deposition pattern of mesh nebulizer device

| Target region | Aerogen SOLO | Aerogen PDAP | Pari 30 V | Pari 35 V | Pari 35 HO V | Pari 40 HO V |
|---|---|---|---|---|---|---|
| Total (%) | 55.2 | 60.2 | 54.7 | 61.8 | 60.5 | 64.6 |
| Head (%) | 16.1 | 15.6 | 11.2 | 18.0 | 19.5 | 26.8 |
| TB (%) | 18.1 | 20.1 | 17.9 | 20.6 | 19.9 | 20.0 |
| P (%) | 20.9 | 24.5 | 25.6 | 23.2 | 21.2 | 17.8 |
| Total (mg/kg) | 0.074 | 0.080 | 0.073 | 0.082 | 0.081 | 0.086 |
| Head (mg/cm²) | 2.7 | 2.7 | 1.9 | 3.1 | 3.3 | 4.6 |
| TB 1-8 (mg/cm²) Trachea + bronchi | 5.0 | 5.5 | 4.9 | 5.7 | 5.5 | 5.5 |

TABLE 11-continued

Deposition pattern of mesh nebulizer device

| Target region | SOLO | Aerogen PDAP | Pari 30 V | Pari 35 V | Pari 35 HO V | Pari 40 HO V |
|---|---|---|---|---|---|---|
| 9-15 bronchioles | 0.6 | 0.7 | 0.6 | 0.7 | 0.7 | 0.7 |
| P (mg/cm$^2$) | 0.0011 | 0.0013 | 0.0014 | 0.0013 | 0.0012 | 0.0010 |

Figure 8A:
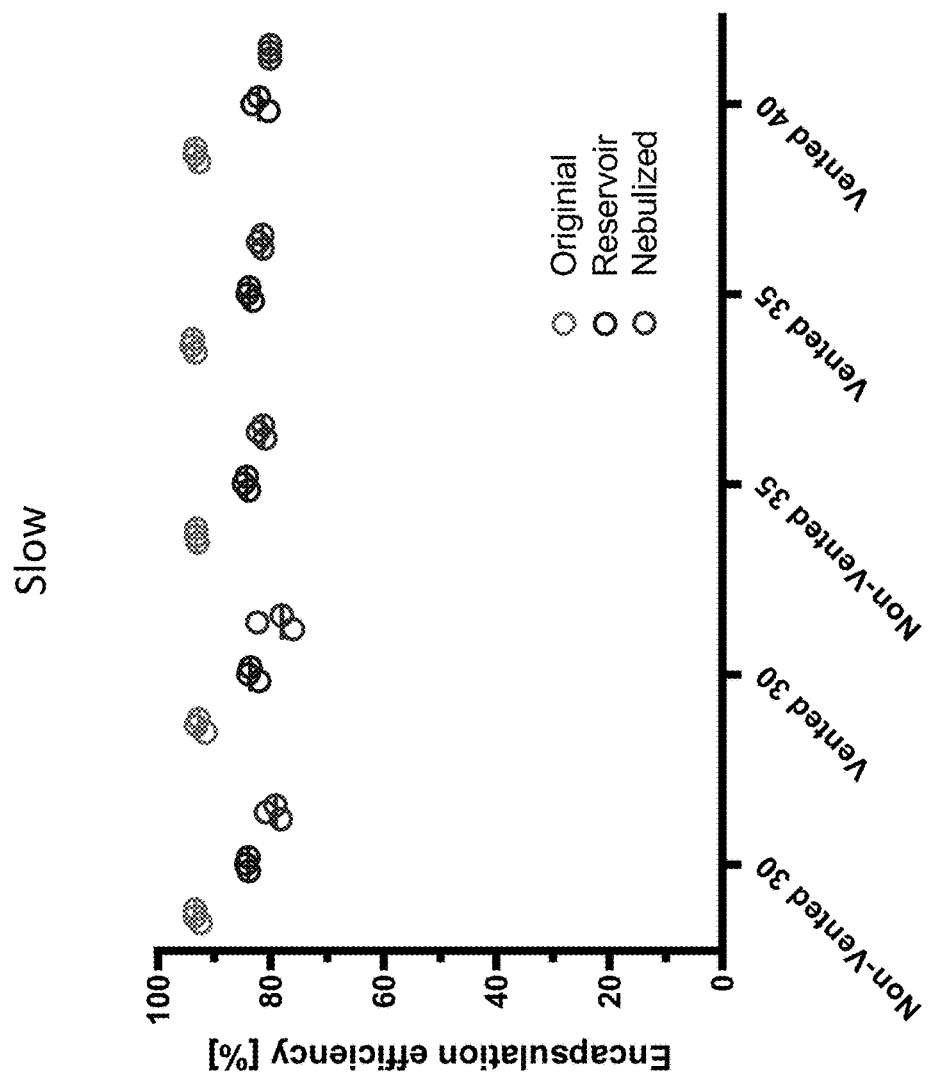
Figure 8B:
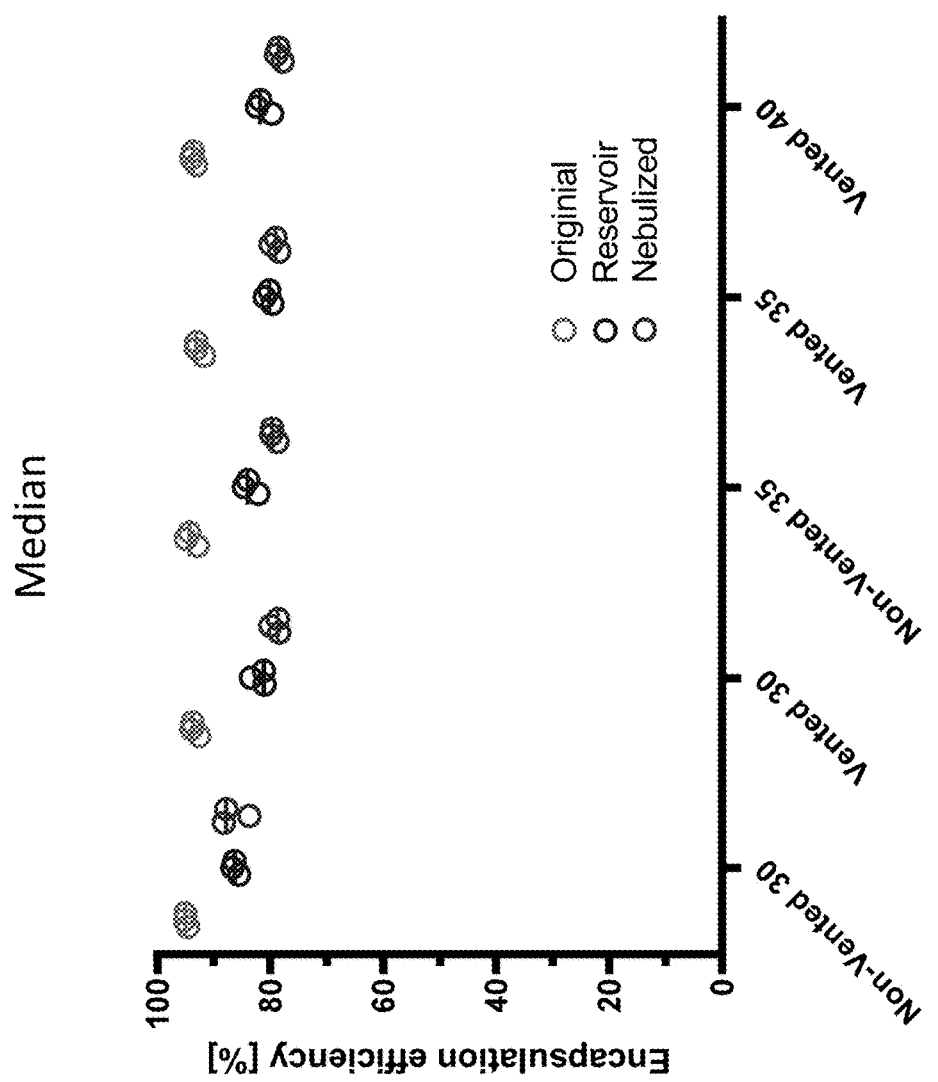
Figure 8C:
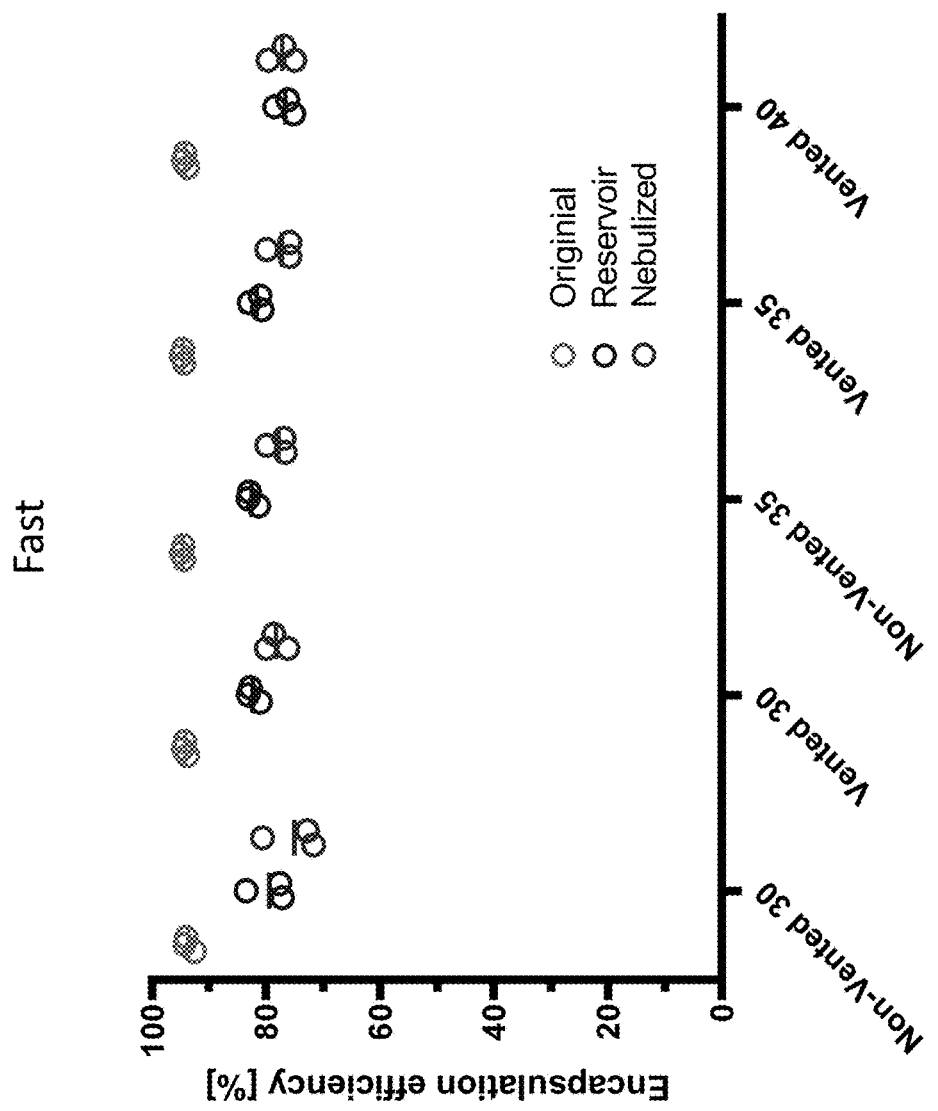

Assuming max fill vol = 8 mL delivery @ 1 mg/mL, BW = 60 kg and Head = 470 cm$^2$, TB = 2,690 cm$^2$ (290 [1-8] + 2400 [9-15] cm$^2$), P = 1,475,000 cm$^2$ Encapsulation efficiency (%) in PARI® eFlow® nebulizer heads were measured using Composition A/DNAI1 at 1.0 mg/ml in 15 mM Tris pH 7.5 containing 10% sucrose (FIGS. 8A-8C). Each head configurations were evaluated at slow, median and fast. Left circles on each column indicate original, middle circles on each column indicate reservoir, and right circles on each column indicate nebulized.

Figure 9A:
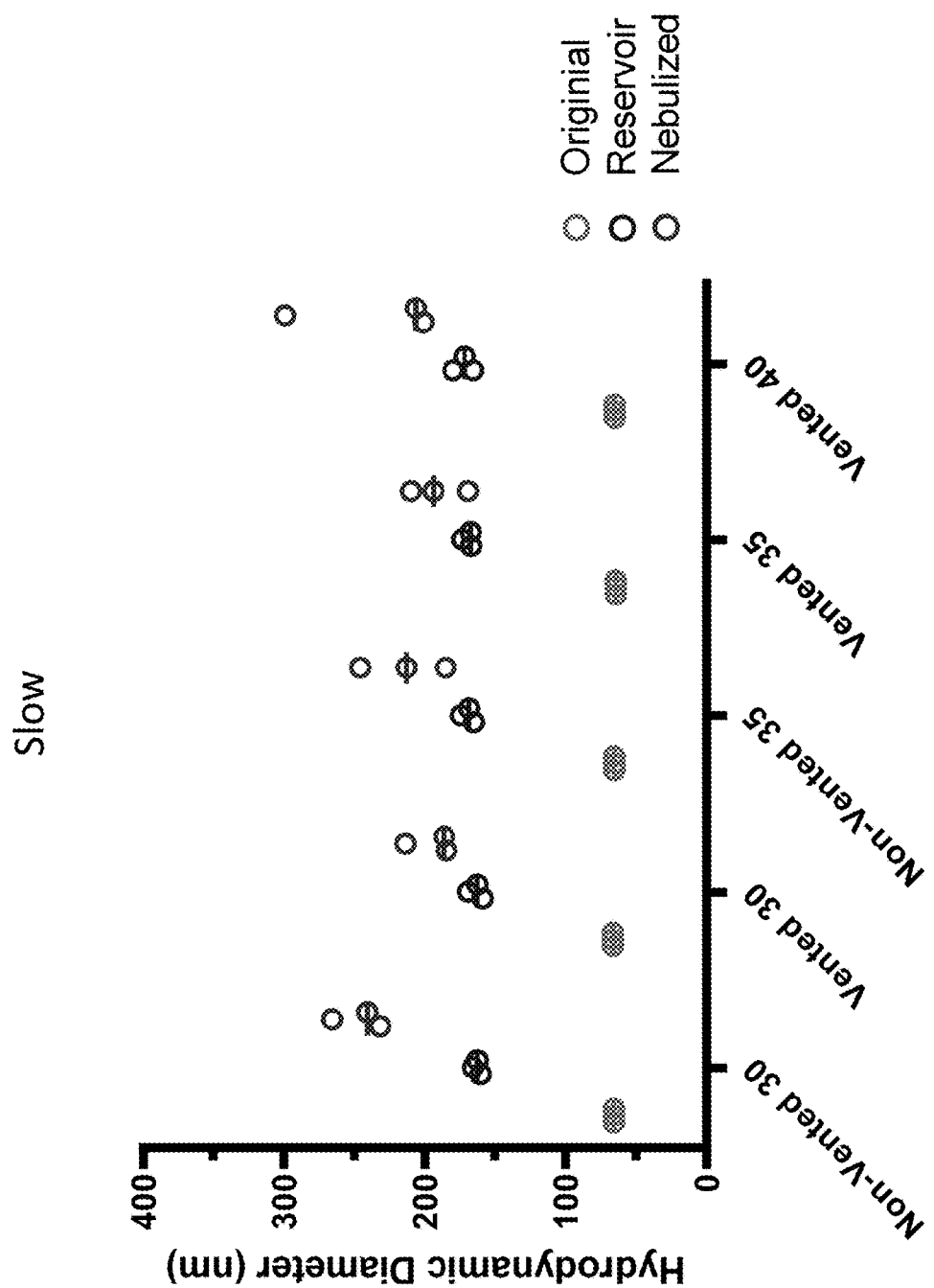
Figure 9B:
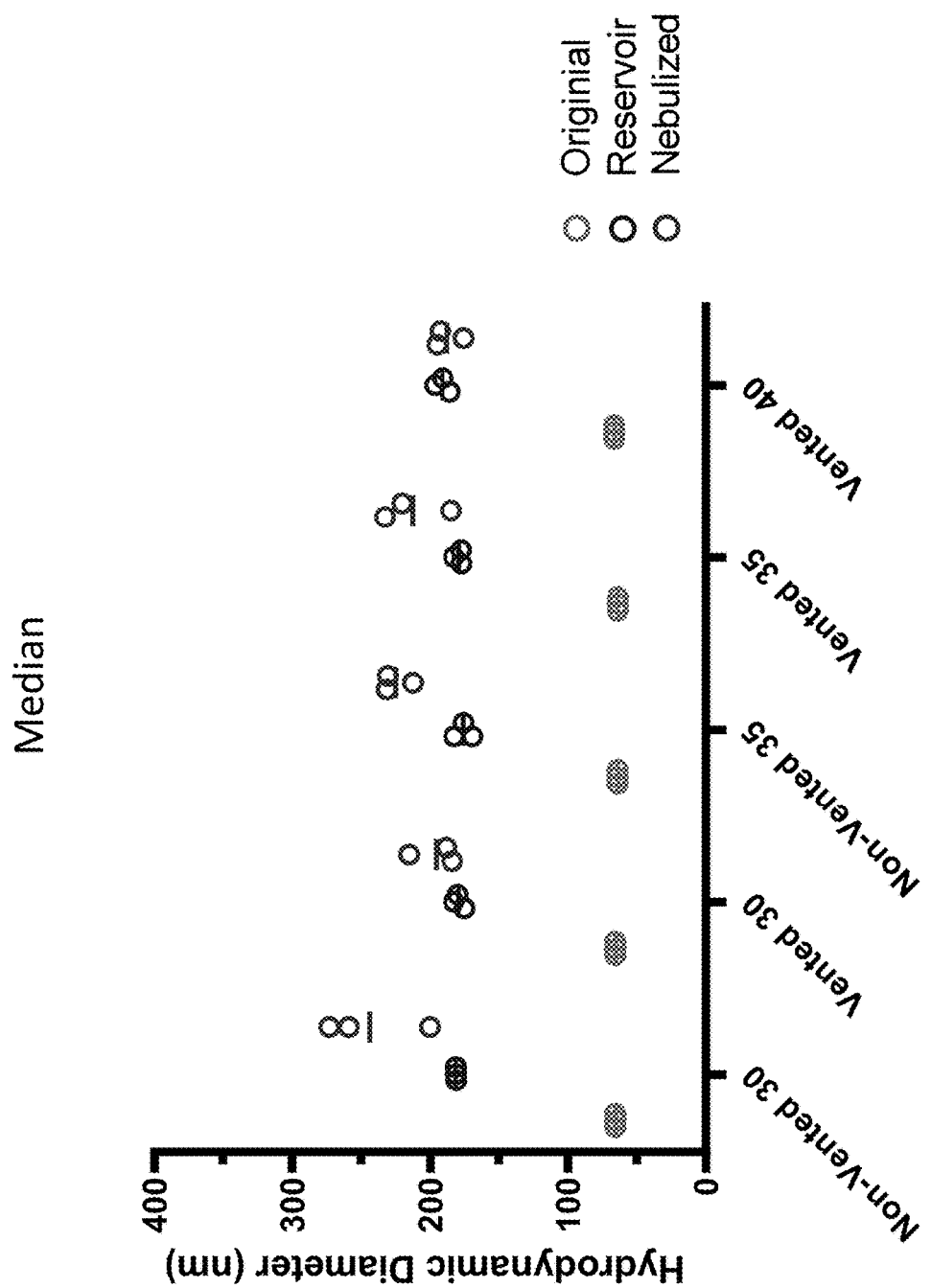
Figure 9C:
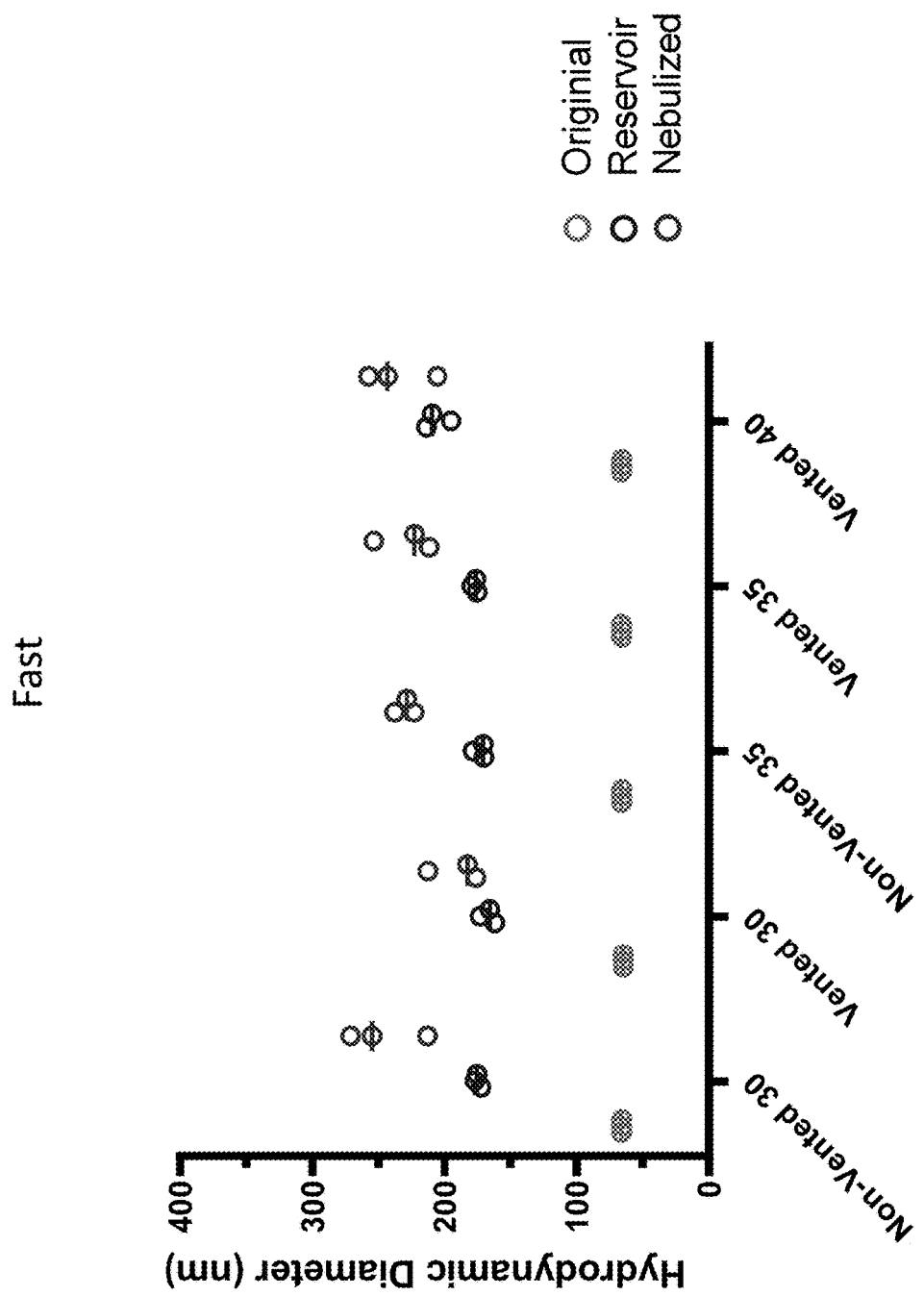

Hydrodynamic diameter (nm) in PARI® eFlow® nebulizer heads were measured using Composition A/DNAI1 at 1.0 mg/ml in 15 mM Tris pH 7.5 containing 10% sucrose (FIGS. 9A-9C). Each head configurations were evaluated at slow, median and fast. Left circles on each column indicate original, middle circles on each column indicate reservoir, and right circles on each column indicate nebulized.

Figure 10A:
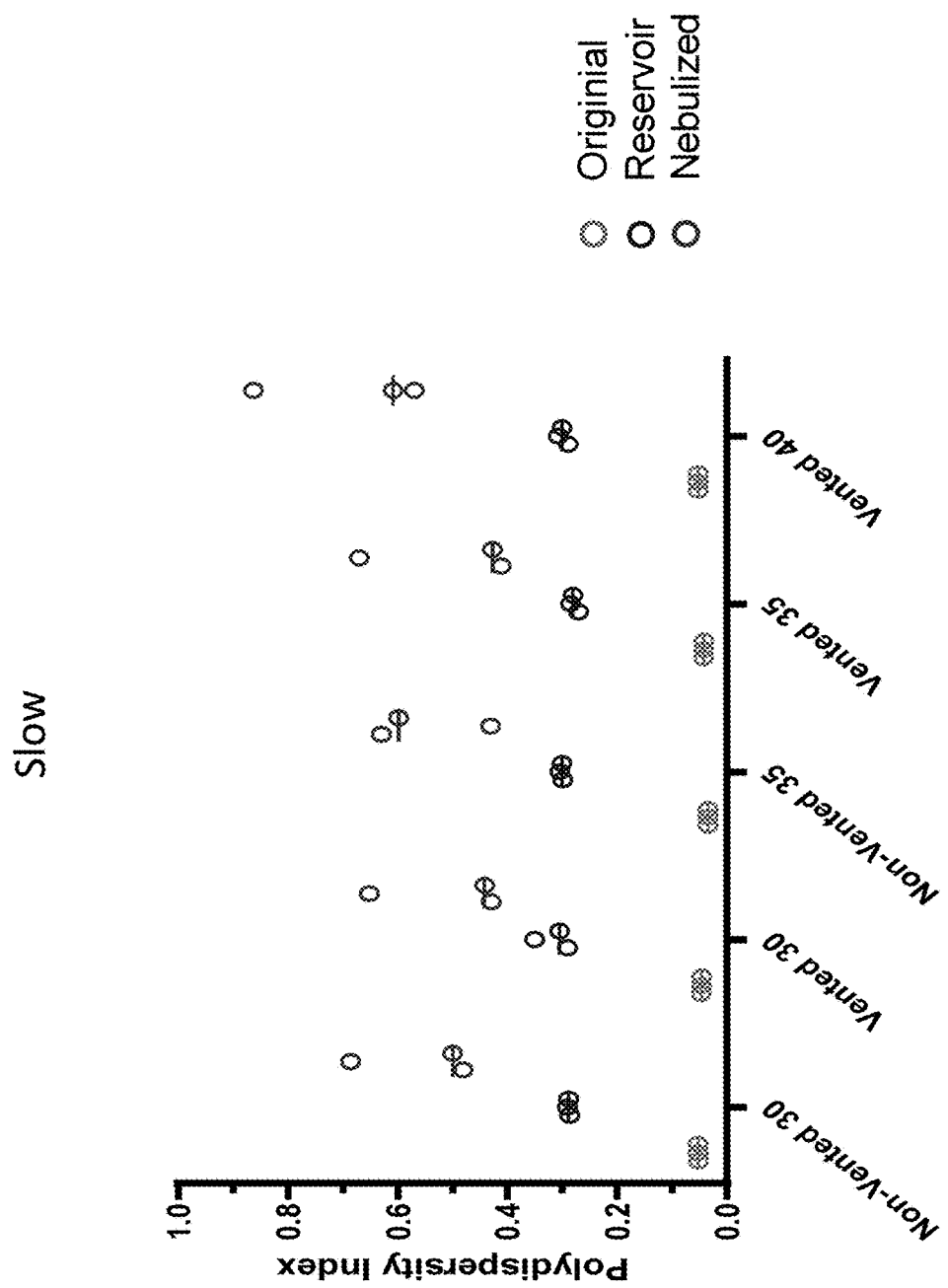
Figure 10B:
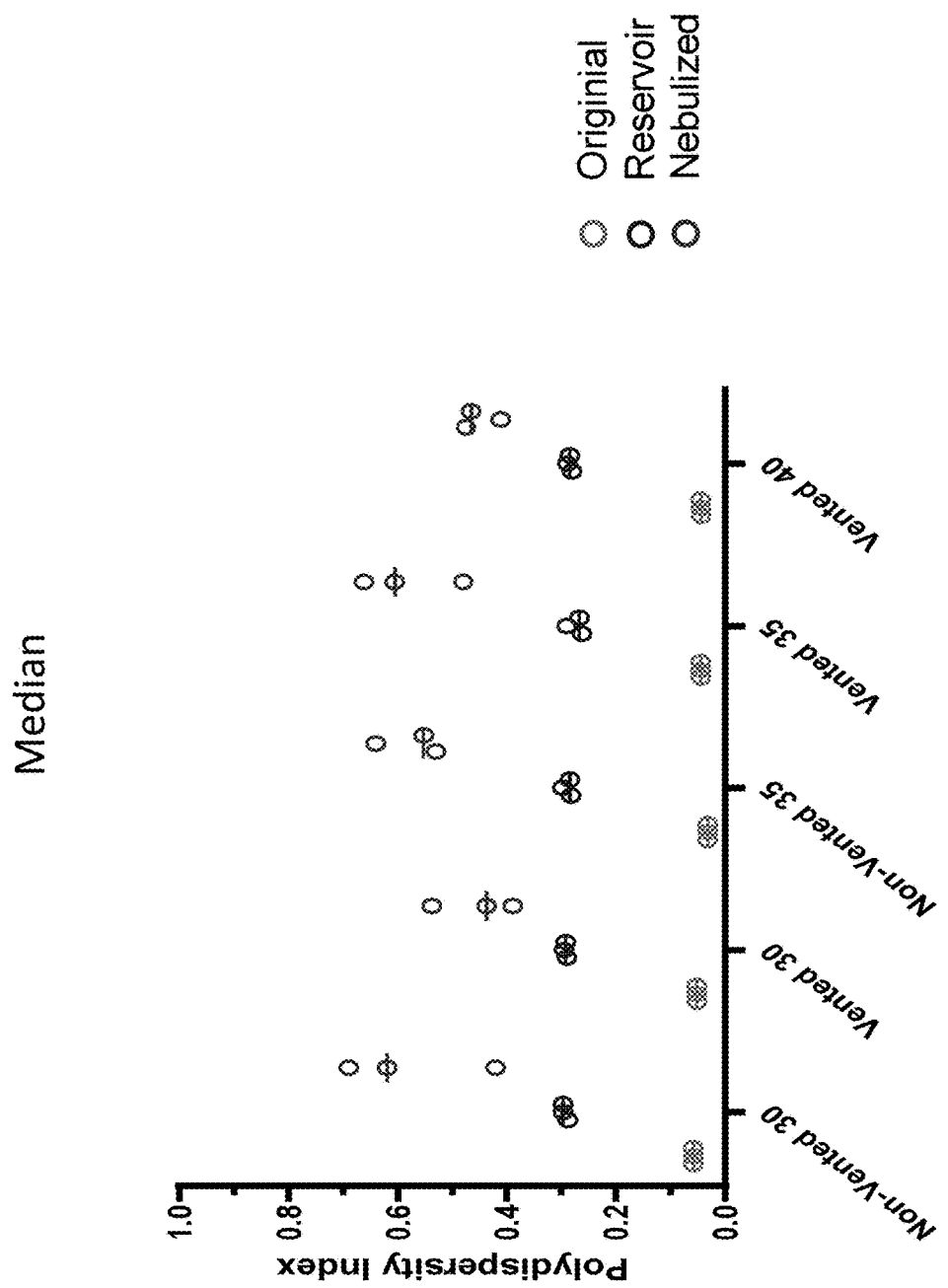
Figure 10C:
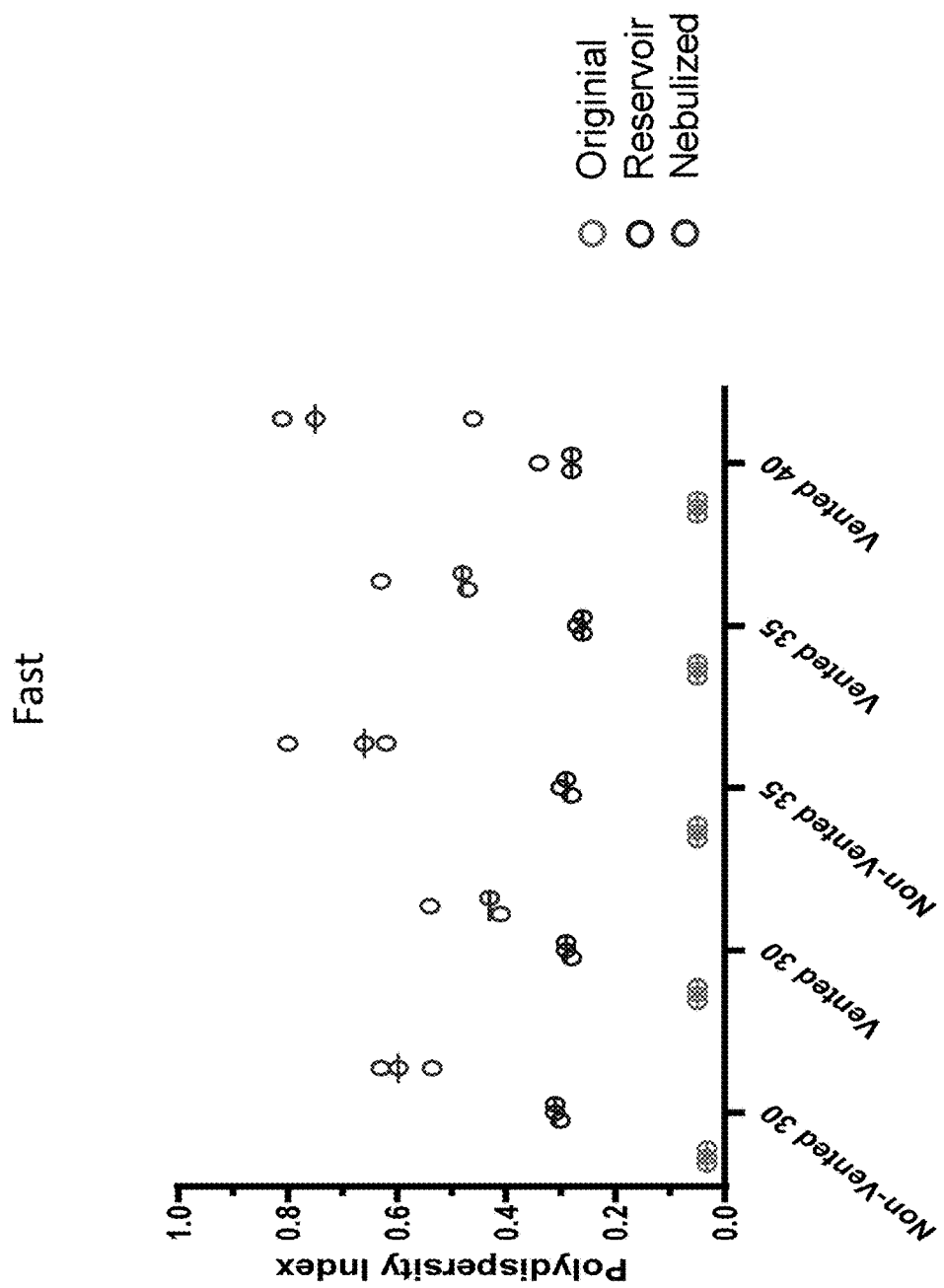

Polydispersity index in PARI® eFlow® nebulizer heads were measured using Composition A/DNAI1 at 1.0 mg/ml in 15 mM Tris pH 7.5 containing 10% sucrose (FIGS. 10A-10C). Each head configurations were evaluated at slow, median and fast. Left circles on each column indicate original, middle circles on each column indicate reservoir, and right circles on each column indicate nebulized.

Figure 11:
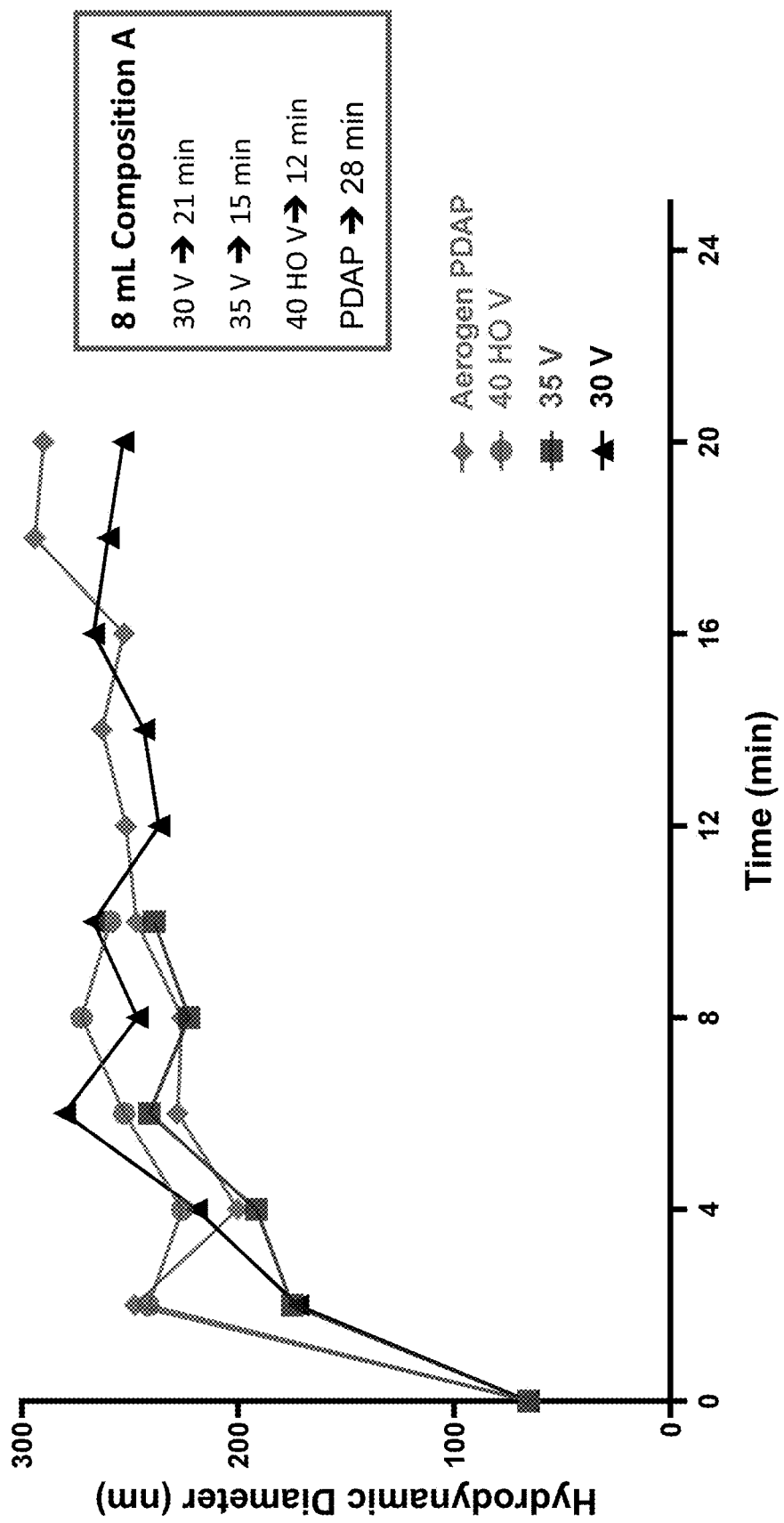

Hydrodynamic diameter (nm) in PARI® nebulizer heads were measured using Composition A/DNAI1 at 1.0 mg/ml in 15 mM Tris pH 7.5 containing 10% sucrose (FIG. 11).

Figure 12:
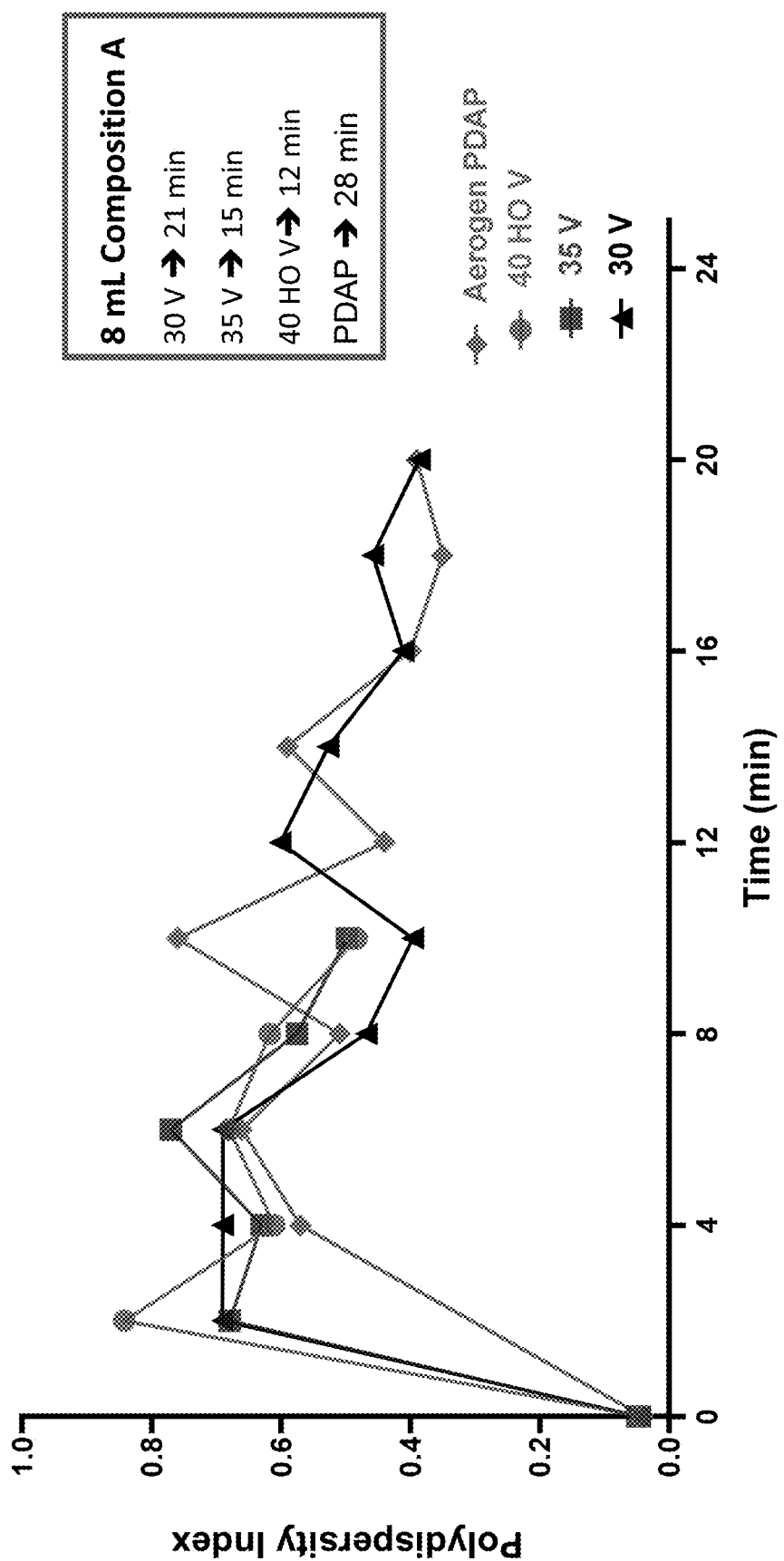
Figures 13A, 13B:
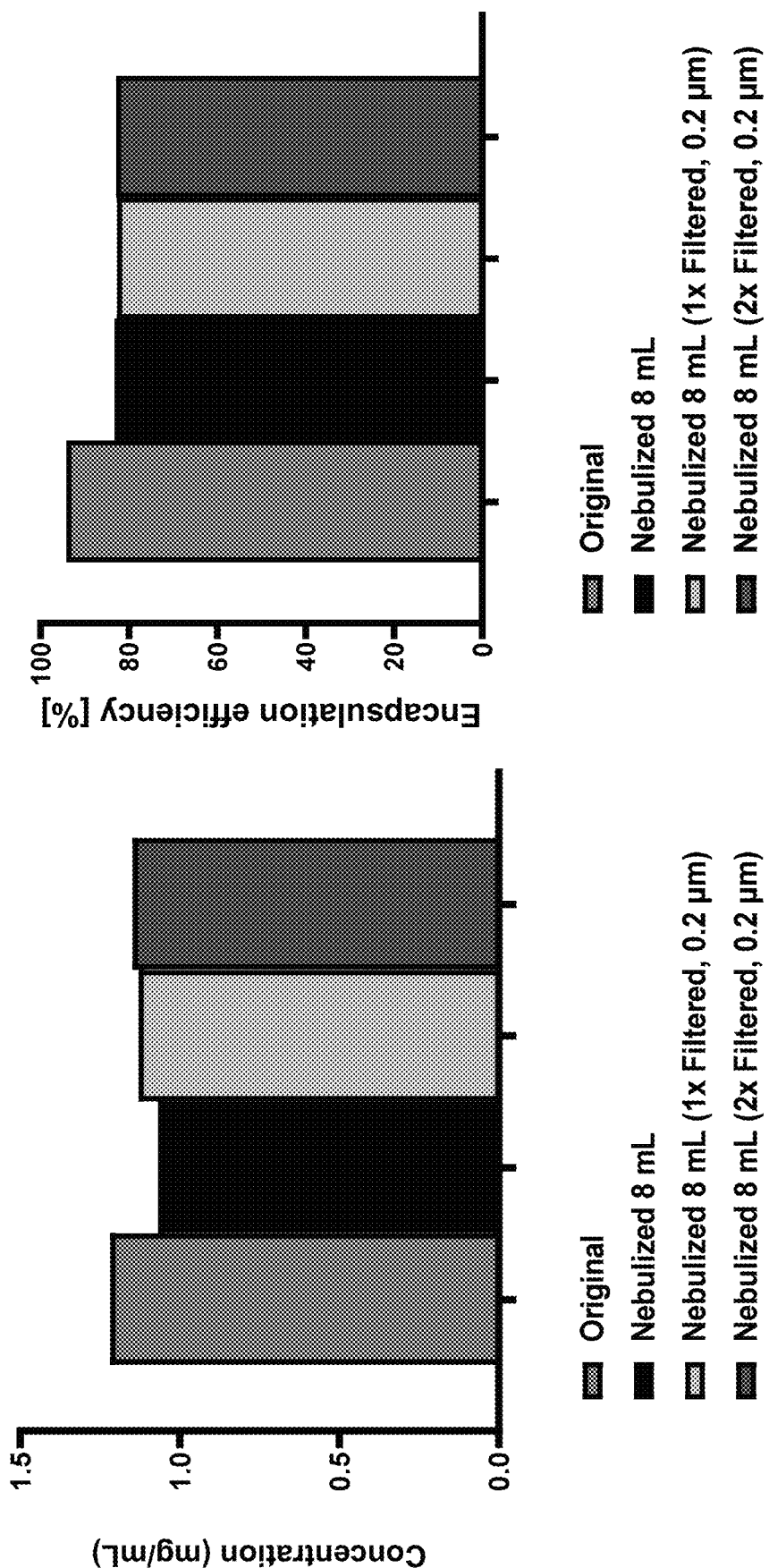
Figures 13C, 13D:
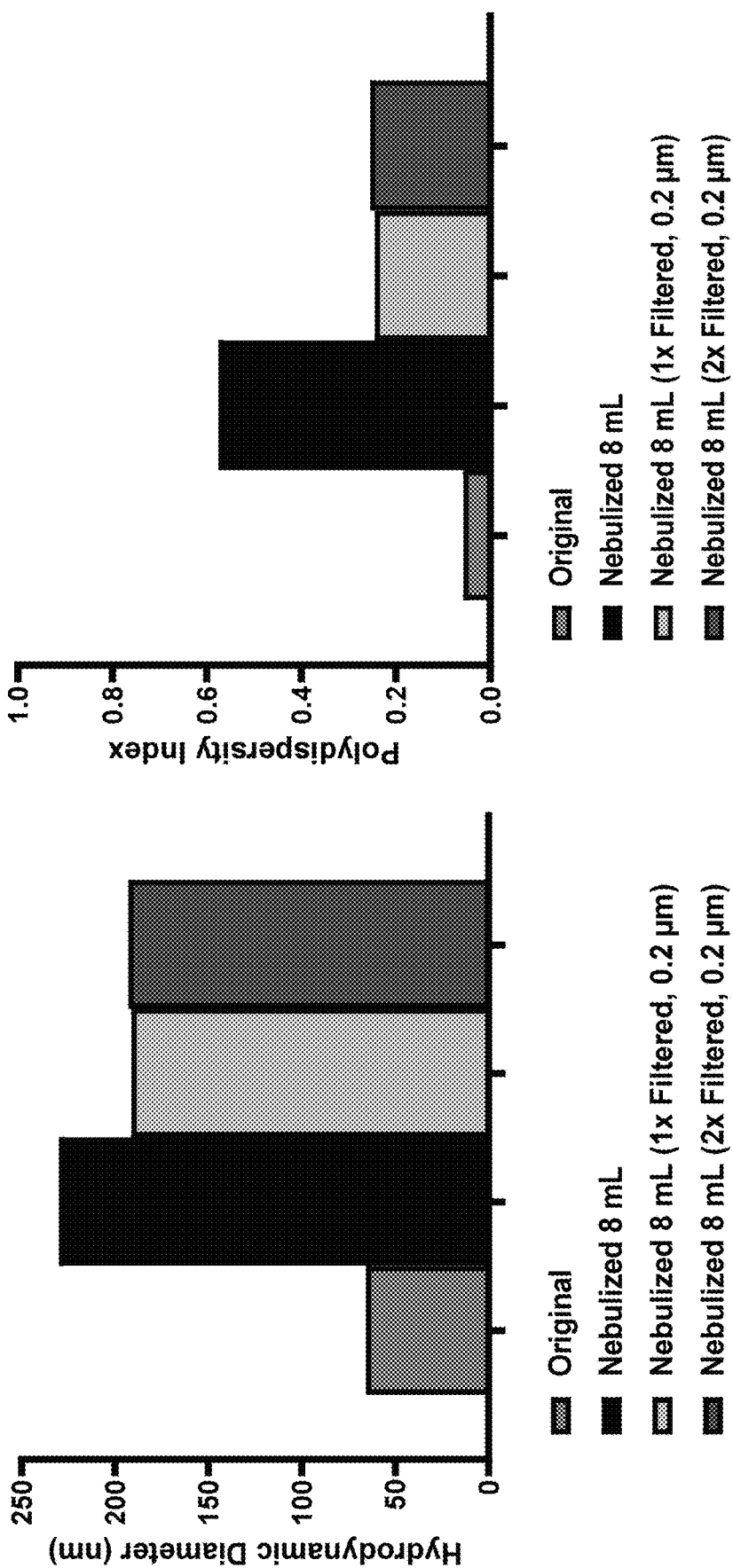

Polydispersity index in PARI® nebulizer heads were measured using Composition A/DNAI1 at 1.0 mg/ml in 15 mM Tris pH 7.5 containing 10% sucrose (FIG. 12).

Composition A/DNAI1 at 1.0 mg/ml in 15 mM Tris pH 7.5 containing 10% sucrose were subjected to PARI® eFlow® nebulizer to determine concentration (mg/mL), encapsulation efficiently (%), hydrodynamic diameter (nm), and polydispersity index (FIGS. 13A-13D) in 40 HO Fastest configuration.

Figure 14A:
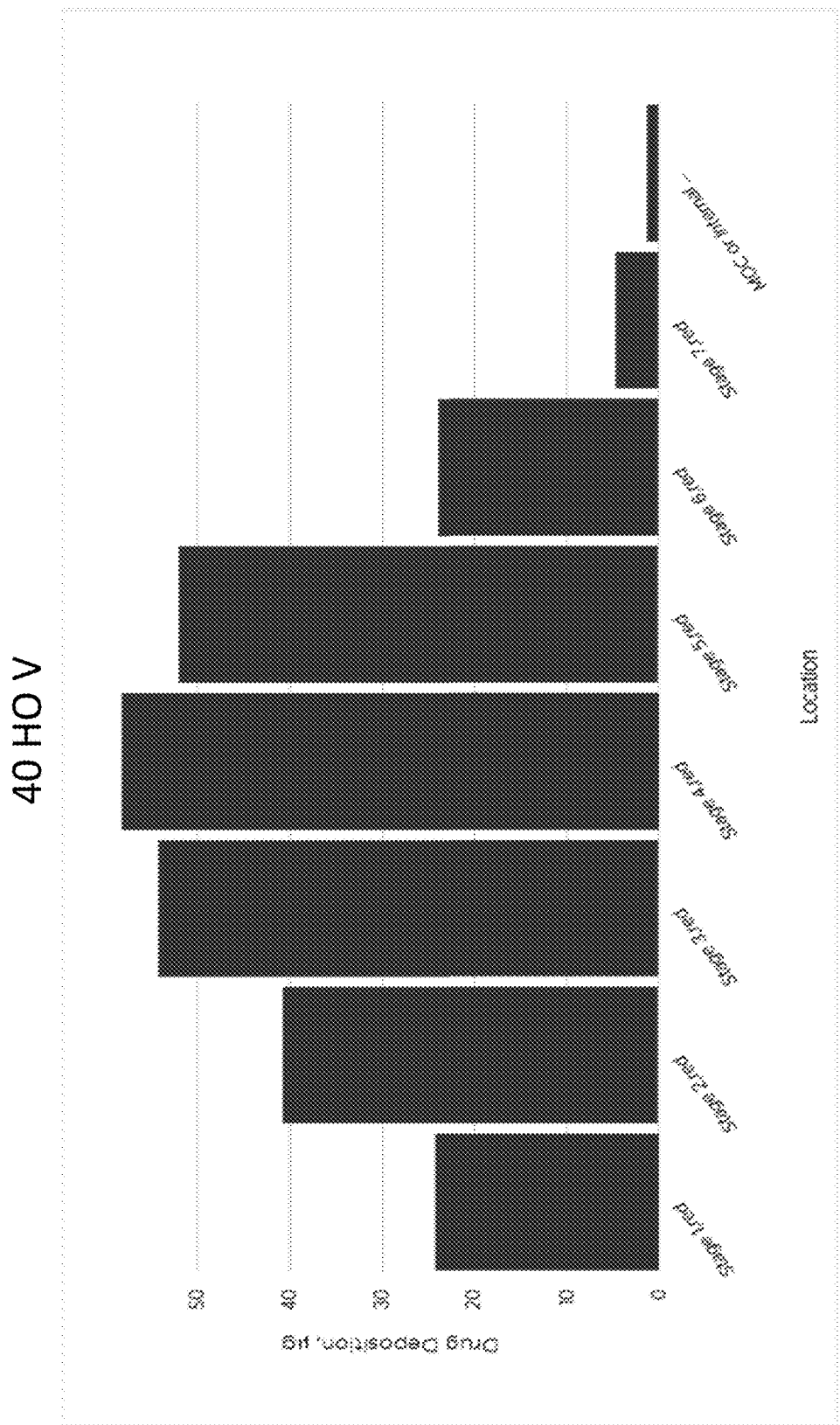
Figure 14B:
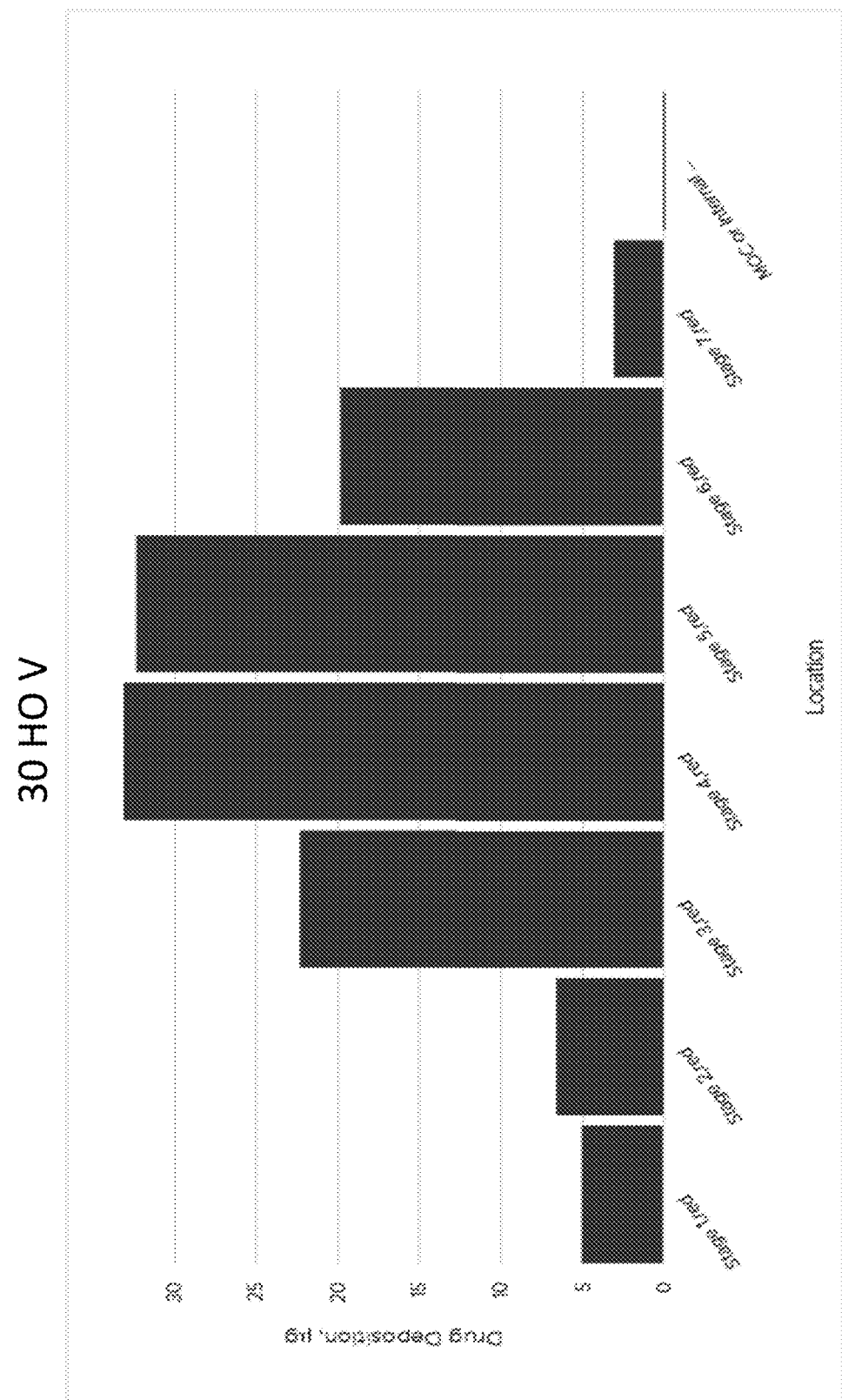
Figure 14C:
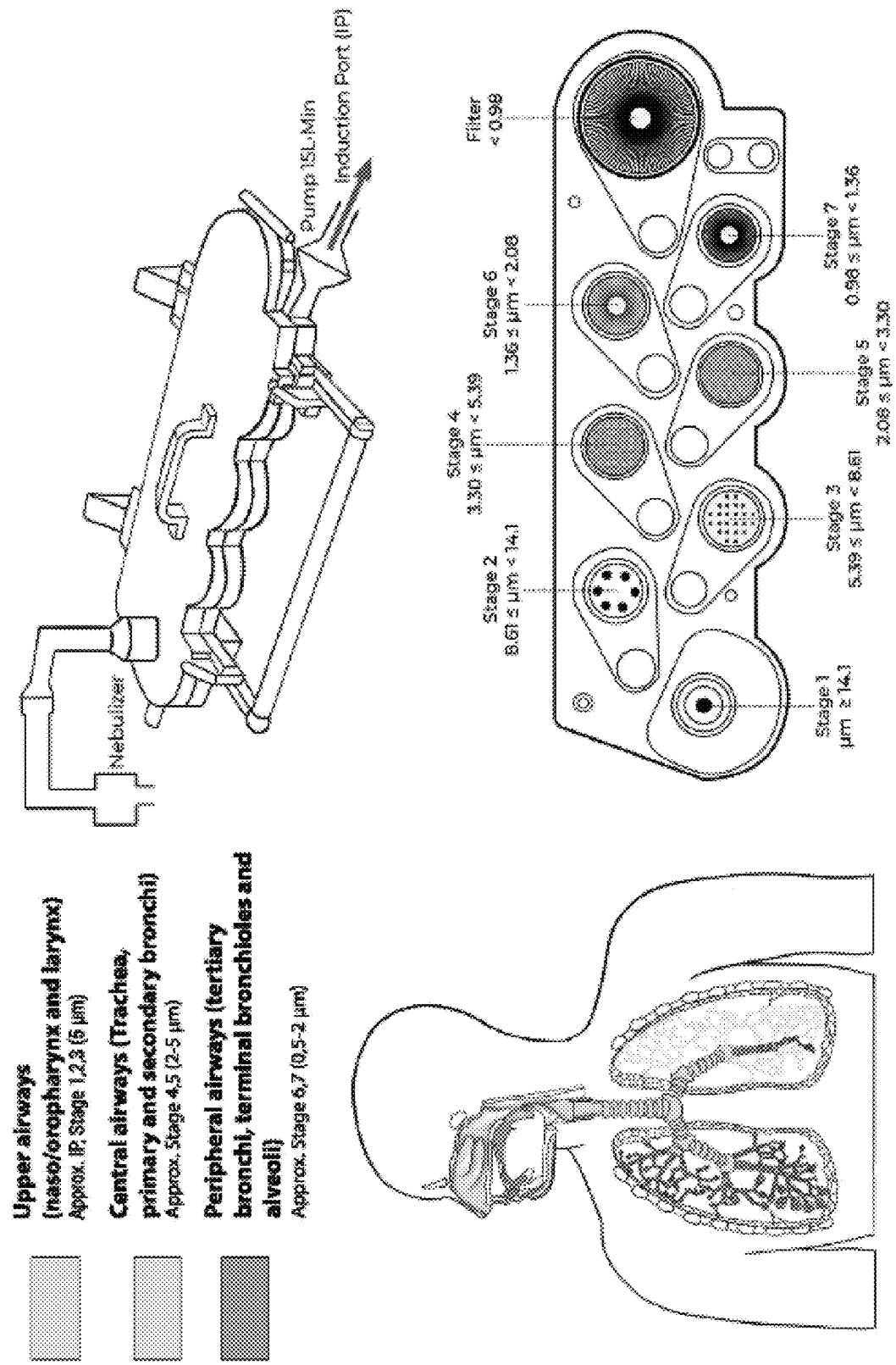

Aerodynamic particle size distribution (aPSD) was determined using a Next Generation Impactor (NGI). Drug deposition (µg) in various stages were measured in 40 HO V (FIG. 14A) and 30 HO V (FIG. 14B) nebulization head configurations. FIG. 14C shows aerosol characterization of each stage. Stage 4 and 5 simulated central airways (Trachea, primary and secondary bronchi), which may be desirable for treatment of disease in that section of the airways. In 40 HO V configuration, more than 50 µg of drug depositions were observed in stage 3, stage 4 and stage 5. Moreover, stage 2 showed about 40 µg of drug deposition and stage 1 and stage 6 showed more than 20 µg of drug deposition. In 30 HO V configuration, stage 4 and stage 5 showed more than 50 µg of drug depositions. However, unlike 40 HO V configuration, 30 HO V showed more than 20 µg of drug deposition in stage 3 and stage 6. These results show that 40 HO V configuration had better desirable treatment effect on lung disease.

The multiple-path particle dosimetry (MPPD) model was adapted to the PARI® nebulizer in various head configurations. Aerodynamic particle size distribution (aPSD) was determined using a Copley® Next Generation Impactor (NGI) according to manufacturer's instructions. Tested nebulizers included the Aerogen® Solo from Aerogen® and the PARI® eFlow® nebulizer device.

Figure 15A:
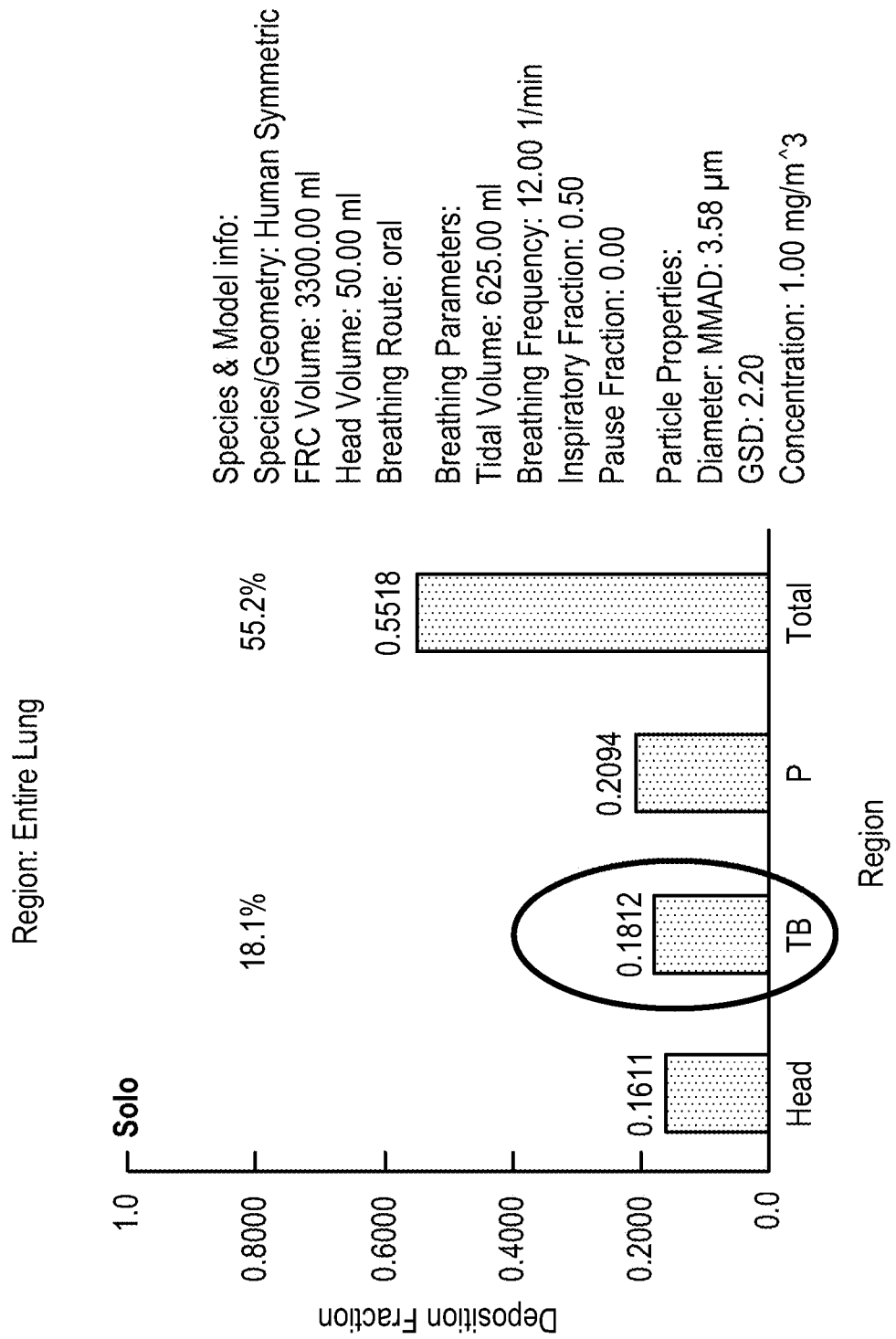
Figure 15B:
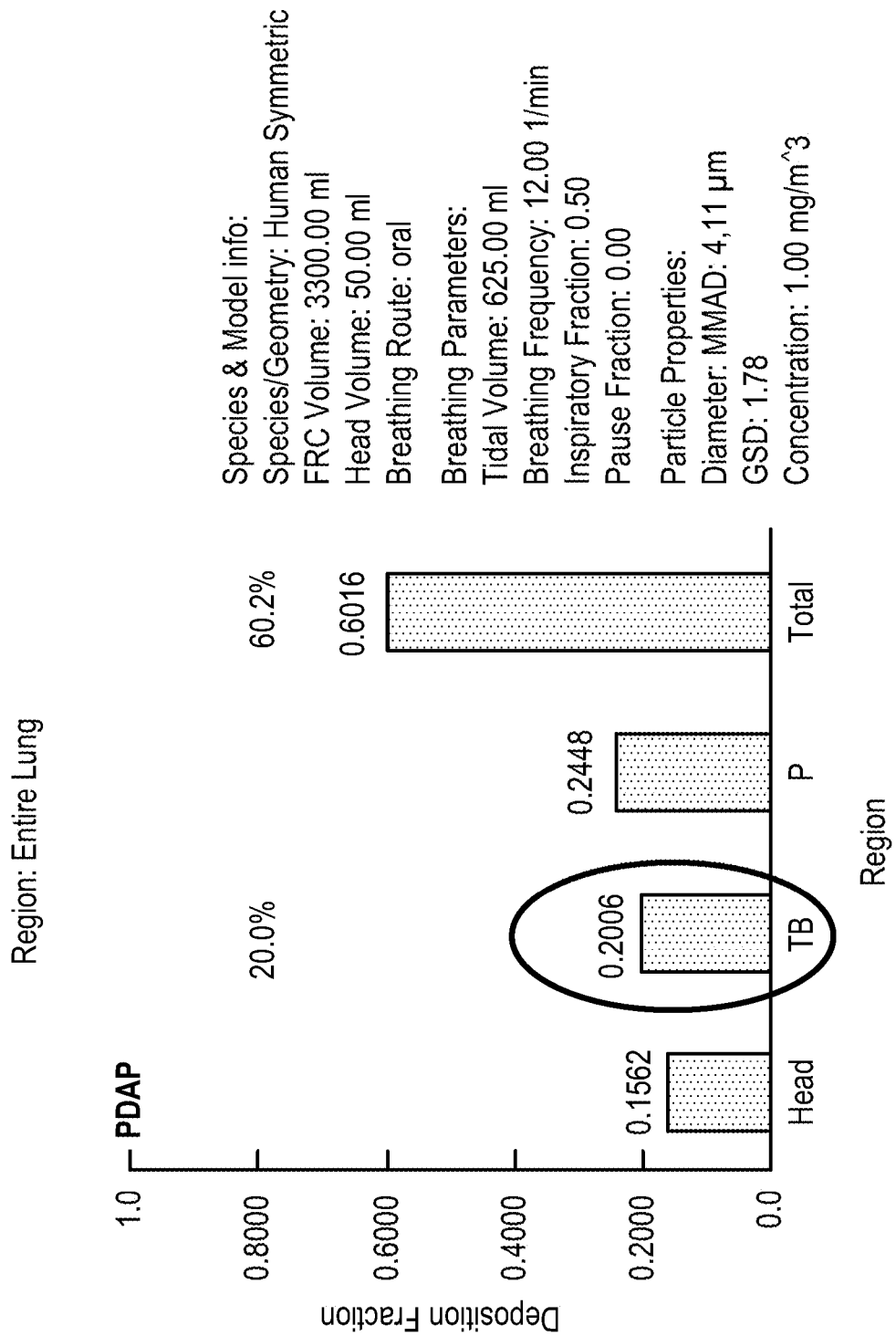
Figure 16A:
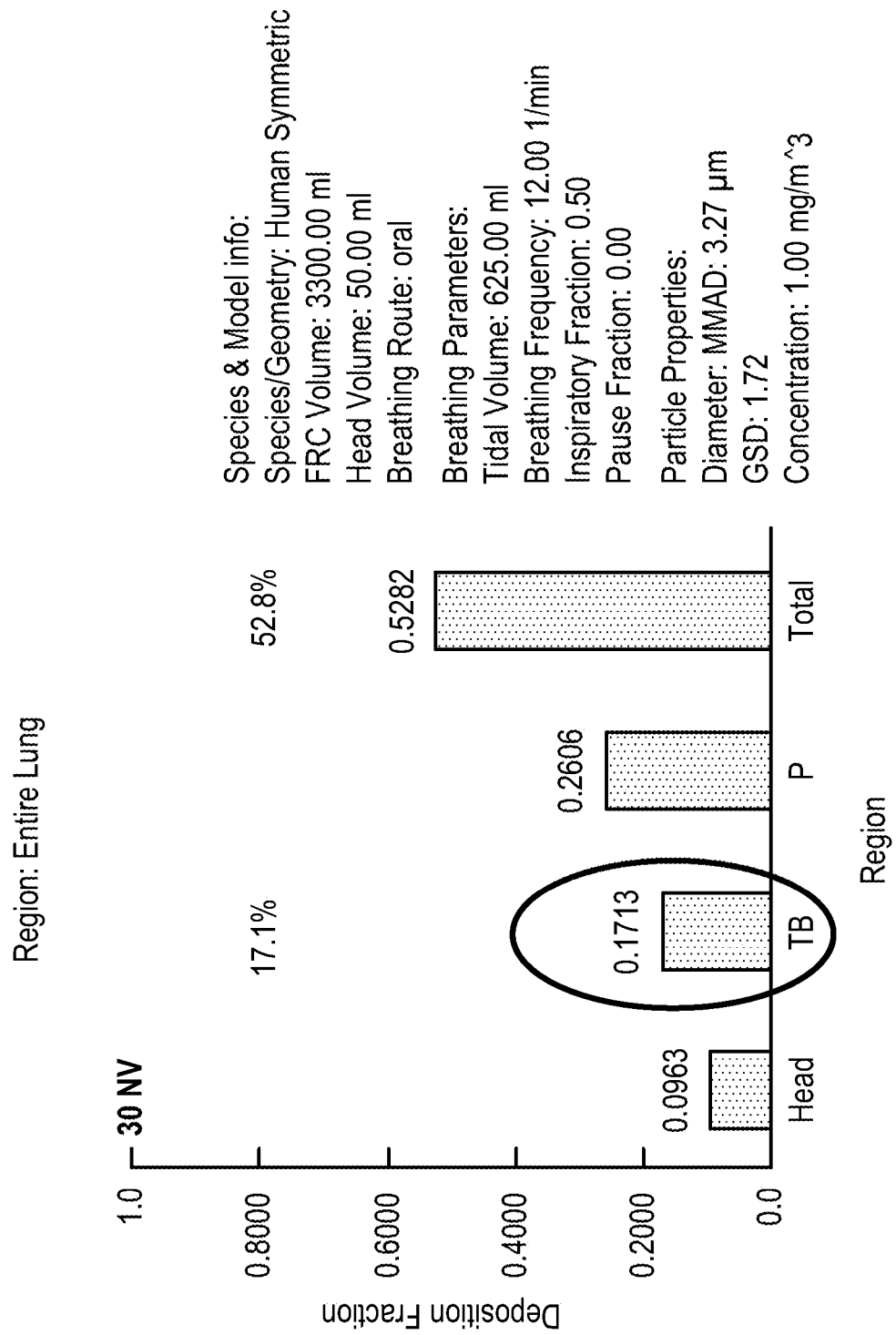
Figure 16B:
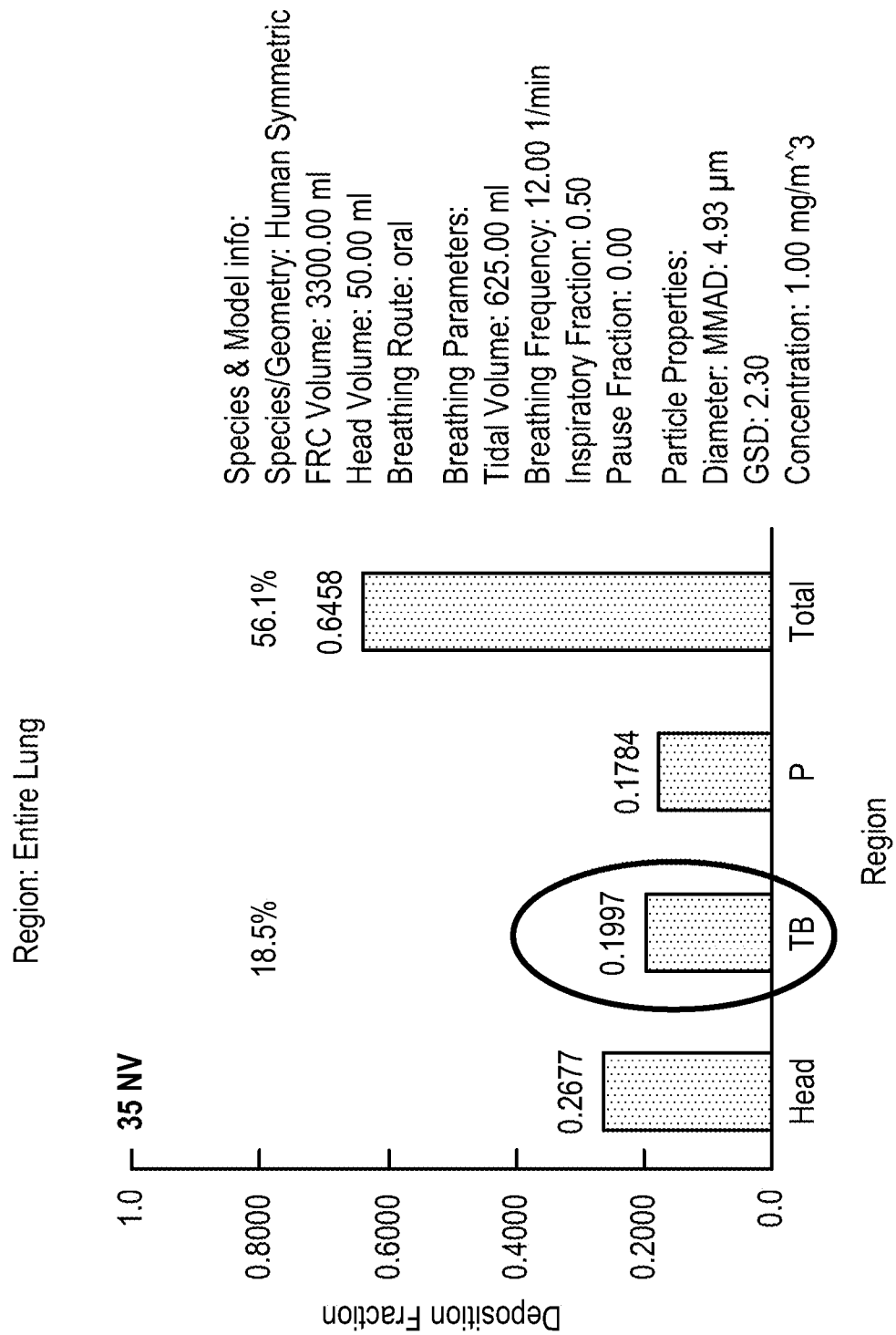
Figure 16C:
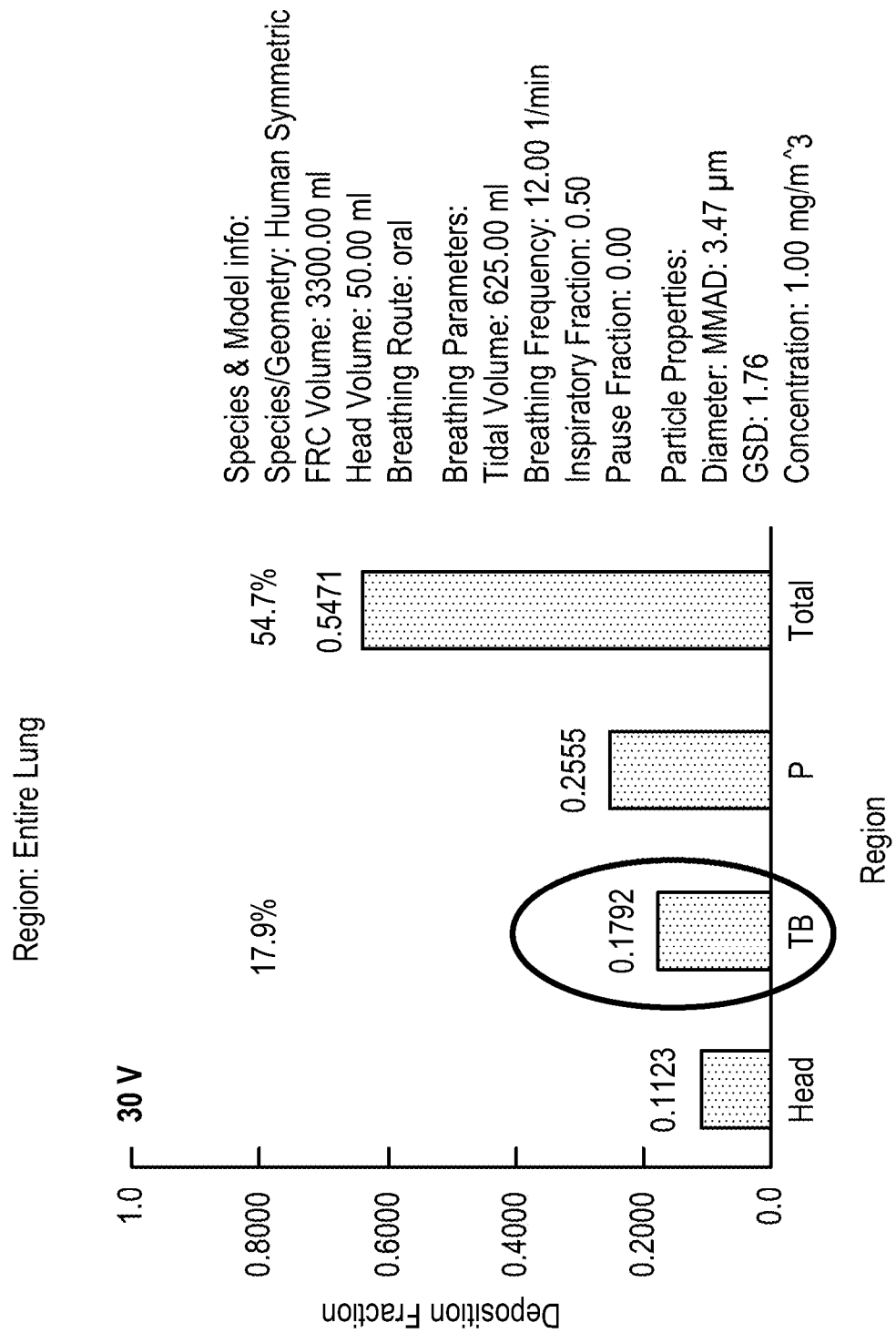
Figure 16D:
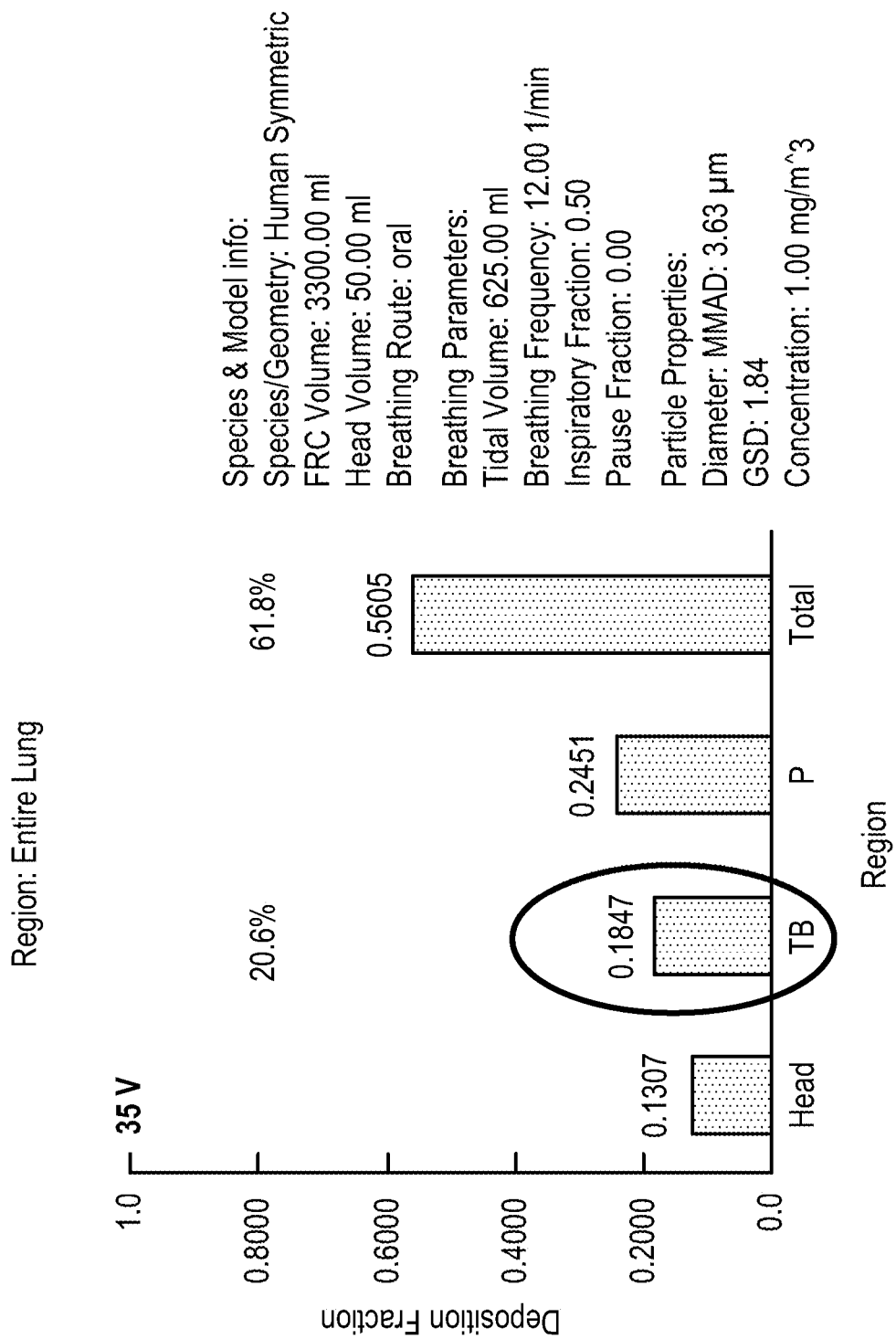
Figure 16E:
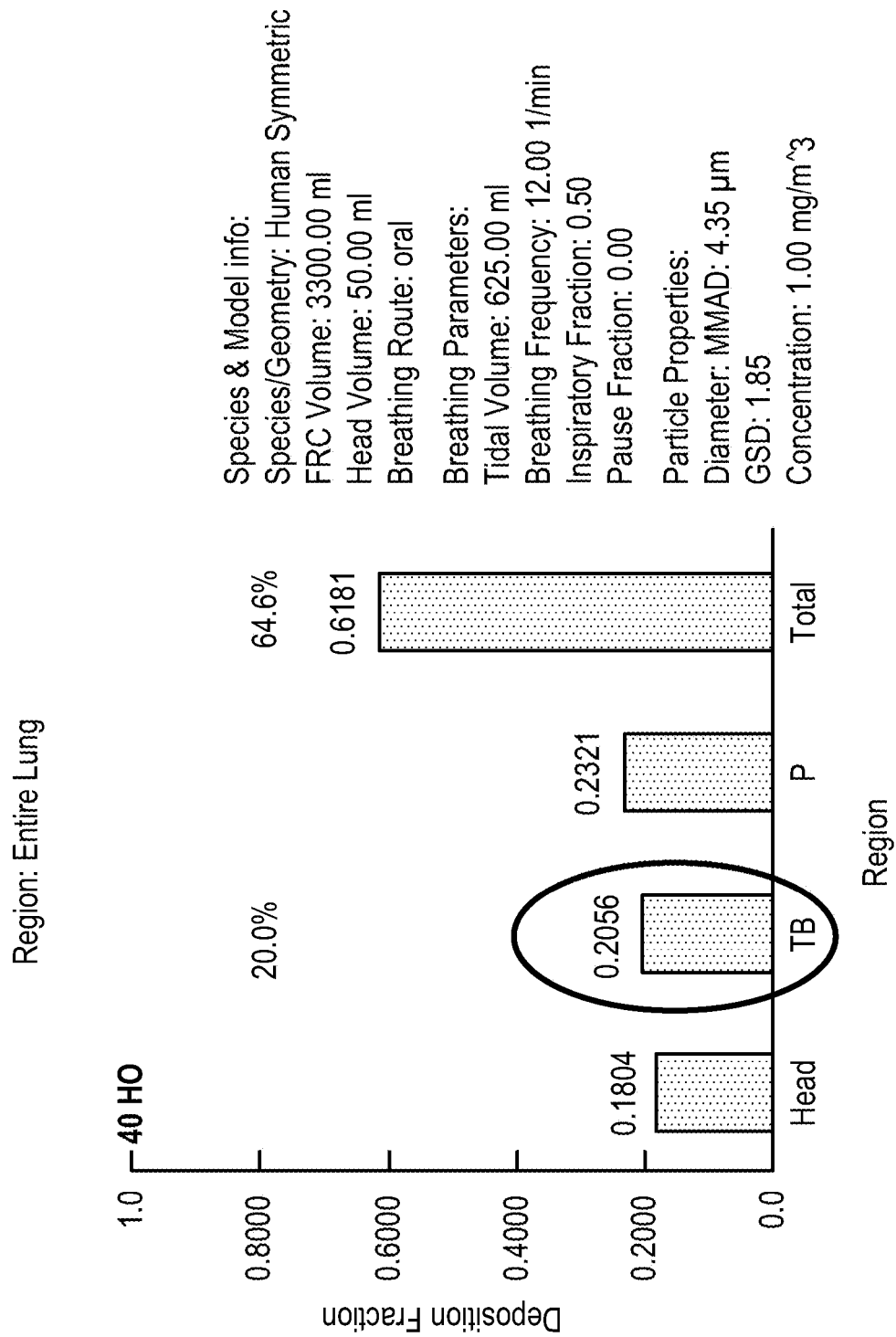

To calculate the deposition and clearance of monodisperse and polydisperse aerosols in the respiratory tracts, the multiple-path particle dosimetry (MPPD) model had been adapted. Results are shown in FIG. 15A (with the Aerogen® Solo), FIG. 15B (Aerogen® PDAP), and FIGS. 16A-E (PARI©eFlow®).

Example 2

Figure 17B:
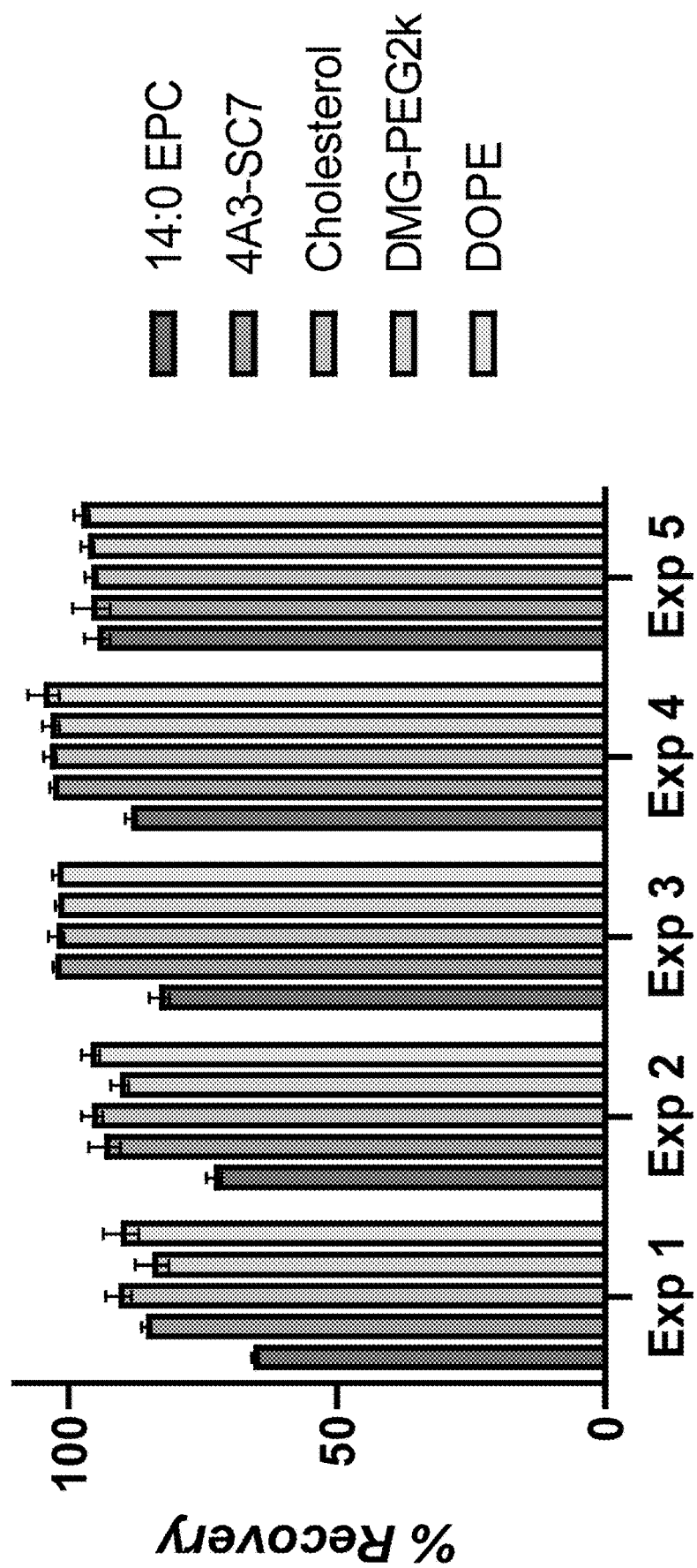

To develop improved methods for determining the amount of lipid nanoparticles (LNPs) in an aerosolized pharmaceutical composition, different compositions of extraction solutions, different volumes of extraction solution, and duration of extraction were evaluated as shown in FIG. 17A. LNP samples were pipetted onto the GF filters, dried at room temperature and were placed in 50 mL polypropylene tubes. The extraction conditions are shown in FIG. 17A. Specified amounts of extraction solutions were added to the tubes and the tubes were shaken at 200 rpm for specified amount of time to extract the lipids from the LNP sample-deposited filters. Controls were prepared for each experiment by directly diluting same amount of LNP sample into the extraction solution in a 50 mL polypropylene tube and were shaken at 200 rpm for the same amount of time. Supernatant were transferred to HPLC vials and were loaded on a HPLC system. Reversed-phase liquid chromatography was used to assess the quantity and the composition of lipids from the LNP samples that were extracted from the glass fiber filters. Samples were injected onto a Waters Acquity UPLC CSH C18, 1.7 µm column with 2.1 mm ID and 50 mm length using water/DFA (100:0.05 v/v) solution as mobile phase A and methanol/acetonitrile/DFA (80:20:0.05 v/v/v) as mobile phase B. Output rate was set to 0.4 mL/min and the column temperature was set to 65° C. Gradient started at 80% B and was ramped up to 100% B in 7 minutes. Lipids were detected using a charged aerosol detector with the evaporator temperature set to 50° C. All five lipids (14:0 EPC, 4A3-SC7, cholesterol, DMG-PEG2k, and DOPE) were baseline separated and the peak area values of each lipid extracted from the filters were compared to that of the control sample to obtain the percent efficiency of extraction. As shown in FIGS. 17A-17B, extraction efficiency was increased when the proportion of water, total volume of extraction solution and the duration of the extraction increased (experiment 1 to 4). However, extraction efficiency of 14:0 EPC lipid, which is positively charged, still showed lower extraction efficiency than the other four lipids. Surprisingly, addition of ammonium acetate in the extraction solution resulted in over 94% extraction yield, similar to that of other neutral lipids in the formulation. Ammonium acetate salt is compatible with reversed-phase chromatography column, charged aerosol detector, mass spectrometry.

An HPLC method was used to quantitate lipids and to evaluate lipid fractions of nebulized LNP samples deposited onto GF filters. For the quantitation of each lipid, a set of standard solutions that contained all five lipids was prepared. Concentrated standard stock solution was prepared by dissolving five lipids into a 100 mL volumetric flask with isopropanol. Aliquots of the standard stock solutions were stored at −80° C. The day of HPLC analysis, an aliquot of stock solution was diluted using the extraction solution to make three or four standard solutions with different concentrations to cover the estimated concentration range of filter extracted samples. Peak areas of lipids were used to generate a standard curve for each lipid. Within the concentration range used in this study the CAD signal is linear for all five lipids. Total lipid weight was obtained by adding lipid weights of all the lipids in the formulation.

Figure 18A:
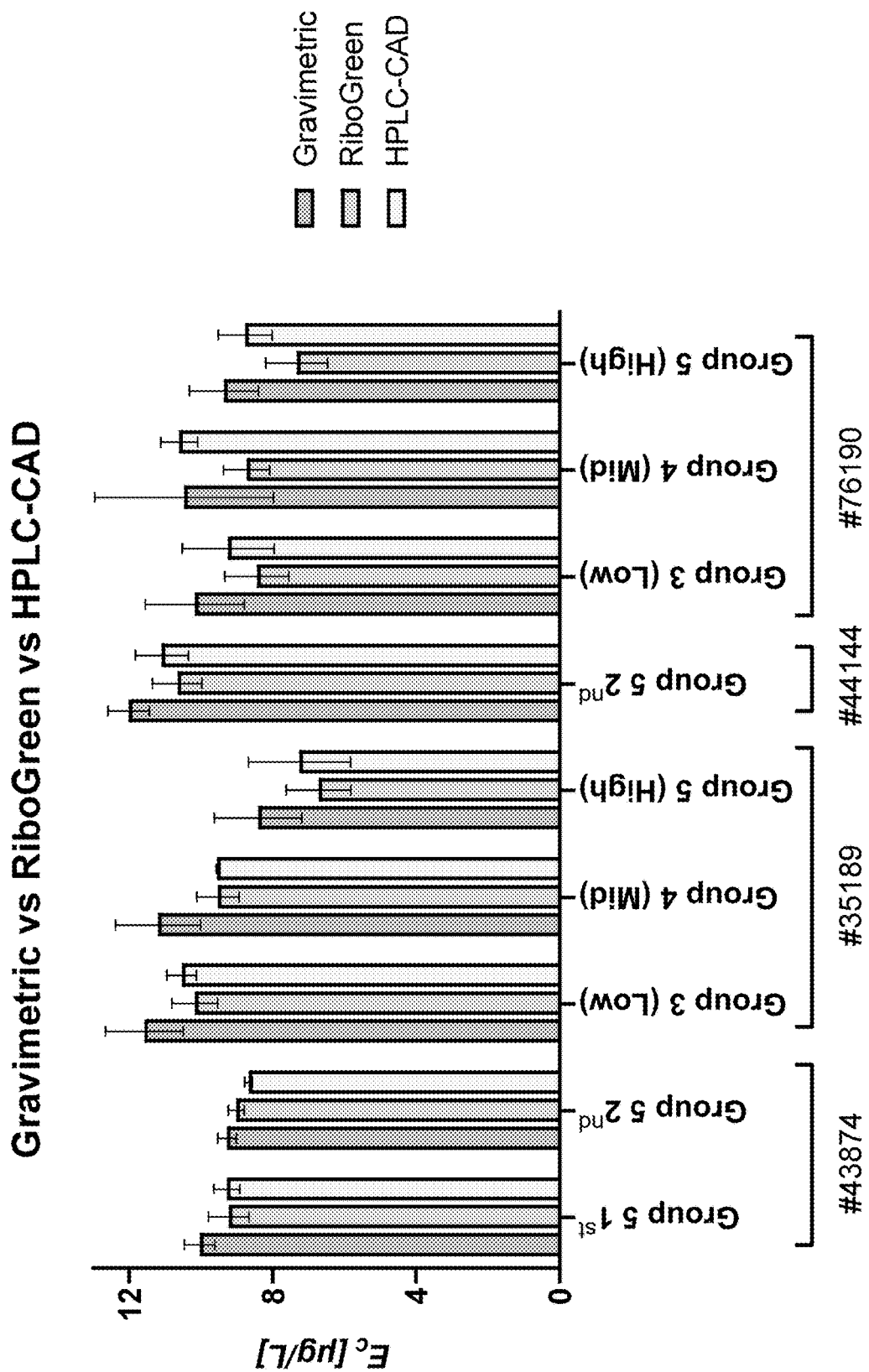
Figure 18C:
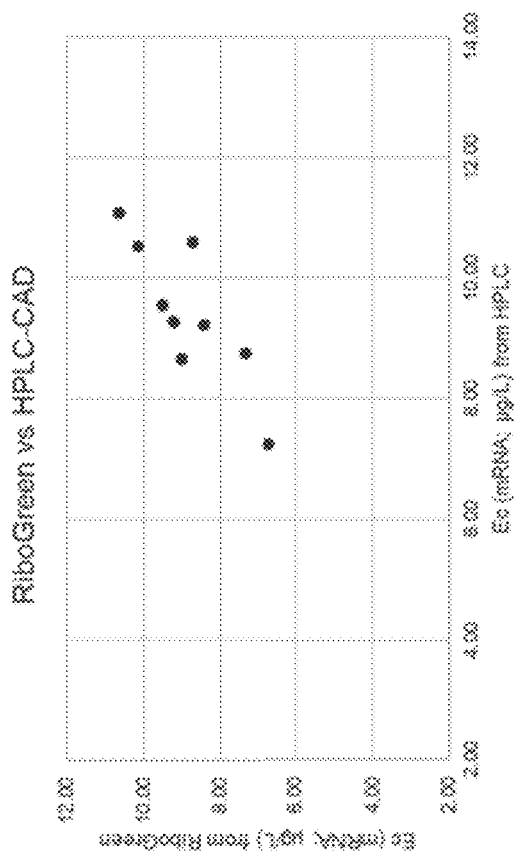
Figure 18B:
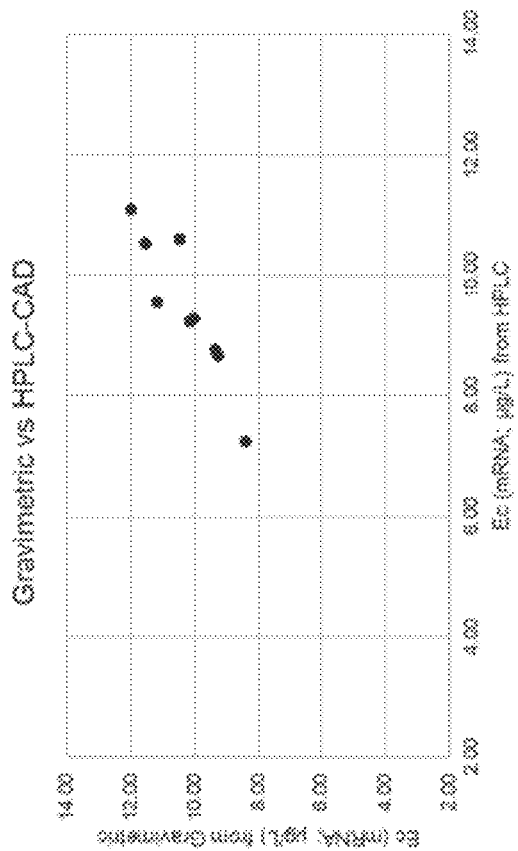

The HPLC-lipid analysis method was compared to two orthogonal methods: gravimetric analysis and RiboGreen assay (FIGS. 18A-18C). Gravimetric data was generated by weighing the GF filters before and after the nebulized LNP samples were deposited and dried. RiboGreen assay was performed to quantitate the amount of mRNA that was deposited onto the filters. Weight of mRNA deposited onto the filters was derived from the gravimetric data based on the theoretical composition of the deposited formulation shown below:

Total dry weight=mRNA (0.75%)+total lipids (22.59%)+sucrose (75.29%)+Tris (1.37%)

Weight of mRNA was calculated from the HPLC-lipid data using the theoretical ratio of mRNA and lipid in the formulation (1:30). Weight of mRNA values obtained from RiboGreen assay, and the weight values derived from gravimetric data as well as HPLC data were then divided by the total sample volume resulting in Ec (mRNA; μg/L) values. Comparison of the calculated Ec (mRNA) values from three different methods are shown in FIG. 18A. Data shows there was a good correlation between the three methods.

Figure 19A:
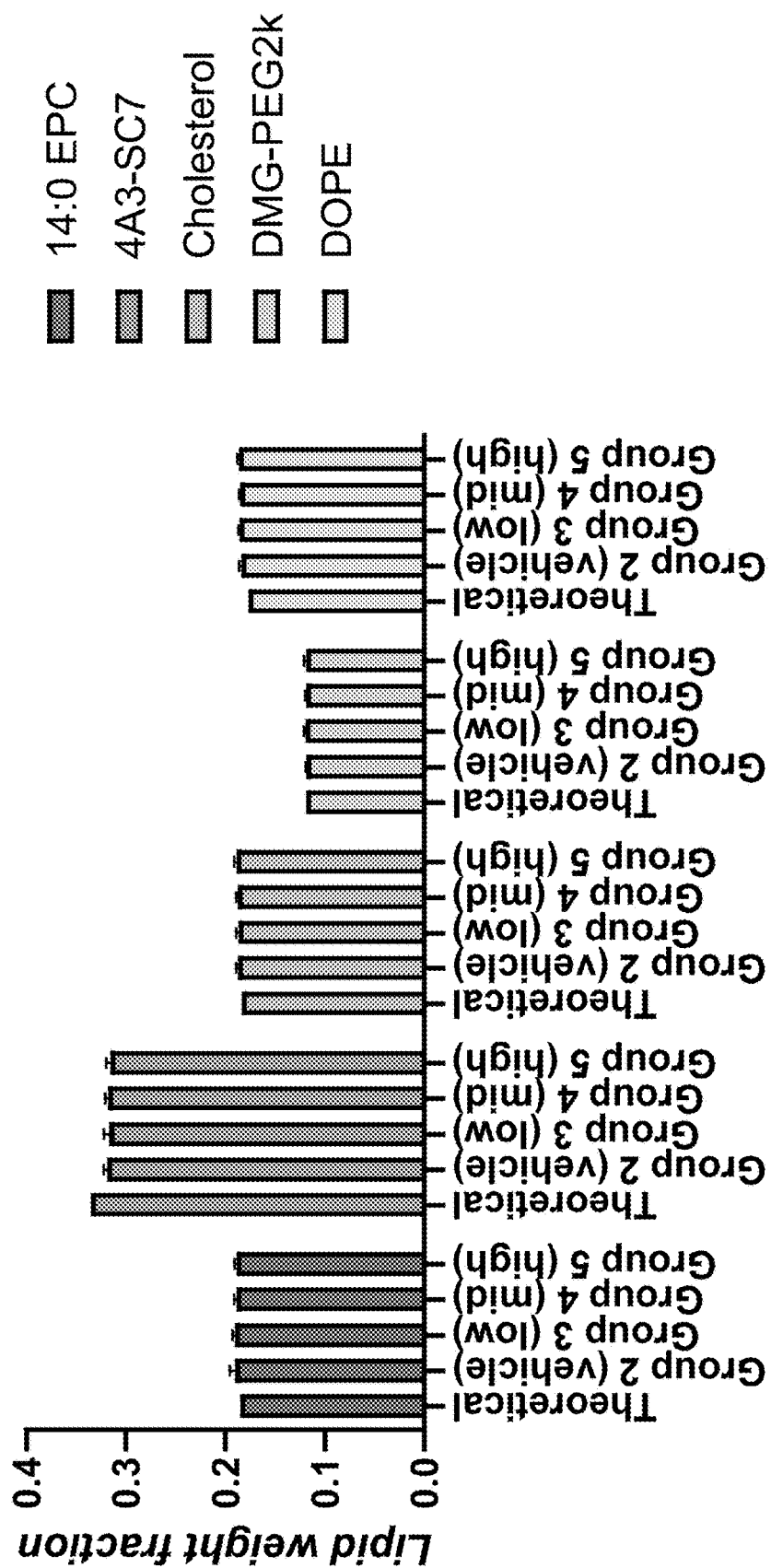
Figure 19B:
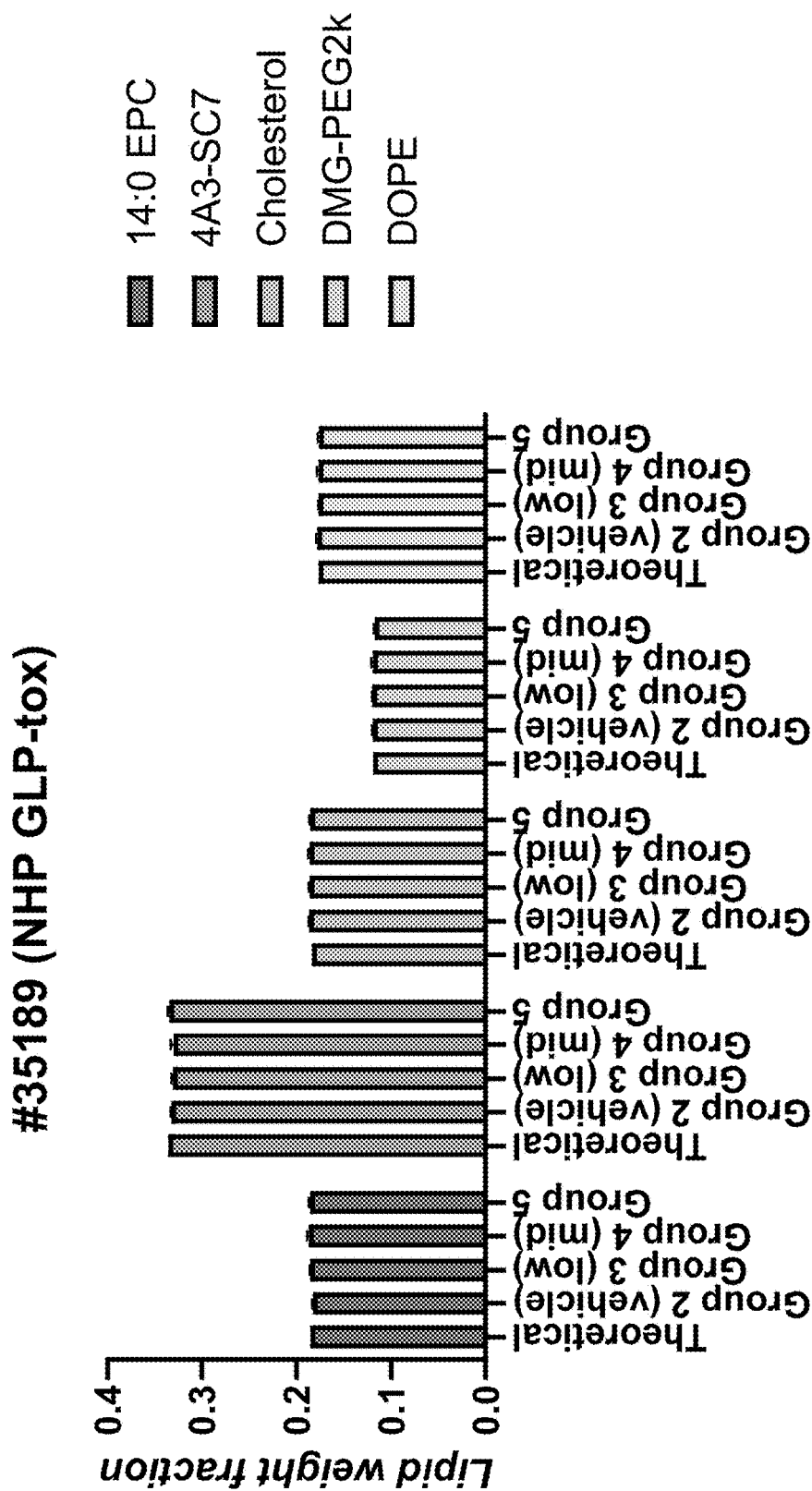
Figure 20B:
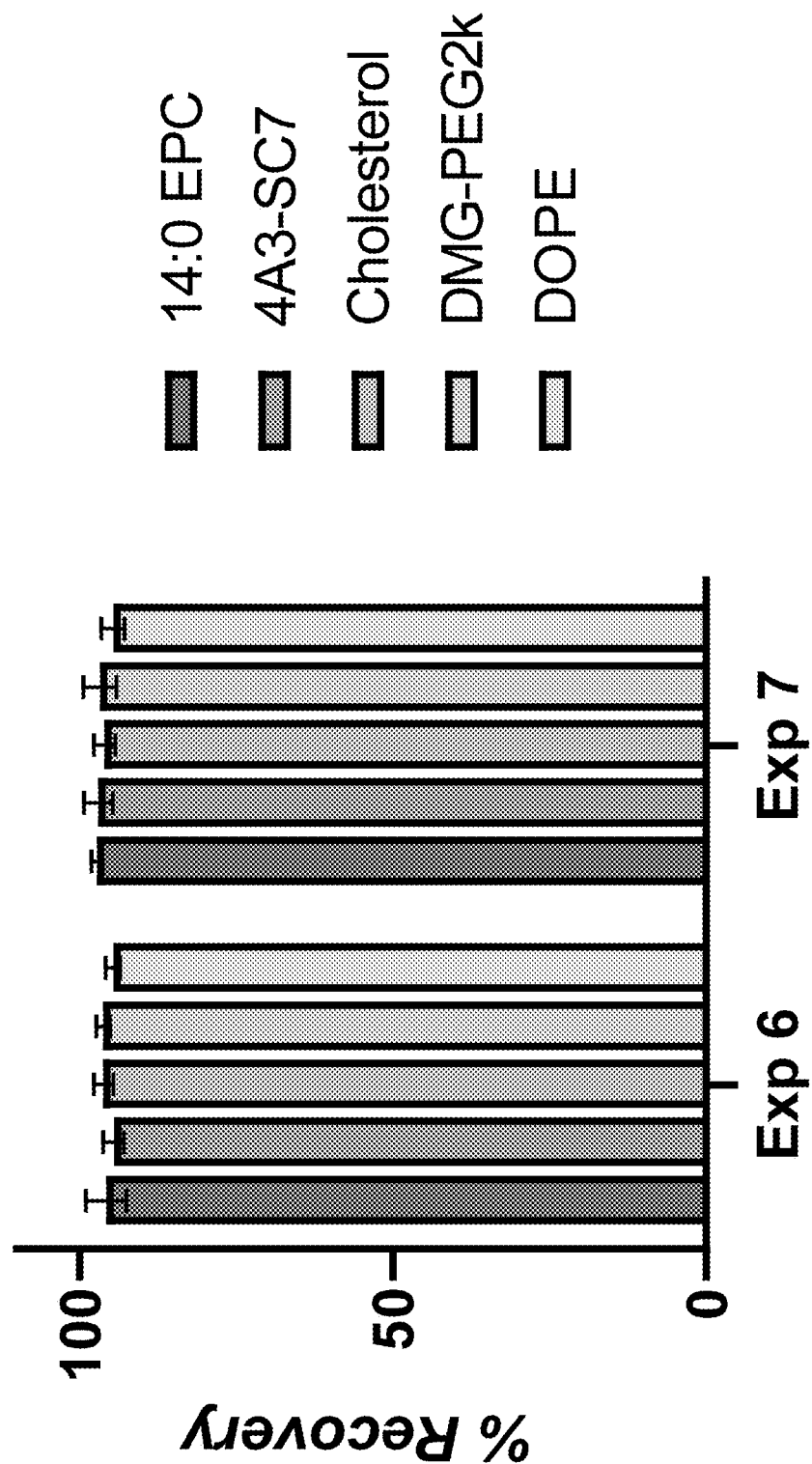

Lipid fraction data obtained from HPLC method were compared to theoretical values in FIGS. 19A-19B. Average lipid weight fraction and standard deviations of each lipid for each study were calculated. The lipid weight fraction of each individual lipid showed small variation between each study and the theoretical values. Filter storage condition study revealed that storage of the filters at 4° C. or −80° C. did not show a significant difference in the recovery percentage (FIGS. 20A-20B).

Figures 21A, 21B:
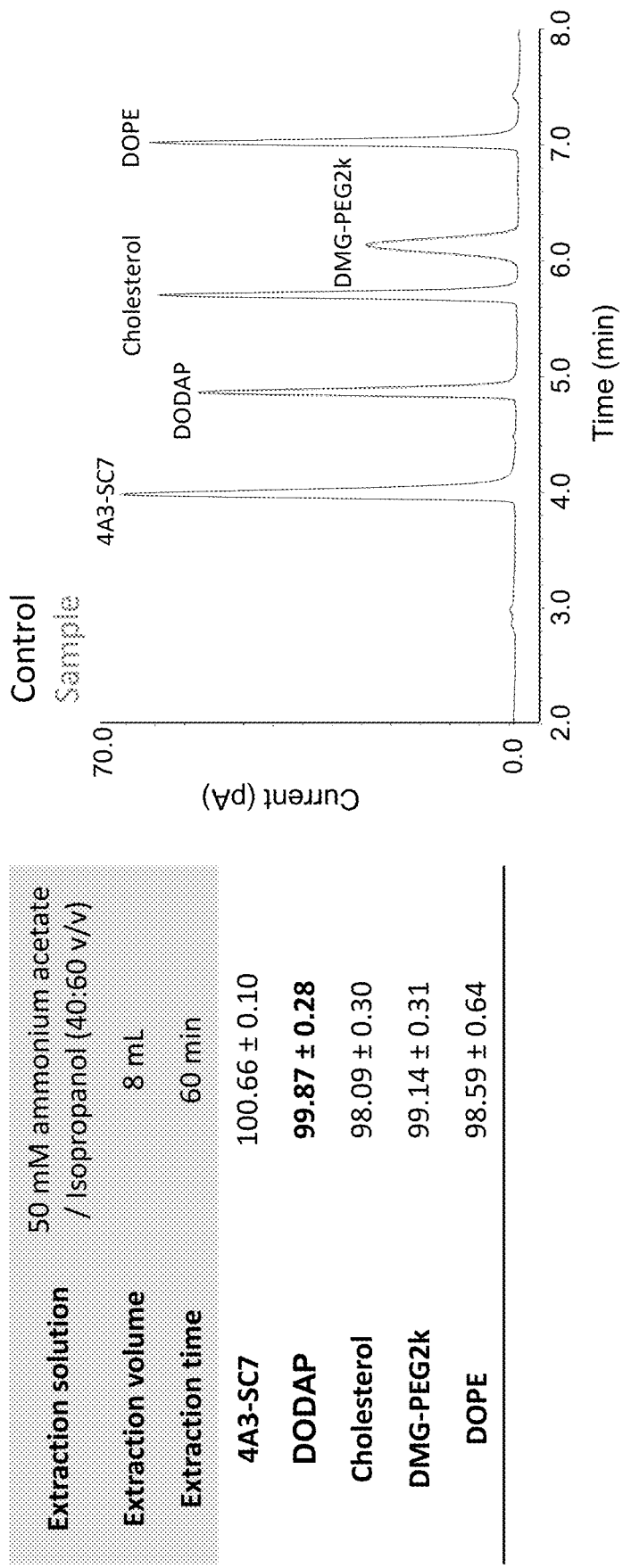
FIG. 21E shows comparison of LC-MS and HPLC-CAD.

In order to assess the generalizability of the lipid extraction method developed herein, extraction efficiency of another LNP formulation was evaluated. Composition B formulation which contains DODAP instead of 14:0 EPC was deposited onto glass fiber filters and extracted with 8 mL of 50 mM ammonium acetate/isopropanol (40:60 v/v) solution for 60 min at 200 rpm. DODAP as well as other lipids in the formulation were all efficiently extracted as shown in FIG. 21A. Chromatograms of control sample and extracted lipid sample are shown in FIG. 21B.

Figure 21C:
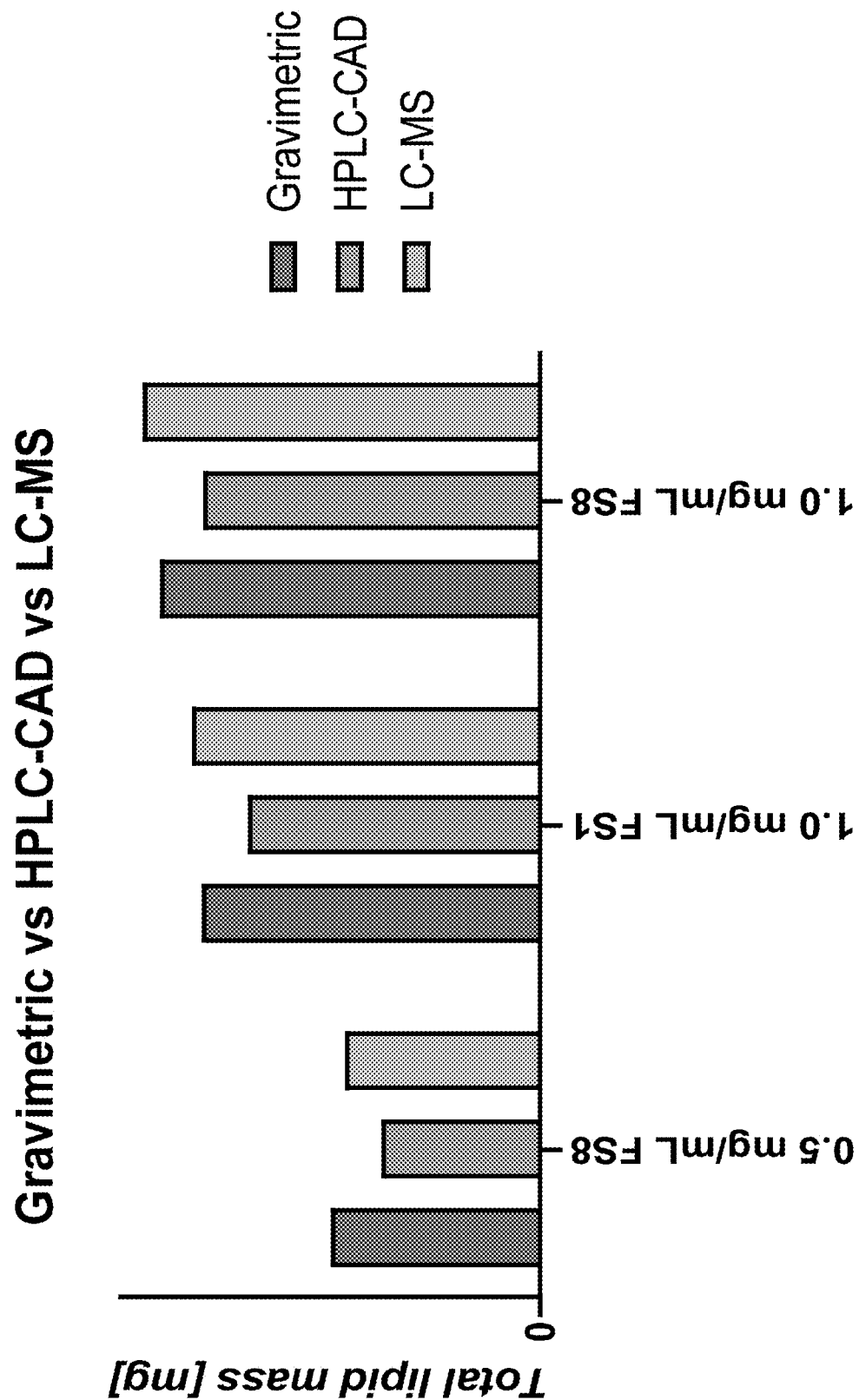
Figures 21D, 21E:
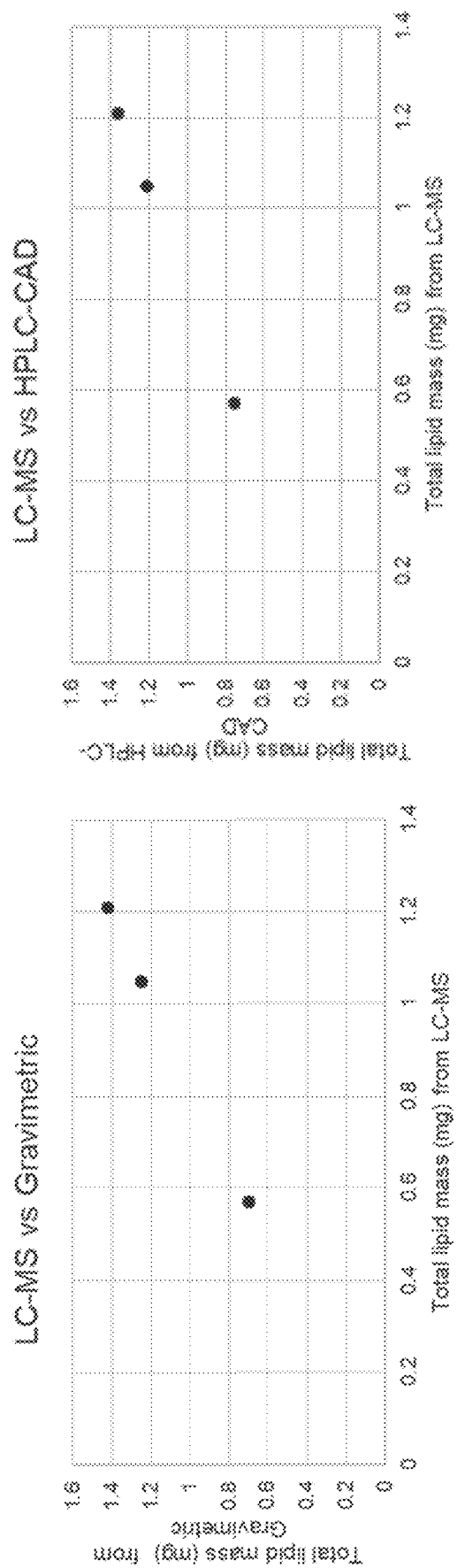
Figure 22:
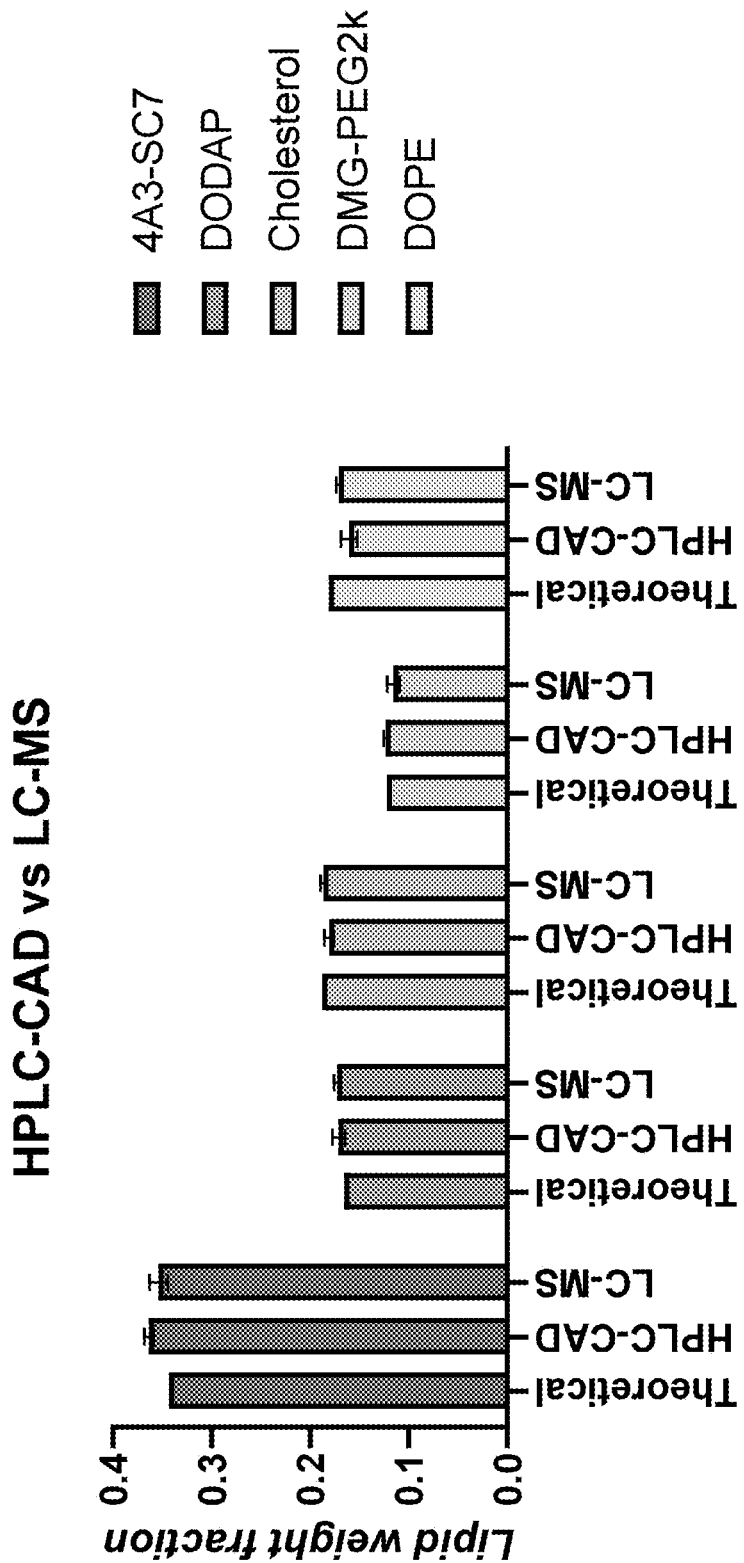
FIG. 22 shows lipid fraction comparison of HPCL-CAD and LC-MS on Composition B.
Figure 23:
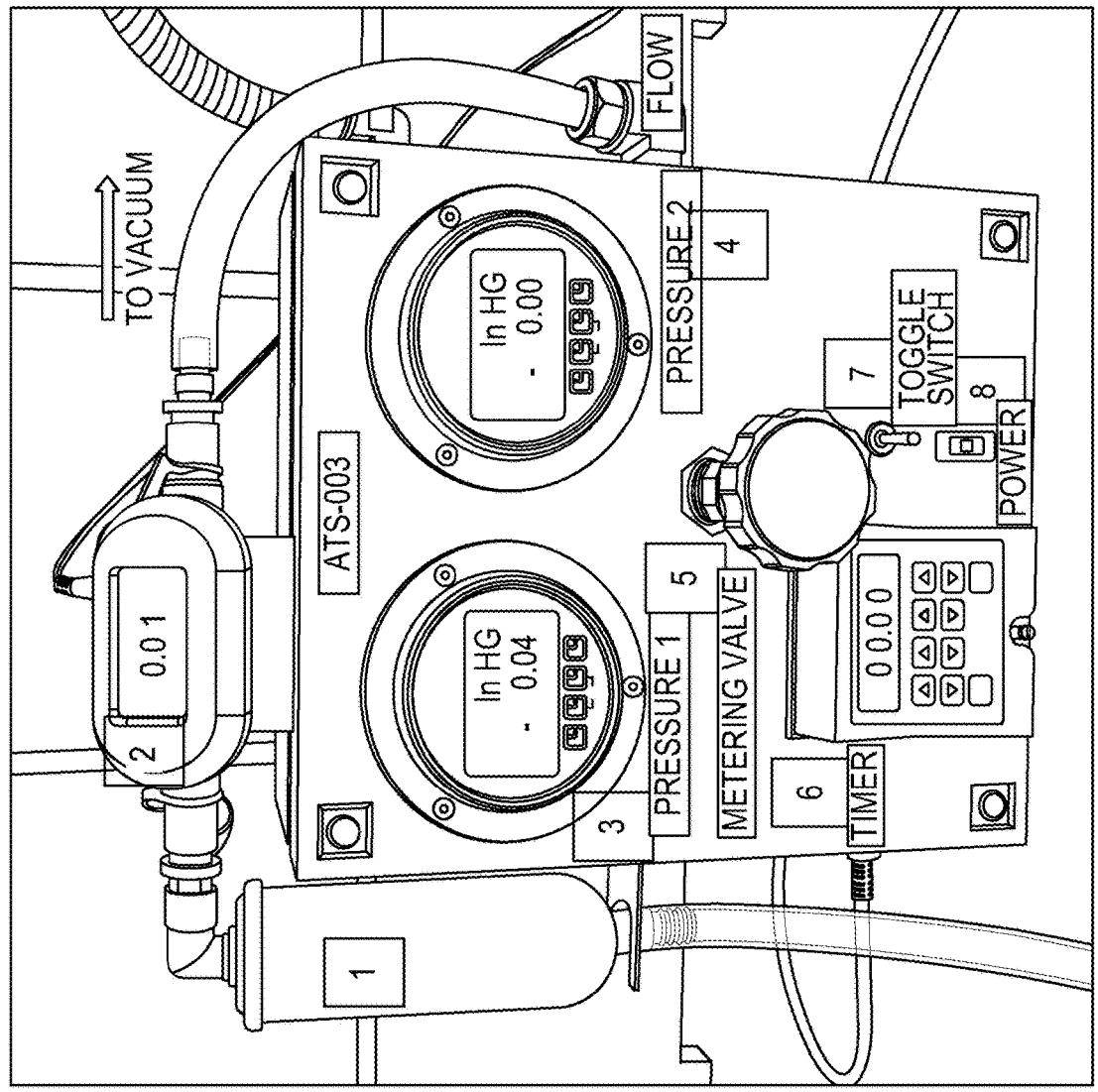
FIG. 23 shows an image of an ATS-003 nebulization device.

A mass spectrometer can be used as an alternative to the charged aerosol detector (CAD). A Liquid chromatography-mass spectrometry (LC-MS) method was developed to quantitate lipids and evaluate lipid fractions. The HPLC system used in LC-MS method was SCIEX ExionLC. All liquid chromatography conditions including column, mobile phase solutions, gradient program, and column temperature were set the same as in HPLC method section. The mass spectrometry system used in LC-MS method was SCIEX Q-Trap 7500 equipped with a triple quadrupole analyzer. The MS was operated in positive-mode and the analyzer was set in the multiple reaction monitoring (MRM) mode for the analysis of lipids. To compare the results with HPLC method, filter extracted samples of formulation Composition B (DODAP, 4A3-SC7, cholesterol, DMG-PEG2k, and DOPE) were analyzed by LC-MS. The LC-MS conditions for quantitation of each lipid are summarized in Table 12. On the day of LC-MS analysis, all filter extracted samples were diluted by 100 times using extraction solution, and an aliquot of stock solution was diluted using the extraction solution to make three or four standard solutions with different concentrations to cover the estimated concentration range of diluted filter extracted samples. Peak areas of lipids were used to generate a standard curve for each lipid. Within the concentration range used in this study the LC-MS signal was linear for all five lipids. Total lipid weight obtained from LC-MS method were compared to values obtained from gravimetric and HPLC method in FIGS. 21C-21E. Lipid fraction data were calculated based on LC-MS results and compared to theoretical values and HPLC results in FIG. 22.

TABLE 12

Parameters for LC-MS Acruisition Method
MS Settings

| Ionization Mode | Electrospray Ionization (ESI), positive ion mode |
| --- | --- |
| Scan Mode | Multiple Reaction Monitoring (MRM) |
| Scan Time (msec) | 250 |
| Voltage | 2700 |
| Ion Source Gas 1 (GS1, psi) | 50 |
| Ion Source Gas 2 (GS2, psi) | 70 |
| Temperature (TEM) | 450° C. |
| Curtain Gas (CUR, psi) | 45 |
| Collision Gas (CAD) | 6 |
| Interface Heater (IHE) | On |

| Components | 4A3-SC7 | DODAP | Cholesterol | DMG-PEG2k | DOPE |
| --- | --- | --- | --- | --- | --- |
| MRM Transitions | 706.4 → 245.2 | 648.9 → 366.4 | 369.7 → 105.0 | 841.2 → 759.4 | 744.8 → 603.5 |
| Collision Energy (CE) | 35 | 40 | 66 | 29 | 30 |
| Entrance Potential (EP) | 10 | 10 | 10 | 10 | 10 |
| Collision Cell Exit Potential (CXP) | 13 | 17 | 13 | 34 | 27 |

Note:
These tune parameters may be adjusted to optimize instrument sensitivity

LNP samples were pipetted onto polypropylene filters, dried for 30 min and were placed in 50 mL polypropylene tubes with 20 mL of the extraction solution (13:1, v/v, 2% Triton X/40 mg/mL Heparin). Samples were placed on a shake plate at 150 rpm for 30 min. diluted as shown in Table 13 and subjected to Ribogreen assay to analyze extracted mRNA (data shown in Table 14).

TABLE 13

Dilution of the samples

| | Volume of HPLC Water (μL) | Volume of sample from step 2 (μL) | Volume of 1:1 (v/v) Water/ES (μL) | Nominal Conc. of RNA (before adding Ribogreen) (μg/mL) |
| --- | --- | --- | --- | --- |
| Sample 1 | 500 | 500 | 4000 | 2.5 |
| Sample 2 | 500 | 500 | 4000 | 2.5 |

TABLE 13-continued

Dilution of the samples

| | Volume of HPLC Water (µL) | Volume of sample from step 2 (µL) | Volume of 1:1 (v/v) Water/ES (µL) | Nominal Conc. of RNA (before adding Ribogreen) (µg/mL) |
|---|---|---|---|---|
| Sample 3 | 500 | 500 | 4000 | 2.5 |
| Control | 500 | 500 | 4000 | 2.5 |

TABLE 14

Ribogreen assay results

| | Intensity | Measured mRNA Conc. in the Assay Plate (µg/mL) | Calculated mRNA Conc. in the formulation (mg/mL) | Mass of mRNA from the Filter/Control (µg) | Recovery (Extraction Efficiency) |
|---|---|---|---|---|---|
| Run 1 | | | | | |
| Sample 1 | 137251 | 1.283 | 1.026 | 513.2 | 92.66% |
| Sample 2 | 11705 | 0.045 | 0.036 | 18.0 | 3.26% |
| Sample 3 | 84403 | 0.762 | 0.609 | 304.7 | 55.03% |
| Control | 147553 | 1.384 | 1.108 | 553.8 | |
| Run 2 | | | | | |
| Sample 1 | 130834 | 1.245 | 0.996 | 497.8 | 90.01% |
| Sample 2 | 11239 | 0.045 | 0.036 | 17.9 | 3.23% |
| Sample 3 | 81835 | 0.753 | 0.602 | 301.2 | 54.46% |
| Control | 144600 | 1.383 | 1.106 | 553.1 | |

The results show that recovery of sample 1 is 92.66% and 90.01%. Sample preparation method is further optimized to improve the extraction efficiency by using RNS-free certified tubes during sample preparation.

Samples were pipetted onto polypropylene filters, dried for 1 h and were placed in 50 mL polypropylene tubes (RNS-free tube) with 20 mL of the extraction solution (13:1, v/v, 2% Triton X/40 mg/mL Heparin). Samples were placed on a shake plate at 180 rpm for 1 h. diluted as shown in Table 13 and subjected to Ribogreen assay to analyze extracted mRNA (data shown in Table 15). Extraction efficiency is calculated by comparing the mRNA content of the samples extracted from the filters with that of control samples. The results showed improved extraction efficiency.

TABLE 15

Ribogreen assay results

| | Intensity | Measured mRNA Conc. in the Assay Plate (µg/mL) | Calculated mRNA Conc. in the formulation (mg/mL) | Mass of mRNA from the Filter/Control (µg) | Recovery (Extraction Efficiency) |
|---|---|---|---|---|---|
| Run 1 | | | | | |
| Sample 1 | 142078 | 1.345 | 1.076 | 538.2 | 99.32% |
| Sample 2 | 142328 | 1.348 | 1.078 | 539.1 | 99.50% |
| Sample 3 | 141766 | 1.342 | 1.074 | 537.0 | 99.10% |
| Control 1 | 143492 | 1.359 | 1.087 | 543.6 | |
| Control 2 | 142574 | 1.350 | 1.080 | 540.1 | |
| Run 2 | | | | | |
| Sample 1 | 146711 | 1.377 | 1.101 | 550.6 | 99.73% |
| Sample 2 | 147398 | 1.383 | 1.107 | 553.3 | 100.21% |
| Sample 3 | 147206 | 1.381 | 1.105 | 552.6 | 100.08% |
| Control 1 | 148148 | 1.390 | 1.112 | 556.2 | |
| Control 2 | 146034 | 1.370 | 1.096 | 548.0 | |

An extraction method was developed to quantitate RNA from LNP deposited polypropylene filters by increasing the filter drying time, extraction time, and shake speed, the percent recovery improved. Second extraction method is efficient to extract mRNA from the formulation-deposited polypropylene filter, the extraction efficiency is within 99.7±0.2% with RiboGreen.

An RP-HPLC method was developed to quantitate mRNA from the extracted solution.

TABLE 16

HPLC method

| | | | |
|---|---|---|---|
| Instrumentation | Agilent 1200 | | |
| Column | DNAPac RP, 4 µm | | |
| Format | 2.1 × 50 mm | | |
| Mobile phase A | 0.1M TEAA, pH 7.0 | | |
| Mobile phase B | Acetonitrile | | |
| Needle wash | Water/Acetonitrile (90:10 v/v) | | |
| Gradient: | Time (min) | % A | % B |
| | 0.0 | 90.0 | 10.0 |
| | 2.0 | 5.0 | 95.0 |
| | 3.0 | 5.0 | 95.0 |
| | 3.1 | 90.0 | 10.0 |
| | 7.0 | 90.0 | 10.0 |
| Flow rate | 0.4 mL/min | | |
| Column Temp | 60° C. | | |
| Detection | UV (260 nm) | | |
| Sample | mRNA | | |
| Injection vol | 4 µL | | |
| Sampler Temp | 5° C. | | |

TABLE 17

| | Peak Area | Recovery HPLC | Recovery RigoGreen (Ave) |
|---|---|---|---|
| Control 1 | 205.9 | | |
| Control 2 | 209.9 | | |
| Sample 1 | 201.5 | 96.9% | 99.5% |
| Sample 2 | 199.9 | 96.2% | 99.9% |
| Sample 3 | 200.1 | 96.2% | 99.6% |

The HPLC results showed similar to RiboGreen results (99.7% with RiboGreen and 96.4% with RP-HPLC).

To demonstrated that this extraction method works for glass fiber filters as well as polypropylene filters, additionally performed experiment using glass fiber filters (data shown in Table 18).

TABLE 18

| | Peak Area | Calculated mRNA Conc. (mg/mL) | Recovery HPLC |
|---|---|---|---|
| Control 1 | 91.70 | 1.078 | |
| Control 2 | 94.65 | 1.114 | |
| Sample 1 | 90.15 | 1.059 | 96.8% |
| Sample 2 | 89.10 | 1.046 | 95.6% |
| Sample 3 | 89.30 | 1.048 | 95.8% |
| Average | | | 96.1% |

Example 3: DODAP VS. NON-DODAP LNPS

Figure 30:
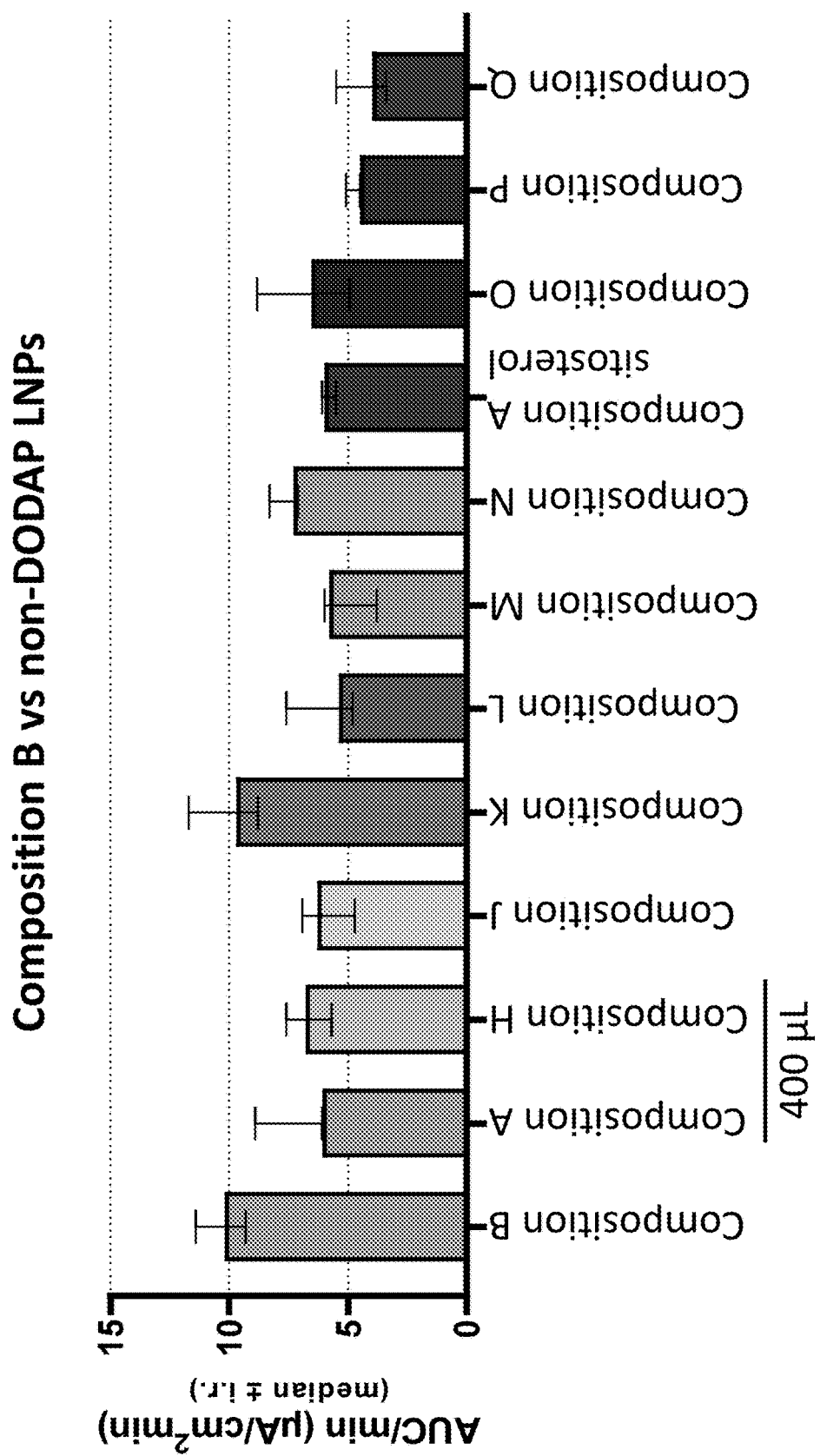

CFTR mRNA was incorporated into various LNP compositions: DODAP-containing Composition B and various non-DODAP lipid nanoparticles (400 3L for Composition A and Composition H) stored in 1× phosphate buffered saline (PBS). The compositions were nebulized using a VitroCell® system with a mesh nebulizer to deliver aerosolized LNPs to primary human Bronchial Epithelialis (hBE). CFTR function was measured. The composition of the nanoparticles used in the study is shown below in Table 13. The result showed DODAP-containing lipid nanoparticle Composition B had the most effect on CFTR function (Data shown in FIG. 30).

TABLE 19

LNP Compositions (mole percent)

| Composition | SORT | 4A3-SC7/ 5A2-SC8 | SORT | DOPE | Cholesterol | DMG-PEG | Lipid:mRNA (wt/wt) |
|---|---|---|---|---|---|---|---|
| B | DODAP | 19.05 | 20 | 19.05 | 38.09 | 3.81 | 40 |
| F | DODAP | 19.05 | 20 | 19.05 | 38.09 | 3.81 | 40 |
| G | non-DODAP | 14.29 | 40 | 14.29 | 28.57 | 2.86 | 40 |
| A | non-DODAP | 19.05 | 20 | 19.05 | 38.09 | 3.81 | 30 |
| H | non-DODAP | 19.05 | 20 | 19.05 | 38.09 | 3.81 | 30 |
| I | non-DODAP | 22.62 | 5 | 22.62 | 45.24 | 4.52 | 40 |
| J | non-DODAP | 24.43 | 10 | 21.43 | 42.85 | 4.29 | 30 |
| K | non-DODAP | 22.62 | 5 | 22.62 | 45.24 | 4.52 | 40 |
| L | DODAP | 23.52 | 27.44 | 24.52 | 20.44 | 4.09 | 27 |
| M | DODAP | 11.99 | 38.97 | 24.52 | 20.44 | 4.09 | 31 |
| N | non-DODAP | 26.16 | 24.79 | 24.52 | 20.44 | 4.09 | 26 |
| A | non-DODAP | 19.05 | 20 | 19.05 | 38.09 | 3.81 | 40 |
| O | non-DODAP | 22.62 | 5 | 22.62 | 45.24 | 4.52 | 30 |
| P | non-DODAP | 19.05 | 20 | 19.05 | 38.09 | 3.81 | 40 |
| Q Sitosterol | non-DODAP | 19.05 | 20 | 19.05 | 38.09 | 3.81 | 40 |

Example 4: DODAP-CONTAINING LIPID NANOPARTICLES

Figure 31:
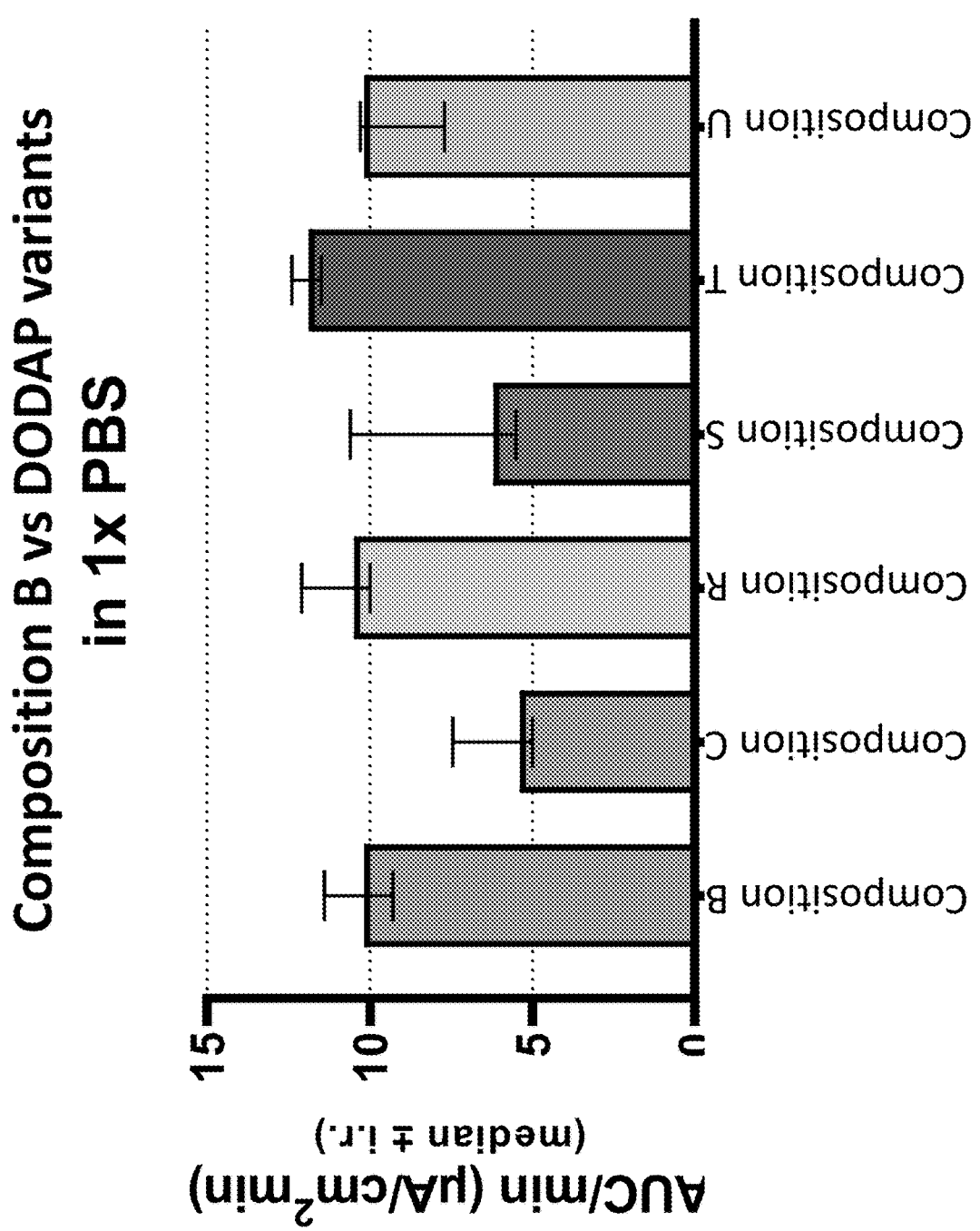

Further experiments were performed on DODAP-containing lipid nanoparticles with lower lipid:RNA ratio (either 30:1 or 25:1), made by adjusting the input amounts used to make the LNPs, and/or higher N/P ratio, achieved by increasing molar percentage of the ionizable lipids, such as 4A3-SC7 and/or DODAP. Among those lipid nanoparticles, Composition R, Composition T, and Composition U performed as well as Composition B (Data shown in FIG. 31). The composition of the nanoparticles used in the study is shown below in Table 14.

TABLE 20

Composition B/Composition C and "derivatives"

| Formulation | 4A3-SC7 | DODAP | DOPE | Cholesterol | DMG-PEG | Lipid:mRNA | N/P |
|---|---|---|---|---|---|---|---|
| Composition B | 19.05$^a$ (5)$^b$ | 20.00 (5.25) | 19.05 (5) | 38.10 (10) | 3.81 (1) | 40:1 | 13.4 |
| Composition C | 19.05$^a$ (5)$^b$ | 20.00 (5.25) | 19.05 (5) | 38.10 (10) | 3.81 (1) | 30:1 | 10.0 |

TABLE 20-continued

Composition B/Composition C and "derivatives"

| Formulation | 4A3-SC7 | DODAP | DOPE | Cholesterol | DMG-PEG | Lipid:mRNA | N/P |
|---|---|---|---|---|---|---|---|
| Composition R | 19.34 (5.83) | 27.62 (8.33) | 16.57 (5) | 33.15 (10) | 3.31 (1) | 30:1 | 11.1 |
| Composition S | 19.34 (5.83) | 27.62 (8.33) | 16.57 (5) | 33.15 (10) | 3.31 (1) | 25:1 | 9.2 |
| Composition T | 18.52 (6.67) | 37.04 (13.33) | 13.89 (5) | 27.78 (10) | 2.78 (1) | 30:1 | 12.1 |
| Composition U | 23.88 (6.67) | 18.81 (5.25) | 17.91 (5) | 35.82 (10) | 3.58 (1) | 30:1 | 11.2 |

$^a$(%)-molar ratio
$^b$molar ratio

Figure 32:
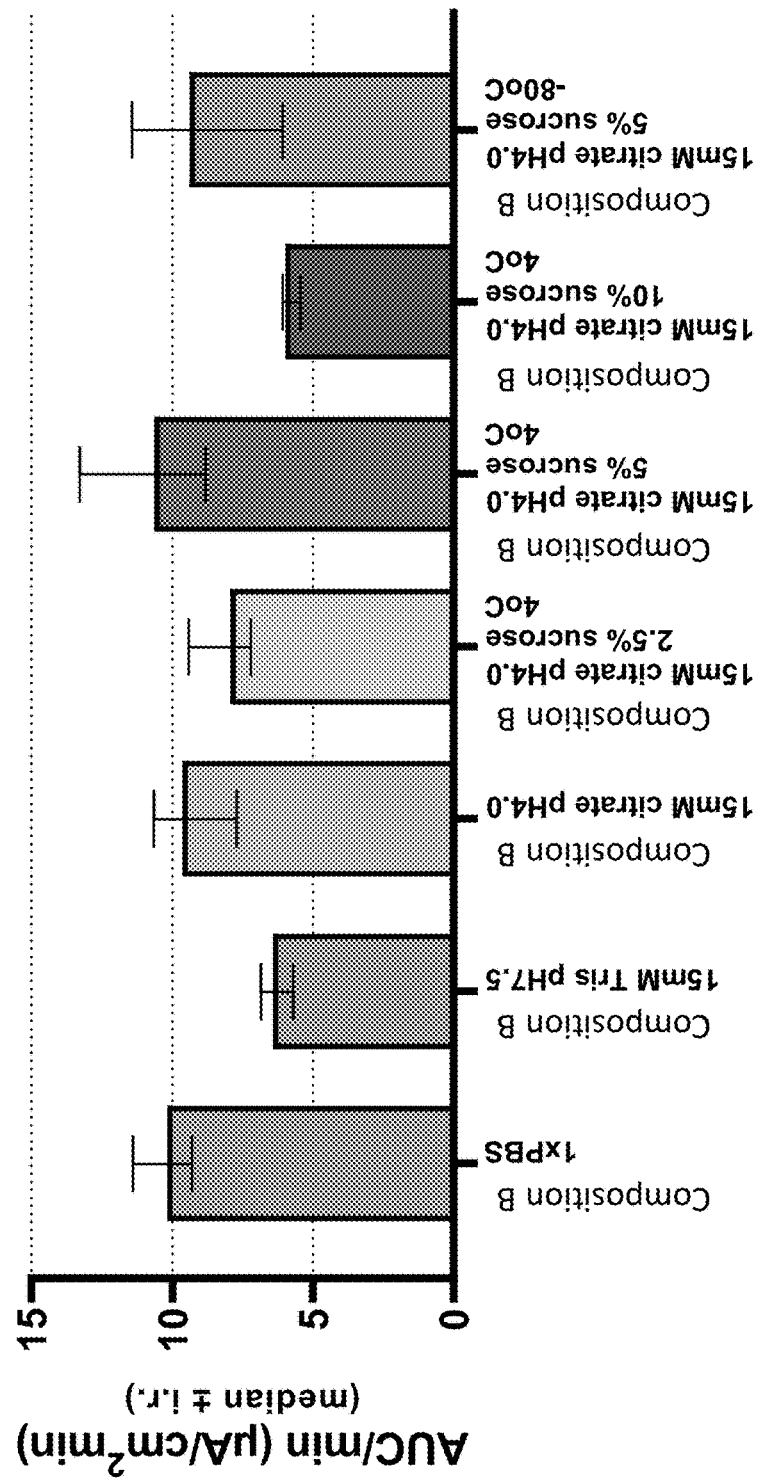

The effect of storage buffer on CFTR function were measured in Composition B lipid nanoparticles. Lipid nanoparticles were stored in either 1× PBS, 15 mM Tris buffer pH 7.5 or 15 mM Citrate buffer pH 4 (at 4° C.) in different sucrose concentration (0%, 2.5%, 5%, or 10%). Composition B lipid nanoparticles in 15 mM Citrate buffer showed similar performance in CFTR function. Addition of 5% sucrose in 15 mM Citrate buffer did not significantly impact Composition B potency. Also, freeze-thaw cycle of lipid nanoparticles before applying to CFTR function analysis did not affect CFTR function (Data shown in FIG. 32).

Figure 33B:
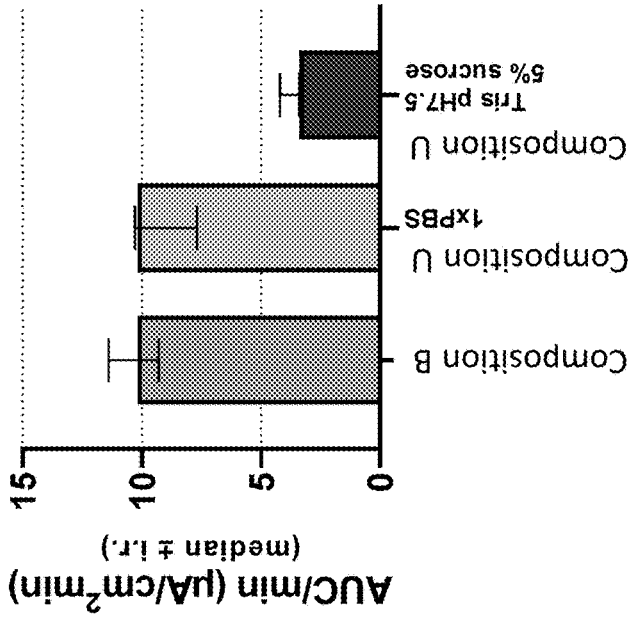
Figure 33A:
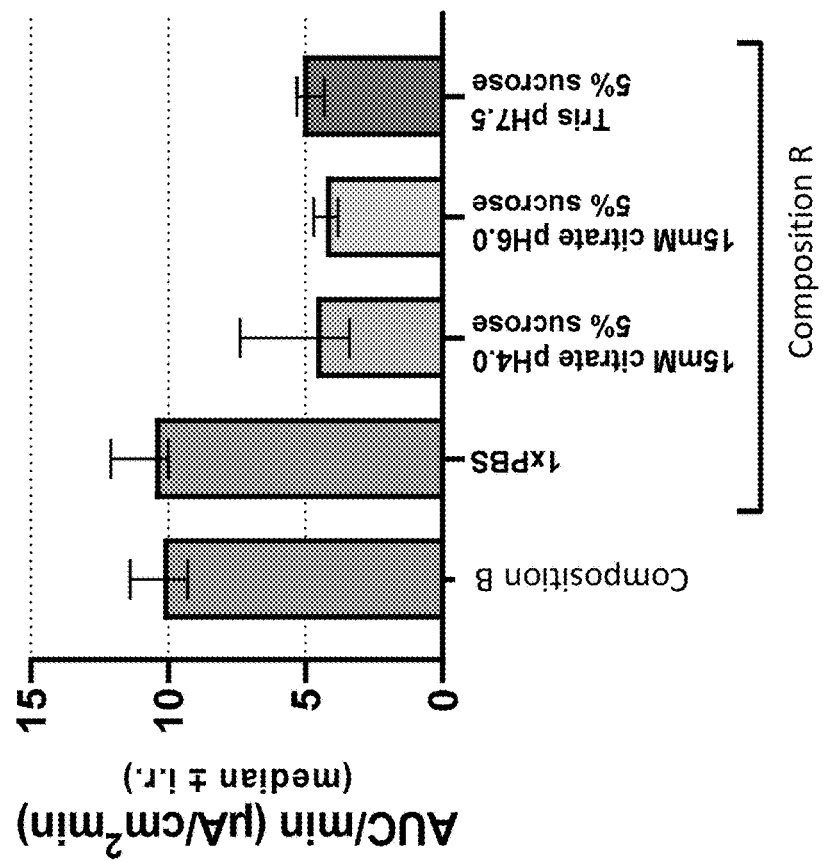
Figure 34A:
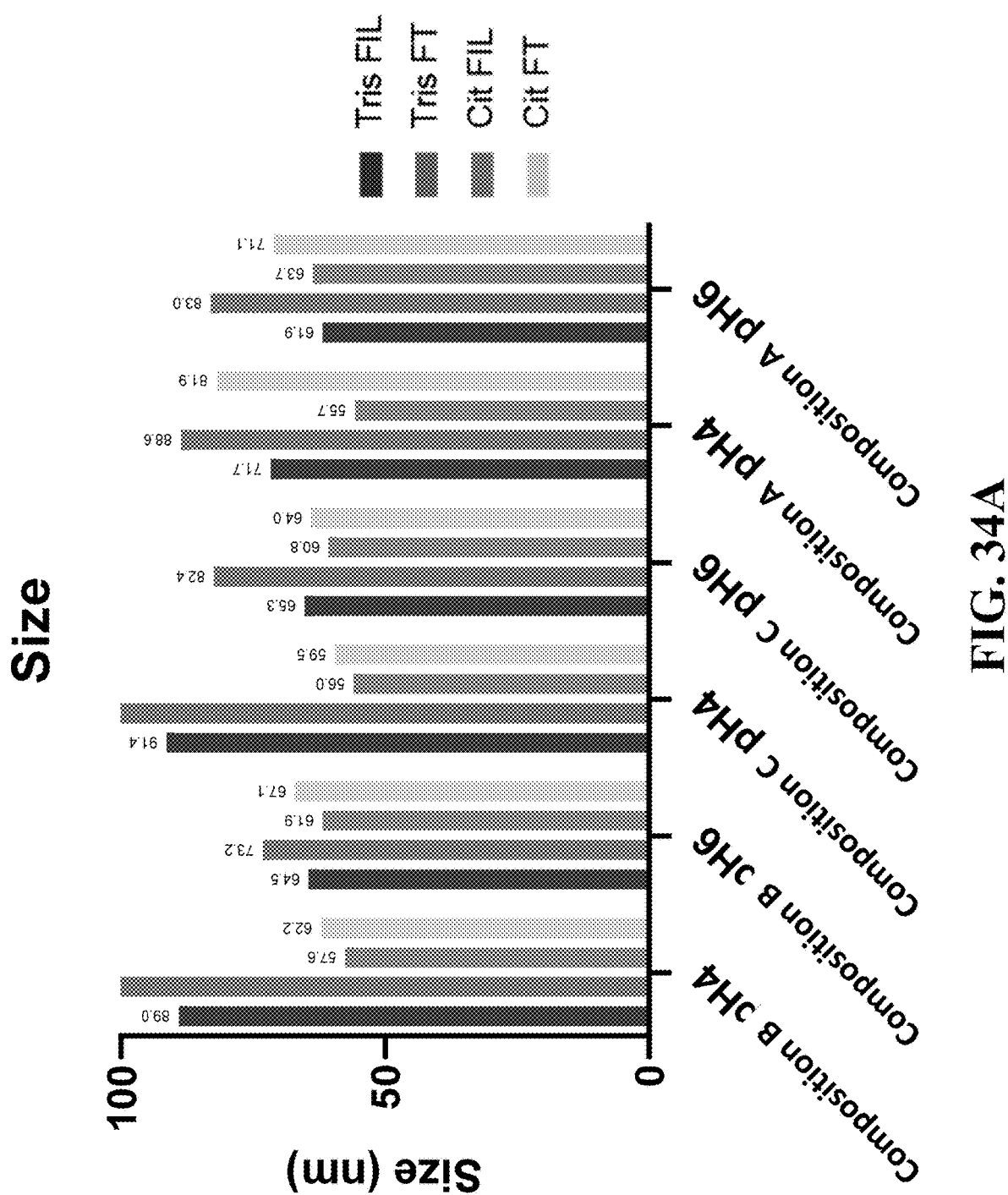
Figure 34B:
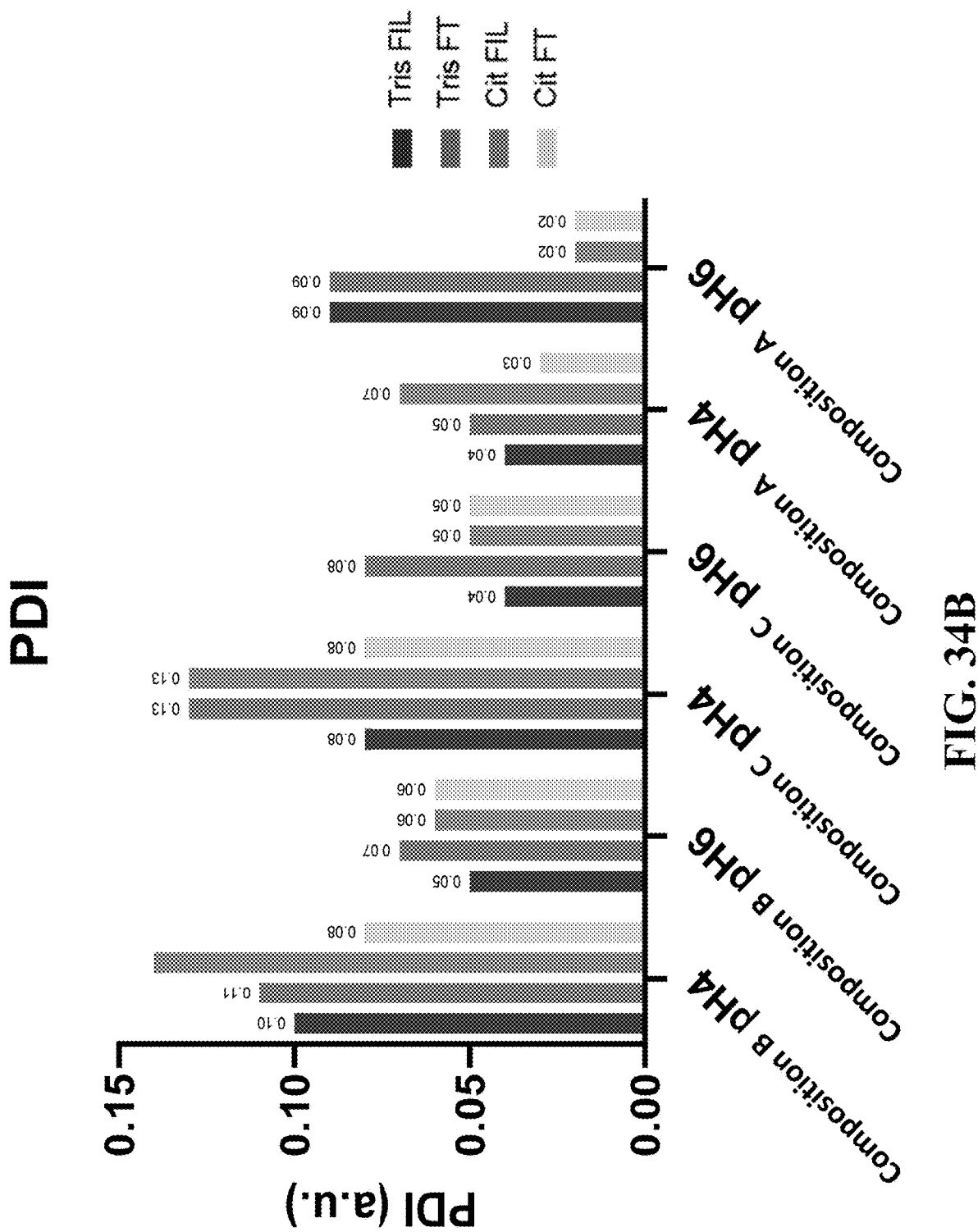
Figure 34C:
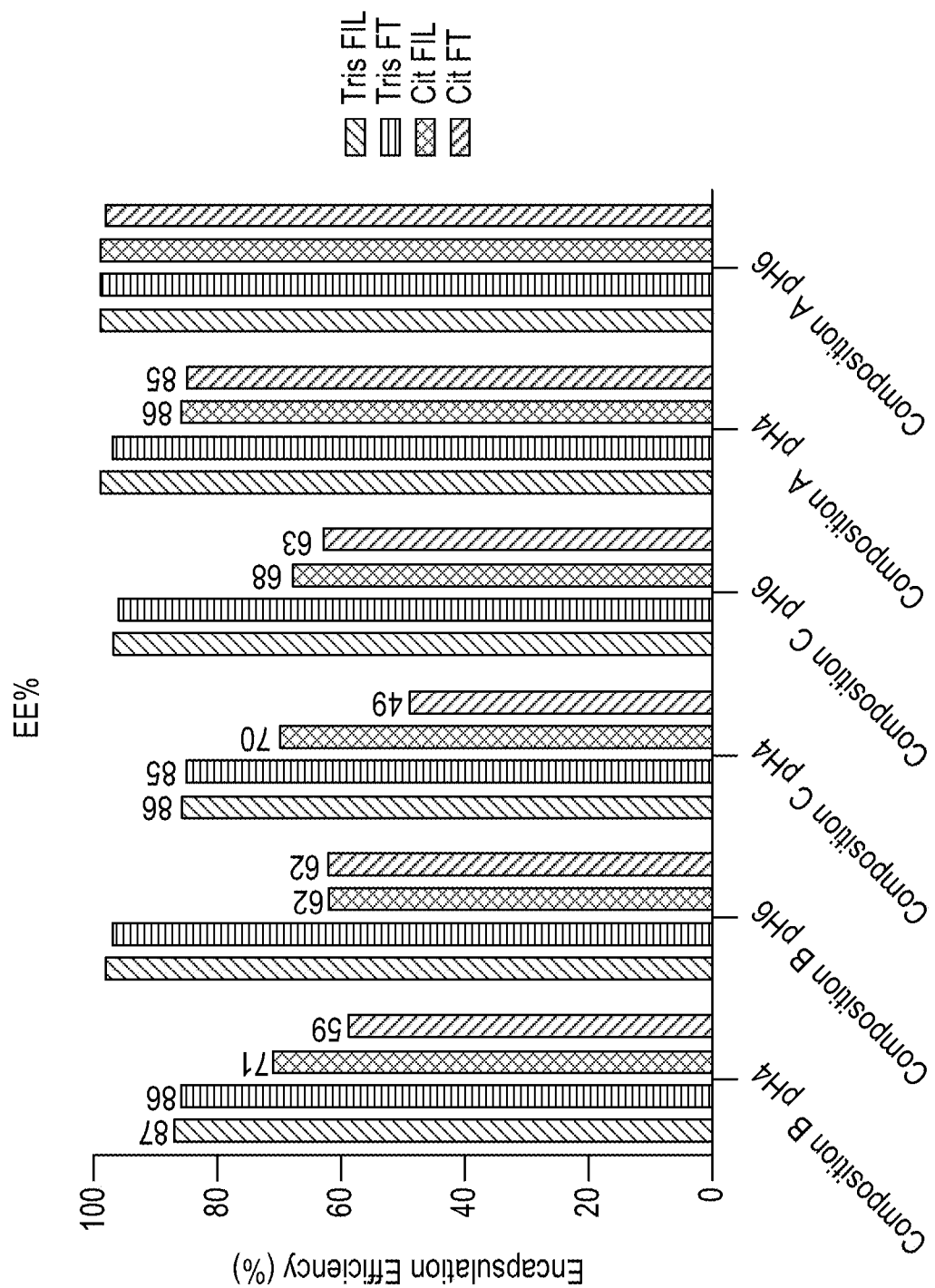
Figure 34D:
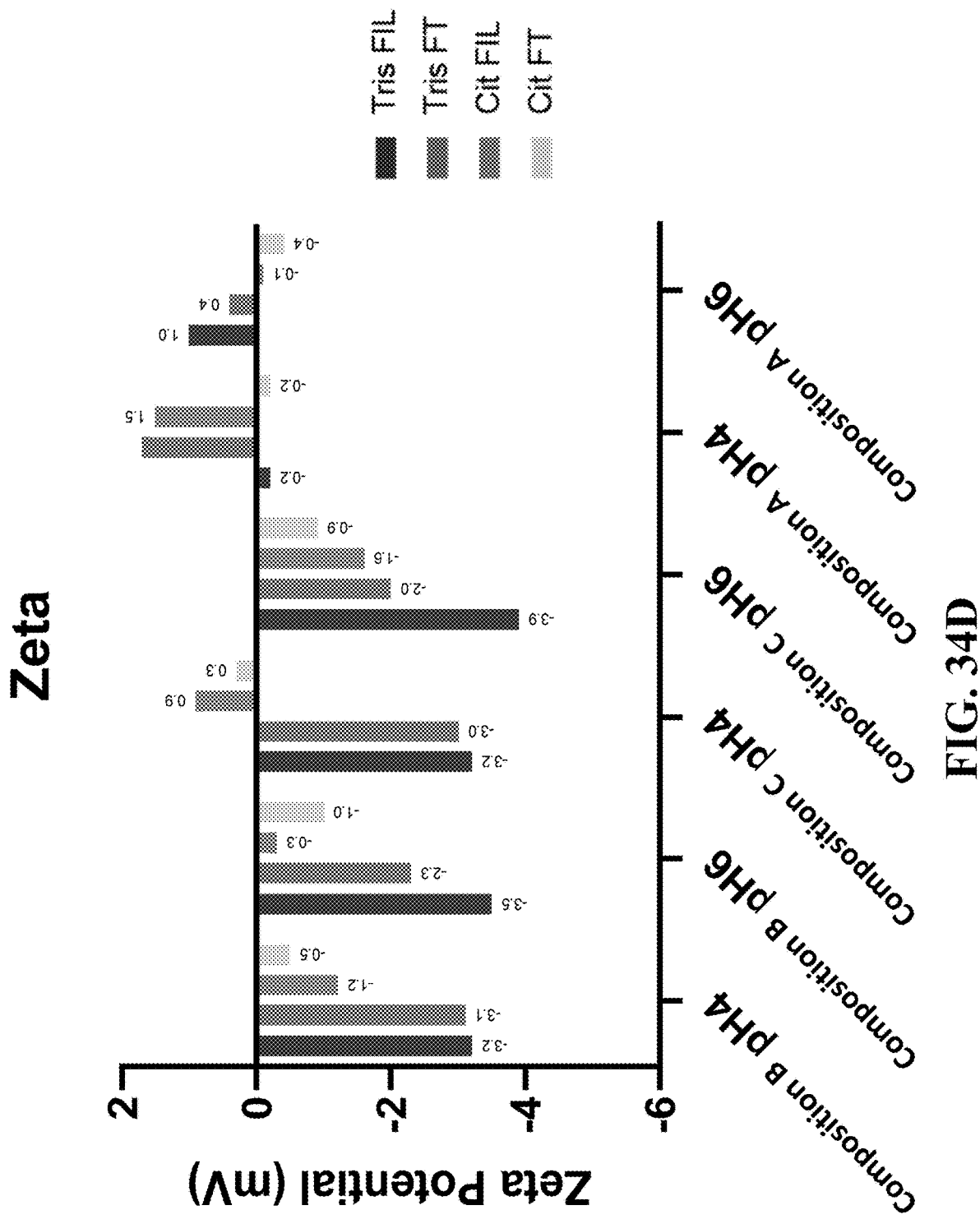

The effect of buffer on CFTR function were further tested in either Composition R or Composition U. Composition R or Composition U performed as well as Composition B when stored in 1× PBS. Addition of 5% sucrose in buffers (15 mM Citrate pH 4, 15 mM Citrate pH 6 or Tris pH 7.5) to Composition R and Composition U was also tested (data shown in FIGS. 33A-33B).

Example 5: Composition X and Composition Y

Figure 40:
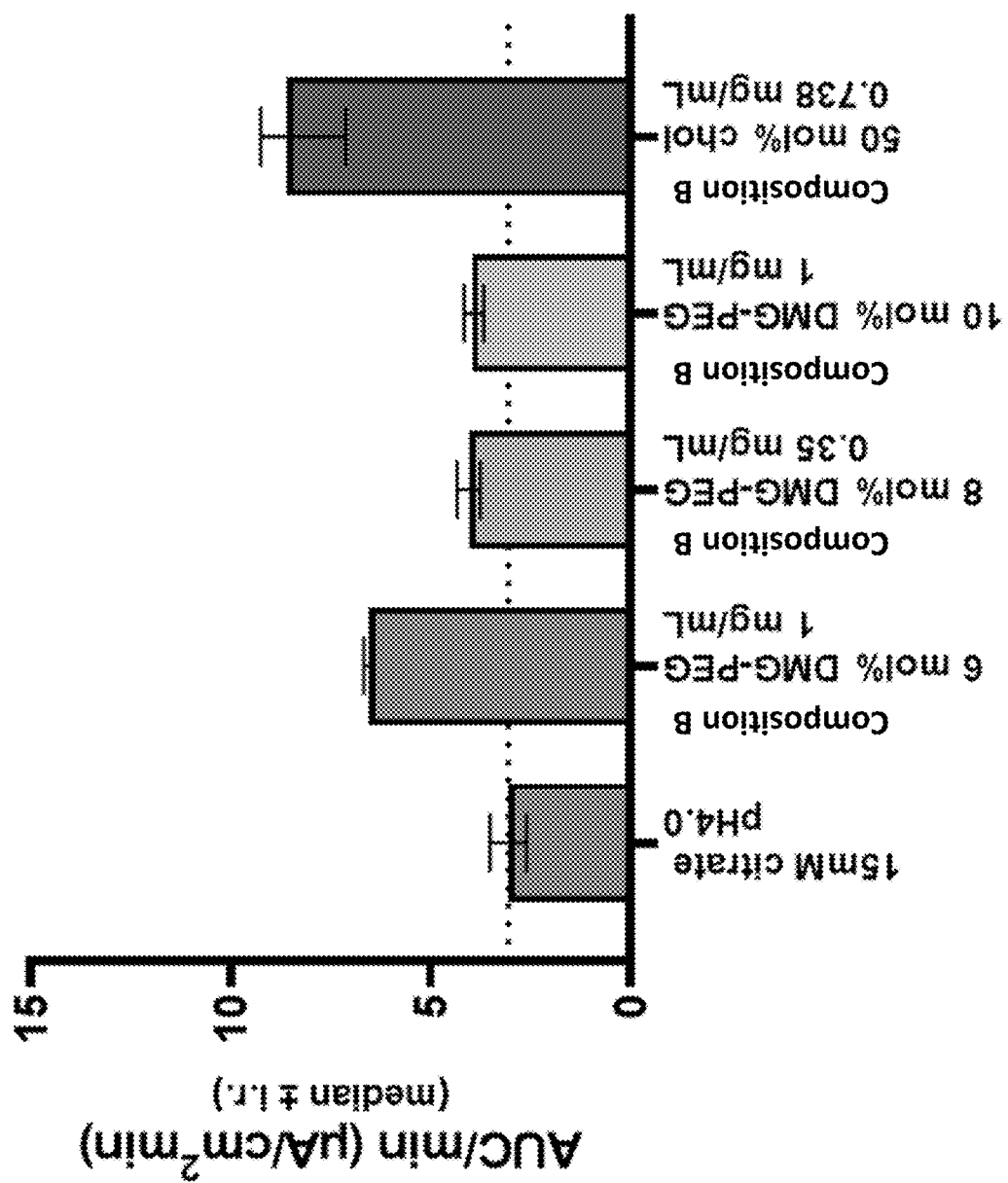
Figure 41:
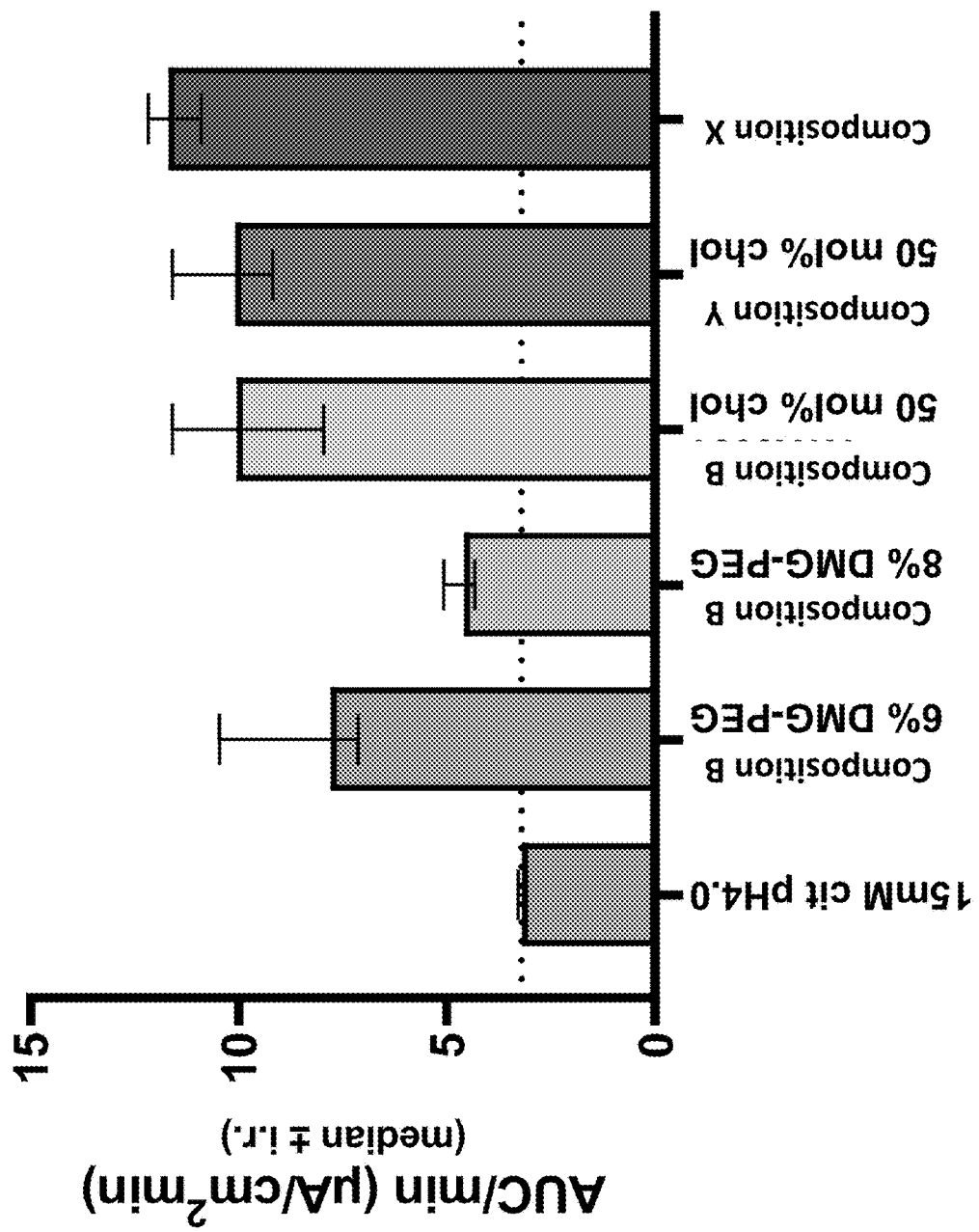

Experiments were conducted to evaluate the impact of cholesterol on the stability and efficacy of lipid nanoparticle (LNP) compositions. Composition B lipid nanoparticles containing higher molar percentage of cholesterol were created and subjected to test its CFTR function. Chloride conductance was measured with multi transepithelial current clamp system (MTECC24). As data shown in FIG. 40, the CFTR function was increased as the molar percentage of cholesterol in lipid nanoparticles were increased. Further, lipid nanoparticles containing 50% molar percentage of cholesterol were created, measured its CFTR function and resulted that increased molar percentage of cholesterol in lipid nanoparticles enhanced CFTR function (FIG. 41). The composition of the nanoparticles used in these studies is shown below in Table 15.

TABLE 21

Test LNP Compositions (mole percent)

| Formulation | 4A3-SC7 | DOPE | Cholesterol | DMG-PEG | DODAP | Lipid:mRNA |
|---|---|---|---|---|---|---|
| Composition B | 19.05 | 19.05 | 38.1 | 3.81 | 20 | 40:1 |
| Composition B-6% | 19.05 | 19.05 | 36 | 6 | 20 | 40:1 |
| Composition B-8% | 19.05 | 19.05 | 34 | 8 | 20 | 40:1 |
| Composition B-10% | 19.05 | 19.05 | 32 | 10 | 20 | 40:1 |
| Composition B-50% cholesterol | 15.08 | 15.08 | 50 | 3.81 | 16.03 | 40:1 |
| Composition S-50% cholesterol* | 13.73 | 10.96 | 50 | 3.31 | 22 | 25:1 |
| Composition X | 14.8 | 22.2 | 44.4 | 3 | 15.6 | 36:1 |

*Composition S-50% cholesterol = Composition Y

Example 6: Effects of Composition X and Composition Y on CFTR

Figure 42:
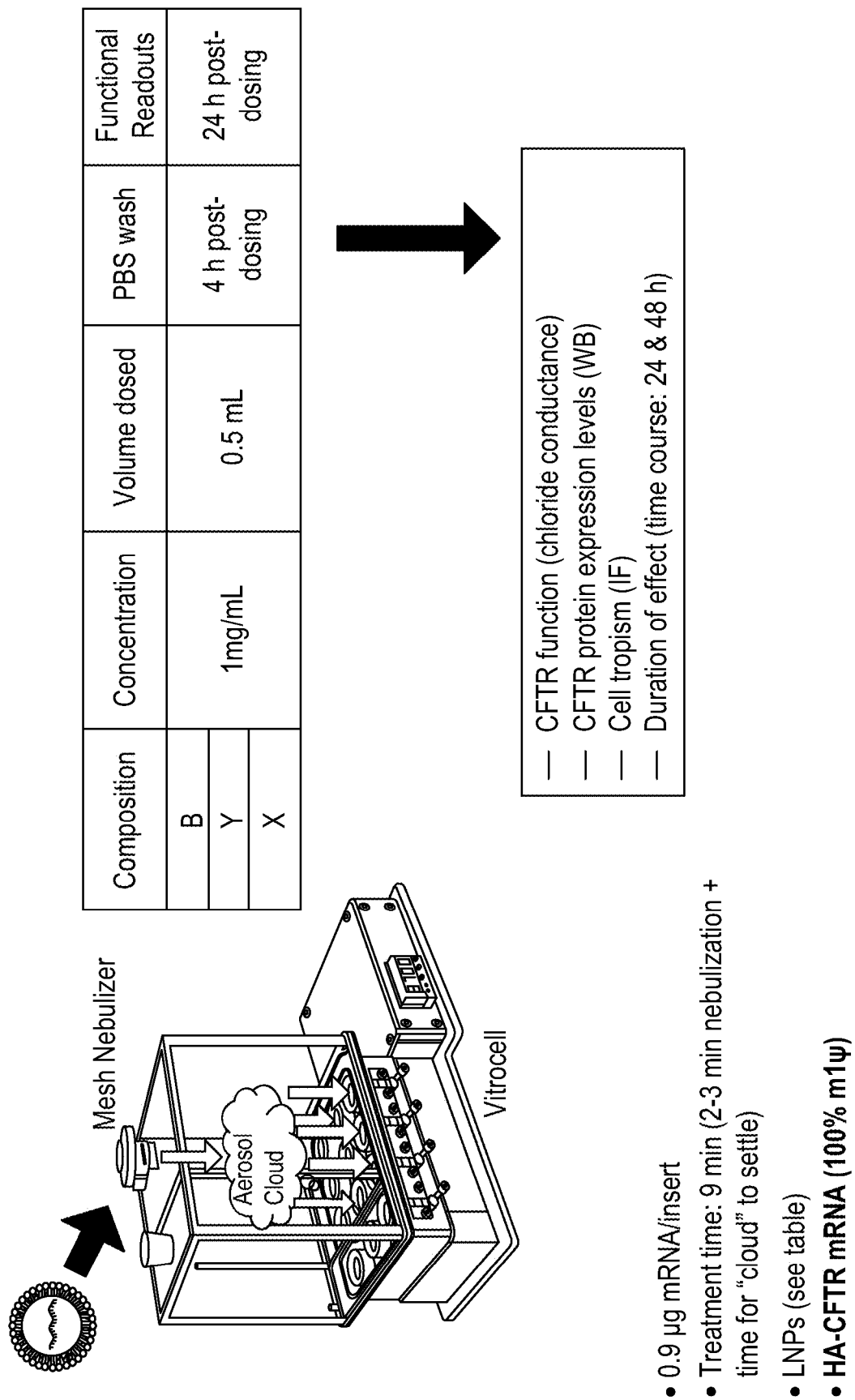
Figure 43B:
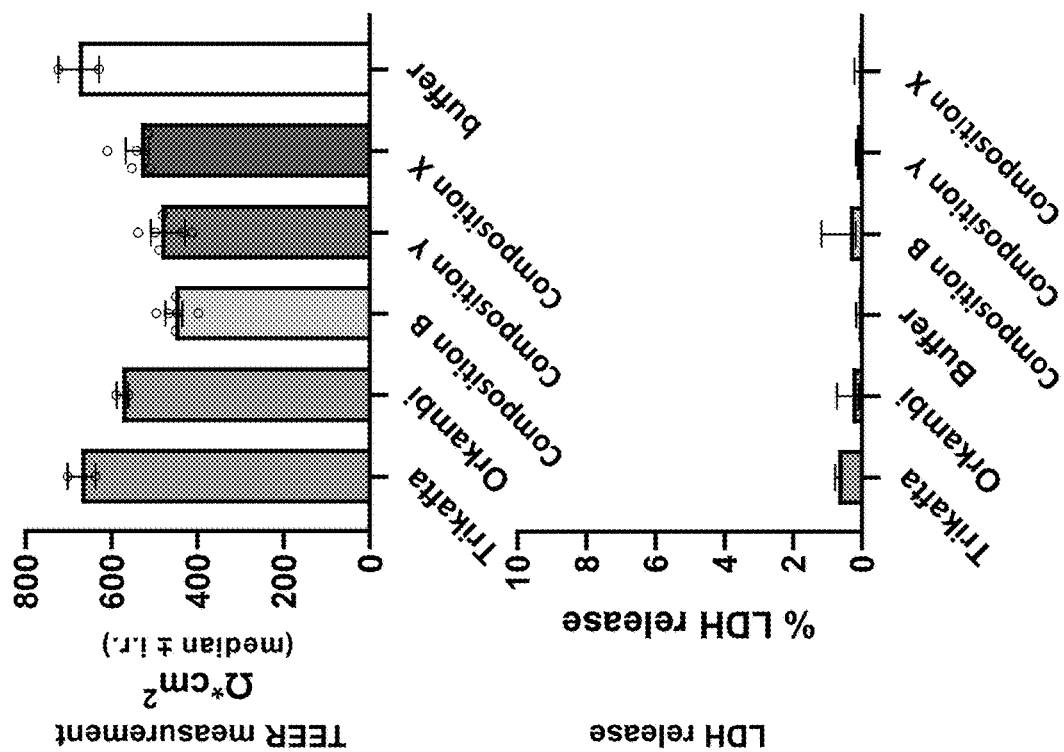
Figure 43A:
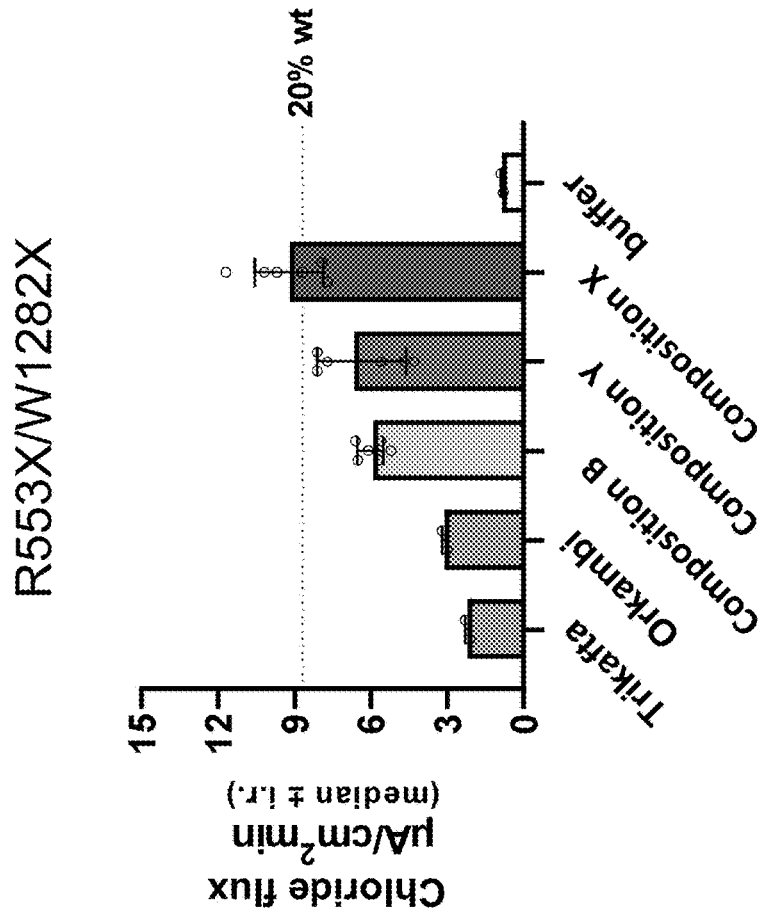
Figure 43D:
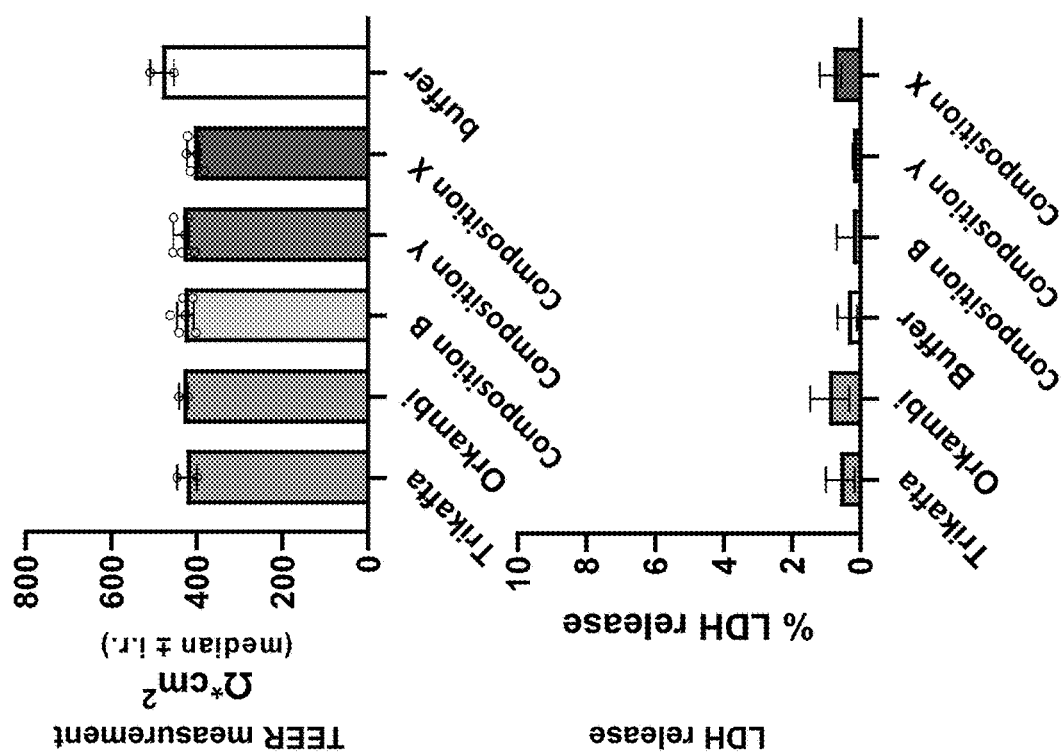
Figure 43C:
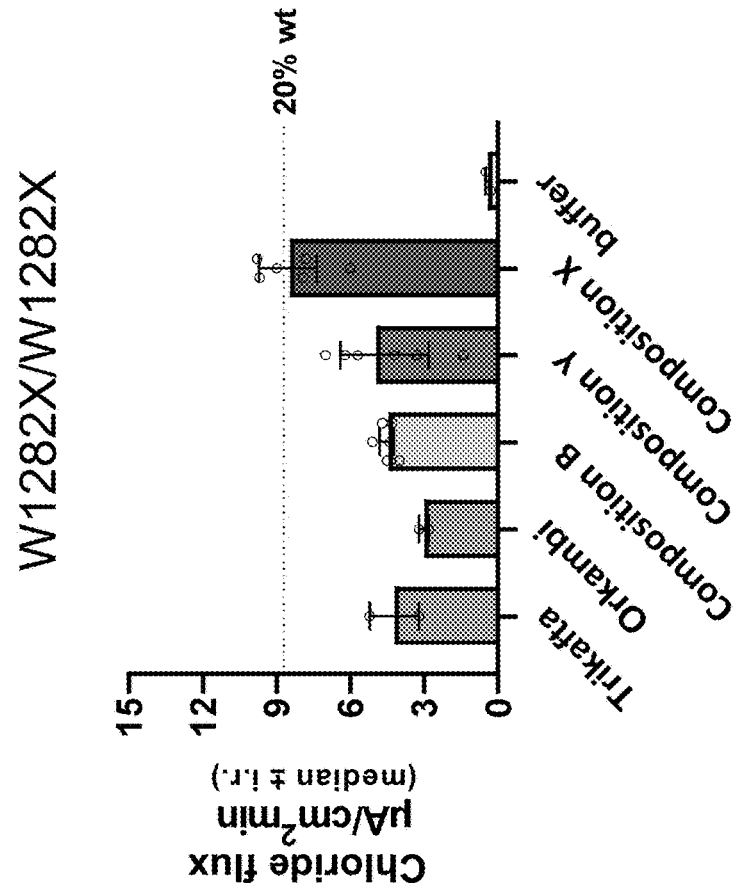

Experimental conditions were shown in FIG. 42. Briefly, human Bronchial Epithelialis (hBEs) (passage 3) with different cystic fibrosis (CF) genotypes were established on TransWell high-throughput screening (HTS) plates (Corning 3378). Then, each mRNA containing lipid nanoparticles (1 mg/mL, 0.5 mL) were subjected to Mesh nebulizer. All nebulizations were performed at 8 weeks post-air liquid interface (ALT). Treatment time for lipid nanoparticles were 9 minutes, including 2-3 minutes of nebulization and additional time for "cloud" to settle. Cells were washed with PBS 4 h post-dosing and subjected to either chloride conductance for CFTR function, Western blotting for CFTR protein expression, or immunofluorescence assay for cell tropism 24 h and 48 h post-dosing.

FIG. 43 shows rescue of CFTR function in two nonresponsive genotypes. hBE cells expressing nonresponsive genotypes were established on TransWell HTS plates (Corning 3378), nebulized with either CFTR mRNA-containing lipid nanoparticles or buffer. Cystic Fibrosis treatment drugs (Trifkafta or Orkambi) were treated at the time of nebulization. At 24 h post-treatment, chloride conductance was measured with multi transepithelial current clamp system (MTECC24). In both cell lines, nebulization of lipid nanoparticles containing CFTR mnRNA rescued CFTR function. Additionally, cells nebulized Composition X showed 20% of wild-type level of CFTR function. Transepithelial electrical resistance (TEER) and lactic acid dehydrogenase (LDH) measurements suggested no indication of toxicity after the delivery of CFTR mRNA-containing lipid nanoparticles (FIGS. 43B and 43D).

To analyze the restoration effect of lipid nanoparticles on CFTR function, various cystic fibrosis genotype cells were further subjected to nebulize with either Composition B, Composition X or Composition Y. Three nonresponsive genotypes (R553X/W1282X, W1282X/W1282X, K710X/L$^{467}$P), six ΔF508/ΔF508 homozygous genotypes (TXCF042716, KKD012K, KKD025L, KKD003K, 20160524CF, KK017N) and one heterozygous genotype (G452X/ΔF508) cells were used in the experiment. Rescue levels in two nonresponsive genotype cells (R553X/W1282X and W1282X/W1282X) dosed with Composition X showed about 20% of wild-type level of CFTR function. Moreover, all ΔF508/ΔF508 homozygous genotype cells (except KKD025L) and heterozygous genotype (G452X/ΔF508) cells dosed with Composition X showed greater than 20% of wild-type level of CFTR function. Heterozygous genotype (G452X/ΔF508) cells dosed with either Composition B or Composition Y also showed more than 20% of wild-type level of CFTR function. (Data shown in FIG. 44).

Increased CFTR function in lipid nanoparticle treated cells might be due to loss of transepithelial resistance. To determine whether aerosolized lipid nanoparticles affect cell toxicity, six ΔF508/ΔF508 homozygous genotypes hBE cells were dosed lipid nanoparticles and measured electrical resistance across a cellular monolayer and released lactic acid dehydrogenase (LDH). No toxicity was observed from aerosolized formulations (Data shown in FIGS. 45A-45K).

Duration of CFTR restoration function in nebulized KKD003K cells were determined at 24 h and 48 h post treatment. CFTR function remained greater than 20% of wild-type level of CFTR function after 48 h of nebulization (FIG. 46A). Also, CFTR protein expression level was detected in cells dosed with lipid nanoparticles at 24 h and decreased at 48 h, but still detected in cells (FIGS. 46B-46C). When analyzing overall protein expression, Composition B seemed to transfect more cells, even though Composition X showed higher chloride flux.

Figure 47B:
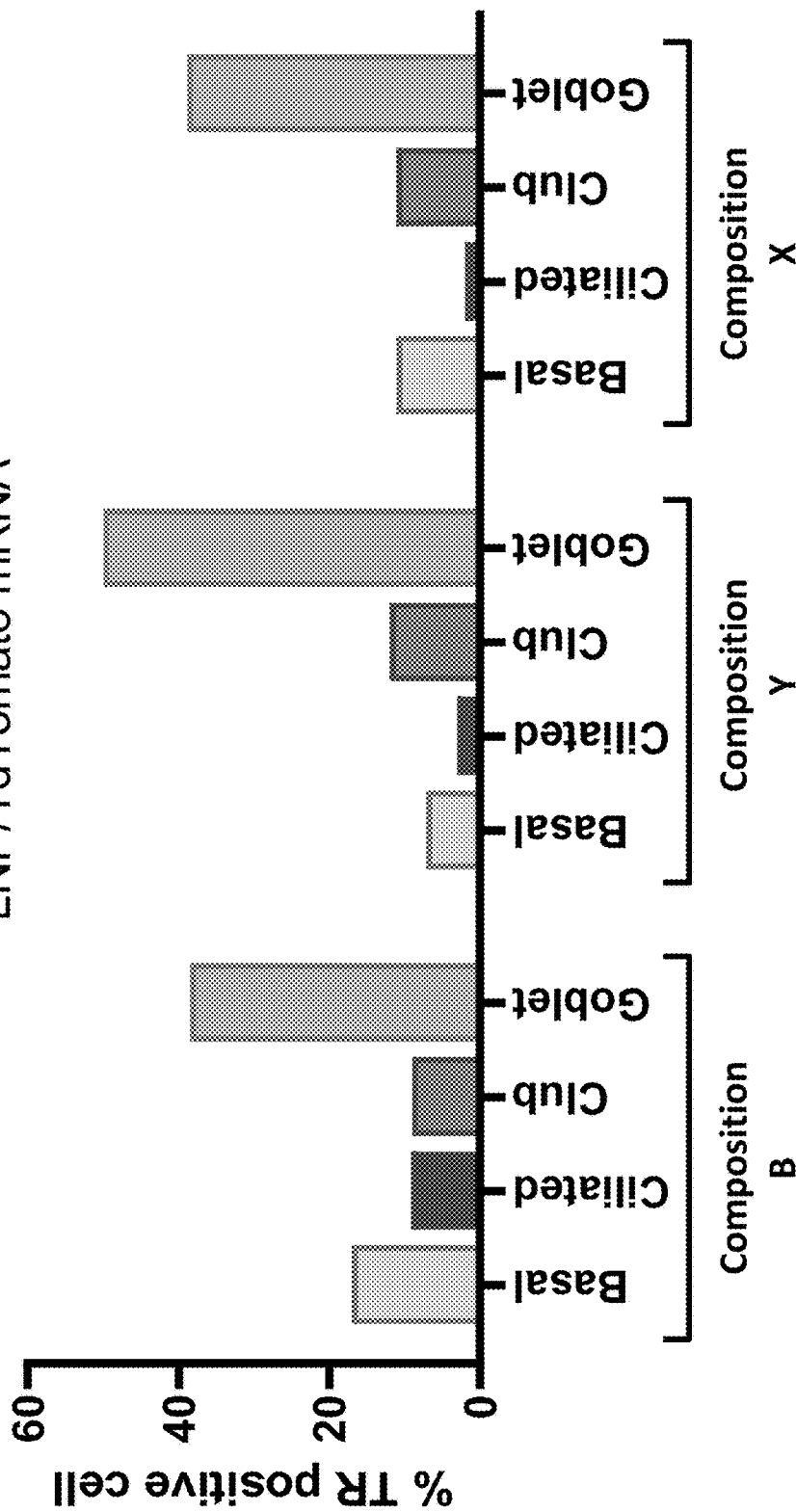

To assess target delivery of lipid nanoparticles, TXCF042716 cells dosed with each lipid nanoparticle were fixed, blocked and probed with primary antibodies for each cell type (Basal=Cytokerain 5 (CK5), Ciliated=Acetylated tubulin, Club=Secretoglobin Family 1A Member 1 (SCGB1A1)/CC10 and Goblet=Mucin 5AC (MUC5AC)) (FIG. 47A). For every field, total number of cells with Tomato Red (TR) signal and colocalized signal were counted and percent of positive Tomato Red signal in each cell type were determined (FIG. 47B). All three compositions showed similar cell tropism profiles, favoring delivery to both basal and secretory cells.

Figure 44:
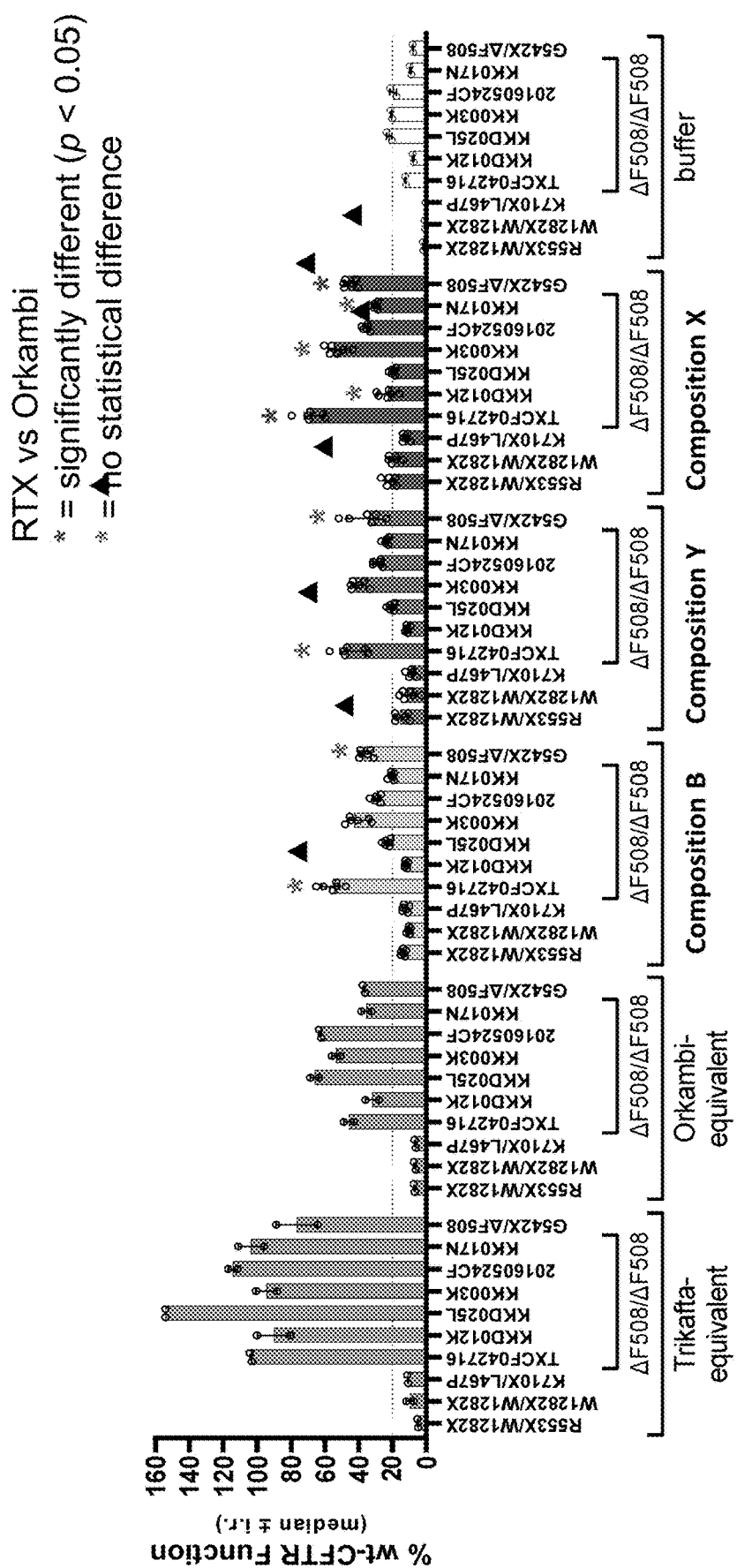
Figures 45A, 45B:
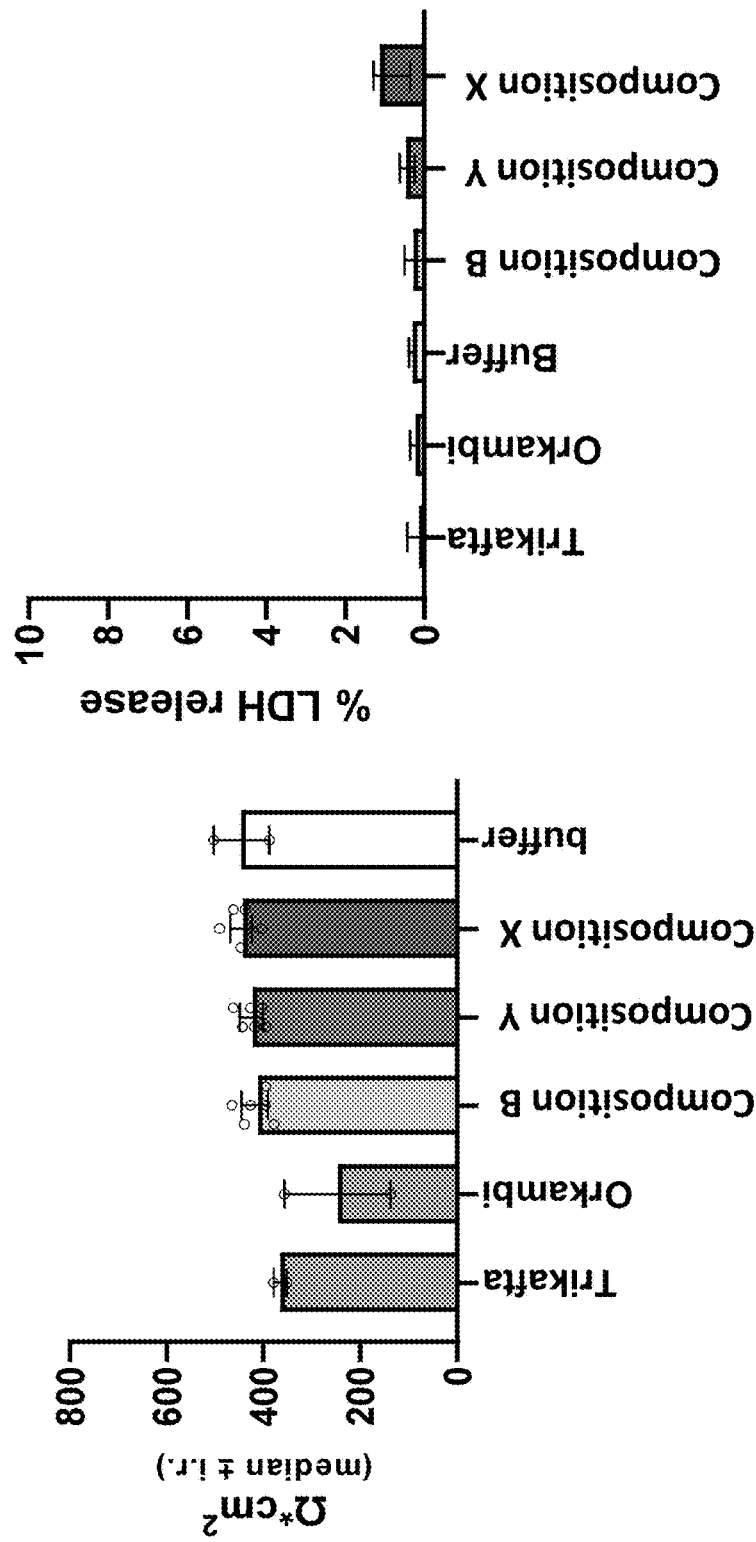
Figures 45C, 45D:
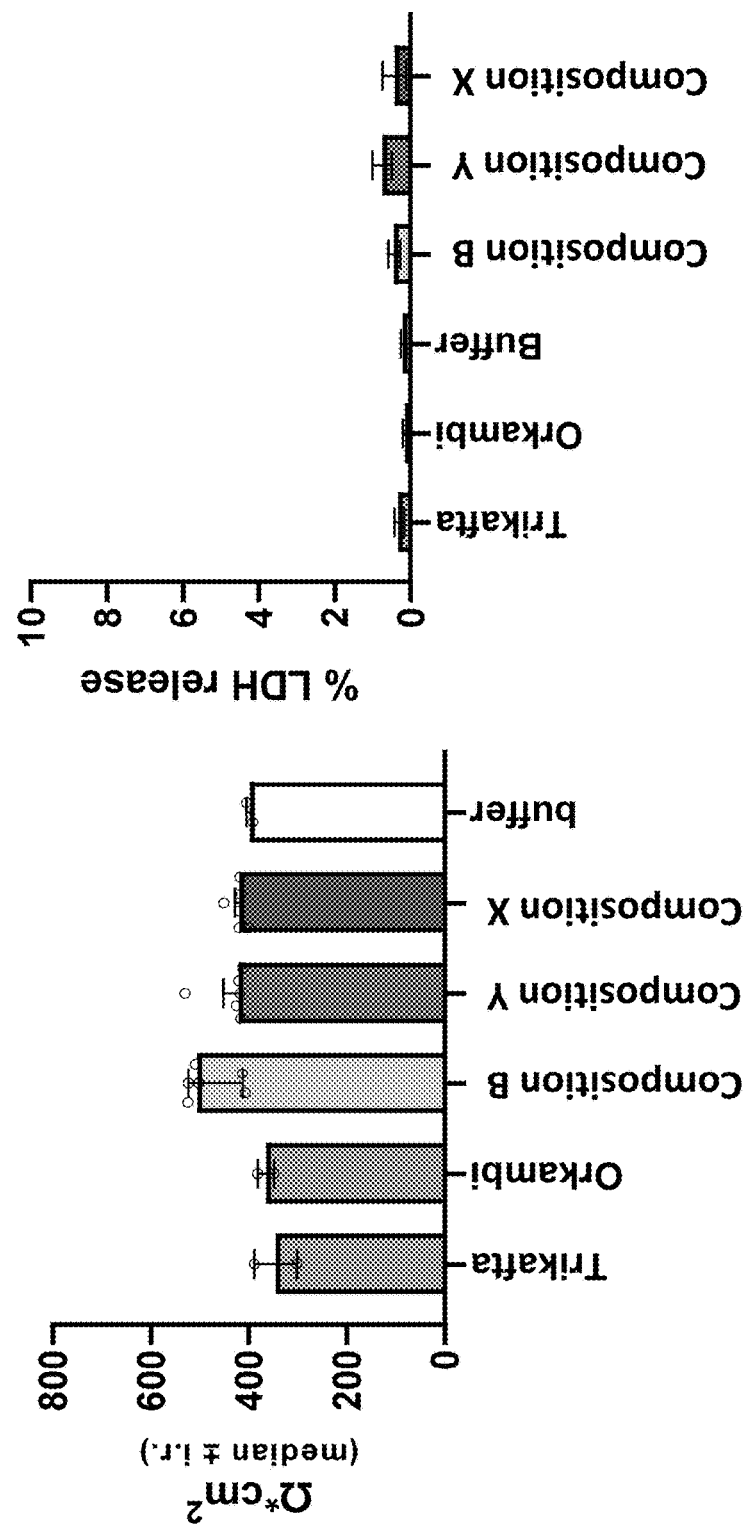
Figures 45E, 45F:
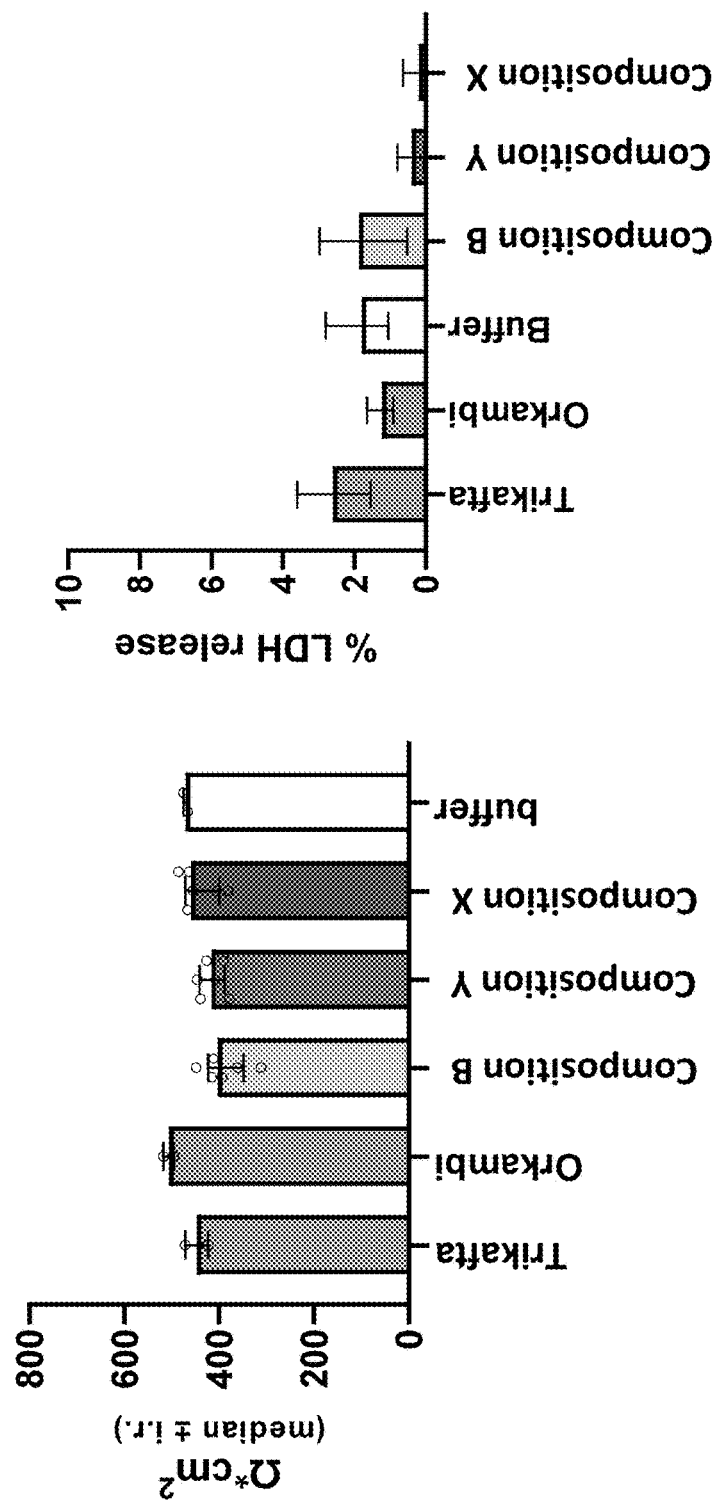
Figures 45G, 45H:
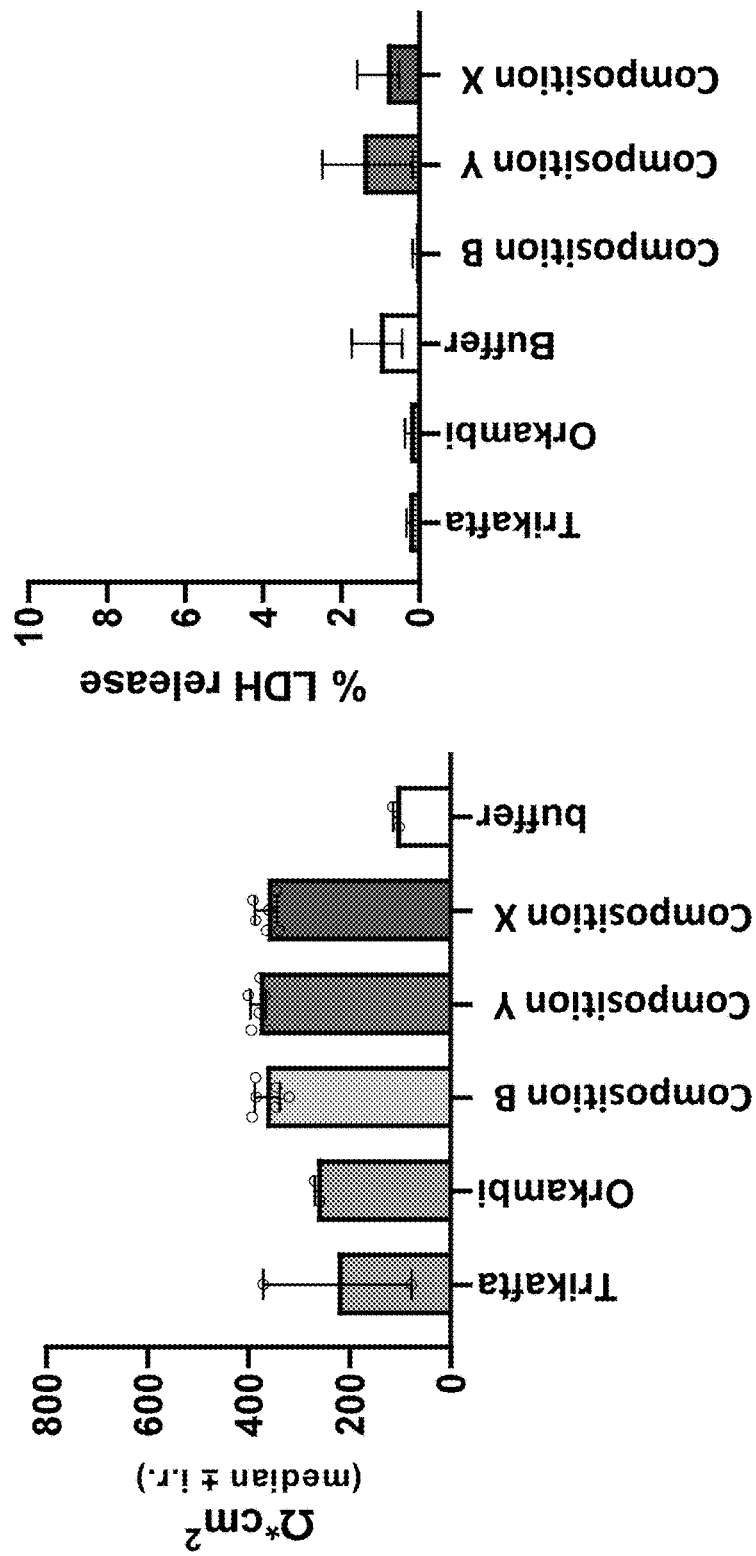
Figures 45I, 45J:
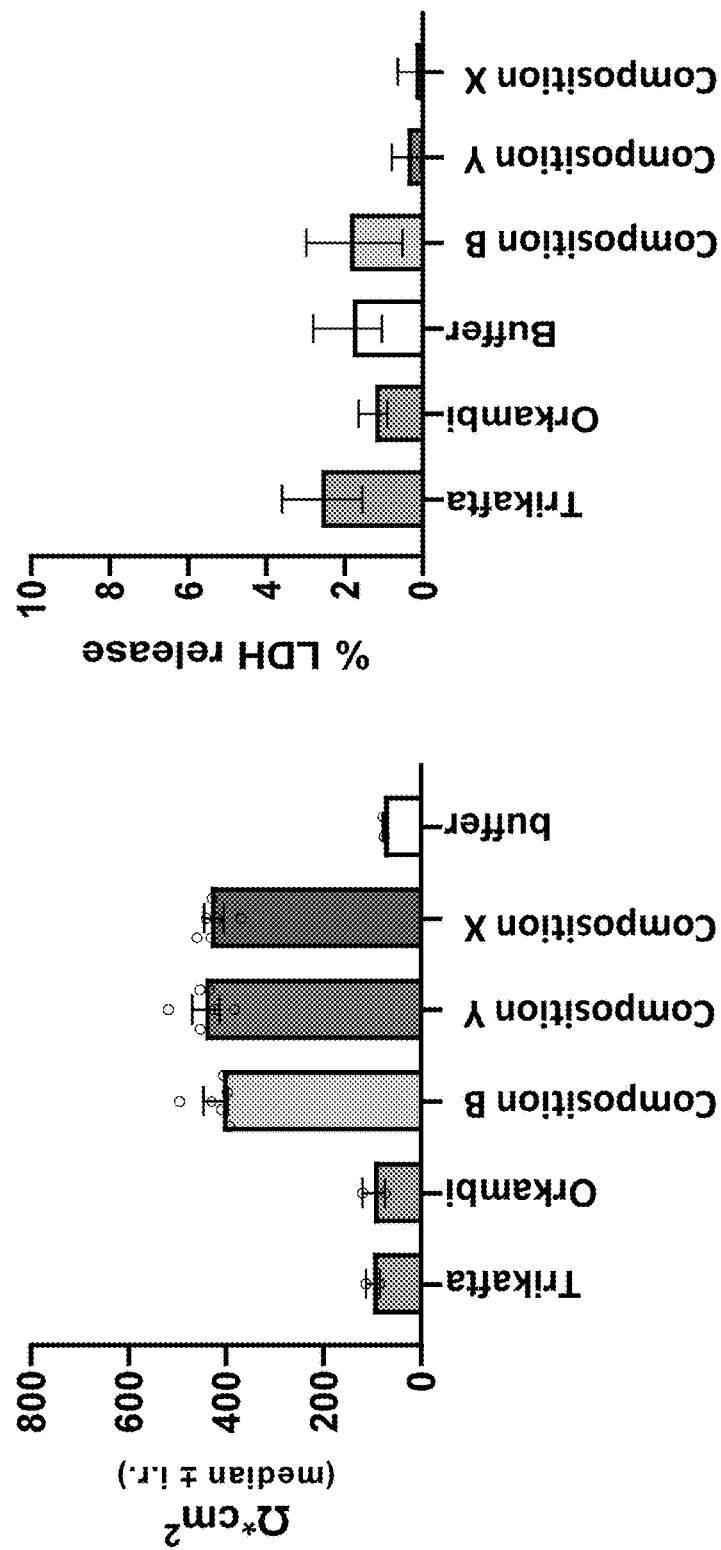
Figure 45K:
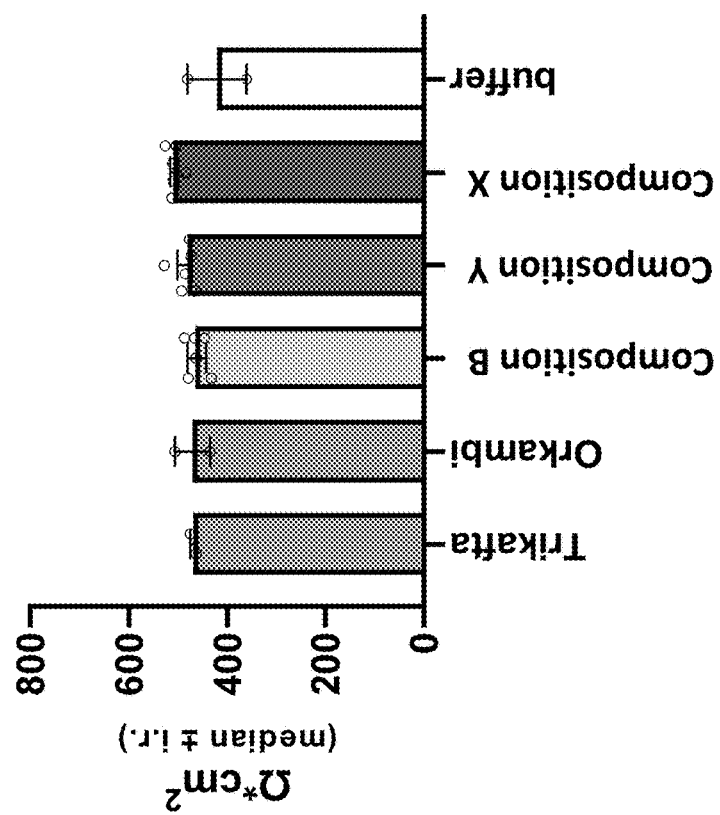

CFTR function restoration assays in FIG. 44 showed similar restoration pattern in each cell type. To determine the relationship between chloride flux and protein expression, either TXCF042716 or KKD012K cells were dosed with lipid nanoparticles and measured CFTR function by chloride conductance and protein expression level by Western blot analysis. Cells with TXCF042716 genotype showed greater restoration of CFTR function compared to cells with KKD012K genotype (FIG. 48A) and Western blot analysis showed expression of CFTR protein was correlated to CFTR functional assay (FIGS. 48B-48C).

To determine whether mucus production affects transfection efficiency of lipid nanoparticles, W1282X/W1282X hBEs and R553X/W1282X hBEs cells were pre-treated Dithiothreitol (DTT) before lipid nanoparticles were nebulized (experimental scheme shown in FIG. 49). The results showed increased pre-treated DTT concentration from 3 mM to 10 mM correlated with higher chloride flux after nebulization of lipid nanoparticles (FIGS. 50-51). Cell toxicities were measured by transepithelial electrical resistance (TEER). The result showed that cell integrity was not affected by DTT treatment (FIGS. 50B and 51B). These data support the idea that differences in mucus production may impact the delivery of lipid nanoparticles.

To establish the addition of CFTR activator further increase CFTR function, two nonresponsive genotypes hBE cells (R553X/W1282X and W1282X/W1282X) were nebulized with lipid nanoparticles either in presence or absence of Ivacaftor (VX-770). Addition of CFTR activator (Ivacaftor) further increased rescue of CFTR function after delivery of lipid nanoparticles (Data shown in FIGS. 52A-52B).

To determine successful delivery of lipid nanoparticles to lungs in vivo, mice were administered via inhalation lipid nanoparticles containing HA-CFTR mRNA and luciferase mRNA. Chemiluminescence signals were gradually increased as the number of injections increased. After six deliveries, Composition B showed the most chemiluminescence image while Composition Y showed the least image (FIG. 53A). These results support the data observed by Western blot in FIGS. 46B-46C. Chemiluminescence images were taken after $2^{nd}$ dose (FIG. 53B).

Composition X was compared to an alternative LNP composition, Composition A. Composition X showed superior ability to restore CFTR function in ΔF508/ΔF508 hBE cells compared to Composition A (FIGS. 54A-54B). There was no significant difference in cell integrity and permeability between Composition A and Composition X treated cells measured by transepithelial electrical resistance (TEER) (FIG. 54C).

Figure 35A:
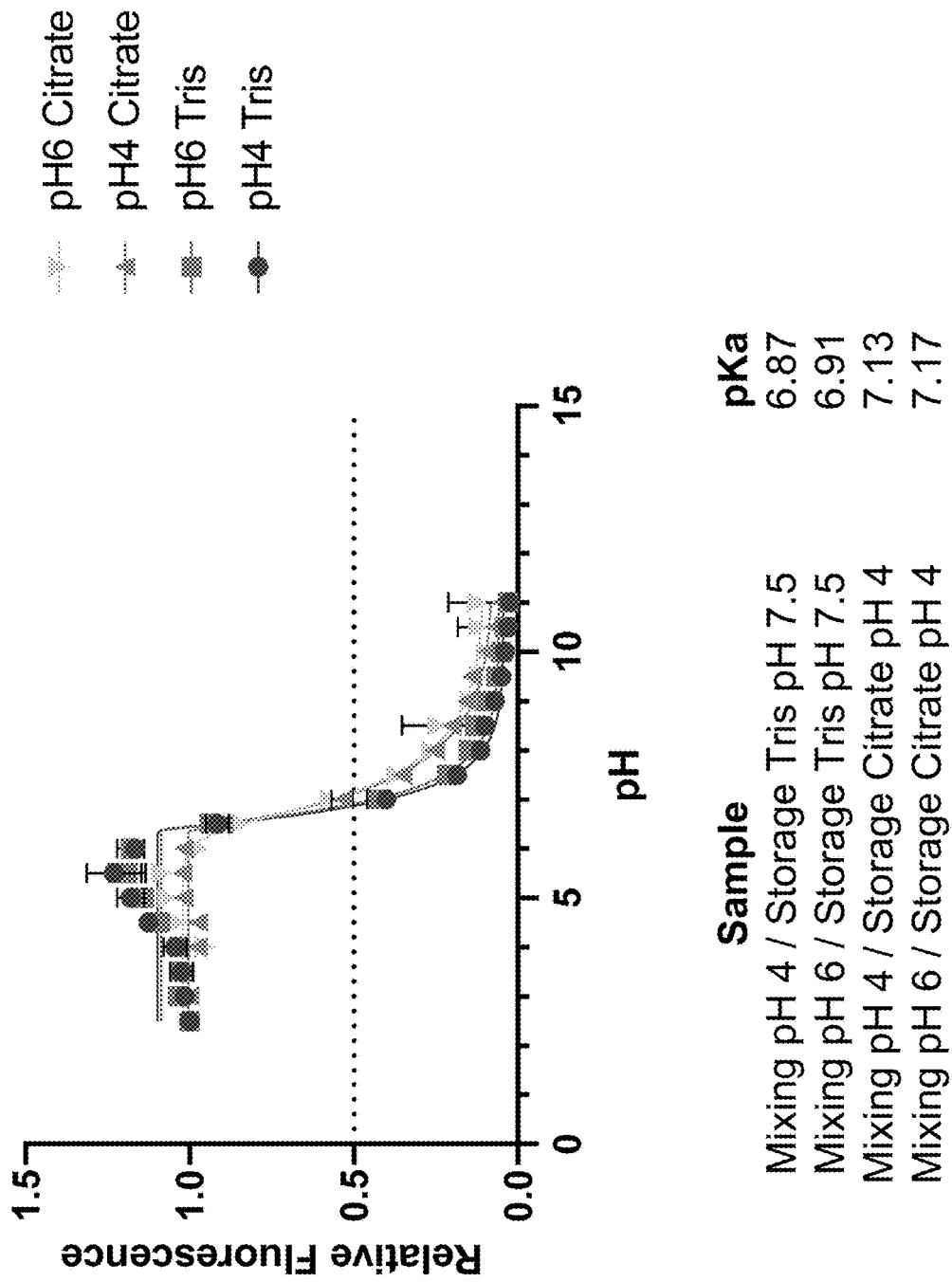
Figure 35B:
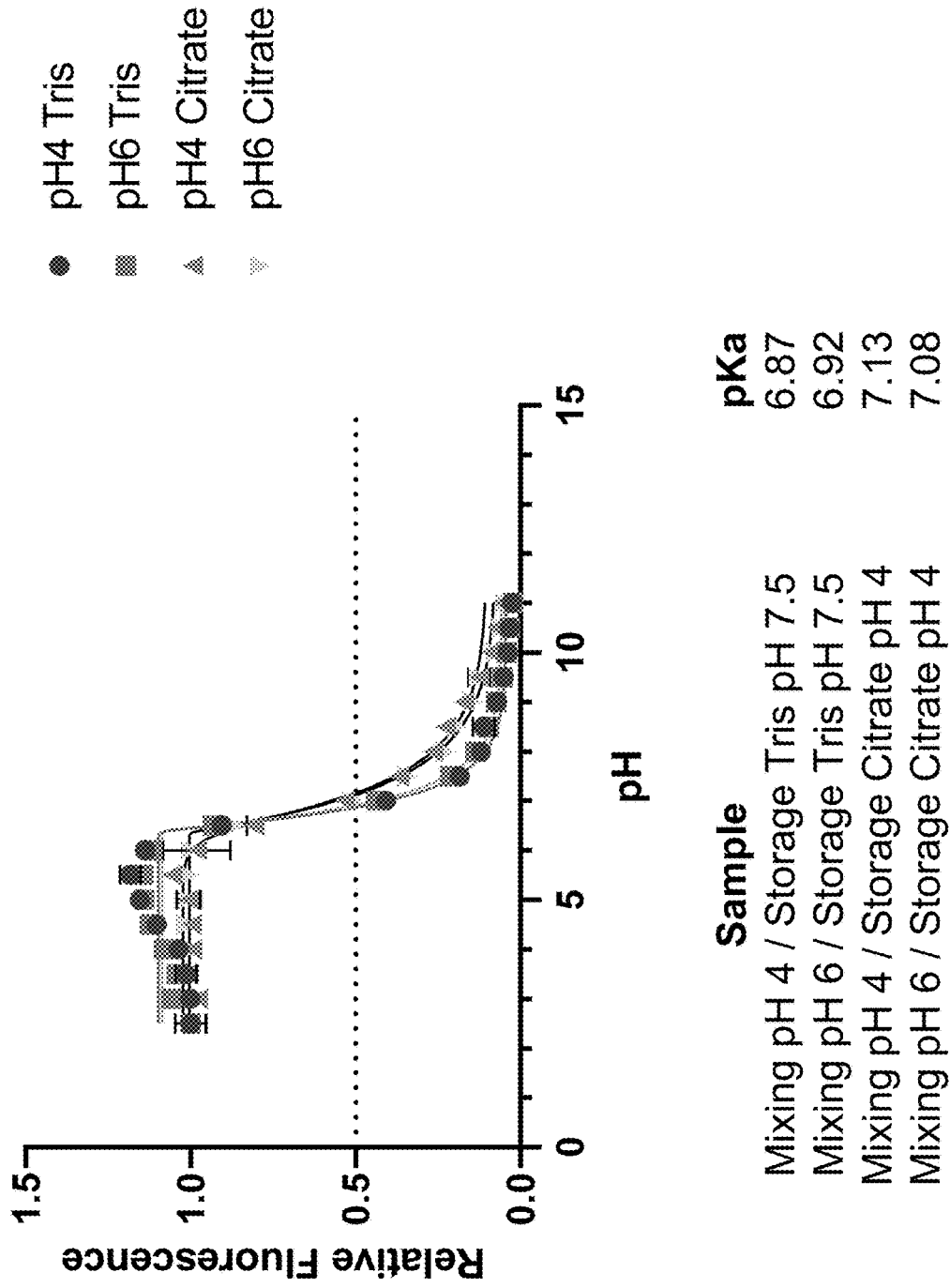
Figure 35C:
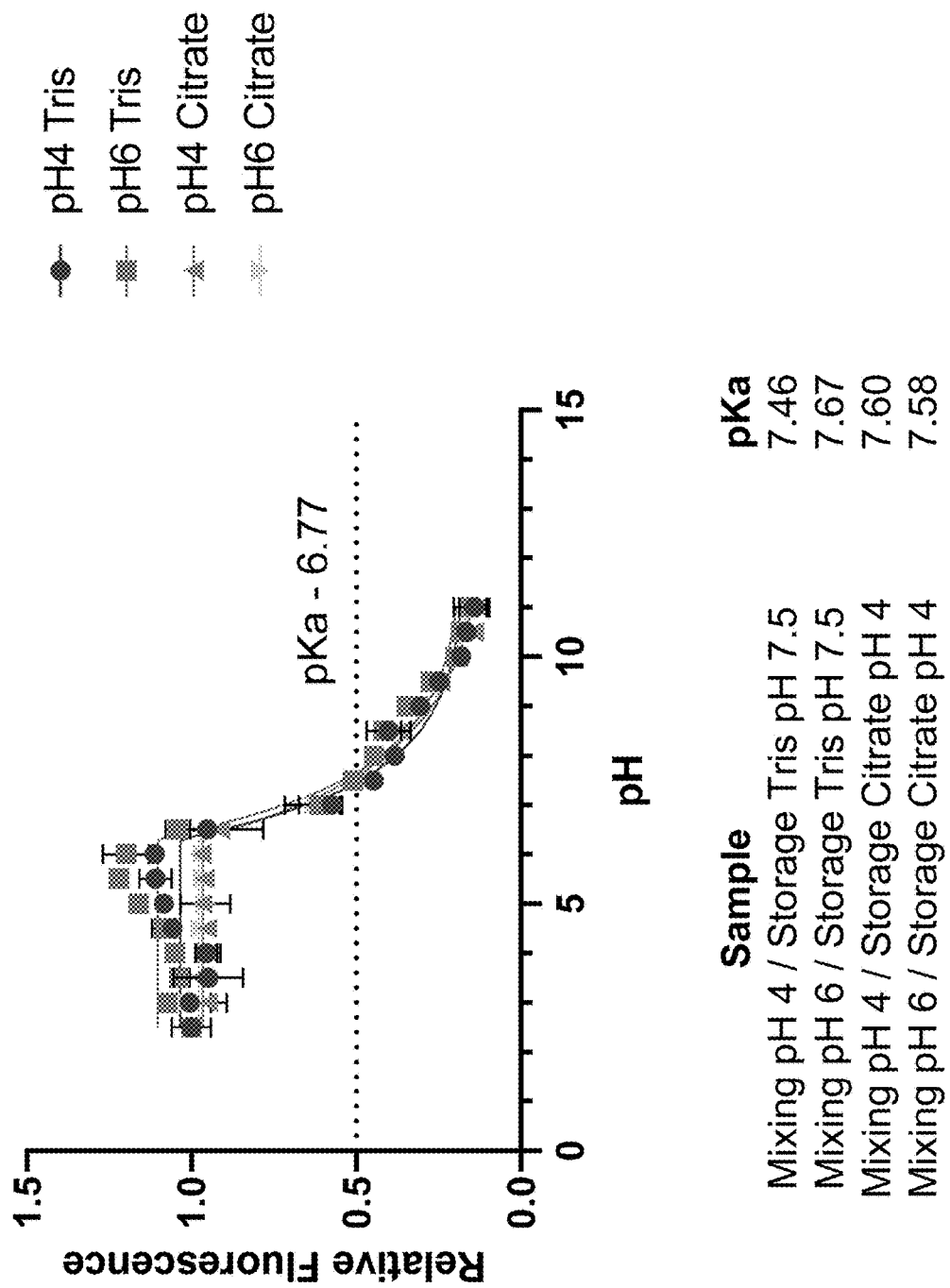
Figure 36A:
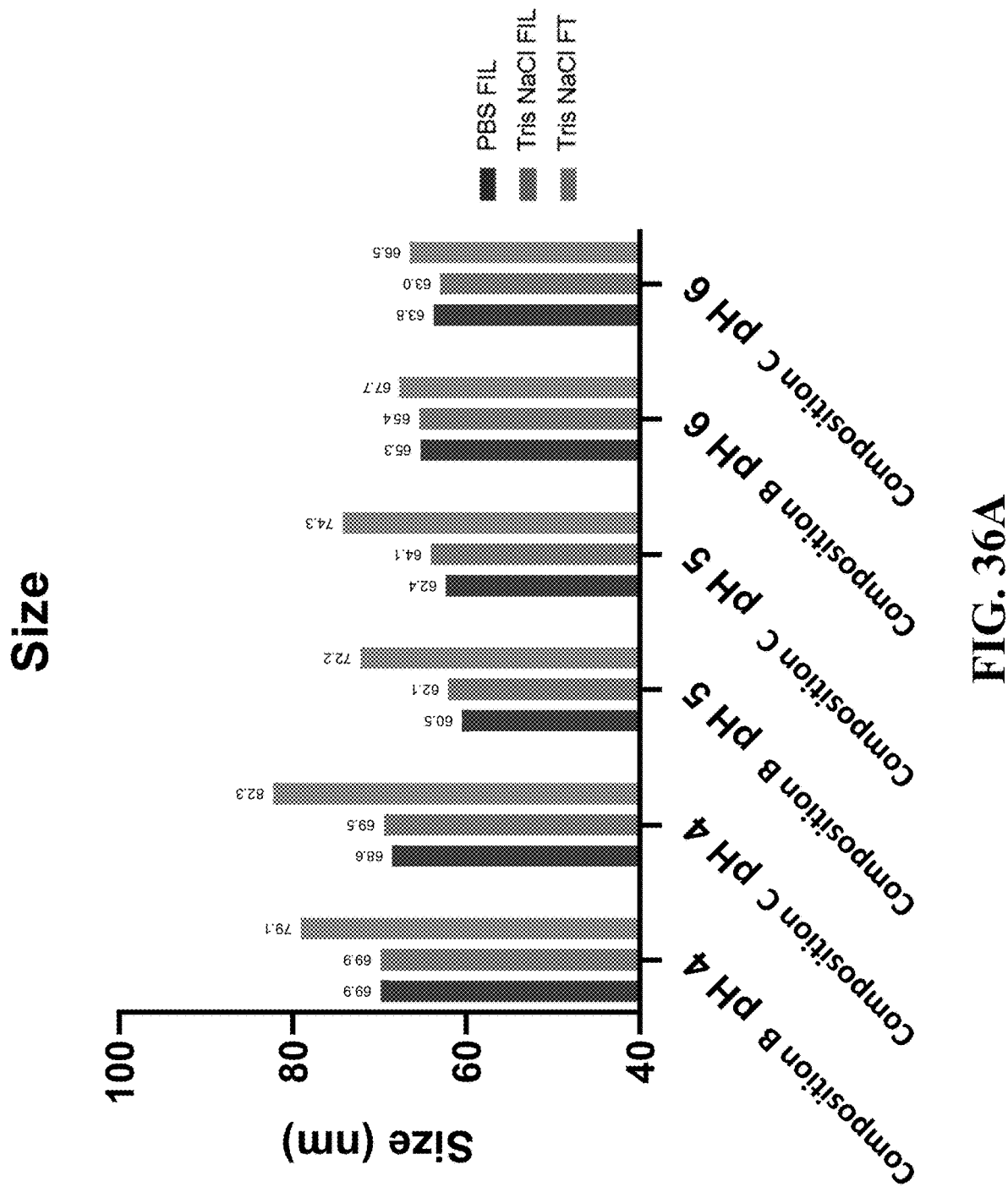
Figure 36B:
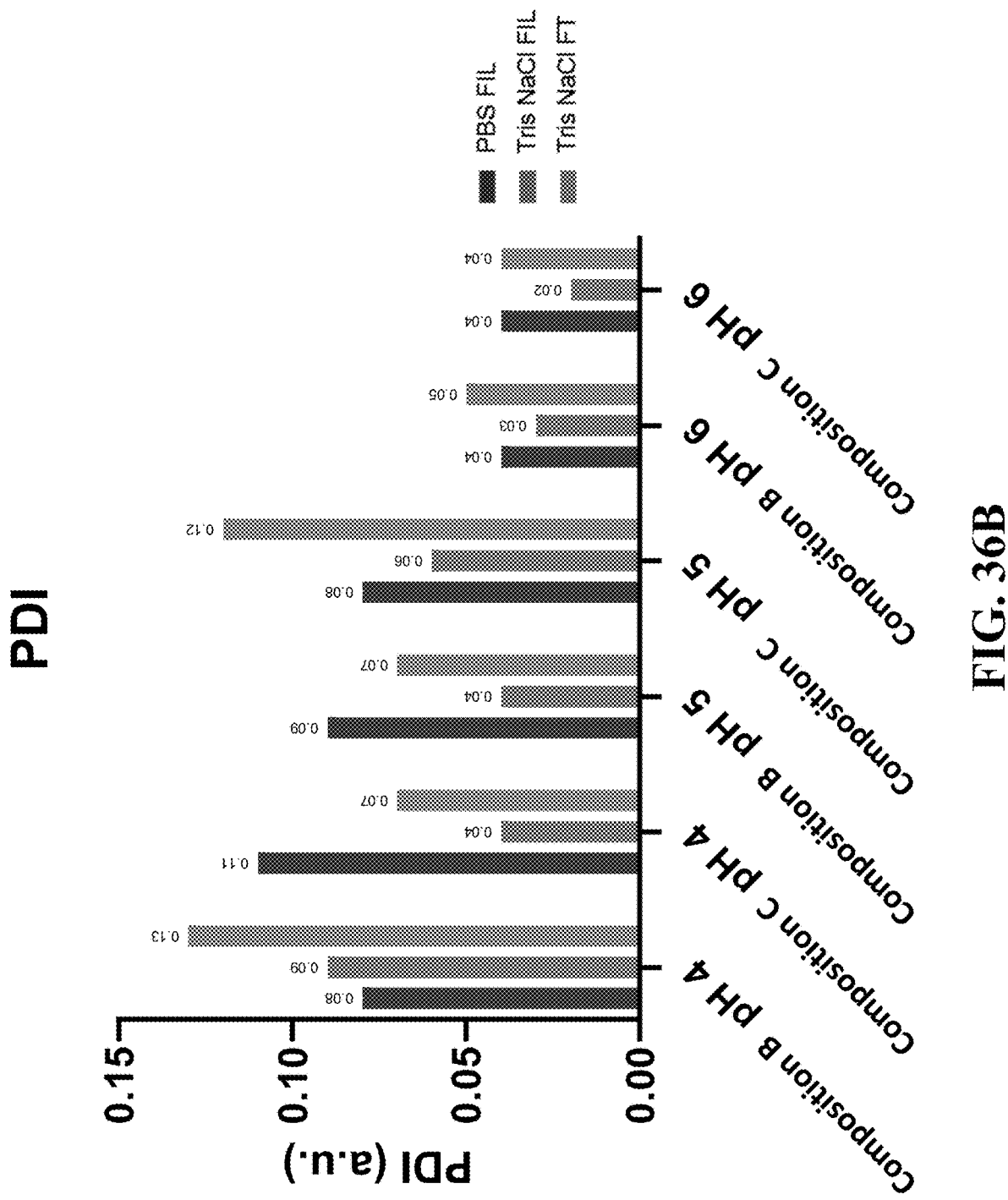
Figure 36C:
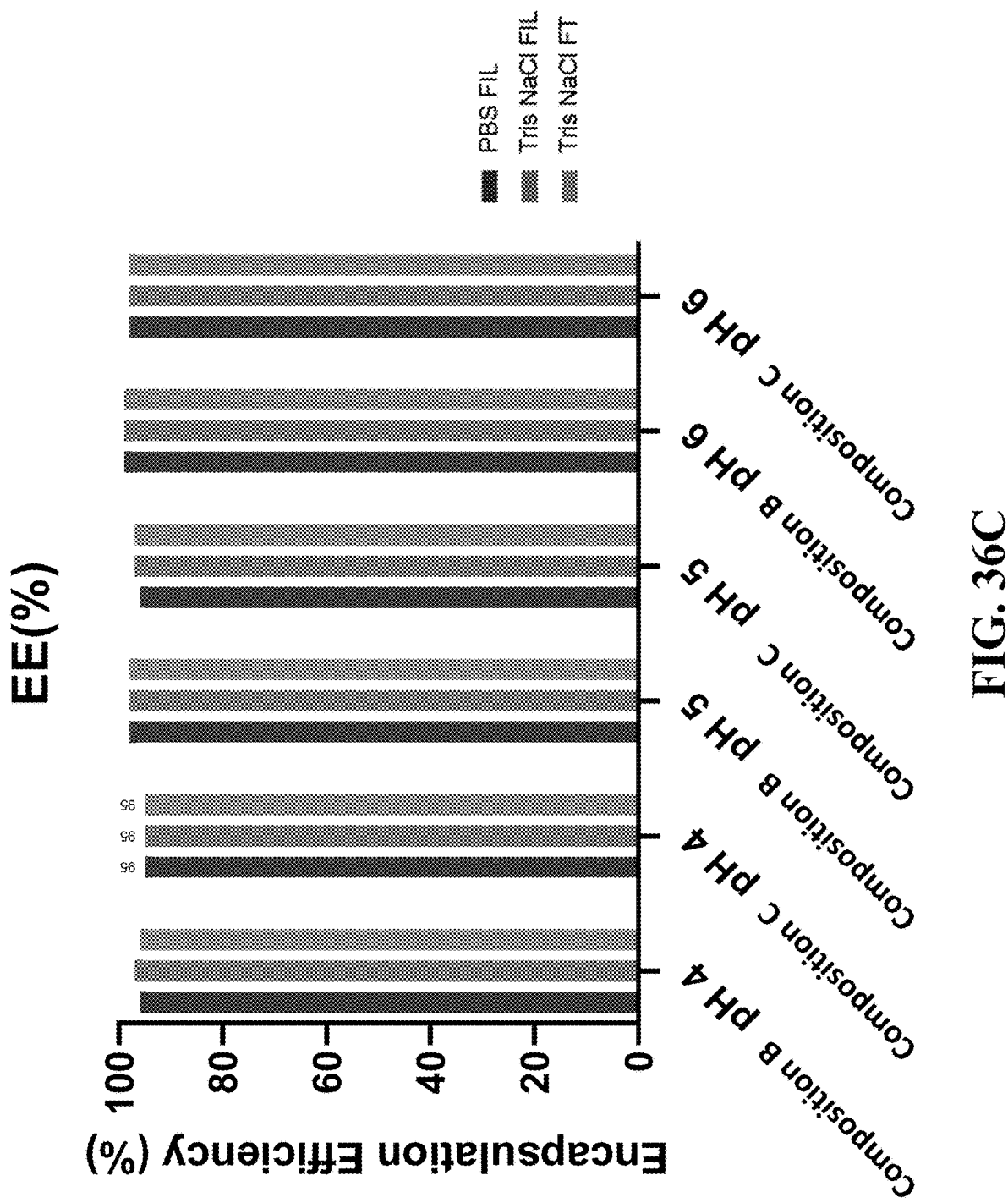
Figure 36D:
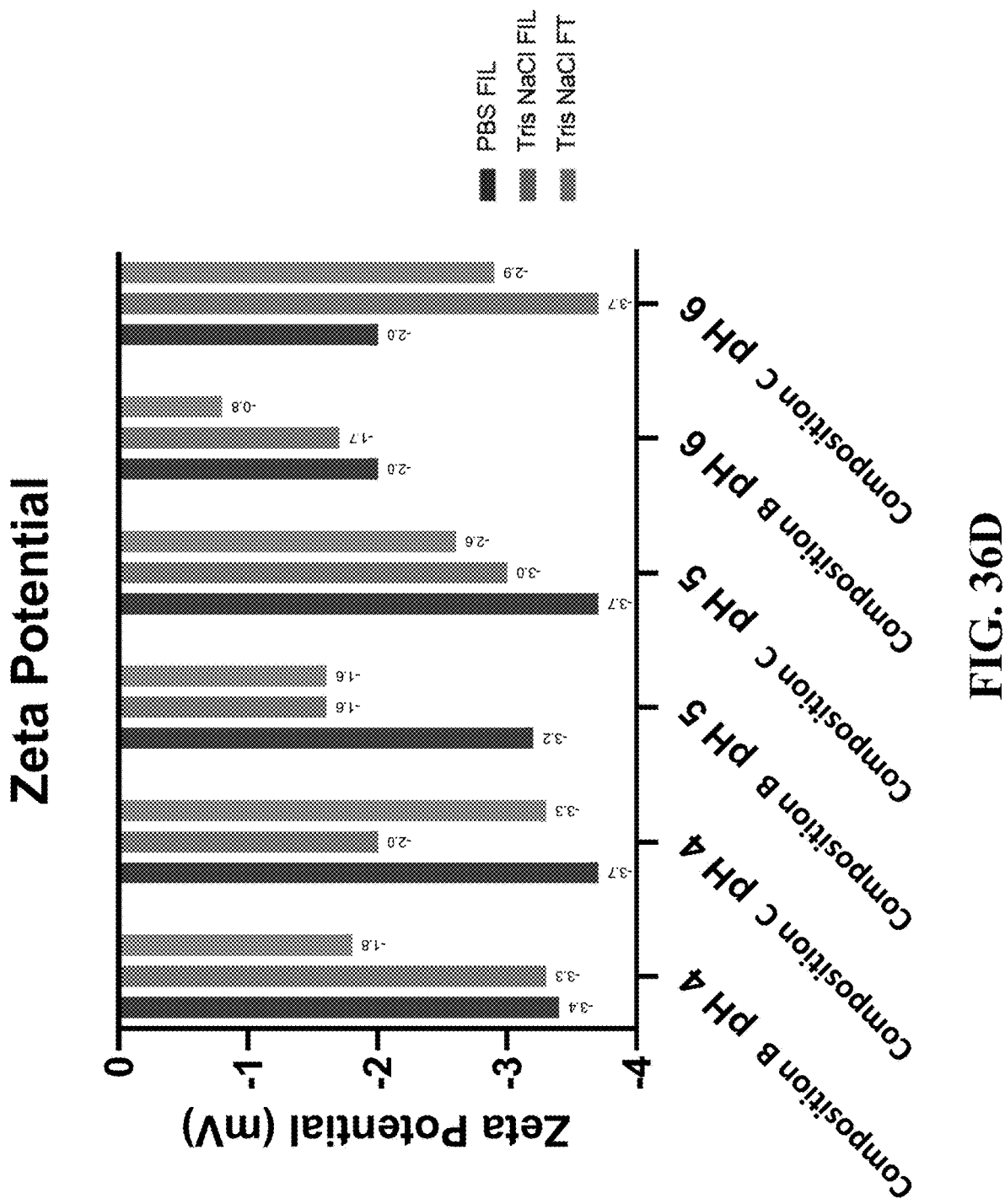

Example 7: Physical Characterization of Composition B, Composition C, Composition F and Composition a and Impact of Mixing Buffer Selection Lipid nanoparticles were characterized by size, polydispersity index (PDI), encapsulation efficiency (EE), and zeta potential (mV). Both LNP composition and the mixing buffer used in the process of making the LNPs were varied. Each lipid nanoparticle composition was prepared by mixing the lipid components with RNA in 10 mM Citrate buffer (in each case at either pH 4 or 6) and stored in either 15 mM Citrate buffer containing 5% sucrose, or 15 mM Tris buffer containing 5% sucrose. The resulting LNP compositions were assayed for size of lipid nanoparticle, polydispersity index (PDI), encapsulation efficiency and Zeta potential (FIGS. 34A-34D). The pH 6 mixing buffers generally resulted in better size control and encapsulation efficiency than pH 4 mixing buffers. Tris storage buffer had better encapsulation efficiency than Citrate storage buffer, while Citrate storage buffer showed better size control. Composition A was less affected by mixing buffer but performed better in Tris storage buffer. FIGS. 35A-35C show assays to determine the apparent acid dissociation constant (pKa)

value of lipid nanoparticle, measured by 6-(p-toluidino)-2-naphthalenesulfonic acid (TNS) Assay.

Figure 37A:
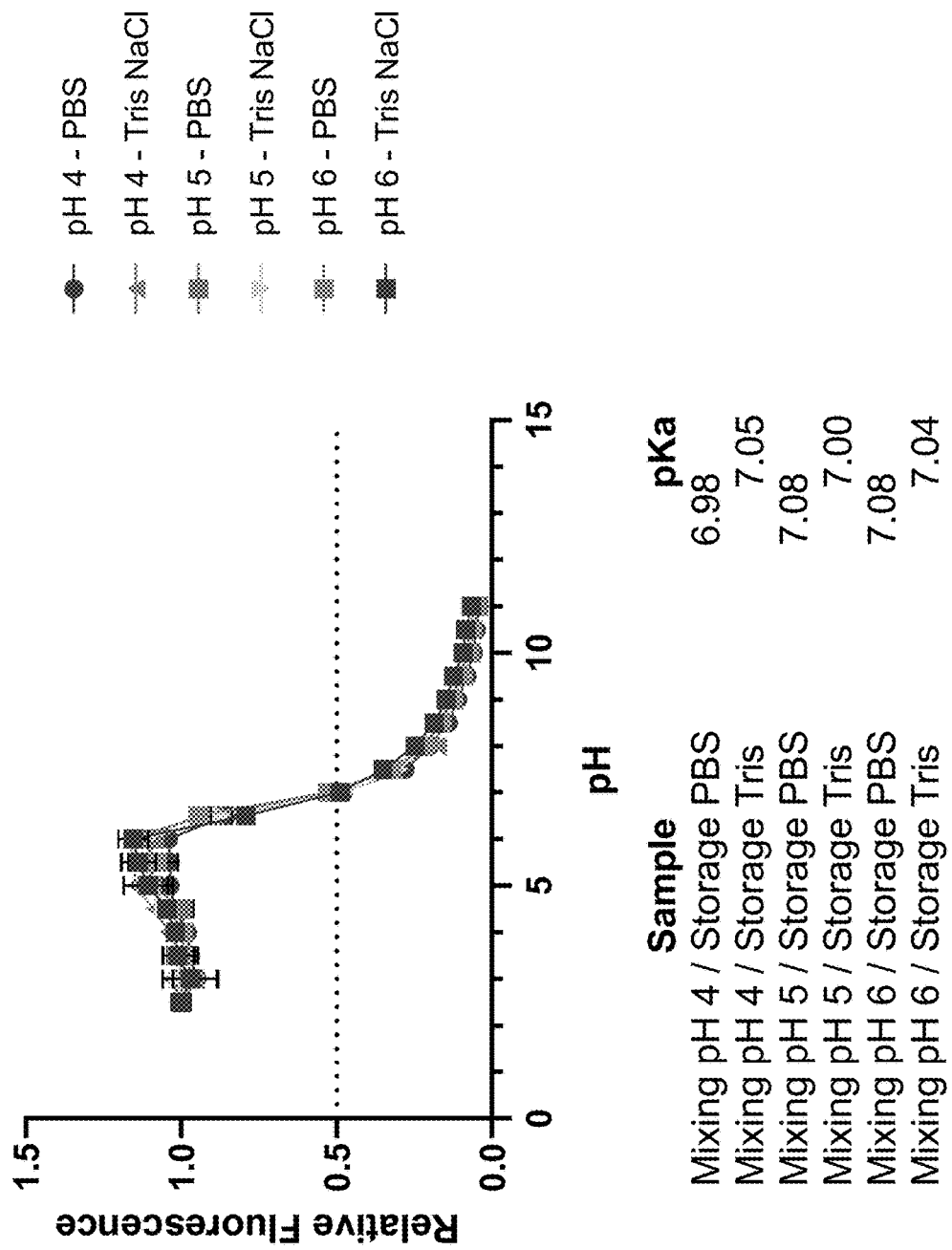
Figure 37B:
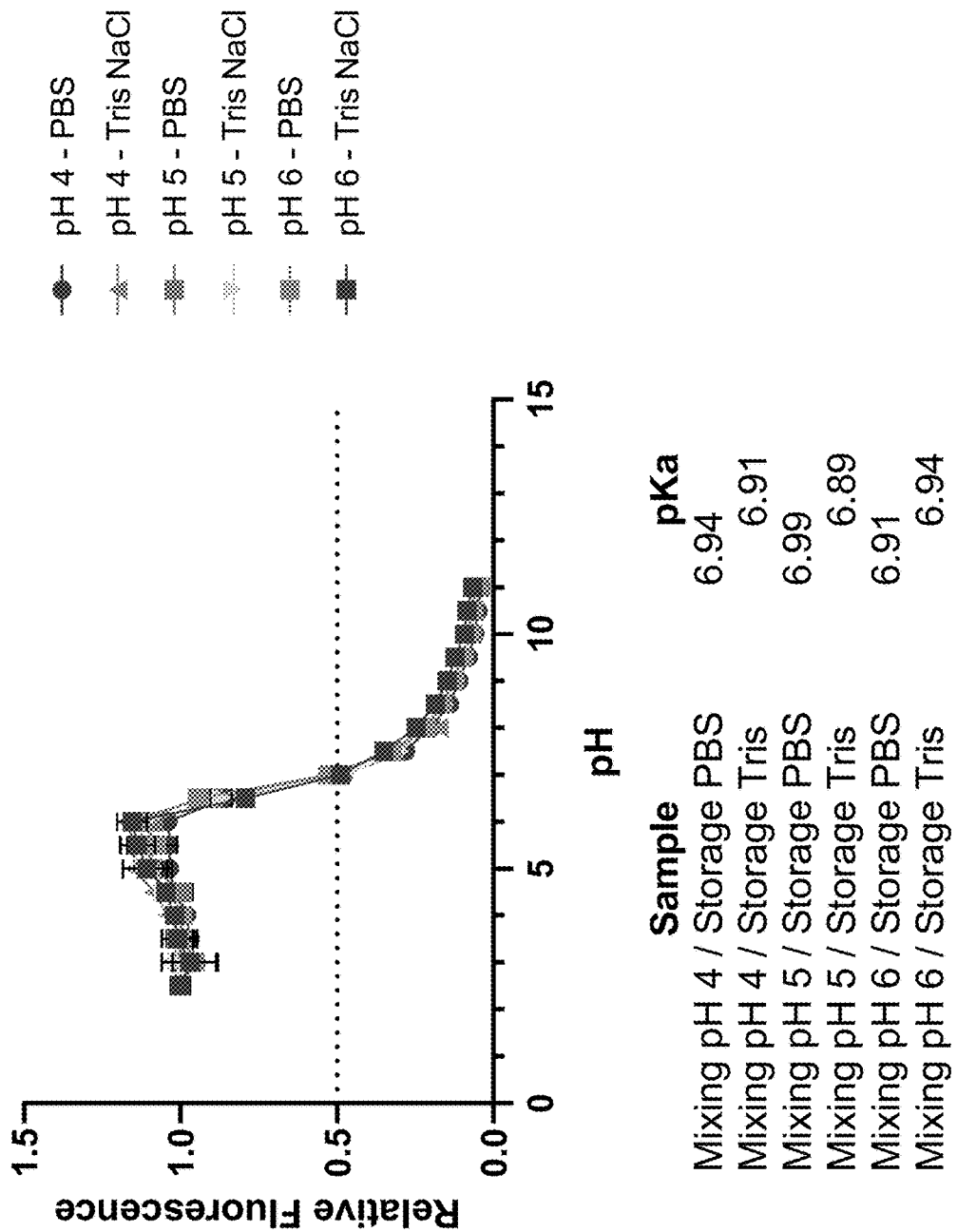
Figure 38A:
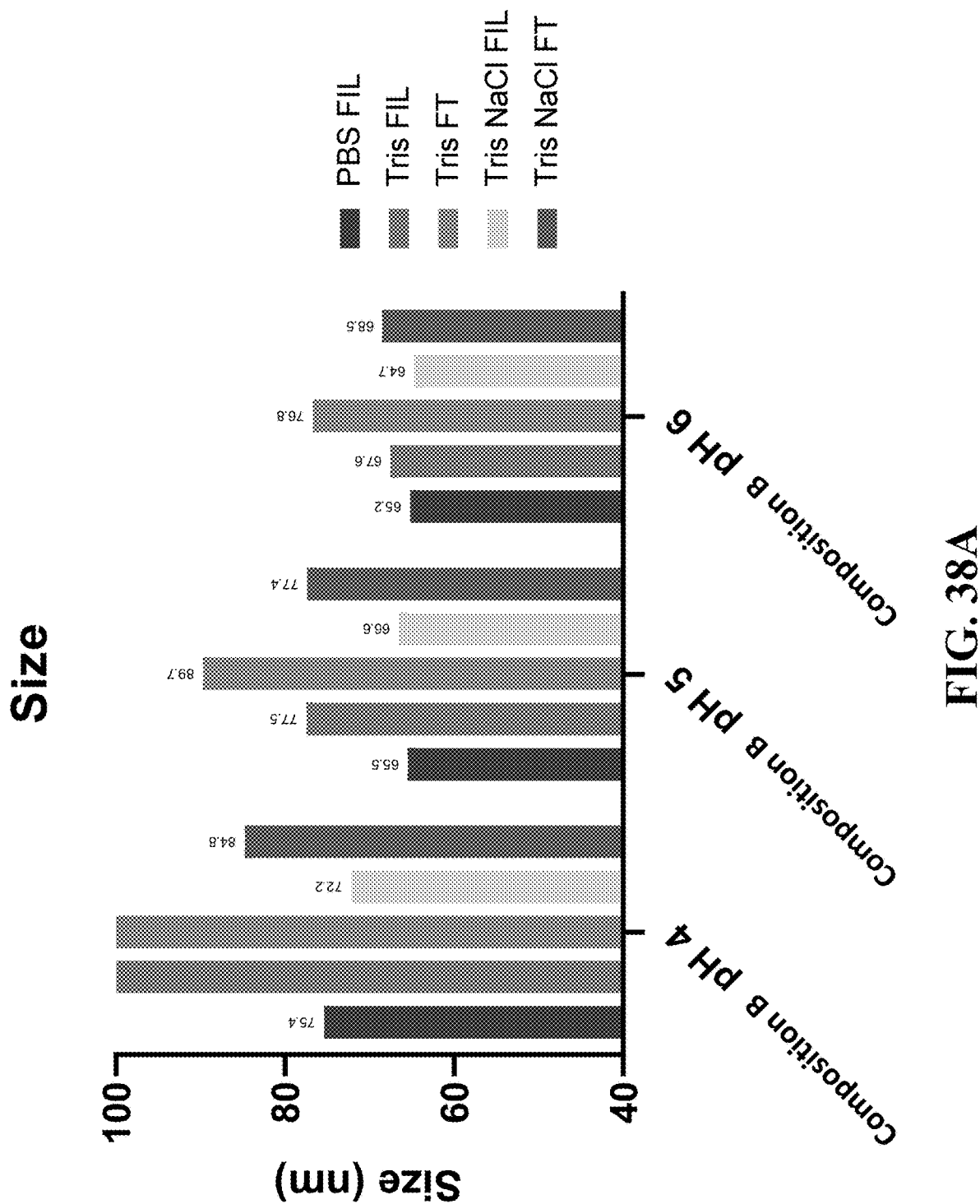
Figure 38B:
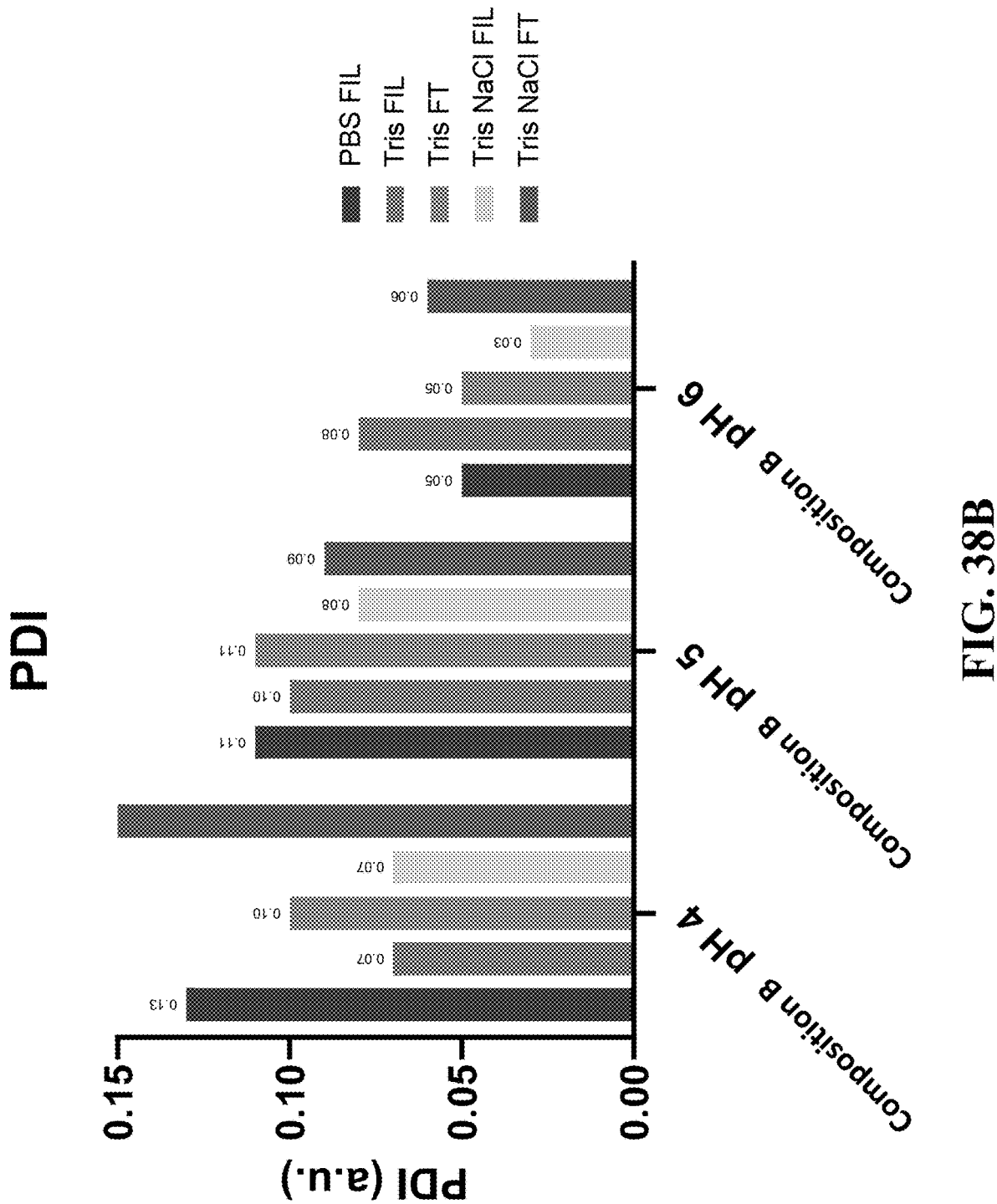
Figure 38C:
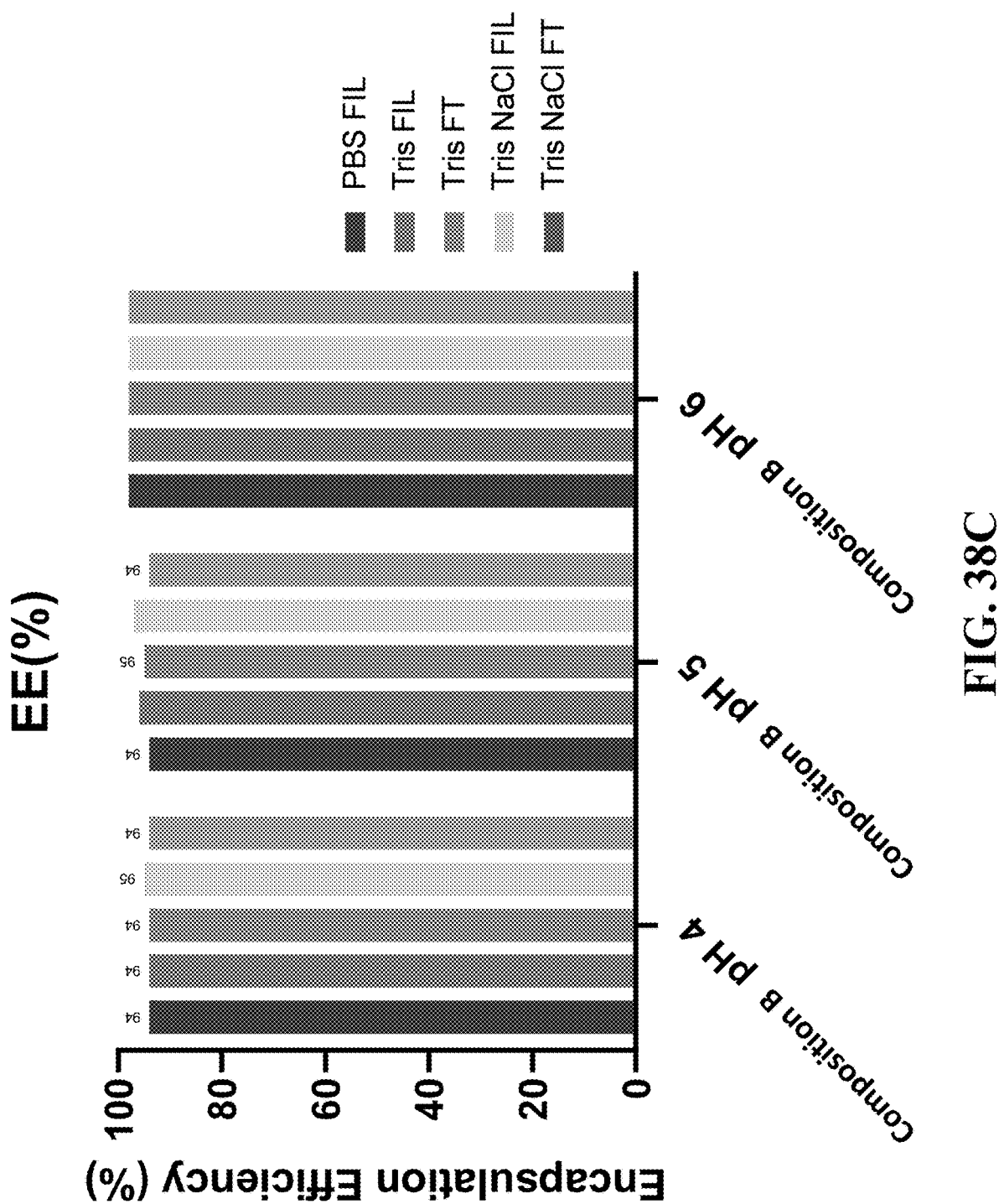
Figure 38D:
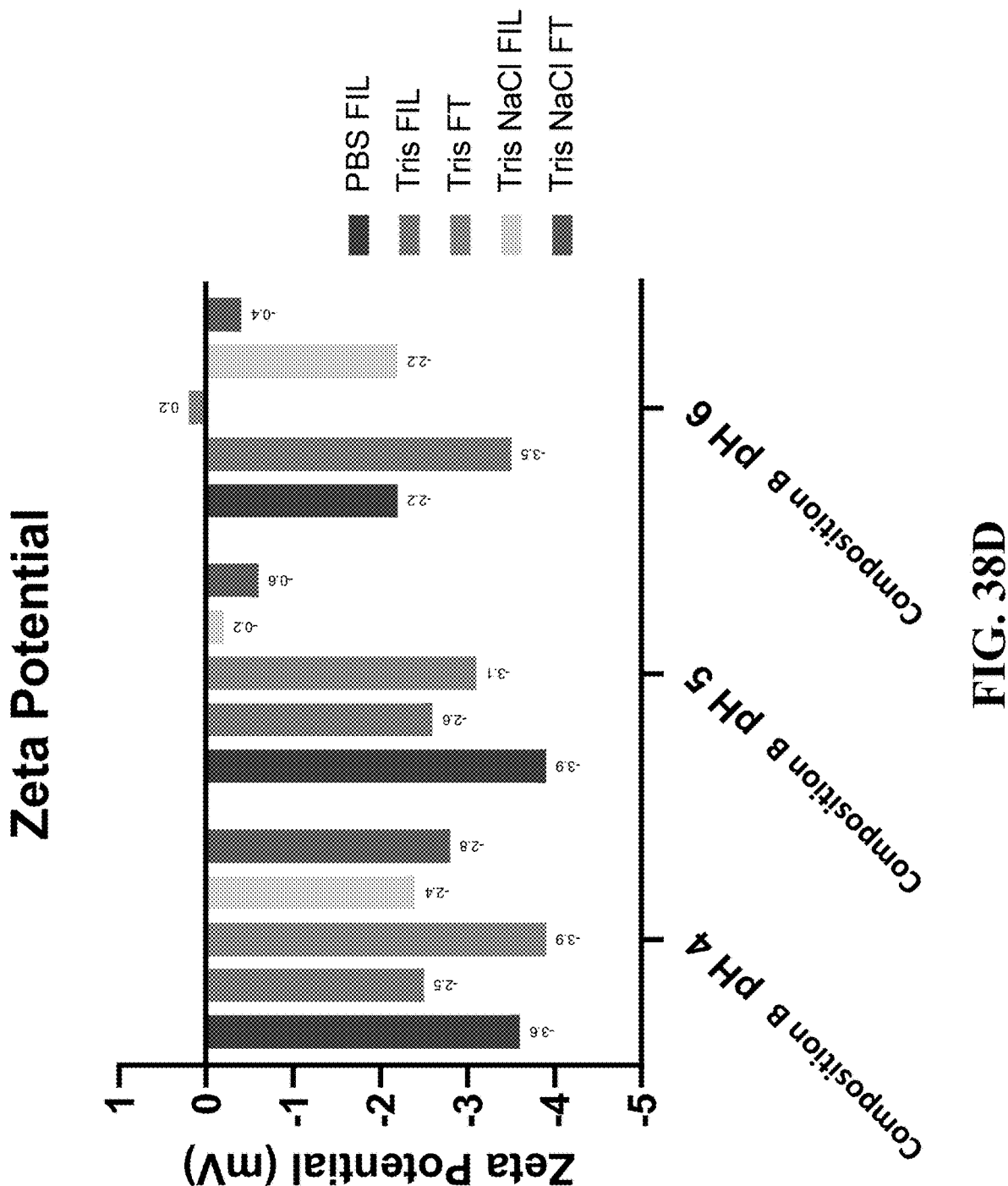
Figure 39A:
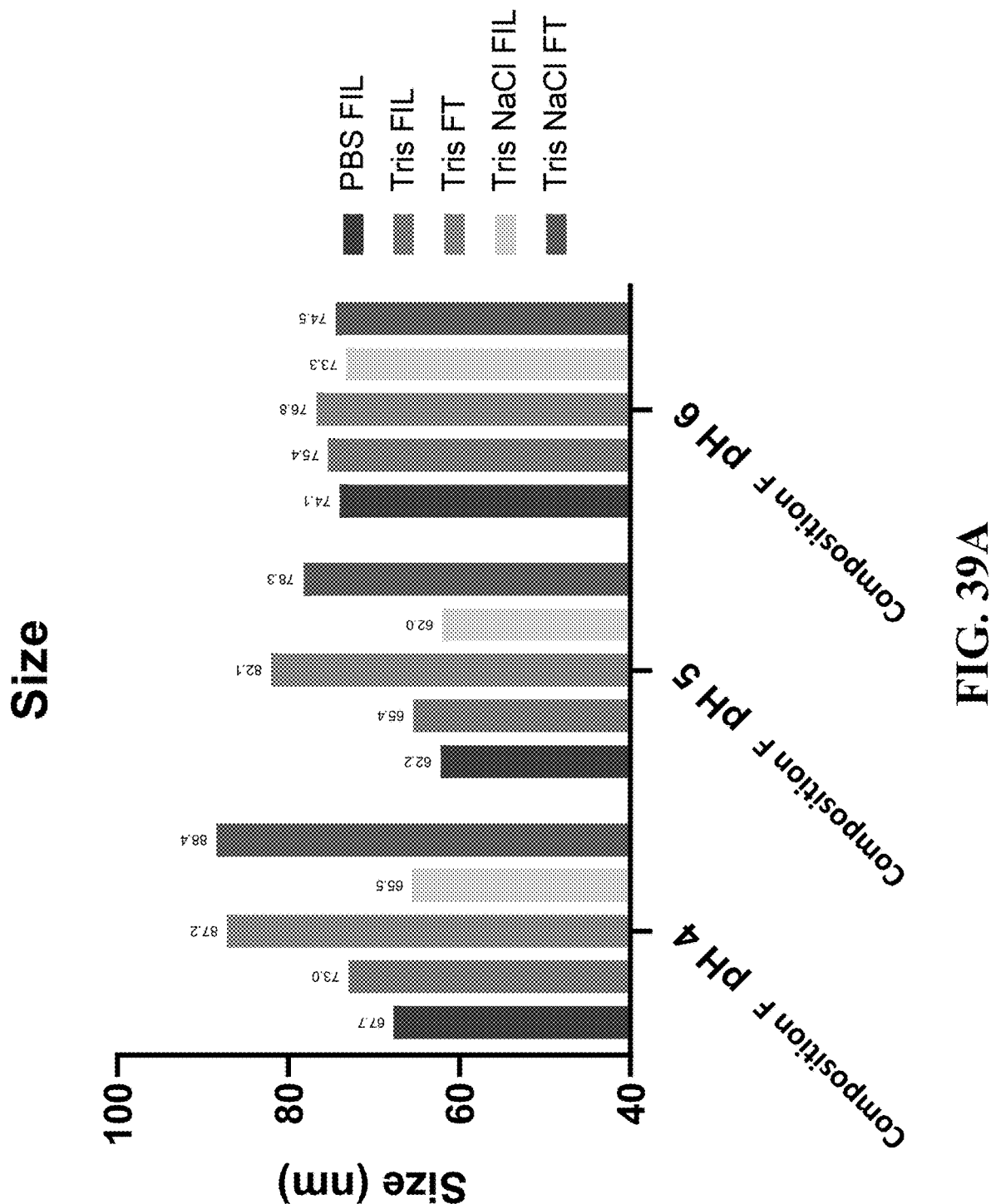
Figure 39B:
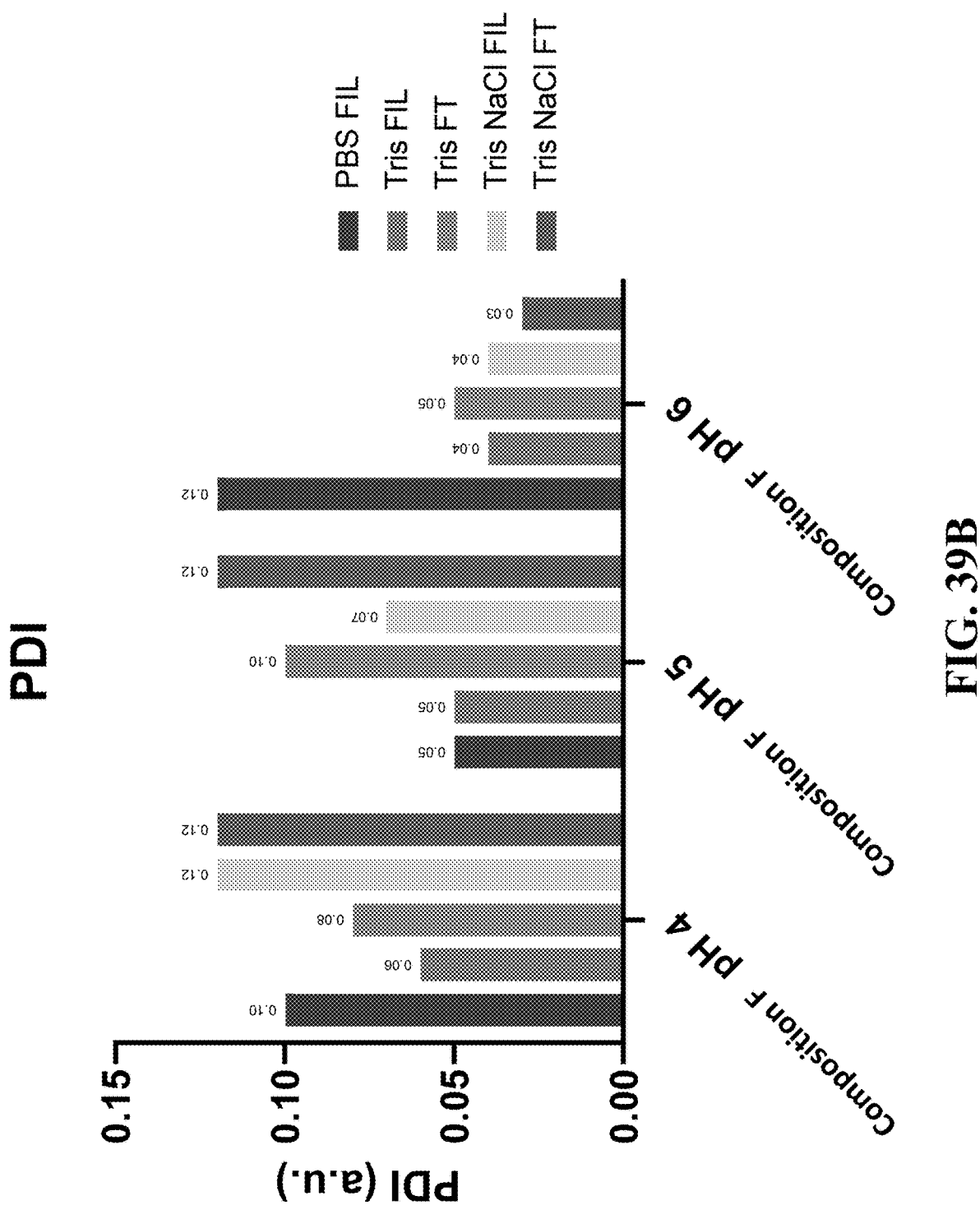
Figure 39C:
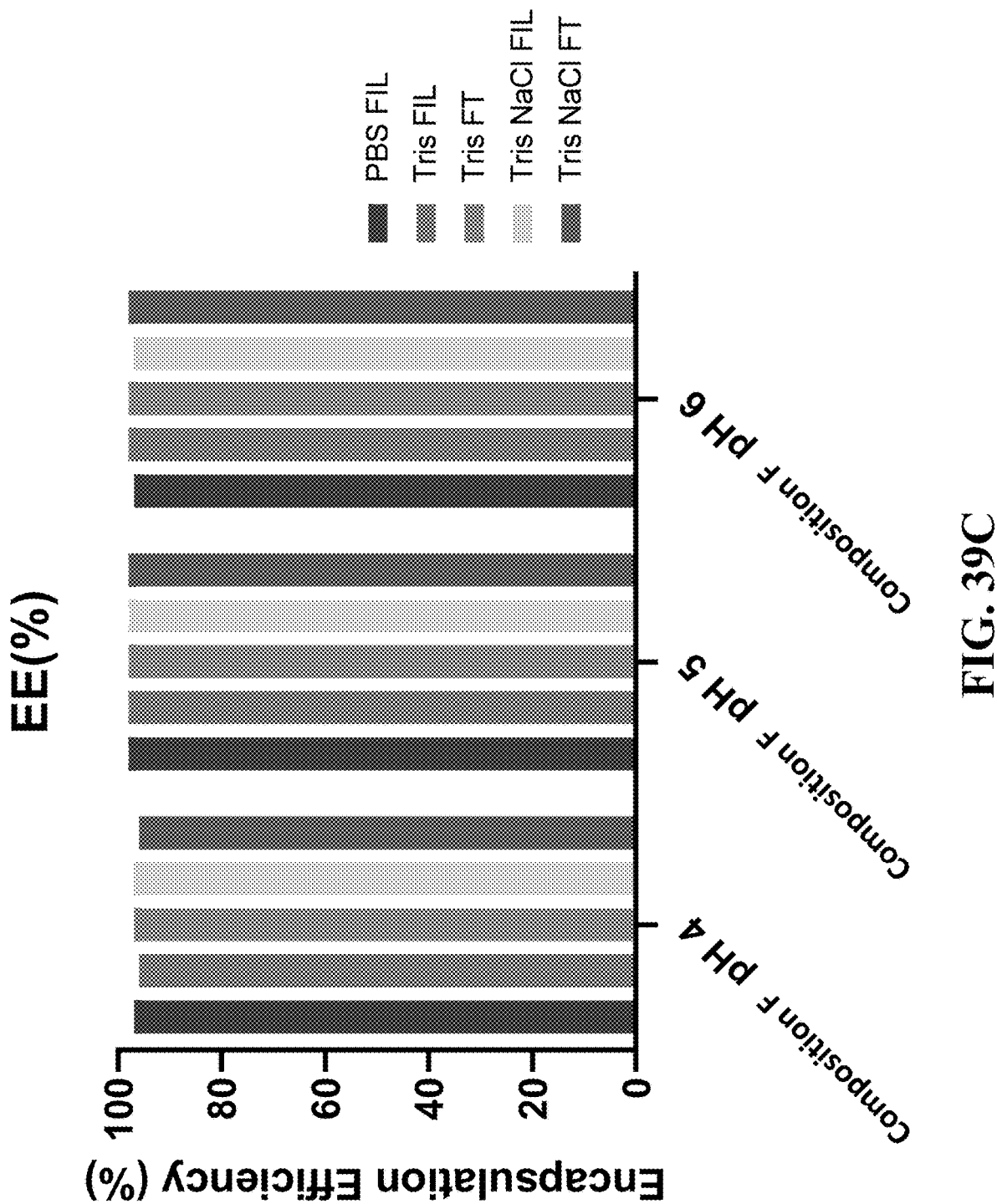
Figure 39D:
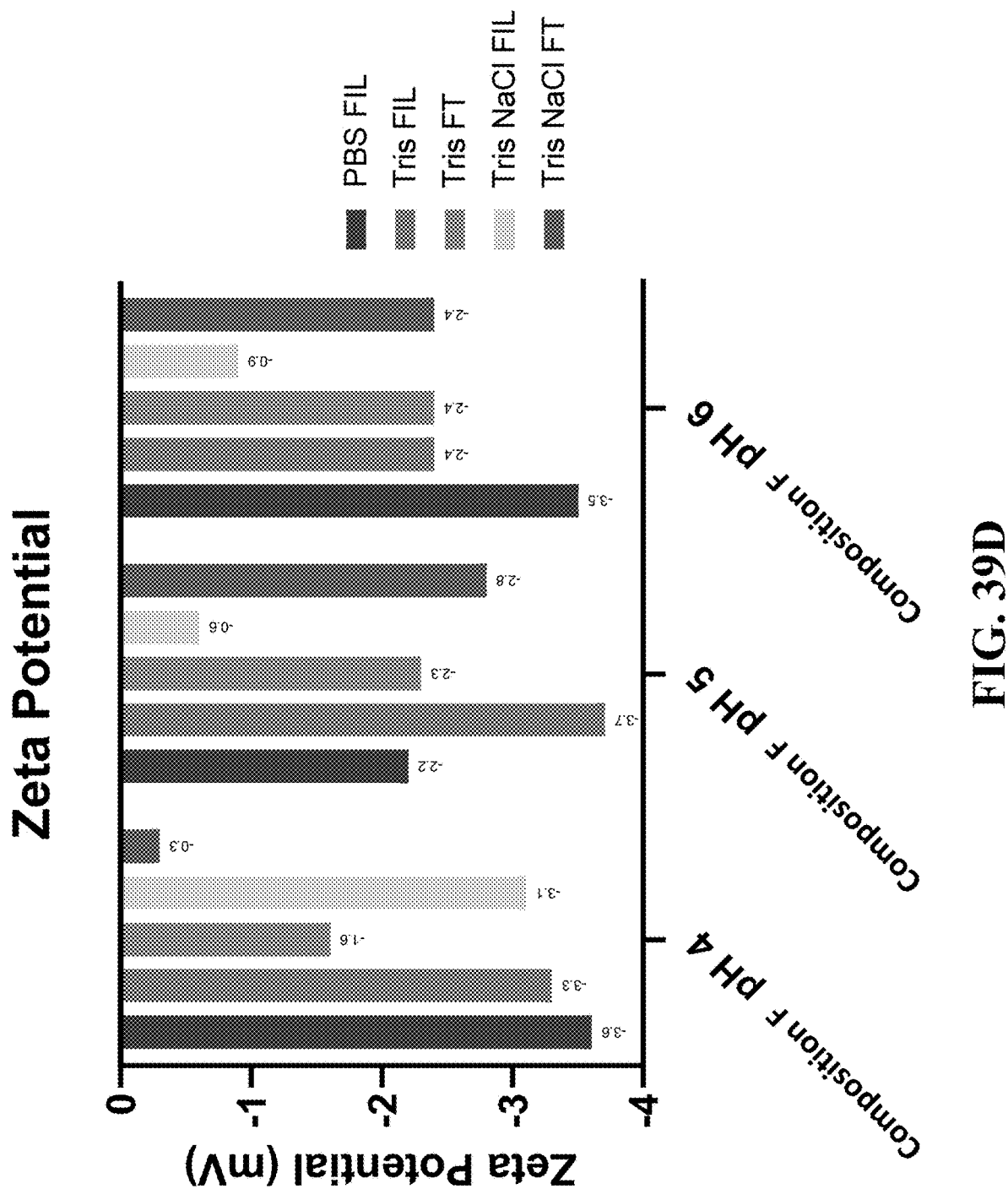

Further analysis on mixing Citrate buffer (10 mM) at pH 4, pH 5 and pH 6 were performed for DODAP-based formulations (FIGS. 36A-36D). The pH 6 mixing buffer had better size control post freeze-thaw, lower polydispersity index (PDI) and higher encapsulation efficiency than pH 4 mixing buffer for both Composition B and Composition C lipid nanoparticles. Adding 75 mM NaCl to Tris storage buffer appears to improve freeze-thaw size stability, and greatly lowered PDI pre and post freeze-thaw with pH 6 mixing buffer. FIGS. 37A-37B further show acid dissociation constant (pKa) value of lipid nanoparticle membrane measured by TNS assay.

Another analysis of Citrate buffer at pH 4, pH 5 and pH 6 was performed to Composition B and Composition F. Both Composition B and Composition F had the same lipid nanoparticle composition, and the only difference was ionizable cationic lipid (FIGS. 38-39). These experiments showed pH 6 mixing buffer resulted in better size stability after freeze-thaw, lower polydispersity index (PDI) and higher encapsulation efficiency. Composition B performed better in Tris-NaCl buffer overall, while Composition F was less affected by storage buffer when mixed at pH 6.

Example 8: Physical Characterization of Composition X and Composition Y and Impact of Buffer Selection To determine the stability of lipid nanoparticles, size of lipid nanoparticles, polydispersity index (PDI), and encapsulated efficiency (EE) of Composition B (FIGS. 55A-55C) or Composition X (FIGS. 56A-56C) lipid nanoparticles were measured over three weeks. These experiments showed that lipid nanoparticles retained their physical characteristics under prolonged storage.

Storable buffer of lipid nanoparticles was tested for optimization. Each formulation was mixed in 10 mM Citrate buffer at either pH 4 or pH 6 (FIGS. 57-59) and stored in either 15 mM Sodium Citrate buffer containing 5% sucrose (Na-Cit) or 15 mM Tris buffer containing 5% sucrose and 75 mM NaCl (Tris-NaCl). Briefly, to make LNPs, formulations were diluted 1:1 with 1× phosphate buffered saline (PBS), incubated 30 minutes after mixing, spun for 1 h at 4° C., concentrated to 1.0 mg/mL, and filtered with a polyvinylidene fluoride (PVDF) membrane filter. The size of lipid nanoparticle, polydispersity index (PDI), and encapsulated efficiency (EE) were measured. The pH 6 mixing buffers resulted in the best size control after freeze-thaw for Composition B. Formulations stored in Na-Citrate buffer showed the best size stability and PDI control overall, regardless of mixing buffer, but had dramatically low encapsulation efficiency. FIGS. 58-59 show the acid dissociation constant (pKa) value of lipid nanoparticle membrane measured by TNS Assay in either pH 4 or pH 6 buffer.

To establish the importance of citrate buffer containing sucrose, further experiments were performed. Lipid nanoparticles were dialyzed into respective buffer vial for 4 h at room temperature and overnight at 2-8° C. pH was measured to ensure that the buffer exchange was completed. Data shown in FIG. 60 illustrate that the particle size of both post dialysis and post nebulization were smaller when lipid nanoparticles were dialyzed in 15 mM citrate buffer at pH 4. Further experiments were established for lipid nanoparticle characterization after freeze-thaw cycle and data showed that the size of lipid nanoparticles in citrate buffer pH 4 with 10% sucrose were smaller after free/thaw storage (Data shown in FIG. 61)

Figure 62A:
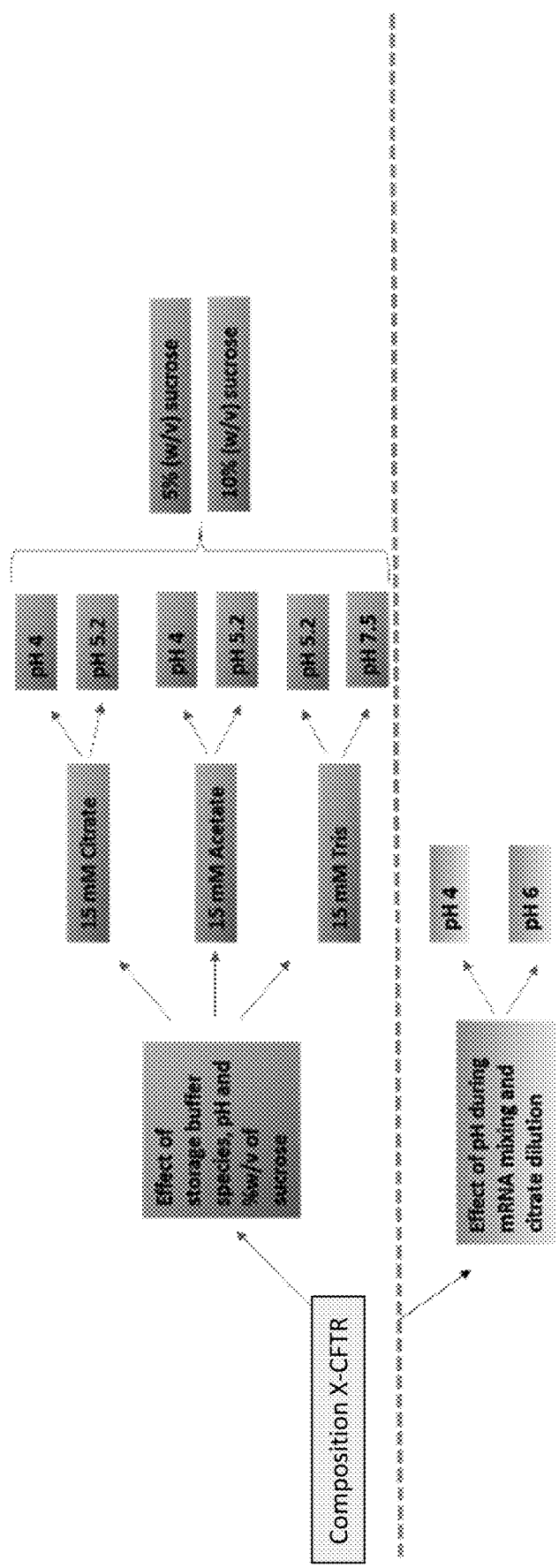

Composition X formulation were further optimized using different buffer containing different sucrose concentration. Schematic of study design for the study is shown in FIG. 62A. Formulations were screened with respect to buffer species, pH and % sucrose for final storage. Stability studies were performed by analyzing particle size (using Wyatt & Malvern) in the respective storage buffer pH and encapsulation efficiency using RiboGreen assay. For freeze-thaw experiments, the same samples were subjected to three freeze-thaw cycles for each formulation. For time course experiments, one aliquot of each formulation was pulled at 1 week, 2 weeks, 3 weeks, 4 weeks, and 7 weeks timepoints. Lipid nanoparticles were formulated either in citrate, sodium acetate or Tris buffer in different pH and sucrose %. Lipid nanoparticle formulated in 15 mM citrate buffer at pH 4 containing 10% sucrose showed improved stability and nebulization (FIGS. 62B-62D). To evaluate the effect of poloxamer 188 (0.005% w/v) in the final formulation storage buffer, three formulations chosen from the previous experiment (either citrate buffer or sodium acetate) and histidine buffer were screened with or without poloxamer 188 (FIGS. 62E-62G)

Figure 65:
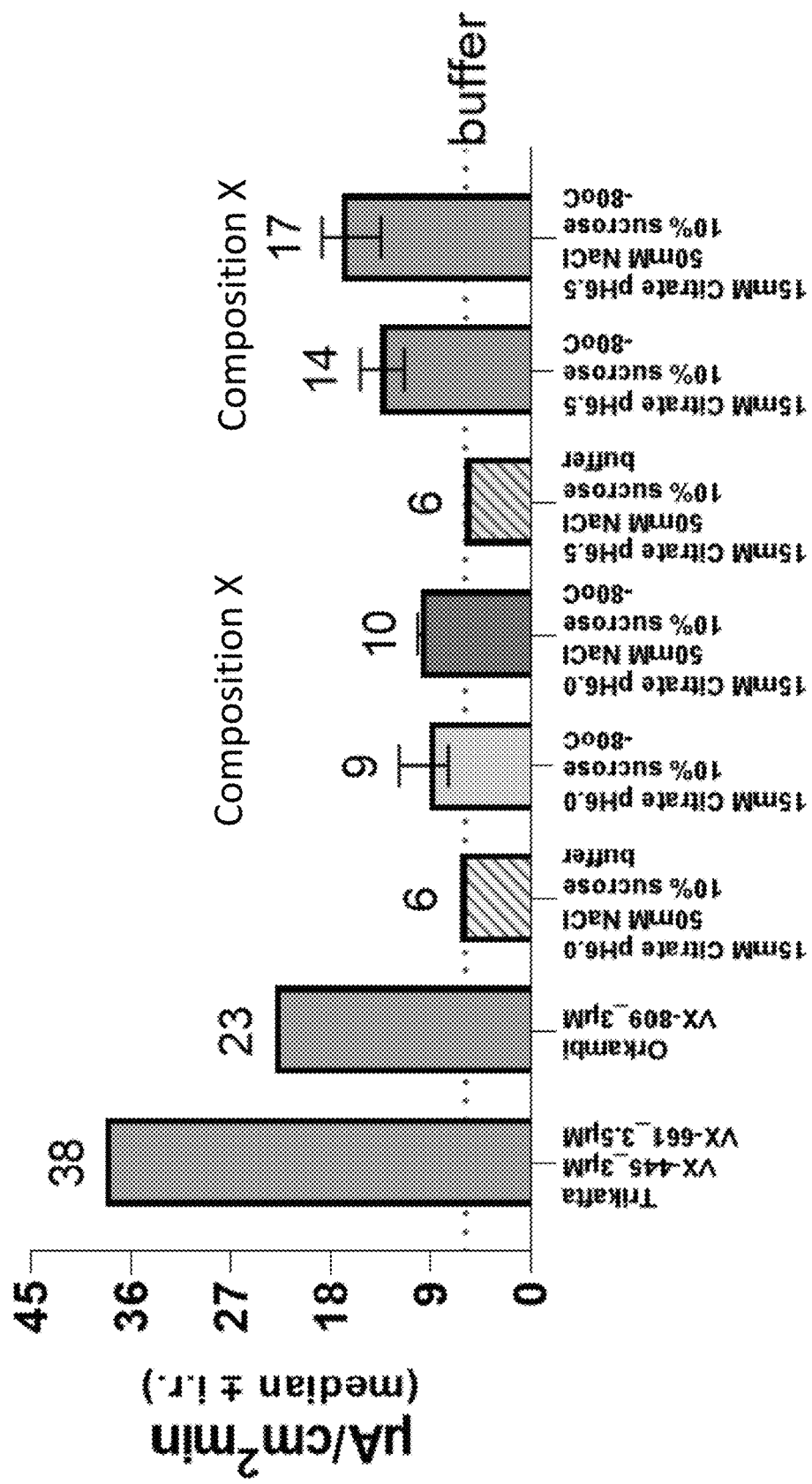

To identify the pH range that yields acceptable nebulization output rate and post-nebulization encapsulation efficiency, Composition X-CFTR formulations were manufactured in between pH 4.0-7.5 in different buffers (15 mM citrate, 15 mM acetate or 15 mM Tris) containing 10% sucrose. All formulations were nebulized using Solo to identify lead candidates. The data showed Composition X formulated and nebulized at pH 6.0 in 15 mM citrate buffer showed the most output rate (FIG. 63). Further experiments were performed to determine the effect of salt on buffer. The data showed that formulations including 50 mM NaCl in buffer had better output rate (FIG. 64). Heterozygous genotype (G452X/ΔF508) cells were dosed with Composition X formulated in different conditions (15 mM Citrate either pH 6.0 or 6.5; presence of 50 mM NaCl), and CFTR function was tested to identify the in vitro potency of lipid nanoparticles. FIG. 65 shows cells dosed with Composition X had increased CFTR function compared to cells dosed without Composition X.

Example 9: Localization of HA-CFTR Protein In Vitro

Figure 66:
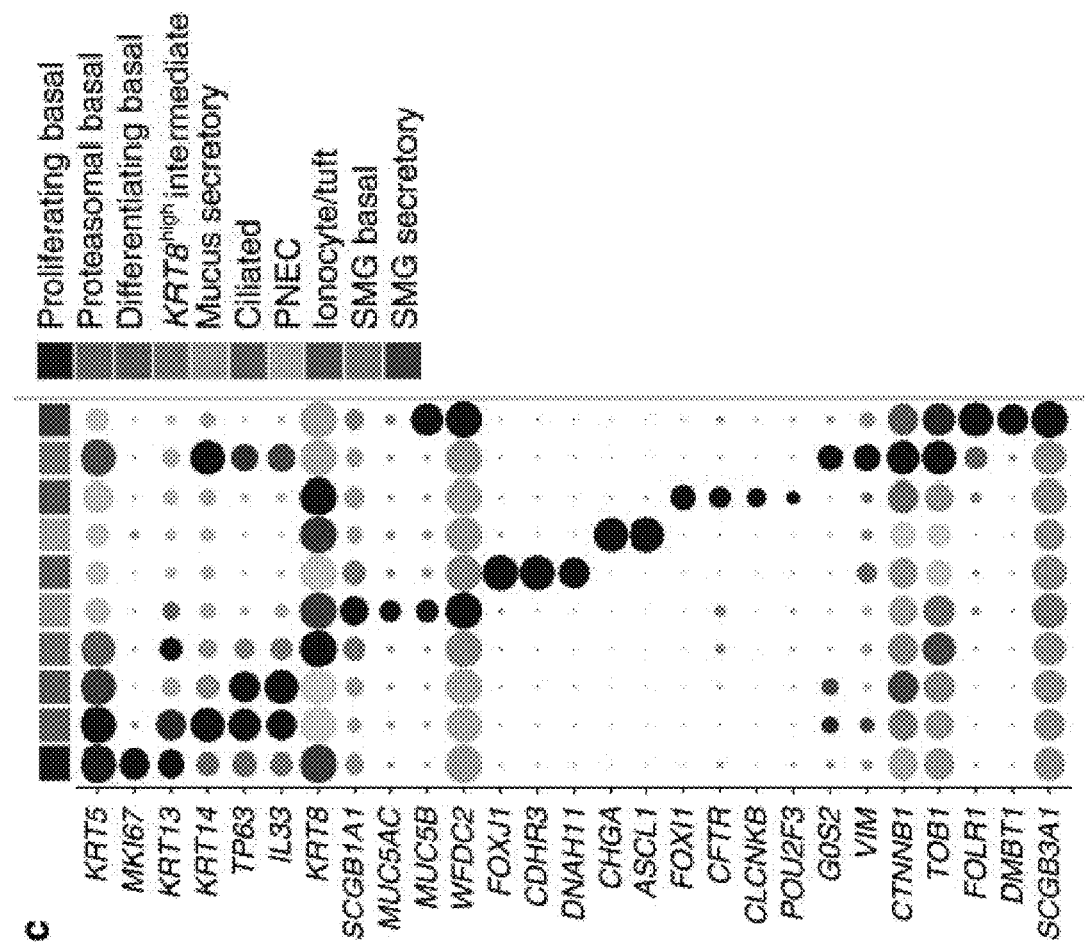
Figure 67A:
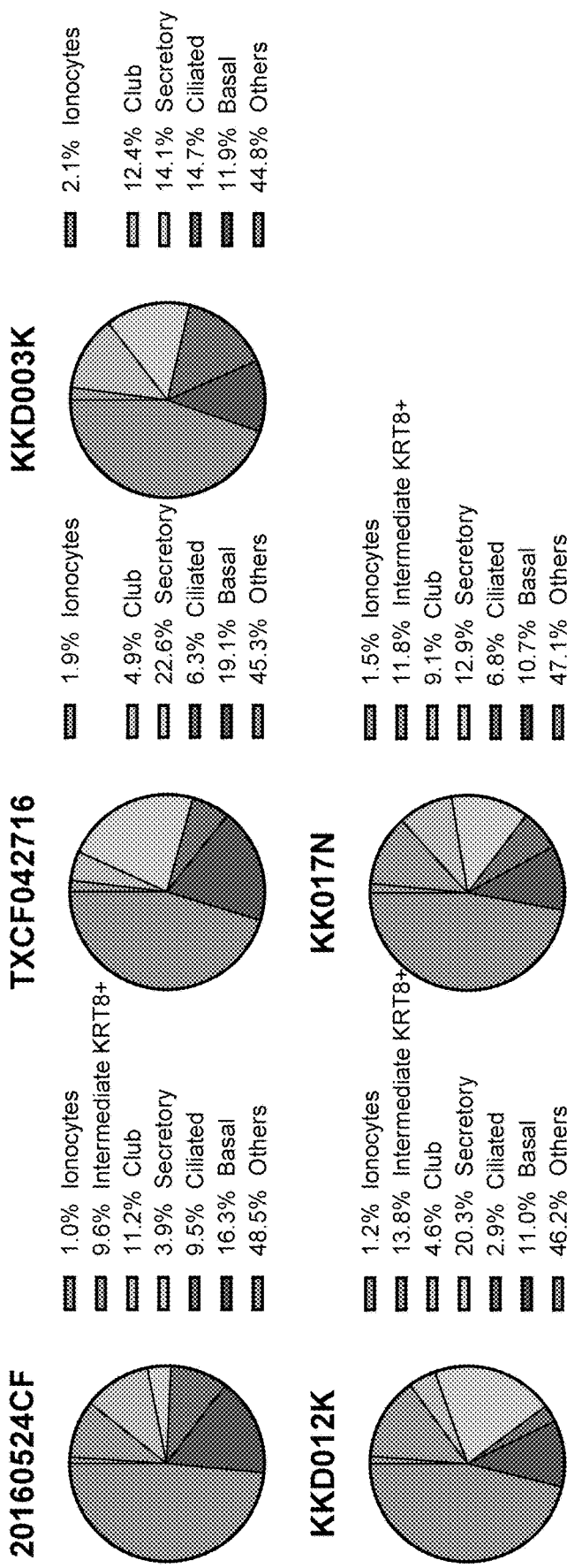

Cells dosed with lipid nanoparticles were further identified by localization of expressed HA-CFTR protein. Reference antibodies selected for the immunofluorescence panels are shown in FIG. 66. FIG. 67A shows cell profile of five ΔF508/ΔF508 homozygous genotype hBE cells. Detection of intermediated cells was not included in TXCF042716 and KKD0003K cells. Genotypes/donors assessed (FIG. 67B) and antibodies used in the experiment (FIG. 67C) were identified.

Figure 68:
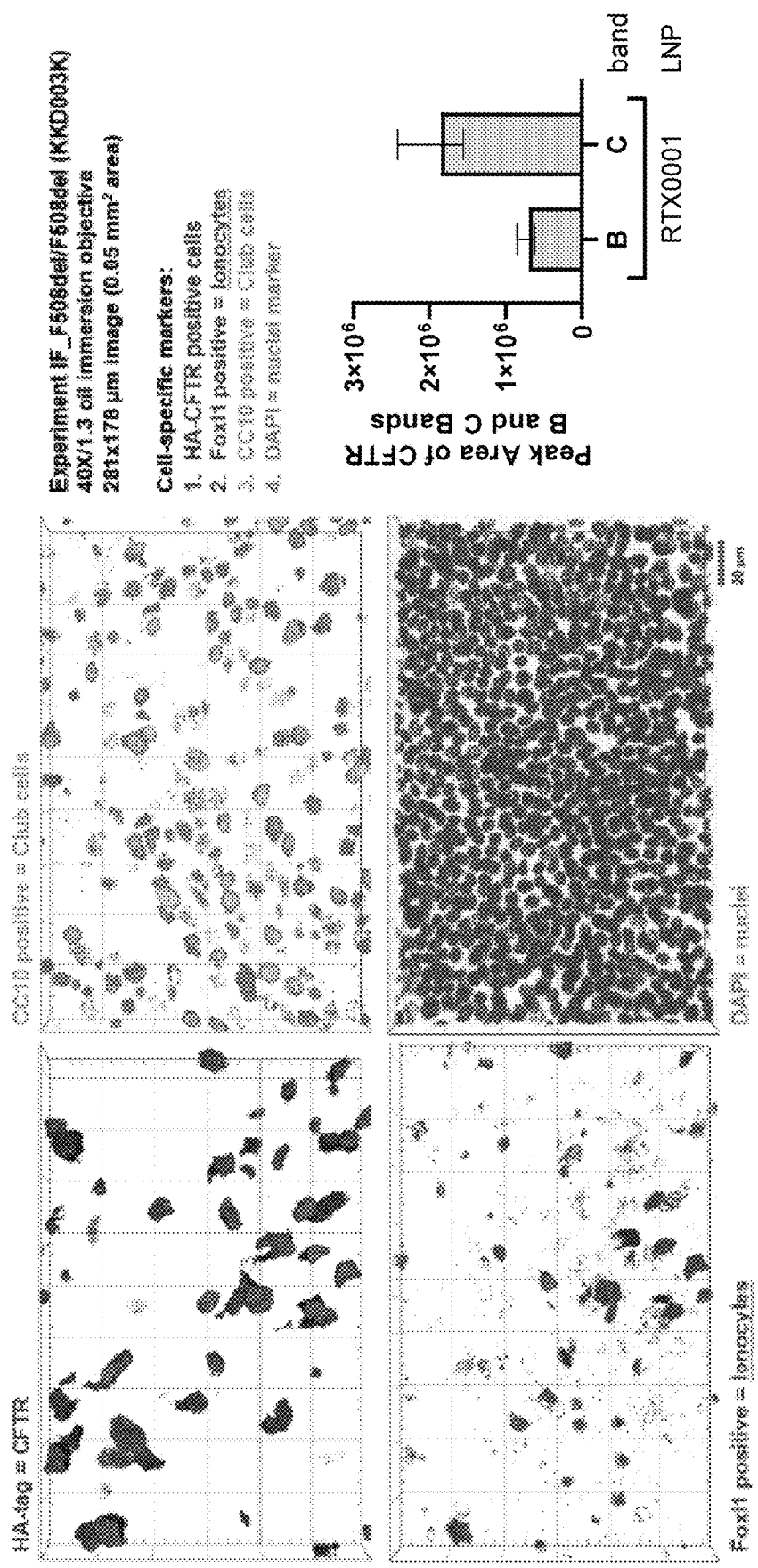

ΔF508/ΔF508 homozygous genotype hBE cells (KKD003K) were dosed with Composition B/HA-CFTR and stained with HA-tag (to detect HA-CFTR protein), FoxI1 (for ionocytes) and CC10 (for club cells). Number of cells expressing HA-CFTR were quantified, and the localization of HA-CFTR was determined by co-staining with different cell markers. Quantification of bands B and C from the transfection were shown on the graph. According to the data, high percentage of ionocytes were positive for HA-CFTR. Most of the HA staining localizes to the apical part of the cells, where we expect to have functional membrane-bound CFTR. In the video, an overlay of all markers is shown. Note that staining for ionocyte (green) co-localizes with HA-staining (purple). A few CC10 positive cells also co-localize with HA marker (Data shown in FIG. 68).

Figure 69:
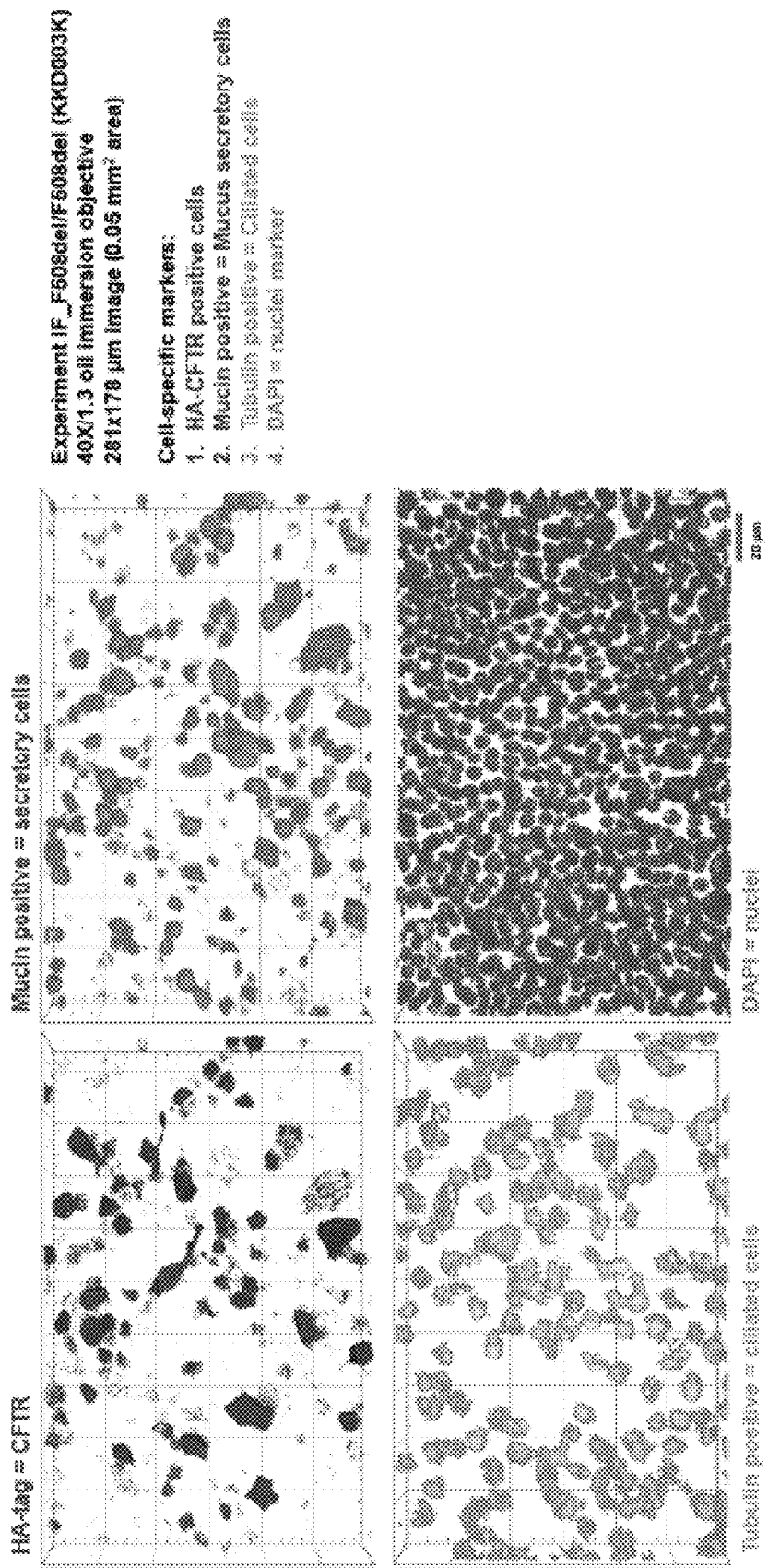
Figure 70:
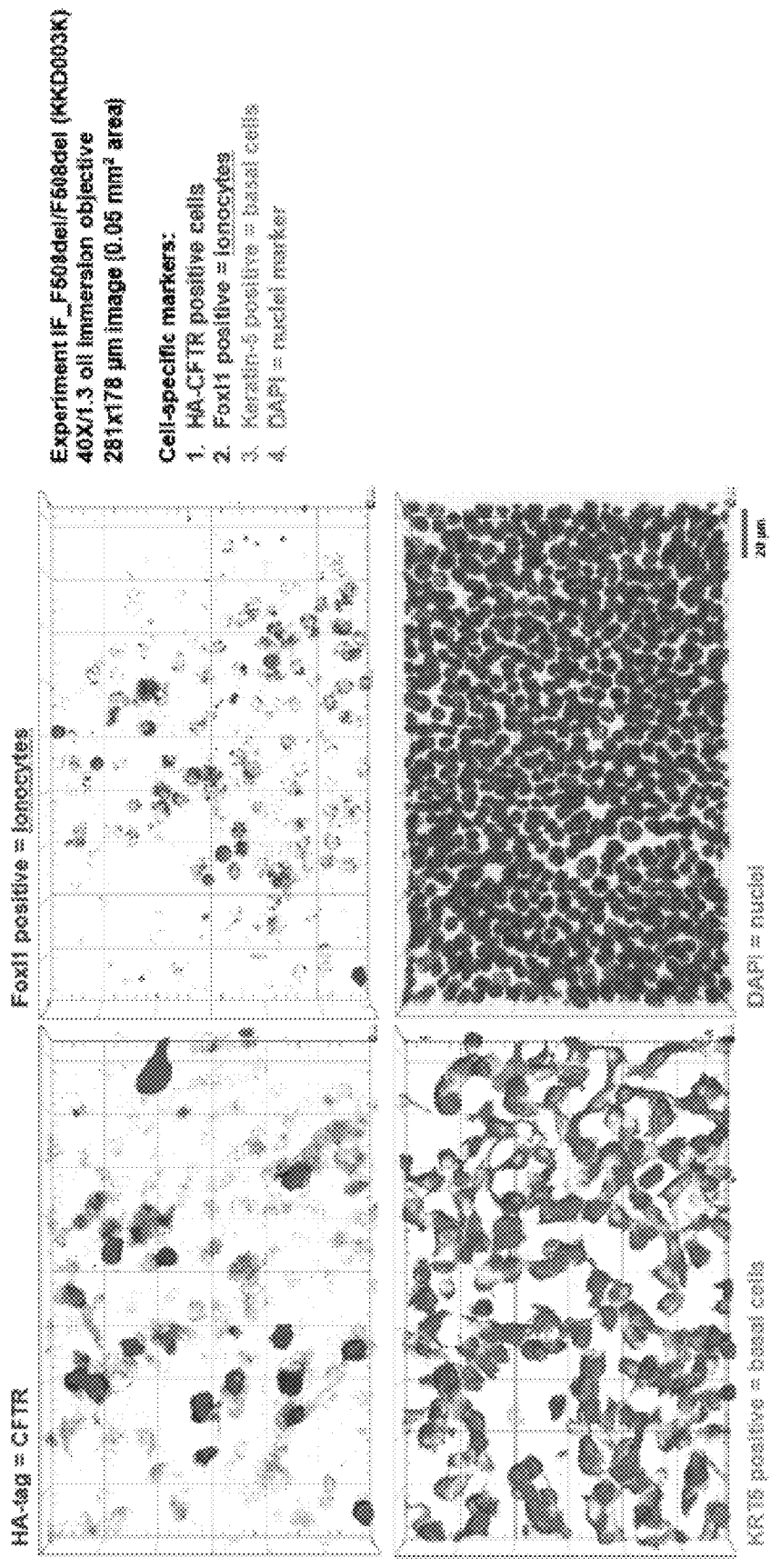

Similar experiments were performed using different antibodies. FIG. 69 shows the number of cells expressing HA-CFTR quantified. The localization of HA-CFTR was determined by co-staining with different cell markers (Mucin for secretory cells; Tubulin for ciliated cells). As in the FIG. 68, most of the HA staining localized to the apical part of the cells. Some mucin-positive cells showed co-localization with HA marker. Few ciliated cells were also observed to co-localize with HA-CFTR (Data shown in FIG. 69). Additional experiments were performed using FoxI1 (for ionocytes) and KRT5 (for basal cells) antibodies. The cells expressing HACFTR were quantified, and the localization of HA-CFTR was determined by co-staining with different cell markers (FoxI for ionocytes; KRT5 for basal cells). Most of the HA-CFTR staining was localized to the apical part of the cells. Some KRT5 positive cells showed co-localization with HA-CFTR. Ionocytes were also observed with co-localization with HA-CFTR (FIG. 70).

Figures 71A, 71B:
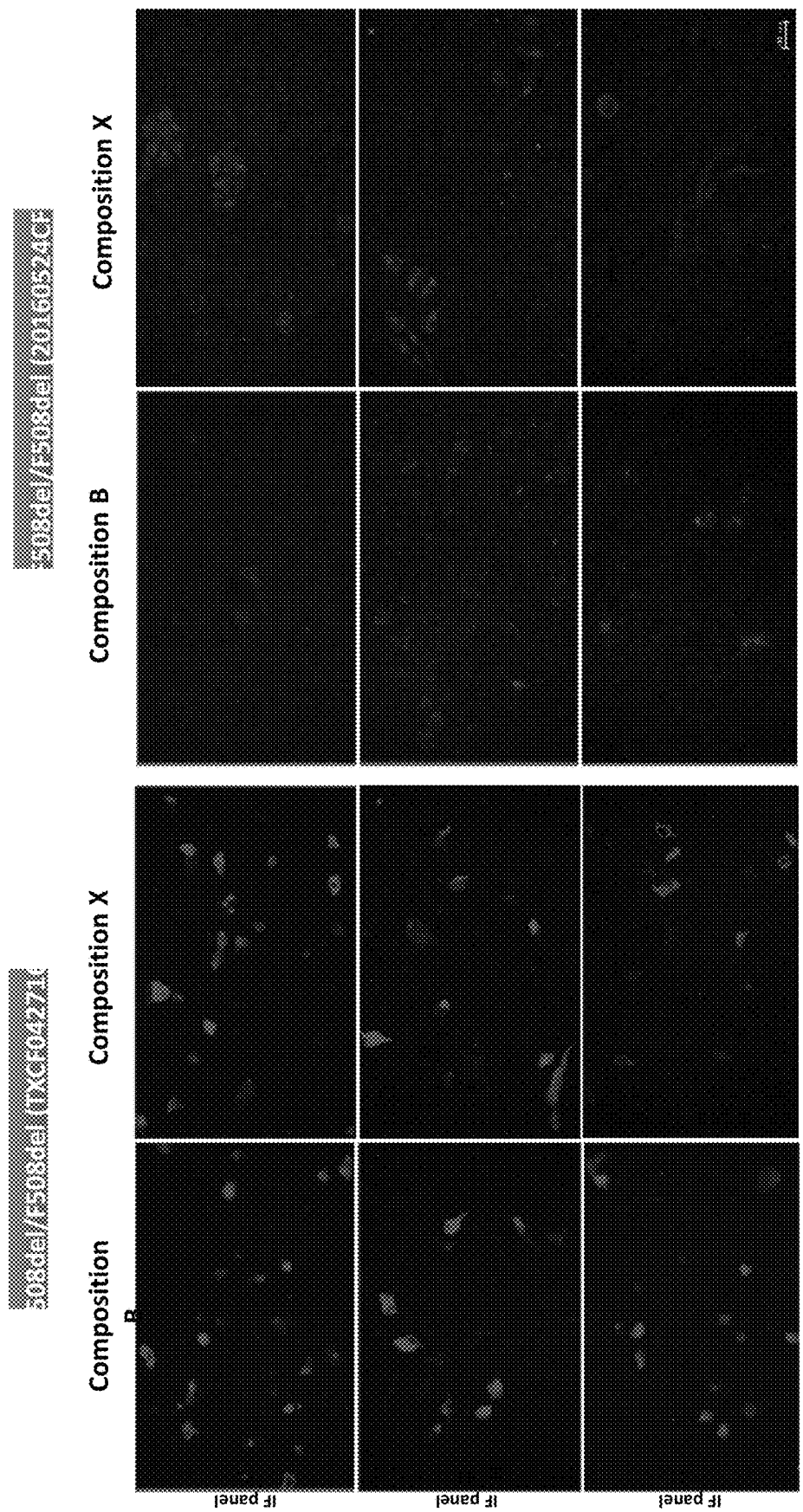

The expression level of HA-CFTR delivered by the lipid nanoparticles was observed in two ΔF508/ΔF508del homozygous genotype hBE cells. TXCF042716 and 20160524CF cells were dosed with HA-CFTR-containing lipid nanoparticles and stained to detect protein expression level of HA-CFTR. FIGS. 71A-71B show that TXCF042716 cells expressed more HA-CFTR protein compared to 20160524CF cells, resulting different donors with the same genotype (ΔF508/ΔF508) showed different HA-CFTR protein expression.

Further studies were performed to analyze the relationship between CFTR expression and its function. TXCF042716 and 20160524CF hBE cells were dosed with HA-CFTR-containing lipid nanoparticles, and CFTR function was determined by measuring chloride flux and CFTR expression level by immunofluorescence. Donor TXCR042716 cells showed significant rescue of chloride flux and strong detection of HA signal, while the opposite was observed with donor 20160524CF, suggesting low transfection efficiency (FIG. 72).

Figure 73A:
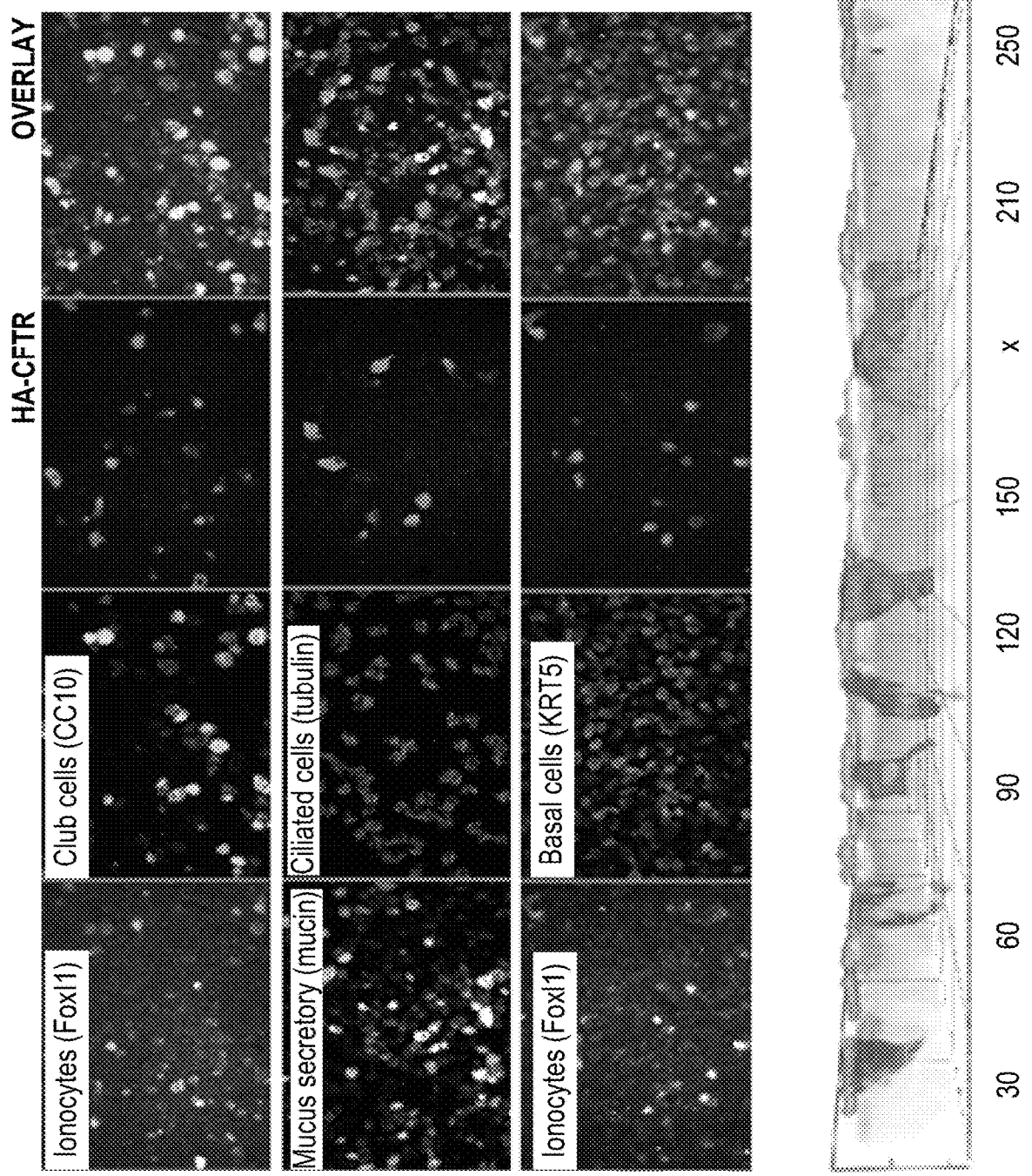
Figures 73B, 73C:
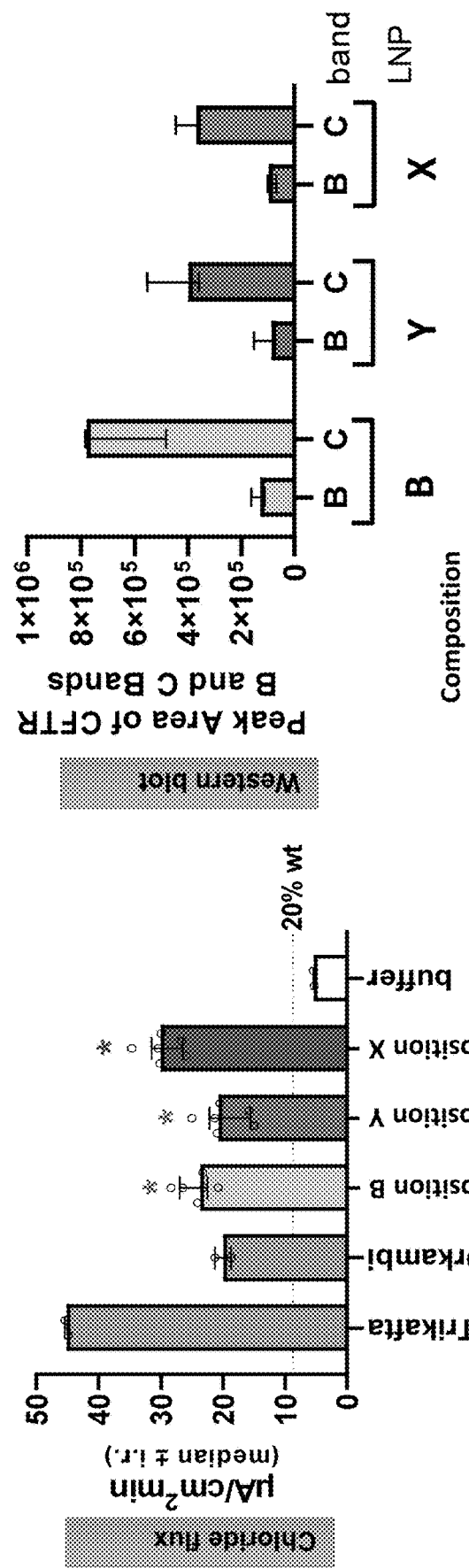
Figure 74A:
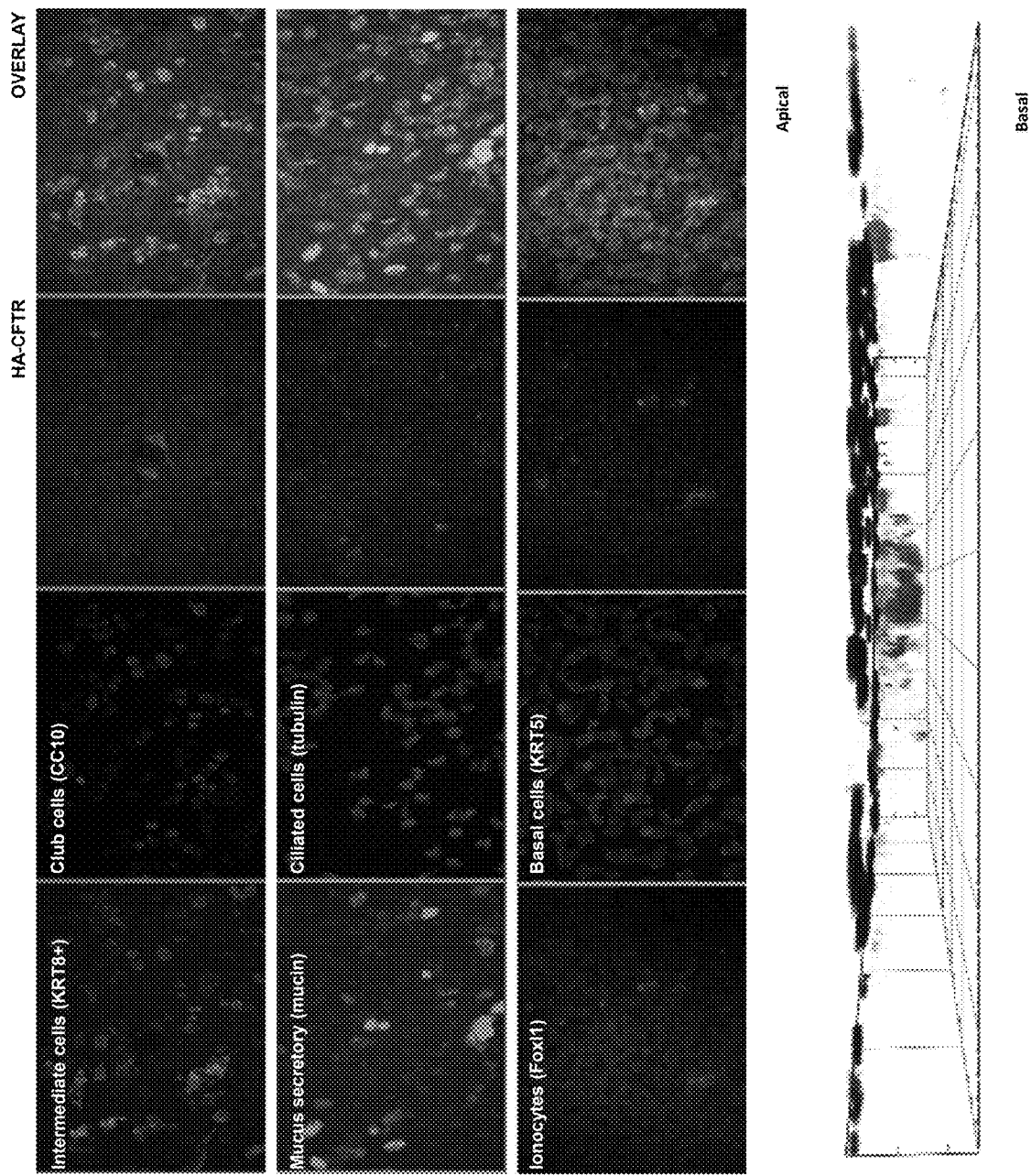
Figures 74B, 74C:
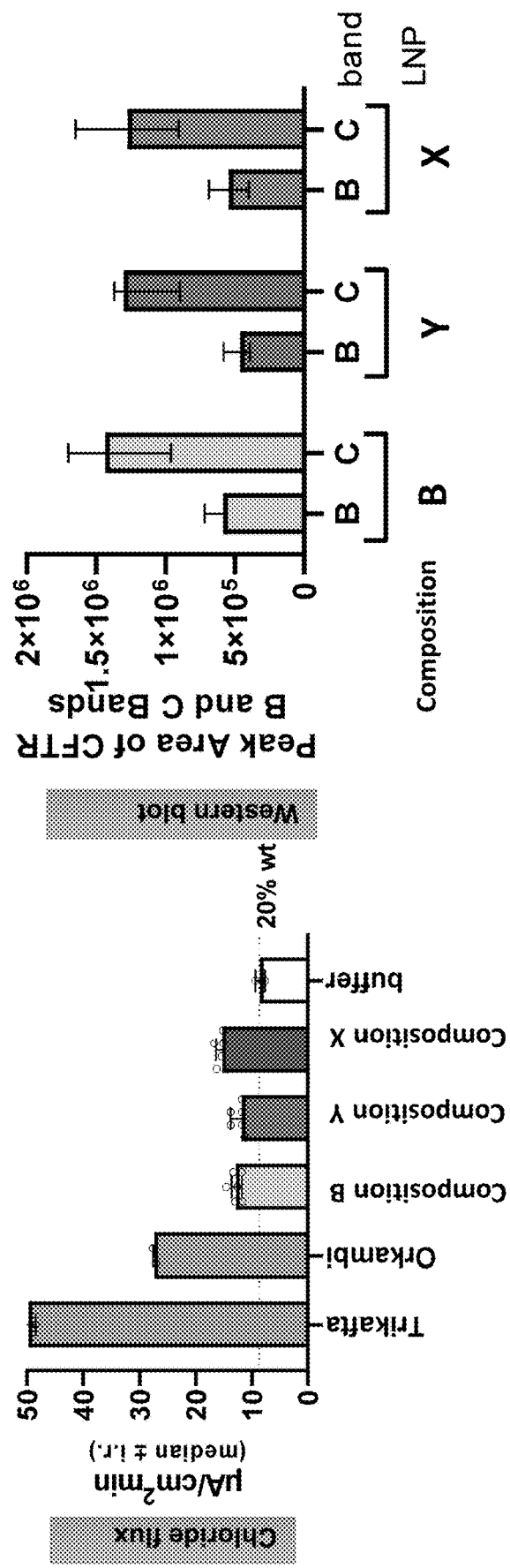
Figures 76B, 76C:
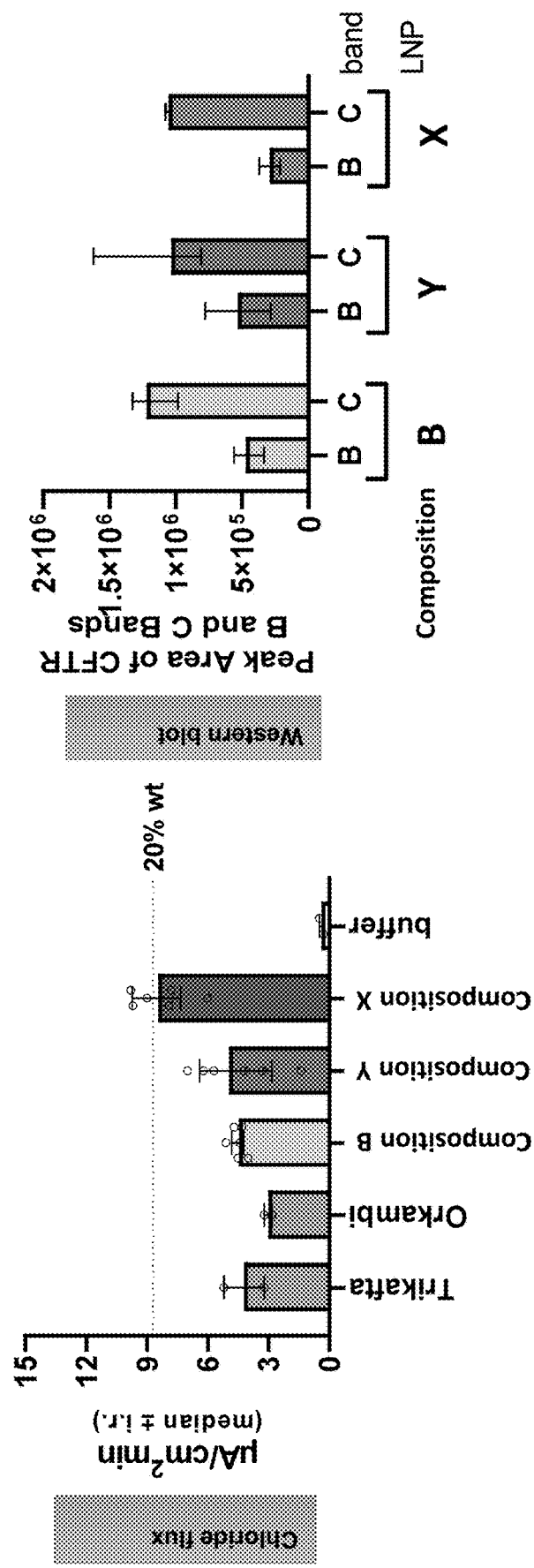

This result led to further experiments to analyze the localization of HA-CFTR in TXCF042716 and 20160524CF hBE cells. TXCF042716 hBE cells were dosed with lipid nanoparticles containing HA-CFTR, and immunostaining assay showed the highest expression and apical translocation of HA-CFTR. HA signal was predominantly detected in ionocytes, and strong HA detection was consistent with high functional rescue of chloride flux (FIGS. 73A-73C). 20160524CF hBE cells dosed with lipid nanoparticles showed the high expression of HA-CFTR (FIG. 74C). HA-CFTR signal was predominantly detected in the body of the cells (FIG. 74A). However, unlike in TXCF042716 hBE cells, HA-CFTR expressed in 20160524CF hBE cells did not translocate to the apical membrane. Low HA detection at the apical membrane was consistent with poor functional rescue of chloride flux (FIG. 74B).

Further experiments were performed to compare the lipid nanoparticles. W1282X/W1282X hBE cells were dosed with either Composition B or Composition X. CFTR expression level was measured using immunofluorescence assay, which showed similar expression level of CFTR protein (FIG. 75).

Further experiments were performed to determine the protein expression by lipid nanoparticle component. W1282X/W1282X (UI0014) hBE cells dosed with either Composition B (FIGS. 77A-77C) or Composition X (FIGS. 76A-77C). Efficient translocation of HA-CFTR protein to the apical membrane was observed in the cells. W1282X/W1282X hBE cells showed high expression and apical translocation of HA-CFTR post exposure to aerosolized lipid nanoparticles. HA signal was predominantly detected in ionocytes, and a few ciliated cells also showed strong apical expression of HA-CFTR.

To determine cell tropism, dF #4 (KKD003K) hBE cells dosed with Composition B showed highest expression by projection area predominantly in ionocytes with proper apical translocation of HA-CFTR. This was consistent with good functional compensation of defective endogenous CFTR comparable to that in dF #1 hBE (FIG. 81). Cell-mediated expression of HA-CFTR in dF #1, dF #4, and dF #4 are shown in FIG. 82.

Further experiments were performed to determine the protein expression level by lipid nanoparticle component. F508del/F508del (TXCF042716) hBE cells dosed with Composition X showed the highest expression and apical translocation of HA-CFTR. HA signal predominantly detected in ionocytes (shown in FIGS. 83A, 83C, and 89), and strong HA detection was consistent with high functional rescue of chloride flux (FIG. 83B). In F508del/F508del (20160524CF) hBE cells dosed with Composition X, the cells showed the high expression of HA-CFTR (FIG. 84C). HA signal was predominantly detected in the body of the cells, and translocation of HA to the apical membrane failed. Low HA detection at the apical membrane was consistent with poor functional rescue of chloride flux (FIG. 84B).

K710X/L$^{467}$ (ND13816) hBE cells showed fibrosis groups in the distribution of basal cell sub-population and elevated density FoxI1-positive cells. K710X/L$^{467}$ (ND13816) hBE cells aerosolized with Composition B showed expression and partial apical translocation of HA-CFTR. HA signal was detected in ionocytes as well as club, goblet, ciliated, and basal cells. However, the signal showed spotted aggregation and reduced intensity. The expression was detected in reduced of FoxI1-positive cells in comparison to other tested hBE samples (FIGS. 85A-85B and 86). Arrows in FIG. 86 indicated intracellular co-segmentation of FoxI1 and Ha-CFTR signals. K710X/L$^{467}$ (ND13816) hBE cells aerosolized with Composition X induced expression of HA-CFTR comparable to cells aerosolized with Composition B (shown in FIGS. 87A-87B and 88).

F508del/F508del hBE cells (KKD017N) were dosed with Composition B/HA-CFTR and stained with HA-tag (to detect HA-CFTR protein), KRT8 (for intermediate cells) and CC10 (for club cells). The number of cells expressing HA-CFTR was quantified, and the localization of HA-CFTR was determined by co-staining with different cell markers. (Data shown in FIG. 90).

All donor cells were dosed with Composition B, Composition Y, or Composition X with HA-CFTR and evaluated the expression level of HA-CFTR by Western blot analysis (FIG. 91). Further experiments were performed to measure dependency of translation level with functional activity of CFTR. All three nonresponsive genotypes analyzed exhibited similar levels of HA-CFTR after being dosed with Composition B, Composition Y, or Composition X, independent of observed functional rescue of chloride flux (FIG. 92).

Composition B and Composition X were compared to an alternative LNP composition, Composition A. Both Composition B and Composition X showed superior ability to restore CFTR function in F508del/F508del hBE cells compared to Composition A (FIGS. 93A-93B). There was no significant difference in cell integrity and permeability between Composition A and Composition X treated cells, measured by transepithelial electrical resistance (TEER) (FIG. 93B upper).

Six A F508del/F508del hBE cells were dosed with either Composition B, Composition Y, or Composition X, and cytotoxicity was measured by LDH assays. Lysed cells showed 100% LDH release. As reference, Composition A resulted in 45% LDH release with significantly reduced ciliary activity, significant increase in IL-6 production, and reduction in cell layer thickness. FIG. 94 shows that no overt toxicity was observed for all three compostions, determined by measuring LDH release.

Example 10: A Phase I Randomized, Double-Blind, Placebo-Controlled, Single Ascending Dose Study to Evaluate the Safety and Tolerability of RCT1100 in Healthy Participants The primary objective of this study is to assess the safety and tolerability of single ascending doses of inhaled RCT1100 administered via nebulizer to healthy participants. The secondary objectives of the study are to characterize biodistribution of RCT1100 components into whole blood and antibodies against polyethylene glycol following single escalating inhaled doses in healthy participant and the potential for development of antidrug antibodies against DNAI1 protein following single escalating inhaled doses. The exploratory objective of this study is to determine the impact of predose short-acting beta 2 agonist bronchodilator (salbutamol) on the tolerability of treatment in healthy participants.

RCT1100-101 is a Phase 1, randomized, double-blind, placebo-controlled single ascending dose study to assess the safety and tolerability of inhaled RCT1100 when administered to healthy participants.

TABLE 22

The drugs used in the study

| Product | Supplied Formulation |
| --- | --- |
| RCT1100 | 1 mg/mL dispersion in 5 mL vials |
| Placebo (normal saline) | sterile, nonpyrogenic, 0.9% sodium chloride with no preservatives |

RCT1100 is an opalescent to off-white, sterile, nonpyrogenic aqueous dispersion. It contains DNAI1 mRNA, a drug substance encapsulated into SORT LNPs. The drug substance is a highly purified single-stranded, 5' capped/3' poly A, nucleotide-modified and sequence optimized mRNA encoding full-length DNAI1 protein. mRNA is optimized for high efficacy with respect to stability and translational efficiency (5'-cap, 1-methyl-pseudouridine used instead of uridine, polyA-tail).

Approximately 32 participants who meet the criteria for study entry will be randomly assigned to 1 of 4 cohorts as shown in FIG. 78 and FIG. 79. Participants in each cohort will receive either RCT1100 or placebo (normal saline). Participants will be pretreated with 2 puffs of an inhaled short-acting beta 2 agonist bronchodilator (salbutamol HFA, 100 mcg per puff), approximately 50 minutes prior to study drug administration. If no bronchospasm is seen and following a review of all safety and tolerability data by the safety review committee (SRC), the decision may be taken to dose without the use of a bronchodilator. All participants will receive the study treatments according to the schedule of events (FIG. 80). A sentinel cohort of 2 participants will be used for each dosing cohort. The sentinel participants will be dosed in a blinded fashion (1 active, 1 placebo) and monitored for at least 48 hours.

The study will consist of a Screening Phase (Day −28 to Day −2), Check-in (Day −1), Treatment Phase (Day 1 to Day 3), and a Follow-up Phase with outpatient visits on Day 8 (±1 day), Day 15 (±1 day), and an end-of-study (EOS) visit on Day 29 (±1 day). The maximum duration of the study for each participant is 57 days, including screening (up to 28 days). Participants will be domiciled at the clinical research unit (CRU) from Day −1 and discharged following completion of all assessments on Day 3, after they are deemed "clinically stable" by the investigator or designee (eg, no ongoing adverse events [AEs] or other safety concerns). The clinical laboratory assessments shown in FIG. 80 will be performed.

Dose escalation will occur only after the safety and tolerability data from at least 14 days after dosing of the preceding dose cohort for at least 6 participants are assessed and the study drug is deemed safe and well tolerated. Dose escalation will be suspended in some condition.

Safety and tolerability endpoints will include monitoring and recording of adverse events, clinical laboratory test results (including but not limited to hematology, serum chemistry including liver function tests, urinalysis), spirometry, vital sign measurements, 12-lead electrocardiogram (ECG) results, and physical examination findings.

For all safety assessments, the investigator will determine whether results are clinically significant, which is defined as any variation in a result that has medical relevance and may result in an alteration in medical care (eg, active observation, diagnostic measures, or therapeutic measures). If clinical significance is noted, the result and reason for significance will be documented and an AE reported on the AE page of the participant's electronic case report form (eCRF). The investigator will monitor the participant until the result has reached the reference range or the result at screening, or until the investigator determines that follow-up is no longer medically necessary.

Each participant must meet all of the following criteria shown in Table 17 to be enrolled in this study

TABLE 23

Study population.

| | |
| --- | --- |
| 1 | The participant is a male or female, 18 to 55 years of age, inclusive, at the time of consent. |
| 2 | The participant has a body mass index 18 to 35 kg/m², inclusive, and a total body weight ≥50 kg, inclusive, at screening. |
| 3 | The participant is considered by the investigator to be in good general health as determined by medical history, clinical laboratory test results, vital sign measurements, 12-lead ECG results, and physical examination findings at screening. |
| 4 | The participant has a percent predicted forced expiratory volume in 1 second (ppFEV$_1$) of at least 80% predicted. |
| 5 | Female participants must be of nonchildbearing potential. |
| 6 | Male participants and their female partners of childbearing potential (defined as women that are neither postmenopausal nor surgically sterile) must agree to use one of the following methods of contraception during the study and until 90 days after the last dose of the study drug. Male participants must also agree not to donate sperm and female participants must agree not to donate eggs, for the duration of the study and until at least 90 days after the last dose of the study drug. |

Example 11: A 13-Week Liquid Inhalation Toxicology Study Followed by a 4-Week Recovery Period in Sprague-Dawley Rats The objective of the study was to determine the toxicity of the DNAI1 mRNA encapsulated in Composition A LNP, following a 13-Week inhalation administration to rats and to assess the persistence, delayed onset or reversibility of any changes following an observation period of 28 days. The test and control/vehicle items and air control were administered to groups of rats three times weekly inhalation administration for 13 weeks.

TABLE 24

The experimental design

| Group Number | Group Designation | Achieved Inhaled Dose Level of RCT1100 (mg/kg/occasion) | Achieved Inhaled Dose Level of RCT1100 (mg/kg/week) | Achieved Aerosol Conc. of RCT1100 (mg/L) | Exposure Duration (minute) | Main Animals M | Main Animals F | Recovery Animals M | Recovery Animals F | TK Animals M | TK Animals F |
|---|---|---|---|---|---|---|---|---|---|---|---|
| 1 | Air Control | 0 | 0 | 0 | 90 | 10 | 10 | 5 | 5 | 10 | 10 |
| 2 | Control/Vehicle# | 0 | 0 | 0 | 90 | 10 | 10 | 5 | 5 | 10 | 10 |
| 3 | Low | 0.16 | 0.48 | 0.01018 | 22 | 10 | 10 | 5 | 5 | 10 | 10 |
| 4 | Mid | 0.34 | 1.02 | 0.01088 | 45 | 10 | 10 | 5 | 5 | 10 | 10 |
| 5 | High | 0.69 | 2.07 | 0.01097 | 90 | 10 | 10 | 5 | 5 | 10 | 10 |

Control/Vehicle animals were administered Composition A-Placebo (LNP formulation with no mRNA).

Following blood collection, the animals were euthanized 24 hours after the last exposure (Day 90) and subjected to a necropsy examination on Day 91. The Recovery animals were observed for 28 days and then euthanized and subjected to a necropsy examination on Day 119. Following blood collection, the TK animals of Groups 1 to 5 were euthanized, and tissue collection was performed at termination after the last exposure.

The overall achieved aerosol concentrations were 0, 0, 0.01018, 0.01088 and 0.01097 mg/L resulting in achieved dosages per occasion of 0, 0, 0.16, 0.34 and 0.69 mg/kg/occasion for air control, control/vehicle, low, mid and high Composition A doses, respectively. The overall achieved dose per week were 0, 0, 0.48, 1.02 and 2.07 mg/kg/week for the air control, control/vehicle, low, mid and high Composition A doses, respectively. The particle size distribution measurements confirmed that Composition A was respirable for the rat, with MMAD values of 1.9, 1.8, 1.8 and 1.8 µm for the control/vehicle, low, mid and high doses, respectively, and corresponding mean σg of 1.91, 1.87, 1.91 and 1.97 for the control/vehicle, low, mid and high doses, respectively. Composition A was administered using the maximum feasible concentration and the high dose level was escalated by increasing the duration of exposure to the maximum feasible dose.

The administration of Composition A by inhalation was well tolerated without any test item-related mortality or adverse clinical signs up to the dose of 2.07 mg/kg/week. Body weights, food consumption, haematology, ophthalmology parameters, hematology clinical chemistry and coagulation were unaffected by treatment with Composition A.

On Day 91, neutrophils were increased in BAL fluid in the control/vehicle (placebo), 1.02 mg/kg/week (mid) and 2.07 mg/kg/week (high) Composition A groups compared to the air control group; these increases were more substantial in the high dose group. There was also a statistically significant decrease in absolute and percent alveolar macrophages control/vehicle (placebo), 1.02 mg/kg/week (mid) and 2.07 mg/kg/week (high) Composition A groups. At the end of the Recovery period (Day 119), all changes observed on Day 91 had generally recovered.

Upon necropsy on Day 91, changes attributed to the administration of Composition A were observed in absolute and relative lung/trachea weights in males at ≥1.02 mg/kg/week and in females at 2.07 mg/kg/week. The increased lung/trachea weights correlated with the microscopic findings of chronic inflammation, increased alveolar macrophages and increased cellularity of the bronchial-associated lymphoid tissue observed in the lungs. At the end of the recovery period, the changes in the lung/trachea weights were reversed in males and females. Chronic inflammation was observed in 3/10 at 0.48 mg/kg/week (minimal), 6/10 at 1.02 mg/kg/week males (minimal to mild), and 10/10 at 2.07 mg/kg/week males (minimal to mild), while in the females, chronic inflammation was observed in 2/10 at 0.48 mg/kg/week females (minimal), 4/10 at 1.02 mg/kg/week (minimal to mild) and 9/10 at 2.07 mg/kg/week females (minimal to mild). Chronic inflammation co-localized with increased alveolar macrophages and pigmented foreign material at the broncho alveolar junction of the lung and was characterized by lymphocytes and mononuclear cells along the walls of the terminal bronchioles and alveolar outpocketings of the terminal bronchioles.

Pigmented foreign material (minimal) was observed in macrophages in the lungs of males (2/10 at 0.48 mg/kg/week; 2/10 at 1.02 mg/kg/week; 7/10 at 2.07 mg/kg/week) and females (2/10 at 0.48 mg/kg/week; 2/10 at 1.02 mg/kg/week; 3/10 at 2.07 mg/kg/week). The foreign material is attributed to phagocytosis and clearance of the test item.

Increased alveolar macrophages in the lung was observed in 6/10 at 2.07 mg/kg/week males (minimal to mild) and 4/10 at 2.07 mg/kg/week females (minimal). Alveolar macrophages were enlarged with foamy granular cytoplasm. In the bronchial associated lymphoid tissue of the lung, increased cellularity was observed in 6/10 at 2.07 mg/kg/week males (minimal to mild) and 3/10 at 2.07 mg/kg/week females (minimal to mild). Chronic inflammation, increased alveolar macrophages and the increased cellularity of the bronchiole associated lymphoid tissue in the lungs of males and females correlated in general with the increased absolute and relative lung/trachea weights observed in males and females administered at 2.07 mg/kg/week Composition A. In the tracheobronchial lymph nodes, an increased incidence of increased lymphocyte cellularity was observed in 8/10 at 2.07 mg/kg/week males (minimal) and 6/9 at 2.07 mg/kg/week females (minimal to mild) and was considered test item related. The increased incidence of increased cellularity correlated in general with the macroscopic finding of enlargement of the tracheobronchial lymph nodes.

Test item-related microscopic finding of minimal pigmented foreign material was observed in the lungs in males ≥1.02 mg/kg/week and in females at 2.07 mg/kg/week Composition A and was partially reversable in males and females. Pigmented foreign material in the lungs and aggregates of pigmented macrophages in the tracheobronchial lymph nodes were considered phagocytosis of test material due to ongoing clearance of the test item. Test item-related finding of aggregates of macrophages (minimal; pigmented) was observed in the tracheobronchial lymph nodes in males (2/4) and females (1/5) at 2.07 mg/kg/week Composition A. Chronic inflammation, increased alveolar macrophages and increased cellularity of the bronchial associated lymphoid tissue in the lungs was fully reversible in Recovery males and females. The increased cellularity of tracheobronchial lymph nodes observed in Main study animals returned to control levels and was reversible following the 28-day recovery period in males and females.

In conclusion, an inhalation administration of Composition A was well-tolerated during the treatment period utilizing a maximum exposure time of 90 minutes three times per week to an achieve dose of 2.07 mg/kg/week. Therefore, the no-adverse effect level (NOAEL) was considered to be 2.07 mg/kg/week Composition A, the highest dose tested.

Example 12: A 13-Week Liquid Inhalation Toxicology Study Followed by a 4-Week Recovery Period in Cynomolgus Monkeys The objective of the study was to determine the toxicity of the DNAI1 mRNA encapsulated in Composition A LNP, following three times weekly inhalation administration to the cynomolgus monkey for 13-weeks and to assess the persistence, delayed onset or reversibility of any changes following a 4-week recovery period.

The test and control/vehicle items and air control were administered to groups of monkeys three times weekly by inhalation administration. At the end of last week of dosing, an additional dose was administered to all groups on the day prior to necropsy, in order to consistently conduct a Day 92 necropsy, approximately 24 hours after the final exposure on Day 91. Therefore, a total of 40 doses were delivered over the course of the study.

TABLE 25

The experimental design

| Group Numbers | Group Designation | Achieved Inhaled Dose Level (mg/kg/occasion) | Achieved Inhaled Dose Level RCT1100 (mg/kg/week) | Achieved Aerosol Conc. of RCT1100 (mg/L) | Exposure Duration (minutes) | Number of Main Animals M | Number of Main Animals F | Number of Recovery Animals M | Number of Recovery Animals F |
|---|---|---|---|---|---|---|---|---|---|
| 1 | Air Control | 0 | 0 | 0 | 48@ | 3 | 3 | 2 | 2 |
| 2 | Control/Vehicle# | 0 | 0 | 0 | 48@ | 3 | 3 | 2 | 2 |
| 3 | Low Dose | 0.038 | 0.11 | 0.00677 | 12@ | 3 | 3 | 2 | 2 |
| 4 | Mid Dose | 0.086 | 0.26 | 0.00741 | 24@ | 3 | 3 | 2 | 2 |
| 5 | High Dose | 0.169 | 0.51 | 0.00733 | 48@ | 3 | 3 | 2 | 2 |

Control animals were administered RTX0051-Placebo (LNP formulation with no mRNA)
Conc = Concentration; M = males; F = females
@Groups 2 and 5 animals were dosed for 40 minutes for Doses 1 to 9; Group 3 animals were dosed for 10 minutes for Doses 1 to 9; Group 4 animals were dosed for 20 minutes for Doses 1 to 9; Group 1animals were dosed for 40 minutes for Doses 1 to 11.

The Main animals were euthanized and subjected to a necropsy examination on Day 92 (approximately 24 hours post-dose). The Recovery animals were observed for 4 weeks and then euthanized and subjected to a necropsy examination on Day 119.

The overall achieved aerosol concentrations were 0, 0, 0.00677, 0.00741 and 0.00733 mg/L resulting in achieved dosages per occasion of 0, 0, 0.038, 0.086 and 0.169 mg/kg/occasion for air control, control/vehicle, low, mid and high Composition A dose, respectively. The overall achieved dose per week were 0, 0, 0.11, 0.26 and 0.51 mg/kg/week for air control, control/vehicle, low, mid and high Composition A dose three times per week respectively. The particle size distribution measurements confirmed that Composition A was respirable for the monkey, with MMAD values of 2.2, 2.0 and 2.2 μm for the low, mid and high dose with corresponding mean σg of 2.37, 2.30 and 2.33 for the low, mid and high dose, respectively. Composition A was administered using the maximum feasible concentration and the low, mid and high dose level was escalated by increasing the duration of exposure.

The administration of Composition A by inhalation was well tolerated without any test item-related mortality or adverse clinical signs up to the dose of 0.51 mg/kg/week. Body weights, ophthalmology, ECG, hematology clinical chemistry, coagulation and urinalysis parameters were unaffected by treatment with Composition A.

On Day 92, $C_3a$ fragment concentrations ranged between 0.61 and 1.49 ng/mL in the air control, from 1.21 to 2.35 ng/mL in the control/vehicle, from 0.83 to 3.07 ng/mL in the low dose, between 3.04 to 5.69 ng/mL in the mid dose and varied from 3.47 to 27.34 ng/mL in the high dose, indicating a dose-dependent response following Composition A inhalation administration. On Day 119, similar results were obtained for the air control, control/vehicle and low dose with $C_3a$ fragment concentration in the BALF samples ranging from 0.91 and 2.18 ng/mL in the air control, from 0.32 to 2.37 ng/mL in the control/vehicle and from 1.19 to 3.78 ng/mL in the low dose. For the mid dose and high doses, $C_3a$ fragment concentrations were similar to both control groups from Day 92 and Day 119 with concentrations ranging from 0.87 to 1.90 ng/mL for Group 4 and from 0.60 to 3.10 ng/mL for Group 5.

On Day 92, sC5b-9 concentrations were <LLOQ (50.00 ng/mL) for air control, vehicle/control and low dose animals, indicating that the administration with Composition A-Placebo (LNP formulation with no mRNA) or low dose level of Composition A had no notable effect on sC5b-9 levels in the bronchoalveolar lavage fluid of the animals. Five out of six (5/6) animals in the mid dose and four out of six (4/6) animals in the high dose showed sC5b-9 levels above the LLOQ, ranging from 56.53 to 102.11 ng/mL and 52.29 to 155.13 ng/mL, respectively. The increase in sC5b-9 concentrations were related to the increased dose levels as compared to the low dose groups. However, similar results were noted between Groups 4 and 5, suggesting a plateau response achieved at 0.26 mg/kg/week. On Day 119, animals in all five groups showed sC5b-9 concentrations <LLOQ, indicating that the changes of sC5b-9 levels in mid and high doses were transient and returned to control values after a four-week recovery period.

On Day 89, exposure to Composition A caused dose-dependent increases in serum and BALF levels of IP-10 in the mid and high doses. IP-10 levels were sustained up to termination in the mid dose while slowly decreased toward baseline in the high dose, but overall IP-10 remained above pre-treatment levels. In addition, increases in BALF levels of IL-6 were observed in the high dose on Day 89 returning to air control levels by Day 119. No effects were reported on the levels of IFN-α2a, IFN-γ, IL-1β, IL-4, IL-10, IL-17A, MCP-1 and TNF-α in either serum or BALF samples as well as on the concentrations of IL-6 in serum samples.

On Day 92, neutrophils were increased in BAL fluid in the control/vehicle, low mid and high doses compared to the air control group; these increases were more substantial in the high dose group. There was also a statistically significant decrease in absolute and percent alveolar macrophages in control/vehicle, mid and high doses. At the end of the Recovery period (Day 119), all changes observed on Day 91 had generally recovered.

Upon necropsy on Day 92, changes attributed to the administration of Composition A were observed in absolute and relative lung/trachea weights in males and females at ≥0.26 mg/kg/week. The increased lung/trachea weights correlated with the microscopic findings of chronic inflammation, increased alveolar macrophages and increased cellularity of the bronchial-associated lymphoid tissue observed in the lungs. At the end of the recovery period, the changes in the lung/trachea weights were reversed in males and females.

Upon necropsy on Day 92, dose-related alveolar inflammatory cell infiltrate (minimal to mild), perivascular mononuclear cell infiltrate (minimal to mild) and alveolar accumulation of vacuolated macrophages (minimal to mild) were observed in all dose levels in a dose-related manner. Dose-related minimal to mild multifocal inflammation was found in 3/6 animals dosed at mid dose and in 6/6 animals dosed at high dose. Alveolar accumulation of vacuolated macrophages was found only in animals treated with Composition A and was considered to be a consequence of pulmonary alveolar accumulation of the test item. Increased cellularity of the tracheo-bronchial lymph node was observed in animal groups treated with Composition A in a dose-related manner. Affected were 1/6 animals dosed at 0.11 mg/kg/week (mild), 2/6 animals dosed at mid dose and 6/6 animals dosed at high dose (mild to moderate). Minimal inflammatory cell infiltrate was found in 1/6 animals dosed at mid dose and in 1/6 animals dosed at high dose. Findings in the tracheo-bronchial lymph node were considered to be a consequence of lesions observed in the lungs.

Upon necropsy on Day 119, minimal accumulation of alveolar vacuolated macrophages in the lungs was observed in 1/4 animals treated with control/vehicle, 2/4 animals dosed at low dose, 0/4 animals dosed at mid dose and 2/4 animals dosed at high dose. Minimal perivascular mononuclear cell infiltrate was found in 2/4 animals dosed at low dose, 4/4 animals dosed at mid dose and 3/4 animals dosed at high dose. Higher incidence of increased alveolar cellularity was observed in animals dosed at high dose, when compared with other animal groups. Affected were 1/4 air control, 0/4 control/vehicle, 0/4 animals dosed at low dose, 1/4 animals dosed at mid dose and 3/4 animals dosed at high dose. Minimal alveolar inflammatory cell infiltrate was observed in one air control animal, one control/vehicle animal, one low dose animal, one mid dose animal and no animal dosed at high dose and was considered to be incidental rather than Composition A-related. There was no evidence of any dose-relationship, and all findings were considered to be continuing to recover.

In conclusion, an inhalation administration of Composition A was well-tolerated during the treatment period utilizing a maximum exposure time of 48 minutes three times per week to an achieved dose of 0.51 mg/kg/week in monkeys. Therefore, the no-adverse effect level (NOAEL) was considered to be 0.51 mg/kg/week Composition A, the highest dose tested.

Example 13: Single Dose Liquid Inhalation Toxicology Study in Cynomolgus Monkeys The experiments were performed to study toxicology of single-dose inhalation of Composition A in Cynomolgus Monkeys. The experimental design is detailed in Table 26.

TABLE 26

| | | The experimental design of Example 13 | | | | |
|---|---|---|---|---|---|---|
| Group Numbers | Group Designation | Achieved Total Inhaled Dose Level Composition A-DHAI1-HA (mg/kg) | Achieved Aerosol Conc. of Composition A-DHAI1-HA (mg/L) | Exposure Duration (minutes) | Number of Animals M | F |
| 1 | Vehicle# Control | 0 | 0 | 90 | 1 | 1 |

TABLE 26-continued

The experimental design of Example 13

| Group Numbers | Group Designation | Achieved Total Inhaled Dose Level Composition A-DHAI1-HA (mg/kg) | Achieved Aerosol Conc. of Composition A-DHAI1-HA (mg/L) | Exposure Duration (minutes) | Number of Animals M | F |
|---|---|---|---|---|---|---|
| 2 | Low Dose | 0.11 | 0.00724 | 30 | 4 | 4 |
| 3 | dose group (group 3) at 6 hr post-administration, levels of 14:0 EPC ranged from 13,860 ng/g to 66,675 ng/g. In the liver samples tested, all values for 14:0 EPC were not detected except for high dose sample at 6 hr, which, while having detectable 14:0 EPC, was below the assay LOQ. For the spleen samples examined, all values for 14:0 EPC were not detected expect for high dose sample at 6 hr, which had a value of 9.56 ng/g. In the blood cell fraction samples, eight samples, all from the high dose group, had detectable levels of 14:0 EPC. For the plasma samples tested, six high dose (group 3) samples had detectable 14:0 EPC (Table 3). Three were below the assay LOQ, while the remaining three gave values of 0.99 ng/mL (1 hr), 1.97 ng/mL (6 hr), and 1.03 ng/mL (1 hr). The remaining plasma samples did not have detectable 14:0 EPC.

A time course of DMG-PEG levels in lung tissue following administration is shown in FIG. 99. Plotted for each animal is the mean of the values from the three sampled lung regions. Peak levels were seen at 6 hr post-exposure and dropped rapidly with levels not detectable by 72 hr. There were some variations in DMG-PEG levels between animals and lung regions sampled. For example, in the high dose (group 3) samples at 6 hr, values ranged from 1830 to 19,150 ng/g.

To examine expression of DNAI1-HA protein in specific airway epithelial cell types, a multiplex immunofluorescence panel consisting of airway cell-type markers and an anti-HA antibody was used. From each animal, eight 5 mm tissue samples from different left lung regions capturing bronchi, large and small conducting airways, and alveoli were collected. Two 5 mm tissue samples from trachea and two 5 mm tissue samples from nasopharynx containing respiratory epithelium were also collected.

Four lung samples for each 6 hr vehicle control (group 1), low dose (group 2), and high dose (group 3) were analyzed in the multiplex immunofluorescence assay. The samples analyzed were taken from the left caudal lobe and were numbered from section 1, most cranially—closest to the attachment of the trachea, to number 8 most caudally—most distal from the trachea. For this analysis, sections 2, 4, 6, and 8 were used to have representative sections across the caudal lobe.

A summary of the DNAI1-HA cell type expression seen in the lung samples analyzed is shown in FIG. 100. The % DNAI1-HA+ population for each cell type was calculated by combining the cell counts from all four examined lung sections per animal. The total number of cells counted per animal ranged from 225,419 to 319,654. From the total of all cells counted, the assay background, as determined by the vehicle control group, was 0.12±0.14% HA+ cells. The low dose group had a total of 0.10±0.11% HA+ cells and the high dose group had a total of 2.28±2.48% HA+ cells.

For the total epithelial cell (EpCAM+) population, the DNAI1-HA+ assay background was 0.50±0.56% (vehicle group). In the low dose group, 0.27±0.26% of epithelial cells was HA+. In the high dose group, 8.00±8.58% of epithelial cells were DNAI1-HA+. In the club cell (SCGB1A1/Uteroglobin+) population, the HA+ assay background was 1.81±1.67% as shown by the vehicle group. In the low dose group 1.26±1.47% of club cells were DNAI1-HA+, while in the high dose group 19.75±19.06% of the club cells were DNAI1-HA+. For the goblet cell (MUCSB+) population, the vehicle control group had 0.10±1.15% HA+ cells, reflecting the assay background. In the low dose group, 0.79±0.83% of the goblet cells were HA+, while in the high dose group, 8.25±11.02% of the cells were DNAI1-HA+. Looking at the basal cell (Cytokeratin 5+) population, the assay background was 0.88±1.05% (vehicle control group). The low dose group had 0.90±1.05% HA+ basal cells and the high dose group had a total of 13.82±17.15% DNAI1-HA+ basal cells. In the ciliated cell (Acetylated tubulin+) population, 0.83±0.92% of the vehicle group ciliated cells were HA+, while in the low dose group 0.49±0.62% of the ciliated cells were HA+. In the high dose group, 3.73±3.55% of the ciliated cells were DNAI1-HA+. For the alveolar type II (ATII) cell (Pro-SP-C+) population, 1.61±1.90% of the ATII cells were scored HA+. In the low dose group, 1.61±2.12% were scored HA+ and in the high dose group 21.00±23.19% of the ATII cells were DNAI1-HA+. Overall, the highest levels of DNAI1-HA expression were seen in samples from the high dose group. For the low dose group, the % HA+ cell populations counted were not significantly different than those seen in the vehicle control group.

To assess airway epithelial cell-specific expression of DNAI1-HA protein in the trachea, two samples were collected from each animal, one from the proximal region and the other from the carina region of the trachea. For the multiplex immunofluorescence analysis, samples taken at 6 hr postadministration were analyzed. For the vehicle control (group 1) and low dose (group 2) groups, one carina trachea sample was analyzed per animal. For the high dose group (group 3), both trachea samples were analyzed.

A summary of the DNAI1-HA cell specific expression detected in the trachea samples examined is shown in FIG. 101. The % DNAI1-HA+ populations for each cell type were calculated for each trachea section examined. The total number of cells counted per section ranged from 5,604 to 25,436. Looking at all cells counted, the assay background, as determined by the vehicle control group, was 0.34±0.31% HA+ cells. In the low dose group, 0.48±0.11% of all cells were HA+, while in the high dose group 1.43±1.55% of all cells were HA+. For the epithelial cell (EpCAM+) population, the DNAI1-HA+ assay background was 0.71±0.64% (vehicle group). In the low dose group, 0.73±0.22% of epithelial cells were HA+. In the high dose group, 3.12±3.27% of epithelial cells were DNAI1-HA+. In the club cell (SCGB1A1/Uteroglobin+) population, the HA+ assay background was 1.23±1.45% as shown by the vehicle group. In the low dose group 0.62±0.87% of club cells were DNAI1-HA+, while in the high dose group 5.84±8.34% of the club cells were DNAI1-HA+.

For the goblet cell (MUCSB+) population, the vehicle control group had 1.40±1.54% HA+ cells, reflecting the assay background. In the low dose group, 0.76±0.59% of the goblet cells were HA+, while in the high dose group 3.73±4.71% of the cells were DNAI1-HA+. In the basal cell (Cytokeratin 5+) population, the assay background was 0.23±0.01% (vehicle control group). The low dose group had 0.50±0.05% HA+ basal cells and the high dose group had a total of 1.46±1.62% DNAI1-HA+ basal cells. Looking at the ciliated cell (Acetylated tubulin+) population, 0.36±0.13% of the vehicle group ciliated cells were HA+, while in the low dose group 0.22±0.09% of the ciliated cells were HA+. In the high dose group, 0.77±0.79% of the ciliated cells were DNAI1-HA+.

Next, the airway epithelial cell-specific expression of DNAI1-HA protein in samples from the nasopharynx or oropharynx was assessed using the multiplex immunofluorescence assay. Two nasopharynx or oropharynx samples were collected from each animal. For the multiplex immunofluorescence analysis, samples taken at 6 hr post-administration were analyzed. For the vehicle control (group 1)

and low dose (group 2) groups, one sample was analyzed per animal. For the high dose group (group 3), both samples were analyzed.

A summary of the DNAI1-HA cell specific expression detected in the naso/oropharynx samples examined is shown in FIG. 102. The % DNAI1-HA+ populations for each cell type were calculated for each section imaged. The total number of cells counted per section ranged from 58,993 to 145,142. For the total cell population, the assay background, as determined by the vehicle control group, was 0.09±0.04% HA+ cells. In the low dose group, 0.51±0.50% of all cells were HA+, while in the high dose group 0.25±0.25% of all cells were HA+. For the epithelial cell (EpCAM+) population, the DNAI1-HA+ assay background was 0.07±0.03% (vehicle group). In the low dose group, 0.52±0.47% of epithelial cells were HA+. In the high dose group, 0.37±0.38% of epithelial cells were DNAI1-HA+. In the club cell (SCGB1A1/Uteroglobin+) population, the HA+ assay background was 0.50±0.15% as shown by the vehicle group. In the low dose group 2.23±3.15% of club cells were DNAI1-HA+, while in the high dose group 0.83±0.67% of the club cells were DNAI1-HA+. For the goblet cell (MUCSB+) population, the vehicle control group had 0.04±0.03% HA+ cells, reflecting the assay background. In the low dose group, 0.18±0.11% of the goblet cells were HA+, while in the high dose group 0.13±0.12% of the cells were DNAI1-HA+. In the basal cell (Cytokeratin 5+) population, the assay background was 0.11±0.04% (vehicle control group). The low dose group had 0.27±0.35% HA+ basal cells and the high dose group had a total of 0.24±0.33% DNAI1-HA+ basal cells. For the ciliated cell (Acetylated tubulin+) population, no HA+ cells were counted in the vehicle group, while in the low dose group 0.13±0.18% of the ciliated cells were HA+. In the high dose group, 1.21±1.69% of the ciliated cells were DNAI1-HA+.

Lung samples from Composition A-DNAI1-HA treated animals were examined for expression of DNAI1-HA protein using both western blot and ELISA assays. Lung samples were taken in duplicate from three different regions of the right lung: Caudal, cranial, and middle lobes. Since previous studies have shown that DNAI1-HA expression peaks at 6 hr postadministration, western blot samples from the high dose (group 3) animals taken at 6 h post-exposure were analyzed (FIGS. 103A-103B). As shown in FIG. 103A, using an anti-HA antibody we were unable to clearly detect a band of the correct size for the DNAI1-HA protein in any of the lung samples. In the same samples, expression of the endogenous monkey DNAI1 protein was also measured (FIGS. 103A-103B). In nine of the samples, a band of the correct size (79.2 kDa) was observed, however, several of them the amount full-length DNAI1 protein present is lower than predicted based on previous analyses of similar samples. In two samples (3001 caudal, 3502 caudal), the 80 kDa band was not detected. In addition, lower molecular weight bands were also detected by the anti-DNAI1 antibody, which could be degradation products of the full-length monkey DNAI1 protein.

These results demonstrate that aerosol delivery to the lung in the NHP model produces high levels of DNAI1-HA mRNA in the lung and low exposure in other tissues; high levels of non-endogenous LNP component lipids were seen in the lung with rapid clearance and low exposure to other tissues, indicating significant cell/tissue tropism and specificity and expression of DNAI1-HA protein in the relevant PCD target cells.

Example 14: Single Dose Liquid Inhalation Toxicology Study Followed by a 14 Day Recovery Period in Sprague-Dawley Rats The experiments were performed to study toxicology of single-dose liquid inhalation followed by a 14 day recovery period of Composition A in Sprague-Dawley rats. The experimental design is detailed in Table 27.

TABLE 27

The experimental design of Example 14

| Group Number | Group Designation | Achieved Inhaled Dose Level of Composition A-DNAI1 (mg/kg) | Main Animals M | Main Animals F | Recovery Animals M | Recovery Animals F | Toxicokinetic Animals M | Toxicokinetic Animals F |
|---|---|---|---|---|---|---|---|---|
| 1 | Air Control | 0 | 10 | 10 | 10 | 10 | 3 | 3 |
| 2 | Control/ Vehicle# | 0 | 10 | 10 | 10 | 10 | 9 | 9 |
| 3 | Low | 0.39 | 10 | 10 | 10 | 10 | 9 | 9 |
| 4 | Mid | 0.80 | 10 | 10 | 10 | 10 | 9 | 9 |
| 5 | High | 1.33 | 10 | 10 | 10 | 10 | 9 | 9 |

Control/Vehicle animals were administered Composition A-DNAI1-Placebo (LNP formulation with no mRNA)
M = males;
F = females Using quantitative RT-PCR, the levels of hDNAI1 mRNA were measured in blood, lung, liver, and spleen tissue following administration of Composition A-DNAI1. Blood samples were collected from 3 male and 3 female animals per group at 0.5 hr, 1 hr, 6 hr, 24 hr, 48 hr, 72 hr, 168 hr, 240 hr, and 336 hr post-administration. Lung, liver, and spleen tissue was collected from 3 male and 3 female animals per group at 24 hr and 336 hr post-administration. Two lung samples, two liver samples, and 1 spleen sample was collected from each animal. For the air control group, blood samples were collected at 1 and 24 hrs and tissues samples only at 24 hrs post-administration.

Levels of hDNAI1 mRNA measured in lung samples at 24 hr and 336 hr post-treatment are shown in FIG. 104. At 24 hr, levels in group 3 (0.39 mg/kg) samples ranged from $2.2\times10^6$ to $2.4\times10^7$ copies/μg total RNA. In group 4 (0.8 mg/kg) samples, levels ranged from $3.6\times10^6$ to $8.3\times10^7$ copies/μg total RNA. For group 5 (1.33 mg/kg) samples, hDNAI1 mRNA levels were between $7.3\times10^6$ to $4.1\times10^8$ copies/μg total RNA. Clearance of the hDNAI1 mRNA was observed at 336 hr with the exception of three samples, one in each treatment group, remaining above the assay LOQ (250 copies/µg total RNA) and representing between 0.001% to 0.04% of 24 hr lung levels. mRNA was not detected in the air or placebo (empty LNP) control groups.

Levels of hDNAI1 mRNA measured in liver samples at 24 hr and 336 hr post-dose administration are shown in FIG. 105. All samples from the control groups, group 1 air control and group 2 placebo (empty LNP) were below the assay LOQ at both time points. For group 3 (0.39 mg/kg) liver samples, 3 of the 12 samples had levels above the assay LOQ, ranging from 530 to 2978 copies/µg total RNA which were 0.01% to 0.02% of the 24 hr lung signal for this group. For group 4 (0.8 mg/kg) liver samples, 7 of the 12 samples had values ranging from 795 to 18,743 copies/µg total RNA, representing 0.02% of the 24 hr lung signal for this group. For group 5 (1.33 mg/kg) liver samples, 8 out 12 were above the assay LOQ with values ranging from 1,255 t 13,790 copies/µg total RNA, representing 0.02% to 0.003% of the 24 hr lung signal for this group, with the exception of one outlier sample (5523S) with high value of $7.2 \times 10^7$ copies/µg total RNA. At 336 hr (14 days), all liver samples tested were below the assay LOQ.

Levels of hDNAI1 mRNA in spleen samples at 24 hr and 336 hr post-treatment are shown in FIG. 106. At both timepoints, all samples from groups 1 (air control) and 2 (placebo/empty LNP) were below the assay LOQ. At 24 hr, one out of six samples from group 3 (0.39 mg/kg) had detectable mRNA with a value of 847 copies/µg total RNA, which was 0.004% of the 24 hr lung level. Levels in five out of six group 4 (0.8 mg/kg) samples ranged from 1,086 to 65,412 copies/µg total RNA, representing 0.03% to 0.08% of the 24 hr lung signal. For group 5 (1.33 mg/kg), four out of six samples had mRNA levels ranging from 913 to 6197 copies/µg total RNA, which was between 0.01% to 0.002% of 24 hr lung levels. At 336 hr, all spleen samples tested were below the assay LOQ.

Levels of hDNAI1 mRNA measured in whole blood are shown in FIG. 107. hDNAI1 mRNA was detected across all dose groups, including similar levels in some animals in the negative control groups (both the air and placebo (empty LNP) groups), likely due to cross-contamination during sample handing/preparation. As such, data on systemic blood exposure of hDNAI1 mRNA are not considered interpretable.

In conclusion, following a single inhalation administration of Composition-DNAI1 in rats, high levels of DNAI1 mRNA are delivered to the lung with minimal systemic exposure in blood, liver, spleen.

Example 15: In Vitro Pharmacology of Composition A

The experiments were performed to demonstrate that DNAI1 mRNA delivered as nebulized Composition A-DNAI1 can be effectively translated in hBE and can restore ciliary function in otherwise non-motile hBE (in an engineered in vitro model of PCD).

Although a DNAI1 knock-out mouse model has been described in the literature (DnaicI KO), this model does not develop the lung phenotype observed in PCD patients that underlies much of the disease-associated morbidity. Therefore, to evaluate the therapeutic potential of Composition A, a human in vitro translational model was developed for PCD patients with pathogenic biallelic mutations in DNAI1 using small hairpin RNA (shRNA) to knockdown DNAI1 in primary human airway (bronchial) epithelial cell cultures (DNAI1-KD hBE). hBEs are considered the most appropriate model available for assessing the therapeutic approach given that these primary human airway cultures reproducibly recapitulate several key features of the respiratory epithelium, including relevant cell types (basal, ciliated, and secretory cells) and cellular characteristics (tight gap junctions, synchronized ciliary activity, mucus secretion). In addition, hBEs cultured at the air-liquid interface have been used for the successful development of new therapies for Cystic Fibrosis.

Primary WT-hBEs used to generate the PCD model had normal ciliated surfaces and representation of all relevant cell types (shown in FIG. 108), as well as ciliated cells with cilia that beat at frequencies consistent with reported literature (7-16 Hz).

To knockdown the expression of DNAI1 in primary WT-hBEs, a commercially available lentiviral system was used to express an shRNA targeting DNAI1 in the cell and puromycin N-acetyltransferase for puromycin resistance, introduced by the shRNA containing plasmid, enabled selection of transduced cells. Importantly, DNAI1-KD hBEs recapitulated the biochemical and functional defects (e.g., loss of ciliary beating) seen in the airways of PCD patients with pathogenic mutations in DNAI1 (FIG. 109; FIG. 110). The ciliated cell number was comparable between DNAI1-KD and WT-hBEs (FIG. 110), but DNAI1-KD hBE cultures lacked or showed reduced levels of DNAI1 protein (FIG. 109), DNAI1 staining in the ciliary axoneme (FIG. 110), and ciliary activity (FIG. 111). Other components of the outer dynein arm such as DNAI2 were also reduced (FIG. 109), consistent with literature descriptions of PCD defects and known interactions between DNAI1 and DNAI2 that together form part of the intermediate dynein complex in the cytoplasm.

Using the DNAI1 KD-hBE model system, we demonstrated that hemagglutinin (HA)-tagged human DNAI (DNAI1-HA) mRNA encapsulated in the Composition A SORT LNP formulation (with identical LNP constituents to Composition A) and delivered via nebulization led to effective translation of DNAI1-HA protein in a dose-dependent manner as confirmed by western blot (FIG. 112) and ELISA. Immunofluorescence of DNAI-HA further demonstrated that newly translated DNAI1-HA protein was detected in ciliated cells and incorporated in a dose-dependent manner into the ciliary axoneme (FIG. 113 and FIG. 114) based on co-staining for acetylated α-tubulin. The number of ciliated cells that stained positive for axonemal incorporation also increased as the dose increased. Incorporated DNAI1-HA protein was detected throughout the length of the cilia within 24 hours of treatment, remaining detectable for up to 24 days, the longest timepoint assessed (FIG. 115).

These data suggest that LNP delivered DNAI1 mRNA can be translated into protein, which can integrate into the human ciliary axoneme and likely remains functional over an extended duration. The number of ciliated cells that stained positive for axonemal incorporation also increased as the dose increased. Thus, increasing the dose and frequency of administration will likely increase the amount of active ciliated surface area in PCD patients.

Importantly, data from WT hBEs indicate that when DNAI1 protein is not incorporated into the ciliary axoneme (including DNAI1 protein expressed in non-ciliated cell types), most of the detectable protein is degraded within 48 h post-treatment (data in FIG. 116).

Ciliary activity in hBEs was recorded and analyzed by Sisson-Ammons Video Analysis (SAVA) software (Ammons Engineering) to yield a ciliary % active surface area score for approximately 700 individual, non-overlapping field of views (FoVs). In DNAI1-KD hBEs, ciliary activity is markedly reduced compared to wild-type. An increase in active ciliated surface area was observed within a week following two administrations by nebulization of Composition A-DNAI1 and continued to increase over time with repeated administrations (2×/week) compared to KD hBE cultures treated with Composition A-TdTomato (FIG. 117). Over time, both control and Composition A-DNAI1 treated cultures showed an increase in background ciliary activity. The increase in background activity was likely a result of the waning effect of the shRNA knockdown over time. The average ciliary beat frequency (CBF) observed in the treated groups ranged between 5-10 Hz and was consistent with the reported normal range in these cells (5-15 Hz), suggesting that translation of DNAI1 protein resulted in restoration of normal ciliary activity.

Example 16: Efficacious Human Dose Prediction of Composition A

The experiments were performed to investigate the deposition of inhaled Composition A in the different regions of the lung and to facilitate the translation between efficacious in vitro exposures in a pharmacologically relevant model of PCD.

The multiple-path particle dosimetry (MPPD, version 3.04) software was employed to simulate inhaled aerosol deposition patterns in human and NHP lungs using the symmetric Yeh/Schum, Weibel, PNNL (Pacific Northwest National Laboratory), and Rhesus airway morphometry models, respectively. Results of MPPD modeling were then compared with experimental results described in in vitro pharmacology studies (Example 15) and an in vivo biodistribution study (Example 13) to estimate doses of Composition A likely to lead to efficacious exposures in humans. Specifically, modeling was performed based on aerosol delivery via either an eFlow 40 HO V device manufactured by PARI (eFlow Nebulizer, intended for clinical use) or an Aerogen Solo device (used in both NHP in vivo and in vitro studies), accounting for characteristic aerodynamic particle profile distribution (APSD) and delivered dose (DD). Comparability of aerosol characteristics generated using the eFlow Nebulizer and Aerogen Solo devices was also established to support this analysis.

Results obtained using the symmetric Yeh-Schum, Weibel and PNNL lung models (Yeh and Schum, 1980) are summarized in FIG. 118. The comparison of simulated deposition fractions (FIG. 118) showed that between 65 (Yeh/Schum) and 73 (PNNL) % of total inhaled Composition A-containing droplets were deposited in the head, tracheobronchial (TB) and pulmonary (P) region combined, while the remaining portion was exhaled. All MPPD model outputs also showed that aerosols generated by the vibrating mesh eFlow Nebulizer System 40 HO V with mass median aerodynamic diameter (MMAD) of 4.93 μm were more likely to deposit in the head and TB regions compared to the P region (FIG. 118). In the primary targeted TB region, model-dependent calculations revealed that about 20 (Yeh/Schum) to 30 (PNNL) % of droplets got deposited. FIG. 119 presents the airway generational deposited fraction of aerosol droplets which clearly distinguishes the PNNL model from both Yeh/Schum and Weibel models based on a characteristic, elevated region surrounding generations 6 and 7. FIG. 120 details airway anatomy and identifies the primary TB target region spanning generations 0-16 of the conducting airways. FIG. 121 illustrates that calculated exposures per surface area were uniformly elevated across all models in the larger conducting airways (generations 0-8) compared to the bronchiolar transition zone (generations 9-16). Employing the PNNL model, the predicted human exposures of Composition A in the trachea, bronchi and bronchioles (generations 0-8) exceeded 1.9 μg/cm$^2$ (shown as top dashed line) with nebulizer loads of 5 mg, which was sufficient to rescue ciliary activity in presently described in vitro PCD model. Similarly, using the Weibel model after nebulizing a 5 mg dose, exposures in the larger conducting airways spanning generations 0-8 exceed the 0.9 μg/cm$^2$ (shown as lower dashed line) needed to enable translation of functional DNAI1 protein and approximate.

Considering predictions based on the Weibel and PNNL models, drug depositions were within the range of exposures needed to enable translation of functional DNAI1 protein (0.9 μg/cm$^2$). When using the PNNL model, doses as low as 5 mg overlapped with exposures sufficient to rescue ciliary function after multiple dose administration in vitro (1.9 μg/cm$^2$ per nebulized administration, see ReCode Report RD100).

The calculated deposition fraction of aerosol particles in different regions of the NHP respiratory tract is shown in FIG. 122.

A representative aerosol droplet size distribution for the high dose group obtained during SD-exposures (ITR 35199 report) showed a MMAD of 2.20 μm with GSD of 2.09. The fraction of particle deposition in the various regions followed the trend: head airway >tracheobronchial region>pulmonary region. While the deposition fraction in the head was the highest, accounting for 50.4% of the total airway deposition, FIG. 122 illustrates that only 6.8% of droplets deposit in the targeted TB region. Such exposures in the target TB region per surface area corresponded to depositions of approximately 1.9 μg/cm$^2$ in trachea, bronchi and bronchioles (generations 0-8) and 0.1 μg/cm$^2$ in the transitional, branching generations 9-15 of facemask wearing NHP.

Predictions of inhaled Composition A deposition fractions in the human lung differed with respect to the varying computational models employed. For example, calculated deposition fractions in the targeted TB region calculated from three symmetric airway morphometry models range from 20.0% (Yeh/Schum) to 24.5% (Weibel) to 30.0% (PNNL). Usage of the less conservative, PNNL model-based estimation would yield a deposition of 2.0 μg/cm$^2$ in trachea, bronchi and bronchioles (generations 0-8) with nebulizer loads as low as 5 mg.

Of note, the lowest dose sufficient to rescue ciliary activity in presently described in vitro PCD model was difficult to establish due to limitations of the in vitro model system (i.e., based on transient viral knockdown of DNAI1) and the nebulization route via Vitrocell (i.e., feasible volume and concentration of Composition A-formulated DNAI1 mRNA for consistency in aerosolization). 1.9 μg/cm$^2$ was the lowest dose tested that could be successfully differentiated from background levels of activity in the DNAI1-KD hBEs. However, in vitro exposures of 0.9 μg/cm$^2$ were shown to be sufficient to detect newly expressed DNAI1-HA protein in the ciliary axoneme.

These results indicate that the human lung exposures following clinical doses ranging from 5 to 8 mg of Composition A were within the range of doses sufficient to enable translation of functional DNAI1 protein (Weibel and PNNL calculations) and to restore ciliary activity in vitro (PNNL-based prediction). Furthermore, predicted human exposures overlapped with inhaled doses sufficient to drive DNAI1 protein production in target cells of the lungs following lung exposure in NHPs in vivo.

Example 17: Six Component Lipid Nanoparticles

This example describes making and testing lipid nanoaparticle having six lipid component.

A five-component lipid nanoparticle (LNP) described herein as Composition X (14.8% 4A3-SC7, 15.6% DODAP, 22.2% DOPE, 44.4% cholesterol, 3.3% DMG-PEG) having an ionizable cationic lipid had been shown to aerosolize well and deliver payloads, such as polynucleotides, to lung cells when administered by inhalation. Compositions having six-components were made. In these compositions, a permanently cationic lipid was added while decreasing the molar percent (mol %) of the cholesterol. By doing so, the percentages of dendrimeric lipid, ionizable lipid, phospholipid and PEG-lipid were maintained, while the charge of the LNP increased.

Various six-component lipid nanoparticles were made as variations of Composition X, in which the ionizable cationic lipid is DODAP. The mol % of ionizable cationic lipid was maintained as constant at 15%, while permanently cationic lipid (either 14:0 TAP or 14:0 EPC) was tested at 2% to 15%. Dendrimeric, phospholipid, and PEG-lipid content was maintained at the same mol %; the mol % of cholesterol was decreased from 43% to 30%.

Two sets of lipid:mRNA (wt/wt) were tested (36:1 or 30:1). Composition X in 15 mM citrate (pH6.5) with 10% sucrose solution was used as control. Each CFTR mRNA-containing compositions (1 mg/mL, 500μL) were nebulized in CF-patient derived hBE cells (G542X/F508del) by Aerogen® Solo nebulized and functional chloride flux was measured (FIG. 124). Several of the six-component lipid nanoparticle showed increased CFTR function compared to Composition X. Encapsulation efficiencies ranges from 90% to 99%.

Encapsulation efficiency (EE %) was measured before and after nebulization using Pari® 35 HOX configuration, resulting significantly improved encapsulation efficiency with increased in cationic component (14:0 TAP or 14:0 EPC) and decreased cholesterol content (FIG. 125). Compositions tested and results are summarized in Table 28 and Table 29.

TABLE 28

Compositions tested in the examples

| Composition | DMG-PEG | DODAP | Cholesterol | 14:0 TAP | 14:0 EPC | DOPE | 4A3-SC7 | Lipid/mRNA |
|---|---|---|---|---|---|---|---|---|
| 2J1 | 3 | 15 | 43 | 2 | X | | | 36 |
| 2J2 | 3 | 15 | 40 | 5 | X | | | 36 |
| 2J3 | 3 | 15 | 37.5 | 7.5 | X | | | 36 |
| 2J4 | 3 | 15 | 35 | 10 | X | | | 36 |
| 2J5 | 3 | 15 | 30 | 15 | X | | | 36 |
| 2J6 | 3 | 15 | 43 | X | 2 | | | 36 |
| 2J7 | 3 | 15 | 40 | X | 5 | | | 36 |
| 2J8 | 3 | 15 | 37.5 | X | 7.5 | | | 36 |
| 2J9 | 3 | 15 | 35 | X | 10 | | | 36 |
| 2J10 | 3 | 15 | 30 | X | 15 | | | 36 |
| 3A1 | 3 | 15 | 43 | 2 | X | | | 30 |
| 3A2 | 3 | 15 | 40 | 5 | X | | | 30 |
| 3A3 | 3 | 15 | 37.5 | 7.5 | X | | | 30 |
| 3A4 | 3 | 15 | 35 | 10 | X | | | 30 |
| 3A5 | 3 | 15 | 30 | 15 | X | | | 30 |
| 3A6 | 3 | 15 | 43 | X | 2 | | | 30 |
| 3A7 | 3 | 15 | 40 | X | 5 | | | 30 |
| 3A8 | 3 | 15 | 37.5 | X | 7.5 | | | 30 |
| 3A9 | 3 | 15 | 35 | X | 10 | | | 30 |
| 3A10 | 3 | 15 | 30 | X | 15 | | | 30 |
| 3B1 | 3 | 15 | 32.5 | 12.5 | X | | | 36 |
| 3B2 | 3 | 15 | 32.5 | 12.5 | X | | | 30 |
| 3B3 | 3 | 15 | 32.5 | X | 12.5 | | | 36 |
| 3B4 | 3 | 15 | 32.5 | X | 12.5 | | | 30 |
| 3B5 | 2.5 | 15 | 30.5 | 15 | X | | | 36 |
| 3B6 | 2 | 15 | 31 | 15 | X | | | 36 |
| 3B7 | 1.5 | 15 | 31.5 | 15 | X | | | 36 |
| 3B8 | 2.5 | 15 | 30.5 | 15 | X | | | 30 |
| 3B9 | 2 | 15 | 31 | 15 | X | | | 30 |
| 3B10 | 1.5 | 15 | 31.5 | 15 | X | | | 30 |
| 3C1 | 2.5 | 15 | 33 | 12.5 | X | | | 36 |
| 3C2 | 2 | 15 | 33.5 | 12.5 | X | | | 36 |
| 3C3 | 1.5 | 15 | 34 | 12.5 | X | | | 36 |
| 3C4 | 2.5 | 15 | 35.5 | 10 | X | | | 36 |
| 3C5 | 2 | 15 | 36 | 10 | X | | | 36 |
| 3C6 | 1.5 | 15 | 36.5 | 10 | X | | | 36 |
| 3C7 | 3 | 17.5 | 35 | 7.5 | X | | | 36 |
| 3C8 | 3 | 12.5 | 40 | 7.5 | X | | | 36 |
| 3C9 | 3 | 17.5 | 30 | 12.5 | X | | | 36 |
| 3C10 | 3 | 12.5 | 35 | 12.5 | X | | | 36 |
| 3D1 | 3 | 17.5 | 35 | X | 7.5 | | | 36 |
| 3D2 | 3 | 12.5 | 40 | X | 7.5 | | | 36 |
| 3D3 | 3 | 17.5 | 30 | X | 12.5 | | | 36 |
| 3D4 | 3 | 12.5 | 35 | X | 12.5 | | | 36 |
| 3D5 | 3.5 | 15 | 32 | 12.5 | X | | | 36 |
| 3B1 | 3 | 15 | 32.5 | 12.5 | X | | | 36 |
| 3D6 | 3.5 | 15 | 32 | 12.5 | X | | | 33 |
| 3D7 | 3 | 15 | 32.5 | 12.5 | X | | | 33 |

TABLE 28-continued Compositions tested in the examples

| Composition | DMG-PEG | DODAP | Cholesterol | 14:0 TAP | 14:0 EPC | DOPE | 4A3-SC7 | Lipid/mRNA |
|---|---|---|---|---|---|---|---|---|
| 3D8 | 3.5 | 15 | 32 | 12.5 | X | | | 30 |
| 3B2 | 3 | 15 | 32.5 | 12.5 | X | | | 30 |
| 3D9 | 3 | 15 | 30 | X | 15 | | | 40 |
| 3D10 | 2.5 | 15 | 30.5 | X | 15 | | | 40 |
| 2J10 | 3 | 15 | 30 | X | 15 | | | 36 |
| 3E1 | 2.5 | 15 | 30.5 | X | 15 | | | 36 |
| 3E2 | 3 | 15 | 30 | X | 15 | | | 33 |
| 3E3 | 2.5 | 15 | 30.5 | X | 15 | | | 33 |

TABLE 29

Summary of LNP composition tested in the example

| Experiment | Composition | Particle Size (Zetasizer) PS (nm) | PDI | Ribo green % EE | Post Freeze Thaw Nebulization (PARI 35 HOX) % EE | Output rate (ul/min) | In vitro Functionality Test (uA/cm2min) Heterozygous | Homozygous |
|---|---|---|---|---|---|---|---|---|
| 14:0 TAP Mol % Titration | 2J1 | 92 | 0.144 | 94 | NA | NA | 9 | |
| | 2J2 | 98 | 0.157 | 91 | 26 | 546 | 17 | |
| | 2J3 | 91 | 0.153 | 92 | NA | NA | 15 | 7 |
| | 2J4 | 84 | 0.172 | 94 | 59 | 546 | 15/12.5 | |
| | 3B1 | 64 | 0.135 | 96 | 80 | 536 | | 23.7/13.5 (TFF)/ 12.5 |
| | 2J5 | 86 | 0.181 | 98 | 91 | 537 | 10.3/13.5 | |
| | 3A1 | 91 | 0.145 | 92 | NA | NA | | |
| | 3A2 | 98 | 0.107 | 82 | NA | | | |
| | 3A3 | 88 | 0.108 | 87 | NA | | | |
| | 3A4 | 74 | 0.130 | 91 | NA | | 12.7/16.1 | |
| | 3B2 | 66 | 0.138 | 94 | 73 | 600 | | 17.9 |
| | 3A5 | 70 | 0.165 | 97 | NA | NA | 13.9/14.5 | NA |
| 14:0 EPC Mol % Titration | 2J6 | 83 | 0.173 | 94 | 18.5 | 492 | | |
| | 2J7 | 85 | 0.154 | 95 | 24.5 | 504 | 15 | |
| | 2J8 | 86 | 0.177 | 95 | 12.5 | 548 | 12 | 8 |
| | 2J9 | 84 | 0.167 | 95 | 34.5 | 510 | 14.5/12.0 | |
| | 3B3 | 72 | 0.116 | 93 | 65.0 | 606 | | 31.3/14.3 (TFF)/ 9.3/12.5 (TT) |
| | 2J10 | 79 | 0.159 | 94 | 74.0 | 522 | | 29.9 |
| | 3A6 | 99 | 0.176 | 93 | NA | NA | | NA |
| | 3A7 | 101 | 0.176 | 92 | NA | | | |
| | 3A8 | 95 | 0.17 | 92 | NA | | | |
| | 3A9 | 89 | 0.186 | 92 | NA | | 15.2/8.1 | |
| | 3B4 | 75 | 0.122 | 93 | 60 | 659 | | 18.2 |
| | 3A10 | 83 | 0.172 | 92 | NA | NA | 12.7/4.3 | |
| PEG Titration (14:0 TAP) | 3B5 | 67 | 0.14 | 99 | 88 | 444 | | 19.3 |
| | 3B6 | 74 | 0.134 | 99 | 89 | 435 | | 23.2 |
| | 3B7 | 87 | 0.145 | 99 | 89 | 251 (clogged) | | |
| | 3B8 | 71 | 0.166 | 99 | 86 | 513 | | |
| | 3B9 | 81 | 0.169 | 99 | 86 | 513 | | |
| | 3B10 | 89 | 0.147 | 99 | 88 | 295 (clogged) | | |
| | 3C1 | 69 | 0.145 | 98 | 83 | 444 | | 18.6 |
| | 3C2 | 76 | 0.135 | 98 | 84 | 469 | | 29.1/8.9 |
| | 3C3 | 84 | 0.137 | 98 | 89 | 405 | | 13.6 |
| | 3C4 | 83 | 0.166 | 96 | 68 | 517 | | 15.7 |
| | 3C5 | 86 | 0.163 | 96 | 75 | 50 | | 26.1 |
| | 3C6 | 89 | 0.129 | 97 | 84 | 259 (clogged) | | |

TABLE 29-continued

Summary of LNP composition tested in the example

| | | Particle Size (Zetasizer) | | Ribo green % | Post Freeze Thaw Nebulization (PARI 35 HOX) | | In vitro Functionality Test (uA/cm2min) | |
|---|---|---|---|---|---|---|---|---|
| Experiment | Composition | PS (nm) | PDI | EE | % EE | Output rate (ul/min) | Heterozygous | Homozygous |
| DODAP | 3C7 | 77 | 0.084 | 93 | 29 | 500 | | 7.1 |
| Titration | 3C8 | 82 | 0.097 | 94 | 29 | 522 | | 7.1 |
| (14:0 TAP) | 3C9 | 62 | 0.093 | 97 | 85 | 508 | | 13.1 |
| | 3C10 | 63 | 0.102 | 96 | 79 | 504 | | 13.4 |
| DODAP | 3D1 | 76 | 0.142 | 98 | 19 | 508 | | 8.6 |
| Titration | 3D2 | 79 | 0.135 | 98 | 18 | 504 | | 9.7 |
| (14:0 EPC) | 3D3 | 70 | 0.123 | 98 | 67 | 504 | | 10.0 |
| | 3D4 | 78 | 0.183 | 97 | 66 | 571 | | 12.1 |
| Lipid Ratio | 3D5 | 64 | 0.158 | 98 | 82 | 522 | | 9.2 |
| Evaluation | 3B1 | 66 | 0.110 | 98 | 83 | 517 | | 14/8.7/8.7 |
| (14:0 TAP) | 3D6 | 63 | 0.145 | 98 | 78 | 577 | | 8.2 |
| | 3D7 | 68 | 0.120 | 97 | 80 | 561 | | 14.4/11.5/ 12.3/10.6 |
| | 3D8 | 73 | 0.148 | 96 | 76 | 588 | | 8.2 |
| | 3B2 | 79 | 0.176 | 96 | 76 | 570 | | 13.6 |
| Lipid Ratio | 3D9 | 73 | 0.128 | 97 | 80 | 508 | | 14.7 |
| Evaluation | 3D10 | 71 | 0.094 | 96 | 80 | 536 | | 8.6 |
| (14:0 EPC) | 2J10 | 68 | 0.110 | 97 | 80 | 556 | | 13.1/8.6/8.6/ 10.8 |
| | 3E1 | 74 | 0.119 | 96 | 79 | 600 | | 9.8 |
| | 3E2 | 75 | 0.126 | 95 | 73 | 619 | | 11.1 |
| | 3E3 | 77 | 0.120 | 95 | 74 | 606 | | 6.4 |
| Biodistribution Study | 3B1 | 72.3 | 0.110 | 97 | | | | 12.1/21.0/ 12.7/11.6/ 17.6 |
| | 3B3 | 69.1 | 0.120 | 98 | | | | 9.7/17.6/ 10.2/9.9/9.9 |

Example 18

This example describes dose-response and functional half-life of delivered CFTR mRNA by Composition 3D7 in CF-patient derived hBE cells.

Composition 3D7 comprised 14.84% 4A3-SC7, 22.2% DOPE, 32.5% cholesterol, 3% DMG-PEG, 15% DODAP, and 12.5% 14:0 TAP (Lipid:mRNA ratio 33:1).

F508del/F508del hBEs were dosed with CFTR mRNA-containing Composition 3D7. At 24 h after dosing, a functional chloride flux was measured resulting a dose-dependent functional CFTR activity (FIG. 126A). CFTR protein expression was measured by Western blot analysis showing correlated results of protein expression and its functional activity (FIG. 126B).

To determine functional half-life, F508del/F508del hBEs were dosed with CFTR mRNA-containing Composition 3D7 using Tecan D300 dispenser. A functional chloride flux was measured at 6, 24, 48 or 72 h post-dosing. FIG. 127A shows detection of ≥50% of CFTR function at 48 h post-dosing, while 33% is still observed at 72 h post-dosing. FIG. 127B shows the measurement of transepithelial electrical resistance (TEER) at 6, 24, 48 or 72 h post-dosing. This results are correlated to protein expression analysis in Western blot analysis (FIG. 127C).

Example 19

This example describes nebulized delivery of Composition 3D7 to nose, trachea, and lungs in rats.

Luciferase mRNA-containing Composition 3D7 was formulated in 10 mM citrate buffer (pH 4) and stored in 15 mM Tris with 10% sucrose (pH 7.5). Characterization of Composition 3D7 before and after freeze/thaw cycle is shown in Table 30.

TABLE 30

| Z avg (nm) | PDI | EE (%) |
|---|---|---|
| Storage at 2-8° C. | | |
| 54.28 | 0.168 | 98.70 |
| Freeze-Thaw (storage at −80° C.) | | |
| 55.16 | 0.162 | 97.95 |

For aerosol delivery, DSI tower was setup. Composition 3D7 (1 mg/mL) was nebulized with Aerogen Solo at flow rate 0.123 mL/min (total 13 mL for 105 mins). Two animals positioned in the top (L1), middle (L2), and bottom levels (L3) of the tower. In vivo images showed Composition 3D7 can be delivered via nebulized aerosol to the nose, trachea, and lungs in rats (FIG. 128A). Quantitative results are shown in FIG. 128B.

Example 20

This example describes evaluation of Composition 3D7 efficacy in Cystic Fibrosis transgenic ferrets.

$CFTR^{G551D/G551D}$ ferrets leads to dehydrated mucus, a mucociliary clearance defect, and subsequently chronic *Pseudomonas aeruginosa* lung infections and accompanying lung disease due to loss of CFTR activity. Composition 3D7 was delivered using the MADgiC® Laryngo-Tracheal Mucosal Atomization Device to CF transgenic ferrets. Characterization of Composition 3A before and after atomized into a tube is shown in Table 31.

TABLE 31

| Composition 3A—CFTR mRNA 1 mg/mL | EE (%) | Size (nm) | PDI |
|---|---|---|---|
| Original | 98.76 ± 0.51 | 61.9 ± 0.4 | 0.12 |
| Atomized | 98.69 ± 0.47 | 62.2 ± 0.0 | 0.13 |

Cre mRNA and CFTR mRNA-containing Composition 3D7 were intratracheally delivered via a laryngo-tracheal mucosal atomizer device and Mucociliary clearance (MCC) was observed at 1, 8, 15, and 48 days (FIG. 129A). Increase in MCC was observed in 1 day post dosing, further improvement in MCC in 8 days post treatment (A from baseline 43%). MCC was maintained at 15 and 48 days but slowly declined to 35% and eventually 29%. The rate of change MCC is fastest at 8 days post-dosing and declined afterwards to lowest at 48 days post-dose (FIG. 129B).

Immunohistochemistry results showed proliferative growth of ionocytes in CF. Also colocalization ionocytes with cre mRNA-induced GFP in CF ferrets were observed (FIG. 130A). Further, colocalization of cre-induced GFP with ionocytes and CFTR at apical cap was observed (FIG. 130B). FIG. 130C shows expression of cre-induced GFP in trachea resulting that Composition 3A efficiently delivers its target gene to ciliated cells in CF ferrets.

Example 21: Characterizations of Lipid Nanoparticle Composition Containing Gene-Editing Payload This example describes characterizations of gene-editing payload containing Composition 3D7.

Lipid compositions are mixed on Cross-Tee using 10 mM Na-citrate (pH 4, 30 mL/min total flowrate), formulated with either Cas9:sgRNA (1:1 wt/wt) or Cas9:sgRNA:ssDNA (1:1:1 wt/wt/wt), concentrated to 0.5 mg/mL using filters, and stored in either 15 mM Tris (10% sucrose pH 7.5) or 1× PBS. Characterizations of formulations in each stage are shown in Table 32. Encapsulation efficiency and concentration measurements were obtained using Ribogreen R&D assay protocol.

TABLE 32

| | Post mix | | Post-Filter | | 2-8° C. | | | | F/T | | | |
|---|---|---|---|---|---|---|---|---|---|---|---|---|
| Formulation | Size | PDI | Size | PDI | Size | PDI | EE % | Conc | Size | PDI | EE % | Conc |
| Composition 3D7-Cas9 + sgRNA (1:1) 1X PBS | 51.01 | 0.139 | 61.85 | 0.176 | 60.67 | 50.67 | 98.28 | 0.54 | | | | |
| Composition 3D7-Cas9 + sgRNA (1:1) 15 mM Tris, 10% suc pH 7.5 | | | 61.41 | 0.128 | 61.68 | 0.128 | 97.56 | 0.53 | 59.32 | 0.111 | 96.96 | 0.46 |
| Composition 3D7-Cas9 + sgRNA + DNA (1:1:1) 1X PBS | 57.8 | 0.170 | 60.31 | 0.142 | 64.25 | 0.190 | 97.96 | 0.57 | | | | |
| Composition 3D7 Cas9 + sgRNA + DNA (1:1:1) 15 mM Tris, 10% suc pH 7.5 | | | 58.58 | 0.130 | 63.43 | 0.197 | 97.65 | 0.58 | 61.40 | 0.122 | 96.72 | 0.57 |

Characterization after nebulization of lipid nanoparticles are shown in Table 33 and Table 34.

TABLE 33

| | Post mix | | Post-Filter | | Pre-Nebulization | | | | |
|---|---|---|---|---|---|---|---|---|---|
| Formulation | Size | PDI | Size | PDI | Size | PDI | EE % | Conc | pH |
| Composition 3D7-Cas9 + sgRNA (1:1) 15 mM Tris, 10% suc pH 7.5 | 51.0 | 0.139 | 61.41 | 0.128 | 59.32 | 0.111 | 96.96 | 0.46 | 7.44 |

TABLE 33-continued

|  | Post mix | | Post-Filter | | Pre-Nebulization | | | | |
|---|---|---|---|---|---|---|---|---|---|
| Formulation | Size | PDI | Size | PDI | Size | PDI | EE % | Conc | pH |
| Composition 3D7-Cas9 + sgRNA + DNA (1:1:1) 15 mM Tris, 10% suc pH 7.5 | 57.8 | 0.170 | 58.58 | 0.130 | 61.40 | 0.122 | 96.72 | 0.57 | 7.47 |

TABLE 34

|  | Post-Nebulization-PARI 35 HO | | | | Post-Nebulization-Aerogen Solo | | | |
|---|---|---|---|---|---|---|---|---|
| Formulation | Size | PDI | EE % | Conc | Size | PDI | EE % | Conc |
| Composition 3D7-Cas9 + sgRNA (1:1) 15 mM Tris, 10% suc pH 7.5 | 290.0 | 0.652 | 85.27 | 0.48 | 246.1 | 0.570 | 85.1 | 0.53 |
| Composition 3D7-Cas9 + sgRNA + DNA (1:1:1) 15 mM Tris, 10% suc pH 7.5 | 244.1 | 0.581 | 84.85 | 0.44 | 223.9 | 0.419 | 85.68 | 0.46 |

|  | TOR (µL/min) | MMD (µm) | GSD | FPF < 5 µm (%) | TOR (µL/min) | MMD (µm) | GSD | FPF < 5 µm (%) |
|---|---|---|---|---|---|---|---|---|
| Composition 3D7-Cas9 + sgRNA (1:1) 15 mM Tris, 10% suc pH 7.5 | 732 | 3.88 | 1.62 | 70.81 | 207 | 4.19 | 1.77 | 61.70 |
| Composition 3D7-Cas9 + sgRNA + DNA (1:1:1) 15 mM Tris, 10% suc pH 7.5 | 789 | 4.04 | 1.65 | 66.93 | 195 | 4.28 | 1.77 | 60.73 |

TOR: Total output rate
MMD: Mass median diameter
GSD: Geometric standard deviation
FPF < 5 µm: Fine particle fraction smaller than 5 µm

Example 22: Fragment Analyzer Analysis

This example describes fragment analysis delivered by Composition 3D7.

Samples were nebulized using different heads (PAR % 35 HO or Aerogen Solo) and Cas9 mRNA, sgRNA, and ssDNA was extracted from LNP using isopropanol precipitation (IPA) protocol (all 3 cargo co-isolated) or Macherey-Nagel Nucleospin miRNA columns protocol (Cas9 isolated separately). 50 ng of total transcript was analyzed using Agilent 5200 Fragment Analyzer. The results of nucleotides size and integrity are shown in Table 35, Table 36 and FIGS. 131A-131B.

TABLE 35

| | Composition 3D7-Cas9 + sgRNA (1:1) | | | | | |
|---|---|---|---|---|---|---|
| | Size | Average Size (nt) | Std | Integrity (%) | Average Integrity | Std |
| Cas9 std | 4254 | 4292 | 24 | 67.8 | 67 | 1.9 |
| | 4291 | | | 66.2 | | |
| | 4287 | | | 68.2 | | |

TABLE 35-continued

| | Composition 3D7-Cas9 + sgRNA (1:1) | | | | | |
|---|---|---|---|---|---|---|
| | Size | Average Size (nt) | Std | Integrity (%) | Average Integrity | Std |
| | 4315 | | | 68.5 | | |
| | 4311 | | | 63.9 | | |
| Pre-neb-nucleoSpin | 4190 | 4374 | 27 | 60.7 | 58.3 | 2.3 |
| | 4190 | | | 59.4 | | |
| | 4190 | | | 57.7 | | |
| | 4190 | | | 55.4 | | |
| PARI-NucleoSpin | 4209 | 4349 | 24 | 40.1 | 42.4 | 3.1 |
| | 4235 | | | 40.6 | | |
| | 4209 | | | 46.9 | | |
| | 4183 | | | 41.9 | | |
| SOLO-NucleoSpin | 4232 | 4351 | 36 | 46.4 | 45.5 | 1.6 |
| | 4257 | | | 45.9 | | |
| | 4232 | | | 46.5 | | |
| | 4206 | | | 43.1 | | |

TABLE 36

Composition 3D7-Cas9 + sgRNA + ssDNA (1:1:1)

| | Size | Average Size (nt) | Std | Integrity (%) | Average Integrity | Std |
|---|---|---|---|---|---|---|
| Cas9 std | 4254 | 4292 | 24 | 67.8 | 67 | 1.9 |
| | 4291 | | | 66.2 | | |
| | 4287 | | | 68.2 | | |
| | 4315 | | | 68.5 | | |
| | 4311 | | | 63.9 | | |
| Pre-neb-nucleoSpin | 4209 | 4353 | 16 | 62 | 55.8 | 4.2 |
| | 4235 | | | 53.6 | | |
| | 4209 | | | 52.7 | | |
| | 4183 | | | 54.7 | | |
| PARI-NucleoSpin | 4349 | 4364 | 17 | 31.3 | 31 | 1.2 |
| | 4378 | | | 32.6 | | |
| | 4349 | | | 30.3 | | |
| | 4378 | | | 29.8 | | |
| SOLO-NucleoSpin | 4232 | 4351 | 27 | 42.3 | 40.4 | 1.7 |
| | 4180 | | | 40.3 | | |
| | 4206 | | | 40.8 | | |
| | 4257 | | | 38.1 | | |

Example 23: In Vitro Analysis of Gene Editing Payload

This example describes in vitro efficacy data for 2- and 3-component formulations Composition 3D7 by comparing against 2 and 3 component delivery with cell control formulation.

GFP-expressing HEK293 cells were plated in 24-well plates at 100,000 cells/well. 18 h later, lipid nanoparticle formulations were diluted to the desired concentrations in ThermoFischer's Opti-MEM to a final volume of 50 μl. Transfections were subsequently cared out by layering all 50 μl onto a well of plated cells. 24 h later, 50 μl of supernatant was collected and stored at −80° C. for the LDH analysis. 72 hours after transfection, the cells were harvested and analyzed for green and blue fluorescence using the Sony flow cytometer. The following day the supernatant samples were thawed at 4° C. for 30 minutes and LDH levels were assayed using the Promega CytoTox96 Nonradioactive Cytotoxicity Assay.

Figure 132A:
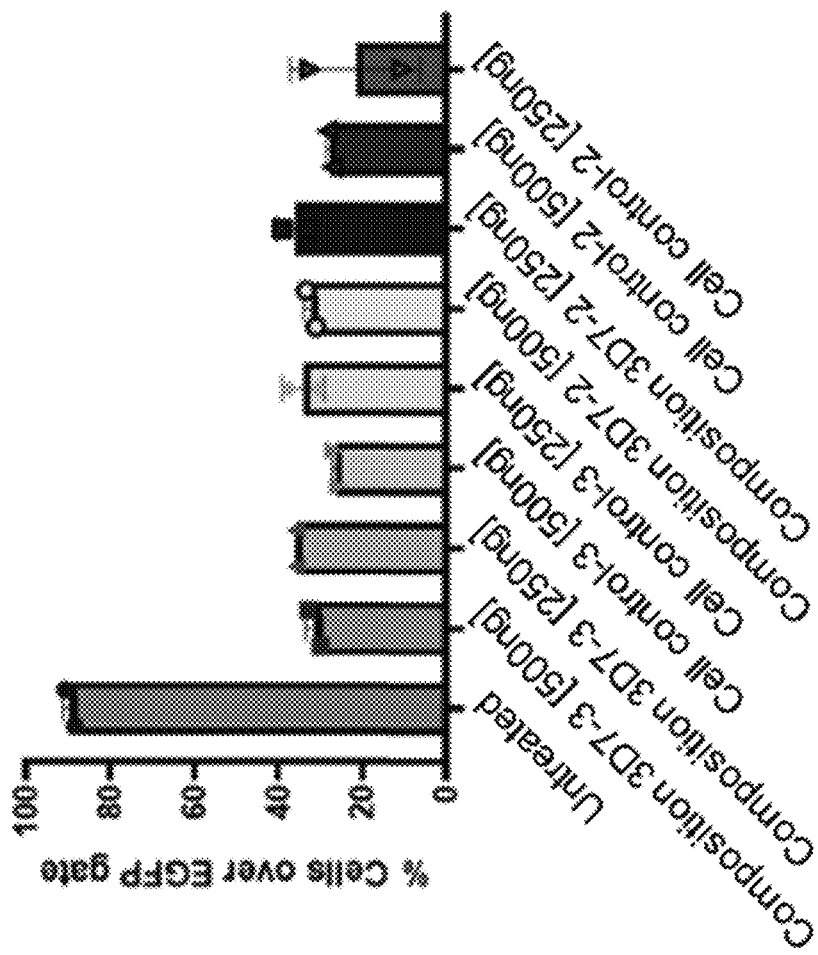
Figure 132B:
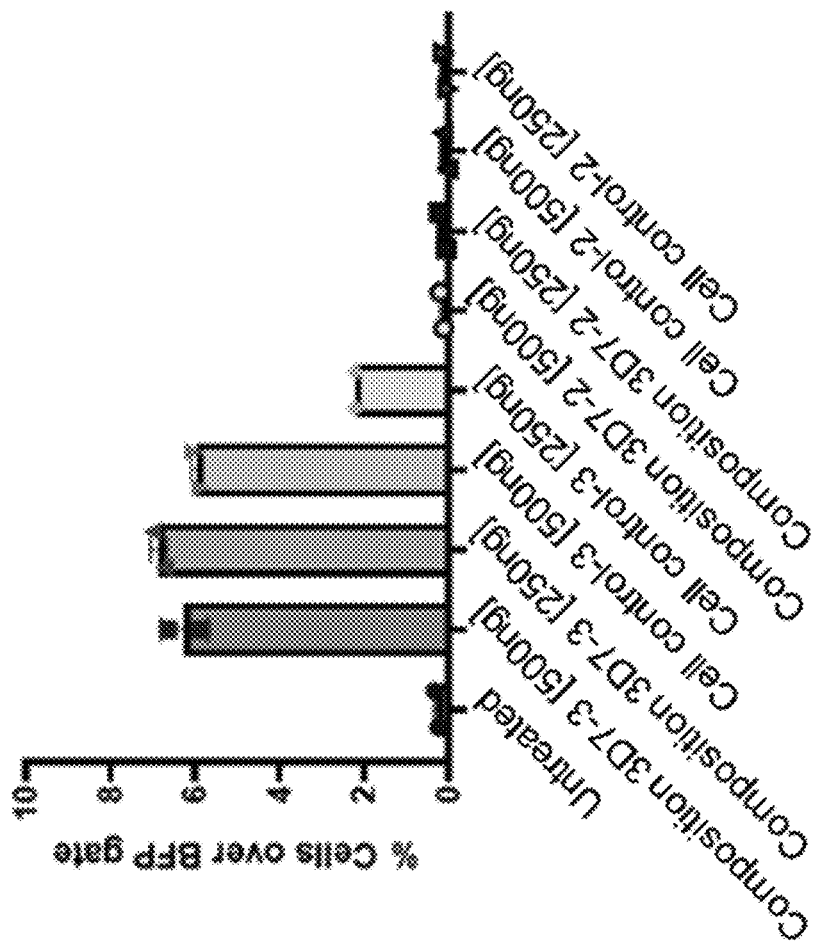
Figure 132C:
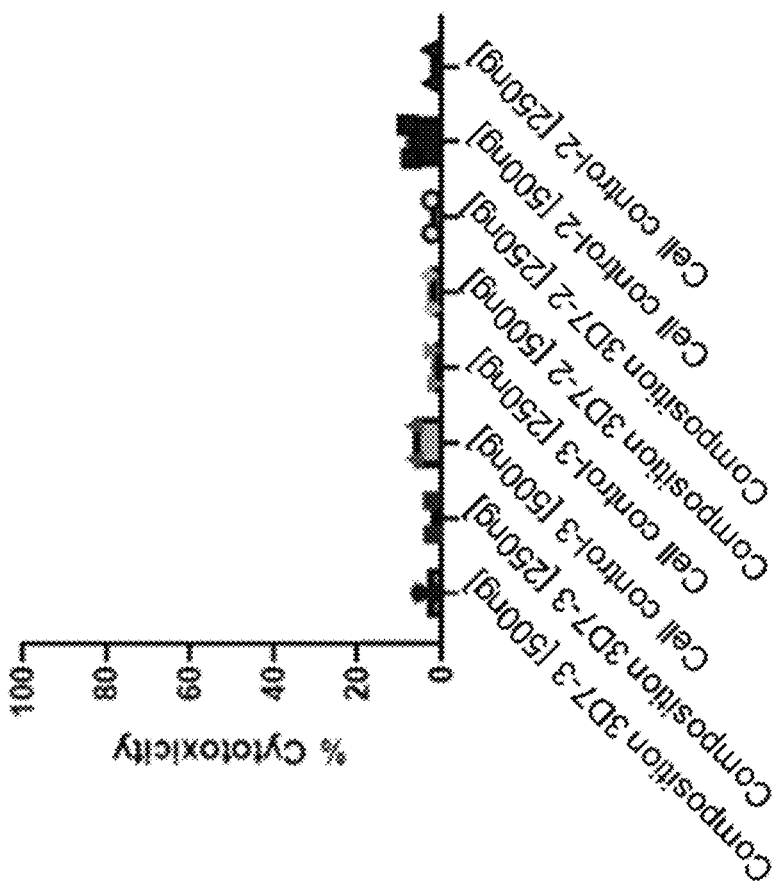

The results showed that both 2- and 3-component systems were able to deliver gene editing material through either Composition 3D7 or cell control formulations resulting in a roughly similar level of EGFP knockdown in all treated cell populations (FIG. 132A). Further, it demonstrates that only 3-component formulations have the capacity to convert EGFP signal to BFP through repair pathway usage of the introduced ssODN. Composition 3D7 demonstrates robust conversion at both concentrations whereas cell control sees a marked drop-off at the lower level (FIG. 132B). LDH assay showed very little toxicity within cell populations transfected by lipid nanoparticle formulations (FIG. 132C).

Example 24: 4 Week Treatment/4 Week Recovery Inhalation Toxicity

This example describes genotoxicity study results by 4 week treatment/4 week recovery inhalation in either Rat and NHP.

Inhaled CFTR mRNA-containing Composition 3D7 was administered via nebulizer using the PARI eFlow® Nebulizer System. The CFTR mRNA is optimized for high efficacy with respect to stability and translational efficiency (5'-cap, 1-methyl-pseudouridine used instead of uridine, polyA-tail) as compared to the wild-type mRNA Bacterial reverse mutation test (Ames) showed Composition 3D7 was not mutagenic when tested on *S. typhimurium* strains TA98, TA100, TA1535, and TA1537 and in the *E. coli* strain WP2 uvrA, with and without metabolic activation. Furthermore, In vitro Micronucleus Test (MNT) showed Composition 3D7-CFTR was considered negative for elastogenic or an eugenic activity in the in vitro micronucleus assay based on the lack of increased micronuclei or hypodiploid frequencies in CHO-K1 cells following 4-hour incubation with and without metabolic activation and 26-hour incubation without metabolic activation.

While the disclosure has been described in connection with proposed specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

What is claimed is:

1. A lipid nanoparticle (LNP) composition, wherein the LNP composition comprises:

(a)

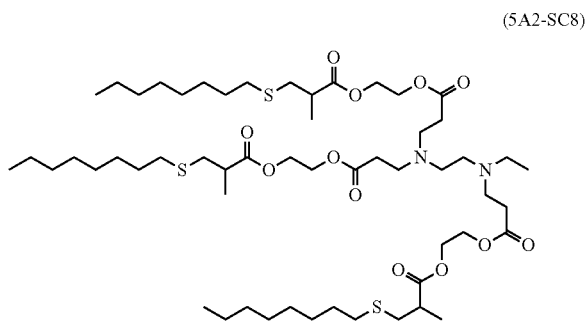
(5A2-SC8)

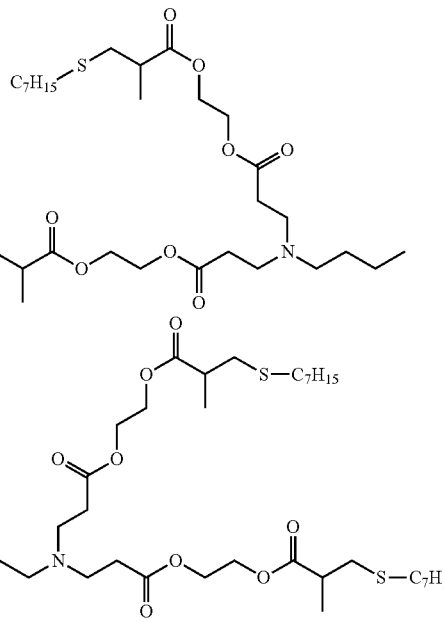
(4A3-SC7)

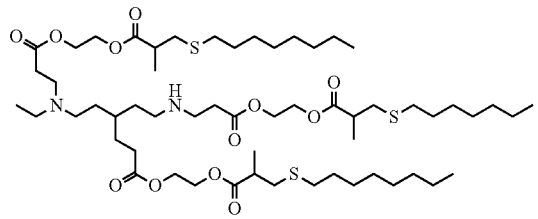
or (b) 1,2-dioleoyl-3-dimethylammonium-propane (DODAP);
(c) 1,2-dimyristoyl-3-trimethylammonium-propane (14:0 TAP) or 1,2-dimyristoyl-sn-glycero-3-ethylphosphocholine (14:0 EPC);
(d) 1,2-dioleoyl-sn-glycero-3-phosphoethanolamine (DOPE) or 1,2-distearoyl-sn-glycero-3-phosphocholine (DSPC);
(e) cholesterol or sitosterol; and
(f) a DMG-PEG.

2. The LNP composition of claim 1, wherein the LNP composition comprises:
   (a) 4A3-SC7 at a molar percentage between about 10% and about 30%;
   (b) DODAP at a molar percentage between about 5% and about 40%;
   (c) 14:0 TAP at a molar percentage between about 5% and about 25%;
   (d) DOPE at a molar percentage between about 10% and about 30%;
   (e) cholesterol at a molar percentage between about 30% and about 50%; and
   (f) a DMG-PEG at a molar percentage between about 0.5% and about 10%.

3. The LNP composition of claim 1, wherein the LNP composition comprises:
   (a) 4A3-SC7 at a molar percentage of about 15%;
   (b) DODAP at a molar percentage of about 15%;
   (c) 14:0 TAP at a molar percentage of about 15%;
   (d) DOPE at a molar percentage of about 22%;
   (e) cholesterol at a molar percentage of about 30%; and
   (f) a DMG-PEG at a molar percentage of about 3%.

4. The LNP composition of claim 1, wherein the LNP composition comprises:
   (a) 4A3-SC7 at a molar percentage of about 15%;
   (b) DODAP at a molar percentage of about 15%;
   (c) 14:0 TAP at a molar percentage of about 12%;
   (d) DOPE at a molar percentage of about 22%;
   (e) cholesterol at a molar percentage of about 32%; and
   (f) a DMG-PEG at a molar percentage of about 3%.

5. The LNP composition of claim 1, wherein the LNP composition is an aerosolized composition.

6. The LNP composition of claim 5, wherein the LNP composition has an encapsulation efficiency of between 50% and 99%, between 60% and 99%, between 70% and 99%, or between 80% and 99%.

7. The LNP composition of claim 1, wherein the LNP composition further comprises an mRNA at a lipid:mRNA ratio less than 40:1.

8. The LNP composition of claim 1, comprising:
   (a) 4A3-SC7 at a molar percentage between 10% and 30%;
   (b) DODAP at a molar percentage of between 12.5% and 17.5%;
   (c) 14:0 TAP at a molar percentage between 10% and 15%;
   (d) DOPE at a molar percentage between 15% and 25%;
   (e) cholesterol at a molar percentage between 30% and 40%; and
   (f) a DMG-PEG at a molar percentage between 1% and 5%.

9. The LNP composition of claim 8, wherein the LNP composition further comprises a payload.

10. The LNP composition of claim 1, wherein the payload is a messenger RNA (mRNA).

11. The LNP composition of claim 10, wherein the LNP composition comprises the mRNA at a lipid:mRNA ratio of less than 40:1.

12. The LNP composition of claim 10, wherein the LNP composition comprises the mRNA at a lipid:mRNA ratio of 33:1.

13. The LNP composition of claim 10, wherein the mRNA encodes a cystic fibrosis transmembrane conductance regulator (CFTR) protein.

14. The LNP composition of claim 13, wherein the LNP composition comprises the mRNA at a lipid:mRNA ratio of less than 40:1.

15. The LNP composition of claim 1, wherein the LNP composition comprises the mRNA at a lipid:mRNA ratio of 33:1.

16. The LNP composition of claim 10, wherein the mRNA encodes a dynein axonemal intermediate chain 1 (DNAI1) protein.

17. The LNP composition of claim 1, wherein the LNP composition comprises
   (a) 4A3-SC7 at a molar percentage of about 15%;
   (b) DODAP at a molar percentage of about 15%;
   (c) 14:0 TAP at a molar percentage of about 12%;
   (d) DOPE at a molar percentage between 15% and 25%;
   (e) cholesterol at a molar percentage between 30% and 40%; and
   (f) a DMG-PEG at a molar percentage between 1% and 5%.

18. The LNP composition of claim 17, wherein the LNP composition further comprises a payload.

19. The LNP composition of claim 18, wherein the payload is a messenger RNA (mRNA).

20. The LNP composition of claim 19, wherein the LNP composition comprises the mRNA at a lipid:mRNA ratio of less than 40:1.

21. The LNP composition of claim 19, wherein the LNP composition comprises the mRNA at a lipid:mRNA ratio of 33:1.

22. The LNP composition of claim 19, wherein the mRNA encodes a cystic fibrosis transmembrane conductance regulator (CFTR) protein.

23. The LNP composition of claim 22, wherein the LNP composition comprises the mRNA at a lipid:mRNA ratio of less than 40:1.

24. The LNP composition of claim 22, wherein the LNP composition comprises the mRNA at a lipid:mRNA ratio of 33:1.

25. The LNP composition of claim 19, wherein the mRNA encodes a dynein axonemal intermediate chain 1 (DNAI1) protein.

26. The LNP composition of claim 4, wherein the LNP composition further comprises a payload.

27. The LNP composition of claim 26, wherein the payload is a messenger RNA (mRNA).

28. The LNP composition of claim 27, wherein the LNP composition comprises the mRNA at a lipid:mRNA ratio of less than 40:1.

29. The LNP composition of claim 27, wherein the LNP composition comprises the mRNA at a lipid:mRNA ratio of 33:1.

30. The LNP composition of claim 27, wherein the mRNA encodes a cystic fibrosis transmembrane conductance regulator (CFTR) protein.

31. The LNP composition of claim 27, wherein the LNP composition comprises the mRNA at a lipid:mRNA ratio of less than 40:1.

32. The LNP composition of claim 30, wherein the LNP composition comprises the mRNA at a lipid:mRNA ratio of 33:1.

33. The LNP composition of claim 27, wherein the mRNA encodes a dynein axonemal intermediate chain 1 (DNAI1) protein.

34. The LNP composition of claim 1, wherein the DMG-PEG is DMG-PEG2000.

35. The LNP composition of claim 2, wherein the DMG-PEG is DMG-PEG2000.

36. The LNP composition of claim 3, wherein the DMG-PEG is DMG-PEG2000.

37. The LNP composition of claim 4, wherein the DMG-PEG is DMG-PEG2000.

38. The LNP composition of claim 8, wherein the DMG-PEG is DMG-PEG2000.

39. The LNP composition of claim 17, wherein the DMG-PEG is DMG-PEG2000.

* * * * *

SEQUENCE LISTING

```
Sequence total quantity: 7
SEQ ID NO: 1             moltype = DNA  length = 4647
FEATURE                  Location/Qualifiers
source                   1..4647
                         mol_type = other DNA
                         organism = synthetic construct
SEQUENCE: 1
gggagaccca agctggctag cgtttaaact tcagcttggc aatccggtac tgttggtaaa    60
gccaccatgc agagaagccc cctggaaaag gccagcgtgg tgagcaagct gttcttcagc   120
tggacccggc ccatcctgcg gaagggctac agacagagac tggaactgag cgacatctac   180
cagatcccca gcgtggacag cgccgacaac ctgagcgaga agctggaaag agagtgggac   240
agagagctgg ccagcaagaa gaaccccaag ctgatcaacg ccctgcggcg gtgcttcttc   300
tggcggttca tgttctacgg catcttcctg tacctgggcg aagtgaccaa agccgtgcag   360
cccctgctgc tgggcagaat catcgccagc tacgaccccg acaacaaaga ggaacggagc   420
atcgccatct acctcggcat cggcctgtgc ctgctgttca tcgtcagaac cctgctgctg   480
caccccgcca tcttcggact gcaccacatc ggcatgcaga tgcggatcgc catgttcagc   540
ctgatctaca agaaaacccT gaagctgagc agcagagtgc tggacaagat cagcatcgga   600
cagctggtga gcctgctgag caacaacctg aacaagttcg acgaaggcct ggccctggcc   660
cacttcgtgt ggatcgcccc cctgcaagtg gccctgctga tgggcctgat ctgggaactg   720
ctgcaggcca gcgccttctg cggactggga ttcctgatcg tgctggccct gttccaggcc   780
ggactgggga gaatgatgat gaagtaccgg gaccagagag ccggcaagat cagcgagaga   840
```

```
ctggtcatca ccagcgagat gatcgagaac atccagagcg tgaaggccta ctgctgggaa    900
gaggccatgg aaaagatgat cgagaacctg cggcagaccg agctgaagct gacaagaaag    960
gccgcctacg tgcgctactt caacagcagc gccttcttct tcagcggctt cttcgtggtg   1020
ttcctgagcg tgctgcccta cgccctgatc aagggcatca tcctgagaaa gatcttcacc   1080
accatcagct tctgcatcgt gctgcggatg gccgtgacca gacagttccc ctgggccgtg   1140
cagacctggt acgacagcct gggcgccatc aacaagatcc aggacttcct gcagaagcaa   1200
gagtacaaga ccctcgagta caacctgacc accaccgagg tggtcatgga aaacgtgacc   1260
gccttctggg aggaaggctt cggcgagctg ttcgagaagg ccaagcagaa caacaacaac   1320
cgcaagacca gcaacggcga cgacgcctg ttcttcagca acttcagcct gctggggacc   1380
cccgtgctga aggacatcaa cttcaagatc gagcgggac agctgctggc cgtggccgga   1440
agcacaggcg ccggaaaaac cagcctgctc atggtcatca tgggcgagct ggaacccagc   1500
gagggcaaga tcaagcacag cggcaggatc agcttctgca gccagttcag ctggatcatg   1560
cccggcacca tcaaagagaa catcatcttc ggcgtgagct acgacgagta cagataccgc   1620
agcgtgatca aggcctgcca gctggaagag gacatcagca gttcgccga gaaggacaac   1680
atcgtgctcg gcgaaggcgg catcacactg agcggcggac agagggccag aatcagcctg   1740
gccagagccg tgtacaagga cgccgacctg tacctgctgg acagccctt cggctacctg   1800
gacgtgctga ccgagaaaga gatcttcgag agctgcgtgt gcaagctgat ggccaacaag   1860
acccggatcc tggtcaccag caagatgaa cacctgaaga ggccgacaa gatcctgatc   1920
ctgcacgagg gcagcagcta cttctacggc accttcagcg agctgcagaa cctgcagccc   1980
gacttcagca gcaaactgat gggctgcgac agcttcgacc agttcagcgc cgagcggaga   2040
aacagcatcc tgacagagac actgcaccgg ttcagcctgg aaggcgacgc ccccgtgagc   2100
tggaccgaga caaagaagca gagcttcaag cagaccggcg agttcggcga agcggaag    2160
aacagcatcc tgaaccccat caacagcatc cggaagttca gcatcgtcca gaaaaccccc   2220
ctgcagatga acggcatcga gaggacagc gacgagcccc tggaaagacg gctgagcctg   2280
gtgcccgaca gcgaacaggg cgaagccatc ctgccccgga tcagcgtgat cagcacaggc   2340
cccacactgc aggcccggag aaggcaggac gtgctgaacc tgatgaccca gcgcgtgaac   2400
cagggacaga acatccacag aaagaccacc gccagcacac ggaaagtgag cctggcccc    2460
caggccaacc tgactgagct ggacatctac agcagacggc tgagccaaga gacaggcctg   2520
gaaatcagcg aggaaatcaa cgaagaggac ctgaagagt gcttcttcga cgacatggaa   2580
agcatccccg ccgtgacaac ctggaacacc tacctgcgat acatcaccgt gcacaagagc   2640
ctgatcttcg tgctgatctg tgcctcgtg atcttcctgg ccgaagtggc cgccagcctg   2700
gtggtgctgt ggctgctcgg aaacacccca ctgcaggaca agggcaacag cacccacagc   2760
cggaacaaca gctacgccgt gatcatcacc agcaccagca gctactacgt gttctacatc   2820
tacgtgggcg tcgccgacac tctgctcgcc atgggcttct tcagaggact gccccctggtg   2880
cacaccctga tcaccgtgag caagatcctg caccacaaga tgctgcacgg cgtcctgcag   2940
gccccccatga gcacactgaa caccctgaaa gccggcggaa tcctgaacag attcagcaag   3000
gacatcgcca tcctggacga cctgctgccc ctgaccatct tcgacttcat ccagctgctg   3060
ctgatcgtga tcggcgccat cgccgtggtg gccgtgctgc agccctacat cttcgtggcc   3120
accgtccccg tgatcgtgg cttcatcatg ctgcgggacct acttcctgca gaccgccag   3180
cagctgaagc agctcgagag cgagggcaga agccccatct tcacccacct cgtgaccagc   3240
ctgaaaggcc tgtggaccct gagagccttc ggcagacagc cctacttcga cactgttcc   3300
cacaaggccc tgaacctgca caccgccaac tggttcctgt acctgagcac cctgcggtgg   3360
ttccagatga ggatcgagat gatcttcgtc atcttcttca tcgccgtgac cttcatcagc   3420
atcctcacca ctggcgaagg cgagggcaga gtgggaatca tcctgaccct ggccatgaac   3480
atcatgagca cactccagtg ggccgtgaac agcagcatcg acgtggacag cctgatgcgg   3540
agcgtgagcc gggtgttcaa gttcatcgac atgcccacag agggcaagcc caccaagagc   3600
accaagccct acaagaacgg ccagctgagc aaagtcatga tcatcgagaa cagccacgtc   3660
aagaaggacg acatctggcc cagcggagc cagatgaccg tgaaggacct gaccgccaag   3720
tacaccgaag gcgaaacgc catcctgaa aacatcagct tcagcatcag ccccggccag   3780
cgcgtgggac tcctgggaag aaccggaagc ggcaagagca ctctgctgag cgccttcctg   3840
agactgctga acaccgaggg cgagatccag atcgacgggg tgagctggga cagcatcgcc   3900
ctgcaacaat ggcggaaggc cttcggcgtg atccccaga aggtgttcat cttcagcggc   3960
acgttccgga agaacctgga ccccacgag cagtggagcg accaagagat ctggaaggtg   4020
gccgacgaag tgggactgag aagcgtgatc gagcagttcc ccggcaagct ggacttcgtg   4080
ctggtggacg gcggctgcgt gctgagccac ggacacaaga gctgatgtg cctggccaga   4140
agcgtgctga gcaaggccaa gatcctgctg ctcgacgagc ccagcgccca cctggacccc   4200
gtgacctacc agatcatccg gcggacactg aagcaggcct tcgccgactg caccgtgatc   4260
ctgtgcgagc acagaatcga ggccatgctg gaatgccagc agttcctggt gatcgaagag   4320
aacaaagtgc ggcagtacga cagcatccag aagctgctga acgagcggag cctgttcaga   4380
caggccatca gcccccagcga cagagtgaag ctgttccccc accggaacag cagcaagtgc   4440
aagagcaagc cccagatcgc cgccctgaaa gaagaaaccg aggaagaggt gcaggacaca   4500
cggctgtgag aattctgcag aaaaaaaaaa aaaaaaaaaa aaaaaaaaaa aaaaaaaaaa   4560
aaaaaaaaaa aaaaaaaaaa aaaaaaaaaa aaaaaaaaaa aaaaaaaaaa aaaaaaaaaa   4620
aaaaaaaaaa aaaaaaaaaa aaattcg                                      4647

SEQ ID NO: 2           moltype = DNA   length = 66
FEATURE                Location/Qualifiers
source                 1..66
                       mol_type = other DNA
                       organism = synthetic construct
SEQUENCE: 2
gggagaccca agctggctag cgtttaaact tcagcttggc aatccggtac tgttggtaaa   60
gccacc                                                              66

SEQ ID NO: 3           moltype = DNA   length = 141
FEATURE                Location/Qualifiers
source                 1..141
                       mol_type = other DNA
                       organism = synthetic construct
```

```
SEQUENCE: 3
tgagaattct gcagaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaattc g                                             141

SEQ ID NO: 4            moltype = DNA   length = 2301
FEATURE                 Location/Qualifiers
source                  1..2301
                        mol_type = other DNA
                        organism = synthetic construct
SEQUENCE: 4
gggagaccca agctggctag cgtttaaact tcagcttggc aatccggtac tgttggtaaa     60
gccaccatga tcccagcaag cgccaaggca ccacacaagc agccccacaa gcagagcatc    120
agcatcggca ggggcacaag gaagagggac gaggacagcg gaaccgaagt gggagaggga    180
acagacgagt gggcacagag caaggcaacc gtgcgcccac ccgaccagct ggagctgaca    240
gacgccgagc tgaaggagga gttcaccagg atcctgacag ccaacaaccc acacgccccc    300
cagaacatcg tgcgctacag cttcaaggag ggcacataca agccaatcgg cttcgtgaac    360
cagctggccg tgcactacac ccaagtgggc aacctgatcc ccaaggacag cgacgagggc    420
cggagacagc actacaggga cgagctggtg gcaggaagcc aggagagcgt gaaagtgatc    480
agcgagaccg gcaacctgga ggaggacgag gagccaaagg agctggagac cgagccagga    540
agccagacag acgtgcccgc agcaggagca gcagagaagg tgaccgagga ggagctgatg    600
acacccaagc agccaaagga gcggaagctg accaaccagt tcaacttcag cgagagagcc    660
agccagacat acaacaaccc agtgcggac agagagtgcc agaccgagcc acccccaga     720
accaacttca gcgccacagc caaccagtgg gagatctacg acgcctacgt ggaggagctg    780
gagaagcagg agaagaccaa ggagaaggag aaggccaaga caccgtggc caagaagagc    840
ggcaagatgg ccatgcggaa gctgaccagc atggagagcc agacagacga cctgatcaag    900
ctgagccagg ccgccaagat catggagaga atggtgaacc agaacaccta cgacgacatc    960
gcccaggact tcaagtacta cgacgacgca cagacgagt acaggacca agtgggcaca    1020
ctgctgcccc tgtggaagtt ccagaacgac aaggccaaga gctgagcgt gaccgccctg   1080
tgctggaacc caagtacag ggacctgttc gcagtggcac tacggaagcta cgacttcatg   1140
aagcagagca gaggcatgct gctgctgtac agcctgaaga accccagctt ccccgagtac   1200
atgttcagca gcaacagcgg cgtgatgtgc ctggacatcc acgtggacca ccctacctg   1260
gtggccgtgg gccactacga cggcaacgtg gccatctaca acctgaagaa gccccacagc   1320
cagcccagct tctgcagcag cgccaagagc ggcaaggaca cgcaccccgt gtggcaggtg   1380
aagtggcaga aggacgacat ggaccagaac ctgaacttct tcagcgtgag cagcgacggc   1440
aggatcgtga gctggaccct ggtgaagcgc aagctggtgc acatcgacgt gatcaagctg   1500
aaggtggagg gcagcaccac agaggtgcca gagggactgc agctgcaccc agtgggatgc   1560
ggcacagcct tcgacttcca caaggagatc gactacatgt tcctggtggg caccgaggag   1620
ggcaagatct acaagtgcag caagagctac agcagccagt tcctggacac atacgacgcc   1680
cacaacatga gcgtggacac cgtgagctgg aaccccatacc acacaaaggt gttcatgagc   1740
tgcagcagcg actggaccgt gaagatctgg gaccacacca tcaagacacc catgttcatc   1800
tacgacctga acagcgccgt gggcgacgtg gcatgggcac catacagcag cacagtgttc   1860
gcagcagtca ccagcagcgg caaggcacac atcttcgaca tggccatcaa caagtacgag   1920
gccatctgca accagcccgt ggccgccaag aagaacaggc tgacccacgt gcagttcaac   1980
ctgatccacc ccatcatcat cgtgggcgac gaccgggggcc acatcatcag cctgaagctg   2040
agccccaacc tgaaaagat gcccaaggag aagagggac aggaggtgca gaagggacca    2100
gcagtggaga tcgcaaagct ggacaagctg ctgaacctgg tgcgcgaggt gaagatcaag   2160
acctgagaat tctgcagaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaattc g                                           2301

SEQ ID NO: 5            moltype = DNA   length = 66
FEATURE                 Location/Qualifiers
source                  1..66
                        mol_type = other DNA
                        organism = synthetic construct
SEQUENCE: 5
gggagaccca agctggctag cgtttaaact tcagcttggc aatccggtac tgttggtaaa     60
gccacc                                                               66

SEQ ID NO: 6            moltype = DNA   length = 2097
FEATURE                 Location/Qualifiers
source                  1..2097
                        mol_type = other DNA
                        organism = synthetic construct
SEQUENCE: 6
atgatcccag caagcgccaa ggcaccacac aagcagcccc acaagcagag catcagcatc     60
ggcagggca caaggaagag ggacgaggac agcggaaccg aagtgggaga gggaacagac    120
gagtgggcac agagcaaggc aaccgtgcgc ccacccgacc agctggagct gacagacgac    180
gagctgaagg aggagttcac caggatcctg acagccaaca acccacacgc ccccccagaac    240
atcgtgcgct acagcttcaa ggagggcaca tacaagccaa tcggcttcgt gaaccagctg    300
gccgtgcact acacccaagt gggcaacctg atccccaagg acagcgacga gggccggaga    360
cagcactaca gggacgagct ggtggcagga agccaggaga gcgtgaaagt gatcagcgag    420
accggcaacc tggaggagga cgaggagcca aaggagctgg agaccgagcc aggaagccag    480
acagacgtgc ccgcagcagg agcagcagag aaggtgaccg aggaggagct gatgacaccc    540
aagcagccaa aggagcggaa gctgaccaac cagttcaact tcagcgagag agccagccag    600
acatacaaca acccagtgcg ggacagagag tgccagaccg agccaccccc agaaccaac    660
ttcagcgcca cagccaacca gtgggagatc tacgacgcct acgtggagga gctggagaag    720
caggagaaga ccaaggagaa ggagaaggcc aagacacccg tggccaagaa gagcggcaag    780
```

```
atggccatgc ggaagctgac cagcatggag agccagacag acgacctgat caagctgagc    840
caggccgcca agatcatgga gagaatggtg aaccagaaca cctacgacga catcgcccag    900
gacttcaagt actacgacga cgcagcagac gagtacaggg accaagtggg cacactgctg    960
cccctgtgga agttccagaa cgacaaggcc aagaggctga gcgtgaccgc cctgtgctgg   1020
aacccaaagt acagggacct gttcgcagtg ggatacggaa gctacgactt catgaagcag   1080
agcagaggca tgctgctgct gtacagcctg aagaacccca gcttccccga gtacatgttc   1140
agcagcaaca gcgcgtgat gtgcctggac atccacgtgg accacccta cctggtggcc    1200
gtgggccact acgacggcaa cgtggccatc tacaacctga agaagcccca cagccagccc   1260
agcttctgca gcagcgccaa gagcggcaag cacagcgacc ccgtgtggca ggtgaagtgg   1320
cagaaggacg acatggacca gaacctgaac ttcttcagcg tgagcagcga cggcaggatc   1380
gtgagctgga ccctggtgaa gcgcaagctg gtgcacatcg acgtgatcaa gctgaaggtg   1440
gagggcagca ccacagaggt gccagaggga ctgcagctgc acccagtggg atgcggcaca   1500
gccttcgact tccacaagga gatcgactac atgttcctgg tgggcaccga ggagggcaag   1560
atctacaagt gcagcaagag ctacacagc cagttcctgg acacatacga cgcccacaac   1620
atgagcgtgg acaccgtgag ctggaacccc taccacacaa aggtgttcat gagctgcagc   1680
agcgactgga ccgtgaagat ctgggaccac accatcaaga cacccatgtt catctacgac   1740
ctgaacagcg ccgtgggcga cgtggcatgg gcaccataca gcagcacagt gttcgcagca   1800
gtgaccacag acggcaaggc acacatcttc gacctggcca tcaacaagta cgaggccatc   1860
tgcaaccagc ccgtggccgc caagaagaac aggctgaccc acgtgcagtt caacctgatc   1920
cacccatca tcatcgtggg cgacgaccgg ggccacatca tcagcctgaa gctgagcccc   1980
aacctgagaa agatgcccaa ggagaagaag ggacaggagg tgcagaaggg accagcagtg   2040
gagatcgcaa agctggacaa gctgctgaac ctggtgcgcg aggtgaagat caagacc      2097

SEQ ID NO: 7             moltype = DNA  length = 138
FEATURE                  Location/Qualifiers
source                   1..138
                         mol_type = other DNA
                         organism = synthetic construct
SEQUENCE: 7
tgagaattct gcagaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaattcg                                                  138
```